(12) United States Patent
English et al.

(10) Patent No.: US 7,722,718 B2
(45) Date of Patent: May 25, 2010

(54) METHODS FOR CRYSTALLIZING ERK2 POLYPEPTIDES

(75) Inventors: Jessie English, Cambridge, MA (US); Thierry Oliver Fischmann, Scotch Plains, NJ (US); Thomas Hesson, Kendall Park, NJ (US); Alan William Hruza, Hackettstown, NJ (US); Weihong Jin, Fanwood, NJ (US); Paul Reichert, Montville, NJ (US); Catherine Smith, Union, NJ (US); Shahriar Shane Taremi, Cambridge, MA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/873,831

(22) Filed: Oct. 17, 2007

(65) Prior Publication Data

US 2008/0081360 A1 Apr. 3, 2008

Related U.S. Application Data

(62) Division of application No. 11/233,581, filed on Sep. 23, 2005, now Pat. No. 7,312,061.

(60) Provisional application No. 60/612,704, filed on Sep. 24, 2004.

(51) Int. Cl.
 *C30B 27/02* (2006.01)
 *C12N 9/12* (2006.01)
(52) U.S. Cl. .............. 117/68; 435/194; 117/70
(58) Field of Classification Search .................. None
 See application file for complete search history.

(56) References Cited

U.S. PATENT DOCUMENTS

2008/0201123 A1* 8/2008 Cosgrove ............. 703/11

OTHER PUBLICATIONS

GenBank Accession No. P27703, Dec. 1992.*
McPherson, Eur. J. Biochem. 189:1-23, 1990.*
Seah et al., J. Biol. Chem. 273:22943-22949, 1998.*
Cioci et al., FEBS Lett. 555:297-301, 2003.*
Canagarajah et al., "Activation mechanism of the MAP kinase ERK2 by dual phosphorylation". Cell. Sep. 5, 1997;90(5):859-869.
Eblen et al., "Identification of novel ERK2 substrates through use of an engineered kinase and ATP analogs". J. Biol. Chem. Apr. 25, 2003;278(17):14926-14935. Epub Feb. 19, 2003.
Fox et al., "A single amino acid substitution makes ERK2 susceptible to pyridinyl imidazole inhibitors of p38 MAP kinase". Protein Sci. 1998; 7: 2249-2255.
Gilliland et al., "Crystallization of biological macromolecules for X-ray diffraction studies". Curr Opin Struct Biol. Oct. 1996;6(5):595-603.
Ke et al., "Crystallization of RNA and RNA-protein complexes". Methods. Nov. 2004;34(3):408-414.
Szedlacsek et al., "Crystal structure of PTP-SL/PTPBR7 catalytic domain: implications for MAP kinase regulation". J. Mol. Biol. Aug. 17, 2001;311(3):557-568.
Vesely et al., "Inhibition of cyclin-dependent kinases by purine analogues". Eur. J. Biochem. Sep. 1, 1994;224(2):771-786.
Wang et al., "Structural basis of inhibitor selectivity in MAP kinases". Structure. Sep. 15, 1998;6(9):1117-1128.
Wiencek et al., "New strategies for protein crystal growth". Ann. Rev. Biomed. Eng. 1999; 1: 505-534.
Zhang et al., "Crystallization and preliminary X-ray studies of extracellular signal-regulated kinase-2/MAP kinase with an incorporated His-tag". J. Mol. Biol. Oct. 5, 1993;233(3):550-552.
Zhang et al., "Atomic structure of the MAP kinase ERK2 at 2.3 A resolution". Nature. Feb. 24, 1994;367(6465):704-711.
Zhang et al., "Activity of the MAP kinase ERK2 is controlled by a flexible surface loop". Structure. Mar. 15, 1995;3(3):299-307.

* cited by examiner

*Primary Examiner*—David J Steadman

(57) ABSTRACT

The present invention relates to crystals of the ERK2 polypeptide and complexes thereof which are useful, inter alia, for structure assisted drug design.

5 Claims, No Drawings

METHODS FOR CRYSTALLIZING ERK2 POLYPEPTIDES

The present application is a division of U.S. patent application Ser. No. 11/233,581; filed Sep. 23, 2005, now U.S. Pat. No. 7,312,061, which claims the benefit of U.S. provisional patent application No. 60/612,704; filed Sep. 24, 2004, each of which is incorporated herein by reference in its entirety.

FIELD OF THE INVENTION

The present invention relates crystals of ERK2 polypeptides, complexes thereof and methods of synthesis thereof.

BACKGROUND OF THE INVENTION

The protein kinases that constitute mitogen activated protein kinases (MAPK) pathways are currently studied by the pharmaceutical industry because of the central role MAPK modules play in mediating cellular responses to stimuli such as growth factors and cytokines. The MAPK kinases, ERK1 and ERK2, are activated by a phosphorylation signaling cascade in response to hormones and growth factors. Specifically, ERK1 and ERK2 are activated by the kinase MEK1 and MEK2 through dual phosphorylation on conserved threonine and tyrosine residues in the ERK's activation loop. Known oncogenes such as Ras and Raf are upstream activators of ERKs 1 and 2. ERK2 is aberrantly activated in multiple common tumor types, and its inhibition reverses cellular transformation. Hence, there is considerable interest in the role ERK1,2 signaling plays in oncogenic transformation and in targeting ERK1,2 for cancer therapies using small molecules. Structure assisted drug design is a tool used to optimize the success of identifying such therapeutic compounds. However, use of this powerful methodology requires three-dimensional structural information (e.g., as obtained via X-ray diffraction of the target protein). The crystal structure of unphosphorylated ERK2 (Zhang et al., J. Mol. Bio. 233: 550-552 (1993); Zhang et al., Nature 367:704-711 (1994); Wang et al., Structure 6(9): 1117-1128 (1998)) and of diphosphorylated ERK2 (Canagarajah et al., Cell 90:859-869 (1997)) was determined. The crystal structure of ERK2 complexed with olomoucine was also determined (Wang et al., Structure 6(9): 1117-1128 (1998)). Nevertheless, there is a need in the art for crystals with which high resolution structural determination can be performed. The present invention addresses this need by providing such crystals.

SUMMARY OF THE INVENTION

The present invention includes new crystal forms of the unphosphorylated, di-phosphorylated and di-thio phosphorylated ERK2. These crystal forms are suitable for structure assisted drug design.

The present invention provides an isolated crystal comprising mouse diphosphorylated $Ah_6$-ERK2 polypeptide wherein threonine 190 is phosphorylated and tyrosine 192 is phosphorylated (e.g., SEQ ID NO: 5) and an isolated crystal comprising mouse diphosphorylated ERK2 polypeptide (e.g., SEQ ID NO: 6) wherein threonine 183 is phosphorylated and tyrosine 185 is phosphorylated wherein said crystals comprise (a) unit cell dimensions: a=71.710 Å, b=72.076 Å, c=84.466 Å, α=76.119°, β=84.738° γ=80.343°; and (b) Space Group: P1 (number 1). In an embodiment of the invention, the crystal is characterized by structural coordinates comprising a root mean square deviation of conserved residue backbone atoms or alpha carbon atoms of less than about 1.5 Å, 1.0 Å, 0.5 Å or 0.1 Å, when superimposed on backbone atoms or alpha carbon atoms described by structural coordinates of Table 2. In another embodiment, the crystal is characterized by the structural coordinates of Table 2.

The present invention also provides an isolated crystal comprising mouse $Ah_6$-ERK2 polypeptide (e.g., SEQ ID NO: 5) and an isolated crystal comprising mouse ERK2 polypeptide (e.g., SEQ ID NO: 6) wherein said crystals comprise (a) unit cell dimensions: a=70.611 Å, b=92.158 Å, c=63.735 Å, α=β=γ=90°; and (b) Space Group: $P2_12_12$ (Number 18). In an embodiment of the invention, the crystal is characterized by structural coordinates comprising a root mean square deviation of conserved residue backbone atoms or alpha carbon atoms of less than about 1.5 Å, 1.0 Å, 0.5 Å or 0.1 Å, when superimposed on backbone atoms or alpha carbon atoms described by structural coordinates of Table 1. In an embodiment of the invention, the crystal is characterized by the structural coordinates of Table 1.

The invention also provides an isolated crystal comprising mouse dithiophosphorylated $Ah_6$-ERK2 polypeptide wherein threonine 190 is thiophosphorylated and tyrosine 192 is thiophosphorylated (e.g., SEQ ID NO: 5) and an isolated crystal comprising mouse dithiophosphorylated ERK2 polypeptide (e.g., SEQ ID NO: 6) wherein threonine 183 is thiophosphorylated and tyrosine 185 is thiophosphorylated wherein said crystals comprise (a) Unit Cell: a=92.892 Å, b=92.892 Å, c=99.829 Å, α=β=90° γ=120°; and (b) Space Group: $P3_221$ (number 154). In an embodiment of the invention, the crystal is characterized by structural coordinates comprising a root mean square deviation of conserved residue backbone atoms or alpha carbon atoms of less than about 1.5 Å, 1.0 Å, 0.5 Å or 0.1 Å when superimposed on backbone atoms or alpha carbon atoms described by structural coordinates of Table 3. In an embodiment of the invention, the crystal is characterized by the structural coordinates of Table 3.

The present invention also comprises an isolated crystal comprising mouse $Ah_6$-ERK2 (e.g., SEQ ID NO: 5) complexed with 1-olomoucine

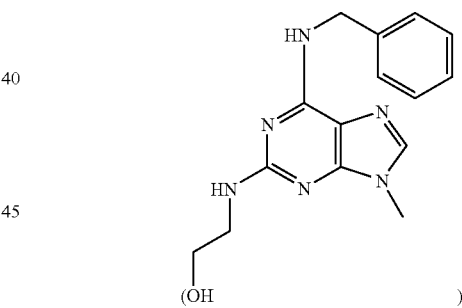

and an isolated crystal comprising mouse ERK2 (e.g., SEQ ID NO: 6) complexed with 1-olomoucine

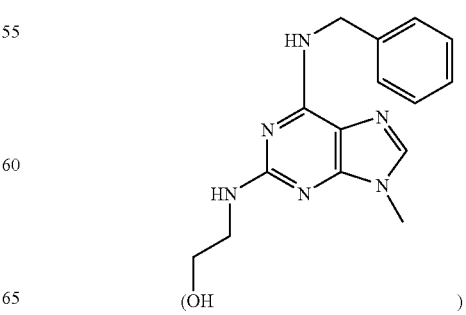

comprising (a) Unit Cell: a=70.622 Å, b=92.154 Å, c=63.103 Å, α=β=γ=90°; and (b) Space Group: P2₁2₁2 (Number 18). In an embodiment of the invention, the crystal is characterized by structural coordinates comprising a root mean square deviation of conserved residue backbone atoms or alpha carbon atoms of less than about 1.5 Å, 1.0 Å, 0.5 Å or 0.1 Å when superimposed on backbone atoms or alpha carbon atoms described by structural coordinates of Table 4. In an embodiment of the invention, the crystal is characterized by the structural coordinates of Table 4.

Also provided by the present invention is a method for crystallizing a mouse ERK2 polypeptide or mouse $Ah_6$-ERK2 polypeptide (e.g., comprising the amino acid sequence of SEQ ID NO: 5 or 6) comprising placing said polypeptide (e.g., wherein the polypeptide was expressed recombinantly, for example, in bacteria) in an aqueous buffered solution comprising from about 1% to about 8% PEG 400 (v/v), about 2.4M ammonium sulfate and a pH of from about 5.5 to about 6.7 (e.g., by the hanging-drop vapor diffusion method). In an embodiment of the invention, the polypeptide is at a concentration of about 5 mg/ml to about 25 mg/ml. In an embodiment, the crystallization is carried out at 22° C. Any crystal produced by any embodiment of the method is also within the scope of the present invention.

The present invention also provides a method for crystallizing a diphosphorylated mouse ERK2 polypeptide, wherein threonine 183 is phosphorylated and tyrosine 185 is phosphorylated or diphosphorylated mouse $Ah_6$-ERK2 polypeptide wherein threonine 190 is phosphorylated and tyrosine 192 is phosphorylated (e.g., comprising the amino acid sequence of SEQ ID NO: 5 or 6), comprising placing said polypeptide (e.g., wherein the polypeptide was expressed recombinantly, for example, in bacteria) in an aqueous buffered solution of having a pH of from about 5 to about 6.2 and a concentration of from about 5% to about 30% isopropanol (v/v) (e.g., by the hanging-drop vapor diffusion method). In an embodiment of the invention, the polypeptide is at a concentration of about 3 mg/ml to about 25 mg/ml. Any crystal produced by any embodiment of the method is also within the scope of the present invention.

The present invention further provides a method for crystallizing a dithiophosphorylated mouse ERK2 polypeptide, wherein threonine 183 is thiophosphorylated and tyrosine 185 is thiophosphorylated or dithiophosphorylated mouse $Ah_6$-ERK2, wherein threonine 190 is thiophosphorylated and tyrosine 192 is thiophosphorylated (e.g., comprising the amino acid sequence of SEQ ID NO: 5 or 6), comprising placing said polypeptide (e.g., wherein the polypeptide was expressed recombinantly, for example, in bacteria) in an aqueous buffered solution of having a pH of from about 5 to about 6.2 and a concentration of from about 5% to about 30% isopropanol (v/v) (e.g., by the hanging-drop vapor diffusion method). In an embodiment of the invention, the polypeptide is at a concentration of about 3 mg/ml to about 25 mg/ml. Any crystal produced by any embodiment of the method is also within the scope of the present invention.

Also provided by the present invention is a method for making a crystal comprising mouse ERK2 or mouse $Ah_6$-ERK2 polypeptide complexed with olomoucine

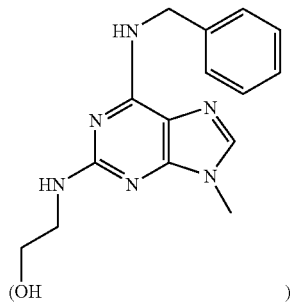

(OH                    )

(e.g., comprising the amino acid sequence of SEQ ID NO: 5 or 6) comprising placing said polypeptide (e.g., wherein the polypeptide was expressed recombinantly, for example, in bacteria) in an aqueous buffered solution comprising from about 1% to about 8% PEG 400 (v/v), about 2.4M ammonium sulfate and a pH of from about 5.5 to about 6.7, crystallizing the polypeptide by the hanging drop vapor diffusion method and soaking said crystal in a solution comprising olomoucine. Any crystal produced by any embodiment of the method is also within the scope of the present invention.

The present invention also provides a computer for producing a three-dimensional representation of (i) unphosphorylated mouse $Ah_6$-ERK2 or a homologue thereof, (ii) unphosphorylated mouse ERK2 or a homologue thereof, (iii) diphosphorylated mouse $Ah_6$-ERK2 or a homologue thereof, (iv) diphosphorylated mouse ERK2 or a homologue thereof, (v) dithiophosphorylated mouse $Ah_6$-ERK2 or a homologue thereof, (vi) dithiophosphorylated mouse ERK2 or a homologue thereof, (vii) unphosphorylate mouse $Ah_6$-ERK2 complexed with olomoucine

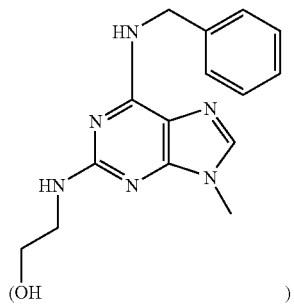

(OH                    )

or a homologue thereof; or (viii) unphosphorylated mouse ERK2 complexed with olomoucine

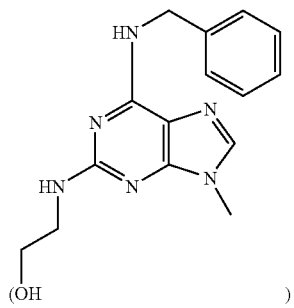

(OH                    )

or a homologue thereof; wherein said computer comprises: (a) a machine-readable data storage medium comprising a data storage material encoded with machine-readable data, wherein said data comprises the structure coordinates of Table 1, 2, 3, or 4; (b) a working memory for storing instructions for processing said machine-readable data; (c) a central-processing unit coupled to said working memory and to said machine-readable data storage medium for processing said machine readable data into said three-dimensional representation; and (d) a display unit coupled to said central-processing unit for displaying said three-dimensional representation. In an embodiment of the invention, the root mean square deviation between said homologue and the structure coordinates set forth in Table 1, 2, 3, or 4 is less than about 1 Å; less than about 0.5 Å or less than about 0.1 Å. In an embodiment of the invention, the display unit is displaying the three dimensional representation.

The present invention also provides a method of using the three-dimensional structure coordinates of any one of Tables 1-4, comprising: (a) determining structure factors from the coordinates; and (b) applying said structure factor information to a set of X-ray diffraction data obtained from a crystal of a protein homologous to mouse ERK2 (e.g., SEQ ID NO: 5 or 6); and (c) solving the three-dimensional structure of the protein homologous to mouse ERK2 (e.g., SEQ ID NO: 5 or 6).

The present invention also provides a method for identifying a potential inhibitor of a kinase comprising: (a) selecting or designing a potential inhibitor by performing rational drug design with a computer readable data storage material encoded with computer readable data comprising structure coordinates of any of Tables 1-4, wherein said selecting is performed in conjunction with computer modeling; (b) contacting the potential inhibitor with a kinase; and (c) detecting the ability of the potential inhibitor for inhibiting the kinase.

The present invention also provides as method for producing phosphorylated ERK2 (e.g., Ah6-ERK2) comprising contacting an ERK2 polypeptide with MEK1 and ATP with $Mg^{2+}$ (e.g., $MgCl_2$). In an embodiment of the invention, ATP is present at a molar amount that is more than $Mg^{2+}$ (e.g., $MgCl_2$). For example, in an embodiment of the invention, ATP is present at an equal molar to that of $Mg^{2+}$ (e.g., $MgCl_2$) wherein EDTA (a divalent cation chelator) is also present. In an embodiment of the invention, a phosphatase inhibitor, such as orthovanadate of potassium fluoride is also present. The present method further, optionally comprises isolating or purifying the phosphorylated ERK2 from the phosphorylation reaction components. In an embodiment of the invention, the concentration of ATP is 200-fold that of the ERK2 polypeptide. In an embodiment of the invention, ERK2 is completely, quantitatively phosphorylated at T190 and Y192 of Ah6-ERK2 (corresponding to T183 and Y185 of unfused ERK2). The present invention further comprises any diphosphorylated ERK2 produced by the foregoing method.

The present invention further provides a method for producing dithiophosphorylated ERK2 (e.g., Ah6-ERK2) comprising contacting ERK2 polypeptide with MEK1 and ATPγS and $Mg^{2+}$ (e.g., $MgCl_2$). The present method further, optionally comprises isolating or purifying the di-thiophosphorylated ERK2 from the thiophosphorylation reaction components. In an embodiment of the invention, the concentration of ATPγS is at a 10-fold excess over ERK2 polypeptide. In an embodiment of the invention, ERK2 is completely, quantitatively thiophosphorylated at T190 and Y192 of Ah6-ERK2 (corresponding to T183 and Y185 of unfused ERK2). The present invention further comprises any dithiophosphorylated ERK2 produced by the foregoing method.

DETAILED DESCRIPTION OF THE INVENTION

In accordance with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1996) (herein "Ausubel et al., 1996").

"$Ah_6$-ERK2" or "mouse $Ah_6$-ERK2" is mouse ERK2 comprising N-terminal Ala-His$_6$-. For example, in an embodiment of the invention, $Ah_6$-ERK2 comprises the amino acid sequence of SEQ ID NO: 5. In an embodiment of the invention, "mouse ERK2", not fused to an $Ah_6$ tag, comprises the amino acid sequence of SEQ ID NO: 6. In some embodiments of the invention, $Ah_6$-ERK2 comprises an N-terminal Methionine (e.g., SEQ ID NO: 3).

Mouse ERK2 polypeptide is well known in the art. For example, a mouse ERK2 polypeptide sequence is set forth under Genbank Accession No. BAA01733. The present invention includes ERK2 crystals comprising unphosphorylated, phosphorylated (e.g., diphosphorylated at T183 and Y185) or thiophosphorylated (e.g., dithiophosphorylated at T183 and Y185) ERK2. The present invention also includes $Ah_6$-ERK2 that is unphosphorylated, di-phosphorylated at T190 and at Y192 (i.e., residues corresponding to T183 and Y185 in the unfused ERK2 polypeptide) or di-thiophosphorylated at T190 and at Y192.

The term "olomoucine" or "1-olomoucine" refers to

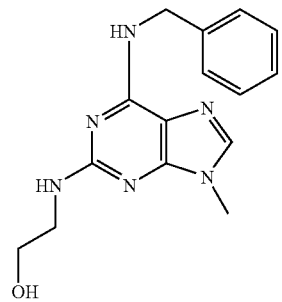

(Vesely et al., Eur. J. Biochem. 224: 771-786 (1994)). The present invention includes crystals comprising $Ah_6$-ERK2 or ERK2 complexed with olomoucine.

The term "enzymatically active" means a protein is catalytically active and, preferably, can phosphorylate a protein or peptide substrate (e.g., EtsΔ138; Waas et al.; Biochim Biophys Acta. 1697(1-2):81-87 (2004)).

In addition to ERK2 polypeptides described in the art, various mutant forms, homologues and variants of ERK2 can be employed; and crystals comprising such variants are within the scope of the present invention. The terms "mutant" and "mutation" refer to any detectable change in genetic material or amino acid sequence. This includes gene mutations, in which the structure (e.g., DNA sequence) of a gene is altered, any gene or DNA arising from any mutation process, and any expression product (e.g., RNA or protein) expressed by a modified gene or DNA sequence. The term "variant" may also be used to indicate a modified or altered gene, DNA sequence, polypeptide or enzyme, etc., i.e., any kind of mutant. Sequence- and function-conservative variants of ERK2 polypeptides are contemplated for use in the present invention and the present invention includes any crystal comprising any ERK2 variant. A natural allelic variant is one of several alternate naturally occurring forms of a gene occupying a given locus on a chromosome of an organism (Genes II, Lewin, B., ed., John Wiley & Sons, New York (1985)). "Function-conservative variants" of ERK2 are those in which a given amino acid residue in a ERK2 polypeptide has been changed without significantly altering the overall conformation and/or function of the polypeptide, including, but not limited to, replacement of an amino acid with one having similar properties (such as, for example, polarity, hydrogen bonding potential, acidic, basic, hydrophobic, aromatic (see infra)).

Protein or polypeptide sequence homology, or sequence identity, is determined by optimizing residue matches, if necessary, by introducing gaps as required. See, e.g., Needleham, et al. *J. Mol. Biol.* 48:443-453 (1970); Sankoff et al., "Time Warps, String Edits, and Macromolecules: The Theory and Practice of Sequence Comparison", Ch. 1, Addison-Wesley, Reading, Mass. (1983); and software packages from Intelli-Genetics, Mountain View, Calif. and the University of Wisconsin Genetics Computer Group (GCG), Madison, Wis.

The present invention includes any ERK2 polypeptide crystal wherein the amino acid sequence comprises less than 100% homology or identity to, for example, the ERK2 sequence of SEQ ID NO: 5 or 6 (e.g., natural allelic variations or homologues of ERK2). Preferably, an ERK2 polypeptide that is less than 100% homologous or identical to SEQ ID NO: 5 or 6 is enzymatically active. Sequence "identity" refers to exact matches between the amino acids of two sequences which are being compared. Sequence similarity refers to both exact matches between the amino acids of two polypeptides which are being compared in addition to matches between nonidentical, biochemically related amino acids. For example, biochemically related amino acids which share similar properties can fall within the following groups: polar/hydrophilic amino acids including asparagine, glutamine, serine, cysteine, threonine, lysine, arginine, histidine, aspartic acid and glutamic acid; nonpolar/hydrophobic amino acids including glycine, alanine, valine, leucine, isoleucine, proline, tyrosine, phenylalanine, tryptophan and methionine; acidic amino acids including aspartic acid and glutamic acid and basic amino acids including histidine, lysine and arginine. Typical ERK2 polypeptides and homologues thereof used in this invention will have from 50-100% homology or identity, to 60-100% homology or identity, e.g., with ERK2 comprising the amino acid sequence of SEQ ID NO: 5 or 6. The present invention includes crystals comprising ERK2 polypeptide or a homologue thereof comprising at least about 70% homology or identity, generally at least 76% homology or identity, more generally at least 81% homology or identity, often at least 85% homology or identity, more often at least 88% homology or identity, typically at least 90% homology or identity, more typically at least 92% homology or identity, usually at least 94% homology or identity, more usually at least 95% homology or identity, preferably at least 96% homology or identity, and more preferably at least 97% homology or identity, and in particularly preferred embodiments, at least 98% or more (e.g., 99%) homology or identity to the amino acid sequence of SEQ ID NO: 5 or 6.

The terms "express" and "expression" mean allowing or causing the information in a gene or DNA sequence to become manifest, e.g., producing a protein by activating the cellular functions involved in transcription and, optionally, translation of a corresponding gene or DNA sequence. A DNA sequence can be expressed using in vitro translation systems (e.g., rabbit reticulocyte lysate-based systems) or in or by a cell (e.g., an insect cell) to form an "expression product" such as a mRNA or a protein. The expression product, e.g. the resulting protein, may also be referred to as "expressed".

An insect cell used in this invention includes any cell derived from an organism of the class Insecta. In an embodiment of the invention, the insect is *Spodoptera fruigiperda* (e.g., Sf9 or Sf21) or *Trichoplusia ni* (e.g., High Five™ cells; Invitrogen; Carlsbad, Calif.)). Other examples of insect expression systems that can be used with the present invention, for example to produce ERK2 polypeptide, include Bac-To-Bac (Invitrogen Corporation, Carlsbad, Calif.) or Gateway (Invitrogen Corporation, Carlsbad, Calif.).

An ERK2 polypeptide can also be produced by any conventional method, including synthetic methods, such as solid phase, liquid phase and combination solid/liquid phase polypeptide syntheses; recombinant DNA methods, including cDNA cloning, optionally combined with site-directed mutagenesis; and/or purification of the natural products, optionally combined with enzymatic or chemical cleavage methods to produce fragments of naturally-occurring ERK2.

It may also be desirable to add amino acids at the amino- or carboxy-terminus of a ERK2 polypeptide, e.g., to prepare a fusion protein. In one embodiment, the addition is a polyhistidine tag of 5-20 amino acids, preferably 6 amino acids, in length. For example, the present invention includes crystals comprising $Ah_6$-ERK2, wherein Met-Ala-$His_6$ is appended to the ERK2 N-terminus (e.g., SEQ ID NO: 3) and crystals wherein the Met has been cleaved off (e.g., SEQ ID NO: 5). A histidine tag for aiding in purification of a ERK2 polypeptide can be located at the carboxy-terminus. In another embodiment, a myc tag is added to the carboxy-terminus of ERK2. A myc tag may be used for detection or immunopurification of ERK2. The myc tag and a polyhistidine tag may both be located at the carboxy-terminus or amino-terminus in a doubly-tagged ERK2.

The present invention contemplates crystals comprising ERK which has been modified (e.g., post-translationally modified) (e.g., phosphorylation, thiophosphorylation, sulfonation, PEGylation). Although ERK2 may be produced, for example, in mammalian cells (e.g., CHO cells, NIH3T3 cells), it is preferable to produce the protein recombinantly in an insect cell expression system (e.g., High Five™ cells). Initial purification may be accomplished by nickel chelate chromatography, as previously described in: Ausubel et al. supra. The ERK2 preparation may be subjected to anion exchange chromatography (e.g., MonoQ) for further purification. It may also be desirable to subject the ERK2 preparation to standard size exclusion gel filtration. The protein preparation may be further concentrated using standard techniques.

An ERK2 preparation can contain a protein stabilizing agent, a salt, a buffering agent and, optionally, a reducing agent or oxygen scavenger. Examples of suitable reducing agents are dithiothreitol (DTT), dithioerythritol (DET) and β-mercaptoethanol (BME).

A "precipitant" is a compound that decreases the solubility of a polypeptide in a concentrated solution. Alternatively, the term "precipitant" can be used to refer to a change in physical or chemical parameters which decreases polypeptide solubility, including temperature, pH and salt concentrations. Precipitants induce crystallization by forming an energetically unfavorable precipitant-depleted layer around the polypeptide molecules. To minimize the relative amount of this depletion layer, the polypeptides form associations and, ultimately, crystals. This process is explained in Weber, *Advances in Protein Chemistry* 41:1-36 (1991) which is incorporated by reference. In addition to precipitants, other materials are sometimes added to the polypeptide crystallization solution. These include buffers, such as Tris or Hepes, to adjust the pH of the solution (and hence surface charge on the peptide) and salts, such as sodium chloride, lithium chloride and sodium citrate, to reduce the solubility of the polypeptide. Various precipitants are known in the art and include the following: ammonium sulfate, ethanol, isopropanol, 3-ethyl-2,4 pentanediol; and many of the polyglycols, such as polyethylene glycol (e.g., PEG 400).

Crystallization may be accomplished by using any of the known methods in the art (Giegé, et al., (1994) *Acta Crystallogr.* D50: 339-350; McPherson, (1990) *Eur. J. Biochem.* 189: 1-23). Such techniques include hanging drop vapor diffusion, sitting drop vapor diffusion, microbatch and dialysis. Preferably, hanging-drop vapor diffusion (see e.g., McPherson, (1976) *J. Biol. Chem.* 251: 6300-6303) is used. Both hanging drop and sitting drop vapor diffusion entail a droplet containing purified protein, buffer, and precipitant being allowed to equilibrate with a larger reservoir containing similar buffers and precipitants in higher concentrations. Initially, the droplet of protein solution contains an insufficient concentration of precipitant for crystallization, but as water vaporizes from the drop and transfers to the reservoir, the precipitant concentration increases to a level optimal for crystallization. Since the system is in equilibrium, these optimum conditions are maintained until the crystallization is complete. The hanging drop method differs from the sitting drop method in the vertical orientation of the protein solution drop within the system. In the microbatch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels. It is desirable to use a ERK2 protein preparation having a concentration of at least about 1 mg/mL and preferably about 10 mg/mL to about 20 mg/mL.

The crystals of the present invention have a wide range of uses. For example, high quality crystals are suitable for X-ray or neutron diffraction analysis to determine the three dimensional structure of ERK2 and, in particular, to assist in the identification of the protein's active and effector sites. Knowledge of these sites and solvent accessible residues allow structure-based design and construction of agonists and antagonists for ERK2.

In addition, crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing high-quality crystals which are preferred for diffraction analysis.

Once a crystal of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of a ERK2 polypeptide. The present invention includes crystals which effectively diffract X-rays for the determination of the atomic coordinates of ERK2 to a resolution of greater than about 5.0 Ångströms (e.g., about 4.5 Å, about 4.0 Å, about 3 Å, about 2.5 Å, about 2 Å, about 1 Å, about 0.5 Å, about 0.1 Å), preferably greater than about 4.0 Ångströms (e.g., about 3 Å, about 2.5 Å, about 2 Å, about 1 Å, about 0.5 Å, about 0.1 Å), more preferably greater than about 2.8 Ångströms (e.g., about 2.5 Å, about 2 Å, about 1 Å, about 0.5 Å, about 0.1 Å) and most preferably greater than about 2.0 Ångströms (e.g., about 1.5 Å, about 1.0 Å, about 0.5 Å, about 0.1 Å).

The present invention includes ERK2 crystals whose three-dimensional structure is described by the structure coordinates set forth in Tables 14. The scope of the present invention also includes crystals which possess structural coordinates which are similar to those set forth in Table 1-4; preferably, the crystals or the soluble polypeptides which are used to form the crystals exhibit ERK2 catalytic activity (see above). Most preferably, the crystals include a polypeptide which includes the amino acid sequence of SEQ ID NO: 5 or 6. Structural similarity between crystals is discussed in detail below.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The present invention includes crystals exhibiting structural coordinates which are similar to those set forth in Tables 14 but for crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Tables 1-4, the resulting three-dimensional shape is considered to be the same and, accordingly, the modified crystal is considered to be within the scope of the present invention.

Various computational analyses may be necessary to determine whether a crystal is sufficiently similar to the crystals whose structural coordinates are set forth in Tables 1-4 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results.

Generally, each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) for all conserved residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Ångströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

For the purpose of this invention, any set of structure coordinates of a molecule that has a RMSD of conserved residue backbone atoms (N, Cα, C, O) or alpha carbon atoms only of less than about 1.5 Å when superimposed—using backbone atoms—on the relevant structure coordinates of Table 1, 2, 3 or 4 are considered identical and the crystals which they characterize are both within the scope of the present invention. Preferably, the root mean square deviation is less than about 1.0 Å, even more preferably, the root mean square deviation is less than about 0.5 Å and most preferably, the root mean square deviation is less than about 0.1 Å.

The term "least squares" refers to a method based on the principle that the best estimate of a value is that in which the sum of the squares of the deviations of observed values is a minimum.

In accordance with the present invention, the structure coordinates of the ERK2 polypeptide and portions thereof may be stored in a machine-readable storage medium. Such data may be used for a variety of purposes, such as drug discovery and X-ray crystallographic analysis of a protein crystal (e.g., for producing a three-dimensional representation of ERK2). Accordingly, one aspect of this invention provides a machine-readable data storage medium comprising a data storage material encoded with the structure coordinates set forth in Table 1, 2, 3 or 4. The machine-readable data storage medium may also include any set of structure coordinates of a molecule that has a root mean square deviation of conserved residue backbone atoms (N, Cα, C, O) or alpha carbon atoms only of less than about 1.5 Å, preferably, less than about 1.0 Å, more preferably less than about 0.5 Å and even more preferably less than about 0.1 Å when superimposed—using backbone atoms—on the relevant structure coordinates of Table 1, 2, 3 or 4.

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages will be known to those skilled in the art.

Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of ERK2 or a portion thereof using a program such as INSIGHT (Molecular Simulations Inc., San Diego, Calif.) or QUANTA as described herein. Output hardware might also include a printer, so that hard copy output may be produced, or a disk drive, to store system output for later use. In preferred embodiments, the computer possesses a display that is displaying a three dimensional representation of ERK2 or a fragment or homologue thereof.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which preferably is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

"Structure factors" are mathematical expressions derived from three-dimensional structure coordinates of a molecule. These mathematical expressions include, for example, amplitude and phase information. The term "structure factors" is known to those of ordinary skill in the art.

The present invention permits the use of structure-assisted drug design techniques to design, select, and synthesize chemical entities, including inhibitory compounds that are capable of binding to a ERK2 polypeptide. Also, de novo and iterative drug design methods can be used to develop drugs from the structure of the ERK2 crystals of this invention.

One particularly useful drug design technique enabled by this invention is structure-assisted drug design. Structure-assisted drug design is a method for optimizing associations between a protein and a compound by determining and evaluating the three-dimensional structures of successive sets of protein/compound complexes.

Numerous computer programs are available and suitable for structure-assisted drug design and the processes of computer modeling, model building, and computationally identifying, selecting and evaluating potential inhibitors in the methods described herein. These include, for example, GRID (available form Oxford University, UK), MCSS (available from Molecular Simulations Inc., Burlington, Mass.), AUTODOCK (available from Oxford Molecular Group), FLEX X (available from Tripos, St. Louis. Mo.), DOCK (available from University of California, San Francisco), CAVEAT (available from University of California, Berkeley), HOOK (available from Molecular Simulations Inc., Burlington, Mass.), and 3D database systems such as MACCS-3D (available from MDL Information Systems, San Leandro, Calif.), UNITY (available from Tripos, St. Louis. Mo.), and CATALYST (available from Molecular Simulations Inc., Burlington, Mass.). Potential inhibitors may also be computationally designed "de novo" using such software packages as LUDI (available from Biosym Technologies, San Diego, Calif.), LEGEND (available from Molecular Simulations Inc., Burlington, Mass.), and LEAPFROG (Tripos Associates, St. Louis, Mo.). Compound deformation energy and electrostatic repulsion, may be evaluated using programs such as GAUSSIAN 92, AMBER, QUANTA/CHARMM, AND INSIGHT II/DISCOVER. These computer evaluation and modeling techniques may be performed on any suitable hardware including for example, workstations available from Silicon Graphics, Sun Microsystems, and the like. These techniques, methods, hardware and software packages are representative and are not intended to be comprehensive listing. Other modeling techniques known in the art may also be employed in accordance with this invention. See for example, N.C. Cohen, Molecular Modeling in Drug Design, Academic Press (1996) (and references therein), and software identified at internet sites including the CAOS/CAMM Center Cheminformatics Suite, and the NIH Molecular Modeling Home Page.

Those skilled in the art will appreciate that association of natural ligands or substrates with the binding pockets of their corresponding receptors or enzymes is the basis of many biological mechanisms of action. The term "binding pocket", as used herein, includes any region of a molecule or molecular complex, that, as a result of its shape, favorably associates with another chemical entity or compound. Similarly, drugs may exert their biological effects through association with the binding pockets of receptors and enzymes. Such association may occur with all or any part of the binding pockets. An understanding of such associations will help lead to the design of drugs having more favorable associations with the target enzyme, and thus, improved biological effects. Therefore, this information is valuable in designing potential enzyme inhibitors, such as inhibitors of ERK2.

In iterative structure-assisted drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of a new polypeptide, solving the three-dimensional structure of the polypeptide, and comparing the associations between the new protein and previously solved protein. By observing how changes in the compound affected the protein/compound associations, these associations may be optimized.

In some cases, iterative structure-assisted drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, ERK2 crystals provided by this invention may be soaked in the presence of a compound or compounds, such as an ERK2 inhibitor (e.g., olomoucine), substrates or other ligands to provide novel ERK2/compound crystal complexes. As used herein, the term "soaked" includes a process in which the crystal is transferred to a solution containing the compound of interest.

The structure coordinates set forth in Tables 1-4 can also be used to aid in obtaining structural information about another crystallized molecule or molecular complex. This may be achieved by any of a number of well-known techniques, including molecular replacement.

The structure coordinates set forth in Tables 1-4 can also be used for determining at least a portion of the three-dimensional structure of molecules or molecular complexes which contain at least some structurally similar features to ERK2. In particular, structural information about another crystallized molecule or molecular complex may be obtained by well-known techniques, including molecular replacement.

Therefore, another aspect of this invention provides a method of utilizing molecular replacement to obtain structural information about a crystallized molecule or molecular complex, whose structure is unknown, comprising the steps of generating an X-ray diffraction pattern from said crystallized molecule or molecular complex and applying crystallographic phases derived from at least a portion of the structure coordinates set forth in Table 1, 2, 3 or 4 to the X-ray diffraction pattern to generate a three-dimensional electron density map of the molecule or molecular complex whose structure is unknown. Once the structure coordinates of a protein crystal have been determined, they are useful in solving the structures of other crystals. For example, polypeptides may be crystallized and their structure elucidated by, for example, difference Fourier techniques and molecular replacement.

By using molecular replacement, all or part of the structure coordinates of, for example, the ERK2 polypeptide provided by this invention (and set forth in Tables 1-4) can be used to determine the previously unknown structure of a crystallized molecule or molecular complex more quickly and efficiently than attempting to determine such information ab initio.

In a preferred embodiment, the method of molecular replacement is utilized to obtain structural information about a molecule wherein the molecule comprises an ERK2 polypeptide complex. The structure coordinates of ERK2 provided by this invention are particularly useful in solving the structure of other crystal forms of ERK2 polypeptide complexes. This approach enables the determination of the optimal sites for interaction between chemical entities, including interaction of candidate inhibitors with ERK2.

Molecular replacement provides an accurate estimation of the phases for an unknown structure. Phases are a factor in equations used to solve crystal structures that cannot be measured experimentally. Obtaining accurate values for the phases, by methods other than molecular replacement, is a time-consuming process. However, when the crystal structure of a protein containing a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the ERK2 crystal according to Table 1, 2, 3 or 4 within the unit cell of the crystal of the unknown molecule or molecular complex so as best to account for the observed X-ray diffraction pattern amplitudes to generate an election density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in *Meth. Enzymol.*, 115: 55-77 (1985); Rossman, ed., "The Molecular Replacement Method", *Int. Sci. Rev. Ser.*, No. 13, Gordon & Breach, New York (1972)).

Phase information from the structure coordinates of the present invention may be used to elucidate the structure of other crystals. For example, the structure of ERK2 in complex with other atoms or molecules (other than olomoucine) may be elucidated. Such complexes include, for example, those containing atoms soaked into or co-crystallized within the crystal lattice. Other structures which can be elucidated using the phase information of the present invention include for example other kinases or homologues or mutants thereof having sufficient three-dimensional structure similarity to ERK2 complex as to be solved using molecular replacement. Also, these protein molecules in a complex with a small molecule substrate(s), inhibitor(s), transition state analog(s), product(s) or analog(s) of any of these may also be solved using the phase information of the present invention.

The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

ERK2 crystals may be studied using well-known X-ray diffraction techniques and may be refined versus X-ray data to 3 Å resolution or better to an $R_{free}$ value of about 0.40 or less using computer software such as X-PLOR (Yale University, 1992, distributed by Molecular Simulations, Inc.; see e.g., Blundell & Johnson, supra; *Meth, Enzymol.*, vol. 114 & 115, H. W. Wyckoff et al., eds., Academic Press (1985)). This information may be used to optimize known ERK2 inhibitors and to design new ERK2 inhibitors.

EXAMPLES

The following examples are intended to exemplify the present invention and should not be construed to limit it. The scope of the invention included all polypeptides and polynucleotides, including crystals, described in the examples along with all methods exemplified.

Example 1

The Cloning of Ah₆-ERK2 Construct

Mouse ERK2 cDNA was cloned into the bacterial expression vector NpT7-5-6His using EcoRI and HindIII sites. Prior to cloning into NpT7-5-6His an internal EcoRI site in mouse ERK2 was eliminated by site directed mutagenesis changing 621 T to C. The C to which the T was changed is underlined and in sequence below (SEQ ID NO: 4). This is a silent mutation yielding an AAC codon for the amino acid 207 aspargine. This construct was used as the template for PCR of mouse ERK2 using a pair of primers (listed below) that encoding a start Met, 6H is tag and the initial 12 amino acids of mouse ERK2. The resulting PCR product was cloned into NpT7-5-6H is digested with EcoRI and HindIII. The construct was verified by sequencing. The final nucleotide and amino acid sequences encoded are shown below.

```
Primer NpT7-5 mouse Erk2 forward:
                                    (SEQ ID NO: 1)
CCG GAA TTC TAA GGA GGT TTA ACC ATG GCA CAT CAC

CAT CAC CAT CAC ATG GCG GCG GCG GCG GCG GCG GGC

CCG GAG ATG GTC

Primer Mouse Erk2 reverse:
                                    (SEQ ID NO: 2)
CCC AAG CTT TTA AGA TCT GTA TCC TGG CTG GAA TCT

AGC AGT CTC TTC AA

Mouse ERK2 in NpT7-5-6His
                                    (SEQ ID NO: 3)
MAHHHHHHMAAAAAAGPEMVRGQVFDVGPRYTNLSYIGEGAYGMVCSAYD

NLNKVRVAIKKISPFEHQTYCQRTLREIKILLRFRHENIIGINDIIRAPT

IEQMKDVYIVQDLMETDLYKLLKTQHLSNDHICYFLYQILRGLKYIHSAN

VLHRDLKPSNLLLNTTCDLKICDFGLARVADPDHDHTGFLTEYVATRWYR

APEIMLNSKGYTKSIDIWSVGCILAEMLSNRPIFPGKHYLDQLNHILGIL

GSPSQEDLNCIINLKARNYLLSLPHKNKVPWNRLFPNADSKALDLLDKML

TFNPHKRIEVEQALAHPYLEQYYDPSDEPIAEAPFKFDMELDDLPKEKLK

ELIFEETARFQPGYRS (SEQ ID NO: 4)
ATGGCACATCACCATCACCATCACATGGCGGCGGCGGCGGCGGCGGGCCC

GGAGATGGTCCGCGGGCAGGTGTTCGACGTAGGGCCGCGCTACACCAACC

TCTCGTACATCGGAGAAGGCGCCTACGGCATGGTTTGCTCTGCTTATGAT

AATCTCAACAAAGTTCGAGTTGCTATCAAGAAAATCAGTCCTTTTGAGCA

CCAGACCTACTGTCAAAGAACCCTAAGAGAGATAAAAATCTTACTGCGCT

TCAGACATGAGAACATCATTGGCATCAATGACATCATCCGGGCACCAACC

ATTGAGCAAATGAAAGATGTATATATAGTACAGGACCTCATGGAGACGGA

CCTTTACAAGCTCTTGAAGACACAGCACCTCAGCAATGACCACATCTGCT
```

```
                          -continued
ATTTTCTTTATCAGATCCTGAGAGGGCTAAAGTATATCCATTCAGCTAAC

GTTCTGCACCGTGACCTCAAGCCTTCCAACCTCCTGCTGAACACCACTTG

TGATCTCAAGATCTGTGACTTTGGCCTTGCCCGTGTTGCAGATCCAGATC

ATGATCACACAGGGTTCTTGACAGAGTACGTAGCCACACGTTGGTACAGA

GCTCCAGAAATTATGTTGAACTCCAAGGGTTATACCAAGTCCATTGATAT

TTGGTCTGTGGGCTGCATCCTGGCAGAGATGCTATCCAACAGGCCTATCT

TCCCAGGAAAGCATTACCTTGACCAGCTGAATCACATCCTGGGTATTCTT

GGATCTCCATCACAGGAAGATCTGAATTGTATAATAAATTTAAAAGCTAG

AAACTATTTGCTTTCTCTCCCGCACAAAAATAAGGTGCCATGGAACAGGT

TGTTCCCAAATGCTGACTCCAAAGCTCTGGATTTACTGGATAAAATGTTG

ACATTTAACCCTCACAAGAGGATTGAACTTGAACAGGCTCTGGCCCACCC

ATACCTGGAGCAGTATTATGACCCAAGTGATGAGCCCATTGCTGAAGCGC

CATTCAAGTTTGACATGGAGTTGGACGACTTACCTAAGGAGAAGCTCAAA

GAACTCATTTTTGAAGAGACTGCTAGATTCCAGCCAGGATACAGATCTTA

A
```

Example 2

Amino Acid Sequence of Ah$_6$-ERK2

The amino terminal methionine of this ERK2 construct expressed in *E. coli* BL21-DE3 cells is processed after translation.

```
                                                        (SEQ ID NO: 5)
  1 AHHHHHHMAA AAAAGPEMVR GQVFDVGPRY TNLSYIGEGA YGMVCSAYDN LNKVRVAIKK

61 ISPFEHQTYC QRTLREIKIL LRFRHENIIG INDITRAPTI RQMKDVYIVQ DLMETDLYKL

121 LKTQHLSNDH ICYFLYQILR GLKYIHSANV LHRDLKPSNL LLNTTCDLKI CDFGLARVAD

181 PDHDHTGFLT EYVATRWYRA PEIMLNSKGY TKSIDIWSVG CILAEMLSNR PIFPGKHYLD

241 QLNHILGILG SPSQEDLNCI INLKARNYLL SLPHKNKVPW NRLFPNADSK ALDLLDKMLT

301 FNPHKRIEVE QALAHPYLEQ YYDPSDEPIA EAPFKFDMEL DDLPKEKLKE LIFEETARFQ

361 PGYRS

Number of amino acids: 365
Molecular weight: 42169.5
```

Example 3

Expression of Ah$_6$-ERK2 Construct

A 250 milliliter starter culture of BL-21 (DE3) cells containing the pNpT7-5 plasmid was grown to an OD$_{600}$ of 0.8 at 37° C. in Miller's LB broth (Mediatech, Inc.) with 100 ug/ml carbenicillin. The 250 milliliter culture was stored at 4° C. overnight for inoculation of 10×1 liter of terrific broth (Mediatech, Inc.) with 100 ug/ml carbenicillin in 2 liter baffled flasks. The cultures were grown to a OD of 1.8 at 37° C., and the temperature was then lowered to 23° C. prior to induction with 1 mM IPTG. Cells were harvested 18 hours after induction by centrifugation at 2700×g for 10 minutes.

Example 4

Purification of Ah$_6$-ERK2 Construct

The cell pellet from 2.25 L of cell culture was suspended in 230 ml of Lysis Buffer, passed 3 times through an Omni-Mixer and then 3 times through a Microfluidizer. All purification steps were carried out at 4° C., or on ice. Lysis Buffer: 0.05 M sodium phosphate, pH 8.0, 0.3 M NaCl, 10 mM β-mercaptoethanol, 11,000 U/liter benzonase (endonuclease), and 5 ml/liter of Calbiochem Protease Inhibitor Cocktail Set III (final concentrations: 500 µM AEBSF, 25 µM Bestatin, 0.4 µM aprotinin, 7.5 µM E-64, 10 µM leupeptin and 5 µM pepstatin A with 0.5% DMSO).

The cell lysate was centrifuged at of 200,000×g (TI-45 rotor at 42,000 rpm) for 1 hour at 4° C. The supernatant was applied to a 1.6×8 cm column (16 ml) of Qiagen Ni-NTA superflow agarose, at 3.6 ml/minute. The column had been equilibrated with Ni-NTA Buffer.

Ni-NTA Buffer: Lysis Buffer without protease inhibitors or endonuclease.

The column was washed first with Ni-NTA Buffer, then with Ni-NTA Buffer, pH 7.5, 25 mM imidazole, followed by of Ni-NTA Buffer, pH 7.5, 25 mM imidazole, 1 M NaCl and then with Ni-NTA Buffer, pH 7.5, 45 mM imidazole. The column was then eluted with Ni-NTA Buffer, pH 7.5, with 250 mM imidazole.

The eluted pool was diluted to 1 mg/ml of protein with Ni-NTA Buffer, and then dialyzed versus 3 changes of 32 volumes of MonoQ Buffer (25 mM Tris-Cl, pH 7.8$_{(rt)}$, 0.05 M NaCl, 10% (v/v) glycerol, 1 mM EDTA and 5 mM DTT).

The dialyzed pool was then centrifuged for 1 hour as described above, and then applied to a MonoQ HR 16/10 column (Amersham/Pharmacia), at 1 ml/minute. The column was washed with 1 bed volume of MonoQ Buffer and then eluted with a linear 30 bed volume gradient between MonoQ Buffer and MonoQ Buffer with 0.5 M NaCl. Eluted peak 1 (at ~0.18 M NaCl) was pooled, diluted with MonoQ Buffers to a final protein concentration of 1 mg/ml (by OD$_{276}$) and NaCl concentration of 0.26 M, and frozen in aliquots at −80° C. The yield of pure unphosphorylated ERK2=28 mg/liter. The protein concentration was determined using E$_{276}$=43,750 M$^{-1}$ cm$^{-1}$, in 20 mM sodium phosphate, pH 6.5, 6 M guanidine hydrochloride (ExPASy-ProtParam Tool). These values were correlated with the protein concentrations of the purified pro-

Example 5

Crystallization of Ah$_6$-ERK2 Un-Phosphorlylated Construct (Form 1)

The Ah$_6$-ERK2 un-phosphorlylated construct was crystallized using a hanging-drop vapor diffusion method. The protein (0.5 µl; 11 mg/ml) in 20 mM Tris-HCl, pH 7.5, 0.20 M sodium chloride, 0.03% sodium azide, 5 mM DTT buffer was mixed with an equal volume of precipitant solution containing 100 mM MES, pH 6.4, 4% PEG 400, and 2.4 M ammonium sulfate placed on the underside of a siliconized glass coverslip and sealed in close proximity to 1 ml of the precipitant solution. Crystallization plates were incubated at 4° C.; crystals grew over 2-30 days.

Example 6

Photomicrograph of Ah$_6$-ERK2 Un-Phosphorlylated Crystals (Form 1)

A photomicrograph of the Ah$_6$-ERK2 un-phosphorlylated crystals (form 1) was taken. Rectangular rod crystals (0.02× 0.2 mm) were observed.

Example 7

Crystallization of Ah$_6$-ERK2 Un-Phosphorlylated Construct (Form 2)

The Ah$_6$-ERK2 un-phosphorlylated construct was be crystallized using a hanging-drop vapor diffusion method. The protein (0.5 µl; 11 mg/ml) in 20 mM Tris-HCl, pH 7.5, 0.20 M sodium chloride, 0.03% sodium azide, 5 mM DTT buffer was mixed with an equal volume of precipitant solution containing 100 mM MES, pH 6.4, 4% PEG 400, and 2.4 M ammonium sulfate placed on the underside of a siliconized glass coverslip and sealed in close proximity to 1 ml of the precipitant solution. Crystallization plates were incubated at 22° C.; crystals grew over 2-30 days.

Example 8

Photomicrograph of Ah$_6$-ERK2 Un-Phosphorlylated Crystals (Form 2)

A photomicrograph of the Ah$_6$-ERK2 un-phosphorlylated crystals (form 2) was taken. Rectangular rod crystals (0.02× 0.2 mm) were observed.

Example 9

Crystallographic Analysis of Ah$_6$-ERK2 [Un-Phosphorlylated] Form 1

Prior to data collection, crystals were washed with the reservoir solution of the crystallization setup and transferred into the same solution with 25% glycerol added. The crystals were then flash-cooled in a nitrogen stream at 95 K or in liquid nitrogen. X-ray diffraction was collected using a Rigaku generator equipped with a Raxis 4 detector. Data were integrated and scaled using the HKL package.

| Data collection statistics: | |
| --- | --- |
| Resolution | 30.0-1.50 Å |
| No. of collected reflections | 435438 |
| No. of unique reflections (F >= 0) | 65681 |
| R-sym | 6.1% |
| Percent of theoretical (I/s >= 1) | 98.1% |
| Unit Cell | a = 70.611 Å, b = 92.158 Å, c = 63.735 Å, α = β = γ = 90° |
| Space Group | P2$_1$2$_1$2 (Number 18) |
| Asymmetric unit | 1 molecule |

TABLE 1

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
| --- | --- | --- | --- | --- | --- | --- | --- |
| 6 | A | CB | 40.4 | 17.5 | −21.9 | 56 | A |
| 6 | A | C | 39.7 | 16.8 | −19.6 | 56 | A |
| 6 | A | O | 39.2 | 17.9 | −19.2 | 56 | A |
| 6 | A | N | 41.2 | 15.4 | −20.9 | 57 | A |
| 6 | A | CA | 40.8 | 16.8 | −20.6 | 56 | A |
| 7 | A | N | 39.2 | 15.7 | −19.2 | 55 | A |
| 7 | A | CA | 38.1 | 15.5 | −18.2 | 54 | A |
| 7 | A | CB | 38.2 | 14.2 | −17.5 | 54 | A |
| 7 | A | C | 38.1 | 16.6 | −17.2 | 53 | A |
| 7 | A | O | 37.5 | 17.7 | −17.4 | 53 | A |
| 8 | G | N | 38.8 | 16.4 | −16.0 | 52 | A |
| 8 | G | CA | 38.8 | 17.4 | −15.0 | 51 | A |
| 8 | G | C | 39.4 | 16.8 | −13.7 | 50 | A |
| 8 | G | O | 40.0 | 15.7 | −13.7 | 49 | A |
| 9 | P | N | 39.4 | 17.5 | −12.6 | 49 | A |
| 9 | P | CD | 38.8 | 18.9 | −12.5 | 49 | A |
| 9 | P | CA | 40.0 | 17.1 | −11.3 | 49 | A |
| 9 | P | CB | 40.0 | 18.4 | −10.5 | 49 | A |
| 9 | P | CG | 38.8 | 19.1 | −11.0 | 49 | A |
| 9 | P | C | 39.2 | 16.0 | −10.6 | 49 | A |
| 9 | P | O | 38.0 | 15.9 | −10.8 | 49 | A |
| 10 | E | N | 39.8 | 15.2 | −9.8 | 48 | A |
| 10 | E | CA | 39.2 | 14.1 | −9.1 | 49 | A |
| 10 | E | CB | 40.2 | 13.1 | −8.5 | 50 | A |
| 10 | E | CG | 41.0 | 12.4 | −9.6 | 51 | A |
| 10 | E | CD | 41.9 | 11.4 | −9.0 | 52 | A |
| 10 | E | OE1 | 41.5 | 10.4 | −8.3 | 52 | A |
| 10 | E | OE2 | 43.2 | 11.5 | −9.2 | 53 | A |
| 10 | E | C | 38.4 | 14.7 | −8.0 | 48 | A |
| 10 | E | O | 38.8 | 15.8 | −7.4 | 48 | A |
| 11 | M | N | 37.3 | 14.1 | −7.6 | 46 | A |
| 11 | M | CA | 36.4 | 14.6 | −6.5 | 45 | A |
| 11 | M | CB | 35.0 | 14.9 | −7.1 | 43 | A |
| 11 | M | CG | 35.0 | 15.8 | −8.3 | 41 | A |
| 11 | M | SD | 35.5 | 17.5 | −8.0 | 39 | A |
| 11 | M | CE | 34.1 | 18.2 | −7.2 | 39 | A |
| 11 | M | C | 36.3 | 13.6 | −5.4 | 46 | A |
| 11 | M | O | 36.5 | 12.4 | −5.5 | 46 | A |
| 12 | V | N | 36.0 | 14.2 | −4.2 | 46 | A |
| 12 | V | CA | 35.9 | 13.4 | −3.0 | 46 | A |
| 12 | V | CB | 37.2 | 13.3 | −2.1 | 45 | A |
| 12 | V | CG1 | 37.0 | 12.6 | −0.8 | 44 | A |
| 12 | V | CG2 | 38.3 | 12.7 | −3.0 | 44 | A |
| 12 | V | C | 34.8 | 14.0 | −2.1 | 47 | A |
| 12 | V | O | 34.9 | 15.1 | −1.5 | 47 | A |
| 13 | R | N | 33.6 | 13.3 | −2.0 | 49 | A |
| 13 | R | CA | 32.5 | 13.8 | −1.3 | 50 | A |
| 13 | R | CB | 32.9 | 13.9 | 0.2 | 52 | A |
| 13 | R | CG | 32.8 | 12.6 | 1.0 | 56 | A |
| 13 | R | CD | 33.7 | 11.5 | 0.3 | 61 | A |
| 13 | R | NE | 33.7 | 10.2 | 1.0 | 64 | A |
| 13 | R | CZ | 34.3 | 9.2 | 0.6 | 65 | A |
| 13 | R | NH1 | 35.1 | 9.2 | −0.4 | 66 | A |
| 13 | R | NH2 | 34.2 | 8.0 | 1.3 | 65 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 13 | R | C | 32.0 | 15.2 | −1.8 | 50 | A |
| 13 | R | O | 31.7 | 16.1 | −1.0 | 50 | A |
| 14 | G | N | 32.0 | 15.3 | −3.1 | 50 | A |
| 14 | G | CA | 31.5 | 16.5 | −3.7 | 49 | A |
| 14 | G | C | 32.5 | 17.7 | −3.7 | 49 | A |
| 14 | G | O | 32.2 | 18.8 | −4.1 | 48 | A |
| 15 | Q | N | 33.7 | 17.4 | −3.1 | 48 | A |
| 15 | Q | CA | 34.7 | 18.4 | −3.1 | 47 | A |
| 15 | Q | CB | 35.2 | 18.6 | −1.6 | 49 | A |
| 15 | Q | CG | 34.1 | 19.0 | −0.7 | 52 | A |
| 15 | Q | CD | 34.6 | 19.3 | 0.8 | 54 | A |
| 15 | Q | OE1 | 35.1 | 18.4 | 1.4 | 55 | A |
| 15 | Q | NE2 | 34.4 | 20.5 | 1.2 | 54 | A |
| 15 | Q | C | 35.9 | 18.0 | −3.9 | 45 | A |
| 15 | Q | O | 36.2 | 16.9 | −4.2 | 45 | A |
| 16 | V | N | 36.6 | 19.1 | −4.5 | 43 | A |
| 16 | V | CA | 37.8 | 18.9 | −5.3 | 40 | A |
| 16 | V | CB | 38.1 | 20.1 | −6.1 | 40 | A |
| 16 | V | CG1 | 39.4 | 19.9 | −6.9 | 39 | A |
| 16 | V | CG2 | 36.9 | 20.5 | −7.0 | 39 | A |
| 16 | V | C | 39.0 | 18.4 | −4.6 | 40 | A |
| 16 | V | O | 39.4 | 19.0 | −3.5 | 40 | A |
| 17 | F | N | 39.7 | 17.4 | −5.1 | 39 | A |
| 17 | F | CA | 40.9 | 16.8 | −4.5 | 39 | A |
| 17 | F | CB | 40.6 | 15.6 | −3.7 | 38 | A |
| 17 | F | CG | 41.6 | 15.3 | −2.6 | 38 | A |
| 17 | F | CD1 | 41.6 | 16.1 | −1.4 | 37 | A |
| 17 | F | CD2 | 42.6 | 14.3 | −2.7 | 37 | A |
| 17 | F | CE1 | 42.5 | 15.9 | −0.4 | 37 | A |
| 17 | F | CE2 | 43.5 | 14.1 | −1.7 | 38 | A |
| 17 | F | CZ | 43.5 | 14.9 | −0.6 | 37 | A |
| 17 | F | C | 41.8 | 16.5 | −5.7 | 40 | A |
| 17 | F | O | 42.0 | 15.3 | −6.0 | 40 | A |
| 18 | D | N | 42.2 | 17.5 | −6.4 | 41 | A |
| 18 | D | CA | 43.0 | 17.4 | −7.6 | 42 | A |
| 18 | D | CB | 42.9 | 18.7 | −8.4 | 43 | A |
| 18 | D | CG | 43.6 | 18.6 | −9.8 | 43 | A |
| 18 | D | OD1 | 43.4 | 17.5 | −10.4 | 44 | A |
| 18 | D | OD2 | 44.3 | 19.6 | −10.1 | 46 | A |
| 18 | D | C | 44.5 | 17.1 | −7.3 | 42 | A |
| 18 | D | O | 45.3 | 18.0 | −7.2 | 42 | A |
| 19 | V | N | 44.8 | 15.8 | −7.1 | 43 | A |
| 19 | V | CA | 46.2 | 15.4 | −6.8 | 44 | A |
| 19 | V | CB | 46.3 | 14.6 | −5.5 | 43 | A |
| 19 | V | CG1 | 45.7 | 15.4 | −4.3 | 43 | A |
| 19 | V | CG2 | 45.4 | 13.3 | −5.7 | 43 | A |
| 19 | V | C | 46.8 | 14.6 | −7.9 | 45 | A |
| 19 | V | O | 48.0 | 14.5 | −8.0 | 44 | A |
| 20 | G | N | 45.9 | 14.0 | −8.7 | 46 | A |
| 20 | G | CA | 46.4 | 13.2 | −9.8 | 46 | A |
| 20 | G | C | 47.4 | 13.8 | −10.7 | 47 | A |
| 20 | G | O | 47.7 | 15.0 | −10.5 | 47 | A |
| 21 | P | N | 48.1 | 13.1 | −11.6 | 48 | A |
| 21 | P | CD | 48.7 | 13.7 | −12.8 | 48 | A |
| 21 | P | CA | 47.8 | 11.7 | −11.9 | 48 | A |
| 21 | P | CB | 48.1 | 11.5 | −13.4 | 48 | A |
| 21 | P | CG | 48.1 | 13.0 | −13.9 | 48 | A |
| 21 | P | C | 48.6 | 10.7 | −11.0 | 49 | A |
| 21 | P | O | 48.2 | 9.6 | −10.8 | 49 | A |
| 22 | R | N | 49.8 | 11.2 | −10.6 | 49 | A |
| 22 | R | CA | 50.7 | 10.4 | −9.8 | 50 | A |
| 22 | R | CB | 51.9 | 11.3 | −9.3 | 51 | A |
| 22 | R | CG | 52.9 | 10.6 | −8.4 | 53 | A |
| 22 | R | CD | 54.0 | 11.6 | −8.0 | 54 | A |
| 22 | R | NE | 54.9 | 11.0 | −7.0 | 56 | A |
| 22 | R | CZ | 55.9 | 11.6 | −6.5 | 56 | A |
| 22 | R | NH1 | 56.1 | 12.9 | −6.7 | 57 | A |
| 22 | R | NH2 | 56.7 | 11.0 | −5.6 | 56 | A |
| 22 | R | C | 50.0 | 9.8 | −8.5 | 49 | A |
| 22 | R | O | 50.5 | 8.8 | −8.0 | 50 | A |
| 23 | Y | N | 49.0 | 10.4 | −8.1 | 48 | A |
| 23 | Y | CA | 48.3 | 9.9 | −6.9 | 48 | A |
| 23 | Y | CB | 48.4 | 11.0 | −5.8 | 46 | A |
| 23 | Y | CG | 49.8 | 11.4 | −5.4 | 44 | A |
| 23 | Y | CD1 | 50.7 | 10.5 | −4.8 | 42 | A |
| 23 | Y | CE1 | 52.0 | 10.9 | −4.5 | 42 | A |
| 23 | Y | CD2 | 50.2 | 12.7 | −5.8 | 43 | A |
| 23 | Y | CE2 | 51.5 | 13.1 | −5.5 | 41 | A |
| 23 | Y | CZ | 52.4 | 12.2 | −4.9 | 41 | A |
| 23 | Y | OH | 53.7 | 12.6 | −4.6 | 40 | A |
| 23 | Y | C | 46.8 | 9.6 | −7.2 | 49 | A |
| 23 | Y | O | 46.0 | 10.5 | −7.5 | 49 | A |
| 24 | T | N | 46.5 | 8.3 | −7.1 | 50 | A |
| 24 | T | CA | 45.1 | 7.9 | −7.3 | 50 | A |
| 24 | T | CB | 45.0 | 7.0 | −8.6 | 50 | A |
| 24 | T | OG1 | 45.9 | 5.9 | −8.5 | 51 | A |
| 24 | T | CG2 | 45.4 | 7.9 | −9.8 | 50 | A |
| 24 | T | C | 44.6 | 7.0 | −6.2 | 51 | A |
| 24 | T | O | 45.2 | 6.8 | −5.2 | 51 | A |
| 25 | N | N | 43.3 | 6.5 | −6.3 | 52 | A |
| 25 | N | CA | 42.7 | 5.7 | −5.3 | 53 | A |
| 25 | N | CB | 43.5 | 4.4 | −5.0 | 53 | A |
| 25 | N | CG | 43.8 | 3.6 | −6.3 | 54 | A |
| 25 | N | OD1 | 44.3 | 4.1 | −7.3 | 54 | A |
| 25 | N | ND2 | 43.3 | 2.3 | −6.2 | 54 | A |
| 25 | N | C | 42.5 | 6.5 | −4.0 | 53 | A |
| 25 | N | O | 42.8 | 6.0 | −2.9 | 53 | A |
| 26 | L | N | 42.0 | 7.7 | −4.2 | 53 | A |
| 26 | L | CA | 41.7 | 8.5 | −3.0 | 53 | A |
| 26 | L | CB | 41.2 | 9.9 | −3.5 | 52 | A |
| 26 | L | CG | 42.0 | 10.7 | −4.4 | 52 | A |
| 26 | L | CD1 | 41.3 | 12.0 | −4.8 | 51 | A |
| 26 | L | CD2 | 43.4 | 11.0 | −3.8 | 51 | A |
| 26 | L | C | 40.7 | 7.9 | −2.0 | 53 | A |
| 26 | L | O | 39.8 | 7.2 | −2.5 | 53 | A |
| 27 | S | N | 41.0 | 8.1 | −0.7 | 53 | A |
| 27 | S | CA | 40.1 | 7.6 | 0.3 | 53 | A |
| 27 | S | CB | 40.7 | 6.2 | 0.8 | 53 | A |
| 27 | S | OG | 39.8 | 5.7 | 1.8 | 53 | A |
| 27 | S | C | 40.0 | 8.6 | 1.4 | 54 | A |
| 27 | S | O | 40.9 | 8.8 | 2.1 | 54 | A |
| 28 | Y | N | 38.8 | 9.1 | 1.6 | 54 | A |
| 28 | Y | CA | 38.5 | 10.0 | 2.7 | 55 | A |
| 28 | Y | CB | 37.0 | 10.3 | 2.8 | 55 | A |
| 28 | Y | CG | 36.6 | 11.5 | 3.7 | 56 | A |
| 28 | Y | CD1 | 37.1 | 12.8 | 3.5 | 56 | A |
| 28 | Y | CE1 | 36.7 | 13.8 | 4.3 | 56 | A |
| 28 | Y | CD2 | 35.9 | 11.2 | 4.9 | 56 | A |
| 28 | Y | CE2 | 35.6 | 12.3 | 5.8 | 56 | A |
| 28 | Y | CZ | 36.0 | 13.5 | 5.5 | 56 | A |
| 28 | Y | OH | 35.7 | 14.6 | 6.3 | 57 | A |
| 28 | Y | C | 39.0 | 9.5 | 4.1 | 55 | A |
| 28 | Y | O | 38.9 | 8.4 | 4.4 | 55 | A |
| 29 | I | N | 39.5 | 10.5 | 4.9 | 56 | A |
| 29 | I | CA | 40.0 | 10.1 | 6.2 | 56 | A |
| 29 | I | CB | 41.6 | 10.2 | 6.2 | 56 | A |
| 29 | I | CG2 | 42.0 | 9.9 | 7.7 | 55 | A |
| 29 | I | CG1 | 42.1 | 9.1 | 5.3 | 55 | A |
| 29 | I | CD1 | 43.6 | 9.1 | 5.3 | 55 | A |
| 29 | I | C | 39.5 | 11.1 | 7.2 | 57 | A |
| 29 | I | O | 39.1 | 10.7 | 8.3 | 57 | A |
| 30 | G | N | 39.5 | 12.4 | 6.9 | 59 | A |
| 30 | G | CA | 39.0 | 13.4 | 7.8 | 61 | A |
| 30 | G | C | 39.0 | 14.8 | 7.2 | 62 | A |
| 30 | G | O | 39.4 | 14.9 | 6.1 | 62 | A |
| 31 | E | N | 38.6 | 15.8 | 8.0 | 63 | A |
| 31 | E | CA | 38.6 | 17.2 | 7.5 | 64 | A |
| 31 | E | CB | 37.3 | 17.5 | 6.8 | 65 | A |
| 31 | E | CG | 37.3 | 18.6 | 5.9 | 68 | A |
| 31 | E | CD | 35.9 | 19.0 | 5.4 | 69 | A |
| 31 | E | OE1 | 35.2 | 18.1 | 4.8 | 70 | A |
| 31 | E | OE2 | 35.5 | 20.2 | 5.5 | 70 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 31 | E | C | 39.0 | 18.1 | 8.6 | 65 | A |
| 31 | E | O | 39.5 | 17.7 | 9.7 | 65 | A |
| 32 | G | N | 38.7 | 19.4 | 8.4 | 64 | A |
| 32 | G | CA | 38.9 | 20.4 | 9.4 | 64 | A |
| 32 | G | C | 38.6 | 21.8 | 8.9 | 64 | A |
| 32 | G | O | 38.1 | 22.0 | 7.8 | 63 | A |
| 36 | M | N | 40.8 | 19.1 | 4.4 | 49 | A |
| 36 | M | CA | 40.4 | 17.7 | 4.2 | 48 | A |
| 36 | M | CB | 39.5 | 17.7 | 3.0 | 49 | A |
| 36 | M | CG | 39.1 | 16.2 | 2.6 | 50 | A |
| 36 | M | SD | 37.8 | 16.2 | 1.4 | 50 | A |
| 36 | M | CE | 38.6 | 16.6 | −0.1 | 50 | A |
| 36 | M | C | 41.6 | 16.8 | 4.0 | 48 | A |
| 36 | M | O | 42.6 | 17.2 | 3.2 | 49 | A |
| 37 | V | N | 41.6 | 15.7 | 4.6 | 48 | A |
| 37 | V | CA | 42.7 | 14.7 | 4.5 | 48 | A |
| 37 | V | CB | 43.3 | 14.4 | 5.8 | 47 | A |
| 37 | V | CG1 | 44.5 | 13.4 | 5.7 | 47 | A |
| 37 | V | CG2 | 43.8 | 15.7 | 6.5 | 47 | A |
| 37 | V | C | 42.2 | 13.4 | 3.8 | 48 | A |
| 37 | V | O | 41.2 | 12.9 | 4.2 | 48 | A |
| 38 | C | N | 43.0 | 12.9 | 2.9 | 48 | A |
| 38 | C | CA | 42.6 | 11.7 | 2.2 | 48 | A |
| 38 | C | CB | 41.9 | 11.9 | 0.9 | 48 | A |
| 38 | C | SG | 40.4 | 12.9 | 1.0 | 47 | A |
| 38 | C | C | 43.9 | 10.8 | 1.9 | 48 | A |
| 38 | C | O | 45.0 | 11.4 | 1.8 | 48 | A |
| 39 | S | N | 43.7 | 9.5 | 1.9 | 47 | A |
| 39 | S | CA | 44.9 | 8.6 | 1.6 | 47 | A |
| 39 | S | CB | 44.8 | 7.4 | 2.4 | 47 | A |
| 39 | S | OG | 43.5 | 6.7 | 2.2 | 46 | A |
| 39 | S | C | 44.8 | 8.3 | 0.1 | 47 | A |
| 39 | S | O | 43.8 | 8.2 | −0.5 | 48 | A |
| 40 | A | N | 46.0 | 8.1 | −0.5 | 48 | A |
| 40 | A | CA | 46.1 | 7.8 | −1.9 | 48 | A |
| 40 | A | CB | 46.3 | 9.1 | −2.7 | 48 | A |
| 40 | A | C | 47.3 | 6.9 | −2.2 | 49 | A |
| 40 | A | O | 48.0 | 6.5 | −1.3 | 49 | A |
| 41 | Y | N | 47.4 | 6.5 | −3.4 | 51 | A |
| 41 | Y | CA | 48.5 | 5.6 | −3.8 | 52 | A |
| 41 | Y | CB | 47.9 | 4.4 | −4.6 | 53 | A |
| 41 | Y | CG | 48.9 | 3.4 | −5.0 | 53 | A |
| 41 | Y | CD1 | 49.6 | 2.6 | −4.1 | 54 | A |
| 41 | Y | CE1 | 50.6 | 1.7 | −4.5 | 54 | A |
| 41 | Y | CD2 | 49.2 | 3.1 | −6.4 | 54 | A |
| 41 | Y | CE2 | 50.2 | 2.2 | −6.8 | 54 | A |
| 41 | Y | CZ | 50.9 | 1.5 | −5.8 | 54 | A |
| 41 | Y | OH | 51.8 | 0.6 | −6.2 | 54 | A |
| 41 | Y | C | 49.5 | 6.3 | −4.7 | 53 | A |
| 41 | Y | O | 49.2 | 6.8 | −5.8 | 53 | A |
| 42 | D | N | 50.7 | 6.3 | −4.2 | 53 | A |
| 42 | D | CA | 51.8 | 7.0 | −4.9 | 53 | A |
| 42 | D | CB | 53.0 | 7.2 | −3.9 | 53 | A |
| 42 | D | CG | 54.1 | 8.0 | −4.5 | 53 | A |
| 42 | D | OD1 | 54.6 | 7.6 | −5.6 | 53 | A |
| 42 | D | OD2 | 54.5 | 9.1 | −4.0 | 53 | A |
| 42 | D | C | 52.2 | 6.2 | −6.0 | 54 | A |
| 42 | D | O | 53.1 | 5.3 | −5.9 | 54 | A |
| 43 | N | N | 51.6 | 6.4 | −7.2 | 54 | A |
| 43 | N | CA | 51.9 | 5.6 | −8.4 | 54 | A |
| 43 | N | CB | 51.1 | 6.2 | −9.6 | 55 | A |
| 43 | N | CG | 49.6 | 6.1 | −9.4 | 56 | A |
| 43 | N | OD1 | 49.1 | 5.0 | −9.2 | 57 | A |
| 43 | N | ND2 | 48.9 | 7.2 | −9.5 | 57 | A |
| 43 | N | C | 53.4 | 5.6 | −8.7 | 54 | A |
| 43 | N | O | 53.9 | 4.7 | −9.5 | 54 | A |
| 44 | L | N | 54.2 | 6.6 | −8.2 | 53 | A |
| 44 | L | CA | 55.6 | 6.7 | −8.5 | 53 | A |
| 44 | L | CB | 56.1 | 8.1 | −8.2 | 54 | A |
| 44 | L | CG | 57.5 | 8.4 | −8.7 | 53 | A |
| 44 | L | CD1 | 57.8 | 9.9 | −8.5 | 53 | A |
| 44 | L | CD2 | 58.6 | 7.6 | −8.0 | 54 | A |
| 44 | L | C | 56.3 | 5.7 | −7.6 | 53 | A |
| 44 | L | O | 56.4 | 5.8 | −6.4 | 52 | A |
| 46 | K | N | 55.1 | 3.5 | −5.6 | 51 | A |
| 46 | K | CA | 54.5 | 2.1 | −5.4 | 51 | A |
| 46 | K | CB | 55.5 | 1.1 | −6.0 | 51 | A |
| 46 | K | CG | 56.8 | 0.9 | −5.2 | 50 | A |
| 46 | K | CD | 57.7 | 2.0 | −5.2 | 49 | A |
| 46 | K | CE | 57.5 | 3.1 | −4.1 | 49 | A |
| 46 | K | NZ | 58.4 | 4.3 | −4.3 | 49 | A |
| 46 | K | C | 54.2 | 1.9 | −4.0 | 51 | A |
| 46 | K | O | 54.4 | 0.7 | −3.5 | 51 | A |
| 47 | V | N | 53.7 | 2.9 | −3.3 | 51 | A |
| 47 | V | CA | 53.3 | 2.7 | −1.9 | 51 | A |
| 47 | V | CB | 54.6 | 2.9 | −1.0 | 51 | A |
| 47 | V | CG1 | 55.2 | 4.3 | −1.2 | 51 | A |
| 47 | V | CG2 | 54.2 | 2.7 | 0.5 | 51 | A |
| 47 | V | C | 52.3 | 3.8 | −1.5 | 50 | A |
| 47 | V | O | 52.4 | 4.9 | −2.0 | 51 | A |
| 48 | R | N | 51.3 | 3.4 | −0.7 | 50 | A |
| 48 | R | CA | 50.3 | 4.4 | −0.3 | 49 | A |
| 48 | R | CB | 49.2 | 3.6 | 0.4 | 51 | A |
| 48 | R | CG | 48.4 | 2.6 | −0.4 | 55 | A |
| 48 | R | CD | 47.0 | 2.4 | 0.2 | 58 | A |
| 48 | R | NE | 46.2 | 3.6 | 0.1 | 61 | A |
| 48 | R | CZ | 45.0 | 3.7 | 0.7 | 62 | A |
| 48 | R | NH1 | 44.5 | 2.8 | 1.5 | 63 | A |
| 48 | R | NH2 | 44.4 | 4.9 | 0.6 | 62 | A |
| 48 | R | C | 50.8 | 5.5 | 0.6 | 47 | A |
| 48 | R | O | 51.7 | 5.2 | 1.4 | 47 | A |
| 49 | V | N | 50.3 | 6.7 | 0.4 | 44 | A |
| 49 | V | CA | 50.7 | 7.8 | 1.2 | 41 | A |
| 49 | V | CB | 51.6 | 8.8 | 0.3 | 40 | A |
| 49 | V | CG1 | 52.9 | 8.1 | −0.1 | 40 | A |
| 49 | V | CG2 | 50.8 | 9.3 | −0.9 | 40 | A |
| 49 | V | C | 49.5 | 8.6 | 1.7 | 39 | A |
| 49 | V | O | 48.4 | 8.2 | 1.4 | 38 | A |
| 50 | A | N | 49.8 | 9.7 | 2.4 | 37 | A |
| 50 | A | CA | 48.8 | 10.5 | 3.0 | 35 | A |
| 50 | A | CB | 48.9 | 10.6 | 4.5 | 35 | A |
| 50 | A | C | 48.9 | 11.9 | 2.3 | 35 | A |
| 50 | A | O | 50.0 | 12.5 | 2.2 | 34 | A |
| 51 | I | N | 47.7 | 12.4 | 1.9 | 34 | A |
| 51 | I | CA | 47.7 | 13.7 | 1.2 | 34 | A |
| 51 | I | CB | 47.3 | 13.6 | −0.3 | 33 | A |
| 51 | I | CG2 | 47.4 | 15.0 | −0.9 | 33 | A |
| 51 | I | CG1 | 48.2 | 12.7 | −1.0 | 33 | A |
| 51 | I | CD1 | 47.9 | 12.4 | −2.4 | 32 | A |
| 51 | I | C | 46.8 | 14.7 | 1.9 | 33 | A |
| 51 | I | O | 45.6 | 14.3 | 2.2 | 34 | A |
| 52 | K | N | 47.2 | 15.8 | 2.3 | 33 | A |
| 52 | K | CA | 46.4 | 16.8 | 3.0 | 34 | A |
| 52 | K | CB | 47.1 | 17.3 | 4.3 | 37 | A |
| 52 | K | CG | 46.4 | 18.3 | 5.1 | 40 | A |
| 52 | K | CD | 47.3 | 19.0 | 6.1 | 44 | A |
| 52 | K | CE | 47.8 | 18.0 | 7.1 | 46 | A |
| 52 | K | NZ | 48.8 | 18.6 | 8.0 | 48 | A |
| 52 | K | C | 46.2 | 18.1 | 2.1 | 33 | A |
| 52 | K | O | 47.1 | 18.7 | 1.7 | 32 | A |
| 53 | K | N | 44.9 | 18.4 | 1.9 | 31 | A |
| 53 | K | CA | 44.5 | 19.5 | 1.1 | 31 | A |
| 53 | K | CB | 43.2 | 19.2 | 0.3 | 32 | A |
| 53 | K | CG | 42.7 | 20.5 | −0.5 | 33 | A |
| 53 | K | CD | 41.4 | 20.2 | −1.1 | 35 | A |
| 53 | K | CE | 40.8 | 21.5 | −1.8 | 36 | A |
| 53 | K | NZ | 39.5 | 21.4 | −2.3 | 37 | A |
| 53 | K | C | 44.3 | 20.7 | 2.0 | 30 | A |
| 53 | K | O | 43.5 | 20.6 | 2.9 | 32 | A |
| 54 | I | N | 44.9 | 21.8 | 1.7 | 29 | A |
| 54 | I | CA | 44.8 | 23.0 | 2.5 | 28 | A |
| 54 | I | CB | 46.2 | 23.4 | 3.2 | 28 | A |

TABLE 1-continued

Structural Coordinates of crystalline Ah6-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| 54 | I | CG2 | 46.0 | 24.6 | 4.1 | 29 | A |
|---|---|---|---|---|---|---|---|
| 54 | I | CG1 | 46.7 | 22.2 | 3.9 | 27 | A |
| 54 | I | CD1 | 48.1 | 22.4 | 4.5 | 29 | A |
| 54 | I | C | 44.3 | 24.2 | 1.7 | 28 | A |
| 54 | I | O | 44.9 | 24.6 | 0.6 | 27 | A |
| 55 | S | N | 43.3 | 24.9 | 2.2 | 28 | A |
| 55 | S | CA | 42.7 | 26.1 | 1.6 | 29 | A |
| 55 | S | CB | 41.3 | 25.8 | 1.1 | 29 | A |
| 45 | S | OG | 41.2 | 24.5 | 0.4 | 30 | A |
| 55 | S | C | 42.7 | 27.2 | 2.6 | 30 | A |
| 55 | S | O | 41.7 | 27.4 | 3.3 | 31 | A |
| 56 | P | N | 43.8 | 27.9 | 2.8 | 29 | A |
| 56 | P | CD | 45.2 | 27.5 | 2.4 | 29 | A |
| 56 | P | CA | 43.9 | 29.0 | 3.8 | 29 | A |
| 56 | P | CB | 45.2 | 28.6 | 4.5 | 29 | A |
| 56 | P | CG | 46.1 | 28.3 | 3.3 | 29 | A |
| 56 | P | C | 44.0 | 30.5 | 3.3 | 29 | A |
| 56 | P | O | 44.0 | 31.4 | 4.1 | 28 | A |
| 57 | F | N | 44.1 | 30.7 | 2.0 | 30 | A |
| 57 | F | CA | 44.3 | 32.0 | 1.4 | 30 | A |
| 57 | F | CB | 44.5 | 31.9 | -0.1 | 27 | A |
| 57 | F | CG | 45.7 | 31.0 | -0.4 | 23 | A |
| 57 | F | CD1 | 47.0 | 31.3 | 0.1 | 22 | A |
| 57 | F | CD2 | 45.6 | 29.9 | -1.1 | 21 | A |
| 57 | F | CE1 | 48.1 | 30.5 | -0.1 | 21 | A |
| 57 | F | CE2 | 46.7 | 29.0 | -1.4 | 23 | A |
| 57 | F | CZ | 47.9 | 29.3 | -0.9 | 21 | A |
| 57 | F | C | 43.2 | 33.1 | 1.7 | 33 | A |
| 57 | F | O | 43.3 | 34.2 | 1.3 | 32 | A |
| 58 | E | N | 42.1 | 32.7 | 2.3 | 36 | A |
| 58 | E | CA | 41.0 | 33.6 | 2.6 | 39 | A |
| 58 | E | CB | 39.7 | 32.8 | 2.5 | 42 | A |
| 58 | E | CG | 39.4 | 32.3 | 1.1 | 47 | A |
| 58 | E | CD | 38.5 | 31.1 | 1.0 | 50 | A |
| 58 | E | OE1 | 37.3 | 31.2 | 1.5 | 53 | A |
| 58 | E | OE2 | 38.9 | 30.1 | 0.5 | 53 | A |
| 58 | E | C | 41.1 | 34.2 | 4.0 | 40 | A |
| 58 | E | O | 40.3 | 35.1 | 4.3 | 39 | A |
| 59 | H | N | 42.1 | 33.8 | 4.8 | 40 | A |
| 59 | H | CA | 42.3 | 34.4 | 6.1 | 40 | A |
| 59 | H | CB | 41.5 | 33.5 | 7.2 | 41 | A |
| 59 | H | CG | 40.1 | 33.4 | 6.9 | 42 | A |
| 59 | H | CD2 | 39.3 | 32.3 | 6.5 | 42 | A |
| 59 | H | ND1 | 39.2 | 34.4 | 7.0 | 43 | A |
| 59 | H | CE1 | 38.0 | 34.0 | 6.7 | 43 | A |
| 59 | H | NE2 | 38.0 | 32.7 | 6.4 | 43 | A |
| 59 | H | C | 43.8 | 34.5 | 6.5 | 40 | A |
| 59 | H | O | 44.5 | 33.5 | 6.3 | 39 | A |
| 60 | Q | N | 44.2 | 35.6 | 7.0 | 39 | A |
| 60 | Q | CA | 45.6 | 35.8 | 7.4 | 39 | A |
| 60 | Q | CB | 45.7 | 37.3 | 7.9 | 40 | A |
| 60 | Q | CG | 47.2 | 37.6 | 8.3 | 43 | A |
| 60 | Q | CD | 47.4 | 38.6 | 9.4 | 44 | A |
| 60 | Q | OE1 | 46.9 | 38.4 | 10.5 | 45 | A |
| 60 | Q | NE2 | 48.0 | 39.7 | 9.1 | 45 | A |
| 60 | Q | C | 46.1 | 34.8 | 8.4 | 38 | A |
| 60 | Q | O | 47.2 | 34.4 | 8.3 | 36 | A |
| 61 | T | N | 45.2 | 34.5 | 9.4 | 36 | A |
| 61 | T | CA | 45.6 | 33.6 | 10.4 | 36 | A |
| 61 | T | CB | 44.5 | 33.4 | 11.4 | 36 | A |
| 61 | T | OG1 | 43.3 | 33.0 | 10.7 | 38 | A |
| 61 | T | CG2 | 44.2 | 34.7 | 12.2 | 36 | A |
| 61 | T | C | 46.0 | 32.2 | 9.8 | 35 | A |
| 61 | T | O | 47.0 | 31.6 | 10.2 | 34 | A |
| 62 | Y | N | 45.2 | 31.7 | 8.9 | 34 | A |
| 62 | Y | CA | 45.4 | 30.4 | 8.3 | 34 | A |
| 62 | Y | CB | 44.2 | 30.0 | 7.4 | 37 | A |
| 62 | Y | CG | 43.0 | 29.7 | 8.2 | 41 | A |
| 62 | Y | CD1 | 43.0 | 28.9 | 9.3 | 43 | A |
| 62 | Y | CE1 | 41.8 | 28.6 | 10.0 | 45 | A |
| 62 | Y | CD2 | 41.8 | 30.2 | 7.8 | 43 | A |
| 62 | Y | CE2 | 40.6 | 29.9 | 8.5 | 45 | A |
| 62 | Y | CZ | 40.6 | 29.1 | 9.6 | 45 | A |
| 62 | Y | OH | 39.5 | 28.8 | 10.3 | 47 | A |
| 62 | Y | C | 46.7 | 30.5 | 7.4 | 32 | A |
| 62 | Y | O | 47.4 | 29.5 | 7.4 | 30 | A |
| 63 | C | N | 46.9 | 31.6 | 6.8 | 29 | A |
| 63 | C | CA | 48.1 | 31.8 | 6.0 | 28 | A |
| 63 | C | CB | 48.0 | 33.1 | 5.2 | 28 | A |
| 63 | C | SG | 46.8 | 33.1 | 3.8 | 27 | A |
| 63 | C | C | 49.4 | 31.7 | 6.8 | 28 | A |
| 63 | C | O | 50.4 | 31.2 | 6.4 | 27 | A |
| 64 | Q | N | 49.3 | 32.4 | 8.0 | 27 | A |
| 64 | Q | CA | 50.5 | 32.4 | 8.9 | 26 | A |
| 64 | Q | CB | 50.2 | 33.3 | 10.1 | 27 | A |
| 64 | Q | CG | 50.0 | 34.8 | 9.7 | 30 | A |
| 64 | Q | CD | 49.8 | 35.6 | 10.9 | 31 | A |
| 64 | Q | OE1 | 48.9 | 35.4 | 11.7 | 34 | A |
| 64 | Q | NE2 | 50.6 | 36.7 | 11.1 | 34 | A |
| 64 | Q | C | 50.8 | 31.0 | 9.3 | 25 | A |
| 64 | Q | O | 52.0 | 30.6 | 9.4 | 24 | A |
| 65 | R | N | 49.8 | 30.2 | 9.7 | 24 | A |
| 65 | R | CA | 50.0 | 28.9 | 10.2 | 25 | A |
| 65 | R | CB | 48.6 | 28.3 | 10.7 | 26 | A |
| 65 | R | CG | 47.9 | 29.2 | 11.7 | 30 | A |
| 65 | R | CD | 48.7 | 29.3 | 13.0 | 32 | A |
| 65 | R | NE | 47.9 | 30.0 | 14.1 | 33 | A |
| 65 | R | CZ | 48.4 | 30.3 | 15.3 | 34 | A |
| 65 | R | NH1 | 49.6 | 30.0 | 15.6 | 34 | A |
| 65 | R | NH2 | 47.6 | 30.9 | 16.1 | 33 | A |
| 65 | R | C | 50.5 | 28.0 | 9.1 | 24 | A |
| 65 | R | O | 51.4 | 27.2 | 9.4 | 22 | A |
| 66 | T | N | 50.0 | 28.1 | 7.9 | 23 | A |
| 66 | T | CA | 50.4 | 27.2 | 6.8 | 23 | A |
| 66 | T | CB | 49.5 | 27.5 | 5.5 | 23 | A |
| 66 | T | OG1 | 48.2 | 27.2 | 5.8 | 22 | A |
| 66 | T | CG2 | 50.0 | 26.7 | 4.3 | 22 | A |
| 66 | T | C | 51.9 | 27.5 | 6.4 | 21 | A |
| 66 | T | O | 52.6 | 26.6 | 6.2 | 22 | A |
| 67 | L | N | 52.2 | 28.8 | 6.4 | 21 | A |
| 67 | L | CA | 53.6 | 29.1 | 6.1 | 21 | A |
| 67 | L | CB | 53.8 | 30.7 | 6.0 | 22 | A |
| 67 | L | CG | 55.1 | 31.2 | 5.6 | 22 | A |
| 67 | L | CD1 | 55.6 | 30.6 | 4.3 | 22 | A |
| 67 | L | CD2 | 55.0 | 32.7 | 5.4 | 23 | A |
| 67 | L | C | 54.6 | 28.6 | 7.1 | 21 | A |
| 67 | L | O | 55.6 | 28.0 | 6.8 | 19 | A |
| 68 | R | N | 54.2 | 28.7 | 8.4 | 22 | A |
| 68 | R | CA | 55.1 | 28.2 | 9.5 | 21 | A |
| 68 | R | CB | 54.5 | 28.6 | 10.9 | 21 | A |
| 68 | R | CG | 54.5 | 30.0 | 11.2 | 22 | A |
| 68 | R | CD | 54.7 | 30.3 | 12.7 | 21 | A |
| 68 | R | NE | 54.5 | 31.7 | 13.0 | 22 | A |
| 68 | R | CZ | 53.3 | 32.3 | 13.2 | 21 | A |
| 68 | R | NH1 | 52.2 | 31.5 | 13.0 | 22 | A |
| 68 | R | NH2 | 53.2 | 33.6 | 13.4 | 23 | A |
| 68 | R | C | 55.3 | 26.7 | 9.4 | 20 | A |
| 68 | R | O | 56.5 | 26.3 | 9.5 | 20 | A |
| 69 | E | N | 54.3 | 25.9 | 9.2 | 18 | A |
| 69 | E | CA | 54.4 | 24.5 | 9.1 | 20 | A |
| 69 | E | CB | 53.1 | 23.8 | 9.0 | 21 | A |
| 69 | E | CG | 53.3 | 22.3 | 8.9 | 25 | A |
| 69 | E | CD | 52.0 | 21.5 | 9.0 | 27 | A |
| 69 | E | OE1 | 51.0 | 21.7 | 8.2 | 30 | A |
| 69 | E | OE2 | 51.9 | 20.6 | 9.9 | 25 | A |
| 69 | E | C | 55.3 | 24.1 | 7.9 | 20 | A |
| 69 | E | O | 56.2 | 23.2 | 8.0 | 19 | A |
| 70 | I | N | 55.1 | 24.7 | 6.8 | 19 | A |
| 70 | I | CA | 55.8 | 24.4 | 5.6 | 19 | A |
| 70 | I | CB | 55.3 | 25.1 | 4.3 | 18 | A |
| 70 | I | CG2 | 56.3 | 24.9 | 3.2 | 20 | A |
| 70 | I | CG1 | 53.9 | 24.6 | 4.0 | 19 | A |

TABLE 1-continued

Structural Coordinates of crystalline Ah₆-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| Res | AA | Atom | X | Y | Z | B | Chain |
|---|---|---|---|---|---|---|---|
| 70 | I | CD1 | 53.2 | 25.2 | 2.8 | 19 | A |
| 70 | I | C | 57.3 | 24.7 | 5.8 | 18 | A |
| 70 | I | O | 58.2 | 23.8 | 5.6 | 18 | A |
| 71 | K | N | 57.6 | 25.9 | 6.2 | 18 | A |
| 71 | K | CA | 59.0 | 26.3 | 6.4 | 19 | A |
| 71 | K | CB | 59.1 | 27.8 | 7.0 | 20 | A |
| 71 | K | CG | 58.5 | 28.8 | 6.0 | 25 | A |
| 71 | K | CD | 58.8 | 30.2 | 6.5 | 26 | A |
| 71 | K | CE | 60.2 | 30.5 | 6.5 | 27 | A |
| 71 | K | NZ | 60.5 | 31.9 | 7.0 | 29 | A |
| 71 | K | C | 59.7 | 25.4 | 7.4 | 19 | A |
| 71 | K | O | 60.8 | 25.0 | 7.2 | 19 | A |
| 72 | I | N | 59.0 | 25.1 | 8.5 | 17 | A |
| 72 | I | CA | 59.6 | 24.3 | 9.6 | 17 | A |
| 72 | I | CB | 58.7 | 24.3 | 10.9 | 16 | A |
| 72 | I | CG2 | 59.2 | 23.1 | 11.8 | 16 | A |
| 72 | I | CG1 | 58.8 | 25.6 | 11.6 | 17 | A |
| 72 | I | CD1 | 57.8 | 25.9 | 12.7 | 18 | A |
| 72 | I | C | 59.8 | 22.8 | 9.1 | 17 | A |
| 72 | I | O | 60.9 | 22.3 | 9.3 | 18 | A |
| 73 | L | N | 58.8 | 22.2 | 8.6 | 17 | A |
| 73 | L | CA | 59.0 | 20.8 | 8.1 | 17 | A |
| 73 | L | CB | 57.6 | 20.2 | 7.8 | 18 | A |
| 73 | L | CG | 56.7 | 19.9 | 9.0 | 19 | A |
| 73 | L | CD1 | 55.4 | 19.2 | 8.6 | 22 | A |
| 73 | L | CD2 | 57.4 | 19.1 | 10.1 | 20 | A |
| 73 | L | C | 59.9 | 20.6 | 7.0 | 19 | A |
| 73 | L | O | 60.5 | 19.5 | 6.9 | 19 | A |
| 74 | L | N | 60.1 | 21.6 | 6.1 | 20 | A |
| 74 | L | CA | 61.0 | 21.5 | 5.0 | 21 | A |
| 74 | L | CB | 60.7 | 22.5 | 3.9 | 20 | A |
| 74 | L | CG | 59.5 | 22.3 | 3.1 | 21 | A |
| 74 | L | CD1 | 59.4 | 23.4 | 2.0 | 22 | A |
| 74 | L | CD2 | 59.6 | 20.9 | 2.4 | 22 | A |
| 74 | L | C | 62.5 | 21.6 | 5.5 | 21 | A |
| 74 | L | O | 63.4 | 21.0 | 4.9 | 22 | A |
| 75 | R | N | 62.7 | 22.2 | 6.6 | 20 | A |
| 75 | R | CA | 64.0 | 22.4 | 7.2 | 20 | A |
| 75 | R | CB | 64.2 | 23.7 | 7.9 | 22 | A |
| 75 | R | CG | 65.6 | 23.9 | 8.4 | 24 | A |
| 75 | R | CD | 65.8 | 25.2 | 9.2 | 26 | A |
| 75 | R | NE | 65.6 | 26.4 | 8.3 | 26 | A |
| 75 | R | CZ | 65.9 | 27.6 | 8.7 | 25 | A |
| 75 | R | NH1 | 66.5 | 27.8 | 9.8 | 26 | A |
| 75 | R | NH2 | 65.7 | 28.6 | 7.9 | 28 | A |
| 75 | R | C | 64.4 | 21.2 | 8.1 | 20 | A |
| 75 | R | O | 65.6 | 21.0 | 8.3 | 24 | A |
| 76 | F | N | 63.4 | 20.5 | 8.6 | 18 | A |
| 76 | F | CA | 63.6 | 19.4 | 9.5 | 17 | A |
| 76 | F | CB | 62.4 | 19.2 | 10.5 | 15 | A |
| 76 | F | CG | 62.3 | 20.2 | 11.6 | 15 | A |
| 76 | F | CD1 | 63.2 | 21.3 | 11.7 | 16 | A |
| 76 | F | CD2 | 61.3 | 20.1 | 12.5 | 15 | A |
| 76 | F | CE1 | 63.1 | 22.2 | 12.8 | 18 | A |
| 76 | F | CE2 | 61.2 | 21.0 | 13.6 | 16 | A |
| 76 | F | CZ | 62.1 | 22.0 | 13.7 | 16 | A |
| 76 | F | C | 63.9 | 18.1 | 8.8 | 17 | A |
| 76 | F | O | 63.3 | 17.8 | 7.8 | 17 | A |
| 77 | R | N | 64.7 | 17.2 | 9.4 | 17 | A |
| 77 | R | CA | 65.0 | 15.9 | 8.9 | 19 | A |
| 77 | R | CB | 66.1 | 15.9 | 7.9 | 24 | A |
| 77 | R | CG | 66.3 | 14.6 | 7.1 | 32 | A |
| 77 | R | CD | 67.4 | 14.8 | 6.0 | 40 | A |
| 77 | R | NE | 67.5 | 13.6 | 5.2 | 47 | A |
| 77 | R | CZ | 68.0 | 12.4 | 5.7 | 50 | A |
| 77 | R | NH1 | 68.3 | 12.3 | 6.9 | 52 | A |
| 77 | R | NH2 | 68.1 | 11.4 | 4.8 | 51 | A |
| 77 | R | C | 65.3 | 15.0 | 10.1 | 16 | A |
| 77 | R | O | 66.4 | 15.0 | 10.6 | 18 | A |
| 78 | H | N | 64.3 | 14.3 | 10.6 | 14 | A |
| 78 | H | CA | 64.5 | 13.4 | 11.7 | 14 | A |
| 78 | H | CB | 64.2 | 14.2 | 13.0 | 14 | A |
| 78 | H | CG | 64.6 | 13.6 | 14.3 | 13 | A |
| 78 | H | CD2 | 65.7 | 13.7 | 15.1 | 13 | A |
| 78 | H | ND1 | 63.8 | 12.6 | 14.9 | 12 | A |
| 78 | H | CE1 | 64.4 | 12.2 | 16.0 | 13 | A |
| 78 | H | NE2 | 65.5 | 12.9 | 16.2 | 13 | A |
| 78 | H | C | 63.5 | 12.2 | 11.7 | 13 | A |
| 78 | H | O | 62.4 | 12.3 | 11.2 | 14 | A |
| 79 | E | N | 64.0 | 11.1 | 12.1 | 14 | A |
| 79 | E | CA | 63.2 | 9.8 | 12.1 | 15 | A |
| 79 | E | CB | 64.0 | 8.6 | 12.7 | 17 | A |
| 79 | E | CG | 65.3 | 8.3 | 12.0 | 20 | A |
| 79 | E | CD | 66.0 | 7.1 | 12.5 | 24 | A |
| 79 | E | OE1 | 66.0 | 6.9 | 13.7 | 25 | A |
| 79 | E | OE2 | 66.5 | 6.3 | 11.7 | 27 | A |
| 79 | E | C | 61.9 | 9.9 | 12.9 | 14 | A |
| 79 | E | O | 60.9 | 9.2 | 12.5 | 15 | A |
| 80 | N | N | 61.8 | 10.7 | 13.9 | 13 | A |
| 80 | N | CA | 60.6 | 10.8 | 14.7 | 11 | A |
| 80 | N | CB | 60.9 | 10.7 | 16.2 | 12 | A |
| 80 | N | CG | 61.7 | 9.5 | 16.6 | 13 | A |
| 80 | N | OD1 | 62.8 | 9.5 | 17.0 | 12 | A |
| 80 | N | ND2 | 61.0 | 8.3 | 16.4 | 13 | A |
| 80 | N | C | 59.7 | 12.1 | 14.4 | 10 | A |
| 80 | N | O | 58.9 | 12.5 | 15.3 | 12 | A |
| 81 | I | N | 59.9 | 12.6 | 13.3 | 12 | A |
| 81 | I | CA | 59.2 | 13.8 | 12.9 | 12 | A |
| 81 | I | CB | 60.0 | 15.1 | 12.9 | 12 | A |
| 81 | I | CG2 | 59.2 | 16.3 | 12.4 | 14 | A |
| 81 | I | CG1 | 60.6 | 15.4 | 14.3 | 14 | A |
| 81 | I | CD1 | 61.5 | 16.5 | 14.4 | 15 | A |
| 81 | I | C | 58.7 | 13.6 | 11.4 | 13 | A |
| 81 | I | O | 59.4 | 13.2 | 10.5 | 15 | A |
| 82 | I | N | 57.4 | 13.8 | 11.2 | 14 | A |
| 82 | I | CA | 56.8 | 13.5 | 9.9 | 16 | A |
| 82 | I | CB | 55.3 | 13.7 | 9.8 | 16 | A |
| 82 | I | CG2 | 54.9 | 15.2 | 10.0 | 17 | A |
| 82 | I | CG1 | 54.7 | 13.1 | 8.6 | 18 | A |
| 82 | I | CD1 | 54.8 | 11.6 | 8.5 | 20 | A |
| 82 | I | C | 57.5 | 14.5 | 8.9 | 18 | A |
| 82 | I | O | 57.7 | 15.6 | 9.2 | 18 | A |
| 83 | G | N | 57.8 | 14.0 | 7.7 | 19 | A |
| 83 | G | CA | 58.4 | 14.8 | 6.7 | 22 | A |
| 83 | G | C | 57.4 | 15.2 | 5.6 | 23 | A |
| 83 | G | O | 56.3 | 14.7 | 5.5 | 26 | A |
| 84 | I | N | 57.8 | 16.1 | 4.7 | 23 | A |
| 84 | I | CA | 57.0 | 16.6 | 3.6 | 24 | A |
| 84 | I | CB | 57.0 | 18.1 | 3.5 | 24 | A |
| 84 | I | CG2 | 56.4 | 18.5 | 2.1 | 26 | A |
| 84 | I | CG1 | 56.1 | 18.7 | 4.6 | 24 | A |
| 84 | I | CD1 | 55.9 | 20.2 | 4.5 | 23 | A |
| 84 | I | C | 57.7 | 15.9 | 2.4 | 24 | A |
| 84 | I | O | 58.8 | 16.3 | 2.0 | 26 | A |
| 85 | N | N | 57.0 | 15.0 | 1.8 | 26 | A |
| 85 | N | CA | 57.5 | 14.3 | 0.6 | 27 | A |
| 85 | N | CB | 56.8 | 12.9 | 0.5 | 29 | A |
| 85 | N | CG | 57.0 | 12.0 | 1.7 | 29 | A |
| 85 | N | OD1 | 56.4 | 11.0 | 1.8 | 32 | A |
| 85 | N | ND2 | 57.8 | 12.5 | 2.7 | 31 | A |
| 85 | N | C | 57.3 | 15.0 | −0.7 | 28 | A |
| 85 | N | O | 58.1 | 14.9 | −1.6 | 28 | A |
| 86 | D | N | 56.3 | 15.8 | −0.8 | 27 | A |
| 86 | D | CA | 56.0 | 16.5 | −2.0 | 28 | A |
| 86 | D | CB | 55.5 | 15.6 | −3.1 | 29 | A |
| 86 | D | CG | 55.2 | 16.2 | −4.4 | 30 | A |
| 86 | D | OD1 | 56.0 | 17.1 | −4.8 | 30 | A |
| 86 | D | OD2 | 54.2 | 15.9 | −5.0 | 33 | A |
| 86 | D | C | 54.9 | 17.6 | −1.7 | 26 | A |
| 86 | D | O | 54.1 | 17.4 | −0.7 | 24 | A |
| 87 | I | N | 54.8 | 18.6 | −2.5 | 25 | A |
| 87 | I | CA | 53.8 | 19.7 | −2.3 | 24 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| Residue | AA | Atom | X | Y | Z | B | Chain |
|---|---|---|---|---|---|---|---|
| 87 | I | CB | 54.4 | 21.0 | -1.7 | 24 | A |
| 87 | I | CG2 | 53.3 | 22.0 | -1.6 | 24 | A |
| 87 | I | CG1 | 55.0 | 20.7 | -0.3 | 24 | A |
| 87 | I | CD1 | 55.6 | 21.9 | 0.4 | 24 | A |
| 87 | I | C | 53.3 | 20.0 | -3.7 | 25 | A |
| 87 | I | O | 54.0 | 20.3 | -4.7 | 25 | A |
| 88 | I | N | 51.9 | 19.9 | -3.8 | 25 | A |
| 88 | I | CA | 51.3 | 20.2 | -5.1 | 25 | A |
| 88 | I | CB | 50.3 | 19.0 | -5.4 | 26 | A |
| 88 | I | CG2 | 49.7 | 19.2 | -6.8 | 28 | A |
| 88 | I | CG1 | 51.1 | 17.7 | -5.4 | 28 | A |
| 88 | I | CD1 | 50.2 | 16.5 | -5.5 | 30 | A |
| 88 | I | C | 50.5 | 21.5 | -5.1 | 24 | A |
| 88 | I | O | 49.7 | 21.8 | -4.2 | 24 | A |
| 89 | R | N | 50.7 | 22.3 | -6.1 | 23 | A |
| 89 | R | CA | 49.9 | 23.6 | -6.3 | 21 | A |
| 89 | R | CB | 50.4 | 24.6 | -5.2 | 22 | A |
| 89 | R | CG | 51.9 | 24.9 | -5.1 | 22 | A |
| 89 | R | CD | 52.3 | 25.9 | -6.2 | 21 | A |
| 89 | R | NE | 53.6 | 26.5 | -5.9 | 20 | A |
| 89 | R | CZ | 54.4 | 27.0 | -6.8 | 22 | A |
| 89 | R | NH1 | 54.1 | 27.1 | -8.0 | 21 | A |
| 89 | R | NH2 | 55.6 | 27.6 | -6.4 | 22 | A |
| 89 | R | C | 50.1 | 24.1 | -7.7 | 21 | A |
| 89 | R | O | 51.0 | 23.7 | -8.4 | 21 | A |
| 90 | A | N | 49.2 | 25.0 | -8.1 | 20 | A |
| 90 | A | CA | 49.3 | 25.7 | -9.4 | 20 | A |
| 90 | A | CB | 48.1 | 26.7 | -9.5 | 20 | A |
| 90 | A | C | 50.6 | 26.3 | -9.8 | 20 | A |
| 90 | A | O | 51.3 | 26.8 | -8.9 | 21 | A |
| 91 | P | N | 50.9 | 26.4 | -11.1 | 20 | A |
| 91 | P | CD | 50.1 | 25.9 | -12.2 | 22 | A |
| 91 | P | CA | 52.1 | 27.1 | -11.6 | 20 | A |
| 91 | P | CB | 52.2 | 26.7 | -13.0 | 21 | A |
| 91 | P | CG | 50.7 | 26.6 | -13.4 | 21 | A |
| 91 | P | C | 52.2 | 28.6 | -11.4 | 20 | A |
| 91 | P | O | 53.3 | 29.2 | -11.4 | 21 | A |
| 92 | T | N | 51.1 | 29.2 | -11.1 | 20 | A |
| 92 | T | CA | 51.0 | 30.7 | -10.9 | 20 | A |
| 92 | T | CB | 50.4 | 31.4 | -12.1 | 21 | A |
| 92 | T | OG1 | 49.0 | 31.1 | -12.1 | 20 | A |
| 92 | T | CG2 | 51.0 | 31.0 | -13.4 | 21 | A |
| 92 | T | C | 50.3 | 31.0 | -9.7 | 21 | A |
| 92 | T | O | 49.4 | 30.3 | -9.2 | 20 | A |
| 93 | I | N | 50.7 | 32.2 | -9.1 | 22 | A |
| 93 | I | CA | 50.0 | 32.7 | -7.9 | 23 | A |
| 93 | I | CB | 50.7 | 33.9 | -7.3 | 26 | A |
| 93 | I | CG2 | 50.6 | 35.1 | -8.3 | 27 | A |
| 93 | I | CG1 | 50.1 | 34.3 | -6.0 | 27 | A |
| 93 | I | CD1 | 50.9 | 35.4 | -5.3 | 29 | A |
| 93 | I | C | 48.5 | 32.9 | -8.1 | 24 | A |
| 93 | I | O | 47.7 | 32.6 | -7.3 | 24 | A |
| 94 | E | N | 48.2 | 33.5 | -9.3 | 24 | A |
| 94 | E | CA | 46.9 | 33.8 | -9.7 | 23 | A |
| 94 | E | CB | 46.8 | 34.4 | -11.0 | 24 | A |
| 94 | E | CG | 47.4 | 35.8 | -11.1 | 26 | A |
| 94 | E | CD | 48.9 | 35.9 | -11.4 | 26 | A |
| 94 | E | OE1 | 49.5 | 34.8 | -11.3 | 26 | A |
| 94 | E | OE2 | 49.4 | 36.9 | -11.8 | 29 | A |
| 94 | E | C | 46.0 | 32.5 | -9.7 | 22 | A |
| 94 | E | O | 44.8 | 32.6 | -9.3 | 23 | A |
| 95 | Q | N | 46.5 | 31.4 | -10.1 | 20 | A |
| 95 | Q | CA | 45.7 | 30.2 | -10.2 | 20 | A |
| 95 | Q | CB | 46.2 | 29.3 | -11.4 | 19 | A |
| 95 | Q | CG | 46.1 | 30.1 | -12.7 | 20 | A |
| 95 | Q | CD | 46.7 | 29.3 | -13.9 | 22 | A |
| 95 | Q | OE1 | 45.9 | 28.6 | -14.6 | 22 | A |
| 95 | Q | NE2 | 48.0 | 29.3 | -14.0 | 20 | A |
| 95 | Q | C | 45.8 | 29.3 | -8.9 | 19 | A |
| 95 | Q | O | 45.1 | 28.3 | -8.8 | 20 | A |
| 96 | M | N | 46.7 | 29.6 | -8.0 | 20 | A |
| 96 | M | CA | 46.8 | 28.9 | -6.7 | 21 | A |
| 96 | M | CB | 48.2 | 29.1 | -6.1 | 21 | A |
| 96 | M | CG | 48.4 | 28.4 | -4.8 | 20 | A |
| 96 | M | SD | 50.0 | 28.5 | -4.1 | 21 | A |
| 96 | M | CE | 50.0 | 30.2 | -3.6 | 21 | A |
| 96 | M | C | 45.7 | 29.2 | -5.7 | 21 | A |
| 96 | M | O | 45.7 | 30.3 | -5.2 | 22 | A |
| 97 | K | N | 44.8 | 28.2 | -5.5 | 23 | A |
| 97 | K | CA | 43.7 | 28.4 | -4.6 | 26 | A |
| 97 | K | CB | 42.4 | 28.2 | -5.3 | 28 | A |
| 97 | K | CG | 42.2 | 29.1 | -6.5 | 32 | A |
| 97 | K | CD | 42.4 | 30.6 | -6.1 | 35 | A |
| 97 | K | CE | 42.4 | 31.5 | -7.4 | 38 | A |
| 97 | K | NZ | 42.7 | 32.9 | -7.1 | 39 | A |
| 97 | K | C | 43.8 | 27.5 | -3.4 | 25 | A |
| 97 | K | O | 43.3 | 27.7 | -2.3 | 25 | A |
| 98 | D | N | 44.5 | 26.4 | -3.6 | 26 | A |
| 98 | D | CA | 44.8 | 25.3 | -2.6 | 26 | A |
| 98 | D | CB | 43.8 | 24.2 | -2.8 | 26 | A |
| 98 | D | CG | 42.4 | 24.6 | -3.1 | 28 | A |
| 98 | D | OD1 | 42.1 | 24.8 | -4.3 | 28 | A |
| 98 | D | OD2 | 41.6 | 24.7 | -2.2 | 29 | A |
| 98 | D | C | 46.2 | 24.8 | -2.7 | 26 | A |
| 98 | D | O | 46.9 | 25.1 | -3.7 | 27 | A |
| 99 | V | N | 46.6 | 24.1 | -1.7 | 25 | A |
| 99 | V | CA | 47.9 | 23.5 | -1.6 | 25 | A |
| 99 | V | CB | 48.9 | 24.4 | -0.8 | 26 | A |
| 99 | V | CG1 | 50.3 | 23.7 | -0.8 | 27 | A |
| 99 | V | CG2 | 49.0 | 25.8 | -1.3 | 27 | A |
| 99 | V | C | 47.8 | 22.1 | -1.0 | 25 | A |
| 99 | V | O | 47.2 | 21.9 | 0.0 | 26 | A |
| 100 | Y | N | 48.5 | 21.1 | -1.7 | 25 | A |
| 100 | Y | CA | 48.4 | 19.8 | -1.2 | 25 | A |
| 100 | Y | CB | 48.0 | 18.8 | -2.3 | 27 | A |
| 100 | Y | CG | 46.7 | 19.1 | -2.9 | 30 | A |
| 100 | Y | CD1 | 46.5 | 20.1 | -3.8 | 31 | A |
| 100 | Y | CE1 | 45.3 | 20.4 | -4.5 | 31 | A |
| 100 | Y | CD2 | 45.6 | 18.2 | -2.7 | 31 | A |
| 100 | Y | CE2 | 44.3 | 18.5 | -3.3 | 32 | A |
| 100 | Y | CZ | 44.2 | 19.5 | -4.2 | 33 | A |
| 100 | Y | OH | 43.0 | 19.7 | -4.8 | 34 | A |
| 100 | Y | C | 49.8 | 19.3 | -0.7 | 24 | A |
| 100 | Y | O | 50.8 | 19.4 | -1.3 | 23 | A |
| 101 | I | N | 49.8 | 18.8 | 0.6 | 23 | A |
| 101 | I | CA | 51.0 | 18.3 | 1.2 | 22 | A |
| 101 | I | CB | 51.2 | 18.9 | 2.6 | 22 | A |
| 101 | I | CG2 | 52.4 | 18.4 | 3.3 | 22 | A |
| 101 | I | CG1 | 51.2 | 20.4 | 2.6 | 23 | A |
| 101 | I | CD1 | 51.3 | 21.1 | 3.9 | 25 | A |
| 101 | I | C | 51.0 | 16.8 | 1.3 | 21 | A |
| 101 | I | O | 50.1 | 16.2 | 1.9 | 22 | A |
| 102 | V | N | 52.0 | 16.2 | 0.7 | 22 | A |
| 102 | V | CA | 52.2 | 14.7 | 0.7 | 24 | A |
| 102 | V | CB | 52.7 | 14.2 | -0.7 | 25 | A |
| 102 | V | CG1 | 52.7 | 12.7 | -0.7 | 25 | A |
| 102 | V | CG2 | 51.9 | 14.9 | -1.8 | 25 | A |
| 102 | V | C | 53.1 | 14.3 | 1.8 | 24 | A |
| 102 | V | O | 54.2 | 14.8 | 1.9 | 24 | A |
| 103 | Q | N | 52.7 | 13.3 | 2.6 | 25 | A |
| 103 | Q | CA | 53.5 | 12.8 | 3.7 | 26 | A |
| 103 | Q | CB | 53.0 | 13.4 | 5.0 | 25 | A |
| 103 | Q | CG | 53.0 | 14.9 | 5.0 | 24 | A |
| 103 | Q | CD | 52.5 | 15.6 | 6.3 | 25 | A |
| 103 | Q | OE1 | 51.3 | 15.4 | 6.6 | 28 | A |
| 103 | Q | NE2 | 53.4 | 16.3 | 7.0 | 23 | A |
| 103 | Q | C | 53.4 | 11.3 | 3.8 | 27 | A |
| 103 | Q | O | 52.5 | 10.6 | 3.1 | 28 | A |
| 104 | D | N | 54.2 | 10.6 | 4.6 | 28 | A |
| 104 | D | CA | 54.2 | 9.2 | 4.8 | 29 | A |
| 104 | D | CB | 55.4 | 8.7 | 5.7 | 31 | A |
| 104 | D | CG | 56.7 | 8.9 | 5.0 | 32 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 104 | D | OD1 | 56.9 | 8.6 | 3.8 | 33 | A |
| 104 | D | OD2 | 57.7 | 9.2 | 5.8 | 34 | A |
| 104 | D | C | 52.9 | 8.8 | 5.4 | 29 | A |
| 104 | D | O | 52.4 | 9.5 | 6.2 | 29 | A |
| 105 | L | N | 52.4 | 7.7 | 4.9 | 29 | A |
| 105 | L | CA | 51.1 | 7.2 | 5.4 | 30 | A |
| 105 | L | CB | 50.3 | 6.4 | 4.4 | 30 | A |
| 105 | L | CG | 49.0 | 5.8 | 4.8 | 31 | A |
| 105 | L | CD1 | 48.0 | 6.9 | 5.2 | 31 | A |
| 105 | L | CD2 | 48.4 | 5.0 | 3.7 | 32 | A |
| 105 | L | C | 51.4 | 6.2 | 6.6 | 29 | A |
| 105 | L | O | 52.1 | 5.2 | 6.5 | 30 | A |
| 106 | M | N | 50.8 | 6.6 | 7.8 | 28 | A |
| 106 | M | CA | 51.0 | 5.8 | 9.0 | 28 | A |
| 106 | M | CB | 51.4 | 6.7 | 10.2 | 27 | A |
| 106 | M | CG | 52.7 | 7.5 | 10.0 | 25 | A |
| 106 | M | SD | 54.2 | 6.5 | 9.9 | 25 | A |
| 106 | M | CE | 54.6 | 6.2 | 11.6 | 25 | A |
| 106 | M | C | 49.7 | 5.1 | 9.3 | 28 | A |
| 106 | M | O | 48.6 | 5.6 | 9.0 | 29 | A |
| 107 | E | N | 49.8 | 3.9 | 9.8 | 27 | A |
| 107 | E | CA | 48.6 | 3.0 | 10.1 | 28 | A |
| 107 | E | CB | 49.1 | 1.7 | 10.5 | 30 | A |
| 107 | E | CG | 49.9 | 0.9 | 9.4 | 33 | A |
| 107 | E | CD | 50.8 | −0.2 | 9.9 | 36 | A |
| 107 | E | OE1 | 50.2 | −1.1 | 10.6 | 38 | A |
| 107 | E | OE2 | 52.0 | −0.2 | 9.7 | 36 | A |
| 107 | E | C | 47.6 | 3.6 | 11.1 | 27 | A |
| 107 | E | O | 46.4 | 3.4 | 10.9 | 26 | A |
| 108 | T | N | 48.1 | 4.3 | 12.1 | 24 | A |
| 108 | T | CA | 47.2 | 4.8 | 13.1 | 23 | A |
| 108 | T | CB | 46.7 | 3.7 | 14.1 | 24 | A |
| 108 | T | OG1 | 45.6 | 4.2 | 14.9 | 25 | A |
| 108 | T | CG2 | 47.8 | 3.2 | 15.0 | 23 | A |
| 108 | T | C | 47.8 | 5.9 | 13.9 | 21 | A |
| 108 | T | O | 48.9 | 6.4 | 13.6 | 19 | A |
| 109 | D | N | 47.2 | 6.4 | 15.0 | 21 | A |
| 109 | D | CA | 47.8 | 7.4 | 15.9 | 19 | A |
| 109 | D | CB | 47.2 | 8.8 | 15.6 | 19 | A |
| 109 | D | CG | 45.7 | 8.9 | 15.8 | 20 | A |
| 109 | D | OD1 | 45.3 | 8.6 | 17.0 | 21 | A |
| 109 | D | OD2 | 45.0 | 9.2 | 14.9 | 24 | A |
| 109 | D | C | 47.5 | 7.0 | 17.3 | 19 | A |
| 109 | D | O | 46.7 | 6.0 | 17.6 | 18 | A |
| 110 | L | N | 48.2 | 7.6 | 18.3 | 18 | A |
| 110 | L | CA | 48.0 | 7.2 | 19.7 | 17 | A |
| 110 | L | CB | 49.1 | 8.0 | 20.6 | 17 | A |
| 110 | L | CG | 49.2 | 7.6 | 22.0 | 15 | A |
| 110 | L | CD1 | 49.5 | 6.1 | 22.2 | 17 | A |
| 110 | L | CD2 | 50.2 | 8.4 | 22.8 | 18 | A |
| 110 | L | C | 46.6 | 7.4 | 20.2 | 18 | A |
| 110 | L | O | 46.2 | 6.7 | 21.1 | 17 | A |
| 111 | Y | N | 45.9 | 8.4 | 19.7 | 19 | A |
| 111 | Y | CA | 44.5 | 8.7 | 20.1 | 21 | A |
| 111 | Y | CB | 44.0 | 9.9 | 19.4 | 22 | A |
| 111 | Y | CG | 42.5 | 10.2 | 19.7 | 26 | A |
| 111 | Y | CD1 | 42.1 | 10.8 | 20.9 | 27 | A |
| 111 | Y | CE1 | 40.8 | 11.1 | 21.2 | 30 | A |
| 111 | Y | CD2 | 41.5 | 9.8 | 18.9 | 28 | A |
| 111 | Y | CE2 | 40.1 | 10.0 | 19.2 | 29 | A |
| 111 | Y | CZ | 39.8 | 10.7 | 20.4 | 29 | A |
| 111 | Y | OH | 38.5 | 10.9 | 20.7 | 32 | A |
| 111 | Y | C | 43.7 | 7.4 | 19.8 | 22 | A |
| 111 | Y | O | 43.0 | 6.9 | 20.7 | 22 | A |
| 112 | K | N | 43.7 | 7.0 | 18.6 | 23 | A |
| 112 | K | CA | 42.9 | 5.8 | 18.2 | 24 | A |
| 112 | K | CB | 43.1 | 5.6 | 16.7 | 24 | A |
| 112 | K | CG | 42.6 | 6.7 | 15.8 | 28 | A |
| 112 | K | CD | 42.5 | 6.2 | 14.3 | 31 | A |
| 112 | K | CE | 42.3 | 7.3 | 13.3 | 33 | A |
| 112 | K | NZ | 43.5 | 8.1 | 13.1 | 36 | A |
| 112 | K | C | 43.4 | 4.5 | 18.9 | 24 | A |
| 112 | K | O | 42.5 | 3.7 | 19.3 | 24 | A |
| 113 | L | N | 44.7 | 4.3 | 19.1 | 23 | A |
| 113 | L | CA | 45.2 | 3.2 | 19.8 | 23 | A |
| 113 | L | CB | 46.7 | 3.2 | 19.7 | 23 | A |
| 113 | L | CG | 47.4 | 1.9 | 20.2 | 22 | A |
| 113 | L | CD1 | 47.1 | 0.7 | 19.3 | 24 | A |
| 113 | L | CD2 | 48.9 | 2.1 | 20.2 | 24 | A |
| 113 | L | C | 44.7 | 3.0 | 21.2 | 23 | A |
| 113 | L | O | 44.4 | 2.0 | 21.6 | 23 | A |
| 114 | L | N | 44.7 | 4.2 | 21.9 | 23 | A |
| 114 | L | CA | 44.3 | 4.2 | 23.3 | 24 | A |
| 114 | L | CB | 44.7 | 5.5 | 24.0 | 23 | A |
| 114 | L | CG | 46.2 | 5.7 | 24.2 | 22 | A |
| 114 | L | CD1 | 46.4 | 7.1 | 24.8 | 23 | A |
| 114 | L | CD2 | 46.7 | 4.6 | 25.1 | 23 | A |
| 114 | L | C | 42.8 | 3.9 | 23.5 | 26 | A |
| 114 | L | O | 42.3 | 3.6 | 24.6 | 27 | A |
| 115 | K | N | 42.0 | 4.0 | 22.4 | 29 | A |
| 115 | K | CA | 40.6 | 3.7 | 22.5 | 33 | A |
| 115 | K | CB | 39.8 | 4.6 | 21.5 | 35 | A |
| 115 | K | CG | 39.5 | 6.0 | 21.9 | 39 | A |
| 115 | K | CD | 38.6 | 6.7 | 21.0 | 42 | A |
| 115 | K | CE | 38.1 | 8.0 | 21.6 | 44 | A |
| 115 | K | NZ | 37.0 | 8.6 | 20.7 | 46 | A |
| 115 | K | C | 40.2 | 2.3 | 22.4 | 35 | A |
| 115 | K | O | 39.1 | 1.9 | 22.5 | 36 | A |
| 116 | T | N | 41.2 | 1.5 | 22.1 | 36 | A |
| 116 | T | CA | 41.0 | 0.0 | 21.9 | 37 | A |
| 116 | T | CB | 41.1 | −0.3 | 20.4 | 38 | A |
| 116 | T | OG1 | 40.2 | 0.5 | 19.6 | 39 | A |
| 116 | T | CG2 | 40.7 | −1.8 | 20.1 | 39 | A |
| 116 | T | C | 42.0 | −0.9 | 22.6 | 37 | A |
| 116 | T | O | 41.7 | −2.0 | 22.9 | 37 | A |
| 117 | Q | N | 43.2 | −0.4 | 22.9 | 36 | A |
| 117 | Q | CA | 44.2 | −1.2 | 23.6 | 36 | A |
| 117 | Q | CB | 45.3 | −1.5 | 22.6 | 38 | A |
| 117 | Q | CG | 44.9 | −2.3 | 21.4 | 41 | A |
| 117 | Q | CD | 44.5 | −3.8 | 21.8 | 42 | A |
| 117 | Q | OE1 | 45.3 | −4.5 | 22.3 | 44 | A |
| 117 | Q | NE2 | 43.3 | −4.2 | 21.5 | 43 | A |
| 117 | Q | C | 44.8 | −0.6 | 24.9 | 35 | A |
| 117 | Q | O | 45.0 | 0.7 | 24.9 | 34 | A |
| 118 | H | N | 45.0 | −1.4 | 25.9 | 33 | A |
| 118 | H | CA | 45.7 | −1.0 | 27.1 | 32 | A |
| 118 | H | CB | 45.2 | −1.8 | 28.3 | 35 | A |
| 118 | H | CG | 45.8 | −1.4 | 29.6 | 39 | A |
| 118 | H | CD2 | 45.3 | −0.8 | 30.7 | 41 | A |
| 118 | H | ND1 | 47.2 | −1.5 | 29.8 | 41 | A |
| 118 | H | CE1 | 47.4 | −1.1 | 31.0 | 41 | A |
| 118 | H | NE2 | 46.3 | −0.7 | 31.6 | 41 | A |
| 118 | H | C | 47.1 | −1.3 | 26.8 | 30 | A |
| 118 | H | O | 47.4 | −2.5 | 26.5 | 31 | A |
| 119 | L | N | 48.0 | −0.3 | 26.9 | 26 | A |
| 119 | L | CA | 49.4 | −0.6 | 26.6 | 23 | A |
| 119 | L | CB | 50.1 | 0.8 | 26.1 | 21 | A |
| 119 | L | CG | 49.5 | 1.3 | 24.8 | 22 | A |
| 119 | L | CD1 | 50.2 | 2.6 | 24.5 | 22 | A |
| 119 | L | CD2 | 49.6 | 0.3 | 23.7 | 22 | A |
| 119 | L | C | 50.3 | −1.1 | 27.7 | 21 | A |
| 119 | L | O | 50.1 | −0.7 | 28.9 | 22 | A |
| 120 | S | N | 51.2 | −2.0 | 27.4 | 19 | A |
| 120 | S | CA | 52.1 | −2.6 | 28.4 | 18 | A |
| 120 | S | CB | 52.8 | −3.8 | 27.8 | 18 | A |
| 120 | S | OG | 53.7 | −3.4 | 26.7 | 17 | A |
| 120 | S | C | 53.1 | −1.5 | 28.7 | 17 | A |
| 120 | S | O | 53.3 | −0.6 | 27.9 | 18 | A |
| 121 | N | N | 53.8 | −1.7 | 29.9 | 16 | A |
| 121 | N | CA | 54.8 | −0.8 | 30.3 | 16 | A |
| 121 | N | CB | 55.4 | −1.1 | 31.6 | 17 | A |
| 121 | N | CG | 56.5 | −0.2 | 32.0 | 19 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| 121 | N | OD1 | 56.3 | 1.0 | 32.3 | 18 | A |
|---|---|---|---|---|---|---|---|
| 121 | N | ND2 | 57.8 | −0.7 | 32.0 | 21 | A |
| 121 | N | C | 55.9 | −0.6 | 29.2 | 16 | A |
| 121 | N | O | 56.4 | 0.5 | 29.0 | 15 | A |
| 122 | D | N | 56.4 | −1.7 | 28.7 | 15 | A |
| 122 | D | CA | 57.4 | −1.6 | 27.7 | 15 | A |
| 122 | D | CB | 58.2 | −2.9 | 27.4 | 15 | A |
| 122 | D | CG | 57.4 | −4.0 | 26.8 | 15 | A |
| 122 | D | OD1 | 56.2 | −3.8 | 26.4 | 16 | A |
| 122 | D | OD2 | 57.9 | −5.1 | 26.7 | 15 | A |
| 122 | D | C | 57.1 | −0.9 | 26.4 | 15 | A |
| 122 | D | O | 57.9 | −0.3 | 25.7 | 14 | A |
| 123 | H | N | 55.8 | −0.9 | 26.1 | 15 | A |
| 123 | H | CA | 55.3 | −0.1 | 24.9 | 14 | A |
| 123 | H | CB | 54.0 | −0.5 | 24.4 | 15 | A |
| 123 | H | CG | 54.0 | −1.7 | 23.5 | 17 | A |
| 123 | H | CD2 | 54.2 | −1.8 | 22.1 | 18 | A |
| 123 | H | ND1 | 53.7 | −3.0 | 23.9 | 18 | A |
| 123 | H | CE1 | 53.8 | −3.8 | 22.8 | 18 | A |
| 123 | H | NE2 | 54.1 | −3.1 | 21.7 | 20 | A |
| 123 | H | C | 55.3 | 1.4 | 25.2 | 16 | A |
| 123 | H | O | 55.7 | 2.2 | 24.4 | 14 | A |
| 124 | I | N | 54.8 | 1.7 | 26.5 | 15 | A |
| 124 | I | CA | 54.8 | 3.0 | 26.9 | 15 | A |
| 124 | I | CB | 54.1 | 3.1 | 28.4 | 15 | A |
| 124 | I | CG2 | 54.2 | 4.5 | 28.9 | 16 | A |
| 124 | I | CG1 | 52.7 | 2.6 | 28.3 | 16 | A |
| 124 | I | CD1 | 52.0 | 2.6 | 29.6 | 16 | A |
| 124 | I | C | 56.2 | 3.6 | 27.0 | 15 | A |
| 124 | I | O | 56.4 | 4.8 | 26.6 | 16 | A |
| 125 | C | N | 57.1 | 2.8 | 27.5 | 15 | A |
| 125 | C | CA | 58.5 | 3.3 | 27.6 | 15 | A |
| 125 | C | CB | 59.4 | 2.2 | 28.3 | 15 | A |
| 125 | C | SG | 61.0 | 2.6 | 28.8 | 18 | A |
| 125 | C | C | 59.1 | 3.6 | 26.2 | 13 | A |
| 125 | C | O | 59.8 | 4.7 | 26.0 | 13 | A |
| 126 | Y | N | 59.0 | 2.7 | 25.3 | 13 | A |
| 126 | Y | CA | 59.5 | 2.9 | 23.9 | 14 | A |
| 126 | Y | CB | 59.4 | 1.7 | 23.1 | 14 | A |
| 126 | Y | CG | 60.0 | 1.7 | 21.7 | 14 | A |
| 126 | Y | CD1 | 61.3 | 2.1 | 21.5 | 16 | A |
| 126 | Y | CE1 | 61.9 | 2.2 | 20.3 | 15 | A |
| 126 | Y | CD2 | 59.3 | 1.4 | 20.6 | 13 | A |
| 126 | Y | CE2 | 59.9 | 1.4 | 19.3 | 15 | A |
| 126 | Y | CZ | 61.2 | 1.8 | 19.2 | 15 | A |
| 126 | Y | OH | 61.8 | 1.9 | 17.9 | 19 | A |
| 126 | Y | C | 58.8 | 4.1 | 23.2 | 14 | A |
| 126 | Y | O | 59.5 | 4.9 | 22.5 | 14 | A |
| 127 | F | N | 57.5 | 4.3 | 23.3 | 14 | A |
| 127 | F | CA | 56.8 | 5.4 | 22.7 | 15 | A |
| 127 | F | CB | 55.3 | 5.2 | 22.8 | 15 | A |
| 127 | F | CG | 54.7 | 4.1 | 22.0 | 16 | A |
| 127 | F | CD1 | 55.3 | 3.8 | 20.8 | 17 | A |
| 127 | F | CD2 | 53.5 | 3.5 | 22.4 | 17 | A |
| 127 | F | CE1 | 54.7 | 2.8 | 20.0 | 19 | A |
| 127 | F | CE2 | 52.9 | 2.5 | 21.6 | 18 | A |
| 127 | F | CZ | 53.5 | 2.2 | 20.4 | 18 | A |
| 127 | F | C | 57.3 | 6.7 | 23.3 | 13 | A |
| 127 | F | O | 57.5 | 7.7 | 22.6 | 13 | A |
| 128 | L | N | 57.4 | 6.7 | 24.7 | 13 | A |
| 128 | L | CA | 57.8 | 8.0 | 25.4 | 11 | A |
| 128 | L | CB | 57.8 | 7.8 | 26.9 | 12 | A |
| 128 | L | CG | 58.2 | 9.0 | 27.7 | 12 | A |
| 128 | L | CD1 | 57.2 | 10.2 | 27.4 | 14 | A |
| 128 | L | CD2 | 58.3 | 8.7 | 29.1 | 13 | A |
| 128 | L | C | 59.2 | 8.3 | 24.9 | 12 | A |
| 128 | L | O | 59.5 | 9.5 | 24.7 | 12 | A |
| 129 | Y | N | 60.1 | 7.3 | 24.8 | 11 | A |
| 129 | Y | CA | 61.5 | 7.6 | 24.3 | 12 | A |
| 129 | Y | CB | 62.3 | 6.3 | 24.2 | 12 | A |
| 129 | Y | CG | 63.7 | 6.5 | 23.6 | 12 | A |
| 129 | Y | CD1 | 64.6 | 7.2 | 24.4 | 11 | A |
| 129 | Y | CE1 | 65.9 | 7.5 | 23.8 | 13 | A |
| 129 | Y | CD2 | 64.0 | 6.1 | 22.3 | 12 | A |
| 129 | Y | CE2 | 65.2 | 6.4 | 21.8 | 12 | A |
| 129 | Y | CZ | 66.2 | 7.0 | 22.5 | 12 | A |
| 129 | Y | OH | 67.4 | 7.3 | 21.9 | 14 | A |
| 129 | Y | C | 61.5 | 8.3 | 22.9 | 12 | A |
| 129 | Y | O | 62.2 | 9.3 | 22.8 | 12 | A |
| 130 | Q | N | 60.7 | 7.8 | 22.0 | 11 | A |
| 130 | Q | CA | 60.6 | 8.4 | 20.7 | 11 | A |
| 130 | Q | CB | 59.8 | 7.5 | 19.7 | 12 | A |
| 130 | Q | CG | 60.5 | 6.1 | 19.5 | 14 | A |
| 130 | Q | CD | 59.7 | 5.3 | 18.5 | 12 | A |
| 130 | Q | OE1 | 59.7 | 5.5 | 17.3 | 13 | A |
| 130 | Q | NE2 | 58.9 | 4.4 | 19.0 | 14 | A |
| 130 | Q | C | 60.0 | 9.8 | 20.7 | 11 | A |
| 130 | Q | O | 60.5 | 10.7 | 19.9 | 11 | A |
| 131 | I | N | 59.0 | 10.1 | 21.5 | 11 | A |
| 131 | I | CA | 58.4 | 11.4 | 21.6 | 11 | A |
| 131 | I | CB | 57.3 | 11.4 | 22.6 | 10 | A |
| 131 | I | CG2 | 56.8 | 12.9 | 22.9 | 12 | A |
| 131 | I | CG1 | 56.1 | 10.6 | 22.2 | 12 | A |
| 131 | I | CD1 | 55.0 | 10.4 | 23.2 | 13 | A |
| 131 | I | C | 59.5 | 12.4 | 22.0 | 11 | A |
| 131 | I | O | 59.7 | 13.5 | 21.5 | 11 | A |
| 132 | L | N | 60.3 | 12.0 | 23.1 | 11 | A |
| 132 | L | CA | 61.3 | 12.9 | 23.6 | 10 | A |
| 132 | L | CB | 61.8 | 12.4 | 25.0 | 12 | A |
| 132 | L | CG | 60.7 | 12.6 | 26.1 | 12 | A |
| 132 | L | CD1 | 61.1 | 11.8 | 27.3 | 13 | A |
| 132 | L | CD2 | 60.5 | 14.0 | 26.4 | 12 | A |
| 132 | L | C | 62.5 | 13.0 | 22.6 | 11 | A |
| 132 | L | O | 63.1 | 14.1 | 22.6 | 11 | A |
| 133 | R | N | 62.8 | 11.9 | 21.9 | 10 | A |
| 133 | R | CA | 63.9 | 12.0 | 20.9 | 11 | A |
| 133 | R | CB | 64.1 | 10.6 | 20.3 | 11 | A |
| 133 | R | CG | 65.3 | 10.5 | 19.3 | 10 | A |
| 133 | R | CD | 65.6 | 9.0 | 19.0 | 13 | A |
| 133 | R | NE | 66.8 | 8.9 | 18.1 | 13 | A |
| 133 | R | CZ | 66.7 | 8.6 | 16.8 | 15 | A |
| 133 | R | NH1 | 65.5 | 8.4 | 16.2 | 18 | A |
| 133 | R | NH2 | 67.8 | 8.4 | 16.1 | 17 | A |
| 133 | R | C | 63.6 | 13.0 | 19.8 | 10 | A |
| 133 | R | O | 64.4 | 13.8 | 19.5 | 11 | A |
| 134 | G | N | 62.3 | 13.0 | 19.4 | 11 | A |
| 134 | G | CA | 61.9 | 13.9 | 18.3 | 11 | A |
| 134 | G | C | 61.8 | 15.3 | 18.9 | 10 | A |
| 134 | G | O | 62.2 | 16.3 | 18.2 | 11 | A |
| 135 | L | N | 61.3 | 15.5 | 20.1 | 10 | A |
| 135 | L | CA | 61.2 | 16.8 | 20.8 | 10 | A |
| 135 | L | CB | 60.5 | 16.7 | 22.1 | 11 | A |
| 135 | L | CG | 60.0 | 18.0 | 22.7 | 10 | A |
| 135 | L | CD1 | 59.1 | 18.8 | 21.8 | 12 | A |
| 135 | L | CD2 | 59.4 | 17.8 | 24.1 | 12 | A |
| 135 | L | C | 62.6 | 17.4 | 21.0 | 11 | A |
| 135 | L | O | 62.7 | 18.6 | 20.9 | 10 | A |
| 136 | K | N | 63.6 | 16.6 | 21.3 | 10 | A |
| 136 | K | CA | 65.0 | 17.1 | 21.5 | 10 | A |
| 136 | K | CB | 66.0 | 16.0 | 21.8 | 10 | A |
| 136 | K | CG | 67.4 | 16.5 | 21.9 | 11 | A |
| 136 | K | CD | 68.4 | 15.3 | 22.2 | 11 | A |
| 136 | K | CE | 69.8 | 15.9 | 22.2 | 12 | A |
| 136 | K | NZ | 70.9 | 14.8 | 22.3 | 14 | A |
| 136 | K | C | 65.4 | 17.8 | 20.2 | 10 | A |
| 136 | K | O | 66.0 | 18.9 | 20.3 | 11 | A |
| 137 | Y | N | 65.2 | 17.2 | 19.1 | 11 | A |
| 137 | Y | CA | 65.5 | 17.8 | 17.8 | 10 | A |
| 137 | Y | CB | 65.3 | 16.8 | 16.6 | 11 | A |
| 137 | Y | CG | 65.7 | 17.3 | 15.3 | 11 | A |
| 137 | Y | CD1 | 64.8 | 18.0 | 14.5 | 13 | A |
| 137 | Y | CE1 | 65.1 | 18.4 | 13.2 | 14 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 137 | Y | CD2 | 66.9 | 17.0 | 14.7 | 11 | A |
| 137 | Y | CE2 | 67.3 | 17.4 | 13.4 | 13 | A |
| 137 | Y | CZ | 66.4 | 18.1 | 12.7 | 14 | A |
| 137 | Y | OH | 66.7 | 18.5 | 11.4 | 16 | A |
| 137 | Y | C | 64.7 | 19.1 | 17.5 | 12 | A |
| 137 | Y | O | 65.3 | 20.1 | 17.1 | 12 | A |
| 138 | I | N | 63.4 | 19.1 | 17.8 | 10 | A |
| 138 | I | CA | 62.6 | 20.3 | 17.6 | 10 | A |
| 138 | I | CB | 61.1 | 20.0 | 18.0 | 10 | A |
| 138 | I | CG2 | 60.3 | 21.3 | 17.9 | 11 | A |
| 138 | I | CG1 | 60.6 | 18.9 | 17.1 | 11 | A |
| 138 | I | CD1 | 59.2 | 18.4 | 17.5 | 12 | A |
| 138 | I | C | 63.1 | 21.4 | 18.5 | 12 | A |
| 138 | I | O | 63.4 | 22.5 | 18.0 | 11 | A |
| 139 | H | N | 63.3 | 21.2 | 19.8 | 11 | A |
| 139 | H | CA | 63.8 | 22.2 | 20.7 | 11 | A |
| 139 | H | CB | 63.7 | 21.7 | 22.1 | 12 | A |
| 139 | H | CG | 62.3 | 21.7 | 22.7 | 10 | A |
| 139 | H | CD2 | 61.2 | 22.1 | 22.1 | 11 | A |
| 139 | H | ND1 | 62.0 | 21.4 | 24.0 | 10 | A |
| 139 | H | CE1 | 60.7 | 21.5 | 24.2 | 12 | A |
| 139 | H | NE2 | 60.2 | 21.9 | 23.0 | 11 | A |
| 139 | H | C | 65.2 | 22.7 | 20.3 | 11 | A |
| 139 | H | O | 65.6 | 23.9 | 20.6 | 12 | A |
| 140 | S | N | 66.1 | 21.8 | 19.8 | 11 | A |
| 140 | S | CA | 67.4 | 22.2 | 19.4 | 12 | A |
| 140 | S | CB | 68.3 | 20.9 | 19.1 | 12 | A |
| 140 | S | OG | 68.0 | 20.5 | 17.8 | 12 | A |
| 140 | S | C | 67.4 | 23.1 | 18.2 | 14 | A |
| 140 | S | O | 68.4 | 23.8 | 18.0 | 15 | A |
| 141 | A | N | 66.3 | 23.2 | 17.5 | 13 | A |
| 141 | A | CA | 66.2 | 24.1 | 16.3 | 13 | A |
| 141 | A | CB | 65.3 | 23.4 | 15.2 | 14 | A |
| 141 | A | C | 65.5 | 25.4 | 16.8 | 13 | A |
| 141 | A | O | 65.2 | 26.2 | 15.9 | 14 | A |
| 142 | N | N | 65.4 | 25.6 | 18.1 | 13 | A |
| 142 | N | CA | 64.8 | 26.8 | 18.7 | 14 | A |
| 142 | N | CB | 65.5 | 28.0 | 18.2 | 16 | A |
| 142 | N | CG | 65.3 | 29.2 | 19.1 | 18 | A |
| 142 | N | OD1 | 65.3 | 29.1 | 20.4 | 19 | A |
| 142 | N | ND2 | 65.1 | 30.4 | 18.6 | 19 | A |
| 142 | N | C | 63.3 | 26.9 | 18.3 | 13 | A |
| 142 | N | O | 62.7 | 28.0 | 18.2 | 14 | A |
| 143 | V | N | 62.6 | 25.7 | 18.1 | 12 | A |
| 143 | V | CA | 61.2 | 25.7 | 17.8 | 12 | A |
| 143 | V | CB | 61.0 | 24.9 | 16.4 | 12 | A |
| 143 | V | CG1 | 59.5 | 24.7 | 16.1 | 13 | A |
| 143 | V | CG2 | 61.7 | 25.7 | 15.3 | 14 | A |
| 143 | V | C | 60.4 | 25.0 | 18.9 | 12 | A |
| 143 | V | O | 60.9 | 24.1 | 19.6 | 12 | A |
| 144 | L | N | 59.1 | 25.4 | 19.0 | 12 | A |
| 144 | L | CA | 58.2 | 24.9 | 19.9 | 13 | A |
| 144 | L | CB | 57.7 | 26.0 | 20.8 | 13 | A |
| 144 | L | CG | 58.7 | 26.9 | 21.5 | 13 | A |
| 144 | L | CD1 | 58.0 | 28.0 | 22.2 | 16 | A |
| 144 | L | CD2 | 59.5 | 26.1 | 22.5 | 16 | A |
| 144 | L | C | 57.0 | 24.3 | 19.1 | 12 | A |
| 144 | L | O | 56.5 | 24.9 | 18.2 | 13 | A |
| 145 | H | N | 56.6 | 23.1 | 19.5 | 11 | A |
| 145 | H | CA | 55.4 | 22.4 | 18.8 | 11 | A |
| 145 | H | CB | 55.4 | 20.9 | 19.0 | 10 | A |
| 145 | H | CG | 54.3 | 20.2 | 18.3 | 12 | A |
| 145 | H | CD2 | 54.4 | 19.4 | 17.1 | 11 | A |
| 145 | H | ND1 | 53.0 | 20.2 | 18.6 | 12 | A |
| 145 | H | CE1 | 52.3 | 19.5 | 17.7 | 12 | A |
| 145 | H | NE2 | 53.1 | 19.0 | 16.8 | 12 | A |
| 145 | H | C | 54.1 | 23.1 | 19.2 | 12 | A |
| 145 | H | O | 53.3 | 23.5 | 18.3 | 12 | A |
| 146 | R | N | 53.9 | 23.2 | 20.5 | 11 | A |
| 146 | R | CA | 52.7 | 23.9 | 21.1 | 11 | A |
| 146 | R | CB | 52.6 | 25.3 | 20.6 | 12 | A |
| 146 | R | CG | 53.9 | 26.1 | 20.9 | 14 | A |
| 146 | R | CD | 53.9 | 27.5 | 20.3 | 16 | A |
| 146 | R | NE | 53.1 | 28.5 | 21.1 | 18 | A |
| 146 | R | CZ | 52.0 | 29.1 | 20.6 | 20 | A |
| 146 | R | NH1 | 51.6 | 28.9 | 19.4 | 19 | A |
| 146 | R | NH2 | 51.4 | 30.0 | 21.4 | 20 | A |
| 146 | R | C | 51.4 | 23.2 | 21.0 | 12 | A |
| 146 | R | O | 50.4 | 23.7 | 21.4 | 15 | A |
| 147 | D | N | 51.3 | 22.0 | 20.4 | 11 | A |
| 147 | D | CA | 50.0 | 21.3 | 20.4 | 12 | A |
| 147 | D | CB | 49.2 | 21.7 | 19.1 | 13 | A |
| 147 | D | CG | 47.7 | 21.3 | 19.3 | 13 | A |
| 147 | D | OD1 | 47.2 | 21.2 | 20.4 | 15 | A |
| 147 | D | OD2 | 47.0 | 21.1 | 18.2 | 18 | A |
| 147 | D | C | 50.2 | 19.7 | 20.4 | 12 | A |
| 147 | D | O | 49.6 | 19.0 | 19.7 | 13 | A |
| 148 | L | N | 51.2 | 19.3 | 21.3 | 11 | A |
| 148 | L | CA | 51.4 | 17.9 | 21.4 | 11 | A |
| 148 | L | CB | 52.7 | 17.6 | 22.2 | 11 | A |
| 148 | L | CG | 54.0 | 18.1 | 21.5 | 12 | A |
| 148 | L | CD1 | 55.2 | 18.0 | 22.5 | 12 | A |
| 148 | L | CD2 | 54.3 | 17.3 | 20.3 | 14 | A |
| 148 | L | C | 50.2 | 17.2 | 22.2 | 11 | A |
| 148 | L | O | 49.8 | 17.7 | 23.2 | 12 | A |
| 149 | K | N | 49.7 | 16.1 | 21.6 | 12 | A |
| 149 | K | CA | 48.6 | 15.4 | 22.1 | 13 | A |
| 149 | K | CB | 47.3 | 16.1 | 21.9 | 15 | A |
| 149 | K | CG | 47.0 | 16.5 | 20.5 | 14 | A |
| 149 | K | CD | 45.7 | 17.4 | 20.4 | 16 | A |
| 149 | K | CE | 45.4 | 17.9 | 19.0 | 17 | A |
| 149 | K | NZ | 44.1 | 18.6 | 19.0 | 19 | A |
| 149 | K | C | 48.6 | 14.0 | 21.4 | 13 | A |
| 149 | K | O | 49.2 | 13.9 | 20.4 | 13 | A |
| 150 | P | N | 47.9 | 13.0 | 21.9 | 13 | A |
| 150 | P | CD | 47.1 | 13.0 | 23.2 | 14 | A |
| 150 | P | CA | 47.8 | 11.7 | 21.3 | 14 | A |
| 150 | P | CB | 46.8 | 10.9 | 22.1 | 14 | A |
| 150 | P | CG | 47.0 | 11.5 | 23.5 | 14 | A |
| 150 | P | C | 47.5 | 11.7 | 19.8 | 15 | A |
| 150 | P | O | 48.1 | 10.9 | 19.0 | 15 | A |
| 151 | S | N | 46.6 | 12.5 | 19.3 | 15 | A |
| 151 | S | CA | 46.2 | 12.5 | 17.9 | 16 | A |
| 151 | S | CB | 44.9 | 13.2 | 17.7 | 17 | A |
| 151 | S | OG | 45.0 | 14.6 | 18.0 | 18 | A |
| 151 | S | C | 47.3 | 13.0 | 17.0 | 16 | A |
| 151 | S | O | 47.2 | 12.9 | 15.8 | 17 | A |
| 152 | N | N | 48.3 | 13.7 | 17.5 | 15 | A |
| 152 | N | CA | 49.4 | 14.2 | 16.7 | 15 | A |
| 152 | N | CB | 49.7 | 15.7 | 17.2 | 15 | A |
| 152 | N | CG | 48.7 | 16.7 | 16.7 | 17 | A |
| 152 | N | OD1 | 48.6 | 17.8 | 17.2 | 18 | A |
| 152 | N | ND2 | 48.0 | 16.3 | 15.7 | 15 | A |
| 152 | N | C | 50.6 | 13.3 | 16.8 | 15 | A |
| 152 | N | O | 51.7 | 13.8 | 16.4 | 15 | A |
| 153 | L | N | 50.5 | 12.1 | 17.3 | 13 | A |
| 153 | L | CA | 51.6 | 11.1 | 17.4 | 14 | A |
| 153 | L | CB | 51.8 | 10.7 | 18.8 | 14 | A |
| 153 | L | CG | 52.1 | 11.9 | 19.8 | 12 | A |
| 153 | L | CD1 | 52.2 | 11.3 | 21.2 | 14 | A |
| 153 | L | CD2 | 53.4 | 12.6 | 19.4 | 13 | A |
| 153 | L | C | 51.2 | 9.9 | 16.5 | 15 | A |
| 153 | L | O | 50.4 | 9.1 | 16.9 | 14 | A |
| 154 | L | N | 51.8 | 9.9 | 15.3 | 15 | A |
| 154 | L | CA | 51.5 | 8.8 | 14.4 | 15 | A |
| 154 | L | CB | 51.7 | 9.3 | 12.9 | 15 | A |
| 154 | L | CG | 51.1 | 10.6 | 12.6 | 16 | A |
| 154 | L | CD1 | 51.5 | 11.0 | 11.2 | 18 | A |
| 154 | L | CD2 | 49.6 | 10.6 | 12.8 | 20 | A |
| 154 | L | C | 52.3 | 7.5 | 14.6 | 15 | A |
| 154 | L | O | 53.4 | 7.6 | 15.0 | 15 | A |
| 155 | L | N | 51.7 | 6.4 | 14.4 | 17 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| 155 | L | CA | 52.3 | 5.1 | 14.6 | 18 | A |
|---|---|---|---|---|---|---|---|
| 155 | L | CB | 51.8 | 4.5 | 15.9 | 20 | A |
| 155 | L | CG | 51.7 | 5.3 | 17.2 | 22 | A |
| 155 | L | CD1 | 50.8 | 4.7 | 18.2 | 22 | A |
| 155 | L | CD2 | 53.0 | 5.7 | 17.7 | 22 | A |
| 155 | L | C | 52.1 | 4.0 | 13.5 | 20 | A |
| 155 | L | O | 51.1 | 4.1 | 12.8 | 19 | A |
| 156 | N | N | 53.0 | 3.1 | 13.4 | 21 | A |
| 156 | N | CA | 52.8 | 2.0 | 12.5 | 23 | A |
| 156 | N | CB | 53.9 | 2.1 | 11.3 | 23 | A |
| 156 | N | CG | 55.3 | 2.0 | 11.8 | 23 | A |
| 156 | N | OD1 | 55.6 | 1.4 | 12.9 | 23 | A |
| 156 | N | ND2 | 56.2 | 2.6 | 11.0 | 26 | A |
| 156 | N | C | 53.0 | 0.6 | 13.2 | 23 | A |
| 156 | N | O | 53.2 | 0.6 | 14.4 | 22 | A |
| 157 | T | N | 52.8 | -0.5 | 12.5 | 26 | A |
| 157 | T | CA | 52.9 | -1.8 | 13.2 | 28 | A |
| 157 | T | CB | 52.6 | -3.0 | 12.2 | 30 | A |
| 157 | T | OG1 | 53.1 | -2.6 | 10.9 | 33 | A |
| 157 | T | CG2 | 51.1 | -3.2 | 12.1 | 32 | A |
| 157 | T | C | 54.3 | -2.1 | 13.8 | 27 | A |
| 157 | T | O | 54.4 | -2.8 | 14.8 | 28 | A |
| 158 | T | N | 55.4 | -1.6 | 13.2 | 25 | A |
| 158 | T | CA | 56.7 | -1.8 | 13.8 | 24 | A |
| 158 | T | CB | 57.8 | -1.6 | 12.7 | 26 | A |
| 158 | T | OG1 | 57.5 | -0.3 | 12.0 | 30 | A |
| 158 | T | CG2 | 57.7 | -2.7 | 11.6 | 27 | A |
| 158 | T | C | 56.9 | -0.9 | 15.0 | 22 | A |
| 158 | T | O | 58.1 | -0.8 | 15.5 | 22 | A |
| 159 | C | N | 55.9 | -0.2 | 15.4 | 20 | A |
| 159 | C | CA | 56.0 | 0.7 | 16.6 | 19 | A |
| 159 | C | CB | 56.4 | -0.0 | 17.8 | 19 | A |
| 159 | C | SG | 55.2 | -1.2 | 18.5 | 22 | A |
| 159 | C | C | 56.8 | 2.0 | 16.4 | 17 | A |
| 159 | C | O | 57.2 | 2.6 | 17.3 | 17 | A |
| 160 | D | N | 57.0 | 2.4 | 15.1 | 17 | A |
| 160 | D | CA | 57.8 | 3.6 | 14.9 | 16 | A |
| 160 | D | CB | 58.2 | 3.7 | 13.4 | 18 | A |
| 160 | D | CG | 59.2 | 2.7 | 13.0 | 20 | A |
| 160 | D | OD1 | 60.2 | 2.5 | 13.7 | 21 | A |
| 160 | D | OD2 | 59.0 | 2.0 | 11.9 | 27 | A |
| 160 | D | C | 56.8 | 4.7 | 15.2 | 15 | A |
| 160 | D | O | 55.6 | 4.6 | 14.9 | 17 | A |
| 161 | L | N | 57.3 | 5.8 | 15.8 | 13 | A |
| 161 | L | CA | 56.4 | 6.9 | 16.1 | 13 | A |
| 161 | L | CB | 56.4 | 7.1 | 17.7 | 13 | A |
| 161 | L | CG | 55.6 | 8.2 | 18.3 | 13 | A |
| 161 | L | CD1 | 55.1 | 7.9 | 19.7 | 14 | A |
| 161 | L | CD2 | 56.4 | 9.5 | 18.3 | 13 | A |
| 161 | L | C | 56.9 | 8.2 | 15.5 | 14 | A |
| 161 | L | O | 58.1 | 8.5 | 15.5 | 14 | A |
| 162 | K | N | 56.0 | 9.0 | 14.9 | 14 | A |
| 162 | K | CA | 56.4 | 10.3 | 14.3 | 14 | A |
| 162 | K | CB | 56.3 | 10.2 | 12.7 | 15 | A |
| 162 | K | CG | 57.4 | 9.3 | 12.1 | 17 | A |
| 162 | K | CD | 57.2 | 9.2 | 10.6 | 19 | A |
| 162 | K | CE | 58.2 | 8.2 | 10.0 | 21 | A |
| 162 | K | NZ | 59.6 | 8.6 | 10.1 | 25 | A |
| 162 | K | C | 55.4 | 11.4 | 14.7 | 13 | A |
| 162 | K | O | 54.2 | 11.3 | 14.7 | 14 | A |
| 163 | I | N | 56.0 | 12.5 | 15.1 | 13 | A |
| 163 | I | CA | 55.3 | 13.7 | 15.6 | 13 | A |
| 163 | I | CB | 56.2 | 14.6 | 16.4 | 12 | A |
| 163 | I | CG2 | 55.4 | 15.9 | 16.8 | 13 | A |
| 163 | I | CG1 | 56.6 | 13.9 | 17.7 | 12 | A |
| 163 | I | CD1 | 57.8 | 14.6 | 18.4 | 12 | A |
| 163 | I | C | 54.8 | 14.5 | 14.3 | 14 | A |
| 163 | I | O | 55.6 | 14.7 | 13.4 | 13 | A |
| 164 | C | N | 53.5 | 14.9 | 14.3 | 13 | A |
| 164 | C | CA | 53.0 | 15.6 | 13.2 | 15 | A |
| 164 | C | CB | 52.1 | 14.7 | 12.3 | 16 | A |
| 164 | C | SG | 50.5 | 14.3 | 13.1 | 18 | A |
| 164 | C | C | 52.2 | 16.8 | 13.6 | 15 | A |
| 164 | C | O | 52.1 | 17.1 | 14.8 | 14 | A |
| 165 | D | N | 51.7 | 17.6 | 12.6 | 16 | A |
| 165 | D | CA | 50.8 | 18.8 | 12.8 | 18 | A |
| 165 | D | CB | 49.6 | 18.4 | 13.6 | 21 | A |
| 165 | D | CG | 48.5 | 17.8 | 12.7 | 26 | A |
| 165 | D | OD1 | 48.8 | 16.9 | 12.0 | 29 | A |
| 165 | D | OD2 | 47.3 | 18.3 | 12.8 | 30 | A |
| 165 | D | C | 51.5 | 20.0 | 13.5 | 17 | A |
| 165 | D | O | 51.3 | 20.2 | 14.7 | 18 | A |
| 166 | F | N | 52.4 | 20.7 | 12.8 | 16 | A |
| 166 | F | CA | 53.1 | 21.8 | 13.3 | 16 | A |
| 166 | F | CB | 54.5 | 21.9 | 12.7 | 17 | A |
| 166 | F | CG | 55.4 | 20.8 | 13.3 | 16 | A |
| 166 | F | CD1 | 55.2 | 19.4 | 13.1 | 17 | A |
| 166 | F | CD2 | 56.5 | 21.2 | 14.2 | 16 | A |
| 166 | F | CE1 | 56.0 | 18.5 | 13.6 | 17 | A |
| 166 | F | CE2 | 57.3 | 20.2 | 14.7 | 16 | A |
| 166 | F | CZ | 57.1 | 18.9 | 14.4 | 16 | A |
| 166 | F | C | 52.4 | 23.2 | 12.9 | 16 | A |
| 166 | F | O | 53.1 | 24.2 | 12.8 | 17 | A |
| 167 | G | N | 51.1 | 23.2 | 12.8 | 16 | A |
| 167 | G | CA | 50.4 | 24.4 | 12.5 | 17 | A |
| 167 | G | C | 50.4 | 25.5 | 13.5 | 18 | A |
| 167 | G | O | 50.3 | 26.7 | 13.2 | 18 | A |
| 168 | L | N | 50.6 | 25.1 | 14.8 | 16 | A |
| 168 | L | CA | 50.6 | 26.1 | 15.9 | 15 | A |
| 168 | L | CB | 49.7 | 25.6 | 17.0 | 16 | A |
| 168 | L | CG | 48.2 | 25.5 | 16.7 | 19 | A |
| 168 | L | CD1 | 47.5 | 25.1 | 18.0 | 21 | A |
| 168 | L | CD2 | 47.7 | 26.9 | 16.2 | 19 | A |
| 168 | L | C | 52.0 | 26.3 | 16.4 | 13 | A |
| 168 | L | O | 52.2 | 26.9 | 17.4 | 14 | A |
| 169 | A | N | 53.0 | 25.7 | 15.7 | 14 | A |
| 169 | A | CA | 54.4 | 25.9 | 16.1 | 16 | A |
| 169 | A | CB | 55.3 | 24.9 | 15.3 | 16 | A |
| 169 | A | C | 54.9 | 27.3 | 16.0 | 18 | A |
| 169 | A | O | 54.5 | 28.1 | 15.1 | 20 | A |
| 170 | R | N | 55.9 | 27.6 | 16.8 | 17 | A |
| 170 | R | CA | 56.5 | 29.0 | 16.8 | 16 | A |
| 170 | R | CB | 55.8 | 29.9 | 17.9 | 18 | A |
| 170 | R | CG | 54.3 | 30.0 | 17.7 | 21 | A |
| 170 | R | CD | 54.0 | 30.8 | 16.4 | 25 | A |
| 170 | R | NE | 54.4 | 32.2 | 16.5 | 29 | A |
| 170 | R | CZ | 53.8 | 33.1 | 17.1 | 31 | A |
| 170 | R | NH1 | 52.6 | 32.8 | 17.8 | 34 | A |
| 170 | R | NH2 | 54.2 | 34.4 | 17.2 | 32 | A |
| 170 | R | C | 58.0 | 28.9 | 17.2 | 17 | A |
| 170 | R | O | 58.5 | 27.9 | 17.7 | 15 | A |
| 171 | V | N | 58.7 | 30.0 | 16.9 | 16 | A |
| 171 | V | CA | 60.1 | 30.1 | 17.2 | 15 | A |
| 171 | V | CB | 60.9 | 31.1 | 16.4 | 15 | A |
| 171 | V | CG1 | 62.3 | 31.4 | 16.9 | 16 | A |
| 171 | V | CG2 | 61.0 | 30.6 | 14.9 | 16 | A |
| 171 | V | C | 60.1 | 30.5 | 18.7 | 15 | A |
| 171 | V | O | 59.4 | 31.4 | 19.1 | 18 | A |
| 172 | A | N | 60.9 | 29.8 | 19.5 | 16 | A |
| 172 | A | CA | 60.9 | 30.1 | 21.0 | 16 | A |
| 172 | A | CB | 61.9 | 29.2 | 21.7 | 16 | A |
| 172 | A | C | 61.3 | 31.6 | 21.2 | 17 | A |
| 172 | A | O | 62.1 | 32.2 | 20.5 | 19 | A |
| 173 | D | N | 60.7 | 32.1 | 22.3 | 17 | A |
| 173 | D | CA | 60.9 | 33.5 | 22.6 | 19 | A |
| 173 | D | CB | 60.0 | 34.4 | 21.8 | 20 | A |
| 173 | D | CG | 60.4 | 35.9 | 21.9 | 22 | A |
| 173 | D | OD1 | 61.4 | 36.3 | 22.6 | 24 | A |
| 173 | D | OD2 | 59.6 | 36.7 | 21.3 | 25 | A |
| 173 | D | C | 60.7 | 33.7 | 24.1 | 19 | A |
| 173 | D | O | 59.7 | 34.4 | 24.5 | 18 | A |
| 174 | P | N | 61.5 | 33.2 | 25.0 | 20 | A |

TABLE 1-continued

Structural Coordinates of crystalline Ah₆-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 174 | P | CD | 62.7 | 32.3 | 24.6 | 21 | A |
| 174 | P | CA | 61.4 | 33.3 | 26.4 | 22 | A |
| 174 | P | CB | 62.5 | 32.4 | 27.0 | 23 | A |
| 174 | P | CG | 63.5 | 32.4 | 25.9 | 21 | A |
| 174 | P | C | 61.4 | 34.7 | 27.0 | 23 | A |
| 174 | P | O | 60.8 | 35.0 | 28.0 | 25 | A |
| 175 | D | N | 62.1 | 35.6 | 26.3 | 24 | A |
| 175 | D | CA | 62.2 | 37.0 | 26.8 | 26 | A |
| 175 | D | CB | 63.3 | 37.7 | 26.1 | 29 | A |
| 175 | D | CG | 64.7 | 37.2 | 26.4 | 32 | A |
| 175 | D | OD1 | 64.9 | 37.0 | 27.6 | 35 | A |
| 175 | D | OD2 | 65.5 | 36.9 | 25.5 | 37 | A |
| 175 | D | C | 60.8 | 37.8 | 26.6 | 26 | A |
| 175 | D | O | 60.7 | 38.8 | 27.2 | 26 | A |
| 176 | H | N | 59.9 | 37.2 | 25.8 | 24 | A |
| 176 | H | CA | 58.6 | 37.9 | 25.6 | 24 | A |
| 176 | H | CB | 58.6 | 38.4 | 24.1 | 27 | A |
| 176 | H | CG | 59.6 | 39.4 | 23.8 | 28 | A |
| 176 | H | CD2 | 59.6 | 40.7 | 23.5 | 30 | A |
| 176 | H | ND1 | 61.0 | 39.0 | 23.7 | 30 | A |
| 176 | H | CE1 | 61.7 | 40.1 | 23.3 | 30 | A |
| 176 | H | NE2 | 60.9 | 41.1 | 23.2 | 31 | A |
| 176 | H | C | 57.5 | 37.0 | 25.8 | 22 | A |
| 176 | H | O | 56.4 | 37.0 | 25.2 | 23 | A |
| 177 | D | N | 57.7 | 36.1 | 26.8 | 21 | A |
| 177 | D | CA | 56.7 | 35.1 | 27.2 | 21 | A |
| 177 | D | CB | 57.4 | 33.9 | 27.8 | 20 | A |
| 177 | D | CG | 56.4 | 32.7 | 28.2 | 20 | A |
| 177 | D | OD1 | 56.1 | 32.5 | 29.4 | 21 | A |
| 177 | D | OD2 | 56.0 | 32.0 | 27.2 | 24 | A |
| 177 | D | C | 55.6 | 35.6 | 28.1 | 21 | A |
| 177 | D | O | 54.5 | 35.0 | 28.2 | 19 | A |
| 178 | H | N | 55.9 | 36.6 | 28.9 | 22 | A |
| 178 | H | CA | 54.9 | 37.2 | 29.8 | 23 | A |
| 178 | H | CB | 55.6 | 38.2 | 30.8 | 27 | A |
| 178 | H | CG | 56.5 | 39.1 | 30.1 | 32 | A |
| 178 | H | CD2 | 56.6 | 40.5 | 30.1 | 34 | A |
| 178 | H | ND1 | 57.5 | 38.7 | 29.2 | 34 | A |
| 178 | H | CE1 | 58.2 | 39.8 | 28.8 | 35 | A |
| 178 | H | NE2 | 57.7 | 40.8 | 29.3 | 35 | A |
| 178 | H | C | 53.6 | 37.8 | 29.3 | 22 | A |
| 178 | H | O | 53.7 | 38.6 | 28.3 | 23 | A |
| 179 | T | N | 52.5 | 37.5 | 29.9 | 20 | A |
| 179 | T | CA | 51.2 | 38.1 | 29.6 | 19 | A |
| 179 | T | CB | 50.5 | 37.2 | 28.4 | 20 | A |
| 179 | T | OG1 | 49.3 | 37.9 | 28.0 | 23 | A |
| 179 | T | CG2 | 50.2 | 35.8 | 28.9 | 19 | A |
| 179 | T | C | 50.3 | 38.0 | 30.8 | 18 | A |
| 179 | T | O | 50.8 | 37.6 | 31.9 | 18 | A |
| 180 | G | N | 49.1 | 38.6 | 30.7 | 17 | A |
| 180 | G | CA | 48.2 | 38.6 | 31.8 | 18 | A |
| 180 | G | C | 47.5 | 37.4 | 32.2 | 19 | A |
| 180 | G | O | 47.7 | 36.3 | 31.6 | 21 | A |
| 181 | F | N | 46.7 | 37.5 | 33.3 | 16 | A |
| 181 | F | CA | 46.0 | 36.4 | 33.9 | 15 | A |
| 181 | F | CB | 45.5 | 36.8 | 35.3 | 14 | A |
| 181 | F | CG | 44.6 | 35.9 | 36.1 | 14 | A |
| 181 | F | CD1 | 45.0 | 34.6 | 36.3 | 17 | A |
| 181 | F | CD2 | 43.4 | 36.3 | 36.6 | 15 | A |
| 181 | F | CE1 | 44.2 | 33.7 | 37.1 | 18 | A |
| 181 | F | CE2 | 42.6 | 35.5 | 37.4 | 16 | A |
| 181 | F | CZ | 43.0 | 34.2 | 37.6 | 16 | A |
| 181 | F | C | 44.7 | 36.1 | 33.0 | 16 | A |
| 181 | F | O | 44.0 | 37.0 | 32.6 | 17 | A |
| 182 | L | N | 44.5 | 34.8 | 32.8 | 15 | A |
| 182 | L | CA | 43.3 | 34.3 | 32.0 | 16 | A |
| 182 | L | CB | 42.0 | 34.6 | 32.8 | 18 | A |
| 182 | L | CG | 41.9 | 34.0 | 34.2 | 17 | A |
| 182 | L | CD1 | 40.5 | 34.3 | 34.8 | 19 | A |
| 182 | L | CD2 | 42.1 | 32.4 | 34.1 | 19 | A |
| 182 | L | C | 43.3 | 34.9 | 30.6 | 18 | A |
| 182 | L | O | 42.2 | 35.3 | 30.1 | 20 | A |
| 183 | T | N | 44.4 | 34.9 | 29.9 | 20 | A |
| 183 | T | CA | 44.5 | 35.4 | 28.5 | 23 | A |
| 183 | T | CB | 46.0 | 35.9 | 28.2 | 25 | A |
| 183 | T | OG1 | 46.3 | 37.0 | 29.1 | 27 | A |
| 183 | T | CG2 | 46.1 | 36.3 | 26.7 | 26 | A |
| 183 | T | C | 44.2 | 34.2 | 27.6 | 25 | A |
| 183 | T | O | 44.6 | 33.1 | 27.8 | 27 | A |
| 184 | E | N | 43.4 | 34.5 | 26.6 | 27 | A |
| 184 | E | CA | 43.0 | 33.5 | 25.6 | 29 | A |
| 184 | E | CB | 42.2 | 34.2 | 24.5 | 32 | A |
| 184 | E | CG | 41.6 | 33.2 | 23.4 | 37 | A |
| 184 | E | CD | 40.8 | 33.8 | 22.4 | 40 | A |
| 184 | E | OE1 | 39.8 | 34.5 | 22.7 | 41 | A |
| 184 | E | OE2 | 41.1 | 33.7 | 21.2 | 42 | A |
| 184 | E | C | 44.2 | 32.7 | 25.0 | 28 | A |
| 184 | E | O | 45.2 | 33.3 | 24.7 | 29 | A |
| 185 | Y | N | 43.9 | 31.4 | 24.7 | 28 | A |
| 185 | Y | CA | 45.0 | 30.6 | 24.2 | 28 | A |
| 185 | Y | CB | 45.6 | 29.7 | 25.3 | 26 | A |
| 185 | Y | CG | 46.9 | 29.1 | 24.9 | 25 | A |
| 185 | Y | CD1 | 48.0 | 30.0 | 24.6 | 25 | A |
| 185 | Y | CE1 | 49.3 | 29.5 | 24.3 | 25 | A |
| 185 | Y | CD2 | 47.2 | 27.8 | 24.8 | 26 | A |
| 185 | Y | CE2 | 48.4 | 27.3 | 24.5 | 25 | A |
| 185 | Y | CZ | 49.5 | 28.1 | 24.2 | 25 | A |
| 185 | Y | OH | 50.7 | 27.6 | 23.9 | 25 | A |
| 185 | Y | C | 44.3 | 29.7 | 23.1 | 28 | A |
| 185 | Y | O | 43.1 | 29.4 | 23.2 | 28 | A |
| 186 | V | N | 45.1 | 29.2 | 22.1 | 27 | A |
| 186 | V | CA | 44.6 | 28.4 | 21.0 | 27 | A |
| 186 | V | CB | 45.1 | 28.9 | 19.7 | 28 | A |
| 186 | V | CG1 | 46.6 | 28.9 | 19.7 | 29 | A |
| 186 | V | CG2 | 44.6 | 28.0 | 18.5 | 29 | A |
| 186 | V | C | 44.8 | 26.9 | 21.1 | 26 | A |
| 186 | V | O | 43.9 | 26.1 | 20.7 | 28 | A |
| 187 | A | N | 45.9 | 26.5 | 21.7 | 24 | A |
| 187 | A | CA | 46.2 | 25.0 | 21.8 | 24 | A |
| 187 | A | CB | 47.6 | 24.8 | 22.4 | 25 | A |
| 187 | A | C | 45.2 | 24.2 | 22.6 | 22 | A |
| 187 | A | O | 44.5 | 24.8 | 23.4 | 23 | A |
| 188 | T | N | 45.1 | 22.9 | 22.3 | 20 | A |
| 188 | T | CA | 44.2 | 22.0 | 23.0 | 17 | A |
| 188 | T | CB | 44.5 | 20.6 | 22.5 | 15 | A |
| 188 | T | OG1 | 44.7 | 20.6 | 21.1 | 15 | A |
| 188 | T | CG2 | 43.3 | 19.7 | 22.9 | 15 | A |
| 188 | T | C | 44.2 | 22.1 | 24.5 | 18 | A |
| 188 | T | O | 45.2 | 21.8 | 25.2 | 17 | A |
| 189 | R | N | 43.0 | 22.4 | 25.0 | 16 | A |
| 189 | R | CA | 42.8 | 22.6 | 26.5 | 15 | A |
| 189 | R | CB | 41.3 | 22.7 | 26.8 | 17 | A |
| 189 | R | CG | 41.0 | 23.2 | 28.2 | 19 | A |
| 189 | R | CD | 39.5 | 23.1 | 28.5 | 22 | A |
| 189 | R | NE | 38.7 | 23.8 | 27.5 | 22 | A |
| 189 | R | CZ | 37.7 | 23.2 | 26.9 | 24 | A |
| 189 | R | NH1 | 37.3 | 22.0 | 27.2 | 25 | A |
| 189 | R | NH2 | 37.0 | 23.9 | 26.0 | 27 | A |
| 189 | R | C | 43.4 | 21.6 | 27.5 | 15 | A |
| 189 | R | O | 44.1 | 21.9 | 28.4 | 15 | A |
| 190 | W | N | 43.0 | 20.3 | 27.3 | 16 | A |
| 190 | W | CA | 43.5 | 19.2 | 28.2 | 15 | A |
| 190 | W | CB | 42.9 | 17.9 | 27.8 | 17 | A |
| 190 | W | CG | 41.4 | 17.8 | 27.9 | 18 | A |
| 190 | W | CD2 | 40.6 | 16.7 | 27.4 | 20 | A |
| 190 | W | CE2 | 39.3 | 17.0 | 27.6 | 19 | A |
| 190 | W | CE3 | 40.9 | 15.5 | 26.7 | 20 | A |
| 190 | W | CD1 | 40.6 | 18.7 | 28.4 | 20 | A |
| 190 | W | NE1 | 39.3 | 18.3 | 28.3 | 20 | A |
| 190 | W | CZ2 | 38.2 | 16.2 | 27.3 | 21 | A |
| 190 | W | CZ3 | 39.9 | 14.7 | 26.3 | 22 | A |
| 190 | W | CH2 | 38.5 | 15.0 | 26.6 | 22 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 190 | W | C | 45.0 | 19.1 | 28.4 | 14 | A |
| 190 | W | O | 45.5 | 18.6 | 29.4 | 14 | A |
| 191 | Y | N | 45.8 | 19.6 | 27.4 | 13 | A |
| 191 | Y | CA | 47.3 | 19.5 | 27.4 | 12 | A |
| 191 | Y | CB | 47.7 | 18.8 | 26.1 | 12 | A |
| 191 | Y | CG | 47.0 | 17.5 | 25.8 | 12 | A |
| 191 | Y | CD1 | 47.4 | 16.3 | 26.3 | 12 | A |
| 191 | Y | CE1 | 46.6 | 15.1 | 26.2 | 13 | A |
| 191 | Y | CD2 | 45.8 | 17.6 | 25.1 | 13 | A |
| 191 | Y | CE2 | 45.0 | 16.4 | 24.9 | 13 | A |
| 191 | Y | CZ | 45.4 | 15.2 | 25.5 | 13 | A |
| 191 | Y | OH | 44.6 | 14.1 | 25.4 | 14 | A |
| 191 | Y | C | 48.0 | 20.8 | 27.7 | 12 | A |
| 191 | Y | O | 49.2 | 20.8 | 27.6 | 11 | A |
| 192 | R | N | 47.3 | 21.8 | 28.2 | 12 | A |
| 192 | R | CA | 47.8 | 23.1 | 28.5 | 12 | A |
| 192 | R | CB | 46.7 | 24.2 | 28.5 | 13 | A |
| 192 | R | CG | 46.1 | 24.5 | 27.1 | 17 | A |
| 192 | R | CD | 45.0 | 25.5 | 27.3 | 17 | A |
| 192 | R | NE | 44.3 | 25.8 | 26.0 | 17 | A |
| 192 | R | CZ | 43.1 | 26.2 | 25.9 | 21 | A |
| 192 | R | NH1 | 42.4 | 26.5 | 27.0 | 22 | A |
| 192 | R | NH2 | 42.5 | 26.4 | 24.8 | 23 | A |
| 192 | R | C | 48.5 | 23.2 | 29.9 | 11 | A |
| 192 | R | O | 47.9 | 22.8 | 30.9 | 12 | A |
| 193 | A | N | 49.7 | 23.7 | 29.9 | 11 | A |
| 193 | A | CA | 50.4 | 23.9 | 31.2 | 10 | A |
| 193 | A | CB | 51.8 | 24.3 | 30.9 | 11 | A |
| 193 | A | C | 49.7 | 24.9 | 32.1 | 12 | A |
| 193 | A | O | 49.1 | 25.9 | 31.6 | 12 | A |
| 194 | P | N | 49.8 | 24.8 | 33.4 | 12 | A |
| 194 | P | CD | 50.7 | 23.9 | 34.2 | 12 | A |
| 194 | P | CA | 49.2 | 25.8 | 34.3 | 12 | A |
| 194 | P | CB | 49.6 | 25.3 | 35.7 | 12 | A |
| 194 | P | CG | 50.9 | 24.6 | 35.5 | 13 | A |
| 194 | P | C | 49.5 | 27.2 | 34.0 | 12 | A |
| 194 | P | O | 48.6 | 28.1 | 34.1 | 13 | A |
| 195 | E | N | 50.8 | 27.5 | 33.7 | 12 | A |
| 195 | E | CA | 51.2 | 28.9 | 33.5 | 12 | A |
| 195 | E | CB | 52.7 | 29.0 | 33.3 | 12 | A |
| 195 | E | CG | 53.2 | 28.2 | 32.0 | 11 | A |
| 195 | E | CD | 53.7 | 26.8 | 32.4 | 14 | A |
| 195 | E | OE1 | 53.2 | 26.3 | 33.4 | 13 | A |
| 195 | E | OE2 | 54.5 | 26.3 | 31.6 | 14 | A |
| 195 | E | C | 50.5 | 29.6 | 32.3 | 13 | A |
| 195 | E | O | 50.4 | 30.8 | 32.2 | 14 | A |
| 196 | I | N | 49.9 | 28.8 | 31.4 | 12 | A |
| 196 | I | CA | 49.2 | 29.4 | 30.2 | 13 | A |
| 196 | I | CB | 48.6 | 28.3 | 29.3 | 13 | A |
| 196 | I | CG2 | 47.7 | 28.9 | 28.3 | 15 | A |
| 196 | I | CG1 | 49.8 | 27.6 | 28.5 | 14 | A |
| 196 | I | CD1 | 50.7 | 28.6 | 27.7 | 16 | A |
| 196 | I | C | 48.0 | 30.2 | 30.7 | 13 | A |
| 196 | I | O | 47.7 | 31.3 | 30.2 | 13 | A |
| 197 | M | N | 47.4 | 29.8 | 31.8 | 12 | A |
| 197 | M | CA | 46.2 | 30.5 | 32.4 | 13 | A |
| 197 | M | CB | 45.3 | 29.4 | 33.1 | 14 | A |
| 197 | M | CG | 44.5 | 28.5 | 32.2 | 15 | A |
| 197 | M | SD | 45.4 | 27.2 | 31.4 | 15 | A |
| 197 | M | CE | 45.6 | 26.0 | 32.7 | 16 | A |
| 197 | M | C | 46.6 | 31.5 | 33.4 | 15 | A |
| 197 | M | O | 45.8 | 32.3 | 33.8 | 15 | A |
| 198 | L | N | 47.9 | 31.5 | 33.8 | 13 | A |
| 198 | L | CA | 48.4 | 32.5 | 34.8 | 14 | A |
| 198 | L | CB | 49.1 | 31.7 | 35.9 | 14 | A |
| 198 | L | CG | 48.4 | 30.6 | 36.7 | 15 | A |
| 198 | L | CD1 | 49.4 | 29.7 | 37.4 | 16 | A |
| 198 | L | CD2 | 47.3 | 31.2 | 37.6 | 16 | A |
| 198 | L | C | 49.2 | 33.6 | 34.3 | 14 | A |
| 198 | L | O | 49.0 | 34.8 | 34.8 | 15 | A |
| 199 | N | N | 50.2 | 33.4 | 33.4 | 15 | A |
| 199 | N | CA | 51.1 | 34.4 | 33.0 | 15 | A |
| 199 | N | CB | 52.1 | 34.7 | 34.1 | 16 | A |
| 199 | N | CG | 52.9 | 33.4 | 34.4 | 19 | A |
| 199 | N | OD1 | 53.2 | 32.6 | 33.6 | 19 | A |
| 199 | N | ND2 | 53.3 | 33.3 | 35.7 | 20 | A |
| 199 | N | C | 51.9 | 34.1 | 31.7 | 16 | A |
| 199 | N | O | 52.9 | 34.9 | 31.4 | 17 | A |
| 200 | S | N | 51.6 | 33.1 | 30.9 | 14 | A |
| 200 | S | CA | 52.4 | 32.7 | 29.8 | 15 | A |
| 200 | S | CB | 53.1 | 31.4 | 30.1 | 15 | A |
| 200 | S | OG | 53.8 | 30.9 | 28.9 | 17 | A |
| 200 | S | C | 51.7 | 32.7 | 28.4 | 15 | A |
| 200 | S | O | 50.6 | 32.2 | 28.3 | 16 | A |
| 201 | K | N | 52.4 | 33.1 | 27.4 | 17 | A |
| 201 | K | CA | 51.9 | 33.1 | 26.0 | 16 | A |
| 201 | K | CB | 52.5 | 34.2 | 25.2 | 19 | A |
| 201 | K | CG | 52.0 | 35.6 | 25.6 | 22 | A |
| 201 | K | CD | 52.6 | 36.7 | 24.7 | 23 | A |
| 201 | K | CE | 52.1 | 38.0 | 25.0 | 25 | A |
| 201 | K | NZ | 52.7 | 39.1 | 24.1 | 28 | A |
| 201 | K | C | 52.3 | 31.8 | 25.3 | 16 | A |
| 201 | K | O | 52.0 | 31.5 | 24.2 | 16 | A |
| 202 | G | N | 53.1 | 30.9 | 26.0 | 15 | A |
| 202 | G | CA | 53.5 | 29.6 | 25.5 | 16 | A |
| 202 | G | C | 54.7 | 29.8 | 25.6 | 16 | A |
| 202 | G | O | 54.7 | 29.1 | 23.5 | 15 | A |
| 203 | Y | N | 55.6 | 30.6 | 24.9 | 16 | A |
| 203 | Y | CA | 56.8 | 30.8 | 24.0 | 16 | A |
| 203 | Y | CB | 57.0 | 32.3 | 23.7 | 18 | A |
| 203 | Y | CG | 55.9 | 33.0 | 22.9 | 19 | A |
| 203 | Y | CD1 | 55.0 | 32.2 | 22.2 | 21 | A |
| 203 | Y | CE1 | 54.0 | 32.9 | 21.4 | 24 | A |
| 203 | Y | CD2 | 55.8 | 34.4 | 22.8 | 22 | A |
| 203 | Y | CE2 | 54.8 | 35.0 | 22.0 | 22 | A |
| 203 | Y | CZ | 53.9 | 34.2 | 21.3 | 23 | A |
| 203 | Y | OH | 53.0 | 34.9 | 20.6 | 27 | A |
| 203 | Y | C | 58.1 | 30.3 | 24.6 | 16 | A |
| 203 | Y | O | 59.2 | 30.7 | 24.2 | 17 | A |
| 204 | T | N | 58.0 | 29.3 | 25.6 | 17 | A |
| 204 | T | CA | 59.1 | 28.7 | 26.2 | 16 | A |
| 204 | T | CB | 59.3 | 29.0 | 27.6 | 20 | A |
| 204 | T | OG1 | 58.3 | 28.4 | 28.4 | 25 | A |
| 204 | T | CG2 | 59.2 | 30.6 | 27.8 | 20 | A |
| 204 | T | C | 59.0 | 27.2 | 26.0 | 15 | A |
| 204 | T | O | 57.9 | 26.6 | 26.0 | 16 | A |
| 205 | K | N | 60.2 | 26.5 | 25.9 | 15 | A |
| 205 | K | CA | 60.2 | 25.0 | 25.8 | 13 | A |
| 205 | K | CB | 61.7 | 24.6 | 25.7 | 13 | A |
| 205 | K | CG | 62.4 | 25.1 | 24.4 | 13 | A |
| 205 | K | CD | 63.9 | 24.9 | 24.5 | 14 | A |
| 205 | K | CE | 64.6 | 25.5 | 23.3 | 14 | A |
| 205 | K | NZ | 66.1 | 25.3 | 23.3 | 16 | A |
| 205 | K | C | 59.5 | 24.2 | 26.8 | 12 | A |
| 205 | K | O | 59.0 | 23.1 | 26.5 | 12 | A |
| 206 | S | N | 59.4 | 24.8 | 28.0 | 12 | A |
| 206 | S | CA | 58.7 | 24.1 | 29.1 | 13 | A |
| 206 | S | CB | 58.8 | 24.9 | 30.4 | 14 | A |
| 206 | S | OG | 58.4 | 26.3 | 30.2 | 17 | A |
| 206 | S | C | 57.2 | 23.8 | 28.8 | 12 | A |
| 206 | S | O | 56.6 | 22.9 | 29.4 | 12 | A |
| 207 | I | N | 56.6 | 24.6 | 27.9 | 11 | A |
| 207 | I | CA | 55.2 | 24.3 | 27.3 | 13 | A |
| 207 | I | CB | 54.7 | 25.4 | 26.5 | 15 | A |
| 207 | I | CG2 | 55.3 | 25.3 | 25.2 | 19 | A |
| 207 | I | CG1 | 53.2 | 25.4 | 26.4 | 20 | A |
| 207 | I | CD1 | 52.5 | 25.7 | 27.7 | 23 | A |
| 207 | I | C | 55.0 | 22.9 | 26.9 | 12 | A |
| 207 | I | O | 54.0 | 22.2 | 27.2 | 12 | A |
| 208 | D | N | 56.0 | 22.5 | 26.1 | 10 | A |
| 208 | D | CA | 55.9 | 21.2 | 25.4 | 10 | A |
| 208 | D | CB | 56.9 | 21.1 | 24.3 | 9 | A |

TABLE 1-continued

Structural Coordinates of crystalline Ah₆-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 208 | D | CG | 56.5 | 21.8 | 23.0 | 10 | A |
| 208 | D | OD1 | 55.3 | 22.0 | 22.7 | 11 | A |
| 208 | D | OD2 | 57.4 | 22.2 | 22.2 | 11 | A |
| 208 | D | C | 56.1 | 20.0 | 26.4 | 10 | A |
| 208 | D | O | 55.5 | 19.0 | 26.3 | 10 | A |
| 209 | I | N | 57.0 | 20.2 | 27.4 | 10 | A |
| 209 | I | CA | 57.3 | 19.2 | 28.4 | 11 | A |
| 209 | I | CB | 58.5 | 19.6 | 29.3 | 10 | A |
| 209 | I | CG2 | 58.6 | 18.6 | 30.4 | 12 | A |
| 209 | I | CG1 | 59.8 | 19.6 | 28.5 | 12 | A |
| 209 | I | CD1 | 60.2 | 18.3 | 27.9 | 15 | A |
| 209 | I | C | 56.0 | 18.9 | 29.2 | 10 | A |
| 209 | I | O | 55.7 | 17.7 | 29.4 | 11 | A |
| 210 | W | N | 55.2 | 19.9 | 29.5 | 10 | A |
| 210 | W | CA | 54.0 | 19.7 | 30.3 | 10 | A |
| 210 | W | CB | 53.3 | 21.0 | 30.6 | 11 | A |
| 210 | W | CG | 52.0 | 20.8 | 31.3 | 8 | A |
| 210 | W | CD2 | 51.8 | 20.7 | 32.7 | 10 | A |
| 210 | W | CE2 | 50.4 | 20.4 | 33.0 | 9 | A |
| 210 | W | CE3 | 52.7 | 20.8 | 33.8 | 11 | A |
| 210 | W | CD1 | 50.7 | 20.5 | 30.8 | 10 | A |
| 210 | W | NE1 | 49.8 | 20.3 | 31.8 | 11 | A |
| 210 | W | CZ2 | 49.9 | 20.3 | 34.3 | 10 | A |
| 210 | W | CZ3 | 52.1 | 20.7 | 35.1 | 12 | A |
| 210 | W | CH2 | 50.8 | 20.4 | 35.3 | 11 | A |
| 210 | W | C | 53.1 | 18.8 | 29.4 | 10 | A |
| 210 | W | O | 52.5 | 17.8 | 29.9 | 11 | A |
| 211 | S | N | 52.9 | 19.1 | 28.1 | 10 | A |
| 211 | S | CA | 52.1 | 18.3 | 27.3 | 9 | A |
| 211 | S | CB | 52.0 | 18.9 | 25.8 | 10 | A |
| 211 | S | OG | 51.6 | 20.2 | 25.9 | 11 | A |
| 211 | S | C | 52.5 | 16.8 | 27.2 | 10 | A |
| 211 | S | O | 51.7 | 15.9 | 27.3 | 11 | A |
| 212 | V | N | 53.8 | 16.6 | 27.1 | 10 | A |
| 212 | V | CA | 54.3 | 15.2 | 27.1 | 11 | A |
| 212 | V | CB | 55.9 | 15.2 | 26.9 | 12 | A |
| 212 | V | CG1 | 56.4 | 13.8 | 26.9 | 12 | A |
| 212 | V | CG2 | 56.2 | 15.8 | 25.5 | 13 | A |
| 212 | V | C | 54.0 | 14.5 | 28.4 | 11 | A |
| 212 | V | O | 53.6 | 13.3 | 28.4 | 11 | A |
| 213 | G | N | 54.1 | 15.2 | 29.5 | 10 | A |
| 213 | G | CA | 53.7 | 14.6 | 30.8 | 10 | A |
| 213 | G | C | 52.2 | 14.2 | 30.8 | 11 | A |
| 213 | G | O | 51.9 | 13.1 | 31.3 | 11 | A |
| 214 | C | N | 51.4 | 15.0 | 30.2 | 11 | A |
| 214 | C | CA | 49.9 | 14.7 | 30.1 | 12 | A |
| 214 | C | CB | 49.1 | 15.8 | 29.6 | 12 | A |
| 214 | C | SG | 49.0 | 17.3 | 30.6 | 12 | A |
| 214 | C | C | 49.7 | 13.4 | 29.3 | 14 | A |
| 214 | C | O | 48.9 | 12.6 | 29.6 | 14 | A |
| 215 | I | N | 50.5 | 13.3 | 28.2 | 12 | A |
| 215 | I | CA | 50.5 | 12.1 | 27.3 | 12 | A |
| 215 | I | CB | 51.3 | 12.4 | 26.0 | 12 | A |
| 215 | I | CG2 | 51.4 | 11.1 | 25.2 | 14 | A |
| 215 | I | CG1 | 50.7 | 13.5 | 25.2 | 12 | A |
| 215 | I | CD1 | 51.6 | 14.1 | 24.1 | 14 | A |
| 215 | I | C | 50.9 | 10.9 | 28.0 | 12 | A |
| 215 | I | O | 50.3 | 9.8 | 27.9 | 12 | A |
| 216 | L | N | 52.0 | 11.0 | 28.8 | 12 | A |
| 216 | L | CA | 52.4 | 9.8 | 29.6 | 14 | A |
| 216 | L | CB | 53.7 | 10.1 | 30.4 | 13 | A |
| 216 | L | CG | 54.2 | 9.1 | 31.4 | 13 | A |
| 216 | L | CD1 | 54.5 | 7.8 | 30.7 | 12 | A |
| 216 | L | CD2 | 55.5 | 9.6 | 32.0 | 12 | A |
| 216 | L | C | 51.3 | 9.3 | 30.6 | 14 | A |
| 216 | L | O | 51.1 | 8.1 | 30.6 | 14 | A |
| 217 | A | N | 50.7 | 10.2 | 31.3 | 14 | A |
| 217 | A | CA | 49.6 | 9.9 | 32.2 | 14 | A |
| 217 | A | CB | 49.1 | 11.1 | 32.9 | 14 | A |
| 217 | A | C | 48.5 | 9.2 | 31.5 | 16 | A |
| 217 | A | O | 47.9 | 8.2 | 32.0 | 17 | A |
| 218 | E | N | 48.2 | 9.7 | 30.3 | 14 | A |
| 218 | E | CA | 47.1 | 9.1 | 29.5 | 15 | A |
| 218 | E | CB | 46.8 | 10.0 | 28.3 | 15 | A |
| 218 | E | CG | 45.4 | 9.8 | 27.7 | 17 | A |
| 218 | E | CD | 44.9 | 10.9 | 26.9 | 18 | A |
| 218 | E | OE1 | 45.3 | 12.1 | 27.1 | 16 | A |
| 218 | E | OE2 | 44.0 | 10.7 | 26.0 | 20 | A |
| 218 | E | C | 47.5 | 7.7 | 29.0 | 16 | A |
| 218 | E | O | 46.6 | 6.8 | 28.9 | 16 | A |
| 219 | M | N | 48.7 | 7.4 | 28.7 | 15 | A |
| 219 | M | CA | 49.1 | 6.1 | 28.3 | 16 | A |
| 219 | M | CB | 50.6 | 6.0 | 27.7 | 13 | A |
| 219 | M | CG | 50.7 | 6.7 | 26.4 | 15 | A |
| 219 | M | SD | 52.3 | 6.3 | 25.5 | 15 | A |
| 219 | M | CE | 53.4 | 7.4 | 26.3 | 14 | A |
| 219 | M | C | 49.0 | 5.1 | 29.5 | 17 | A |
| 219 | M | O | 48.8 | 3.9 | 29.3 | 17 | A |
| 220 | L | N | 49.2 | 5.6 | 30.7 | 16 | A |
| 220 | L | CA | 49.2 | 4.8 | 31.9 | 18 | A |
| 220 | L | CB | 49.9 | 5.5 | 33.0 | 18 | A |
| 220 | L | CG | 51.4 | 5.7 | 32.9 | 18 | A |
| 220 | L | CD1 | 51.9 | 6.6 | 34.1 | 19 | A |
| 220 | L | CD2 | 52.1 | 4.4 | 32.9 | 19 | A |
| 220 | L | C | 47.8 | 4.3 | 32.3 | 20 | A |
| 220 | L | O | 47.6 | 3.3 | 32.9 | 21 | A |
| 221 | S | N | 46.8 | 5.1 | 31.9 | 20 | A |
| 221 | S | CA | 45.4 | 4.8 | 32.3 | 21 | A |
| 221 | S | CB | 45.0 | 5.8 | 33.4 | 21 | A |
| 221 | S | OG | 45.0 | 7.1 | 32.9 | 26 | A |
| 221 | S | C | 44.3 | 4.8 | 31.2 | 22 | A |
| 221 | S | O | 43.2 | 4.4 | 31.5 | 24 | A |
| 222 | N | N | 44.7 | 5.2 | 30.0 | 21 | A |
| 222 | N | CA | 43.7 | 5.3 | 28.9 | 21 | A |
| 222 | N | CB | 43.1 | 3.9 | 28.7 | 21 | A |
| 222 | N | CG | 44.0 | 2.9 | 28.0 | 20 | A |
| 222 | N | OD1 | 44.0 | 2.8 | 26.8 | 24 | A |
| 222 | N | ND2 | 44.7 | 2.2 | 28.9 | 22 | A |
| 222 | N | C | 42.7 | 6.4 | 29.1 | 22 | A |
| 222 | N | O | 41.6 | 6.3 | 28.6 | 25 | A |
| 223 | R | N | 43.0 | 7.4 | 29.9 | 22 | A |
| 223 | R | CA | 42.1 | 8.5 | 30.2 | 22 | A |
| 223 | R | CB | 41.3 | 8.2 | 31.5 | 27 | A |
| 223 | R | CG | 42.1 | 8.0 | 32.7 | 34 | A |
| 223 | R | CD | 41.3 | 7.8 | 33.9 | 40 | A |
| 223 | R | NE | 42.1 | 7.5 | 35.1 | 45 | A |
| 223 | R | CZ | 43.0 | 8.4 | 35.6 | 48 | A |
| 223 | R | NH1 | 43.2 | 9.6 | 35.1 | 48 | A |
| 223 | R | NH2 | 43.7 | 8.0 | 36.7 | 49 | A |
| 223 | R | C | 42.9 | 9.7 | 30.4 | 19 | A |
| 223 | R | O | 44.0 | 9.7 | 30.9 | 18 | A |
| 224 | P | N | 42.3 | 10.9 | 29.9 | 18 | A |
| 224 | P | CD | 41.1 | 11.1 | 29.2 | 19 | A |
| 224 | P | CA | 43.1 | 12.1 | 30.1 | 17 | A |
| 224 | P | CB | 42.2 | 13.2 | 29.3 | 18 | A |
| 224 | P | CG | 40.8 | 12.6 | 29.4 | 21 | A |
| 224 | P | C | 43.2 | 12.5 | 31.6 | 17 | A |
| 224 | P | O | 42.2 | 12.3 | 32.4 | 16 | A |
| 225 | I | N | 44.4 | 12.9 | 32.0 | 16 | A |
| 225 | I | CA | 44.6 | 13.2 | 33.4 | 16 | A |
| 225 | I | CB | 46.1 | 13.2 | 33.8 | 16 | A |
| 225 | I | CG2 | 46.9 | 14.2 | 32.9 | 16 | A |
| 225 | I | CG1 | 46.3 | 13.5 | 35.3 | 18 | A |
| 225 | I | CD1 | 47.7 | 13.5 | 35.7 | 21 | A |
| 225 | I | C | 43.9 | 14.5 | 33.9 | 16 | A |
| 225 | I | O | 43.4 | 14.6 | 35.0 | 18 | A |
| 226 | F | N | 43.8 | 15.5 | 33.0 | 16 | A |
| 226 | F | CA | 43.2 | 16.8 | 33.4 | 16 | A |
| 226 | F | CB | 44.3 | 17.9 | 33.4 | 15 | A |
| 226 | F | CG | 45.4 | 17.6 | 34.4 | 13 | A |
| 226 | F | CD1 | 45.2 | 17.4 | 35.7 | 14 | A |
| 226 | F | CD2 | 46.7 | 17.6 | 33.9 | 13 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 226 | F | CE1 | 46.3 | 17.2 | 36.6 | 14 | A |
| 226 | F | CE2 | 47.8 | 17.4 | 34.7 | 14 | A |
| 226 | F | CZ | 47.6 | 17.2 | 36.1 | 15 | A |
| 226 | F | C | 42.1 | 17.2 | 32.3 | 15 | A |
| 226 | F | O | 42.4 | 18.1 | 31.5 | 17 | A |
| 227 | P | N | 41.0 | 16.6 | 32.3 | 18 | A |
| 227 | P | CD | 40.6 | 15.4 | 33.2 | 18 | A |
| 227 | P | CA | 39.9 | 16.9 | 31.4 | 18 | A |
| 227 | P | CB | 39.1 | 15.5 | 31.4 | 19 | A |
| 227 | P | CG | 39.2 | 15.1 | 32.8 | 19 | A |
| 227 | P | C | 39.0 | 18.1 | 31.7 | 20 | A |
| 227 | P | O | 37.8 | 17.9 | 32.0 | 21 | A |
| 228 | G | N | 39.6 | 19.3 | 31.7 | 21 | A |
| 228 | G | CA | 38.8 | 20.5 | 31.9 | 23 | A |
| 228 | G | C | 37.6 | 20.6 | 31.0 | 23 | A |
| 228 | G | O | 37.8 | 20.3 | 29.8 | 23 | A |
| 229 | K | N | 36.5 | 21.1 | 31.5 | 25 | A |
| 229 | K | CA | 35.3 | 21.3 | 30.7 | 27 | A |
| 229 | K | CB | 34.0 | 21.1 | 31.5 | 29 | A |
| 229 | K | CG | 33.8 | 19.7 | 32.1 | 33 | A |
| 229 | K | CD | 32.6 | 19.6 | 32.9 | 36 | A |
| 229 | K | CE | 32.3 | 18.2 | 33.5 | 39 | A |
| 229 | K | NZ | 33.4 | 17.8 | 34.4 | 39 | A |
| 229 | K | C | 35.3 | 22.6 | 30.0 | 26 | A |
| 229 | K | O | 34.6 | 22.8 | 28.9 | 29 | A |
| 230 | H | N | 36.1 | 23.5 | 30.5 | 24 | A |
| 230 | H | CA | 36.2 | 24.9 | 29.9 | 23 | A |
| 230 | H | CB | 35.0 | 25.8 | 30.3 | 23 | A |
| 230 | H | CG | 34.7 | 25.9 | 31.8 | 19 | A |
| 230 | H | CD2 | 35.3 | 26.6 | 32.7 | 20 | A |
| 230 | H | ND1 | 33.8 | 25.1 | 32.4 | 22 | A |
| 230 | H | CE1 | 33.7 | 25.4 | 33.7 | 20 | A |
| 230 | H | NE2 | 34.6 | 26.3 | 33.9 | 22 | A |
| 230 | H | C | 37.5 | 25.5 | 30.4 | 23 | A |
| 230 | H | O | 38.2 | 24.9 | 31.2 | 22 | A |
| 231 | Y | N | 37.8 | 26.7 | 29.9 | 23 | A |
| 231 | Y | CA | 39.1 | 27.4 | 30.2 | 23 | A |
| 231 | Y | CB | 39.0 | 28.8 | 29.7 | 24 | A |
| 231 | Y | CG | 40.3 | 29.6 | 29.7 | 22 | A |
| 231 | Y | CD1 | 40.7 | 30.2 | 30.9 | 23 | A |
| 231 | Y | CE1 | 41.9 | 30.9 | 31.0 | 23 | A |
| 231 | Y | CD2 | 41.2 | 29.6 | 28.6 | 22 | A |
| 231 | Y | CE2 | 42.4 | 30.3 | 28.7 | 21 | A |
| 231 | Y | CZ | 42.8 | 30.9 | 29.9 | 21 | A |
| 231 | Y | OH | 44.0 | 31.6 | 29.9 | 20 | A |
| 231 | Y | C | 39.6 | 27.4 | 31.6 | 23 | A |
| 231 | Y | O | 40.7 | 26.9 | 31.9 | 22 | A |
| 232 | L | N | 38.8 | 28.0 | 32.6 | 23 | A |
| 232 | L | CA | 39.3 | 28.1 | 34.0 | 22 | A |
| 232 | L | CB | 38.4 | 29.1 | 34.8 | 23 | A |
| 232 | L | CG | 38.8 | 29.2 | 36.2 | 24 | A |
| 232 | L | CD1 | 40.2 | 29.6 | 36.4 | 25 | A |
| 232 | L | CD2 | 37.8 | 30.1 | 36.9 | 25 | A |
| 232 | L | C | 39.2 | 26.7 | 34.7 | 22 | A |
| 232 | L | O | 40.0 | 26.4 | 35.6 | 22 | A |
| 233 | D | N | 38.3 | 25.9 | 34.2 | 20 | A |
| 233 | D | CA | 38.2 | 24.5 | 34.8 | 19 | A |
| 233 | D | CB | 37.0 | 23.8 | 34.2 | 20 | A |
| 233 | D | CG | 36.6 | 22.5 | 34.9 | 20 | A |
| 233 | D | OD1 | 36.5 | 22.6 | 36.2 | 21 | A |
| 233 | D | OD2 | 36.3 | 21.5 | 34.3 | 21 | A |
| 233 | D | C | 39.5 | 23.7 | 34.6 | 18 | A |
| 233 | D | O | 39.8 | 22.8 | 35.4 | 17 | A |
| 234 | Q | N | 40.2 | 24.0 | 33.6 | 16 | A |
| 234 | Q | CA | 41.5 | 23.3 | 33.3 | 16 | A |
| 234 | Q | CB | 42.1 | 23.8 | 32.0 | 14 | A |
| 234 | Q | CG | 43.3 | 23.0 | 31.5 | 15 | A |
| 234 | Q | CD | 42.9 | 21.5 | 31.3 | 16 | A |
| 234 | Q | OE1 | 41.7 | 21.3 | 30.8 | 16 | A |
| 234 | Q | NE2 | 43.8 | 20.6 | 31.6 | 15 | A |
| 234 | Q | C | 42.5 | 23.5 | 34.5 | 17 | A |
| 234 | Q | O | 43.1 | 22.6 | 34.9 | 16 | A |
| 235 | L | N | 42.5 | 24.8 | 35.0 | 17 | A |
| 235 | L | CA | 43.4 | 25.0 | 36.1 | 19 | A |
| 235 | L | CB | 43.5 | 26.6 | 36.3 | 20 | A |
| 235 | L | CG | 44.5 | 27.0 | 37.4 | 20 | A |
| 235 | L | CD1 | 45.9 | 26.5 | 37.2 | 22 | A |
| 235 | L | CD2 | 44.5 | 28.6 | 37.5 | 21 | A |
| 235 | L | C | 42.9 | 24.3 | 37.4 | 19 | A |
| 235 | L | O | 43.6 | 23.9 | 38.2 | 21 | A |
| 236 | N | N | 41.5 | 24.2 | 37.5 | 20 | A |
| 236 | N | CA | 40.9 | 23.6 | 38.6 | 21 | A |
| 236 | N | CB | 39.4 | 23.5 | 38.5 | 23 | A |
| 236 | N | CG | 38.7 | 24.9 | 38.6 | 26 | A |
| 236 | N | OD1 | 39.2 | 25.8 | 39.3 | 27 | A |
| 236 | N | ND2 | 37.5 | 25.0 | 38.1 | 26 | A |
| 236 | N | C | 41.4 | 22.1 | 38.7 | 20 | A |
| 236 | N | O | 41.8 | 21.6 | 39.8 | 20 | A |
| 237 | H | N | 41.4 | 21.4 | 37.6 | 18 | A |
| 237 | H | CA | 41.8 | 20.1 | 37.5 | 17 | A |
| 237 | H | CB | 41.6 | 19.5 | 36.1 | 18 | A |
| 237 | H | CG | 40.2 | 19.0 | 35.9 | 20 | A |
| 237 | H | CD2 | 39.1 | 19.7 | 35.6 | 21 | A |
| 237 | H | ND1 | 39.8 | 17.7 | 35.9 | 21 | A |
| 237 | H | CE1 | 38.5 | 17.6 | 35.7 | 23 | A |
| 237 | H | NE2 | 38.0 | 18.8 | 35.5 | 22 | A |
| 237 | H | C | 43.3 | 19.9 | 37.9 | 16 | A |
| 237 | H | O | 43.6 | 19.0 | 38.6 | 17 | A |
| 238 | I | N | 44.2 | 20.7 | 37.3 | 16 | A |
| 238 | I | CA | 45.6 | 20.6 | 37.6 | 14 | A |
| 238 | I | CB | 46.4 | 21.7 | 36.8 | 13 | A |
| 238 | I | CG2 | 47.8 | 21.7 | 37.3 | 13 | A |
| 238 | I | CG1 | 46.3 | 21.4 | 35.3 | 14 | A |
| 238 | I | CD1 | 46.8 | 22.5 | 34.4 | 15 | A |
| 238 | I | C | 45.9 | 20.8 | 39.1 | 16 | A |
| 238 | I | O | 46.6 | 20.0 | 39.7 | 17 | A |
| 239 | L | N | 45.3 | 21.9 | 39.7 | 16 | A |
| 239 | L | CA | 45.5 | 22.1 | 41.2 | 17 | A |
| 239 | L | CB | 45.0 | 23.5 | 41.5 | 17 | A |
| 239 | L | CG | 45.7 | 24.7 | 40.8 | 20 | A |
| 239 | L | CD1 | 45.0 | 26.0 | 41.2 | 21 | A |
| 239 | L | CD2 | 47.2 | 24.7 | 41.2 | 21 | A |
| 239 | L | C | 44.9 | 21.1 | 42.1 | 17 | A |
| 239 | L | O | 45.3 | 20.9 | 43.2 | 18 | A |
| 240 | G | N | 43.8 | 20.4 | 41.6 | 17 | A |
| 240 | G | CA | 43.2 | 19.4 | 42.3 | 18 | A |
| 240 | G | C | 44.1 | 18.2 | 42.6 | 18 | A |
| 240 | G | O | 43.9 | 17.5 | 43.5 | 20 | A |
| 241 | I | N | 45.0 | 18.0 | 41.7 | 19 | A |
| 241 | I | CA | 46.0 | 16.9 | 41.8 | 18 | A |
| 241 | I | CB | 46.2 | 16.2 | 40.4 | 17 | A |
| 241 | I | CG2 | 47.4 | 15.2 | 40.5 | 18 | A |
| 241 | I | CG1 | 44.9 | 15.4 | 40.1 | 19 | A |
| 241 | I | CD1 | 44.9 | 14.7 | 38.7 | 21 | A |
| 241 | I | C | 47.3 | 17.3 | 42.4 | 18 | A |
| 241 | I | O | 47.9 | 16.6 | 43.2 | 18 | A |
| 242 | L | N | 47.9 | 18.4 | 41.9 | 17 | A |
| 242 | L | CA | 49.2 | 18.9 | 42.4 | 17 | A |
| 242 | L | CB | 49.8 | 19.9 | 41.4 | 17 | A |
| 242 | L | CG | 50.4 | 19.4 | 40.1 | 19 | A |
| 242 | L | CD1 | 49.5 | 18.6 | 39.2 | 24 | A |
| 242 | L | CD2 | 51.1 | 20.6 | 39.3 | 18 | A |
| 242 | L | C | 49.1 | 19.6 | 43.7 | 17 | A |
| 242 | L | O | 50.1 | 19.6 | 44.5 | 17 | A |
| 243 | G | N | 47.9 | 20.1 | 44.1 | 17 | A |
| 243 | G | CA | 47.7 | 20.7 | 45.4 | 17 | A |
| 243 | G | C | 48.1 | 22.2 | 45.3 | 18 | A |
| 243 | G | O | 48.5 | 22.7 | 44.2 | 19 | A |
| 244 | S | N | 48.0 | 22.9 | 46.4 | 16 | A |
| 244 | S | CA | 48.3 | 24.4 | 46.4 | 16 | A |
| 244 | S | CB | 48.0 | 25.0 | 47.8 | 16 | A |
| 244 | S | OG | 46.6 | 24.8 | 48.1 | 19 | A |

TABLE 1-continued

Structural Coordinates of crystalline Ah₆-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| Res | AA | Atom | X | Y | Z | B | Chain |
|---|---|---|---|---|---|---|---|
| 244 | S | C | 49.8 | 24.6 | 46.1 | 18 | A |
| 244 | S | O | 50.7 | 23.9 | 46.6 | 18 | A |
| 245 | P | N | 50.1 | 25.6 | 45.3 | 18 | A |
| 245 | P | CD | 49.2 | 26.4 | 44.5 | 19 | A |
| 245 | P | CA | 51.5 | 25.9 | 45.0 | 18 | A |
| 245 | P | CB | 51.4 | 27.0 | 44.0 | 20 | A |
| 245 | P | CG | 50.1 | 26.7 | 43.3 | 21 | A |
| 245 | P | C | 52.3 | 26.4 | 46.3 | 18 | A |
| 245 | P | O | 51.7 | 27.1 | 47.1 | 18 | A |
| 246 | S | N | 53.6 | 26.2 | 46.3 | 19 | A |
| 246 | S | CA | 54.4 | 26.6 | 47.5 | 20 | A |
| 246 | S | CB | 55.8 | 25.9 | 47.4 | 21 | A |
| 246 | S | OG | 56.5 | 26.4 | 46.3 | 21 | A |
| 246 | S | C | 54.6 | 28.1 | 47.5 | 21 | A |
| 246 | S | O | 54.3 | 28.8 | 46.5 | 19 | A |
| 247 | Q | N | 55.0 | 28.6 | 48.6 | 24 | A |
| 247 | Q | CA | 55.3 | 30.0 | 48.7 | 26 | A |
| 247 | Q | CB | 55.7 | 30.4 | 50.2 | 28 | A |
| 247 | Q | CG | 56.2 | 31.8 | 50.3 | 30 | A |
| 247 | Q | CD | 56.5 | 32.2 | 51.7 | 33 | A |
| 247 | Q | OE1 | 55.7 | 32.2 | 52.6 | 34 | A |
| 247 | Q | NE2 | 57.8 | 32.5 | 52.0 | 34 | A |
| 247 | Q | C | 56.3 | 30.5 | 47.7 | 26 | A |
| 247 | Q | O | 56.2 | 31.6 | 47.1 | 26 | A |
| 248 | E | N | 57.3 | 29.7 | 47.5 | 27 | A |
| 248 | E | CA | 58.4 | 30.0 | 46.6 | 28 | A |
| 248 | E | CB | 59.5 | 29.0 | 46.6 | 30 | A |
| 248 | E | CG | 60.7 | 29.3 | 45.8 | 34 | A |
| 248 | E | CD | 61.9 | 28.3 | 46.0 | 36 | A |
| 248 | E | OE1 | 61.7 | 27.2 | 45.6 | 37 | A |
| 248 | E | OE2 | 62.9 | 28.7 | 46.5 | 38 | A |
| 248 | E | C | 57.8 | 30.1 | 45.2 | 28 | A |
| 248 | E | O | 58.2 | 31.0 | 44.4 | 28 | A |
| 249 | D | N | 57.0 | 29.2 | 44.8 | 27 | A |
| 249 | D | CA | 56.4 | 29.2 | 43.5 | 26 | A |
| 249 | D | CB | 55.7 | 27.9 | 43.2 | 26 | A |
| 249 | D | CG | 56.7 | 26.7 | 42.9 | 24 | A |
| 249 | D | OD1 | 57.9 | 27.0 | 42.9 | 25 | A |
| 249 | D | OD2 | 56.2 | 25.6 | 42.8 | 26 | A |
| 249 | D | C | 55.4 | 30.3 | 43.3 | 27 | A |
| 249 | D | O | 55.3 | 30.9 | 42.2 | 26 | A |
| 250 | L | N | 54.8 | 30.7 | 44.4 | 28 | A |
| 250 | L | CA | 53.8 | 31.9 | 44.3 | 30 | A |
| 250 | L | CB | 53.0 | 32.0 | 45.6 | 31 | A |
| 250 | L | CG | 51.7 | 31.2 | 45.6 | 31 | A |
| 250 | L | CD1 | 51.0 | 31.4 | 46.9 | 33 | A |
| 250 | L | CD2 | 50.8 | 31.7 | 44.5 | 32 | A |
| 250 | L | C | 54.6 | 33.2 | 44.1 | 32 | A |
| 250 | L | O | 54.2 | 34.1 | 43.4 | 31 | A |
| 251 | N | N | 55.8 | 33.2 | 44.7 | 33 | A |
| 251 | N | CA | 56.7 | 34.4 | 44.6 | 35 | A |
| 251 | N | CB | 57.9 | 34.3 | 45.5 | 37 | A |
| 251 | N | CG | 57.5 | 34.4 | 47.0 | 38 | A |
| 251 | N | OD1 | 56.4 | 35.0 | 47.3 | 39 | A |
| 251 | N | ND2 | 58.3 | 34.0 | 47.9 | 39 | A |
| 251 | N | C | 57.2 | 34.5 | 43.1 | 35 | A |
| 251 | N | O | 57.6 | 35.6 | 42.7 | 35 | A |
| 252 | C | N | 57.2 | 33.4 | 42.4 | 34 | A |
| 252 | C | CA | 57.7 | 33.5 | 41.0 | 34 | A |
| 252 | C | CB | 58.2 | 32.1 | 40.6 | 34 | A |
| 252 | C | SG | 59.8 | 31.6 | 41.3 | 36 | A |
| 252 | C | C | 56.6 | 34.0 | 40.1 | 33 | A |
| 252 | C | O | 56.9 | 34.2 | 38.9 | 33 | A |
| 253 | I | N | 55.4 | 34.1 | 40.6 | 31 | A |
| 253 | I | CA | 54.3 | 34.6 | 39.8 | 32 | A |
| 253 | I | CB | 53.0 | 34.0 | 40.3 | 34 | A |
| 253 | I | CG2 | 51.8 | 35.1 | 40.1 | 34 | A |
| 253 | I | CG1 | 52.6 | 32.8 | 39.7 | 37 | A |
| 253 | I | CD1 | 53.7 | 31.7 | 39.8 | 38 | A |
| 253 | I | C | 54.4 | 36.2 | 40.0 | 32 | A |
| 253 | I | O | 54.3 | 36.7 | 41.1 | 34 | A |
| 254 | I | N | 54.5 | 36.9 | 38.9 | 29 | A |
| 254 | I | CA | 54.6 | 38.3 | 38.9 | 29 | A |
| 254 | I | CB | 55.6 | 38.9 | 37.9 | 30 | A |
| 254 | I | CG2 | 57.0 | 38.2 | 38.1 | 32 | A |
| 254 | I | CG1 | 55.1 | 38.6 | 36.5 | 30 | A |
| 254 | I | CD1 | 56.0 | 39.2 | 35.4 | 32 | A |
| 254 | I | C | 53.3 | 39.0 | 38.7 | 26 | A |
| 254 | I | O | 53.2 | 40.2 | 39.0 | 27 | A |
| 255 | N | N | 52.2 | 38.4 | 38.2 | 23 | A |
| 255 | N | CA | 51.0 | 39.0 | 37.9 | 19 | A |
| 255 | N | CB | 50.1 | 38.3 | 36.9 | 18 | A |
| 255 | N | CG | 50.6 | 38.5 | 35.5 | 22 | A |
| 255 | N | OD1 | 51.1 | 39.5 | 35.1 | 20 | A |
| 255 | N | ND2 | 50.3 | 37.5 | 34.7 | 20 | A |
| 255 | N | C | 50.2 | 39.2 | 39.2 | 18 | A |
| 255 | N | O | 50.0 | 38.2 | 39.9 | 16 | A |
| 256 | L | N | 49.7 | 40.4 | 39.5 | 16 | A |
| 256 | L | CA | 48.9 | 40.7 | 40.7 | 16 | A |
| 256 | L | CB | 48.6 | 42.2 | 40.7 | 16 | A |
| 256 | L | CG | 47.5 | 42.6 | 41.7 | 17 | A |
| 256 | L | CD1 | 48.0 | 42.5 | 43.1 | 18 | A |
| 256 | L | CD2 | 47.2 | 44.1 | 41.4 | 19 | A |
| 256 | L | C | 47.6 | 39.8 | 40.7 | 15 | A |
| 256 | L | O | 47.3 | 39.3 | 41.8 | 15 | A |
| 257 | K | N | 46.9 | 39.8 | 39.6 | 15 | A |
| 257 | K | CA | 45.7 | 39.0 | 39.5 | 14 | A |
| 257 | K | CB | 45.0 | 39.2 | 38.2 | 16 | A |
| 257 | K | CG | 44.5 | 40.7 | 38.0 | 22 | A |
| 257 | K | CD | 43.8 | 40.8 | 36.6 | 23 | A |
| 257 | K | CE | 43.3 | 42.2 | 36.3 | 25 | A |
| 257 | K | NZ | 42.5 | 42.2 | 35.1 | 25 | A |
| 257 | K | C | 45.9 | 37.5 | 39.7 | 13 | A |
| 257 | K | O | 45.0 | 36.8 | 40.3 | 14 | A |
| 258 | A | N | 47.0 | 37.0 | 39.2 | 14 | A |
| 258 | A | CA | 47.2 | 35.5 | 39.4 | 14 | A |
| 258 | A | CB | 48.4 | 35.1 | 38.4 | 14 | A |
| 258 | A | C | 47.6 | 35.2 | 40.8 | 15 | A |
| 258 | A | O | 47.1 | 34.2 | 41.4 | 13 | A |
| 259 | R | N | 48.4 | 36.0 | 41.4 | 14 | A |
| 259 | R | CA | 48.8 | 35.9 | 42.8 | 15 | A |
| 259 | R | CB | 49.8 | 36.9 | 43.2 | 19 | A |
| 259 | R | CG | 50.1 | 36.9 | 44.7 | 25 | A |
| 259 | R | CD | 51.2 | 38.0 | 45.1 | 31 | A |
| 259 | R | NE | 52.5 | 37.7 | 44.5 | 36 | A |
| 259 | R | CZ | 53.3 | 36.8 | 45.0 | 40 | A |
| 259 | R | NH1 | 52.9 | 36.0 | 46.0 | 42 | A |
| 259 | R | NH2 | 54.5 | 36.5 | 44.4 | 41 | A |
| 259 | R | C | 47.6 | 35.9 | 43.7 | 15 | A |
| 259 | R | O | 47.3 | 35.0 | 44.6 | 15 | A |
| 260 | N | N | 46.7 | 37.0 | 43.5 | 14 | A |
| 260 | N | CA | 45.5 | 37.1 | 44.3 | 14 | A |
| 260 | N | CB | 44.8 | 38.4 | 43.9 | 14 | A |
| 260 | N | CG | 45.4 | 39.7 | 44.4 | 17 | A |
| 260 | N | OD1 | 46.4 | 39.6 | 45.2 | 18 | A |
| 260 | N | ND2 | 45.0 | 40.8 | 43.9 | 18 | A |
| 260 | N | C | 44.6 | 35.9 | 44.2 | 13 | A |
| 260 | N | O | 44.1 | 35.4 | 45.2 | 14 | A |
| 261 | Y | N | 44.4 | 35.4 | 43.0 | 13 | A |
| 261 | Y | CA | 43.6 | 34.2 | 42.7 | 13 | A |
| 261 | Y | CB | 43.5 | 33.9 | 41.2 | 14 | A |
| 261 | Y | CG | 42.7 | 32.7 | 41.0 | 14 | A |
| 261 | Y | CD1 | 41.3 | 32.7 | 41.3 | 15 | A |
| 261 | Y | CE1 | 40.5 | 31.5 | 41.1 | 17 | A |
| 261 | Y | CD2 | 43.2 | 31.5 | 40.5 | 16 | A |
| 261 | Y | CE2 | 42.5 | 30.3 | 40.4 | 15 | A |
| 261 | Y | CZ | 41.1 | 30.4 | 40.7 | 15 | A |
| 261 | Y | OH | 40.3 | 29.2 | 40.6 | 19 | A |
| 261 | Y | C | 44.1 | 33.0 | 43.5 | 12 | A |
| 261 | Y | O | 43.3 | 32.4 | 44.2 | 13 | A |
| 262 | L | N | 45.4 | 32.7 | 43.4 | 12 | A |
| 262 | L | CA | 45.9 | 31.5 | 44.1 | 12 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| 262 | L | CB | 47.4 | 31.3 | 43.6 | 13 | A |
|---|---|---|---|---|---|---|---|
| 262 | L | CG | 47.5 | 30.9 | 42.1 | 14 | A |
| 262 | L | CD1 | 49.0 | 30.9 | 41.7 | 16 | A |
| 262 | L | CD2 | 46.9 | 29.5 | 41.9 | 17 | A |
| 262 | L | C | 45.8 | 31.7 | 45.6 | 14 | A |
| 262 | L | O | 45.5 | 30.7 | 46.3 | 15 | A |
| 263 | L | N | 46.1 | 32.9 | 46.1 | 12 | A |
| 263 | L | CA | 46.0 | 33.1 | 47.6 | 14 | A |
| 263 | L | CB | 46.6 | 34.5 | 47.9 | 15 | A |
| 263 | L | CG | 48.1 | 34.6 | 47.7 | 18 | A |
| 263 | L | CD1 | 48.5 | 36.1 | 48.0 | 20 | A |
| 263 | L | CD2 | 48.8 | 33.7 | 48.7 | 20 | A |
| 263 | L | C | 44.6 | 33.0 | 48.1 | 15 | A |
| 263 | L | O | 44.4 | 32.7 | 49.3 | 17 | A |
| 264 | S | N | 43.6 | 33.2 | 47.2 | 16 | A |
| 264 | S | CA | 42.2 | 33.1 | 47.6 | 15 | A |
| 264 | S | CB | 41.3 | 33.9 | 46.7 | 15 | A |
| 264 | S | OG | 41.1 | 33.2 | 45.5 | 16 | A |
| 264 | S | C | 41.6 | 31.7 | 47.8 | 15 | A |
| 264 | S | O | 40.5 | 31.5 | 48.3 | 15 | A |
| 265 | L | N | 42.3 | 30.7 | 47.2 | 14 | A |
| 265 | L | CA | 41.8 | 29.4 | 47.3 | 15 | A |
| 265 | L | CB | 42.5 | 28.6 | 46.1 | 14 | A |
| 265 | L | CG | 42.3 | 29.0 | 44.7 | 14 | A |
| 265 | L | CD1 | 43.2 | 28.2 | 43.7 | 14 | A |
| 265 | L | CD2 | 40.8 | 28.8 | 44.3 | 16 | A |
| 265 | L | C | 42.1 | 28.6 | 48.6 | 16 | A |
| 265 | L | O | 43.1 | 28.9 | 49.3 | 16 | A |
| 266 | P | N | 41.2 | 27.7 | 49.0 | 16 | A |
| 266 | P | CD | 39.8 | 27.5 | 48.4 | 16 | A |
| 266 | P | CA | 41.4 | 27.0 | 50.2 | 16 | A |
| 266 | P | CB | 40.1 | 26.1 | 50.3 | 17 | A |
| 266 | P | CG | 39.1 | 27.0 | 49.7 | 19 | A |
| 266 | P | C | 42.6 | 26.1 | 50.0 | 17 | A |
| 266 | P | O | 42.9 | 25.7 | 48.8 | 17 | A |
| 267 | H | N | 43.4 | 25.8 | 51.1 | 18 | A |
| 267 | H | CA | 44.5 | 24.9 | 50.9 | 20 | A |
| 267 | H | CB | 45.2 | 24.8 | 52.3 | 21 | A |
| 267 | H | CG | 46.4 | 23.8 | 52.3 | 23 | A |
| 267 | H | CD2 | 47.4 | 23.6 | 51.4 | 25 | A |
| 267 | H | ND1 | 46.6 | 22.9 | 53.3 | 27 | A |
| 267 | H | CE1 | 47.7 | 22.2 | 53.0 | 25 | A |
| 267 | H | NE2 | 48.1 | 22.6 | 51.9 | 26 | A |
| 267 | H | C | 44.1 | 23.5 | 50.4 | 22 | A |
| 267 | H | O | 43.1 | 23.0 | 50.9 | 24 | A |
| 268 | K | N | 44.9 | 23.0 | 49.5 | 22 | A |
| 268 | K | CA | 44.6 | 21.7 | 48.9 | 24 | A |
| 268 | K | CB | 44.1 | 21.8 | 47.5 | 23 | A |
| 268 | K | CG | 43.9 | 20.5 | 46.8 | 29 | A |
| 268 | K | CD | 42.7 | 19.8 | 47.3 | 30 | A |
| 268 | K | CE | 42.3 | 18.5 | 46.5 | 30 | A |
| 268 | K | NZ | 43.5 | 17.6 | 46.3 | 30 | A |
| 268 | K | C | 45.9 | 20.8 | 48.9 | 24 | A |
| 268 | K | O | 47.0 | 21.3 | 48.6 | 23 | A |
| 269 | N | N | 45.8 | 19.6 | 49.4 | 25 | A |
| 269 | N | CA | 47.0 | 18.7 | 49.5 | 26 | A |
| 269 | N | CB | 46.8 | 17.7 | 50.6 | 28 | A |
| 269 | N | CG | 47.2 | 18.3 | 51.9 | 29 | A |
| 269 | N | OD1 | 48.3 | 18.8 | 52.1 | 30 | A |
| 269 | N | ND2 | 46.3 | 18.3 | 52.9 | 30 | A |
| 269 | N | C | 47.1 | 17.9 | 48.2 | 26 | A |
| 269 | N | O | 46.2 | 17.6 | 47.5 | 26 | A |
| 270 | K | N | 48.4 | 17.6 | 47.8 | 28 | A |
| 270 | K | CA | 48.7 | 16.9 | 46.6 | 29 | A |
| 270 | K | CB | 50.3 | 16.9 | 46.5 | 30 | A |
| 270 | K | CG | 50.8 | 16.1 | 45.3 | 33 | A |
| 270 | K | CD | 52.3 | 16.1 | 45.3 | 34 | A |
| 270 | K | CE | 52.9 | 15.4 | 44.1 | 35 | A |
| 270 | K | NZ | 52.7 | 16.1 | 42.8 | 33 | A |
| 270 | K | C | 48.2 | 15.5 | 46.7 | 28 | A |
| 270 | K | O | 48.3 | 14.8 | 47.7 | 29 | A |
| 271 | V | N | 47.8 | 14.9 | 45.5 | 28 | A |
| 271 | V | CA | 47.3 | 13.6 | 45.4 | 27 | A |
| 271 | V | CB | 46.2 | 13.4 | 44.4 | 27 | A |
| 271 | V | CG1 | 45.7 | 12.0 | 44.3 | 27 | A |
| 271 | V | CG2 | 45.0 | 14.3 | 44.8 | 27 | A |
| 271 | V | C | 48.5 | 12.7 | 44.9 | 27 | A |
| 271 | V | O | 49.0 | 12.9 | 43.8 | 27 | A |
| 272 | P | N | 48.9 | 11.7 | 45.7 | 26 | A |
| 272 | P | CD | 48.4 | 11.3 | 47.0 | 26 | A |
| 272 | P | CA | 50.0 | 10.8 | 45.4 | 25 | A |
| 272 | P | CB | 50.0 | 9.8 | 46.5 | 25 | A |
| 272 | P | CG | 49.5 | 10.6 | 47.6 | 27 | A |
| 272 | P | C | 49.9 | 10.2 | 44.0 | 23 | A |
| 272 | P | O | 48.8 | 9.7 | 43.6 | 23 | A |
| 273 | W | N | 51.0 | 10.2 | 43.2 | 23 | A |
| 273 | W | CA | 50.9 | 9.6 | 41.9 | 23 | A |
| 273 | W | CB | 52.2 | 9.8 | 41.2 | 22 | A |
| 273 | W | CG | 52.6 | 11.2 | 40.9 | 22 | A |
| 273 | W | CD2 | 51.8 | 12.1 | 40.0 | 20 | A |
| 273 | W | CE2 | 52.5 | 13.4 | 40.0 | 19 | A |
| 273 | W | CE3 | 50.7 | 12.0 | 39.2 | 21 | A |
| 273 | W | CD1 | 53.6 | 12.0 | 41.4 | 20 | A |
| 273 | W | NE1 | 53.5 | 13.2 | 40.9 | 22 | A |
| 273 | W | CZ2 | 52.0 | 14.5 | 39.3 | 21 | A |
| 273 | W | CZ3 | 50.2 | 13.1 | 38.5 | 23 | A |
| 273 | W | CH2 | 50.9 | 14.3 | 38.6 | 19 | A |
| 273 | W | C | 50.6 | 8.1 | 42.0 | 23 | A |
| 273 | W | O | 49.9 | 7.6 | 41.1 | 23 | A |
| 274 | N | N | 51.1 | 7.4 | 43.0 | 25 | A |
| 274 | N | CA | 50.8 | 6.0 | 43.2 | 27 | A |
| 274 | N | CB | 51.7 | 5.4 | 44.3 | 30 | A |
| 274 | N | CG | 51.6 | 6.2 | 45.6 | 31 | A |
| 274 | N | OD1 | 50.6 | 6.3 | 46.2 | 34 | A |
| 274 | N | ND2 | 52.7 | 6.8 | 46.0 | 36 | A |
| 274 | N | C | 49.4 | 5.7 | 43.5 | 29 | A |
| 274 | N | O | 48.9 | 4.6 | 43.3 | 29 | A |
| 275 | R | N | 48.6 | 6.7 | 44.0 | 30 | A |
| 275 | R | CA | 47.2 | 6.5 | 44.3 | 32 | A |
| 275 | R | CB | 46.7 | 7.5 | 45.3 | 36 | A |
| 275 | R | CG | 47.4 | 7.4 | 46.7 | 43 | A |
| 275 | R | CD | 46.8 | 8.4 | 47.7 | 49 | A |
| 275 | R | NE | 45.4 | 8.2 | 47.9 | 54 | A |
| 275 | R | CZ | 44.6 | 8.9 | 48.7 | 56 | A |
| 275 | R | NH1 | 45.2 | 9.9 | 49.3 | 57 | A |
| 275 | R | NH2 | 43.3 | 8.7 | 48.8 | 57 | A |
| 275 | R | C | 46.4 | 6.6 | 43.0 | 30 | A |
| 275 | R | O | 45.4 | 5.9 | 42.8 | 31 | A |
| 276 | L | N | 46.9 | 7.5 | 42.1 | 28 | A |
| 276 | L | CA | 46.2 | 7.7 | 40.8 | 26 | A |
| 276 | L | CB | 46.6 | 9.0 | 40.2 | 27 | A |
| 276 | L | CG | 45.9 | 10.3 | 40.8 | 28 | A |
| 276 | L | CD1 | 46.7 | 11.5 | 40.3 | 28 | A |
| 276 | L | CD2 | 44.5 | 10.3 | 40.3 | 29 | A |
| 276 | L | C | 46.6 | 6.6 | 39.8 | 24 | A |
| 276 | L | O | 45.8 | 6.2 | 39.0 | 25 | A |
| 277 | F | N | 47.8 | 6.1 | 39.9 | 24 | A |
| 277 | F | CA | 48.3 | 5.0 | 39.1 | 24 | A |
| 277 | F | CB | 49.4 | 5.6 | 38.1 | 24 | A |
| 277 | F | CG | 48.9 | 6.8 | 37.3 | 21 | A |
| 277 | F | CD1 | 47.9 | 6.6 | 36.3 | 22 | A |
| 277 | F | CD2 | 49.3 | 8.1 | 37.6 | 21 | A |
| 277 | F | CE1 | 47.5 | 7.7 | 35.6 | 23 | A |
| 277 | F | CE2 | 48.8 | 9.2 | 36.9 | 22 | A |
| 277 | F | CZ | 47.9 | 9.0 | 35.9 | 21 | A |
| 277 | F | C | 49.0 | 3.9 | 39.9 | 24 | A |
| 277 | F | O | 50.2 | 3.8 | 39.9 | 24 | A |
| 278 | P | N | 48.1 | 3.1 | 40.6 | 25 | A |
| 278 | P | CD | 46.7 | 3.2 | 40.6 | 26 | A |
| 278 | P | CA | 48.6 | 2.1 | 41.5 | 26 | A |
| 278 | P | CB | 47.4 | 1.6 | 42.3 | 26 | A |
| 278 | P | CG | 46.3 | 1.8 | 41.2 | 26 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| Residue | AA | Atom | X | Y | Z | B | Chain |
|---|---|---|---|---|---|---|---|
| 278 | P | C | 49.3 | 0.9 | 40.8 | 27 | A |
| 278 | P | O | 50.0 | 0.1 | 41.4 | 28 | A |
| 279 | N | N | 49.1 | 0.8 | 39.5 | 28 | A |
| 279 | N | CA | 49.7 | −0.3 | 38.7 | 28 | A |
| 279 | N | CB | 48.7 | −1.0 | 37.8 | 30 | A |
| 279 | N | CG | 47.5 | −1.6 | 38.6 | 32 | A |
| 279 | N | OD1 | 46.4 | −1.7 | 38.1 | 34 | A |
| 279 | N | ND2 | 47.8 | −1.9 | 39.9 | 33 | A |
| 279 | N | C | 50.9 | 0.1 | 37.9 | 27 | A |
| 279 | N | O | 51.5 | −0.7 | 37.1 | 28 | A |
| 280 | A | N | 51.3 | 1.4 | 38.0 | 26 | A |
| 280 | A | CA | 52.4 | 1.9 | 37.1 | 25 | A |
| 280 | A | CB | 52.2 | 3.4 | 36.9 | 24 | A |
| 280 | A | C | 53.8 | 1.7 | 37.7 | 24 | A |
| 280 | A | O | 54.0 | 1.5 | 38.9 | 24 | A |
| 281 | D | N | 54.8 | 1.6 | 36.8 | 23 | A |
| 281 | D | CA | 56.2 | 1.4 | 37.2 | 23 | A |
| 281 | D | CB | 57.0 | 1.4 | 35.9 | 26 | A |
| 281 | D | CG | 58.5 | 1.1 | 36.2 | 30 | A |
| 281 | D | OD1 | 59.1 | 1.8 | 37.0 | 32 | A |
| 281 | D | OD2 | 59.0 | 0.1 | 35.7 | 34 | A |
| 281 | D | C | 56.6 | 2.7 | 38.1 | 23 | A |
| 281 | D | O | 56.3 | 3.8 | 37.7 | 22 | A |
| 282 | S | N | 57.3 | 2.4 | 39.1 | 20 | A |
| 282 | S | CA | 57.7 | 3.5 | 40.0 | 21 | A |
| 282 | S | CB | 58.4 | 3.0 | 41.3 | 23 | A |
| 282 | S | OG | 59.7 | 2.4 | 40.9 | 27 | A |
| 282 | S | C | 58.6 | 4.6 | 39.3 | 20 | A |
| 282 | S | O | 58.5 | 5.8 | 39.5 | 19 | A |
| 283 | K | N | 59.5 | 4.1 | 38.4 | 19 | A |
| 283 | K | CA | 60.4 | 5.0 | 37.7 | 19 | A |
| 283 | K | CB | 61.4 | 4.2 | 36.9 | 19 | A |
| 283 | K | CG | 62.5 | 3.6 | 37.8 | 22 | A |
| 283 | K | CD | 63.5 | 2.8 | 37.0 | 24 | A |
| 283 | K | CE | 64.6 | 2.2 | 37.9 | 27 | A |
| 283 | K | NZ | 65.5 | 1.3 | 37.2 | 28 | A |
| 283 | K | C | 59.6 | 5.9 | 36.7 | 18 | A |
| 283 | K | O | 59.9 | 7.1 | 36.5 | 17 | A |
| 284 | A | N | 58.5 | 5.3 | 36.1 | 17 | A |
| 284 | A | CA | 57.6 | 6.1 | 35.2 | 17 | A |
| 284 | A | CB | 56.6 | 5.2 | 34.6 | 17 | A |
| 284 | A | C | 57.0 | 7.2 | 36.0 | 18 | A |
| 284 | A | O | 56.8 | 8.3 | 35.5 | 17 | A |
| 285 | L | N | 56.5 | 6.9 | 37.2 | 17 | A |
| 285 | L | CA | 55.8 | 7.9 | 38.0 | 16 | A |
| 285 | L | CB | 55.1 | 7.3 | 39.2 | 17 | A |
| 285 | L | CG | 54.0 | 6.3 | 38.9 | 16 | A |
| 285 | L | CD1 | 53.3 | 5.8 | 40.2 | 18 | A |
| 285 | L | CD2 | 53.0 | 7.0 | 38.0 | 18 | A |
| 285 | L | C | 56.8 | 9.0 | 38.5 | 15 | A |
| 285 | L | O | 56.4 | 10.2 | 38.7 | 17 | A |
| 286 | D | N | 58.1 | 8.7 | 38.7 | 16 | A |
| 286 | D | CA | 59.0 | 9.7 | 39.1 | 16 | A |
| 286 | D | CB | 60.4 | 9.0 | 39.5 | 18 | A |
| 286 | D | CG | 61.4 | 10.0 | 40.1 | 20 | A |
| 286 | D | OD1 | 62.2 | 10.5 | 39.3 | 20 | A |
| 286 | D | OD2 | 61.3 | 10.3 | 41.3 | 24 | A |
| 286 | D | C | 59.3 | 10.7 | 38.0 | 16 | A |
| 286 | D | O | 59.4 | 11.9 | 38.2 | 16 | A |
| 287 | L | N | 59.3 | 10.1 | 36.8 | 15 | A |
| 287 | L | CA | 59.5 | 11.0 | 35.6 | 15 | A |
| 287 | L | CB | 59.9 | 10.2 | 34.3 | 14 | A |
| 287 | L | CG | 60.0 | 10.9 | 33.0 | 14 | A |
| 287 | L | CD1 | 61.0 | 12.1 | 33.2 | 14 | A |
| 287 | L | CD2 | 60.6 | 10.0 | 32.0 | 13 | A |
| 287 | L | C | 58.3 | 11.9 | 35.4 | 15 | A |
| 287 | L | O | 58.4 | 13.0 | 35.0 | 15 | A |
| 288 | L | N | 57.1 | 11.2 | 35.6 | 15 | A |
| 288 | L | CA | 55.8 | 12.0 | 35.4 | 14 | A |
| 288 | L | CB | 54.7 | 11.0 | 35.7 | 14 | A |
| 288 | L | CG | 53.2 | 11.6 | 35.5 | 13 | A |
| 288 | L | CD1 | 53.0 | 12.1 | 34.1 | 13 | A |
| 288 | L | CD2 | 52.2 | 10.6 | 36.0 | 14 | A |
| 288 | L | C | 55.8 | 13.2 | 36.3 | 15 | A |
| 288 | L | O | 55.4 | 14.3 | 36.0 | 14 | A |
| 289 | D | N | 56.2 | 12.9 | 37.6 | 14 | A |
| 289 | D | CA | 56.2 | 14.0 | 38.6 | 15 | A |
| 289 | D | CB | 56.8 | 13.5 | 39.9 | 17 | A |
| 289 | D | CG | 56.8 | 14.5 | 41.0 | 18 | A |
| 289 | D | OD1 | 55.7 | 15.0 | 41.4 | 20 | A |
| 289 | D | OD2 | 57.9 | 14.9 | 41.4 | 22 | A |
| 289 | D | C | 57.1 | 15.2 | 38.1 | 15 | A |
| 289 | D | O | 56.7 | 16.4 | 38.3 | 15 | A |
| 290 | K | N | 58.2 | 14.9 | 37.6 | 14 | A |
| 290 | K | CA | 59.2 | 16.0 | 37.1 | 15 | A |
| 290 | K | CB | 60.5 | 15.4 | 36.8 | 15 | A |
| 290 | K | CG | 61.2 | 14.9 | 38.1 | 19 | A |
| 290 | K | CD | 62.6 | 14.2 | 37.9 | 20 | A |
| 290 | K | CE | 63.4 | 14.0 | 39.1 | 22 | A |
| 290 | K | NZ | 62.6 | 13.2 | 40.2 | 24 | A |
| 290 | K | C | 58.7 | 16.7 | 35.8 | 13 | A |
| 290 | K | O | 59.0 | 17.9 | 35.7 | 15 | A |
| 291 | M | N | 57.9 | 16.0 | 35.0 | 14 | A |
| 291 | M | CA | 57.3 | 16.7 | 33.8 | 13 | A |
| 291 | M | CB | 56.9 | 15.6 | 32.8 | 14 | A |
| 291 | M | CG | 58.1 | 14.9 | 32.2 | 15 | A |
| 291 | M | SD | 57.6 | 13.7 | 30.9 | 22 | A |
| 291 | M | CE | 58.3 | 14.5 | 29.5 | 24 | A |
| 291 | M | C | 56.1 | 17.5 | 34.2 | 13 | A |
| 291 | M | O | 55.9 | 18.6 | 33.6 | 15 | A |
| 292 | L | N | 55.3 | 17.0 | 35.2 | 13 | A |
| 292 | L | CA | 54.1 | 17.8 | 35.6 | 13 | A |
| 292 | L | CB | 53.0 | 16.8 | 35.8 | 12 | A |
| 292 | L | CG | 52.5 | 16.0 | 34.6 | 12 | A |
| 292 | L | CD1 | 51.3 | 15.2 | 34.9 | 13 | A |
| 292 | L | CD2 | 52.2 | 17.1 | 33.5 | 13 | A |
| 292 | L | C | 54.4 | 18.6 | 36.8 | 15 | A |
| 292 | L | O | 53.7 | 18.5 | 37.8 | 19 | A |
| 293 | T | N | 55.5 | 19.4 | 36.8 | 14 | A |
| 293 | T | CA | 55.9 | 20.2 | 37.9 | 14 | A |
| 293 | T | CB | 57.4 | 20.4 | 37.9 | 16 | A |
| 293 | T | OG1 | 58.0 | 19.1 | 38.3 | 20 | A |
| 293 | T | CG2 | 57.9 | 21.5 | 38.8 | 19 | A |
| 293 | T | C | 55.2 | 21.6 | 37.6 | 14 | A |
| 293 | T | O | 55.3 | 22.1 | 36.5 | 14 | A |
| 294 | F | N | 54.6 | 22.2 | 38.7 | 14 | A |
| 294 | F | CA | 53.9 | 23.5 | 38.6 | 14 | A |
| 294 | F | CB | 53.3 | 23.8 | 39.9 | 15 | A |
| 294 | F | CG | 52.6 | 25.1 | 39.9 | 16 | A |
| 294 | F | CD1 | 51.3 | 25.2 | 39.5 | 16 | A |
| 294 | F | CD2 | 53.2 | 26.3 | 40.3 | 17 | A |
| 294 | F | CE1 | 50.5 | 26.4 | 39.4 | 17 | A |
| 294 | F | CE2 | 52.5 | 27.5 | 40.3 | 17 | A |
| 294 | F | CZ | 51.1 | 27.5 | 39.9 | 15 | A |
| 294 | F | C | 54.8 | 24.6 | 38.0 | 14 | A |
| 294 | F | O | 54.4 | 25.3 | 37.1 | 15 | A |
| 295 | N | N | 55.9 | 24.9 | 38.7 | 15 | A |
| 295 | N | CA | 56.8 | 26.0 | 38.3 | 15 | A |
| 295 | N | CB | 57.8 | 26.3 | 39.4 | 17 | A |
| 295 | N | CG | 58.6 | 27.6 | 39.2 | 20 | A |
| 295 | N | OD1 | 58.8 | 28.0 | 38.0 | 20 | A |
| 295 | N | ND2 | 59.1 | 28.2 | 40.3 | 21 | A |
| 295 | N | C | 57.6 | 25.6 | 37.0 | 14 | A |
| 295 | N | O | 58.4 | 24.7 | 37.0 | 14 | A |
| 296 | P | N | 57.3 | 26.3 | 35.9 | 14 | A |
| 296 | P | CD | 56.5 | 27.5 | 35.6 | 15 | A |
| 296 | P | CA | 58.0 | 25.9 | 34.8 | 16 | A |
| 296 | P | CB | 57.4 | 26.8 | 33.6 | 16 | A |
| 296 | P | CG | 57.1 | 28.1 | 34.4 | 18 | A |
| 296 | P | C | 59.6 | 26.0 | 34.7 | 16 | A |
| 296 | P | O | 60.3 | 25.3 | 34.0 | 18 | A |
| 297 | H | N | 60.0 | 26.9 | 35.7 | 17 | A |

TABLE 1-continued

Structural Coordinates of crystalline Ah₆-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| 297 | H | CA  | 61.5 | 27.0 | 35.8 | 20 | A |
|-----|---|-----|------|------|------|----|---|
| 297 | H | CB  | 61.8 | 28.3 | 36.6 | 23 | A |
| 297 | H | CG  | 61.4 | 29.6 | 36.0 | 27 | A |
| 297 | H | CD2 | 62.1 | 30.5 | 35.2 | 29 | A |
| 297 | H | ND1 | 60.1 | 30.0 | 36.0 | 30 | A |
| 297 | H | CE1 | 60.0 | 31.1 | 35.3 | 30 | A |
| 297 | H | NE2 | 61.2 | 31.4 | 34.8 | 30 | A |
| 297 | H | C   | 62.1 | 25.8 | 36.5 | 20 | A |
| 297 | H | O   | 63.3 | 25.6 | 36.4 | 22 | A |
| 298 | K | N   | 61.3 | 25.0 | 37.2 | 18 | A |
| 298 | K | CA  | 61.8 | 23.9 | 37.9 | 18 | A |
| 298 | K | CB  | 61.2 | 23.8 | 39.3 | 18 | A |
| 298 | K | CG  | 61.5 | 24.9 | 40.2 | 22 | A |
| 298 | K | CD  | 60.8 | 24.7 | 41.6 | 23 | A |
| 298 | K | CE  | 61.1 | 25.9 | 42.5 | 26 | A |
| 298 | K | NZ  | 60.3 | 25.7 | 43.8 | 27 | A |
| 298 | K | C   | 61.5 | 22.6 | 37.1 | 17 | A |
| 298 | K | O   | 61.9 | 21.5 | 37.5 | 18 | A |
| 299 | R | N   | 60.7 | 22.7 | 36.1 | 15 | A |
| 299 | R | CA  | 60.3 | 21.6 | 35.3 | 14 | A |
| 299 | R | CB  | 59.1 | 22.0 | 34.3 | 14 | A |
| 299 | R | CG  | 58.3 | 20.9 | 33.6 | 13 | A |
| 299 | R | CD  | 57.2 | 21.5 | 32.8 | 11 | A |
| 299 | R | NE  | 56.3 | 22.2 | 33.7 | 13 | A |
| 299 | R | CZ  | 55.5 | 23.3 | 33.3 | 12 | A |
| 299 | R | NH1 | 55.6 | 23.7 | 32.1 | 12 | A |
| 299 | R | NH2 | 54.8 | 23.9 | 34.2 | 12 | A |
| 299 | R | C   | 61.4 | 21.0 | 34.5 | 13 | A |
| 299 | R | O   | 62.3 | 21.7 | 34.0 | 14 | A |
| 300 | I | N   | 61.5 | 19.7 | 34.4 | 13 | A |
| 300 | I | CA  | 62.6 | 19.0 | 33.7 | 14 | A |
| 300 | I | CB  | 62.4 | 17.4 | 33.9 | 14 | A |
| 300 | I | CG2 | 61.2 | 16.9 | 33.1 | 15 | A |
| 300 | I | CG1 | 63.7 | 16.7 | 33.5 | 16 | A |
| 300 | I | CD1 | 63.6 | 15.2 | 33.9 | 18 | A |
| 300 | I | C   | 62.6 | 19.3 | 32.2 | 14 | A |
| 300 | I | O   | 61.6 | 19.5 | 31.6 | 14 | A |
| 301 | E | N   | 63.8 | 19.5 | 31.6 | 12 | A |
| 301 | E | CA  | 64.0 | 19.8 | 30.2 | 12 | A |
| 301 | E | CB  | 65.2 | 20.7 | 30.0 | 14 | A |
| 301 | E | CG  | 65.2 | 22.0 | 30.7 | 17 | A |
| 301 | E | CD  | 66.1 | 23.1 | 30.1 | 22 | A |
| 301 | E | OE1 | 67.0 | 22.7 | 29.4 | 24 | A |
| 301 | E | OE2 | 65.8 | 24.3 | 30.3 | 26 | A |
| 301 | E | C   | 64.1 | 18.5 | 29.4 | 13 | A |
| 301 | E | O   | 64.4 | 17.4 | 30.0 | 12 | A |
| 302 | V | N   | 64.0 | 18.6 | 28.1 | 12 | A |
| 302 | V | CA  | 64.0 | 17.4 | 27.3 | 11 | A |
| 302 | V | CB  | 63.7 | 17.7 | 25.8 | 11 | A |
| 302 | V | CG1 | 64.9 | 18.5 | 25.2 | 13 | A |
| 302 | V | CG2 | 63.4 | 16.5 | 25.0 | 13 | A |
| 302 | V | C   | 65.2 | 16.5 | 27.4 | 11 | A |
| 302 | V | O   | 65.1 | 15.3 | 27.4 | 12 | A |
| 303 | E | N   | 66.4 | 17.1 | 27.5 | 13 | A |
| 303 | E | CA  | 67.6 | 16.2 | 27.6 | 14 | A |
| 303 | E | CB  | 68.9 | 17.1 | 27.4 | 15 | A |
| 303 | E | CG  | 69.1 | 17.6 | 26.0 | 20 | A |
| 303 | E | CD  | 70.2 | 18.6 | 25.8 | 23 | A |
| 303 | E | OE1 | 70.1 | 19.6 | 26.5 | 27 | A |
| 303 | E | OE2 | 71.0 | 18.4 | 24.9 | 27 | A |
| 303 | E | C   | 67.7 | 15.5 | 28.9 | 15 | A |
| 303 | E | O   | 68.2 | 14.4 | 29.0 | 15 | A |
| 304 | Q | N   | 67.2 | 16.2 | 30.0 | 14 | A |
| 304 | Q | CA  | 67.1 | 15.6 | 31.3 | 14 | A |
| 304 | Q | CB  | 66.7 | 16.6 | 32.3 | 16 | A |
| 304 | Q | CG  | 67.7 | 17.6 | 32.7 | 14 | A |
| 304 | Q | CD  | 67.1 | 18.6 | 33.7 | 17 | A |
| 304 | Q | OE1 | 66.2 | 19.4 | 33.3 | 17 | A |
| 304 | Q | NE2 | 67.5 | 18.6 | 34.9 | 17 | A |
| 304 | Q | C   | 66.2 | 14.4 | 31.3 | 15 | A |
| 304 | Q | O   | 66.4 | 13.4 | 32.0 | 15 | A |
| 305 | A | N   | 65.0 | 14.6 | 30.6 | 13 | A |
| 305 | A | CA  | 64.0 | 13.5 | 30.6 | 13 | A |
| 305 | A | CB  | 62.8 | 14.1 | 29.9 | 12 | A |
| 305 | A | C   | 64.6 | 12.3 | 29.9 | 14 | A |
| 305 | A | O   | 64.4 | 11.2 | 30.3 | 14 | A |
| 306 | L | N   | 65.3 | 12.5 | 28.8 | 12 | A |
| 306 | L | CA  | 65.9 | 11.4 | 28.1 | 13 | A |
| 306 | L | CB  | 66.6 | 11.9 | 26.8 | 13 | A |
| 306 | L | CG  | 65.7 | 12.2 | 25.6 | 12 | A |
| 306 | L | CD1 | 66.5 | 13.1 | 24.6 | 13 | A |
| 306 | L | CD2 | 65.2 | 10.9 | 25.0 | 13 | A |
| 306 | L | C   | 66.9 | 10.6 | 28.9 | 13 | A |
| 306 | L | O   | 67.0 | 9.4  | 28.8 | 14 | A |
| 307 | A | N   | 67.6 | 11.3 | 29.8 | 14 | A |
| 307 | A | CA  | 68.5 | 10.7 | 30.7 | 14 | A |
| 307 | A | CB  | 69.6 | 11.7 | 31.1 | 15 | A |
| 307 | A | C   | 68.0 | 10.1 | 32.0 | 15 | A |
| 307 | A | O   | 68.7 | 9.6  | 32.9 | 17 | A |
| 308 | H | N   | 66.6 | 10.2 | 32.2 | 16 | A |
| 308 | H | CA  | 66.0 | 9.7  | 33.4 | 16 | A |
| 308 | H | CB  | 64.5 | 10.1 | 33.4 | 15 | A |
| 308 | H | CG  | 63.8 | 9.8  | 34.7 | 15 | A |
| 308 | H | CD2 | 63.6 | 10.6 | 35.8 | 16 | A |
| 308 | H | ND1 | 63.3 | 8.6  | 35.0 | 15 | A |
| 308 | H | CE1 | 62.8 | 8.6  | 36.2 | 14 | A |
| 308 | H | NE2 | 62.9 | 9.8  | 36.7 | 16 | A |
| 308 | H | C   | 66.1 | 8.2  | 33.4 | 16 | A |
| 308 | H | O   | 66.0 | 7.5  | 32.4 | 16 | A |
| 309 | P | N   | 66.2 | 7.6  | 34.7 | 17 | A |
| 309 | P | CD  | 66.4 | 8.2  | 35.9 | 17 | A |
| 309 | P | CA  | 66.2 | 6.1  | 34.8 | 17 | A |
| 309 | P | CB  | 66.2 | 5.9  | 36.3 | 18 | A |
| 309 | P | CG  | 66.9 | 7.1  | 36.8 | 18 | A |
| 309 | P | C   | 65.2 | 5.3  | 34.1 | 17 | A |
| 309 | P | O   | 65.4 | 4.2  | 33.6 | 18 | A |
| 310 | Y | N   | 63.9 | 5.8  | 33.9 | 16 | A |
| 310 | Y | CA  | 62.9 | 5.1  | 33.3 | 15 | A |
| 310 | Y | CB  | 61.6 | 5.9  | 33.3 | 15 | A |
| 310 | Y | CG  | 60.4 | 5.2  | 32.6 | 16 | A |
| 310 | Y | CD1 | 59.9 | 4.0  | 33.1 | 16 | A |
| 310 | Y | CE1 | 58.8 | 3.3  | 32.5 | 17 | A |
| 310 | Y | CD2 | 59.7 | 5.8  | 31.6 | 15 | A |
| 310 | Y | CE2 | 58.6 | 5.2  | 31.0 | 16 | A |
| 310 | Y | CZ  | 58.2 | 3.9  | 31.5 | 16 | A |
| 310 | Y | OH  | 57.1 | 3.3  | 30.9 | 18 | A |
| 310 | Y | C   | 63.2 | 4.8  | 31.8 | 15 | A |
| 310 | Y | O   | 62.8 | 3.7  | 31.3 | 17 | A |
| 311 | L | N   | 64.0 | 5.6  | 31.2 | 16 | A |
| 311 | L | CA  | 64.4 | 5.4  | 29.8 | 15 | A |
| 311 | L | CB  | 64.2 | 6.7  | 29.0 | 16 | A |
| 311 | L | CG  | 62.7 | 7.3  | 29.0 | 15 | A |
| 311 | L | CD1 | 62.7 | 8.7  | 28.4 | 17 | A |
| 311 | L | CD2 | 61.8 | 6.4  | 28.3 | 16 | A |
| 311 | L | C   | 65.8 | 5.0  | 29.6 | 17 | A |
| 311 | L | O   | 66.3 | 5.0  | 28.4 | 17 | A |
| 312 | E | N   | 66.5 | 4.6  | 30.7 | 18 | A |
| 312 | E | CA  | 67.9 | 4.2  | 30.6 | 19 | A |
| 312 | E | CB  | 68.4 | 3.7  | 32.0 | 23 | A |
| 312 | E | CG  | 67.7 | 2.5  | 32.5 | 27 | A |
| 312 | E | CD  | 67.9 | 2.2  | 34.0 | 30 | A |
| 312 | E | OE1 | 69.1 | 2.3  | 34.4 | 32 | A |
| 312 | E | OE2 | 67.0 | 1.9  | 34.7 | 33 | A |
| 312 | E | C   | 68.3 | 3.1  | 29.6 | 19 | A |
| 312 | E | O   | 69.4 | 3.1  | 29.1 | 20 | A |
| 313 | Q | N   | 67.3 | 2.2  | 29.2 | 19 | A |
| 313 | Q | CA  | 67.6 | 1.2  | 28.3 | 21 | A |
| 313 | Q | CB  | 66.6 | 0.1  | 28.3 | 22 | A |
| 313 | Q | CG  | 65.2 | 0.5  | 27.8 | 23 | A |
| 313 | Q | CD  | 64.2 | -0.6 | 27.9 | 25 | A |
| 313 | Q | OE1 | 64.3 | -1.7 | 27.2 | 27 | A |
| 313 | Q | NE2 | 63.2 | -0.5 | 28.8 | 25 | A |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 313 | Q | C | 67.8 | 1.7 | 26.8 | 21 | A |
| 313 | Q | O | 68.4 | 1.0 | 26.0 | 22 | A |
| 314 | Y | N | 67.2 | 2.9 | 26.6 | 18 | A |
| 314 | Y | CA | 67.2 | 3.4 | 25.2 | 18 | A |
| 314 | Y | CB | 65.8 | 3.9 | 24.8 | 17 | A |
| 314 | Y | CG | 64.9 | 2.7 | 24.6 | 17 | A |
| 314 | Y | CD1 | 65.1 | 1.7 | 23.7 | 17 | A |
| 314 | Y | CE1 | 64.3 | 0.6 | 23.6 | 19 | A |
| 314 | Y | CD2 | 63.7 | 2.6 | 25.4 | 17 | A |
| 314 | Y | CE2 | 62.9 | 1.5 | 25.4 | 17 | A |
| 314 | Y | CZ | 63.2 | 0.5 | 24.4 | 18 | A |
| 314 | Y | OH | 62.3 | −0.6 | 24.4 | 19 | A |
| 314 | Y | C | 68.2 | 4.6 | 25.1 | 16 | A |
| 314 | Y | O | 68.7 | 4.9 | 24.0 | 17 | A |
| 315 | Y | N | 68.4 | 5.3 | 26.2 | 16 | A |
| 315 | Y | CA | 69.3 | 6.5 | 26.2 | 15 | A |
| 315 | Y | CB | 69.5 | 7.0 | 27.7 | 17 | A |
| 315 | Y | CG | 70.2 | 8.3 | 27.8 | 17 | A |
| 315 | Y | CD1 | 69.8 | 9.4 | 27.1 | 16 | A |
| 315 | Y | CE1 | 70.5 | 10.6 | 27.3 | 18 | A |
| 315 | Y | CD2 | 71.2 | 8.4 | 28.8 | 18 | A |
| 315 | Y | CE2 | 71.9 | 9.6 | 29.0 | 19 | A |
| 315 | Y | CZ | 71.5 | 10.7 | 28.2 | 17 | A |
| 315 | Y | OH | 72.1 | 11.9 | 28.4 | 22 | A |
| 315 | Y | C | 70.7 | 6.4 | 25.5 | 15 | A |
| 315 | Y | O | 71.4 | 5.5 | 25.9 | 17 | A |
| 316 | D | N | 70.9 | 7.2 | 24.6 | 13 | A |
| 316 | D | CA | 72.2 | 7.2 | 23.8 | 13 | A |
| 316 | D | CB | 72.2 | 6.1 | 22.8 | 15 | A |
| 316 | D | CG | 73.5 | 6.1 | 22.0 | 17 | A |
| 316 | D | OD1 | 74.4 | 6.9 | 22.3 | 16 | A |
| 316 | D | OD2 | 73.7 | 5.2 | 21.1 | 19 | A |
| 316 | D | C | 72.3 | 8.6 | 23.1 | 13 | A |
| 316 | D | O | 71.8 | 8.8 | 22.0 | 13 | A |
| 317 | P | N | 72.9 | 9.6 | 23.8 | 14 | A |
| 317 | P | CD | 73.5 | 9.5 | 25.1 | 14 | A |
| 317 | P | CA | 73.1 | 10.9 | 23.2 | 16 | A |
| 317 | P | CB | 74.0 | 11.6 | 24.2 | 17 | A |
| 317 | P | CG | 73.7 | 11.0 | 25.5 | 18 | A |
| 317 | P | C | 73.6 | 11.0 | 21.8 | 16 | A |
| 317 | P | O | 73.3 | 11.9 | 21.0 | 15 | A |
| 318 | S | N | 74.5 | 10.1 | 21.5 | 15 | A |
| 318 | S | CA | 75.1 | 10.0 | 20.1 | 16 | A |
| 318 | S | CB | 76.4 | 9.1 | 20.1 | 15 | A |
| 318 | S | OG | 76.0 | 7.7 | 20.1 | 16 | A |
| 318 | S | C | 74.2 | 9.6 | 19.1 | 15 | A |
| 318 | S | O | 74.4 | 9.7 | 17.9 | 16 | A |
| 319 | D | N | 73.0 | 9.0 | 19.5 | 14 | A |
| 319 | D | CA | 72.0 | 8.5 | 18.5 | 14 | A |
| 319 | D | CB | 71.7 | 7.0 | 18.8 | 15 | A |
| 319 | D | CG | 70.9 | 6.4 | 17.7 | 17 | A |
| 319 | D | OD1 | 71.0 | 6.8 | 16.5 | 17 | A |
| 319 | D | OD2 | 70.1 | 5.5 | 18.0 | 20 | A |
| 319 | D | C | 70.7 | 9.3 | 18.7 | 14 | A |
| 319 | D | O | 69.6 | 8.9 | 18.4 | 14 | A |
| 320 | E | N | 70.8 | 10.5 | 19.3 | 14 | A |
| 320 | E | CA | 69.7 | 11.5 | 19.5 | 13 | A |
| 320 | E | CB | 69.5 | 11.6 | 21.1 | 14 | A |
| 320 | E | CG | 68.8 | 10.3 | 21.6 | 14 | A |
| 320 | E | CD | 69.1 | 10.0 | 23.1 | 15 | A |
| 320 | E | OE1 | 69.5 | 11.0 | 23.8 | 15 | A |
| 320 | E | OE2 | 68.8 | 8.9 | 23.5 | 13 | A |
| 320 | E | C | 70.2 | 12.8 | 18.9 | 13 | A |
| 320 | E | O | 70.6 | 13.7 | 19.6 | 13 | A |
| 321 | P | N | 70.1 | 12.9 | 17.6 | 14 | A |
| 321 | P | CD | 69.5 | 11.9 | 16.7 | 14 | A |
| 321 | P | CA | 70.6 | 14.1 | 16.9 | 14 | A |
| 321 | P | CB | 70.5 | 13.6 | 15.4 | 16 | A |
| 321 | P | CG | 69.3 | 12.7 | 15.4 | 16 | A |
| 321 | P | C | 69.9 | 15.4 | 17.1 | 15 | A |
| 321 | P | O | 68.7 | 15.5 | 17.5 | 14 | A |
| 322 | I | N | 70.6 | 16.5 | 16.9 | 14 | A |
| 322 | I | CA | 70.1 | 17.8 | 17.0 | 14 | A |
| 322 | I | CB | 71.0 | 18.7 | 18.0 | 15 | A |
| 322 | I | CG2 | 70.8 | 18.1 | 19.4 | 16 | A |
| 322 | I | CG1 | 72.4 | 18.8 | 17.6 | 15 | A |
| 322 | I | CD1 | 73.2 | 19.8 | 18.4 | 18 | A |
| 322 | I | C | 70.1 | 18.5 | 15.6 | 14 | A |
| 322 | I | O | 70.8 | 18.0 | 14.7 | 15 | A |
| 323 | A | N | 69.4 | 19.6 | 15.5 | 14 | A |
| 323 | A | CA | 69.3 | 20.3 | 14.2 | 14 | A |
| 323 | A | CB | 68.1 | 21.3 | 14.3 | 15 | A |
| 323 | A | C | 70.6 | 21.0 | 13.8 | 16 | A |
| 323 | A | O | 71.3 | 21.6 | 14.5 | 17 | A |
| 324 | E | N | 70.8 | 21.0 | 12.5 | 19 | A |
| 324 | E | CA | 72.0 | 21.6 | 11.8 | 22 | A |
| 324 | E | CB | 72.3 | 21.0 | 10.5 | 26 | A |
| 324 | E | CG | 73.3 | 21.7 | 9.7 | 32 | A |
| 324 | E | CD | 73.5 | 21.1 | 8.3 | 35 | A |
| 324 | E | OE1 | 72.5 | 21.1 | 7.5 | 37 | A |
| 324 | E | OE2 | 74.6 | 20.7 | 8.0 | 37 | A |
| 324 | E | C | 71.7 | 23.1 | 11.7 | 24 | A |
| 324 | E | O | 72.6 | 23.9 | 11.8 | 26 | A |
| 325 | A | N | 70.5 | 23.5 | 11.3 | 24 | A |
| 325 | A | CA | 70.1 | 24.9 | 11.1 | 23 | A |
| 325 | A | CB | 69.9 | 25.1 | 9.6 | 24 | A |
| 325 | A | C | 68.9 | 25.4 | 11.9 | 23 | A |
| 325 | A | O | 67.8 | 25.4 | 11.4 | 22 | A |
| 326 | P | N | 69.2 | 25.8 | 13.2 | 22 | A |
| 326 | P | CD | 70.4 | 25.7 | 13.9 | 22 | A |
| 326 | P | CA | 68.1 | 26.3 | 14.0 | 23 | A |
| 326 | P | CB | 68.8 | 26.5 | 15.4 | 22 | A |
| 326 | P | CG | 70.0 | 25.6 | 15.3 | 25 | A |
| 326 | P | C | 67.5 | 27.6 | 13.5 | 23 | A |
| 326 | P | O | 68.2 | 28.3 | 12.7 | 23 | A |
| 327 | F | N | 66.3 | 27.9 | 13.9 | 22 | A |
| 327 | F | CA | 65.6 | 29.2 | 13.5 | 23 | A |
| 327 | F | CB | 64.1 | 29.0 | 13.5 | 22 | A |
| 327 | F | CG | 63.6 | 28.3 | 12.4 | 21 | A |
| 327 | F | CD1 | 63.3 | 28.9 | 11.2 | 21 | A |
| 327 | F | CD2 | 63.4 | 26.9 | 12.4 | 20 | A |
| 327 | F | CE1 | 62.8 | 28.2 | 10.1 | 21 | A |
| 327 | F | CE2 | 62.9 | 26.2 | 11.3 | 20 | A |
| 327 | F | CZ | 62.6 | 26.9 | 10.1 | 22 | A |
| 327 | F | C | 66.1 | 30.2 | 14.6 | 26 | A |
| 327 | F | O | 65.5 | 30.3 | 15.7 | 26 | A |
| 328 | K | N | 67.1 | 30.9 | 14.3 | 29 | A |
| 328 | K | CA | 67.6 | 31.9 | 15.2 | 31 | A |
| 328 | K | CB | 69.1 | 32.3 | 14.8 | 32 | A |
| 328 | K | CG | 70.0 | 31.1 | 14.8 | 34 | A |
| 328 | K | CD | 71.5 | 31.6 | 14.4 | 35 | A |
| 328 | K | CE | 71.5 | 32.3 | 13.1 | 37 | A |
| 328 | K | NZ | 71.1 | 31.4 | 12.0 | 37 | A |
| 328 | K | C | 66.8 | 33.2 | 15.5 | 32 | A |
| 328 | K | O | 66.9 | 33.8 | 16.5 | 33 | A |
| 329 | F | N | 66.0 | 33.6 | 14.5 | 33 | A |
| 329 | F | CA | 65.2 | 34.8 | 14.7 | 34 | A |
| 329 | F | CB | 65.7 | 35.9 | 13.7 | 35 | A |
| 329 | F | CG | 67.2 | 36.1 | 13.7 | 37 | A |
| 329 | F | CD1 | 68.0 | 35.3 | 12.9 | 38 | A |
| 329 | F | CD2 | 67.7 | 37.1 | 14.5 | 38 | A |
| 329 | F | CE1 | 69.4 | 35.4 | 12.9 | 39 | A |
| 329 | F | CE2 | 69.1 | 37.3 | 14.5 | 39 | A |
| 329 | F | CZ | 69.9 | 36.4 | 13.7 | 39 | A |
| 329 | F | C | 63.7 | 34.5 | 14.5 | 33 | A |
| 329 | F | O | 63.3 | 33.5 | 13.8 | 31 | A |
| 330 | D | N | 62.9 | 35.4 | 15.0 | 34 | A |
| 330 | D | CA | 61.5 | 35.3 | 14.8 | 35 | A |
| 330 | D | CB | 60.7 | 36.4 | 15.7 | 36 | A |
| 330 | D | CG | 61.2 | 36.4 | 17.1 | 38 | A |
| 330 | D | OD1 | 61.1 | 35.3 | 17.7 | 38 | A |
| 330 | D | OD2 | 61.5 | 37.5 | 17.6 | 39 | A |

TABLE 1-continued

Structural Coordinates of crystalline Ah$_6$-ERK2 [non-phosphorlylated, SEQ ID NO: 5] form 1.

The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| 330 | D | C | 61.1 | 35.5 | 13.4 | 35 | A |
|---|---|---|---|---|---|---|---|
| 330 | D | O | 61.8 | 36.3 | 12.7 | 35 | A |
| 331 | M | N | 60.1 | 34.9 | 12.9 | 36 | A |
| 331 | M | CA | 59.7 | 35.0 | 11.5 | 37 | A |
| 331 | M | CB | 58.8 | 33.8 | 11.1 | 35 | A |
| 331 | M | CG | 59.5 | 32.5 | 11.4 | 33 | A |
| 331 | M | SD | 58.5 | 31.1 | 10.6 | 32 | A |
| 331 | M | CE | 59.9 | 29.9 | 10.4 | 31 | A |
| 331 | M | C | 58.9 | 36.3 | 11.2 | 39 | A |
| 331 | M | O | 58.8 | 36.7 | 10.1 | 39 | A |
| 332 | E | N | 58.4 | 36.9 | 12.3 | 41 | A |
| 332 | E | CA | 57.7 | 38.2 | 12.2 | 43 | A |
| 332 | E | CB | 58.7 | 39.4 | 12.1 | 45 | A |
| 332 | E | CG | 59.6 | 39.3 | 10.9 | 49 | A |
| 332 | E | CD | 60.8 | 40.2 | 11.0 | 51 | A |
| 332 | E | OE1 | 60.6 | 41.4 | 11.2 | 53 | A |
| 332 | E | OE2 | 62.0 | 39.7 | 10.9 | 53 | A |
| 332 | E | C | 56.7 | 38.2 | 11.0 | 43 | A |
| 332 | E | O | 56.8 | 39.0 | 10.1 | 43 | A |
| 333 | L | N | 55.6 | 37.4 | 11.2 | 43 | A |
| 333 | L | CA | 54.6 | 37.3 | 10.2 | 43 | A |
| 333 | L | CB | 54.3 | 35.8 | 9.9 | 41 | A |
| 333 | L | CG | 55.5 | 34.9 | 9.5 | 39 | A |
| 333 | L | CD1 | 55.0 | 33.4 | 9.4 | 38 | A |
| 333 | L | CD2 | 56.1 | 35.3 | 8.2 | 38 | A |
| 333 | L | C | 53.3 | 38.0 | 10.6 | 45 | A |
| 333 | L | O | 52.4 | 38.2 | 9.8 | 45 | A |
| 334 | D | N | 53.2 | 38.2 | 11.9 | 47 | A |
| 334 | D | CA | 52.0 | 38.9 | 12.4 | 49 | A |
| 334 | D | CB | 52.1 | 39.1 | 13.9 | 49 | A |
| 334 | D | CG | 53.5 | 39.6 | 14.3 | 51 | A |
| 334 | D | OD1 | 54.5 | 39.0 | 14.1 | 51 | A |
| 334 | D | OD2 | 53.5 | 40.8 | 14.9 | 51 | A |
| 334 | D | C | 51.7 | 40.2 | 11.8 | 50 | A |
| 334 | D | O | 50.5 | 40.7 | 11.9 | 50 | A |
| 335 | D | N | 52.6 | 40.9 | 11.1 | 50 | A |
| 335 | D | CA | 52.4 | 42.2 | 10.5 | 50 | A |
| 335 | D | CB | 53.6 | 43.1 | 10.8 | 52 | A |
| 335 | D | CG | 54.9 | 42.5 | 10.2 | 53 | A |
| 335 | D | OD1 | 56.0 | 43.2 | 10.3 | 53 | A |
| 335 | D | OD2 | 54.9 | 41.4 | 9.7 | 53 | A |
| 335 | D | C | 52.2 | 42.1 | 9.0 | 50 | A |
| 335 | D | O | 52.0 | 43.1 | 8.4 | 50 | A |
| 336 | L | N | 52.2 | 40.9 | 8.5 | 48 | A |
| 336 | L | CA | 52.0 | 40.7 | 7.0 | 46 | A |
| 336 | L | CB | 53.0 | 39.6 | 6.5 | 45 | A |
| 336 | L | CG | 54.5 | 39.7 | 6.8 | 45 | A |
| 336 | L | CD1 | 55.2 | 38.5 | 6.3 | 44 | A |
| 336 | L | CD2 | 55.0 | 41.0 | 6.2 | 45 | A |
| 336 | L | C | 50.6 | 40.4 | 6.6 | 46 | A |
| 336 | L | O | 49.9 | 39.6 | 7.2 | 45 | A |
| 337 | P | N | 50.1 | 41.1 | 5.5 | 45 | A |
| 337 | P | CD | 50.8 | 42.1 | 4.8 | 45 | A |
| 337 | P | CA | 48.8 | 40.9 | 5.0 | 44 | A |
| 337 | P | CB | 48.5 | 42.0 | 4.1 | 44 | A |
| 337 | P | CG | 49.9 | 42.3 | 3.6 | 45 | A |
| 337 | P | C | 48.7 | 39.5 | 4.3 | 44 | A |
| 337 | P | O | 49.7 | 39.0 | 3.8 | 43 | A |
| 338 | K | N | 47.5 | 38.9 | 4.3 | 44 | A |
| 338 | K | CA | 47.3 | 37.6 | 3.6 | 44 | A |
| 338 | K | CB | 45.8 | 37.2 | 3.7 | 45 | A |
| 338 | K | CG | 44.9 | 38.2 | 3.1 | 46 | A |
| 338 | K | CD | 43.4 | 37.7 | 3.2 | 48 | A |
| 338 | K | CE | 42.4 | 38.7 | 2.7 | 49 | A |
| 338 | K | NZ | 42.6 | 38.8 | 1.2 | 51 | A |
| 338 | K | C | 47.8 | 37.6 | 2.2 | 43 | A |
| 338 | K | O | 48.2 | 36.6 | 1.7 | 43 | A |
| 339 | E | N | 47.8 | 38.8 | 1.6 | 42 | A |
| 339 | E | CA | 48.3 | 38.9 | 0.2 | 41 | A |
| 339 | E | CB | 48.1 | 40.3 | −0.4 | 42 | A |
| 339 | E | CG | 46.6 | 40.6 | −0.6 | 43 | A |
| 339 | E | CD | 45.8 | 40.8 | 0.7 | 43 | A |
| 339 | E | OE1 | 46.3 | 41.6 | 1.6 | 43 | A |
| 339 | E | OE2 | 44.8 | 40.1 | 0.8 | 44 | A |
| 339 | E | C | 49.8 | 38.6 | 0.1 | 40 | A |
| 339 | E | O | 50.3 | 37.9 | −0.8 | 39 | A |
| 340 | K | N | 50.6 | 39.2 | 1.0 | 38 | A |
| 340 | K | CA | 52.0 | 39.0 | 1.1 | 37 | A |
| 340 | K | CB | 52.7 | 40.0 | 2.0 | 39 | A |
| 340 | K | CG | 54.2 | 39.8 | 2.1 | 42 | A |
| 340 | K | CD | 54.8 | 39.9 | 0.7 | 45 | A |
| 340 | K | CE | 56.3 | 39.7 | 0.8 | 47 | A |
| 340 | K | NZ | 57.0 | 39.7 | −0.5 | 48 | A |
| 340 | K | C | 52.3 | 37.5 | 1.5 | 34 | A |
| 340 | K | O | 53.3 | 36.9 | 1.1 | 32 | A |
| 341 | L | N | 51.5 | 37.0 | 2.4 | 32 | A |
| 341 | L | CA | 51.7 | 35.7 | 3.0 | 30 | A |
| 341 | L | CB | 50.8 | 35.4 | 4.1 | 29 | A |
| 341 | L | CG | 51.1 | 36.2 | 5.4 | 29 | A |
| 341 | L | CD1 | 49.9 | 35.9 | 6.4 | 29 | A |
| 341 | L | CD2 | 52.4 | 35.7 | 6.0 | 30 | A |
| 341 | L | C | 51.5 | 34.6 | 1.9 | 29 | A |
| 341 | L | O | 52.2 | 33.6 | 1.8 | 28 | A |
| 342 | K | N | 50.6 | 34.9 | 1.0 | 29 | A |
| 342 | K | CA | 50.3 | 34.0 | −0.1 | 28 | A |
| 342 | K | CB | 49.1 | 34.4 | −1.0 | 28 | A |
| 342 | K | CG | 48.7 | 33.4 | −2.0 | 27 | A |
| 342 | K | CD | 47.5 | 33.9 | −2.8 | 28 | A |
| 342 | K | CE | 47.0 | 32.9 | −3.7 | 29 | A |
| 342 | K | NZ | 48.0 | 32.4 | −4.7 | 32 | A |
| 342 | K | C | 51.6 | 33.9 | −1.0 | 28 | A |
| 342 | K | O | 51.9 | 32.8 | −1.5 | 27 | A |
| 343 | E | N | 52.2 | 35.0 | −1.2 | 29 | A |
| 343 | E | CA | 53.4 | 35.1 | −2.0 | 30 | A |
| 343 | E | CB | 53.8 | 36.6 | −2.2 | 33 | A |
| 343 | E | CG | 52.8 | 37.5 | −2.9 | 38 | A |
| 343 | E | CD | 53.2 | 38.9 | −3.0 | 40 | A |
| 343 | E | OE1 | 54.3 | 39.2 | −3.5 | 42 | A |
| 343 | E | OE2 | 52.4 | 39.8 | −2.6 | 43 | A |
| 343 | E | C | 54.6 | 34.4 | −1.4 | 29 | A |
| 343 | E | O | 55.3 | 33.7 | −2.1 | 28 | A |
| 344 | L | N | 54.7 | 34.5 | −0.1 | 28 | A |
| 344 | L | CA | 55.7 | 33.8 | 0.6 | 25 | A |
| 344 | L | CB | 55.8 | 34.2 | 2.1 | 25 | A |
| 344 | L | CG | 56.1 | 35.7 | 2.3 | 25 | A |
| 344 | L | CD1 | 56.1 | 36.0 | 3.8 | 26 | A |
| 344 | L | CD2 | 57.5 | 36.0 | 1.7 | 25 | A |
| 344 | L | C | 55.5 | 32.2 | 0.6 | 24 | A |
| 344 | L | O | 56.5 | 31.5 | 0.4 | 23 | A |
| 345 | I | N | 54.3 | 31.8 | 0.6 | 21 | A |
| 345 | I | CA | 53.9 | 30.4 | 0.5 | 21 | A |
| 345 | I | CB | 52.4 | 30.2 | 0.9 | 20 | A |
| 345 | I | CG2 | 51.9 | 28.8 | 0.5 | 19 | A |
| 345 | I | CG1 | 52.2 | 30.5 | 2.4 | 20 | A |
| 345 | I | CD1 | 50.7 | 30.4 | 2.8 | 20 | A |
| 345 | I | C | 54.2 | 29.9 | −0.9 | 21 | A |
| 345 | I | O | 54.6 | 28.8 | −1.1 | 20 | A |
| 346 | F | N | 53.9 | 30.7 | −1.9 | 23 | A |
| 346 | F | CA | 54.2 | 30.3 | −3.3 | 23 | A |
| 346 | F | CB | 53.8 | 31.5 | −4.2 | 23 | A |
| 346 | F | CG | 53.9 | 31.2 | −5.7 | 21 | A |
| 346 | F | CD1 | 53.0 | 30.3 | −6.3 | 21 | A |
| 346 | F | CD2 | 54.9 | 31.8 | −6.5 | 21 | A |
| 346 | F | CE1 | 53.1 | 30.0 | −7.7 | 21 | A |
| 346 | F | CE2 | 55.0 | 31.5 | −7.8 | 21 | A |
| 346 | F | CZ | 54.1 | 30.6 | −8.4 | 21 | A |
| 346 | F | C | 55.7 | 30.1 | −3.5 | 24 | A |
| 346 | F | O | 56.1 | 29.1 | −4.0 | 23 | A |
| 347 | E | N | 56.5 | 31.0 | −3.0 | 25 | A |
| 347 | E | CA | 58.0 | 30.9 | −3.1 | 27 | A |
| 347 | E | CB | 58.6 | 32.2 | −2.6 | 29 | A |
| 347 | E | CG | 58.2 | 33.4 | −3.4 | 34 | A |

TABLE 1-continued

Structural Coordinates of crystalline Ah$_6$-ERK2 [non-phosphorlylated, SEQ ID NO: 5] form 1.

The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 347 | E | CD | 58.8 | 34.7 | −2.9 | 36 | A |
| 347 | E | OE1 | 58.6 | 35.1 | −1.7 | 38 | A |
| 347 | E | OE2 | 59.5 | 35.3 | −3.7 | 39 | A |
| 347 | E | C | 58.6 | 29.7 | −2.3 | 27 | A |
| 347 | E | O | 59.5 | 29.1 | −2.8 | 27 | A |
| 348 | E | N | 58.0 | 29.4 | −1.1 | 26 | A |
| 348 | E | CA | 58.5 | 28.3 | −0.3 | 26 | A |
| 348 | E | CB | 57.8 | 28.5 | 1.1 | 27 | A |
| 348 | E | CG | 58.5 | 27.7 | 2.2 | 30 | A |
| 348 | E | CD | 59.9 | 28.2 | 2.6 | 31 | A |
| 348 | E | OE1 | 60.0 | 29.4 | 2.7 | 31 | A |
| 348 | E | OE2 | 60.8 | 27.4 | 2.8 | 34 | A |
| 348 | E | C | 58.2 | 27.0 | −0.8 | 26 | A |
| 348 | E | O | 58.8 | 26.0 | −0.5 | 25 | A |
| 349 | T | N | 57.2 | 26.9 | −1.7 | 25 | A |
| 349 | T | CA | 56.8 | 25.6 | −2.3 | 25 | A |
| 349 | T | CB | 55.3 | 25.4 | −2.3 | 24 | A |
| 349 | T | OG1 | 54.7 | 26.5 | −3.1 | 22 | A |
| 349 | T | CG2 | 54.7 | 25.5 | −0.9 | 24 | A |
| 349 | T | C | 57.3 | 25.4 | −3.7 | 26 | A |
| 349 | T | O | 57.0 | 24.4 | −4.4 | 26 | A |
| 350 | A | N | 58.1 | 26.3 | −4.2 | 28 | A |
| 350 | A | CA | 58.6 | 26.2 | −5.6 | 31 | A |
| 350 | A | CB | 59.4 | 27.5 | −5.9 | 29 | A |
| 350 | A | C | 59.5 | 25.0 | −5.9 | 33 | A |
| 350 | A | O | 59.4 | 24.5 | −7.0 | 32 | A |
| 351 | R | N | 60.3 | 24.6 | −5.0 | 36 | A |
| 351 | R | CA | 61.2 | 23.5 | −5.2 | 38 | A |
| 351 | R | CB | 62.0 | 23.2 | −3.9 | 42 | A |
| 351 | R | CG | 61.1 | 22.9 | −2.7 | 49 | A |
| 351 | R | CD | 61.9 | 22.3 | −1.5 | 55 | A |
| 351 | R | NE | 62.4 | 21.0 | −1.9 | 60 | A |
| 351 | R | CZ | 63.1 | 20.2 | −1.1 | 63 | A |
| 351 | R | NH1 | 63.3 | 20.6 | 0.2 | 64 | A |
| 351 | R | NH2 | 63.5 | 19.0 | −1.5 | 64 | A |
| 351 | R | C | 60.6 | 22.2 | −5.7 | 38 | A |
| 351 | R | O | 61.3 | 21.3 | −6.3 | 37 | A |
| 352 | F | N | 59.3 | 22.0 | −5.5 | 36 | A |
| 352 | F | CA | 58.6 | 20.8 | −5.9 | 36 | A |
| 352 | F | CB | 57.5 | 20.5 | −4.8 | 34 | A |
| 352 | F | CG | 58.1 | 20.1 | −3.5 | 34 | A |
| 352 | F | CD1 | 58.8 | 18.9 | −3.3 | 34 | A |
| 352 | F | CD2 | 57.9 | 20.9 | −2.4 | 34 | A |
| 352 | F | CE1 | 59.4 | 18.6 | −2.1 | 34 | A |
| 352 | F | CE2 | 58.5 | 20.6 | −1.2 | 34 | A |
| 352 | F | CZ | 59.2 | 19.4 | −1.0 | 34 | A |
| 352 | F | C | 58.0 | 20.9 | −7.3 | 36 | A |
| 352 | F | O | 57.4 | 19.9 | −7.7 | 36 | A |
| 353 | Q | N | 58.1 | 22.0 | −7.9 | 36 | A |
| 353 | Q | CA | 57.6 | 22.2 | −9.3 | 39 | A |
| 353 | Q | CB | 57.4 | 23.7 | −9.6 | 38 | A |
| 353 | Q | CG | 56.3 | 24.4 | −8.8 | 36 | A |
| 353 | Q | CD | 55.0 | 23.8 | −9.1 | 37 | A |
| 353 | Q | OE1 | 54.4 | 23.1 | −8.3 | 36 | A |
| 353 | Q | NE2 | 54.5 | 24.1 | −10.3 | 37 | A |
| 353 | Q | C | 58.5 | 21.6 | −10.3 | 41 | A |
| 353 | Q | O | 59.7 | 21.6 | −10.3 | 41 | A |
| 354 | P | N | 57.8 | 20.9 | −11.3 | 42 | A |
| 354 | P | CD | 56.4 | 20.6 | −11.4 | 43 | A |
| 354 | P | CA | 58.6 | 20.2 | −12.4 | 44 | A |
| 354 | P | CB | 57.4 | 19.7 | −13.3 | 44 | A |
| 354 | P | CG | 56.3 | 19.4 | −12.3 | 44 | A |
| 354 | P | C | 59.5 | 21.2 | −13.1 | 46 | A |
| 354 | P | O | 59.0 | 22.0 | −13.9 | 47 | A |
| 355 | G | N | 60.8 | 21.1 | −12.9 | 48 | A |
| 355 | G | CA | 61.7 | 21.9 | −13.6 | 49 | A |
| 355 | G | C | 63.2 | 21.6 | −13.2 | 50 | A |
| 355 | G | O | 63.9 | 21.2 | −14.1 | 50 | A |
| 355 | G | OXT | 63.5 | 21.8 | −12.0 | 50 | A |
| 1 | O | OH2 | 52.7 | 21.0 | 23.2 | 13 | W |
| 3 | O | OH2 | 65.8 | 22.1 | 26.4 | 16 | W |
| 4 | O | OH2 | 67.1 | 13.4 | 18.6 | 13 | W |
| 5 | O | OH2 | 46.2 | 13.4 | 29.5 | 14 | W |
| 6 | O | OH2 | 63.3 | 21.1 | 26.6 | 13 | W |
| 7 | O | OH2 | 51.3 | 22.9 | 27.6 | 14 | W |
| 8 | O | OH2 | 61.7 | 14.6 | 9.3 | 16 | W |
| 9 | O | OH2 | 48.0 | 20.0 | 22.8 | 14 | W |
| 10 | O | OH2 | 60.3 | 17.1 | 8.9 | 19 | W |
| 11 | O | OH2 | 67.4 | 19.9 | 27.4 | 17 | W |
| 12 | O | OH2 | 46.6 | 28.1 | −17.8 | 18 | W |
| 13 | O | OH2 | 44.9 | 15.9 | 30.4 | 15 | W |
| 14 | O | OH2 | 60.7 | 22.2 | 30.9 | 16 | W |
| 15 | O | OH2 | 46.9 | 20.3 | 31.4 | 13 | W |
| 16 | O | OH2 | 45.0 | 25.9 | −17.3 | 24 | W |
| 17 | O | OH2 | 62.5 | 28.2 | 26.0 | 22 | W |
| 18 | O | OH2 | 62.0 | 22.7 | 28.5 | 16 | W |
| 19 | O | OH2 | 62.3 | 24.2 | 32.5 | 21 | W |
| 20 | O | OH2 | 47.0 | 25.3 | −6.3 | 23 | W |
| 21 | O | OH2 | 54.8 | 21.1 | 41.4 | 23 | W |
| 22 | O | OH2 | 67.9 | 7.3 | 30.5 | 17 | W |
| 23 | O | OH2 | 54.7 | 24.2 | 44.4 | 27 | W |
| 24 | O | OH2 | 60.2 | 0.9 | 15.8 | 22 | W |
| 25 | O | OH2 | 44.4 | 13.9 | 20.9 | 16 | W |
| 26 | O | OH2 | 42.6 | 26.4 | 29.9 | 15 | W |
| 27 | O | OH2 | 49.1 | 28.4 | −16.5 | 18 | W |
| 28 | O | OH2 | 56.2 | 27.7 | 30.2 | 20 | W |
| 29 | O | OH2 | 66.8 | 22.6 | 23.8 | 19 | W |
| 31 | O | OH2 | 56.9 | 23.6 | 41.2 | 17 | W |
| 32 | O | OH2 | 51.5 | 22.6 | 16.2 | 16 | W |
| 33 | O | OH2 | 40.9 | 22.9 | 23.2 | 22 | W |
| 34 | O | OH2 | 46.9 | 33.8 | 30.9 | 20 | W |
| 35 | O | OH2 | 61.5 | 18.7 | 37.7 | 23 | W |
| 36 | O | OH2 | 55.9 | 29.0 | 27.7 | 27 | W |
| 37 | O | OH2 | 54.9 | 23.0 | −5.5 | 23 | W |
| 38 | O | OH2 | 52.5 | 20.8 | −8.2 | 29 | W |
| 39 | O | OH2 | 51.8 | 23.0 | −11.1 | 32 | W |
| 40 | O | OH2 | 60.5 | 17.3 | 5.1 | 24 | W |
| 42 | O | OH2 | 50.0 | 41.7 | 33.8 | 17 | W |
| 43 | O | OH2 | 50.6 | 23.4 | 42.4 | 24 | W |
| 44 | O | OH2 | 47.9 | 22.2 | 24.6 | 22 | W |
| 45 | O | OH2 | 42.9 | 27.4 | −10.3 | 22 | W |
| 46 | O | OH2 | 64.6 | 1.8 | 30.4 | 24 | W |
| 47 | O | OH2 | 53.0 | 22.5 | 43.1 | 26 | W |
| 48 | O | OH2 | 52.6 | 19.1 | 43.6 | 40 | W |
| 49 | O | OH2 | 50.9 | −3.4 | 24.8 | 27 | W |
| 50 | O | OH2 | 59.1 | −6.1 | 29.0 | 17 | W |
| 51 | O | OH2 | 74.0 | 14.0 | 19.3 | 23 | W |
| 52 | O | OH2 | 45.5 | 9.8 | 33.3 | 24 | W |
| 53 | O | OH2 | 72.9 | 11.0 | 15.9 | 26 | W |
| 54 | O | OH2 | 67.1 | 27.1 | 21.2 | 23 | W |
| 55 | O | OH2 | 68.2 | 14.0 | 12.6 | 22 | W |
| 56 | O | OH2 | 73.6 | 15.6 | 16.9 | 19 | W |
| 57 | O | OH2 | 55.7 | 34.1 | 31.5 | 24 | W |
| 58 | O | OH2 | 51.9 | 28.6 | 14.1 | 23 | W |
| 59 | O | OH2 | 47.4 | 2.3 | 27.8 | 29 | W |
| 60 | O | OH2 | 73.3 | 16.2 | 21.6 | 26 | W |
| 61 | O | OH2 | 55.6 | 29.3 | 39.7 | 22 | W |
| 62 | O | OH2 | 60.6 | −1.2 | 29.1 | 22 | W |
| 63 | O | OH2 | 38.8 | 33.5 | 49.6 | 25 | W |
| 64 | O | OH2 | 71.0 | 22.6 | 17.2 | 25 | W |
| 65 | O | OH2 | 58.5 | 10.8 | 7.5 | 32 | W |
| 66 | O | OH2 | 54.4 | 17.3 | 40.1 | 26 | W |
| 67 | O | OH2 | 60.9 | 11.0 | 9.1 | 28 | W |
| 68 | O | OH2 | 70.7 | 28.5 | 11.4 | 28 | W |
| 69 | O | OH2 | 64.6 | 28.8 | 24.4 | 26 | W |
| 70 | O | OH2 | 65.3 | 30.6 | 22.6 | 29 | W |
| 71 | O | OH2 | 59.4 | 36.8 | 29.6 | 33 | W |
| 72 | O | OH2 | 60.7 | 18.2 | 40.3 | 32 | W |
| 73 | O | OH2 | 59.9 | 6.7 | 13.2 | 28 | W |
| 74 | O | OH2 | 51.7 | 21.5 | 46.0 | 38 | W |
| 75 | O | OH2 | 39.7 | 11.4 | 32.9 | 33 | W |
| 76 | O | OH2 | 53.1 | 33.7 | 53.3 | 33 | W |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| | | | | | | | |
|---|---|---|---|---|---|---|---|
| 77  | O | OH2 | 52.4 | 2.5  | 41.3 | 29 | W |
| 78  | O | OH2 | 57.7 | -0.5 | 40.2 | 38 | W |
| 79  | O | OH2 | 60.6 | -0.8 | 26.2 | 19 | W |
| 80  | O | OH2 | 68.7 | 3.7  | 21.7 | 35 | W |
| 81  | O | OH2 | 70.6 | 14.0 | 27.3 | 22 | W |
| 82  | O | OH2 | 70.3 | 13.4 | 24.6 | 19 | W |
| 83  | O | OH2 | 49.9 | 33.1 | 13.7 | 32 | W |
| 84  | O | OH2 | 46.3 | 35.9 | -5.8 | 34 | W |
| 85  | O | OH2 | 57.9 | 6.9  | 42.0 | 36 | W |
| 86  | O | OH2 | 48.5 | 21.9 | 15.5 | 35 | W |
| 87  | O | OH2 | 60.4 | 13.8 | 41.6 | 39 | W |
| 88  | O | OH2 | 63.3 | 32.7 | 11.3 | 43 | W |
| 89  | O | OH2 | 46.4 | 37.2 | -3.5 | 38 | W |
| 90  | O | OH2 | 50.1 | 33.0 | 22.8 | 35 | W |
| 91  | O | OH2 | 45.1 | 16.1 | 15.7 | 36 | W |
| 92  | O | OH2 | 52.9 | 27.5 | 36.6 | 26 | W |
| 93  | O | OH2 | 50.5 | 14.7 | 42.3 | 31 | W |
| 94  | O | OH2 | 42.4 | 38.0 | 40.6 | 21 | W |
| 95  | O | OH2 | 48.3 | 33.9 | 24.8 | 31 | W |
| 96  | O | OH2 | 67.3 | 20.0 | 22.6 | 21 | W |
| 97  | O | OH2 | 56.7 | 30.3 | 31.2 | 23 | W |
| 98  | O | OH2 | 49.3 | 1.8  | 34.8 | 33 | W |
| 99  | O | OH2 | 69.3 | 18.6 | 10.7 | 26 | W |
| 100 | O | OH2 | 41.4 | 26.7 | 40.0 | 30 | W |
| 101 | O | OH2 | 42.8 | 40.5 | 41.9 | 27 | W |
| 102 | O | OH2 | 71.1 | 9.2  | 15.0 | 23 | W |
| 103 | O | OH2 | 70.3 | 6.9  | 31.7 | 24 | W |
| 104 | O | OH2 | 56.5 | 12.1 | 5.3  | 27 | W |
| 105 | O | OH2 | 54.5 | -4.9 | 19.5 | 30 | W |
| 106 | O | OH2 | 61.4 | 26.6 | 29.1 | 32 | W |
| 107 | O | OH2 | 55.7 | 31.3 | 33.5 | 26 | W |
| 108 | O | OH2 | 68.9 | 9.2  | 13.1 | 29 | W |
| 109 | O | OH2 | 63.9 | 28.7 | 28.4 | 42 | W |
| 110 | O | OH2 | 47.9 | 32.6 | 27.3 | 28 | W |
| 111 | O | OH2 | 66.9 | 11.0 | 12.9 | 26 | W |
| 112 | O | OH2 | 63.7 | 35.4 | 23.8 | 27 | W |
| 113 | O | OH2 | 61.5 | 5.0  | 14.8 | 30 | W |
| 114 | O | OH2 | 77.6 | 23.2 | 8.6  | 49 | W |
| 115 | O | OH2 | 42.5 | 22.2 | -5.8 | 36 | W |
| 116 | O | OH2 | 59.1 | 26.4 | -9.4 | 32 | W |
| 117 | O | OH2 | 44.8 | 36.3 | -1.4 | 36 | W |
| 118 | O | OH2 | 55.2 | 35.7 | 13.3 | 35 | W |
| 119 | O | OH2 | 50.8 | 39.0 | -5.1 | 38 | W |
| 120 | O | OH2 | 51.0 | 25.1 | 23.7 | 27 | W |
| 121 | O | OH2 | 50.7 | 11.1 | 7.7  | 39 | W |
| 122 | O | OH2 | 54.3 | 18.7 | -7.3 | 34 | W |
| 123 | O | OH2 | 42.9 | 13.8 | 23.3 | 32 | W |
| 124 | O | OH2 | 39.4 | 26.5 | -2.5 | 46 | W |
| 125 | O | OH2 | 53.8 | 16.1 | -7.6 | 42 | W |
| 126 | O | OH2 | 42.8 | 12.3 | 36.4 | 35 | W |
| 127 | O | OH2 | 44.5 | 22.0 | 17.9 | 42 | W |
| 128 | O | OH2 | 71.5 | 3.6  | 20.4 | 32 | W |
| 129 | O | OH2 | 60.5 | 5.5  | 10.3 | 47 | W |
| 130 | O | OH2 | 42.3 | 29.0 | -0.1 | 28 | W |
| 131 | O | OH2 | 51.4 | 0.9  | 33.3 | 32 | W |
| 132 | O | OH2 | 67.2 | 26.9 | 25.9 | 35 | W |
| 133 | O | OH2 | 54.1 | 1.5  | 34.0 | 25 | W |
| 134 | O | OH2 | 60.8 | 0.1  | 31.7 | 27 | W |
| 135 | O | OH2 | 51.9 | 17.4 | 9.6  | 20 | W |
| 136 | O | OH2 | 40.9 | 19.3 | 25.1 | 24 | W |
| 137 | O | OH2 | 42.6 | 32.4 | 51.4 | 37 | W |
| 138 | O | OH2 | 61.6 | 0.9  | 34.3 | 48 | W |
| 139 | O | OH2 | 41.6 | 15.6 | 36.8 | 24 | W |
| 140 | O | OH2 | 56.5 | 9.9  | 42.3 | 41 | W |
| 141 | O | OH2 | 47.0 | 7.9  | 10.8 | 47 | W |
| 142 | O | OH2 | 62.8 | 27.0 | 5.4  | 54 | W |
| 143 | O | OH2 | 63.8 | 7.1  | 39.2 | 31 | W |
| 144 | O | OH2 | 48.0 | 2.5  | 37.2 | 28 | W |
| 145 | O | OH2 | 57.6 | 35.8 | 19.7 | 35 | W |
| 146 | O | OH2 | 49.2 | 9.0  | 8.2  | 39 | W |
| 147 | O | OH2 | 68.0 | 5.9  | 19.7 | 25 | W |
| 148 | O | OH2 | 48.9 | -4.3 | 30.2 | 59 | W |
| 149 | O | OH2 | 46.6 | 20.3 | -8.2 | 35 | W |
| 150 | O | OH2 | 55.3 | 24.3 | -12.9| 35 | W |
| 151 | O | OH2 | 60.0 | 35.0 | 7.9  | 43 | W |
| 152 | O | OH2 | 52.9 | -4.3 | 17.0 | 47 | W |
| 153 | O | OH2 | 69.9 | 20.0 | 22.5 | 34 | W |
| 154 | O | OH2 | 41.9 | 17.0 | 39.4 | 22 | W |
| 155 | O | OH2 | 58.8 | 34.0 | 18.1 | 37 | W |
| 156 | O | OH2 | 57.3 | 28.5 | -8.6 | 29 | W |
| 157 | O | OH2 | 55.6 | 28.1 | -10.5| 29 | W |
| 158 | O | OH2 | 50.4 | 18.0 | 50.0 | 42 | W |
| 159 | O | OH2 | 42.1 | 8.2  | 23.0 | 38 | W |
| 160 | O | OH2 | 55.0 | 3.5  | 42.6 | 41 | W |
| 161 | O | OH2 | 65.7 | 13.1 | 36.6 | 27 | W |
| 162 | O | OH2 | 44.1 | 25.6 | -6.5 | 27 | W |
| 163 | O | OH2 | 53.7 | 38.8 | 33.4 | 39 | W |
| 164 | O | OH2 | 57.6 | 33.1 | 34.7 | 42 | W |
| 165 | O | OH2 | 36.0 | 27.3 | 27.3 | 34 | W |
| 166 | O | OH2 | 68.4 | 21.8 | 7.4  | 58 | W |
| 167 | O | OH2 | 65.9 | 20.5 | 36.9 | 36 | W |
| 168 | O | OH2 | 52.5 | 41.1 | 27.5 | 40 | W |
| 169 | O | OH2 | 32.0 | 13.3 | -5.0 | 54 | W |
| 170 | O | OH2 | 50.6 | 14.8 | -9.0 | 56 | W |
| 171 | O | OH2 | 42.7 | 8.0  | 25.9 | 31 | W |
| 172 | O | OH2 | 62.4 | 32.5 | 8.9  | 44 | W |
| 173 | O | OH2 | 58.8 | 31.9 | 1.5  | 33 | W |
| 174 | O | OH2 | 48.0 | -3.8 | 24.3 | 38 | W |
| 175 | O | OH2 | 57.7 | 36.8 | 15.1 | 33 | W |
| 176 | O | OH2 | 58.3 | 27.6 | 49.5 | 33 | W |
| 177 | O | OH2 | 71.1 | 22.3 | 21.3 | 35 | W |
| 178 | O | OH2 | 53.0 | 35.6 | 37.2 | 32 | W |
| 179 | O | OH2 | 57.1 | 30.8 | 37.8 | 37 | W |
| 180 | O | OH2 | 76.1 | 4.4  | 20.2 | 32 | W |
| 181 | O | OH2 | 61.2 | 20.7 | 41.5 | 36 | W |
| 182 | O | OH2 | 49.3 | 37.4 | -3.5 | 34 | W |
| 183 | O | OH2 | 56.0 | 35.8 | 36.3 | 44 | W |
| 184 | O | OH2 | 69.6 | -1.7 | 24.8 | 48 | W |
| 185 | O | OH2 | 45.8 | 0.7  | 36.3 | 46 | W |
| 186 | O | OH2 | 68.7 | 26.3 | 19.2 | 31 | W |
| 187 | O | OH2 | 34.0 | 23.9 | 38.1 | 37 | W |
| 188 | O | OH2 | 66.9 | 4.7  | 15.0 | 40 | W |
| 189 | O | OH2 | 44.0 | 19.1 | 16.2 | 32 | W |
| 190 | O | OH2 | 45.4 | 40.7 | 5.6  | 38 | W |
| 191 | O | OH2 | 41.1 | 6.3  | -7.8 | 44 | W |
| 192 | O | OH2 | 62.4 | 6.7  | 41.5 | 44 | W |
| 193 | O | OH2 | 64.7 | 0.9  | 33.6 | 47 | W |
| 194 | O | OH2 | 58.1 | 17.9 | 40.9 | 43 | W |
| 195 | O | OH2 | 54.5 | 6.4  | 2.7  | 40 | W |
| 196 | O | OH2 | 66.0 | 5.0  | 39.9 | 37 | W |
| 197 | O | OH2 | 35.7 | 19.0 | 27.5 | 42 | W |
| 198 | O | OH2 | 61.2 | 19.3 | -8.7 | 41 | W |
| 199 | O | OH2 | 49.0 | 26.4 | 20.2 | 48 | W |
| 200 | O | OH2 | 57.4 | 43.2 | 28.2 | 48 | W |
| 201 | O | OH2 | 41.1 | 30.6 | 25.2 | 33 | W |
| 202 | O | OH2 | 58.9 | 22.0 | 42.3 | 38 | W |
| 203 | O | OH2 | 59.9 | 41.7 | 27.3 | 45 | W |
| 204 | O | OH2 | 42.3 | 37.3 | 26.4 | 38 | W |
| 205 | O | OH2 | 51.1 | 22.8 | 49.1 | 40 | W |
| 206 | O | OH2 | 33.4 | 21.7 | -5.4 | 45 | W |
| 207 | O | OH2 | 44.2 | 1.0  | 12.0 | 47 | W |
| 208 | O | OH2 | 62.0 | 13.2 | 6.9  | 36 | W |
| 209 | O | OH2 | 52.2 | 2.6  | 2.9  | 46 | W |
| 210 | O | OH2 | 62.7 | 30.6 | 30.1 | 41 | W |
| 211 | O | OH2 | 38.0 | 21.8 | 0.1  | 48 | W |
| 212 | O | OH2 | 62.5 | 8.3  | 8.7  | 48 | W |
| 213 | O | OH2 | 43.1 | 5.3  | -10.4| 49 | W |
| 214 | O | OH2 | 57.9 | 18.0 | -10.0| 47 | W |
| 215 | O | OH2 | 63.8 | 25.4 | 45.8 | 45 | W |
| 216 | O | OH2 | 44.1 | 14.5 | 13.9 | 43 | W |
| 217 | O | OH2 | 37.5 | 25.8 | -0.8 | 51 | W |
| 218 | O | OH2 | 63.2 | 1.9  | 13.4 | 46 | W |

TABLE 1-continued

Structural Coordinates of crystalline Ah$_6$-ERK2 [non-phosphorlylated, SEQ ID NO: 5] form 1.
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. The coordinates are arranged in two side-by-side columns.

| 219 | O | OH2 | 61.0 | 32.5 | 48.3 | 50 | W |
|---|---|---|---|---|---|---|---|
| 220 | O | OH2 | 57.4 | 43.5 | 12.4 | 50 | W |
| 221 | O | OH2 | 39.1 | 39.8 | 1.3 | 52 | W |
| 222 | O | OH2 | 37.5 | 9.6 | −6.1 | 50 | W |
| 500 | U | S | 57.5 | 33.2 | 14.8 | 32 | W |
| 500 | U | O1 | 56.8 | 33.5 | 13.6 | 33 | W |
| 500 | U | O2 | 56.9 | 34.0 | 15.9 | 34 | W |
| 500 | U | O3 | 57.3 | 31.8 | 15.2 | 33 | W |
| 500 | U | O4 | 58.9 | 33.4 | 14.7 | 34 | W |
| 501 | U | S | 67.1 | 31.9 | 10.6 | 41 | W |
| 501 | U | O1 | 66.6 | 30.6 | 10.1 | 42 | W |
| 501 | U | O2 | 68.2 | 31.6 | 11.6 | 42 | W |
| 501 | U | O3 | 67.7 | 32.7 | 9.6 | 42 | W |
| 501 | U | O4 | 66.0 | 32.6 | 11.3 | 42 | W |

Example 10

Ah$_6$-ERK2 [Non-Phosphorlylated] (Form 1) Structure Determination

The crystal structure was solved using molecular replacement using the search models 1 ERK and 3ERK and 4ERK from the PDB. Refinement was done using the program CNX.

| Theoretical number of reflections | 67268 |
|---|---|
| Resolution Limits | 30.0-1.50 Å |
| Number of unobserved reflections | 1517 (2.3%) |
| Number of reflections in working set | 62484 (97.7%) |
| Number of reflections in test set | 3267 (4.9%) |
| Number of protein residues | 346 |
| Number of solvent atoms | 219 |
| R-factor | 0.239 |
| R-free | 0.248 |
| RMSD bond length | 0.0058 Å |
| RMSD bond angles | 1.12° |

Example 11

Preparation of Ah$_6$-ERK2 [Di-Phosphorlylated]

Di-phosphorylated ERK2 was prepared by incubation of 30 mg of 5 μM ERK2 at 4° C. with 95 nM MEK1P (active MEK1) in 50 mM sodium Hepes buffer, pH 7.45, 2 mM MgCl$_2$, 1 mM sodium orthovanadate, 4 mM KF, 1 mM TCEP, 5 mM Tris-Cl, 0.2 mM EDTA, 2% glycerol, 1 mM DTT, 52 mM NaCl and 2 mM ATP for 105 minutes. The reaction was quenched with 35 mM EDTA, and the sample was dialyzed against MonoQ buffer (25 mM Tris-Cl, pH 7.8 (rt), 0.05 M NaCl, 1 mM EDTA, 10% (v/v) glycerol, and 5 mM DTT) and applied to a MonoQ HR 16/10 column (Amersham/Pharmacia) at 4° C. The column was washed with 1 bed volume of MonoQ buffer and developed with a linear 30 bed volume gradient between MonoQ Buffer and MonoQ Buffer with 0.5 M NaCl. The yield was 13 mg of di-phosphorylated ERK2.

Pure di-phosphorylated ERK2 was prepared for crystallography by extensive dialysis versus 20 mM Tris-Cl, pH 7.5 (rt), 0.2 M NaCl, 0.03% sodium azide and 5 mM DTT at 4° C., centrifugation at 200,000×g for 40 minutes, and concentration to 11 mg/ml of protein on a YM10 membrane (Millipore).

Example 12

Crystallization of Ah$_6$-ERK2 [Di-Phosphorylated]

The Ah$_6$-ERK2 [di-phosphorylated] construct was crystallized using a hanging-drop vapor diffusion method. The protein (0.5 μl; 10 mg/ml) in 20 mM Tris-HCl, pH 7.5, 0.20 M sodium chloride, 0.03% sodium azide, 5 mM DTT buffer was mixed with an equal volume of precipitant solution containing 10 mM sodium citrate, pH 5.8, 20% iso-propanol placed on the underside of a siliconized glass coverslip and sealed in close proximity to 1 ml of the precipitant solution. Crystallization plates were incubated at 4°-22° for 5 hours followed by incubation at 4° for 48 hours; crystals grew over 4-30 days.

Example 13

Photomicrograph of Ah$_6$-ERK2 [Di-Phosphorlylated] Crystals

A protomicrograph of the Ah$_6$-ERK2 [di-phosphorylated crystals was taken (magnification about 200×). Rectangular rod crystals (0.02×0.2 mm) were observed.

Example 14

Crystallographic Analysis of Ah$_6$-ERK2 [Di-Phosphorlylated]

Prior to data collection, crystals were washed with the reservoir solution of the crystallization setup and transferred into the same solution with 20% glycerol added. The crystals were then flash-cooled in a nitrogen stream at 95 K. X-ray diffraction was collected using a Rigaku generator equipped with a Raxis 4++ detector. Data were integrated and scaled using the HKL package.

Data Collection Statistics:

| Resolution | 30.0-1.97 Å |
|---|---|
| No. of collected reflections | 1308217 |
| No. of unique reflections (F >= 0) | 113309 |
| R-sym | 3.6% |
| Percent of theoretical (I/s >= 1) | 84.7% |
| Unit Cell | a = 71.710 Å, b = 72.076 Å, c = 84.466 Å, α = 76.119°, β = 84.738° γ = 80.343° |
| Space Group | P1 (number 1) |
| Asymmetric unit | 4 molecule |

TABLE 2

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 6 | A | CB | 2.1 | 5.1 | 18.1 | 91 | A |
|---|---|---|---|---|---|---|---|
| 6 | A | C | 0.2 | 5.6 | 19.7 | 91 | A |
| 6 | A | O | 0.6 | 5.7 | 20.8 | 92 | A |
| 6 | A | N | 1.7 | 7.4 | 18.9 | 91 | A |
| 6 | A | CA | 1.0 | 6.1 | 18.5 | 91 | A |
| 7 | A | N | −0.9 | 4.9 | 19.3 | 90 | A |
| 7 | A | CA | −1.8 | 4.3 | 20.3 | 89 | A |
| 7 | A | CB | −2.6 | 3.2 | 19.7 | 88 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 7  | A | C   | -1.1 | 3.9  | 21.6 | 87 | A |
|----|---|-----|------|------|------|----|---|
| 7  | A | O   | -1.4 | 4.4  | 22.7 | 87 | A |
| 8  | G | N   | -0.2 | 2.9  | 21.4 | 85 | A |
| 8  | G | CA  | 0.6  | 2.4  | 22.5 | 81 | A |
| 8  | G | C   | 1.8  | 3.2  | 22.7 | 79 | A |
| 8  | G | O   | 1.8  | 4.4  | 23.1 | 79 | A |
| 9  | P | N   | 3.0  | 2.6  | 22.4 | 76 | A |
| 9  | P | CD  | 3.2  | 1.2  | 22.0 | 75 | A |
| 9  | P | CA  | 4.3  | 3.3  | 22.6 | 73 | A |
| 9  | P | CB  | 5.3  | 2.1  | 22.6 | 74 | A |
| 9  | P | CG  | 4.7  | 1.2  | 21.6 | 75 | A |
| 9  | P | C   | 4.6  | 4.3  | 21.5 | 71 | A |
| 9  | P | O   | 4.2  | 4.1  | 20.3 | 71 | A |
| 10 | E | N   | 5.3  | 5.4  | 21.8 | 69 | A |
| 10 | E | CA  | 5.7  | 6.4  | 20.8 | 66 | A |
| 10 | E | CB  | 6.2  | 7.7  | 21.6 | 67 | A |
| 10 | E | CG  | 5.2  | 8.2  | 22.6 | 67 | A |
| 10 | E | CD  | 5.7  | 9.4  | 23.3 | 67 | A |
| 10 | E | OE1 | 6.0  | 10.4 | 22.6 | 66 | A |
| 10 | E | OE2 | 5.8  | 9.4  | 24.5 | 66 | A |
| 10 | E | C   | 6.8  | 5.8  | 20.0 | 65 | A |
| 10 | E | O   | 7.6  | 5.0  | 20.5 | 64 | A |
| 11 | M | N   | 7.0  | 6.3  | 18.8 | 64 | A |
| 11 | M | CA  | 8.0  | 5.8  | 17.9 | 62 | A |
| 11 | M | CB  | 7.4  | 5.1  | 16.7 | 62 | A |
| 11 | M | CG  | 6.4  | 4.0  | 17.0 | 59 | A |
| 11 | M | SD  | 7.1  | 2.6  | 18.0 | 58 | A |
| 11 | M | CE  | 8.0  | 1.7  | 16.7 | 59 | A |
| 11 | M | C   | 9.0  | 6.8  | 17.4 | 61 | A |
| 11 | M | O   | 8.6  | 8.0  | 17.1 | 61 | A |
| 12 | V | N   | 10.2 | 6.5  | 17.3 | 60 | A |
| 12 | V | CA  | 11.3 | 7.4  | 16.8 | 60 | A |
| 12 | V | CB  | 12.1 | 8.0  | 18.0 | 59 | A |
| 12 | V | CG1 | 13.3 | 8.7  | 17.4 | 58 | A |
| 12 | V | CG2 | 11.3 | 8.9  | 18.8 | 58 | A |
| 12 | V | C   | 12.2 | 6.5  | 16.0 | 60 | A |
| 12 | V | O   | 12.8 | 5.6  | 16.5 | 61 | A |
| 13 | R | N   | 12.3 | 6.8  | 14.7 | 59 | A |
| 13 | R | CA  | 13.1 | 6.1  | 13.7 | 59 | A |
| 13 | R | CB  | 14.6 | 6.4  | 14.0 | 59 | A |
| 13 | R | CG  | 15.0 | 7.8  | 13.6 | 58 | A |
| 13 | R | CD  | 16.5 | 7.8  | 13.7 | 58 | A |
| 13 | R | NE  | 17.1 | 8.9  | 12.8 | 58 | A |
| 13 | R | CZ  | 18.4 | 8.9  | 12.4 | 60 | A |
| 13 | R | NH1 | 19.2 | 7.9  | 12.8 | 60 | A |
| 13 | R | NH2 | 18.8 | 9.8  | 11.6 | 59 | A |
| 13 | R | C   | 12.8 | 4.6  | 13.8 | 58 | A |
| 13 | R | O   | 13.7 | 3.8  | 14.0 | 59 | A |
| 14 | G | N   | 11.6 | 4.2  | 13.6 | 57 | A |
| 14 | G | CA  | 11.2 | 2.8  | 13.6 | 57 | A |
| 14 | G | C   | 11.4 | 2.1  | 14.9 | 56 | A |
| 14 | G | O   | 11.2 | 0.9  | 15.0 | 57 | A |
| 15 | Q | N   | 11.9 | 2.8  | 16.0 | 56 | A |
| 15 | Q | CA  | 12.2 | 2.1  | 17.2 | 54 | A |
| 15 | Q | CB  | 13.5 | 2.4  | 17.8 | 55 | A |
| 15 | Q | CG  | 14.7 | 1.8  | 17.0 | 57 | A |
| 15 | Q | CD  | 15.9 | 1.6  | 17.9 | 59 | A |
| 15 | Q | OE1 | 17.0 | 1.4  | 17.4 | 61 | A |
| 15 | Q | NE2 | 15.7 | 1.7  | 19.2 | 58 | A |
| 15 | Q | C   | 11.1 | 2.5  | 18.3 | 53 | A |
| 15 | Q | O   | 10.5 | 3.5  | 18.2 | 50 | A |
| 16 | V | N   | 11.0 | 1.6  | 19.3 | 51 | A |
| 16 | V | CA  | 10.2 | 1.9  | 20.4 | 51 | A |
| 16 | V | CB  | 9.7  | 0.6  | 21.1 | 51 | A |
| 16 | V | CG1 | 8.9  | 0.9  | 22.3 | 50 | A |
| 16 | V | CG2 | 8.8  | -0.2 | 20.1 | 54 | A |
| 16 | V | C   | 10.9 | 2.7  | 21.4 | 50 | A |
| 16 | V | O   | 12.0 | 2.4  | 21.9 | 49 | A |
| 17 | F | N   | 10.3 | 3.9  | 21.8 | 51 | A |
| 17 | F | CA  | 10.8 | 4.8  | 22.8 | 50 | A |
| 17 | F | CB  | 11.1 | 6.1  | 22.1 | 49 | A |
| 17 | F | CG  | 12.4 | 6.8  | 22.6 | 48 | A |
| 17 | F | CD1 | 13.6 | 6.2  | 22.3 | 47 | A |
| 17 | F | CD2 | 12.3 | 7.8  | 23.5 | 48 | A |
| 17 | F | CE1 | 14.8 | 6.7  | 22.8 | 45 | A |
| 17 | F | CE2 | 13.5 | 8.4  | 24.1 | 48 | A |
| 17 | F | CZ  | 14.7 | 7.8  | 23.7 | 47 | A |
| 17 | F | C   | 9.6  | 4.9  | 23.7 | 49 | A |
| 17 | F | O   | 9.0  | 6.0  | 23.8 | 49 | A |
| 18 | D | N   | 9.3  | 3.8  | 24.4 | 49 | A |
| 18 | D | CA  | 8.2  | 3.8  | 25.4 | 50 | A |
| 18 | D | CB  | 7.9  | 2.3  | 25.5 | 50 | A |
| 18 | D | CG  | 6.5  | 2.1  | 26.3 | 53 | A |
| 18 | D | OD1 | 5.6  | 2.9  | 26.1 | 52 | A |
| 18 | D | OD2 | 6.4  | 1.1  | 27.0 | 54 | A |
| 18 | D | C   | 8.4  | 4.4  | 26.7 | 50 | A |
| 18 | D | O   | 8.6  | 3.8  | 27.7 | 49 | A |
| 19 | V | N   | 8.4  | 5.8  | 26.7 | 49 | A |
| 19 | V | CA  | 8.5  | 6.5  | 28.0 | 50 | A |
| 19 | V | CB  | 9.5  | 7.7  | 27.7 | 48 | A |
| 19 | V | CG1 | 10.9 | 7.2  | 27.5 | 46 | A |
| 19 | V | CG2 | 9.0  | 8.6  | 26.6 | 46 | A |
| 19 | V | C   | 7.2  | 7.0  | 28.5 | 52 | A |
| 19 | V | O   | 7.0  | 8.2  | 28.6 | 52 | A |
| 20 | G | N   | 6.3  | 6.1  | 28.8 | 52 | A |
| 20 | G | CA  | 5.0  | 6.4  | 29.4 | 50 | A |
| 20 | G | C   | 4.3  | 7.6  | 28.8 | 49 | A |
| 20 | G | O   | 4.6  | 8.0  | 27.6 | 48 | A |
| 21 | P | N   | 3.4  | 8.2  | 29.5 | 49 | A |
| 21 | P | CD  | 2.7  | 7.6  | 30.7 | 48 | A |
| 21 | P | CA  | 2.6  | 9.4  | 29.1 | 49 | A |
| 21 | P | CB  | 1.3  | 9.2  | 29.7 | 47 | A |
| 21 | P | CG  | 1.7  | 8.7  | 31.1 | 47 | A |
| 21 | P | C   | 3.3  | 10.7 | 29.4 | 48 | A |
| 21 | P | O   | 3.2  | 11.7 | 28.8 | 48 | A |
| 22 | R | N   | 4.1  | 10.7 | 30.5 | 47 | A |
| 22 | R | CA  | 4.8  | 11.8 | 31.0 | 48 | A |
| 22 | R | CB  | 5.6  | 11.5 | 32.3 | 47 | A |
| 22 | R | CG  | 6.3  | 12.7 | 32.9 | 48 | A |
| 22 | R | CD  | 7.1  | 12.2 | 34.1 | 47 | A |
| 22 | R | NE  | 8.0  | 13.3 | 34.6 | 47 | A |
| 22 | R | CZ  | 8.8  | 13.2 | 35.6 | 48 | A |
| 22 | R | NH1 | 8.9  | 12.0 | 36.3 | 46 | A |
| 22 | R | NH2 | 9.6  | 14.2 | 36.0 | 47 | A |
| 22 | R | C   | 5.7  | 12.5 | 30.0 | 48 | A |
| 22 | R | O   | 5.8  | 13.7 | 29.9 | 49 | A |
| 23 | Y | N   | 6.5  | 11.7 | 29.2 | 46 | A |
| 23 | Y | CA  | 7.4  | 12.2 | 28.3 | 45 | A |
| 23 | Y | CB  | 8.7  | 11.5 | 28.4 | 41 | A |
| 23 | Y | CG  | 9.3  | 11.6 | 29.8 | 37 | A |
| 23 | Y | CD1 | 9.9  | 12.8 | 30.2 | 38 | A |
| 23 | Y | CE1 | 10.4 | 12.8 | 31.5 | 37 | A |
| 23 | Y | CD2 | 9.3  | 10.5 | 30.6 | 38 | A |
| 23 | Y | CE2 | 9.8  | 10.6 | 31.9 | 35 | A |
| 23 | Y | CZ  | 10.4 | 11.7 | 32.4 | 37 | A |
| 23 | Y | OH  | 10.9 | 11.8 | 33.6 | 35 | A |
| 23 | Y | C   | 6.8  | 12.1 | 26.9 | 45 | A |
| 23 | Y | O   | 6.3  | 11.0 | 26.5 | 46 | A |
| 24 | T | N   | 6.8  | 13.2 | 26.1 | 48 | A |
| 24 | T | CA  | 6.2  | 13.2 | 24.8 | 50 | A |
| 24 | T | CB  | 4.8  | 13.7 | 24.8 | 51 | A |
| 24 | T | OG1 | 4.8  | 15.1 | 25.0 | 52 | A |
| 24 | T | CG2 | 4.0  | 13.0 | 25.9 | 49 | A |
| 24 | T | C   | 7.0  | 14.1 | 23.8 | 52 | A |
| 24 | T | O   | 8.1  | 14.5 | 24.1 | 55 | A |
| 25 | N | N   | 6.4  | 14.4 | 22.6 | 53 | A |
| 25 | N | CA  | 7.0  | 15.2 | 21.6 | 54 | A |
| 25 | N | CB  | 6.9  | 16.7 | 22.0 | 55 | A |
| 25 | N | CG  | 5.4  | 17.0 | 22.4 | 57 | A |
| 25 | N | OD1 | 4.6  | 16.9 | 21.5 | 57 | A |

TABLE 2-continued

Structural Coordinates of Ah₆-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 25 | N | ND2 | 5.2 | 17.5 | 23.6 | 57 | A |
| 25 | N | C | 8.5 | 14.9 | 21.4 | 55 | A |
| 25 | N | O | 9.3 | 15.8 | 21.1 | 56 | A |
| 26 | L | N | 8.8 | 13.6 | 21.5 | 56 | A |
| 26 | L | CA | 10.2 | 13.1 | 21.3 | 56 | A |
| 26 | L | CB | 10.2 | 11.6 | 21.2 | 55 | A |
| 26 | L | CG | 10.1 | 10.7 | 22.4 | 55 | A |
| 26 | L | CD1 | 9.2 | 11.3 | 23.4 | 56 | A |
| 26 | L | CD2 | 9.7 | 9.3 | 22.1 | 56 | A |
| 26 | L | C | 10.8 | 13.8 | 20.1 | 57 | A |
| 26 | L | O | 10.2 | 14.2 | 19.2 | 57 | A |
| 27 | S | N | 12.2 | 13.8 | 20.1 | 58 | A |
| 27 | S | CA | 12.9 | 14.4 | 19.0 | 57 | A |
| 27 | S | CB | 13.0 | 15.9 | 19.1 | 57 | A |
| 27 | S | OG | 13.7 | 16.5 | 18.1 | 56 | A |
| 27 | S | C | 14.3 | 13.8 | 19.0 | 58 | A |
| 27 | S | O | 15.2 | 14.2 | 19.8 | 59 | A |
| 28 | Y | N | 14.6 | 12.9 | 18.1 | 57 | A |
| 28 | Y | CA | 15.9 | 12.2 | 17.9 | 57 | A |
| 28 | Y | CB | 15.9 | 11.4 | 16.6 | 56 | A |
| 28 | Y | CG | 17.2 | 10.7 | 16.4 | 55 | A |
| 28 | Y | CD1 | 17.5 | 9.5 | 17.1 | 56 | A |
| 28 | Y | CE1 | 18.7 | 8.8 | 16.8 | 55 | A |
| 28 | Y | CD2 | 18.1 | 11.2 | 15.5 | 56 | A |
| 28 | Y | CE2 | 19.3 | 10.5 | 15.2 | 56 | A |
| 28 | Y | CZ | 19.6 | 9.3 | 15.9 | 55 | A |
| 28 | Y | OH | 20.8 | 8.7 | 15.7 | 55 | A |
| 28 | Y | C | 17.1 | 13.2 | 17.9 | 56 | A |
| 28 | Y | O | 17.0 | 14.3 | 17.3 | 56 | A |
| 29 | I | N | 18.2 | 12.8 | 18.5 | 55 | A |
| 29 | I | CA | 19.4 | 13.7 | 18.6 | 55 | A |
| 29 | I | CB | 19.5 | 14.4 | 19.9 | 55 | A |
| 29 | I | CG2 | 18.5 | 15.5 | 20.0 | 57 | A |
| 29 | I | CG1 | 19.4 | 13.5 | 21.1 | 55 | A |
| 29 | I | CD1 | 19.4 | 14.2 | 22.4 | 53 | A |
| 29 | I | C | 20.6 | 12.9 | 18.3 | 54 | A |
| 29 | I | O | 21.6 | 13.4 | 17.8 | 53 | A |
| 30 | G | N | 20.6 | 11.6 | 18.5 | 53 | A |
| 30 | G | CA | 21.8 | 10.8 | 18.2 | 52 | A |
| 30 | G | C | 21.8 | 9.4 | 18.9 | 52 | A |
| 30 | G | O | 21.0 | 9.0 | 19.7 | 51 | A |
| 31 | E | N | 22.8 | 8.6 | 18.4 | 53 | A |
| 31 | E | CA | 23.0 | 7.2 | 18.9 | 54 | A |
| 31 | E | CB | 23.5 | 6.3 | 17.8 | 54 | A |
| 31 | E | CG | 22.6 | 6.0 | 16.6 | 55 | A |
| 31 | E | CD | 21.3 | 5.3 | 17.1 | 56 | A |
| 31 | E | OE1 | 21.5 | 4.2 | 17.8 | 56 | A |
| 31 | E | OE2 | 20.2 | 5.7 | 16.7 | 55 | A |
| 31 | E | C | 23.9 | 7.2 | 20.1 | 55 | A |
| 31 | E | O | 24.9 | 7.9 | 20.1 | 54 | A |
| 32 | G | N | 23.6 | 6.4 | 21.1 | 55 | A |
| 32 | G | CA | 24.4 | 6.2 | 22.3 | 55 | A |
| 32 | G | C | 25.0 | 4.9 | 22.3 | 55 | A |
| 32 | G | O | 24.8 | 4.0 | 21.4 | 56 | A |
| 33 | A | N | 25.9 | 4.6 | 23.3 | 54 | A |
| 33 | A | CA | 26.6 | 3.3 | 23.4 | 53 | A |
| 33 | A | CB | 27.2 | 3.2 | 24.8 | 53 | A |
| 33 | A | C | 25.7 | 2.1 | 23.2 | 53 | A |
| 33 | A | O | 25.9 | 1.3 | 22.3 | 53 | A |
| 34 | Y | N | 24.6 | 2.1 | 24.0 | 52 | A |
| 34 | Y | CA | 23.7 | 0.9 | 23.8 | 52 | A |
| 34 | Y | CB | 23.7 | 0.1 | 25.1 | 52 | A |
| 34 | Y | CG | 25.0 | 0.0 | 25.8 | 53 | A |
| 34 | Y | CD1 | 26.1 | −0.6 | 25.1 | 53 | A |
| 34 | Y | CE1 | 27.4 | −0.6 | 25.7 | 54 | A |
| 34 | Y | CD2 | 25.2 | 0.5 | 27.1 | 52 | A |
| 34 | Y | CE2 | 26.5 | 0.5 | 27.7 | 53 | A |
| 34 | Y | CZ | 27.6 | −0.1 | 27.0 | 53 | A |
| 34 | Y | OH | 28.8 | −0.1 | 27.5 | 52 | A |
| 34 | Y | C | 22.2 | 1.3 | 23.5 | 50 | A |
| 34 | Y | O | 21.3 | 0.6 | 24.0 | 50 | A |
| 35 | G | N | 22.0 | 2.3 | 22.7 | 49 | A |
| 35 | G | CA | 20.7 | 2.7 | 22.3 | 48 | A |
| 35 | G | C | 20.7 | 4.2 | 21.8 | 48 | A |
| 35 | G | O | 21.7 | 4.8 | 21.8 | 49 | A |
| 36 | M | N | 19.5 | 4.6 | 21.3 | 46 | A |
| 36 | M | CA | 19.4 | 6.0 | 20.8 | 45 | A |
| 36 | M | CB | 18.5 | 6.1 | 19.7 | 46 | A |
| 36 | M | CG | 17.0 | 5.8 | 20.0 | 46 | A |
| 36 | M | SD | 15.9 | 6.6 | 18.8 | 49 | A |
| 36 | M | CE | 16.2 | 5.6 | 17.3 | 48 | A |
| 36 | M | C | 19.0 | 7.0 | 21.9 | 44 | A |
| 36 | M | O | 18.4 | 6.6 | 23.0 | 40 | A |
| 37 | V | N | 19.4 | 8.3 | 21.7 | 44 | A |
| 37 | V | CA | 19.1 | 9.3 | 22.6 | 45 | A |
| 37 | V | CB | 20.4 | 10.0 | 23.1 | 45 | A |
| 37 | V | CG1 | 20.1 | 11.1 | 24.1 | 44 | A |
| 37 | V | CG2 | 21.4 | 9.0 | 23.6 | 44 | A |
| 37 | V | C | 18.2 | 10.4 | 22.0 | 45 | A |
| 37 | V | O | 18.4 | 10.8 | 20.9 | 44 | A |
| 38 | C | N | 17.1 | 10.7 | 22.7 | 46 | A |
| 38 | C | CA | 16.2 | 11.7 | 22.2 | 48 | A |
| 38 | C | CB | 14.8 | 11.0 | 21.9 | 49 | A |
| 38 | C | SG | 14.9 | 9.8 | 20.6 | 51 | A |
| 38 | C | C | 15.9 | 12.8 | 23.2 | 48 | A |
| 38 | C | O | 16.3 | 12.6 | 24.4 | 49 | A |
| 39 | S | N | 15.2 | 13.9 | 22.8 | 48 | A |
| 39 | S | CA | 14.9 | 14.9 | 23.8 | 50 | A |
| 39 | S | CB | 15.4 | 16.3 | 23.3 | 49 | A |
| 39 | S | OG | 14.9 | 16.6 | 22.0 | 48 | A |
| 39 | S | C | 13.4 | 15.0 | 23.8 | 50 | A |
| 39 | S | O | 12.7 | 15.4 | 22.9 | 52 | A |
| 40 | A | N | 12.8 | 14.6 | 25.0 | 51 | A |
| 40 | A | CA | 11.4 | 14.6 | 25.2 | 51 | A |
| 40 | A | CB | 11.0 | 13.5 | 26.1 | 49 | A |
| 40 | A | C | 11.0 | 15.9 | 25.8 | 53 | A |
| 40 | A | O | 11.8 | 16.9 | 25.9 | 51 | A |
| 41 | Y | N | 9.7 | 16.0 | 26.2 | 56 | A |
| 41 | Y | CA | 9.2 | 17.2 | 26.9 | 59 | A |
| 41 | Y | CB | 8.2 | 17.9 | 26.0 | 62 | A |
| 41 | Y | CG | 7.5 | 19.0 | 26.6 | 64 | A |
| 41 | Y | CD1 | 8.1 | 20.2 | 26.8 | 66 | A |
| 41 | Y | CE1 | 7.5 | 21.3 | 27.5 | 67 | A |
| 41 | Y | CD2 | 6.2 | 18.9 | 27.1 | 66 | A |
| 41 | Y | CE2 | 5.5 | 19.9 | 27.8 | 68 | A |
| 41 | Y | CZ | 6.2 | 21.1 | 28.0 | 68 | A |
| 41 | Y | OH | 5.6 | 22.1 | 28.7 | 69 | A |
| 41 | Y | C | 8.5 | 16.7 | 28.1 | 59 | A |
| 41 | Y | O | 7.4 | 16.1 | 28.0 | 61 | A |
| 42 | D | N | 9.1 | 16.9 | 29.3 | 59 | A |
| 42 | D | CA | 8.4 | 16.4 | 30.5 | 59 | A |
| 42 | D | CB | 9.3 | 16.7 | 31.7 | 57 | A |
| 42 | D | CG | 8.9 | 15.9 | 32.9 | 58 | A |
| 42 | D | OD1 | 7.8 | 15.5 | 33.0 | 57 | A |
| 42 | D | OD2 | 9.8 | 15.6 | 33.8 | 56 | A |
| 42 | D | C | 7.1 | 17.2 | 30.6 | 60 | A |
| 42 | D | O | 7.1 | 18.4 | 30.5 | 62 | A |
| 43 | N | N | 6.0 | 16.5 | 30.8 | 60 | A |
| 43 | N | CA | 4.7 | 17.1 | 30.9 | 60 | A |
| 43 | N | CB | 3.6 | 16.2 | 30.5 | 60 | A |
| 43 | N | CG | 3.6 | 16.0 | 29.0 | 61 | A |
| 43 | N | OD1 | 3.5 | 17.0 | 28.2 | 60 | A |
| 43 | N | ND2 | 3.7 | 14.8 | 28.5 | 60 | A |
| 43 | N | C | 4.5 | 17.5 | 32.4 | 60 | A |
| 43 | N | O | 3.6 | 18.3 | 32.7 | 61 | A |
| 44 | L | N | 5.3 | 17.0 | 33.3 | 60 | A |
| 44 | L | CA | 5.3 | 17.2 | 34.7 | 59 | A |
| 44 | L | CB | 5.8 | 16.1 | 35.5 | 57 | A |
| 44 | L | CG | 6.0 | 16.3 | 37.0 | 56 | A |
| 44 | L | CD1 | 4.9 | 17.1 | 37.6 | 56 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| Residue | AA | Atom | x | y | z | B | Chain |
|---|---|---|---|---|---|---|---|
| 44 | L | CD2 | 6.2 | 15.0 | 37.7 | 54 | A |
| 44 | L | C | 6.1 | 18.5 | 35.0 | 59 | A |
| 44 | L | O | 5.5 | 19.4 | 35.6 | 60 | A |
| 45 | N | N | 7.3 | 18.5 | 34.6 | 58 | A |
| 45 | N | CA | 8.2 | 19.7 | 34.9 | 57 | A |
| 45 | N | CB | 9.6 | 19.3 | 35.3 | 55 | A |
| 45 | N | CG | 9.6 | 18.3 | 36.4 | 53 | A |
| 45 | N | OD1 | 8.9 | 18.5 | 37.4 | 53 | A |
| 45 | N | ND2 | 10.4 | 17.2 | 36.3 | 53 | A |
| 45 | N | C | 8.2 | 20.6 | 33.7 | 56 | A |
| 45 | N | O | 9.2 | 21.5 | 33.6 | 58 | A |
| 46 | K | N | 7.2 | 20.5 | 32.8 | 56 | A |
| 46 | K | CA | 7.1 | 21.4 | 31.6 | 57 | A |
| 46 | K | CB | 6.3 | 22.6 | 31.9 | 59 | A |
| 46 | K | CG | 4.8 | 22.4 | 32.3 | 60 | A |
| 46 | K | CD | 4.7 | 21.8 | 33.7 | 60 | A |
| 46 | K | CE | 3.2 | 21.7 | 34.2 | 60 | A |
| 46 | K | NZ | 2.4 | 20.8 | 33.3 | 60 | A |
| 46 | K | C | 8.4 | 21.8 | 30.9 | 57 | A |
| 46 | K | O | 8.5 | 22.8 | 30.3 | 56 | A |
| 47 | V | N | 9.5 | 21.0 | 31.1 | 56 | A |
| 47 | V | CA | 10.8 | 21.3 | 30.5 | 55 | A |
| 47 | V | CB | 11.9 | 21.5 | 31.6 | 55 | A |
| 47 | V | CG1 | 11.7 | 22.8 | 32.2 | 56 | A |
| 47 | V | CG2 | 11.8 | 20.4 | 32.6 | 55 | A |
| 47 | V | C | 11.2 | 20.1 | 29.6 | 54 | A |
| 47 | V | O | 11.1 | 18.9 | 30.0 | 53 | A |
| 48 | R | N | 11.8 | 20.4 | 28.4 | 53 | A |
| 48 | R | CA | 12.3 | 19.4 | 27.6 | 53 | A |
| 48 | R | CB | 12.6 | 19.9 | 26.2 | 53 | A |
| 48 | R | CG | 11.4 | 20.3 | 25.4 | 52 | A |
| 48 | R | CD | 11.7 | 20.7 | 24.0 | 53 | A |
| 48 | R | NE | 12.3 | 19.7 | 23.1 | 53 | A |
| 48 | R | CZ | 11.6 | 18.6 | 22.8 | 52 | A |
| 48 | R | NH1 | 10.3 | 18.4 | 23.2 | 52 | A |
| 48 | R | NH2 | 12.1 | 17.6 | 22.0 | 52 | A |
| 48 | R | C | 13.5 | 18.8 | 28.2 | 53 | A |
| 48 | R | O | 14.5 | 19.6 | 28.4 | 54 | A |
| 49 | V | N | 13.5 | 17.5 | 28.5 | 51 | A |
| 49 | V | CA | 14.7 | 16.9 | 29.1 | 49 | A |
| 49 | V | CB | 14.3 | 15.9 | 30.2 | 49 | A |
| 49 | V | CG1 | 13.7 | 16.7 | 31.4 | 47 | A |
| 49 | V | CG2 | 13.2 | 14.9 | 29.7 | 48 | A |
| 49 | V | C | 15.4 | 16.1 | 28.0 | 47 | A |
| 49 | V | O | 15.1 | 16.2 | 26.8 | 47 | A |
| 50 | A | N | 16.3 | 15.2 | 28.4 | 46 | A |
| 50 | A | CA | 17.1 | 14.4 | 27.5 | 43 | A |
| 50 | A | CB | 18.6 | 14.7 | 27.5 | 43 | A |
| 50 | A | C | 16.9 | 12.9 | 28.0 | 40 | A |
| 50 | A | O | 16.9 | 12.7 | 29.2 | 38 | A |
| 51 | I | N | 16.7 | 12.0 | 27.1 | 38 | A |
| 51 | I | CA | 16.5 | 10.6 | 27.5 | 38 | A |
| 51 | I | CB | 15.0 | 10.2 | 27.4 | 37 | A |
| 51 | I | CG2 | 14.8 | 8.8 | 27.9 | 33 | A |
| 51 | I | CG1 | 14.2 | 11.2 | 28.2 | 36 | A |
| 51 | I | CD1 | 12.7 | 10.9 | 28.1 | 38 | A |
| 51 | I | C | 17.3 | 9.7 | 26.6 | 38 | A |
| 51 | I | O | 17.5 | 9.9 | 25.4 | 38 | A |
| 52 | K | N | 17.9 | 8.7 | 27.2 | 37 | A |
| 52 | K | CA | 18.7 | 7.7 | 26.4 | 37 | A |
| 52 | K | CB | 20.2 | 7.9 | 26.6 | 38 | A |
| 52 | K | CG | 20.7 | 7.6 | 28.0 | 40 | A |
| 52 | K | CD | 21.9 | 8.5 | 28.2 | 44 | A |
| 52 | K | CE | 22.9 | 7.9 | 29.3 | 48 | A |
| 52 | K | NZ | 23.8 | 6.9 | 28.6 | 49 | A |
| 52 | K | C | 18.2 | 6.3 | 26.6 | 34 | A |
| 52 | K | O | 18.1 | 5.9 | 27.8 | 31 | A |
| 53 | K | N | 17.9 | 5.6 | 25.5 | 35 | A |
| 53 | K | CA | 17.4 | 4.2 | 25.6 | 36 | A |
| 53 | K | CB | 16.6 | 3.9 | 24.4 | 35 | A |
| 53 | K | CG | 15.9 | 2.6 | 24.4 | 36 | A |
| 53 | K | CD | 15.1 | 2.3 | 23.1 | 35 | A |
| 53 | K | CE | 14.6 | 0.9 | 23.0 | 36 | A |
| 53 | K | NZ | 14.1 | 0.6 | 21.6 | 34 | A |
| 53 | K | C | 18.6 | 3.3 | 25.7 | 35 | A |
| 53 | K | O | 19.5 | 3.4 | 24.9 | 34 | A |
| 54 | I | N | 18.6 | 2.5 | 26.7 | 36 | A |
| 54 | I | CA | 19.8 | 1.6 | 26.9 | 36 | A |
| 54 | I | CB | 20.5 | 2.0 | 28.2 | 35 | A |
| 54 | I | CG2 | 21.7 | 1.1 | 28.4 | 32 | A |
| 54 | I | CG1 | 20.9 | 3.4 | 28.1 | 36 | A |
| 54 | I | CD1 | 21.6 | 4.0 | 29.4 | 38 | A |
| 54 | I | C | 19.3 | 0.1 | 27.0 | 37 | A |
| 54 | I | O | 18.6 | −0.2 | 28.0 | 39 | A |
| 55 | S | N | 19.8 | −0.7 | 26.1 | 39 | A |
| 55 | S | CA | 19.4 | −2.1 | 26.0 | 42 | A |
| 55 | S | CB | 18.7 | −2.4 | 24.7 | 42 | A |
| 55 | S | OG | 17.9 | −1.3 | 24.3 | 40 | A |
| 55 | S | C | 20.7 | −2.9 | 26.1 | 44 | A |
| 55 | S | O | 21.3 | −3.4 | 25.1 | 46 | A |
| 56 | P | N | 21.2 | −3.1 | 27.4 | 45 | A |
| 56 | P | CD | 20.8 | −2.3 | 28.6 | 45 | A |
| 56 | P | CA | 22.5 | −3.8 | 27.6 | 45 | A |
| 56 | P | CB | 23.1 | −2.9 | 28.7 | 46 | A |
| 56 | P | CG | 22.0 | −2.7 | 29.6 | 44 | A |
| 56 | P | C | 22.4 | −5.3 | 28.1 | 47 | A |
| 56 | P | O | 23.4 | −6.0 | 27.9 | 47 | A |
| 57 | F | N | 21.3 | −5.7 | 28.6 | 48 | A |
| 57 | F | CA | 21.1 | −7.0 | 29.1 | 50 | A |
| 57 | F | CB | 19.6 | −7.2 | 29.4 | 50 | A |
| 57 | F | CG | 19.1 | −6.1 | 30.3 | 51 | A |
| 57 | F | CD1 | 19.6 | −5.8 | 31.5 | 52 | A |
| 57 | F | CD2 | 18.1 | −5.3 | 29.8 | 52 | A |
| 57 | F | CE1 | 19.2 | −4.8 | 32.3 | 53 | A |
| 57 | F | CE2 | 17.6 | −4.2 | 30.6 | 53 | A |
| 57 | F | CZ | 18.2 | −3.9 | 31.8 | 52 | A |
| 57 | F | C | 21.6 | −8.2 | 28.3 | 50 | A |
| 57 | F | O | 21.6 | −9.4 | 28.8 | 50 | A |
| 58 | E | N | 22.1 | −8.0 | 27.1 | 50 | A |
| 58 | E | CA | 22.6 | −9.1 | 26.2 | 52 | A |
| 58 | E | CB | 22.6 | −8.7 | 24.8 | 54 | A |
| 58 | E | CG | 21.2 | −8.3 | 24.3 | 57 | A |
| 58 | E | CD | 20.3 | −9.5 | 24.3 | 60 | A |
| 58 | E | OE1 | 20.5 | −10.5 | 23.5 | 61 | A |
| 58 | E | OE2 | 19.3 | −9.6 | 25.0 | 60 | A |
| 58 | E | C | 24.1 | −9.4 | 26.6 | 52 | A |
| 58 | E | O | 24.5 | −10.6 | 26.5 | 52 | A |
| 59 | H | N | 24.9 | −8.5 | 27.0 | 50 | A |
| 59 | H | CA | 26.3 | −8.7 | 27.4 | 50 | A |
| 59 | H | CB | 27.2 | −8.0 | 26.4 | 52 | A |
| 59 | H | CG | 26.9 | −8.2 | 25.0 | 55 | A |
| 59 | H | CD2 | 27.5 | −8.9 | 24.0 | 55 | A |
| 59 | H | ND1 | 25.7 | −7.7 | 24.4 | 55 | A |
| 59 | H | CE1 | 25.7 | −8.1 | 23.1 | 56 | A |
| 59 | H | NE2 | 26.7 | −8.8 | 22.8 | 57 | A |
| 59 | H | C | 26.6 | −8.3 | 28.8 | 49 | A |
| 59 | H | O | 26.1 | −7.3 | 29.3 | 49 | A |
| 60 | Q | N | 27.5 | −9.0 | 29.4 | 47 | A |
| 60 | Q | CA | 27.9 | −8.7 | 30.8 | 46 | A |
| 60 | Q | CB | 28.9 | −9.7 | 31.3 | 45 | A |
| 60 | Q | CG | 29.6 | −9.3 | 32.6 | 46 | A |
| 60 | Q | CD | 30.9 | −10.0 | 32.8 | 46 | A |
| 60 | Q | OE1 | 31.8 | −10.0 | 32.0 | 48 | A |
| 60 | Q | NE2 | 31.1 | −10.6 | 34.0 | 46 | A |
| 60 | Q | C | 28.6 | −7.3 | 30.9 | 46 | A |
| 60 | Q | O | 28.2 | −6.5 | 31.8 | 47 | A |
| 61 | T | N | 29.6 | −7.0 | 30.0 | 46 | A |
| 61 | T | CA | 30.3 | −5.8 | 30.1 | 46 | A |
| 61 | T | CB | 31.4 | −5.7 | 29.1 | 44 | A |
| 61 | T | OG1 | 31.0 | −6.0 | 27.8 | 50 | A |

TABLE 2-continued

Structural Coordinates of Ah₆-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 61 | T | CG2 | 32.4 | −6.8 | 29.4 | 43 | A |
| 61 | T | C | 29.3 | −4.6 | 29.8 | 46 | A |
| 61 | T | O | 29.5 | −3.5 | 30.3 | 47 | A |
| 62 | Y | N | 28.3 | −4.8 | 29.0 | 46 | A |
| 62 | Y | CA | 27.3 | −3.8 | 28.8 | 46 | A |
| 62 | Y | CB | 26.3 | −4.3 | 27.7 | 49 | A |
| 62 | Y | CG | 26.8 | −4.1 | 26.3 | 51 | A |
| 62 | Y | CD1 | 28.2 | −4.0 | 26.0 | 51 | A |
| 62 | Y | CE1 | 28.7 | −3.9 | 24.7 | 52 | A |
| 62 | Y | CD2 | 26.0 | −4.0 | 25.2 | 51 | A |
| 62 | Y | CE2 | 26.5 | −3.9 | 23.9 | 51 | A |
| 62 | Y | CZ | 27.9 | −3.8 | 23.7 | 51 | A |
| 62 | Y | OH | 28.4 | −3.6 | 22.4 | 51 | A |
| 62 | Y | C | 26.5 | −3.6 | 30.1 | 46 | A |
| 62 | Y | O | 26.2 | −2.4 | 30.4 | 45 | A |
| 63 | C | N | 26.2 | −4.7 | 30.8 | 43 | A |
| 63 | C | CA | 25.5 | −4.6 | 32.1 | 41 | A |
| 63 | C | CB | 25.1 | −6.0 | 32.5 | 42 | A |
| 63 | C | SG | 23.7 | −6.7 | 31.6 | 41 | A |
| 63 | C | C | 26.4 | −3.9 | 33.2 | 40 | A |
| 63 | C | O | 25.9 | −3.1 | 33.9 | 39 | A |
| 64 | Q | N | 27.7 | −4.3 | 33.2 | 38 | A |
| 64 | Q | CA | 28.6 | −3.7 | 34.2 | 38 | A |
| 64 | Q | CB | 30.0 | −4.2 | 34.0 | 38 | A |
| 64 | Q | CG | 30.3 | −5.6 | 34.5 | 42 | A |
| 64 | Q | CD | 31.8 | −5.9 | 34.4 | 44 | A |
| 64 | Q | OE1 | 32.4 | −5.6 | 33.3 | 46 | A |
| 64 | Q | NE2 | 32.4 | −6.4 | 35.4 | 44 | A |
| 64 | Q | C | 28.6 | −2.2 | 34.2 | 37 | A |
| 64 | Q | O | 28.4 | −1.5 | 35.2 | 36 | A |
| 65 | R | N | 28.7 | −1.7 | 33.0 | 35 | A |
| 65 | R | CA | 28.8 | −0.2 | 32.7 | 37 | A |
| 65 | R | CB | 29.3 | 0.0 | 31.3 | 36 | A |
| 65 | R | CG | 30.7 | −0.5 | 31.1 | 38 | A |
| 65 | R | CD | 31.3 | −0.4 | 29.7 | 40 | A |
| 65 | R | NE | 32.7 | −0.8 | 29.6 | 43 | A |
| 65 | R | CZ | 33.4 | −0.8 | 28.5 | 44 | A |
| 65 | R | NH1 | 32.8 | −0.5 | 27.3 | 41 | A |
| 65 | R | NH2 | 34.6 | −1.2 | 28.5 | 40 | A |
| 65 | R | C | 27.5 | 0.5 | 33.0 | 37 | A |
| 65 | R | O | 27.5 | 1.6 | 33.4 | 39 | A |
| 66 | T | N | 26.4 | −0.2 | 32.7 | 37 | A |
| 66 | T | CA | 25.1 | 0.4 | 32.9 | 35 | A |
| 66 | T | CB | 24.0 | −0.5 | 32.3 | 35 | A |
| 66 | T | OG1 | 24.1 | −0.5 | 30.9 | 35 | A |
| 66 | T | CG2 | 22.6 | 0.0 | 32.7 | 33 | A |
| 66 | T | C | 24.8 | 0.5 | 34.4 | 35 | A |
| 66 | T | O | 24.4 | 1.6 | 34.9 | 35 | A |
| 67 | L | N | 25.1 | −0.5 | 35.2 | 33 | A |
| 67 | L | CA | 25.0 | −0.5 | 36.7 | 32 | A |
| 67 | L | CB | 25.2 | −1.9 | 37.2 | 31 | A |
| 67 | L | CG | 24.7 | −2.4 | 38.6 | 32 | A |
| 67 | L | CD1 | 25.8 | −2.2 | 39.6 | 32 | A |
| 67 | L | CD2 | 23.4 | −1.8 | 38.9 | 29 | A |
| 67 | L | C | 25.9 | 0.5 | 37.3 | 32 | A |
| 67 | L | O | 25.5 | 1.3 | 38.2 | 29 | A |
| 68 | R | N | 27.2 | 0.6 | 36.8 | 31 | A |
| 68 | R | CA | 28.2 | 1.5 | 37.3 | 29 | A |
| 68 | R | CB | 29.5 | 1.3 | 36.6 | 25 | A |
| 68 | R | CG | 30.4 | 0.2 | 37.2 | 23 | A |
| 68 | R | CD | 31.5 | −0.1 | 36.3 | 20 | A |
| 68 | R | NE | 32.3 | −1.3 | 36.8 | 19 | A |
| 68 | R | CZ | 33.3 | −1.9 | 36.2 | 20 | A |
| 68 | R | NH1 | 33.8 | −1.4 | 35.1 | 16 | A |
| 68 | R | NH2 | 33.9 | −2.9 | 36.8 | 18 | A |
| 68 | R | C | 27.7 | 3.0 | 37.1 | 28 | A |
| 68 | R | O | 27.6 | 3.7 | 38.1 | 26 | A |
| 69 | E | N | 27.4 | 3.4 | 35.9 | 28 | A |
| 69 | E | CA | 26.9 | 4.7 | 35.7 | 29 | A |
| 69 | E | CB | 26.6 | 4.9 | 34.2 | 30 | A |
| 69 | E | CG | 25.9 | 6.2 | 33.9 | 34 | A |
| 69 | E | CD | 26.0 | 6.7 | 32.5 | 36 | A |
| 69 | E | OE1 | 25.6 | 5.9 | 31.6 | 36 | A |
| 69 | E | OE2 | 26.4 | 7.8 | 32.2 | 34 | A |
| 69 | E | C | 25.7 | 5.1 | 36.5 | 30 | A |
| 69 | E | O | 25.7 | 6.2 | 37.1 | 31 | A |
| 70 | I | N | 24.8 | 4.2 | 36.7 | 26 | A |
| 70 | I | CA | 23.6 | 4.4 | 37.5 | 25 | A |
| 70 | I | CB | 22.6 | 3.2 | 37.3 | 25 | A |
| 70 | I | CG2 | 21.5 | 3.4 | 38.3 | 22 | A |
| 70 | I | CG1 | 22.0 | 3.2 | 35.9 | 22 | A |
| 70 | I | CD1 | 21.3 | 2.0 | 35.6 | 21 | A |
| 70 | I | C | 23.9 | 4.6 | 39.0 | 25 | A |
| 70 | I | O | 23.5 | 5.5 | 39.6 | 27 | A |
| 71 | K | N | 24.6 | 3.6 | 39.6 | 25 | A |
| 71 | K | CA | 24.9 | 3.7 | 41.0 | 28 | A |
| 71 | K | CB | 25.7 | 2.5 | 41.5 | 30 | A |
| 71 | K | CG | 24.8 | 1.2 | 41.4 | 33 | A |
| 71 | K | CD | 25.6 | −0.0 | 41.9 | 34 | A |
| 71 | K | CE | 25.9 | 0.1 | 43.4 | 37 | A |
| 71 | K | NZ | 26.6 | −1.2 | 43.9 | 39 | A |
| 71 | K | C | 25.7 | 5.0 | 41.3 | 29 | A |
| 71 | K | O | 25.4 | 5.7 | 42.2 | 29 | A |
| 72 | I | N | 26.7 | 5.2 | 40.5 | 27 | A |
| 72 | I | CA | 27.5 | 6.4 | 40.6 | 26 | A |
| 72 | I | CB | 28.7 | 6.4 | 39.7 | 26 | A |
| 72 | I | CG2 | 29.4 | 7.8 | 39.6 | 21 | A |
| 72 | I | CG1 | 29.7 | 5.4 | 40.1 | 22 | A |
| 72 | I | CD1 | 30.7 | 5.0 | 38.9 | 22 | A |
| 72 | I | C | 26.7 | 7.7 | 40.5 | 25 | A |
| 72 | I | O | 26.7 | 8.6 | 41.3 | 25 | A |
| 73 | L | N | 26.1 | 7.9 | 39.3 | 24 | A |
| 73 | L | CA | 25.3 | 9.1 | 39.0 | 26 | A |
| 73 | L | CB | 24.9 | 9.0 | 37.5 | 25 | A |
| 73 | L | CG | 25.4 | 10.1 | 36.6 | 25 | A |
| 73 | L | CD1 | 26.9 | 10.2 | 36.9 | 21 | A |
| 73 | L | CD2 | 25.1 | 9.8 | 35.2 | 21 | A |
| 73 | L | C | 24.1 | 9.3 | 39.9 | 27 | A |
| 73 | L | O | 23.6 | 10.4 | 40.1 | 29 | A |
| 74 | L | N | 23.6 | 8.2 | 40.5 | 28 | A |
| 74 | L | CA | 22.5 | 8.3 | 41.4 | 30 | A |
| 74 | L | CB | 21.8 | 6.9 | 41.6 | 28 | A |
| 74 | L | CG | 20.3 | 6.7 | 41.3 | 31 | A |
| 74 | L | CD1 | 19.8 | 7.7 | 40.2 | 25 | A |
| 74 | L | CD2 | 20.1 | 5.3 | 40.9 | 32 | A |
| 74 | L | C | 22.9 | 8.8 | 42.7 | 30 | A |
| 74 | L | O | 22.2 | 9.6 | 43.4 | 30 | A |
| 75 | R | N | 24.1 | 8.5 | 43.2 | 30 | A |
| 75 | R | CA | 24.7 | 9.0 | 44.4 | 31 | A |
| 75 | R | CB | 25.7 | 8.0 | 45.0 | 34 | A |
| 75 | R | CG | 26.3 | 8.5 | 46.3 | 37 | A |
| 75 | R | CD | 27.3 | 7.5 | 46.9 | 40 | A |
| 75 | R | NE | 26.7 | 6.2 | 47.2 | 42 | A |
| 75 | R | CZ | 27.3 | 5.3 | 48.0 | 43 | A |
| 75 | R | NH1 | 28.5 | 5.6 | 48.5 | 44 | A |
| 75 | R | NH2 | 26.7 | 4.1 | 48.2 | 42 | A |
| 75 | R | C | 25.3 | 10.4 | 44.3 | 30 | A |
| 75 | R | O | 25.2 | 11.1 | 45.3 | 30 | A |
| 76 | F | N | 25.9 | 10.7 | 43.2 | 27 | A |
| 76 | F | CA | 26.6 | 12.0 | 43.0 | 26 | A |
| 76 | F | CB | 27.3 | 12.0 | 41.7 | 23 | A |
| 76 | F | CG | 28.7 | 11.3 | 41.8 | 23 | A |
| 76 | F | CD1 | 29.1 | 10.7 | 42.9 | 20 | A |
| 76 | F | CD2 | 29.5 | 11.4 | 40.7 | 20 | A |
| 76 | F | CE1 | 30.4 | 10.1 | 43.0 | 22 | A |
| 76 | F | CE2 | 30.8 | 10.8 | 40.7 | 23 | A |
| 76 | F | CZ | 31.2 | 10.2 | 41.9 | 21 | A |
| 76 | F | C | 25.6 | 13.2 | 43.0 | 26 | A |
| 76 | F | O | 24.5 | 13.1 | 42.5 | 26 | A |
| 77 | R | N | 26.0 | 14.3 | 43.6 | 28 | A |

TABLE 2-continued

Structural Coordinates of Ah₆-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 77 | R | CA | 25.2 | 15.5 | 43.7 | 29 | A |
| 77 | R | CB | 24.6 | 15.6 | 45.1 | 34 | A |
| 77 | R | CG | 25.6 | 15.7 | 46.3 | 43 | A |
| 77 | R | CD | 25.4 | 14.6 | 47.3 | 49 | A |
| 77 | R | NE | 26.7 | 14.0 | 47.7 | 53 | A |
| 77 | R | CZ | 27.7 | 14.5 | 48.3 | 55 | A |
| 77 | R | NH1 | 27.7 | 15.8 | 48.6 | 58 | A |
| 77 | R | NH2 | 28.8 | 13.8 | 48.5 | 55 | A |
| 77 | R | C | 26.2 | 16.7 | 43.5 | 26 | A |
| 77 | R | O | 26.7 | 17.3 | 44.5 | 25 | A |
| 78 | H | N | 26.3 | 17.2 | 42.3 | 24 | A |
| 78 | H | CA | 27.2 | 18.3 | 42.0 | 22 | A |
| 78 | H | CB | 28.6 | 17.8 | 41.8 | 19 | A |
| 78 | H | CG | 29.7 | 18.8 | 41.8 | 21 | A |
| 78 | H | CD2 | 30.1 | 19.7 | 40.8 | 19 | A |
| 78 | H | ND1 | 30.5 | 19.1 | 42.8 | 21 | A |
| 78 | H | CE1 | 31.4 | 20.0 | 42.5 | 20 | A |
| 78 | H | NE2 | 31.2 | 20.4 | 41.3 | 24 | A |
| 78 | H | C | 26.8 | 19.1 | 40.8 | 22 | A |
| 78 | H | O | 26.2 | 18.6 | 39.8 | 22 | A |
| 79 | E | N | 27.0 | 20.4 | 40.9 | 21 | A |
| 79 | E | CA | 26.6 | 21.4 | 39.8 | 21 | A |
| 79 | E | CB | 26.9 | 22.8 | 40.2 | 23 | A |
| 79 | E | CG | 26.1 | 23.3 | 41.4 | 27 | A |
| 79 | E | CD | 26.5 | 24.7 | 41.7 | 30 | A |
| 79 | E | OE1 | 25.7 | 25.4 | 42.5 | 33 | A |
| 79 | E | OE2 | 27.6 | 25.2 | 41.3 | 33 | A |
| 79 | E | C | 27.3 | 21.1 | 38.5 | 22 | A |
| 79 | E | O | 26.7 | 21.3 | 37.4 | 20 | A |
| 80 | N | N | 28.5 | 20.5 | 38.5 | 21 | A |
| 80 | N | CA | 29.2 | 20.2 | 37.3 | 21 | A |
| 80 | N | CB | 30.7 | 20.7 | 37.5 | 18 | A |
| 80 | N | CG | 30.8 | 22.2 | 37.9 | 21 | A |
| 80 | N | OD1 | 31.3 | 22.5 | 38.9 | 23 | A |
| 80 | N | ND2 | 30.3 | 23.1 | 37.0 | 15 | A |
| 80 | N | C | 29.2 | 18.8 | 36.8 | 22 | A |
| 80 | N | O | 30.0 | 18.3 | 36.0 | 22 | A |
| 81 | I | N | 28.2 | 18.0 | 37.4 | 19 | A |
| 81 | I | CA | 28.0 | 16.6 | 37.0 | 18 | A |
| 81 | I | CB | 28.4 | 15.7 | 38.2 | 19 | A |
| 81 | I | CG2 | 28.1 | 14.2 | 37.8 | 14 | A |
| 81 | I | CG1 | 29.9 | 15.9 | 38.6 | 18 | A |
| 81 | I | CD1 | 30.3 | 15.0 | 39.7 | 17 | A |
| 81 | I | C | 26.6 | 16.3 | 36.6 | 18 | A |
| 81 | I | O | 25.7 | 16.6 | 37.4 | 15 | A |
| 82 | I | N | 26.4 | 15.9 | 35.4 | 19 | A |
| 82 | I | CA | 25.0 | 15.6 | 35.0 | 20 | A |
| 82 | I | CB | 25.0 | 14.9 | 33.6 | 22 | A |
| 82 | I | CG2 | 25.5 | 13.5 | 33.6 | 18 | A |
| 82 | I | CG1 | 23.5 | 15.0 | 33.0 | 23 | A |
| 82 | I | CD1 | 22.9 | 16.3 | 32.9 | 22 | A |
| 82 | I | C | 24.4 | 14.6 | 36.0 | 21 | A |
| 82 | I | O | 25.1 | 13.7 | 36.6 | 21 | A |
| 83 | G | N | 23.1 | 14.7 | 36.3 | 23 | A |
| 83 | G | CA | 22.5 | 13.8 | 37.2 | 26 | A |
| 83 | G | C | 21.4 | 13.0 | 36.5 | 29 | A |
| 83 | G | O | 21.1 | 13.3 | 35.3 | 29 | A |
| 84 | I | N | 20.7 | 12.1 | 37.2 | 30 | A |
| 84 | I | CA | 19.6 | 11.3 | 36.6 | 31 | A |
| 84 | I | CB | 19.8 | 9.8 | 36.8 | 31 | A |
| 84 | I | CG2 | 18.6 | 9.0 | 36.3 | 30 | A |
| 84 | I | CG1 | 21.1 | 9.3 | 36.2 | 27 | A |
| 84 | I | CD1 | 21.3 | 7.8 | 36.4 | 26 | A |
| 84 | I | C | 18.3 | 11.8 | 37.3 | 32 | A |
| 84 | I | O | 18.1 | 11.6 | 38.5 | 33 | A |
| 85 | N | N | 17.4 | 12.4 | 36.5 | 34 | A |
| 85 | N | CA | 16.2 | 12.9 | 37.1 | 37 | A |
| 85 | N | CB | 15.6 | 14.1 | 36.3 | 36 | A |
| 85 | N | CG | 16.7 | 15.0 | 35.8 | 39 | A |
| 85 | N | OD1 | 17.7 | 15.2 | 36.5 | 38 | A |
| 85 | N | ND2 | 16.5 | 15.6 | 34.7 | 39 | A |
| 85 | N | C | 15.1 | 11.8 | 37.2 | 38 | A |
| 85 | N | O | 14.1 | 12.0 | 37.9 | 40 | A |
| 86 | D | N | 15.2 | 10.7 | 36.5 | 38 | A |
| 86 | D | CA | 14.2 | 9.6 | 36.5 | 38 | A |
| 86 | D | CB | 12.9 | 10.2 | 36.0 | 35 | A |
| 86 | D | CG | 11.7 | 9.3 | 36.0 | 35 | A |
| 86 | D | OD1 | 11.7 | 8.3 | 36.8 | 33 | A |
| 86 | D | OD2 | 10.8 | 9.4 | 35.2 | 35 | A |
| 86 | D | C | 14.7 | 8.5 | 35.6 | 40 | A |
| 86 | D | O | 15.5 | 8.6 | 34.7 | 42 | A |
| 87 | I | N | 14.1 | 7.3 | 35.9 | 40 | A |
| 87 | I | CA | 14.4 | 6.1 | 35.1 | 40 | A |
| 87 | I | CB | 15.4 | 5.2 | 35.8 | 39 | A |
| 87 | I | CG2 | 15.6 | 3.9 | 35.0 | 37 | A |
| 87 | I | CG1 | 16.7 | 5.9 | 36.0 | 37 | A |
| 87 | I | CD1 | 17.8 | 5.1 | 36.6 | 35 | A |
| 87 | I | C | 13.1 | 5.2 | 34.9 | 42 | A |
| 87 | I | O | 12.5 | 4.7 | 35.8 | 42 | A |
| 88 | I | N | 12.8 | 5.1 | 33.6 | 43 | A |
| 88 | I | CA | 11.6 | 4.3 | 33.2 | 44 | A |
| 88 | I | CB | 10.9 | 5.0 | 32.0 | 44 | A |
| 88 | I | CG2 | 9.8 | 4.1 | 31.4 | 43 | A |
| 88 | I | CG1 | 10.3 | 6.3 | 32.5 | 42 | A |
| 88 | I | CD1 | 9.6 | 7.1 | 31.4 | 41 | A |
| 88 | I | C | 12.0 | 2.9 | 32.7 | 45 | A |
| 88 | I | O | 12.8 | 2.8 | 31.8 | 45 | A |
| 89 | R | N | 11.5 | 1.9 | 33.3 | 47 | A |
| 89 | R | CA | 11.8 | 0.5 | 33.0 | 48 | A |
| 89 | R | CB | 13.1 | -0.0 | 33.6 | 48 | A |
| 89 | R | CG | 13.1 | 0.1 | 35.1 | 47 | A |
| 89 | R | CD | 12.2 | -1.0 | 35.8 | 48 | A |
| 89 | R | NE | 12.6 | -1.1 | 37.2 | 50 | A |
| 89 | R | CZ | 11.9 | -1.7 | 38.1 | 50 | A |
| 89 | R | NH1 | 10.7 | -2.3 | 37.8 | 52 | A |
| 89 | R | NH2 | 12.3 | -1.8 | 39.4 | 49 | A |
| 89 | R | C | 10.6 | -0.4 | 33.3 | 49 | A |
| 89 | R | O | 9.8 | -0.1 | 34.3 | 49 | A |
| 90 | A | N | 10.4 | -1.5 | 32.6 | 51 | A |
| 90 | A | CA | 9.3 | -2.4 | 32.8 | 52 | A |
| 90 | A | CB | 9.5 | -3.7 | 32.0 | 51 | A |
| 90 | A | C | 9.0 | -2.8 | 34.2 | 52 | A |
| 90 | A | O | 9.9 | -2.9 | 35.1 | 52 | A |
| 91 | P | N | 7.7 | -2.9 | 34.6 | 53 | A |
| 91 | P | CD | 6.5 | -2.7 | 33.7 | 53 | A |
| 91 | P | CA | 7.2 | -3.2 | 35.9 | 53 | A |
| 91 | P | CB | 5.7 | -3.3 | 35.8 | 53 | A |
| 91 | P | CG | 5.4 | -2.4 | 34.6 | 53 | A |
| 91 | P | C | 7.8 | -4.6 | 36.4 | 52 | A |
| 91 | P | O | 8.0 | -4.7 | 37.6 | 52 | A |
| 92 | T | N | 7.9 | -5.5 | 35.5 | 53 | A |
| 92 | T | CA | 8.5 | -6.8 | 35.9 | 56 | A |
| 92 | T | CB | 7.5 | -7.9 | 35.5 | 56 | A |
| 92 | T | OG1 | 7.4 | -8.1 | 34.1 | 58 | A |
| 92 | T | CG2 | 6.1 | -7.6 | 36.0 | 56 | A |
| 92 | T | C | 9.8 | -7.1 | 35.1 | 57 | A |
| 92 | T | O | 9.9 | -6.8 | 34.0 | 57 | A |
| 93 | I | N | 10.8 | -7.6 | 35.9 | 57 | A |
| 93 | I | CA | 12.1 | -7.9 | 35.3 | 58 | A |
| 93 | I | CB | 12.9 | -8.7 | 36.3 | 58 | A |
| 93 | I | CG2 | 12.3 | -10.0 | 36.5 | 57 | A |
| 93 | I | CG1 | 14.4 | -8.8 | 35.7 | 58 | A |
| 93 | I | CD1 | 15.4 | -9.3 | 36.8 | 58 | A |
| 93 | I | C | 12.0 | -8.5 | 33.9 | 58 | A |
| 93 | I | O | 12.7 | -8.1 | 33.0 | 58 | A |
| 94 | E | N | 11.2 | -9.6 | 33.8 | 58 | A |
| 94 | E | CA | 11.1 | -10.3 | 32.5 | 56 | A |
| 94 | E | CB | 10.0 | -11.4 | 32.5 | 57 | A |
| 94 | E | CG | 10.4 | -12.7 | 33.3 | 56 | A |
| 94 | E | CD | 10.5 | -12.5 | 34.8 | 57 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 94 | E | OE1 | 9.6 | −11.8 | 35.4 | 56 | A |
|---|---|---|---|---|---|---|---|
| 94 | E | OE2 | 11.5 | −13.0 | 35.4 | 56 | A |
| 94 | E | C | 10.8 | −9.3 | 31.4 | 56 | A |
| 94 | E | O | 11.3 | −9.5 | 30.2 | 56 | A |
| 95 | Q | N | 10.0 | −8.3 | 31.7 | 56 | A |
| 95 | Q | CA | 9.6 | −7.3 | 30.7 | 57 | A |
| 95 | Q | CB | 8.3 | −6.6 | 31.1 | 59 | A |
| 95 | Q | CG | 7.1 | −7.5 | 31.4 | 61 | A |
| 95 | Q | CD | 5.9 | −6.8 | 31.7 | 62 | A |
| 95 | Q | OE1 | 5.3 | −6.1 | 30.9 | 63 | A |
| 95 | Q | NE2 | 5.5 | −6.8 | 33.0 | 61 | A |
| 95 | Q | C | 10.6 | −6.3 | 30.4 | 55 | A |
| 95 | Q | O | 10.5 | −5.5 | 29.4 | 57 | A |
| 96 | M | N | 11.6 | −6.2 | 31.3 | 53 | A |
| 96 | M | CA | 12.7 | −5.2 | 31.2 | 51 | A |
| 96 | M | CB | 13.3 | −4.9 | 32.5 | 50 | A |
| 96 | M | CG | 14.4 | −3.8 | 32.5 | 45 | A |
| 96 | M | SD | 15.0 | −3.5 | 34.2 | 42 | A |
| 96 | M | CE | 16.0 | −4.9 | 34.4 | 40 | A |
| 96 | M | C | 13.7 | −5.6 | 30.1 | 50 | A |
| 96 | M | O | 14.6 | −6.5 | 30.4 | 47 | A |
| 97 | K | N | 13.7 | −5.0 | 29.0 | 50 | A |
| 97 | K | CA | 14.6 | −5.2 | 27.9 | 52 | A |
| 97 | K | CB | 13.9 | −5.6 | 26.6 | 53 | A |
| 97 | K | CG | 12.8 | −6.6 | 26.8 | 56 | A |
| 97 | K | CD | 13.3 | −8.0 | 27.0 | 59 | A |
| 97 | K | CE | 12.2 | −9.0 | 27.1 | 60 | A |
| 97 | K | NZ | 12.8 | −10.4 | 27.3 | 61 | A |
| 97 | K | C | 15.4 | −3.9 | 27.7 | 51 | A |
| 97 | K | O | 16.5 | −3.9 | 27.2 | 51 | A |
| 98 | D | N | 14.8 | −2.8 | 28.1 | 49 | A |
| 98 | D | CA | 15.3 | −1.5 | 27.9 | 49 | A |
| 98 | D | CB | 14.6 | −0.8 | 26.8 | 50 | A |
| 98 | D | CG | 14.5 | −1.6 | 25.6 | 51 | A |
| 98 | D | OD1 | 15.6 | −2.1 | 25.0 | 52 | A |
| 98 | D | OD2 | 13.4 | −1.9 | 25.1 | 53 | A |
| 98 | D | C | 15.2 | −0.6 | 29.2 | 48 | A |
| 98 | D | O | 14.4 | −0.9 | 30.1 | 50 | A |
| 99 | V | N | 16.1 | 0.4 | 29.2 | 46 | A |
| 99 | V | CA | 16.1 | 1.3 | 30.3 | 43 | A |
| 99 | V | CB | 17.2 | 1.0 | 31.3 | 44 | A |
| 99 | V | CG1 | 17.1 | 2.0 | 32.5 | 43 | A |
| 99 | V | CG2 | 17.1 | −0.4 | 31.8 | 42 | A |
| 99 | V | C | 16.2 | 2.7 | 29.8 | 42 | A |
| 99 | V | O | 17.1 | 3.0 | 28.9 | 42 | A |
| 100 | Y | N | 15.3 | 3.6 | 30.2 | 40 | A |
| 100 | Y | CA | 15.4 | 5.0 | 29.7 | 38 | A |
| 100 | Y | CB | 14.1 | 5.5 | 29.1 | 38 | A |
| 100 | Y | CG | 13.5 | 4.6 | 28.0 | 38 | A |
| 100 | Y | CD1 | 12.9 | 3.4 | 28.3 | 37 | A |
| 100 | Y | CE1 | 12.4 | 2.5 | 27.3 | 38 | A |
| 100 | Y | CD2 | 13.7 | 4.9 | 26.7 | 37 | A |
| 100 | Y | CE2 | 13.1 | 4.1 | 25.6 | 39 | A |
| 100 | Y | CZ | 12.5 | 2.9 | 26.0 | 39 | A |
| 100 | Y | OH | 12.0 | 2.2 | 25.0 | 42 | A |
| 100 | Y | C | 15.8 | 5.9 | 30.8 | 38 | A |
| 100 | Y | O | 15.1 | 6.1 | 31.8 | 39 | A |
| 101 | I | N | 17.0 | 6.5 | 30.7 | 35 | A |
| 101 | I | CA | 17.5 | 7.4 | 31.7 | 33 | A |
| 101 | I | CB | 19.0 | 7.2 | 32.0 | 33 | A |
| 101 | I | CG2 | 19.5 | 8.1 | 33.0 | 32 | A |
| 101 | I | CG1 | 19.2 | 5.7 | 32.4 | 34 | A |
| 101 | I | CD1 | 20.7 | 5.3 | 32.5 | 34 | A |
| 101 | I | C | 17.3 | 8.9 | 31.3 | 33 | A |
| 101 | I | O | 17.8 | 9.3 | 30.3 | 33 | A |
| 102 | V | N | 16.4 | 9.5 | 32.1 | 33 | A |
| 102 | V | CA | 16.1 | 10.9 | 31.8 | 35 | A |
| 102 | V | CB | 14.7 | 11.3 | 32.4 | 37 | A |
| 102 | V | CG1 | 14.4 | 12.7 | 32.0 | 39 | A |
| 102 | V | CG2 | 13.7 | 10.4 | 31.8 | 36 | A |
| 102 | V | C | 17.2 | 11.8 | 32.6 | 34 | A |
| 102 | V | O | 17.5 | 11.6 | 33.7 | 35 | A |
| 103 | Q | N | 17.7 | 12.8 | 31.8 | 32 | A |
| 103 | Q | CA | 18.7 | 13.7 | 32.4 | 31 | A |
| 103 | Q | CB | 20.1 | 13.3 | 31.9 | 29 | A |
| 103 | Q | CG | 20.5 | 12.0 | 32.4 | 27 | A |
| 103 | Q | CD | 21.9 | 11.6 | 32.0 | 27 | A |
| 103 | Q | OE1 | 22.2 | 11.5 | 30.9 | 28 | A |
| 103 | Q | NE2 | 22.8 | 11.4 | 33.0 | 32 | A |
| 103 | Q | C | 18.3 | 15.1 | 31.8 | 32 | A |
| 103 | Q | O | 17.6 | 15.2 | 30.9 | 32 | A |
| 104 | D | N | 19.0 | 16.2 | 32.4 | 32 | A |
| 104 | D | CA | 18.7 | 17.5 | 31.9 | 32 | A |
| 104 | D | CB | 19.4 | 18.6 | 32.8 | 34 | A |
| 104 | D | CG | 18.8 | 18.7 | 34.2 | 36 | A |
| 104 | D | OD1 | 17.5 | 18.7 | 34.3 | 37 | A |
| 104 | D | OD2 | 19.6 | 18.7 | 35.1 | 37 | A |
| 104 | D | C | 19.2 | 17.7 | 30.5 | 33 | A |
| 104 | D | O | 20.3 | 17.1 | 30.1 | 33 | A |
| 105 | L | N | 18.5 | 18.5 | 29.7 | 33 | A |
| 105 | L | CA | 18.8 | 18.7 | 28.3 | 32 | A |
| 105 | L | CB | 17.5 | 19.0 | 27.5 | 30 | A |
| 105 | L | CG | 17.7 | 19.4 | 26.1 | 31 | A |
| 105 | L | CD1 | 18.5 | 18.2 | 25.4 | 29 | A |
| 105 | L | CD2 | 16.4 | 19.6 | 25.4 | 31 | A |
| 105 | L | C | 19.7 | 20.0 | 28.3 | 33 | A |
| 105 | L | O | 19.2 | 21.1 | 28.4 | 34 | A |
| 106 | M | N | 21.0 | 19.8 | 28.0 | 33 | A |
| 106 | M | CA | 21.9 | 20.9 | 27.9 | 33 | A |
| 106 | M | CB | 23.3 | 20.5 | 28.2 | 33 | A |
| 106 | M | CG | 23.5 | 20.0 | 29.7 | 32 | A |
| 106 | M | SD | 23.2 | 21.4 | 30.9 | 29 | A |
| 106 | M | CE | 24.8 | 22.1 | 31.2 | 29 | A |
| 106 | M | C | 21.9 | 21.4 | 26.4 | 34 | A |
| 106 | M | O | 21.5 | 20.7 | 25.5 | 36 | A |
| 107 | E | N | 22.2 | 22.7 | 26.3 | 36 | A |
| 107 | E | CA | 22.2 | 23.4 | 25.0 | 35 | A |
| 107 | E | CB | 22.4 | 24.9 | 25.3 | 39 | A |
| 107 | E | CG | 21.6 | 25.8 | 24.4 | 46 | A |
| 107 | E | CD | 21.0 | 27.0 | 25.2 | 50 | A |
| 107 | E | OE1 | 21.6 | 27.4 | 26.2 | 46 | A |
| 107 | E | OE2 | 19.9 | 27.5 | 24.8 | 54 | A |
| 107 | E | C | 23.2 | 22.9 | 24.0 | 35 | A |
| 107 | E | O | 22.9 | 22.8 | 22.8 | 35 | A |
| 108 | T | N | 24.4 | 22.6 | 24.4 | 32 | A |
| 108 | T | CA | 25.5 | 22.1 | 23.5 | 27 | A |
| 108 | T | CB | 26.0 | 23.3 | 22.7 | 25 | A |
| 108 | T | OG1 | 26.7 | 22.9 | 21.6 | 25 | A |
| 108 | T | CG2 | 26.9 | 24.2 | 23.6 | 24 | A |
| 108 | T | C | 26.6 | 21.4 | 24.3 | 27 | A |
| 108 | T | O | 26.4 | 21.0 | 25.5 | 24 | A |
| 109 | D | N | 27.7 | 21.2 | 23.6 | 24 | A |
| 109 | D | CA | 28.9 | 20.6 | 24.3 | 25 | A |
| 109 | D | CB | 28.9 | 19.0 | 24.2 | 24 | A |
| 109 | D | CG | 29.1 | 18.6 | 22.7 | 25 | A |
| 109 | D | OD1 | 30.2 | 19.0 | 22.2 | 24 | A |
| 109 | D | OD2 | 28.3 | 17.8 | 22.2 | 20 | A |
| 109 | D | C | 30.2 | 21.2 | 23.8 | 26 | A |
| 109 | D | O | 30.2 | 21.9 | 22.8 | 29 | A |
| 110 | L | N | 31.3 | 21.0 | 24.5 | 25 | A |
| 110 | L | CA | 32.5 | 21.6 | 24.2 | 23 | A |
| 110 | L | CB | 33.6 | 21.2 | 25.2 | 21 | A |
| 110 | L | CG | 34.9 | 22.0 | 25.0 | 18 | A |
| 110 | L | CD1 | 34.6 | 23.5 | 25.1 | 17 | A |
| 110 | L | CD2 | 35.9 | 21.7 | 26.2 | 17 | A |
| 110 | L | C | 33.0 | 21.2 | 22.8 | 24 | A |
| 110 | L | O | 33.6 | 22.0 | 22.0 | 27 | A |
| 111 | Y | N | 32.8 | 19.9 | 22.4 | 21 | A |
| 111 | Y | CA | 33.2 | 19.4 | 21.1 | 23 | A |
| 111 | Y | CB | 32.7 | 18.0 | 20.9 | 25 | A |

TABLE 2-continued

Structural Coordinates of Ah₆-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 111 | Y | CG  | 32.9 | 17.4 | 19.5 | 30 | A |
|-----|---|-----|------|------|------|----|---|
| 111 | Y | CD1 | 34.2 | 17.0 | 19.1 | 29 | A |
| 111 | Y | CE1 | 34.4 | 16.5 | 17.8 | 32 | A |
| 111 | Y | CD2 | 31.9 | 17.4 | 18.6 | 34 | A |
| 111 | Y | CE2 | 32.1 | 16.9 | 17.3 | 34 | A |
| 111 | Y | CZ  | 33.3 | 16.4 | 16.9 | 36 | A |
| 111 | Y | OH  | 33.5 | 15.9 | 15.6 | 39 | A |
| 111 | Y | C   | 32.6 | 20.4 | 20.0 | 24 | A |
| 111 | Y | O   | 33.4 | 21.0 | 19.3 | 23 | A |
| 112 | K | N   | 31.3 | 20.5 | 20.0 | 23 | A |
| 112 | K | CA  | 30.6 | 21.3 | 19.0 | 25 | A |
| 112 | K | CB  | 29.1 | 21.2 | 19.2 | 28 | A |
| 112 | K | CG  | 28.6 | 20.0 | 18.6 | 31 | A |
| 112 | K | CD  | 27.0 | 19.9 | 18.6 | 35 | A |
| 112 | K | CE  | 26.5 | 19.5 | 20.0 | 36 | A |
| 112 | K | NZ  | 25.1 | 19.2 | 19.9 | 40 | A |
| 112 | K | C   | 31.0 | 22.8 | 19.1 | 26 | A |
| 112 | K | O   | 31.2 | 23.5 | 18.1 | 26 | A |
| 113 | L | N   | 31.3 | 23.3 | 20.3 | 27 | A |
| 113 | L | CA  | 31.6 | 24.7 | 20.5 | 28 | A |
| 113 | L | CB  | 31.7 | 25.0 | 22.0 | 28 | A |
| 113 | L | CG  | 31.5 | 26.5 | 22.5 | 32 | A |
| 113 | L | CD1 | 31.8 | 26.6 | 23.9 | 31 | A |
| 113 | L | CD2 | 32.3 | 27.4 | 21.7 | 34 | A |
| 113 | L | C   | 33.0 | 25.0 | 19.9 | 30 | A |
| 113 | L | O   | 33.1 | 26.0 | 19.2 | 30 | A |
| 114 | L | N   | 34.0 | 24.1 | 20.2 | 30 | A |
| 114 | L | CA  | 35.3 | 24.3 | 19.6 | 29 | A |
| 114 | L | CB  | 36.3 | 23.3 | 20.3 | 27 | A |
| 114 | L | CG  | 36.7 | 23.6 | 21.8 | 23 | A |
| 114 | L | CD1 | 37.6 | 22.5 | 22.2 | 19 | A |
| 114 | L | CD2 | 37.4 | 25.0 | 21.8 | 20 | A |
| 114 | L | C   | 35.4 | 24.2 | 18.1 | 31 | A |
| 114 | L | O   | 36.3 | 24.6 | 17.5 | 32 | A |
| 115 | K | N   | 34.4 | 23.5 | 17.6 | 34 | A |
| 115 | K | CA  | 34.3 | 23.2 | 16.2 | 37 | A |
| 115 | K | CB  | 33.4 | 22.0 | 15.9 | 37 | A |
| 115 | K | CG  | 33.5 | 21.4 | 14.6 | 43 | A |
| 115 | K | CD  | 32.7 | 20.1 | 14.5 | 47 | A |
| 115 | K | CE  | 31.2 | 20.2 | 14.9 | 50 | A |
| 115 | K | NZ  | 30.5 | 21.2 | 14.1 | 52 | A |
| 115 | K | C   | 33.8 | 24.5 | 15.4 | 38 | A |
| 115 | K | O   | 33.8 | 24.5 | 14.2 | 37 | A |
| 116 | T | N   | 33.3 | 25.4 | 16.1 | 38 | A |
| 116 | T | CA  | 32.7 | 26.6 | 15.5 | 39 | A |
| 116 | T | CB  | 31.2 | 26.5 | 15.4 | 40 | A |
| 116 | T | OG1 | 30.7 | 26.5 | 16.8 | 42 | A |
| 116 | T | CG2 | 30.8 | 25.2 | 14.8 | 39 | A |
| 116 | T | C   | 33.0 | 28.0 | 16.2 | 40 | A |
| 116 | T | O   | 32.5 | 29.0 | 15.8 | 41 | A |
| 117 | Q | N   | 33.9 | 28.0 | 17.2 | 40 | A |
| 117 | Q | CA  | 34.2 | 29.2 | 17.9 | 41 | A |
| 117 | Q | CB  | 33.1 | 29.5 | 18.9 | 45 | A |
| 117 | Q | CG  | 33.4 | 30.6 | 19.9 | 52 | A |
| 117 | Q | CD  | 33.2 | 32.0 | 19.3 | 58 | A |
| 117 | Q | OE1 | 32.2 | 32.2 | 18.6 | 59 | A |
| 117 | Q | NE2 | 34.2 | 32.9 | 19.5 | 60 | A |
| 117 | Q | C   | 35.6 | 29.2 | 18.6 | 39 | A |
| 117 | Q | O   | 36.0 | 28.2 | 19.1 | 37 | A |
| 118 | H | N   | 36.3 | 30.3 | 18.5 | 38 | A |
| 118 | H | CA  | 37.6 | 30.4 | 19.2 | 38 | A |
| 118 | H | CB  | 38.5 | 31.3 | 18.3 | 39 | A |
| 118 | H | CG  | 39.9 | 31.5 | 19.0 | 43 | A |
| 118 | H | CD2 | 41.1 | 30.9 | 18.8 | 43 | A |
| 118 | H | ND1 | 40.1 | 32.4 | 20.0 | 45 | A |
| 118 | H | CE1 | 41.3 | 32.3 | 20.4 | 44 | A |
| 118 | H | NE2 | 42.0 | 31.5 | 19.7 | 45 | A |
| 118 | H | C   | 37.3 | 31.1 | 20.5 | 37 | A |
| 118 | H | O   | 36.9 | 32.2 | 20.6 | 41 | A |
| 119 | L | N   | 37.6 | 30.4 | 21.6 | 33 | A |
| 119 | L | CA  | 37.4 | 30.8 | 23.0 | 30 | A |
| 119 | L | CB  | 37.4 | 29.7 | 23.9 | 25 | A |
| 119 | L | CG  | 36.4 | 28.5 | 23.7 | 21 | A |
| 119 | L | CD1 | 36.7 | 27.4 | 24.7 | 17 | A |
| 119 | L | CD2 | 35.0 | 28.9 | 23.7 | 20 | A |
| 119 | L | C   | 38.4 | 31.9 | 23.4 | 31 | A |
| 119 | L | O   | 39.6 | 31.8 | 23.1 | 30 | A |
| 120 | S | N   | 37.9 | 32.8 | 24.2 | 32 | A |
| 120 | S | CA  | 38.7 | 33.9 | 24.8 | 31 | A |
| 120 | S | CB  | 37.9 | 35.1 | 25.2 | 31 | A |
| 120 | S | OG  | 37.0 | 34.8 | 26.2 | 33 | A |
| 120 | S | C   | 39.3 | 33.2 | 26.0 | 31 | A |
| 120 | S | O   | 38.9 | 32.2 | 26.5 | 30 | A |
| 121 | N | N   | 40.4 | 33.9 | 26.6 | 29 | A |
| 121 | N | CA  | 41.0 | 33.3 | 27.7 | 30 | A |
| 121 | N | CB  | 42.2 | 34.2 | 28.1 | 30 | A |
| 121 | N | CG  | 43.0 | 33.6 | 29.2 | 30 | A |
| 121 | N | OD1 | 43.3 | 34.2 | 30.2 | 36 | A |
| 121 | N | ND2 | 43.5 | 32.4 | 29.0 | 28 | A |
| 121 | N | C   | 40.1 | 33.2 | 28.9 | 30 | A |
| 121 | N | O   | 40.2 | 32.3 | 29.7 | 28 | A |
| 122 | D | N   | 39.1 | 34.2 | 29.0 | 29 | A |
| 122 | D | CA  | 38.2 | 34.2 | 30.1 | 32 | A |
| 122 | D | CB  | 37.3 | 35.4 | 30.1 | 34 | A |
| 122 | D | CG  | 38.1 | 36.7 | 30.4 | 38 | A |
| 122 | D | OD1 | 38.8 | 36.7 | 31.4 | 38 | A |
| 122 | D | OD2 | 37.9 | 37.7 | 29.7 | 42 | A |
| 122 | D | C   | 37.3 | 32.9 | 30.1 | 31 | A |
| 122 | D | O   | 37.1 | 32.3 | 31.2 | 30 | A |
| 123 | H | N   | 36.8 | 32.5 | 28.9 | 29 | A |
| 123 | H | CA  | 36.0 | 31.3 | 28.8 | 29 | A |
| 123 | H | CB  | 35.4 | 31.2 | 27.4 | 29 | A |
| 123 | H | CG  | 34.2 | 32.1 | 27.2 | 33 | A |
| 123 | H | CD2 | 32.9 | 31.8 | 27.1 | 35 | A |
| 123 | H | ND1 | 34.3 | 33.5 | 27.1 | 38 | A |
| 123 | H | CE1 | 33.1 | 34.0 | 26.9 | 37 | A |
| 123 | H | NE2 | 32.2 | 33.0 | 26.9 | 37 | A |
| 123 | H | C   | 36.8 | 30.1 | 29.2 | 26 | A |
| 123 | H | O   | 36.4 | 29.3 | 30.0 | 28 | A |
| 124 | I | N   | 37.9 | 29.9 | 28.5 | 23 | A |
| 124 | I | CA  | 38.8 | 28.8 | 28.8 | 21 | A |
| 124 | I | CB  | 40.1 | 29.0 | 28.1 | 19 | A |
| 124 | I | CG2 | 41.1 | 27.9 | 28.6 | 22 | A |
| 124 | I | CG1 | 40.0 | 28.9 | 26.6 | 18 | A |
| 124 | I | CD1 | 41.2 | 29.3 | 25.8 | 14 | A |
| 124 | I | C   | 39.0 | 28.6 | 30.3 | 20 | A |
| 124 | I | O   | 38.8 | 27.6 | 30.8 | 19 | A |
| 125 | C | N   | 39.5 | 29.7 | 30.9 | 20 | A |
| 125 | C | CA  | 39.7 | 29.7 | 32.3 | 22 | A |
| 125 | C | CB  | 40.2 | 31.1 | 32.8 | 23 | A |
| 125 | C | SG  | 40.6 | 31.2 | 34.5 | 25 | A |
| 125 | C | C   | 38.5 | 29.3 | 33.2 | 22 | A |
| 125 | C | O   | 38.7 | 28.5 | 34.1 | 21 | A |
| 126 | Y | N   | 37.4 | 29.8 | 32.8 | 20 | A |
| 126 | Y | CA  | 36.1 | 29.4 | 33.5 | 21 | A |
| 126 | Y | CB  | 35.0 | 30.4 | 33.2 | 22 | A |
| 126 | Y | CG  | 33.7 | 30.1 | 33.9 | 24 | A |
| 126 | Y | CD1 | 33.7 | 29.8 | 35.3 | 26 | A |
| 126 | Y | CE1 | 32.5 | 29.6 | 36.0 | 26 | A |
| 126 | Y | CD2 | 32.5 | 30.2 | 33.3 | 25 | A |
| 126 | Y | CE2 | 31.3 | 30.0 | 33.9 | 27 | A |
| 126 | Y | CZ  | 31.3 | 29.7 | 35.3 | 27 | A |
| 126 | Y | OH  | 30.2 | 29.4 | 36.0 | 32 | A |
| 126 | Y | C   | 35.7 | 28.0 | 33.2 | 20 | A |
| 126 | Y | O   | 35.2 | 27.3 | 34.1 | 18 | A |
| 127 | F | N   | 35.9 | 27.5 | 32.0 | 19 | A |
| 127 | F | CA  | 35.5 | 26.2 | 31.6 | 19 | A |
| 127 | F | CB  | 35.6 | 25.9 | 30.1 | 18 | A |
| 127 | F | CG  | 34.5 | 26.5 | 29.3 | 22 | A |
| 127 | F | CD1 | 33.2 | 26.6 | 29.9 | 17 | A |

TABLE 2-continued

Structural Coordinates of Ah₆-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 127 | F | CD2 | 34.6 | 26.9 | 28.0 | 18 | A |
|---|---|---|---|---|---|---|---|
| 127 | F | CE1 | 32.1 | 27.1 | 29.2 | 19 | A |
| 127 | F | CE2 | 33.5 | 27.4 | 27.2 | 20 | A |
| 127 | F | CZ | 32.3 | 27.5 | 27.8 | 21 | A |
| 127 | F | C | 36.4 | 25.2 | 32.3 | 17 | A |
| 127 | F | O | 36.0 | 24.1 | 32.8 | 15 | A |
| 128 | L | N | 37.7 | 25.5 | 32.4 | 16 | A |
| 128 | L | CA | 38.7 | 24.7 | 33.0 | 17 | A |
| 128 | L | CB | 40.1 | 25.2 | 32.8 | 17 | A |
| 128 | L | CG | 41.2 | 24.3 | 33.4 | 19 | A |
| 128 | L | CD1 | 41.2 | 23.0 | 32.5 | 21 | A |
| 128 | L | CD2 | 42.5 | 25.0 | 33.3 | 22 | A |
| 128 | L | C | 38.4 | 24.5 | 34.5 | 18 | A |
| 128 | L | O | 38.4 | 23.4 | 35.0 | 15 | A |
| 129 | Y | N | 38.0 | 25.7 | 35.1 | 17 | A |
| 129 | Y | CA | 37.7 | 25.6 | 36.5 | 17 | A |
| 129 | Y | CB | 37.2 | 27.0 | 37.0 | 17 | A |
| 129 | Y | CG | 36.7 | 27.0 | 38.4 | 16 | A |
| 129 | Y | CD1 | 37.7 | 26.6 | 39.4 | 17 | A |
| 129 | Y | CE1 | 37.3 | 26.5 | 40.8 | 19 | A |
| 129 | Y | CD2 | 35.4 | 27.2 | 38.8 | 16 | A |
| 129 | Y | CE2 | 35.0 | 27.1 | 40.2 | 15 | A |
| 129 | Y | CZ | 36.0 | 26.8 | 41.1 | 17 | A |
| 129 | Y | OH | 35.6 | 26.6 | 42.5 | 15 | A |
| 129 | Y | C | 36.5 | 24.6 | 36.8 | 19 | A |
| 129 | Y | O | 36.7 | 23.7 | 37.6 | 18 | A |
| 130 | Q | N | 35.4 | 24.8 | 36.0 | 19 | A |
| 130 | Q | CA | 34.3 | 23.9 | 36.2 | 19 | A |
| 130 | Q | CB | 33.2 | 24.3 | 35.3 | 21 | A |
| 130 | Q | CG | 32.7 | 25.8 | 35.6 | 19 | A |
| 130 | Q | CD | 31.4 | 26.1 | 34.8 | 22 | A |
| 130 | Q | OE1 | 30.3 | 25.7 | 35.1 | 25 | A |
| 130 | Q | NE2 | 31.7 | 26.9 | 33.7 | 20 | A |
| 130 | Q | C | 34.6 | 22.4 | 35.9 | 19 | A |
| 130 | Q | O | 34.1 | 21.5 | 36.6 | 20 | A |
| 131 | I | N | 35.5 | 22.1 | 35.0 | 18 | A |
| 131 | I | CA | 35.9 | 20.8 | 34.7 | 18 | A |
| 131 | I | CB | 36.8 | 20.6 | 33.5 | 16 | A |
| 131 | I | CG2 | 37.3 | 19.2 | 33.4 | 18 | A |
| 131 | I | CG1 | 36.1 | 21.1 | 32.2 | 18 | A |
| 131 | I | CD1 | 37.1 | 21.4 | 31.0 | 13 | A |
| 131 | I | C | 36.6 | 20.2 | 35.9 | 15 | A |
| 131 | I | O | 36.3 | 19.0 | 36.3 | 13 | A |
| 132 | L | N | 37.5 | 20.9 | 36.5 | 14 | A |
| 132 | L | CA | 38.3 | 20.5 | 37.6 | 12 | A |
| 132 | L | CB | 39.6 | 21.3 | 37.8 | 9 | A |
| 132 | L | CG | 40.6 | 21.1 | 36.7 | 12 | A |
| 132 | L | CD1 | 41.7 | 22.1 | 36.9 | 8 | A |
| 132 | L | CD2 | 41.1 | 19.7 | 36.6 | 10 | A |
| 132 | L | C | 37.5 | 20.5 | 38.9 | 10 | A |
| 132 | L | O | 37.8 | 19.7 | 39.9 | 15 | A |
| 133 | R | N | 36.5 | 21.3 | 39.0 | 13 | A |
| 133 | R | CA | 35.6 | 21.4 | 40.2 | 11 | A |
| 133 | R | CB | 34.7 | 22.6 | 40.1 | 12 | A |
| 133 | R | CG | 33.9 | 22.9 | 41.4 | 13 | A |
| 133 | R | CD | 33.2 | 24.2 | 41.3 | 15 | A |
| 133 | R | NE | 32.3 | 24.5 | 42.4 | 18 | A |
| 133 | R | CZ | 30.9 | 24.4 | 42.3 | 21 | A |
| 133 | R | NH1 | 30.4 | 24.1 | 41.1 | 22 | A |
| 133 | R | NH2 | 30.1 | 24.6 | 43.3 | 16 | A |
| 133 | R | C | 34.8 | 20.1 | 40.2 | 13 | A |
| 133 | R | O | 34.7 | 19.4 | 41.2 | 12 | A |
| 134 | G | N | 34.3 | 19.8 | 39.0 | 13 | A |
| 134 | G | CA | 33.5 | 18.5 | 38.9 | 14 | A |
| 134 | G | C | 34.4 | 17.3 | 39.1 | 16 | A |
| 134 | G | O | 34.0 | 16.4 | 39.8 | 14 | A |
| 135 | L | N | 35.6 | 17.4 | 38.6 | 15 | A |
| 135 | L | CA | 36.6 | 16.2 | 38.8 | 16 | A |
| 135 | L | CB | 37.8 | 16.4 | 37.8 | 15 | A |
| 135 | L | CG | 38.8 | 15.2 | 37.8 | 17 | A |
| 135 | L | CD1 | 38.0 | 14.0 | 37.2 | 16 | A |
| 135 | L | CD2 | 40.0 | 15.5 | 36.9 | 9 | A |
| 135 | L | C | 37.0 | 16.1 | 40.2 | 16 | A |
| 135 | L | O | 37.4 | 15.0 | 40.6 | 15 | A |
| 136 | K | N | 37.1 | 17.2 | 40.9 | 15 | A |
| 136 | K | CA | 37.5 | 17.2 | 42.3 | 14 | A |
| 136 | K | CB | 37.6 | 18.6 | 42.9 | 15 | A |
| 136 | K | CG | 37.9 | 18.6 | 44.3 | 14 | A |
| 136 | K | CD | 37.9 | 20.1 | 44.8 | 15 | A |
| 136 | K | CE | 38.0 | 20.2 | 46.3 | 13 | A |
| 136 | K | NZ | 38.0 | 21.6 | 46.7 | 14 | A |
| 136 | K | C | 36.5 | 16.3 | 43.1 | 15 | A |
| 136 | K | O | 36.9 | 15.5 | 43.8 | 13 | A |
| 137 | Y | N | 35.2 | 16.6 | 42.8 | 17 | A |
| 137 | Y | CA | 34.2 | 15.9 | 43.5 | 17 | A |
| 137 | Y | CB | 32.8 | 16.5 | 43.1 | 17 | A |
| 137 | Y | CG | 31.7 | 15.7 | 43.7 | 20 | A |
| 137 | Y | CD1 | 31.1 | 16.1 | 44.9 | 19 | A |
| 137 | Y | CE1 | 30.0 | 15.4 | 45.5 | 18 | A |
| 137 | Y | CD2 | 31.1 | 14.6 | 43.1 | 19 | A |
| 137 | Y | CE2 | 30.1 | 13.9 | 43.6 | 21 | A |
| 137 | Y | CZ | 29.5 | 14.3 | 44.8 | 22 | A |
| 137 | Y | OH | 28.4 | 13.6 | 45.3 | 27 | A |
| 137 | Y | C | 34.2 | 14.4 | 43.1 | 19 | A |
| 137 | Y | O | 34.2 | 13.5 | 44.0 | 17 | A |
| 138 | I | N | 34.4 | 14.1 | 41.8 | 19 | A |
| 138 | I | CA | 34.4 | 12.7 | 41.3 | 21 | A |
| 138 | I | CB | 34.7 | 12.7 | 39.8 | 18 | A |
| 138 | I | CG2 | 34.8 | 11.2 | 39.3 | 22 | A |
| 138 | I | CG1 | 33.6 | 13.4 | 39.0 | 18 | A |
| 138 | I | CD1 | 33.9 | 13.5 | 37.5 | 15 | A |
| 138 | I | C | 35.6 | 12.0 | 42.0 | 21 | A |
| 138 | I | O | 35.3 | 10.9 | 42.6 | 23 | A |
| 139 | H | N | 36.8 | 12.5 | 42.0 | 21 | A |
| 139 | H | CA | 37.9 | 11.9 | 42.6 | 21 | A |
| 139 | H | CB | 39.2 | 12.7 | 42.3 | 20 | A |
| 139 | H | CG | 39.8 | 12.4 | 40.9 | 22 | A |
| 139 | H | CD2 | 39.3 | 11.6 | 39.9 | 23 | A |
| 139 | H | ND1 | 40.9 | 13.0 | 40.5 | 22 | A |
| 139 | H | CE1 | 41.2 | 12.6 | 39.2 | 20 | A |
| 139 | H | NE2 | 40.2 | 11.8 | 38.9 | 26 | A |
| 139 | H | C | 37.8 | 11.7 | 44.1 | 19 | A |
| 139 | H | O | 38.4 | 10.7 | 44.6 | 19 | A |
| 140 | S | N | 37.1 | 12.6 | 44.8 | 19 | A |
| 140 | S | CA | 36.9 | 12.5 | 46.2 | 15 | A |
| 140 | S | CB | 36.2 | 13.7 | 46.8 | 15 | A |
| 140 | S | OG | 34.9 | 13.8 | 46.3 | 14 | A |
| 140 | S | C | 36.1 | 11.3 | 46.5 | 17 | A |
| 140 | S | O | 36.2 | 10.7 | 47.6 | 18 | A |
| 141 | A | N | 35.3 | 10.8 | 45.5 | 17 | A |
| 141 | A | CA | 34.4 | 9.7 | 45.7 | 18 | A |
| 141 | A | CB | 33.1 | 9.9 | 44.9 | 16 | A |
| 141 | A | C | 35.1 | 8.4 | 45.3 | 20 | A |
| 141 | A | O | 34.4 | 7.3 | 45.3 | 23 | A |
| 142 | N | N | 36.4 | 8.4 | 45.0 | 20 | A |
| 142 | N | CA | 37.1 | 7.3 | 44.5 | 20 | A |
| 142 | N | CB | 37.0 | 6.1 | 45.5 | 23 | A |
| 142 | N | CG | 37.7 | 6.4 | 46.9 | 27 | A |
| 142 | N | OD1 | 38.7 | 7.1 | 47.0 | 25 | A |
| 142 | N | ND2 | 37.0 | 5.9 | 47.9 | 26 | A |
| 142 | N | C | 36.7 | 6.8 | 43.1 | 20 | A |
| 142 | N | O | 37.0 | 5.6 | 42.7 | 16 | A |
| 143 | V | N | 36.1 | 7.6 | 42.4 | 17 | A |
| 143 | V | CA | 35.6 | 7.3 | 41.0 | 16 | A |
| 143 | V | CB | 34.2 | 7.9 | 40.8 | 17 | A |
| 143 | V | CG1 | 33.9 | 7.7 | 39.3 | 17 | A |
| 143 | V | CG2 | 33.2 | 7.1 | 41.6 | 16 | A |
| 143 | V | C | 36.6 | 7.9 | 40.0 | 19 | A |
| 143 | V | O | 37.2 | 9.0 | 40.2 | 17 | A |
| 144 | L | N | 36.9 | 7.1 | 39.0 | 21 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 144 | L | CA  | 37.7 | 7.5  | 37.9 | 20 | A |
| 144 | L | CB  | 38.8 | 6.5  | 37.4 | 19 | A |
| 144 | L | CG  | 39.7 | 5.7  | 38.3 | 19 | A |
| 144 | L | CD1 | 41.0 | 5.4  | 37.5 | 13 | A |
| 144 | L | CD2 | 40.1 | 6.4  | 39.6 | 18 | A |
| 144 | L | C   | 36.7 | 7.6  | 36.7 | 20 | A |
| 144 | L | O   | 36.0 | 6.7  | 36.5 | 21 | A |
| 145 | H | N   | 36.7 | 8.8  | 36.0 | 19 | A |
| 145 | H | CA  | 35.8 | 8.9  | 34.9 | 16 | A |
| 145 | H | CB  | 35.7 | 10.4 | 34.5 | 14 | A |
| 145 | H | CG  | 34.7 | 10.6 | 33.4 | 15 | A |
| 145 | H | CD2 | 33.4 | 11.2 | 33.5 | 13 | A |
| 145 | H | ND1 | 34.8 | 10.3 | 32.1 | 14 | A |
| 145 | H | CE1 | 33.8 | 10.6 | 31.4 | 17 | A |
| 145 | H | NE2 | 32.9 | 11.2 | 32.2 | 15 | A |
| 145 | H | C   | 36.2 | 8.0  | 33.8 | 19 | A |
| 145 | H | O   | 35.4 | 7.2  | 33.3 | 17 | A |
| 146 | R | N   | 37.4 | 8.2  | 33.3 | 20 | A |
| 146 | R | CA  | 38.0 | 7.4  | 32.2 | 18 | A |
| 146 | R | CB  | 37.7 | 6.0  | 32.4 | 22 | A |
| 146 | R | CG  | 38.3 | 5.3  | 33.6 | 19 | A |
| 146 | R | CD  | 37.5 | 4.1  | 33.8 | 19 | A |
| 146 | R | NE  | 38.3 | 2.9  | 34.0 | 17 | A |
| 146 | R | CZ  | 37.9 | 1.7  | 34.0 | 22 | A |
| 146 | R | NH1 | 36.5 | 1.5  | 33.9 | 12 | A |
| 146 | R | NH2 | 38.7 | 0.7  | 34.2 | 20 | A |
| 146 | R | C   | 37.7 | 7.8  | 30.8 | 18 | A |
| 146 | R | O   | 38.2 | 7.2  | 29.9 | 21 | A |
| 147 | D | N   | 36.7 | 8.7  | 30.6 | 17 | A |
| 147 | D | CA  | 36.4 | 9.0  | 29.2 | 17 | A |
| 147 | D | CB  | 35.2 | 8.2  | 28.7 | 15 | A |
| 147 | D | CG  | 35.1 | 8.1  | 27.2 | 19 | A |
| 147 | D | OD1 | 36.2 | 8.4  | 26.6 | 14 | A |
| 147 | D | OD2 | 34.1 | 7.8  | 26.7 | 16 | A |
| 147 | D | C   | 36.1 | 10.5 | 29.0 | 18 | A |
| 147 | D | O   | 35.3 | 10.9 | 28.3 | 18 | A |
| 148 | L | N   | 37.0 | 11.3 | 29.7 | 15 | A |
| 148 | L | CA  | 36.9 | 12.7 | 29.6 | 16 | A |
| 148 | L | CB  | 37.7 | 13.4 | 30.7 | 16 | A |
| 148 | L | CG  | 37.0 | 13.9 | 31.9 | 16 | A |
| 148 | L | CD1 | 35.7 | 13.3 | 32.2 | 15 | A |
| 148 | L | CD2 | 38.0 | 13.7 | 33.1 | 13 | A |
| 148 | L | C   | 37.4 | 13.2 | 28.2 | 19 | A |
| 148 | L | O   | 38.5 | 12.8 | 27.8 | 19 | A |
| 149 | K | N   | 36.5 | 14.0 | 27.5 | 19 | A |
| 149 | K | CA  | 36.8 | 14.5 | 26.2 | 20 | A |
| 149 | K | CB  | 36.7 | 13.4 | 25.1 | 18 | A |
| 149 | K | CG  | 35.5 | 12.6 | 25.1 | 18 | A |
| 149 | K | CD  | 35.5 | 11.5 | 24.0 | 17 | A |
| 149 | K | CE  | 34.3 | 10.6 | 23.9 | 14 | A |
| 149 | K | NZ  | 34.3 | 9.8  | 22.7 | 19 | A |
| 149 | K | C   | 35.8 | 15.6 | 25.9 | 21 | A |
| 149 | K | O   | 34.7 | 15.7 | 26.5 | 23 | A |
| 150 | P | N   | 36.1 | 16.5 | 25.0 | 19 | A |
| 150 | P | CD  | 37.3 | 16.5 | 24.1 | 16 | A |
| 150 | P | CA  | 35.2 | 17.6 | 24.6 | 20 | A |
| 150 | P | CB  | 35.8 | 18.2 | 23.4 | 19 | A |
| 150 | P | CG  | 37.3 | 18.0 | 23.6 | 19 | A |
| 150 | P | C   | 33.7 | 17.3 | 24.5 | 19 | A |
| 150 | P | O   | 32.9 | 18.1 | 25.0 | 20 | A |
| 151 | S | N   | 33.3 | 16.2 | 23.9 | 20 | A |
| 151 | S | CA  | 31.9 | 15.9 | 23.7 | 20 | A |
| 151 | S | CB  | 31.7 | 14.9 | 22.6 | 20 | A |
| 151 | S | OG  | 32.3 | 13.6 | 22.9 | 29 | A |
| 151 | S | C   | 31.2 | 15.4 | 25.0 | 19 | A |
| 151 | S | O   | 30.0 | 15.1 | 25.0 | 21 | A |
| 152 | N | N   | 32.0 | 15.2 | 26.1 | 20 | A |
| 152 | N | CA  | 31.4 | 14.8 | 27.3 | 18 | A |
| 152 | N | CB  | 32.2 | 13.6 | 27.9 | 20 | A |
| 152 | N | CG  | 31.9 | 12.3 | 27.3 | 20 | A |
| 152 | N | OD1 | 30.9 | 12.2 | 26.5 | 23 | A |
| 152 | N | ND2 | 32.7 | 11.3 | 27.5 | 18 | A |
| 152 | N | C   | 31.3 | 15.9 | 28.3 | 18 | A |
| 152 | N | O   | 31.2 | 15.7 | 29.5 | 20 | A |
| 153 | L | N   | 31.5 | 17.1 | 27.8 | 21 | A |
| 153 | L | CA  | 31.4 | 18.3 | 28.6 | 20 | A |
| 153 | L | CB  | 32.7 | 19.1 | 28.5 | 20 | A |
| 153 | L | CG  | 34.0 | 18.3 | 28.9 | 21 | A |
| 153 | L | CD1 | 35.2 | 19.2 | 28.8 | 21 | A |
| 153 | L | CD2 | 33.8 | 17.9 | 30.4 | 19 | A |
| 153 | L | C   | 30.3 | 19.1 | 28.0 | 20 | A |
| 153 | L | O   | 30.4 | 19.9 | 27.0 | 22 | A |
| 154 | L | N   | 29.1 | 19.0 | 28.7 | 20 | A |
| 154 | L | CA  | 27.9 | 19.7 | 28.2 | 20 | A |
| 154 | L | CB  | 26.7 | 19.0 | 28.8 | 19 | A |
| 154 | L | CG  | 26.8 | 17.5 | 28.5 | 19 | A |
| 154 | L | CD1 | 25.6 | 16.7 | 29.2 | 17 | A |
| 154 | L | CD2 | 26.8 | 17.2 | 27.0 | 18 | A |
| 154 | L | C   | 27.9 | 21.2 | 28.7 | 20 | A |
| 154 | L | O   | 28.4 | 21.5 | 29.8 | 19 | A |
| 155 | L | N   | 27.4 | 22.0 | 27.8 | 21 | A |
| 155 | L | CA  | 27.3 | 23.5 | 28.1 | 24 | A |
| 155 | L | CB  | 28.3 | 24.2 | 27.2 | 24 | A |
| 155 | L | CG  | 29.8 | 24.3 | 27.5 | 23 | A |
| 155 | L | CD1 | 30.3 | 23.2 | 28.4 | 25 | A |
| 155 | L | CD2 | 30.5 | 24.3 | 26.1 | 15 | A |
| 155 | L | C   | 25.9 | 24.0 | 27.8 | 25 | A |
| 155 | L | O   | 25.1 | 23.4 | 27.2 | 23 | A |
| 156 | N | N   | 25.7 | 25.3 | 28.2 | 28 | A |
| 156 | N | CA  | 24.5 | 26.0 | 27.9 | 28 | A |
| 156 | N | CB  | 23.5 | 25.9 | 29.0 | 28 | A |
| 156 | N | CG  | 23.9 | 26.5 | 30.3 | 31 | A |
| 156 | N | OD1 | 24.8 | 27.4 | 30.4 | 32 | A |
| 156 | N | ND2 | 23.3 | 26.1 | 31.4 | 27 | A |
| 156 | N | C   | 24.9 | 27.4 | 27.7 | 29 | A |
| 156 | N | O   | 26.1 | 27.8 | 27.9 | 29 | A |
| 157 | T | N   | 24.0 | 28.3 | 27.2 | 32 | A |
| 157 | T | CA  | 24.2 | 29.7 | 26.8 | 34 | A |
| 157 | T | CB  | 22.9 | 30.4 | 26.5 | 36 | A |
| 157 | T | OG1 | 22.3 | 29.8 | 25.4 | 42 | A |
| 157 | T | CG2 | 23.1 | 31.9 | 26.3 | 37 | A |
| 157 | T | C   | 25.0 | 30.5 | 27.8 | 32 | A |
| 157 | T | O   | 25.8 | 31.4 | 27.5 | 34 | A |
| 158 | T | N   | 24.7 | 30.3 | 29.1 | 28 | A |
| 158 | T | CA  | 25.4 | 31.0 | 30.2 | 27 | A |
| 158 | T | CB  | 24.4 | 31.2 | 31.4 | 26 | A |
| 158 | T | OG1 | 23.8 | 29.9 | 31.7 | 30 | A |
| 158 | T | CG2 | 23.4 | 32.2 | 31.1 | 28 | A |
| 158 | T | C   | 26.7 | 30.4 | 30.7 | 25 | A |
| 158 | T | O   | 27.2 | 30.8 | 31.8 | 21 | A |
| 159 | C | N   | 27.3 | 29.5 | 29.9 | 26 | A |
| 159 | C | CA  | 28.6 | 28.9 | 30.3 | 26 | A |
| 159 | C | CB  | 29.6 | 30.0 | 30.6 | 27 | A |
| 159 | C | SG  | 30.0 | 31.1 | 29.2 | 29 | A |
| 159 | C | C   | 28.6 | 27.9 | 31.4 | 26 | A |
| 159 | C | O   | 29.7 | 27.6 | 31.9 | 28 | A |
| 160 | D | N   | 27.4 | 27.4 | 31.7 | 26 | A |
| 160 | D | CA  | 27.4 | 26.3 | 32.8 | 27 | A |
| 160 | D | CB  | 26.0 | 26.0 | 33.2 | 30 | A |
| 160 | D | CG  | 25.4 | 27.1 | 33.9 | 31 | A |
| 160 | D | OD1 | 25.9 | 27.5 | 34.9 | 31 | A |
| 160 | D | OD2 | 24.3 | 27.6 | 33.5 | 31 | A |
| 160 | D | C   | 28.0 | 25.1 | 32.1 | 25 | A |
| 160 | D | O   | 27.7 | 24.9 | 30.9 | 26 | A |
| 161 | L | N   | 28.8 | 24.3 | 32.8 | 22 | A |
| 161 | L | CA  | 29.4 | 23.1 | 32.2 | 19 | A |
| 161 | L | CB  | 30.9 | 23.3 | 32.0 | 17 | A |
| 161 | L | CG  | 31.7 | 22.2 | 31.5 | 17 | A |
| 161 | L | CD1 | 33.1 | 22.7 | 30.9 | 16 | A |
| 161 | L | CD2 | 31.9 | 21.1 | 32.6 | 12 | A |

TABLE 2-continued

Structural Coordinates of Ah₆-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| Res | AA | Atom | X | Y | Z | B | Ch |
|---|---|---|---|---|---|---|---|
| 161 | L | C | 29.1 | 21.9 | 33.1 | 17 | A |
| 161 | L | O | 29.1 | 22.1 | 34.3 | 14 | A |
| 162 | K | N | 28.9 | 20.8 | 32.5 | 18 | A |
| 162 | K | CA | 28.6 | 19.6 | 33.2 | 20 | A |
| 162 | K | CB | 27.1 | 19.3 | 33.3 | 20 | A |
| 162 | K | CG | 26.2 | 20.1 | 34.2 | 19 | A |
| 162 | K | CD | 25.2 | 19.3 | 34.8 | 21 | A |
| 162 | K | CE | 24.3 | 20.0 | 35.9 | 20 | A |
| 162 | K | NZ | 23.4 | 20.9 | 35.2 | 20 | A |
| 162 | K | C | 29.3 | 18.4 | 32.6 | 19 | A |
| 162 | K | O | 29.2 | 18.2 | 31.4 | 19 | A |
| 163 | I | N | 29.9 | 17.6 | 33.4 | 20 | A |
| 163 | I | CA | 30.6 | 16.4 | 33.0 | 20 | A |
| 163 | I | CB | 31.7 | 15.9 | 34.0 | 18 | A |
| 163 | I | CG2 | 32.2 | 14.6 | 33.6 | 14 | A |
| 163 | I | CG1 | 32.8 | 17.0 | 34.1 | 17 | A |
| 163 | I | CD1 | 33.8 | 16.7 | 35.2 | 17 | A |
| 163 | I | C | 29.5 | 15.3 | 32.9 | 21 | A |
| 163 | I | O | 28.8 | 15.0 | 33.9 | 22 | A |
| 164 | C | N | 29.4 | 14.6 | 31.8 | 22 | A |
| 164 | C | CA | 28.4 | 13.6 | 31.6 | 21 | A |
| 164 | C | CB | 27.3 | 14.0 | 30.6 | 19 | A |
| 164 | C | SG | 27.9 | 14.1 | 28.9 | 23 | A |
| 164 | C | C | 29.1 | 12.3 | 31.1 | 19 | A |
| 164 | C | O | 30.3 | 12.3 | 31.0 | 17 | A |
| 165 | D | N | 28.3 | 11.3 | 30.8 | 22 | A |
| 165 | D | CA | 28.8 | 10.0 | 30.2 | 24 | A |
| 165 | D | CB | 29.4 | 10.3 | 28.8 | 27 | A |
| 165 | D | CG | 29.6 | 9.0 | 28.0 | 32 | A |
| 165 | D | OD1 | 30.0 | 9.0 | 26.9 | 33 | A |
| 165 | D | OD2 | 29.2 | 7.9 | 28.6 | 32 | A |
| 165 | D | C | 29.8 | 9.3 | 31.1 | 25 | A |
| 165 | D | O | 31.0 | 9.3 | 30.8 | 26 | A |
| 166 | F | N | 29.2 | 8.7 | 32.2 | 26 | A |
| 166 | F | CA | 30.0 | 7.9 | 33.1 | 24 | A |
| 166 | F | CB | 29.5 | 8.1 | 34.5 | 22 | A |
| 166 | F | CG | 29.9 | 9.4 | 35.1 | 21 | A |
| 166 | F | CD1 | 29.4 | 10.6 | 34.6 | 19 | A |
| 166 | F | CD2 | 30.8 | 9.4 | 36.2 | 17 | A |
| 166 | F | CE1 | 29.8 | 11.8 | 35.2 | 17 | A |
| 166 | F | CE2 | 31.2 | 10.6 | 36.8 | 18 | A |
| 166 | F | CZ | 30.7 | 11.8 | 36.3 | 19 | A |
| 166 | F | C | 29.9 | 6.4 | 32.7 | 25 | A |
| 166 | F | O | 30.0 | 5.5 | 33.6 | 24 | A |
| 167 | G | N | 29.7 | 6.1 | 31.5 | 26 | A |
| 167 | G | CA | 29.6 | 4.7 | 31.0 | 28 | A |
| 167 | G | C | 30.9 | 3.9 | 31.3 | 28 | A |
| 167 | G | O | 30.9 | 2.7 | 31.5 | 31 | A |
| 168 | L | N | 32.0 | 4.6 | 31.2 | 27 | A |
| 168 | L | CA | 33.3 | 4.0 | 31.5 | 27 | A |
| 168 | L | CB | 34.3 | 4.4 | 30.4 | 31 | A |
| 168 | L | CG | 35.6 | 3.6 | 30.1 | 38 | A |
| 168 | L | CD1 | 35.2 | 2.2 | 29.7 | 38 | A |
| 168 | L | CD2 | 36.4 | 4.3 | 29.0 | 39 | A |
| 168 | L | C | 33.8 | 4.2 | 32.9 | 25 | A |
| 168 | L | O | 34.9 | 3.7 | 33.3 | 24 | A |
| 169 | A | N | 33.1 | 5.0 | 33.6 | 24 | A |
| 169 | A | CA | 33.5 | 5.3 | 35.0 | 24 | A |
| 169 | A | CB | 32.6 | 6.4 | 35.6 | 22 | A |
| 169 | A | C | 33.6 | 4.1 | 35.9 | 24 | A |
| 169 | A | O | 32.9 | 3.1 | 35.6 | 21 | A |
| 170 | R | N | 34.4 | 4.1 | 36.9 | 24 | A |
| 170 | R | CA | 34.6 | 3.0 | 37.8 | 25 | A |
| 170 | R | CB | 35.6 | 2.0 | 37.3 | 28 | A |
| 170 | R | CG | 36.3 | 1.1 | 38.3 | 32 | A |
| 170 | R | CD | 37.6 | 0.7 | 37.8 | 32 | A |
| 170 | R | NE | 37.7 | −0.8 | 37.6 | 34 | A |
| 170 | R | CZ | 37.9 | −1.6 | 38.6 | 32 | A |
| 170 | R | NH1 | 37.9 | −1.2 | 39.9 | 33 | A |
| 170 | R | NH2 | 38.0 | −2.9 | 38.4 | 36 | A |
| 170 | R | C | 35.1 | 3.5 | 39.2 | 26 | A |
| 170 | R | O | 35.6 | 4.6 | 39.3 | 28 | A |
| 171 | V | N | 34.9 | 2.6 | 40.2 | 26 | A |
| 171 | V | CA | 35.3 | 2.9 | 41.6 | 25 | A |
| 171 | V | CB | 34.3 | 2.4 | 42.6 | 23 | A |
| 171 | V | CG1 | 34.9 | 2.5 | 44.0 | 24 | A |
| 171 | V | CG2 | 33.0 | 3.2 | 42.5 | 20 | A |
| 171 | V | C | 36.6 | 2.2 | 41.8 | 24 | A |
| 171 | V | O | 36.8 | 1.0 | 41.4 | 20 | A |
| 172 | A | N | 37.6 | 2.8 | 42.5 | 24 | A |
| 172 | A | CA | 38.9 | 2.3 | 42.8 | 26 | A |
| 172 | A | CB | 39.9 | 2.7 | 41.8 | 26 | A |
| 172 | A | C | 39.3 | 2.7 | 44.2 | 28 | A |
| 172 | A | O | 39.9 | 3.8 | 44.3 | 30 | A |
| 173 | D | N | 38.9 | 2.0 | 45.2 | 28 | A |
| 173 | D | CA | 39.1 | 2.3 | 46.6 | 29 | A |
| 173 | D | CB | 38.5 | 1.2 | 47.5 | 31 | A |
| 173 | D | CG | 38.3 | 1.6 | 48.9 | 31 | A |
| 173 | D | OD1 | 39.2 | 2.3 | 49.5 | 28 | A |
| 173 | D | OD2 | 37.3 | 1.2 | 49.5 | 32 | A |
| 173 | D | C | 40.6 | 2.3 | 46.9 | 32 | A |
| 173 | D | O | 41.3 | 1.3 | 46.7 | 33 | A |
| 174 | P | N | 41.2 | 3.5 | 47.3 | 35 | A |
| 174 | P | CD | 40.4 | 4.6 | 47.8 | 35 | A |
| 174 | P | CA | 42.6 | 3.6 | 47.6 | 38 | A |
| 174 | P | CB | 42.7 | 5.1 | 48.1 | 37 | A |
| 174 | P | CG | 41.4 | 5.7 | 47.7 | 38 | A |
| 174 | P | C | 43.1 | 2.6 | 48.6 | 40 | A |
| 174 | P | O | 44.3 | 2.3 | 48.7 | 42 | A |
| 175 | D | N | 42.2 | 2.1 | 49.5 | 42 | A |
| 175 | D | CA | 42.7 | 1.2 | 50.6 | 44 | A |
| 175 | D | CB | 41.6 | 1.0 | 51.6 | 43 | A |
| 175 | D | CG | 41.3 | 2.3 | 52.4 | 45 | A |
| 175 | D | OD1 | 42.3 | 3.1 | 52.6 | 44 | A |
| 175 | D | OD2 | 40.2 | 2.5 | 53.0 | 44 | A |
| 175 | D | C | 43.0 | −0.2 | 50.0 | 46 | A |
| 175 | D | O | 43.5 | −1.0 | 50.7 | 46 | A |
| 176 | H | N | 42.8 | −0.4 | 48.7 | 45 | A |
| 176 | H | CA | 43.1 | −1.6 | 48.1 | 47 | A |
| 176 | H | CB | 41.9 | −2.3 | 47.6 | 47 | A |
| 176 | H | CG | 41.1 | −3.0 | 48.7 | 49 | A |
| 176 | H | CD2 | 40.4 | −2.4 | 49.7 | 51 | A |
| 176 | H | ND1 | 40.9 | −4.3 | 48.8 | 50 | A |
| 176 | H | CE1 | 40.2 | −4.6 | 49.9 | 51 | A |
| 176 | H | NE2 | 39.8 | −3.5 | 50.4 | 52 | A |
| 176 | H | C | 44.1 | −1.4 | 46.9 | 47 | A |
| 176 | H | O | 43.8 | −0.6 | 46.0 | 48 | A |
| 177 | D | N | 45.2 | −2.1 | 46.9 | 47 | A |
| 177 | D | CA | 46.1 | −2.1 | 45.8 | 46 | A |
| 177 | D | CB | 47.4 | −2.9 | 46.1 | 49 | A |
| 177 | D | CG | 48.2 | −3.2 | 44.8 | 52 | A |
| 177 | D | OD1 | 48.7 | −2.2 | 44.2 | 54 | A |
| 177 | D | OD2 | 48.4 | −4.4 | 44.5 | 54 | A |
| 177 | D | C | 45.4 | −2.6 | 44.5 | 45 | A |
| 177 | D | O | 45.0 | −3.8 | 44.5 | 45 | A |
| 178 | H | N | 45.3 | −1.7 | 43.5 | 42 | A |
| 178 | H | CA | 44.6 | −2.1 | 42.3 | 39 | A |
| 178 | H | CB | 43.7 | −1.0 | 41.8 | 38 | A |
| 178 | H | CG | 42.3 | −1.0 | 42.5 | 36 | A |
| 178 | H | CD2 | 41.1 | −1.5 | 42.0 | 33 | A |
| 178 | H | ND1 | 42.1 | −0.5 | 43.7 | 36 | A |
| 178 | H | CE1 | 40.9 | −0.7 | 44.1 | 36 | A |
| 178 | H | NE2 | 40.2 | −1.3 | 43.1 | 34 | A |
| 178 | H | C | 45.5 | −2.6 | 41.2 | 37 | A |
| 178 | H | O | 45.1 | −2.8 | 40.1 | 38 | A |
| 179 | T | N | 46.8 | −2.7 | 41.5 | 36 | A |
| 179 | T | CA | 47.8 | −3.1 | 40.5 | 37 | A |
| 179 | T | CB | 49.2 | −3.4 | 41.1 | 37 | A |
| 179 | T | OG1 | 49.6 | −2.2 | 41.9 | 39 | A |
| 179 | T | CG2 | 50.2 | −3.7 | 40.0 | 36 | A |

TABLE 2-continued

Structural Coordinates of Ah₆-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 179 | T | C | 47.3 | −4.4 | 39.8 | 36 | A |
| 179 | T | O | 47.0 | −5.4 | 40.5 | 38 | A |
| 180 | G | N | 47.2 | −4.4 | 38.5 | 36 | A |
| 180 | G | CA | 46.7 | −5.5 | 37.7 | 34 | A |
| 180 | G | C | 45.2 | −5.8 | 37.7 | 36 | A |
| 180 | G | O | 44.8 | −6.8 | 37.1 | 38 | A |
| 181 | F | N | 44.4 | −4.9 | 38.2 | 36 | A |
| 181 | F | CA | 43.0 | −5.1 | 38.2 | 38 | A |
| 181 | F | CB | 42.4 | −5.0 | 39.7 | 41 | A |
| 181 | F | CG | 43.0 | −6.0 | 40.6 | 44 | A |
| 181 | F | CD1 | 43.0 | −7.4 | 40.2 | 46 | A |
| 181 | F | CD2 | 43.5 | −5.7 | 41.9 | 44 | A |
| 181 | F | CE1 | 43.5 | −8.3 | 41.1 | 47 | A |
| 181 | F | CE2 | 44.0 | −6.6 | 42.7 | 45 | A |
| 181 | F | CZ | 44.0 | −7.9 | 42.4 | 48 | A |
| 181 | F | C | 42.1 | −4.1 | 37.4 | 36 | A |
| 181 | F | O | 40.9 | −4.4 | 37.2 | 37 | A |
| 182 | L | N | 42.7 | −3.1 | 36.8 | 34 | A |
| 182 | L | CA | 42.0 | −2.2 | 36.0 | 33 | A |
| 182 | L | CB | 42.6 | −0.8 | 36.1 | 34 | A |
| 182 | L | CG | 42.6 | −0.2 | 37.5 | 34 | A |
| 182 | L | CD1 | 43.1 | 1.2 | 37.5 | 34 | A |
| 182 | L | CD2 | 41.3 | −0.3 | 38.2 | 33 | A |
| 182 | L | C | 41.7 | −2.6 | 34.6 | 32 | A |
| 182 | L | O | 42.3 | −3.2 | 33.9 | 34 | A |
| 183 | T | N | 40.5 | −2.3 | 34.1 | 32 | A |
| 183 | T | CA | 40.1 | −2.6 | 32.7 | 28 | A |
| 183 | T | CB | 38.7 | −2.1 | 32.5 | 30 | A |
| 183 | T | OG1 | 37.8 | −2.5 | 33.6 | 21 | A |
| 183 | T | CG2 | 38.2 | −2.6 | 31.2 | 22 | A |
| 183 | T | C | 41.2 | −1.9 | 31.8 | 30 | A |
| 183 | T | O | 41.5 | −0.8 | 31.9 | 28 | A |
| 184 | E | N | 41.6 | −2.7 | 30.7 | 30 | A |
| 184 | E | CA | 42.7 | −2.3 | 29.8 | 33 | A |
| 184 | E | CB | 43.3 | −3.5 | 29.2 | 33 | A |
| 184 | E | CG | 44.7 | −3.3 | 28.8 | 38 | A |
| 184 | E | CD | 45.4 | −4.6 | 28.3 | 41 | A |
| 184 | E | OE1 | 45.2 | −5.7 | 28.8 | 41 | A |
| 184 | E | OE2 | 46.0 | −4.5 | 27.2 | 44 | A |
| 184 | E | C | 42.5 | −1.2 | 28.7 | 33 | A |
| 184 | E | O | 43.2 | −0.1 | 28.8 | 37 | A |
| 185 | Y | N | 41.7 | −1.4 | 27.7 | 30 | A |
| 185 | Y | CA | 41.5 | −0.4 | 26.6 | 30 | A |
| 185 | Y | CB | 41.1 | −1.2 | 25.3 | 28 | A |
| 185 | Y | CG | 41.0 | −0.4 | 24.0 | 25 | A |
| 185 | Y | CD1 | 42.0 | 0.0 | 23.3 | 25 | A |
| 185 | Y | CE1 | 42.2 | 0.6 | 22.1 | 22 | A |
| 185 | Y | CD2 | 39.8 | −0.2 | 23.3 | 24 | A |
| 185 | Y | CE2 | 39.8 | 0.5 | 22.0 | 23 | A |
| 185 | Y | CZ | 41.0 | 0.9 | 21.4 | 23 | A |
| 185 | Y | OH | 40.9 | 1.6 | 20.2 | 21 | A |
| 185 | Y | C | 40.5 | 0.7 | 27.0 | 29 | A |
| 185 | Y | O | 39.4 | 0.7 | 26.4 | 32 | A |
| 186 | V | N | 40.9 | 1.6 | 27.9 | 30 | A |
| 186 | V | CA | 40.0 | 2.7 | 28.3 | 27 | A |
| 186 | V | CB | 40.0 | 2.8 | 29.8 | 29 | A |
| 186 | V | CG1 | 39.5 | 1.4 | 30.4 | 30 | A |
| 186 | V | CG2 | 41.4 | 3.1 | 30.4 | 29 | A |
| 186 | V | C | 40.4 | 4.1 | 27.8 | 26 | A |
| 186 | V | O | 41.4 | 4.3 | 27.2 | 18 | A |
| 187 | A | N | 39.4 | 5.0 | 27.9 | 25 | A |
| 187 | A | CA | 39.5 | 6.4 | 27.4 | 24 | A |
| 187 | A | CB | 40.8 | 7.0 | 28.0 | 23 | A |
| 187 | A | C | 39.5 | 6.4 | 25.9 | 24 | A |
| 187 | A | O | 39.9 | 5.4 | 25.2 | 25 | A |
| 188 | T | N | 39.1 | 7.6 | 25.3 | 22 | A |
| 188 | T | CA | 39.1 | 7.7 | 23.9 | 19 | A |
| 188 | T | CB | 38.1 | 8.9 | 23.5 | 20 | A |
| 188 | T | OG1 | 36.8 | 8.5 | 23.9 | 21 | A |
| 188 | T | CG2 | 38.2 | 9.2 | 22.0 | 17 | A |
| 188 | T | C | 40.6 | 8.0 | 23.5 | 20 | A |
| 188 | T | O | 41.2 | 8.8 | 24.0 | 18 | A |
| 189 | R | N | 41.0 | 7.3 | 22.4 | 20 | A |
| 189 | R | CA | 42.4 | 7.4 | 22.0 | 20 | A |
| 189 | R | CB | 42.5 | 6.9 | 20.5 | 21 | A |
| 189 | R | CG | 44.0 | 6.6 | 20.2 | 22 | A |
| 189 | R | CD | 44.2 | 6.4 | 18.7 | 24 | A |
| 189 | R | NE | 43.3 | 5.5 | 18.1 | 23 | A |
| 189 | R | CZ | 42.6 | 5.6 | 17.0 | 25 | A |
| 189 | R | NH1 | 42.9 | 6.7 | 16.2 | 19 | A |
| 189 | R | NH2 | 41.8 | 4.7 | 16.5 | 21 | A |
| 189 | R | C | 43.1 | 8.7 | 22.1 | 20 | A |
| 189 | R | O | 44.1 | 8.8 | 22.8 | 19 | A |
| 190 | W | N | 42.6 | 9.8 | 21.5 | 18 | A |
| 190 | W | CA | 43.3 | 11.1 | 21.6 | 19 | A |
| 190 | W | CB | 42.6 | 12.1 | 20.8 | 17 | A |
| 190 | W | CG | 42.4 | 11.8 | 19.3 | 20 | A |
| 190 | W | CD2 | 41.6 | 12.5 | 18.4 | 18 | A |
| 190 | W | CE2 | 41.8 | 11.9 | 17.1 | 18 | A |
| 190 | W | CE3 | 40.7 | 13.6 | 18.5 | 22 | A |
| 190 | W | CD1 | 43.1 | 10.9 | 18.6 | 19 | A |
| 190 | W | NE1 | 42.7 | 10.9 | 17.3 | 18 | A |
| 190 | W | CZ2 | 41.1 | 12.4 | 15.9 | 16 | A |
| 190 | W | CZ3 | 40.0 | 14.0 | 17.3 | 21 | A |
| 190 | W | CH2 | 40.3 | 13.4 | 16.1 | 21 | A |
| 190 | W | C | 43.5 | 11.6 | 23.0 | 17 | A |
| 190 | W | O | 44.4 | 12.3 | 23.2 | 20 | A |
| 191 | Y | N | 42.7 | 11.1 | 23.9 | 17 | A |
| 191 | Y | CA | 42.7 | 11.6 | 25.3 | 16 | A |
| 191 | Y | CB | 41.3 | 12.0 | 25.7 | 14 | A |
| 191 | Y | CG | 40.7 | 13.0 | 24.8 | 18 | A |
| 191 | Y | CD1 | 40.0 | 12.6 | 23.6 | 19 | A |
| 191 | Y | CE1 | 39.6 | 13.5 | 22.6 | 18 | A |
| 191 | Y | CD2 | 41.0 | 14.4 | 24.9 | 18 | A |
| 191 | Y | CE2 | 40.6 | 15.3 | 23.9 | 14 | A |
| 191 | Y | CZ | 39.9 | 14.9 | 22.8 | 19 | A |
| 191 | Y | OH | 39.6 | 15.7 | 21.8 | 18 | A |
| 191 | Y | C | 43.3 | 10.5 | 26.3 | 15 | A |
| 191 | Y | O | 43.2 | 10.6 | 27.5 | 15 | A |
| 192 | R | N | 43.9 | 9.5 | 25.7 | 15 | A |
| 192 | R | CA | 44.5 | 8.4 | 26.4 | 14 | A |
| 192 | R | CB | 44.6 | 7.2 | 25.5 | 18 | A |
| 192 | R | CG | 44.7 | 5.8 | 26.2 | 20 | A |
| 192 | R | CD | 43.6 | 4.9 | 25.6 | 22 | A |
| 192 | R | NE | 44.0 | 4.4 | 24.3 | 26 | A |
| 192 | R | CZ | 43.1 | 3.9 | 23.4 | 26 | A |
| 192 | R | NH1 | 41.8 | 3.8 | 23.6 | 21 | A |
| 192 | R | NH2 | 43.6 | 3.5 | 22.2 | 23 | A |
| 192 | R | C | 45.9 | 8.7 | 27.0 | 13 | A |
| 192 | R | O | 46.8 | 9.1 | 26.3 | 17 | A |
| 193 | A | N | 46.0 | 8.6 | 28.3 | 12 | A |
| 193 | A | CA | 47.3 | 8.9 | 29.0 | 12 | A |
| 193 | A | CB | 47.1 | 8.9 | 30.5 | 14 | A |
| 193 | A | C | 48.3 | 7.8 | 28.6 | 15 | A |
| 193 | A | O | 48.0 | 6.7 | 28.3 | 11 | A |
| 194 | P | N | 49.6 | 8.2 | 28.6 | 16 | A |
| 194 | P | CD | 50.2 | 9.5 | 29.2 | 12 | A |
| 194 | P | CA | 50.6 | 7.3 | 28.3 | 16 | A |
| 194 | P | CB | 51.9 | 8.1 | 28.5 | 15 | A |
| 194 | P | CG | 51.5 | 9.5 | 28.5 | 15 | A |
| 194 | P | C | 50.6 | 6.0 | 29.1 | 18 | A |
| 194 | P | O | 50.7 | 4.9 | 28.5 | 18 | A |
| 195 | E | N | 50.4 | 6.1 | 30.4 | 17 | A |
| 195 | E | CA | 50.4 | 4.9 | 31.2 | 18 | A |
| 195 | E | CB | 50.3 | 5.3 | 32.7 | 15 | A |
| 195 | E | CG | 49.0 | 5.9 | 33.2 | 13 | A |
| 195 | E | CD | 49.1 | 7.4 | 33.2 | 17 | A |
| 195 | E | OE1 | 49.9 | 8.0 | 32.5 | 20 | A |
| 195 | E | OE2 | 48.2 | 8.0 | 33.9 | 19 | A |
| 195 | E | C | 49.3 | 3.9 | 30.9 | 19 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 195 | E | O | 49.5 | 2.7 | 31.2 | 21 | A |
| 196 | I | N | 48.2 | 4.3 | 30.2 | 20 | A |
| 196 | I | CA | 47.2 | 3.3 | 29.9 | 22 | A |
| 196 | I | CB | 46.0 | 4.0 | 29.3 | 24 | A |
| 196 | I | CG2 | 45.1 | 3.0 | 28.5 | 23 | A |
| 196 | I | CG1 | 45.2 | 4.7 | 30.4 | 23 | A |
| 196 | I | CD1 | 44.1 | 5.6 | 29.9 | 23 | A |
| 196 | I | C | 47.8 | 2.3 | 28.9 | 23 | A |
| 196 | I | O | 47.4 | 1.2 | 28.8 | 24 | A |
| 197 | M | N | 48.8 | 2.8 | 28.1 | 25 | A |
| 197 | M | CA | 49.5 | 2.0 | 27.1 | 22 | A |
| 197 | M | CB | 50.0 | 2.8 | 25.9 | 23 | A |
| 197 | M | CG | 49.1 | 3.1 | 24.8 | 28 | A |
| 197 | M | SD | 48.1 | 4.6 | 25.0 | 32 | A |
| 197 | M | CE | 49.3 | 5.8 | 24.5 | 30 | A |
| 197 | M | C | 50.8 | 1.3 | 27.7 | 23 | A |
| 197 | M | O | 51.1 | 0.2 | 27.3 | 21 | A |
| 198 | L | N | 51.4 | 1.9 | 28.7 | 24 | A |
| 198 | L | CA | 52.6 | 1.4 | 29.3 | 25 | A |
| 198 | L | CB | 53.7 | 2.5 | 29.5 | 27 | A |
| 198 | L | CG | 54.4 | 3.2 | 28.3 | 28 | A |
| 198 | L | CD1 | 54.5 | 2.3 | 27.1 | 24 | A |
| 198 | L | CD2 | 53.7 | 4.5 | 27.9 | 27 | A |
| 190 | L | C | 52.5 | 0.6 | 30.6 | 24 | A |
| 198 | L | O | 53.4 | -0.1 | 31.0 | 25 | A |
| 199 | N | N | 51.3 | 0.8 | 31.2 | 24 | A |
| 199 | N | CA | 51.1 | 0.1 | 32.5 | 24 | A |
| 199 | N | CB | 51.4 | 1.0 | 33.7 | 23 | A |
| 199 | N | CG | 51.3 | 0.3 | 35.0 | 25 | A |
| 199 | N | OD1 | 51.3 | 1.0 | 36.1 | 25 | A |
| 199 | N | ND2 | 51.3 | -1.0 | 35.0 | 23 | A |
| 199 | N | C | 49.6 | -0.3 | 32.4 | 26 | A |
| 199 | N | O | 48.8 | -0.1 | 33.4 | 27 | A |
| 200 | S | N | 49.2 | -0.8 | 31.3 | 29 | A |
| 200 | S | CA | 47.8 | -1.2 | 30.9 | 31 | A |
| 200 | S | CB | 47.9 | -2.3 | 29.9 | 32 | A |
| 200 | S | OG | 48.5 | -3.5 | 30.4 | 34 | A |
| 200 | S | C | 46.9 | -1.6 | 32.0 | 30 | A |
| 200 | S | O | 45.7 | -1.2 | 31.9 | 30 | A |
| 201 | K | N | 47.3 | -2.2 | 33.1 | 27 | A |
| 201 | K | CA | 46.4 | -2.6 | 34.1 | 28 | A |
| 201 | K | CB | 46.2 | -4.1 | 34.2 | 28 | A |
| 201 | K | CG | 45.9 | -4.8 | 32.8 | 30 | A |
| 201 | K | CD | 45.1 | -6.1 | 33.0 | 34 | A |
| 201 | K | CE | 43.7 | -5.8 | 33.6 | 37 | A |
| 201 | K | NZ | 42.9 | -6.9 | 33.9 | 39 | A |
| 201 | K | C | 46.7 | -2.0 | 35.5 | 26 | A |
| 201 | K | O | 46.0 | -2.4 | 36.5 | 25 | A |
| 202 | G | N | 47.6 | -1.1 | 35.6 | 23 | A |
| 202 | G | CA | 47.9 | -0.5 | 36.8 | 23 | A |
| 202 | G | C | 47.9 | 1.0 | 36.9 | 25 | A |
| 202 | G | O | 48.5 | 1.6 | 37.7 | 24 | A |
| 203 | Y | N | 47.1 | 1.6 | 36.0 | 26 | A |
| 203 | Y | CA | 47.0 | 3.1 | 35.9 | 24 | A |
| 203 | Y | CB | 46.4 | 3.6 | 34.6 | 22 | A |
| 203 | Y | CG | 45.1 | 3.0 | 34.3 | 20 | A |
| 203 | Y | CD1 | 43.9 | 3.5 | 34.9 | 18 | A |
| 203 | Y | CE1 | 42.7 | 3.0 | 34.6 | 13 | A |
| 203 | Y | CD2 | 45.0 | 1.9 | 33.4 | 17 | A |
| 203 | Y | CE2 | 43.7 | 1.3 | 33.1 | 12 | A |
| 203 | Y | CZ | 42.6 | 1.9 | 33.7 | 14 | A |
| 203 | Y | OH | 41.3 | 1.3 | 33.5 | 15 | A |
| 203 | Y | C | 46.1 | 3.5 | 37.1 | 26 | A |
| 203 | Y | O | 45.5 | 2.6 | 37.8 | 26 | A |
| 204 | T | N | 46.0 | 4.8 | 37.3 | 25 | A |
| 204 | T | CA | 45.2 | 5.3 | 38.4 | 20 | A |
| 204 | T | CB | 46.1 | 5.9 | 39.6 | 22 | A |
| 204 | T | OG1 | 46.7 | 7.1 | 39.1 | 21 | A |
| 204 | T | CG2 | 47.1 | 4.9 | 40.0 | 21 | A |
| 204 | T | C | 44.3 | 6.5 | 37.9 | 21 | A |
| 204 | T | O | 44.2 | 6.7 | 36.7 | 20 | A |
| 205 | K | N | 43.7 | 7.1 | 38.9 | 21 | A |
| 205 | K | CA | 42.8 | 8.3 | 38.6 | 21 | A |
| 205 | K | CB | 42.3 | 8.8 | 40.0 | 26 | A |
| 205 | K | CG | 43.4 | 9.5 | 40.8 | 28 | A |
| 205 | K | CD | 43.1 | 9.6 | 42.3 | 33 | A |
| 205 | K | CE | 41.8 | 10.2 | 42.6 | 35 | A |
| 205 | K | NZ | 41.4 | 10.0 | 44.0 | 37 | A |
| 205 | K | C | 43.5 | 9.4 | 37.9 | 20 | A |
| 205 | K | O | 42.8 | 10.2 | 37.2 | 20 | A |
| 206 | S | N | 44.8 | 9.5 | 37.9 | 20 | A |
| 206 | S | CA | 45.5 | 10.6 | 37.2 | 20 | A |
| 206 | S | CB | 47.0 | 10.8 | 37.6 | 23 | A |
| 206 | S | OG | 47.8 | 9.8 | 37.0 | 27 | A |
| 206 | S | C | 45.3 | 10.6 | 35.7 | 19 | A |
| 206 | S | O | 45.7 | 11.6 | 35.0 | 21 | A |
| 207 | I | N | 44.8 | 9.5 | 35.1 | 16 | A |
| 207 | I | CA | 44.6 | 9.5 | 33.7 | 17 | A |
| 207 | I | CB | 44.2 | 8.1 | 33.1 | 16 | A |
| 207 | I | CG2 | 45.1 | 7.0 | 33.7 | 14 | A |
| 207 | I | CG1 | 42.7 | 7.7 | 33.6 | 19 | A |
| 207 | I | CD1 | 42.2 | 6.4 | 33.1 | 18 | A |
| 207 | I | C | 43.5 | 10.5 | 33.3 | 17 | A |
| 207 | I | O | 43.4 | 11.0 | 32.2 | 18 | A |
| 208 | D | N | 42.7 | 10.8 | 34.3 | 17 | A |
| 208 | D | CA | 41.6 | 11.8 | 34.1 | 15 | A |
| 208 | D | CB | 40.6 | 11.8 | 35.2 | 16 | A |
| 208 | D | CG | 39.6 | 10.6 | 35.2 | 15 | A |
| 208 | D | OD1 | 39.3 | 10.2 | 34.1 | 12 | A |
| 208 | D | OD2 | 39.3 | 10.1 | 36.3 | 19 | A |
| 208 | D | C | 42.2 | 13.2 | 34.0 | 16 | A |
| 208 | D | O | 41.7 | 14.0 | 33.2 | 17 | A |
| 209 | I | N | 43.3 | 13.4 | 34.8 | 14 | A |
| 209 | I | CA | 44.0 | 14.7 | 34.8 | 15 | A |
| 209 | I | CB | 45.0 | 14.8 | 35.9 | 15 | A |
| 209 | I | CG2 | 45.9 | 16.1 | 35.7 | 16 | A |
| 209 | I | CG1 | 44.4 | 14.8 | 37.3 | 17 | A |
| 209 | I | CD1 | 43.6 | 16.1 | 37.5 | 19 | A |
| 209 | I | C | 44.7 | 14.9 | 33.4 | 16 | A |
| 209 | I | O | 44.7 | 16.0 | 32.8 | 17 | A |
| 210 | W | N | 45.2 | 13.8 | 32.9 | 16 | A |
| 210 | W | CA | 45.9 | 13.8 | 31.6 | 16 | A |
| 210 | W | CB | 46.5 | 12.4 | 31.2 | 16 | A |
| 210 | W | CG | 47.0 | 12.4 | 29.8 | 15 | A |
| 210 | W | CD2 | 48.4 | 12.7 | 29.5 | 12 | A |
| 210 | W | CE2 | 48.5 | 12.6 | 28.1 | 13 | A |
| 210 | W | CE3 | 49.5 | 13.0 | 30.2 | 14 | A |
| 210 | W | CD1 | 46.4 | 12.2 | 28.7 | 15 | A |
| 210 | W | NE1 | 47.2 | 12.3 | 27.6 | 13 | A |
| 210 | W | CZ2 | 49.7 | 12.8 | 27.4 | 15 | A |
| 210 | W | CZ3 | 50.7 | 13.2 | 29.6 | 14 | A |
| 210 | W | CH2 | 50.8 | 13.1 | 28.2 | 15 | A |
| 210 | W | C | 44.9 | 14.2 | 30.5 | 16 | A |
| 210 | W | O | 45.2 | 15.0 | 29.6 | 14 | A |
| 211 | S | N | 43.7 | 13.7 | 30.6 | 17 | A |
| 211 | S | CA | 42.6 | 14.0 | 29.7 | 17 | A |
| 211 | S | CB | 41.4 | 13.2 | 30.0 | 16 | A |
| 211 | S | OG | 41.6 | 11.8 | 29.6 | 12 | A |
| 211 | S | C | 42.3 | 15.5 | 29.7 | 16 | A |
| 211 | S | O | 42.1 | 16.1 | 28.7 | 18 | A |
| 212 | V | N | 42.1 | 16.0 | 30.9 | 15 | A |
| 212 | V | CA | 41.8 | 17.4 | 31.1 | 16 | A |
| 212 | V | CB | 41.6 | 17.8 | 32.5 | 17 | A |
| 212 | V | CG1 | 41.4 | 19.4 | 32.6 | 17 | A |
| 212 | V | CG2 | 40.5 | 17.1 | 33.2 | 15 | A |
| 212 | V | C | 42.9 | 18.2 | 30.4 | 19 | A |
| 212 | V | O | 42.6 | 19.3 | 29.8 | 18 | A |
| 213 | G | N | 44.1 | 17.7 | 30.5 | 20 | A |
| 213 | G | CA | 45.2 | 18.3 | 29.9 | 19 | A |
| 213 | G | C | 45.0 | 18.4 | 28.4 | 19 | A |

TABLE 2-continued

Structural Coordinates of Ah6-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 213 | G | O   | 45.2 | 19.5 | 27.8 | 23 | A |
|-----|---|-----|------|------|------|----|---|
| 214 | C | N   | 44.6 | 17.3 | 27.8 | 17 | A |
| 214 | C | CA  | 44.4 | 17.3 | 26.3 | 17 | A |
| 214 | C | CB  | 44.0 | 15.9 | 25.8 | 16 | A |
| 214 | C | SG  | 45.2 | 14.7 | 26.1 | 17 | A |
| 214 | C | C   | 43.2 | 18.3 | 26.0 | 17 | A |
| 214 | C | O   | 43.3 | 19.0 | 25.0 | 18 | A |
| 215 | I | N   | 42.2 | 18.4 | 26.9 | 20 | A |
| 215 | I | CA  | 41.1 | 19.3 | 26.7 | 18 | A |
| 215 | I | CB  | 40.0 | 18.9 | 27.6 | 15 | A |
| 215 | I | CG2 | 38.9 | 20.0 | 27.6 | 11 | A |
| 215 | I | CG1 | 39.4 | 17.6 | 27.3 | 13 | A |
| 215 | I | CD1 | 38.5 | 17.0 | 28.4 | 13 | A |
| 215 | I | C   | 41.5 | 20.7 | 26.8 | 20 | A |
| 215 | I | O   | 41.0 | 21.6 | 26.0 | 22 | A |
| 216 | L | N   | 42.4 | 21.1 | 27.7 | 19 | A |
| 216 | L | CA  | 42.8 | 22.4 | 27.8 | 19 | A |
| 216 | L | CB  | 43.8 | 22.6 | 29.0 | 19 | A |
| 216 | L | CG  | 44.0 | 23.9 | 29.7 | 19 | A |
| 216 | L | CD1 | 45.5 | 24.0 | 30.1 | 18 | A |
| 216 | L | CD2 | 43.6 | 25.1 | 28.9 | 13 | A |
| 216 | L | C   | 43.5 | 22.8 | 26.5 | 21 | A |
| 216 | L | O   | 43.2 | 23.8 | 25.9 | 23 | A |
| 217 | A | N   | 44.4 | 22.0 | 26.0 | 21 | A |
| 217 | A | CA  | 45.2 | 22.3 | 24.8 | 21 | A |
| 217 | A | CB  | 46.1 | 21.1 | 24.5 | 22 | A |
| 217 | A | C   | 44.2 | 22.5 | 23.6 | 23 | A |
| 217 | A | O   | 44.4 | 23.3 | 22.8 | 22 | A |
| 218 | E | N   | 43.1 | 21.8 | 23.6 | 21 | A |
| 218 | E | CA  | 42.1 | 21.9 | 22.5 | 22 | A |
| 218 | E | CB  | 41.1 | 20.8 | 22.5 | 21 | A |
| 218 | E | CG  | 40.9 | 20.2 | 21.1 | 24 | A |
| 218 | E | CD  | 40.2 | 18.9 | 21.1 | 23 | A |
| 218 | E | OE1 | 40.7 | 17.9 | 21.6 | 21 | A |
| 218 | E | OE2 | 39.1 | 18.8 | 20.4 | 25 | A |
| 218 | E | C   | 41.4 | 23.3 | 22.7 | 22 | A |
| 218 | E | O   | 41.1 | 23.9 | 21.6 | 24 | A |
| 219 | M | N   | 41.1 | 23.7 | 23.9 | 22 | A |
| 219 | M | CA  | 40.4 | 25.0 | 24.1 | 22 | A |
| 219 | M | CB  | 40.0 | 25.2 | 25.6 | 20 | A |
| 219 | M | CG  | 38.9 | 24.2 | 26.0 | 22 | A |
| 219 | M | SD  | 38.1 | 24.7 | 27.6 | 18 | A |
| 219 | M | CE  | 39.2 | 24.0 | 28.8 | 20 | A |
| 219 | M | C   | 41.3 | 26.1 | 23.7 | 20 | A |
| 219 | M | O   | 40.9 | 27.2 | 23.3 | 21 | A |
| 220 | L | N   | 42.6 | 25.9 | 23.8 | 22 | A |
| 220 | L | CA  | 43.6 | 26.9 | 23.4 | 22 | A |
| 220 | L | CB  | 44.9 | 26.6 | 24.1 | 19 | A |
| 220 | L | CG  | 45.0 | 26.8 | 25.7 | 16 | A |
| 220 | L | CD1 | 46.3 | 26.0 | 26.2 | 13 | A |
| 220 | L | CD2 | 45.1 | 28.2 | 26.1 | 16 | A |
| 220 | L | C   | 43.9 | 27.1 | 21.9 | 22 | A |
| 220 | L | O   | 44.3 | 28.1 | 21.5 | 23 | A |
| 221 | S | N   | 43.6 | 26.0 | 21.2 | 21 | A |
| 221 | S | CA  | 43.9 | 26.0 | 19.8 | 22 | A |
| 221 | S | CB  | 45.2 | 25.3 | 19.5 | 26 | A |
| 221 | S | OG  | 45.0 | 23.9 | 19.7 | 29 | A |
| 221 | S | C   | 42.8 | 25.4 | 18.8 | 23 | A |
| 221 | S | O   | 43.0 | 25.5 | 17.6 | 25 | A |
| 222 | N | N   | 41.8 | 24.9 | 19.4 | 21 | A |
| 222 | N | CA  | 40.7 | 24.3 | 18.6 | 23 | A |
| 222 | N | CB  | 40.1 | 25.4 | 17.6 | 21 | A |
| 222 | N | CG  | 39.4 | 26.5 | 18.4 | 22 | A |
| 222 | N | OD1 | 40.1 | 27.4 | 18.9 | 20 | A |
| 222 | N | ND2 | 38.1 | 26.4 | 18.5 | 23 | A |
| 222 | N | C   | 41.2 | 23.1 | 17.8 | 22 | A |
| 222 | N | O   | 40.7 | 22.9 | 16.7 | 22 | A |
| 223 | R | N   | 42.2 | 22.4 | 18.3 | 24 | A |
| 223 | R | CA  | 42.7 | 21.3 | 17.5 | 25 | A |
| 223 | R | CB  | 44.0 | 21.8 | 16.7 | 31 | A |
| 223 | R | CG  | 44.2 | 21.0 | 15.5 | 39 | A |
| 223 | R | CD  | 45.7 | 21.3 | 15.0 | 43 | A |
| 223 | R | NE  | 46.6 | 20.5 | 15.8 | 49 | A |
| 223 | R | CZ  | 46.8 | 19.1 | 15.7 | 50 | A |
| 223 | R | NH1 | 46.0 | 18.5 | 14.8 | 51 | A |
| 223 | R | NH2 | 47.7 | 18.5 | 16.4 | 45 | A |
| 223 | R | C   | 43.2 | 20.2 | 18.5 | 23 | A |
| 223 | R | O   | 43.8 | 20.6 | 19.6 | 22 | A |
| 224 | P | N   | 42.9 | 18.9 | 18.2 | 21 | A |
| 224 | P | CD  | 42.1 | 18.3 | 17.2 | 19 | A |
| 224 | P | CA  | 43.4 | 18.0 | 19.2 | 16 | A |
| 224 | P | CB  | 42.8 | 16.6 | 18.7 | 13 | A |
| 224 | P | CG  | 42.6 | 16.9 | 17.2 | 22 | A |
| 224 | P | C   | 44.9 | 18.0 | 19.2 | 14 | A |
| 224 | P | O   | 45.5 | 18.1 | 18.1 | 14 | A |
| 225 | I | N   | 45.6 | 17.9 | 20.3 | 12 | A |
| 225 | I | CA  | 47.0 | 18.0 | 20.5 | 14 | A |
| 225 | I | CB  | 47.4 | 18.5 | 21.9 | 17 | A |
| 225 | I | CG2 | 46.9 | 17.5 | 23.0 | 15 | A |
| 225 | I | CG1 | 48.9 | 18.7 | 22.1 | 19 | A |
| 225 | I | CD1 | 49.4 | 19.9 | 21.2 | 24 | A |
| 225 | I | C   | 47.7 | 16.6 | 20.1 | 16 | A |
| 225 | I | O   | 48.8 | 16.7 | 19.6 | 15 | A |
| 226 | F | N   | 47.1 | 15.5 | 20.4 | 16 | A |
| 226 | F | CA  | 47.7 | 14.2 | 20.1 | 11 | A |
| 226 | F | CB  | 47.9 | 13.4 | 21.4 | 13 | A |
| 226 | F | CG  | 48.8 | 14.2 | 22.4 | 13 | A |
| 226 | F | CD1 | 50.0 | 14.8 | 22.0 | 15 | A |
| 226 | F | CD2 | 48.3 | 14.3 | 23.7 | 12 | A |
| 226 | F | CE1 | 50.7 | 15.5 | 22.9 | 14 | A |
| 226 | F | CE2 | 49.1 | 15.0 | 24.6 | 14 | A |
| 226 | F | CZ  | 50.3 | 15.6 | 24.3 | 10 | A |
| 226 | F | C   | 46.7 | 13.4 | 19.2 | 14 | A |
| 226 | F | O   | 46.2 | 12.3 | 19.7 | 13 | A |
| 227 | P | N   | 46.5 | 13.7 | 18.0 | 14 | A |
| 227 | P | CD  | 47.1 | 14.9 | 17.2 | 13 | A |
| 227 | P | CA  | 45.6 | 13.0 | 17.1 | 16 | A |
| 227 | P | CB  | 45.3 | 14.0 | 16.0 | 13 | A |
| 227 | P | CG  | 46.6 | 14.7 | 15.8 | 13 | A |
| 227 | P | C   | 46.1 | 11.6 | 16.6 | 18 | A |
| 227 | P | O   | 46.3 | 11.4 | 15.4 | 20 | A |
| 228 | G | N   | 46.3 | 10.7 | 17.5 | 17 | A |
| 228 | G | CA  | 46.8 | 9.4  | 17.1 | 18 | A |
| 228 | G | C   | 45.9 | 8.7  | 16.1 | 19 | A |
| 228 | G | O   | 44.6 | 8.9  | 16.3 | 19 | A |
| 229 | K | N   | 46.4 | 7.9  | 15.2 | 18 | A |
| 229 | K | CA  | 45.6 | 7.2  | 14.2 | 22 | A |
| 229 | K | CB  | 46.2 | 7.3  | 12.8 | 23 | A |
| 229 | K | CG  | 46.4 | 8.8  | 12.4 | 29 | A |
| 229 | K | CD  | 47.3 | 8.9  | 11.2 | 36 | A |
| 229 | K | CE  | 47.3 | 10.3 | 10.6 | 36 | A |
| 229 | K | NZ  | 48.2 | 10.4 | 9.5  | 37 | A |
| 229 | K | C   | 45.2 | 5.8  | 14.6 | 21 | A |
| 229 | K | O   | 44.3 | 5.2  | 14.1 | 24 | A |
| 230 | H | N   | 46.1 | 5.1  | 15.4 | 21 | A |
| 230 | H | CA  | 45.9 | 3.8  | 15.8 | 20 | A |
| 230 | H | CB  | 46.7 | 2.8  | 14.9 | 21 | A |
| 230 | H | CG  | 46.3 | 2.9  | 13.4 | 25 | A |
| 230 | H | CD2 | 46.9 | 3.4  | 12.4 | 24 | A |
| 230 | H | ND1 | 45.1 | 2.4  | 13.0 | 26 | A |
| 230 | H | CE1 | 45.0 | 2.7  | 11.7 | 26 | A |
| 230 | H | NE2 | 46.1 | 3.3  | 11.3 | 24 | A |
| 230 | H | C   | 46.4 | 3.7  | 17.2 | 18 | A |
| 230 | H | O   | 46.9 | 4.7  | 17.7 | 20 | A |
| 231 | Y | N   | 46.3 | 2.5  | 17.8 | 19 | A |
| 231 | Y | CA  | 46.7 | 2.3  | 19.2 | 18 | A |
| 231 | Y | CB  | 46.6 | 0.9  | 19.6 | 16 | A |
| 231 | Y | CG  | 46.8 | 0.6  | 21.0 | 21 | A |
| 231 | Y | CD1 | 45.9 | 1.1  | 22.0 | 18 | A |
| 231 | Y | CE1 | 46.0 | 0.8  | 23.3 | 22 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 231 | Y | CD2 | 47.8 | −0.2 | 21.5 | 23 | A |
|---|---|---|---|---|---|---|---|
| 231 | Y | CE2 | 48.0 | −0.5 | 22.8 | 22 | A |
| 231 | Y | CZ | 47.1 | 0.0 | 23.7 | 21 | A |
| 231 | Y | OH | 47.3 | −0.3 | 25.1 | 23 | A |
| 231 | Y | C | 48.1 | 2.8 | 19.6 | 18 | A |
| 231 | Y | O | 48.3 | 3.7 | 20.4 | 14 | A |
| 232 | L | N | 49.1 | 2.3 | 19.0 | 17 | A |
| 232 | L | CA | 50.5 | 2.7 | 19.3 | 19 | A |
| 232 | L | CB | 51.5 | 1.6 | 18.7 | 20 | A |
| 232 | L | CG | 51.4 | 0.2 | 19.3 | 22 | A |
| 232 | L | CD1 | 52.5 | −0.6 | 18.7 | 23 | A |
| 232 | L | CD2 | 51.5 | 0.2 | 20.8 | 21 | A |
| 232 | L | C | 50.8 | 4.0 | 18.7 | 21 | A |
| 232 | L | O | 51.6 | 4.8 | 19.3 | 19 | A |
| 233 | D | N | 50.2 | 4.4 | 17.6 | 22 | A |
| 233 | D | CA | 50.5 | 5.7 | 17.0 | 22 | A |
| 233 | D | CB | 49.7 | 5.9 | 15.7 | 23 | A |
| 233 | D | CG | 50.1 | 7.1 | 14.9 | 26 | A |
| 233 | D | OD1 | 51.3 | 7.3 | 14.6 | 26 | A |
| 233 | D | OD2 | 49.2 | 8.0 | 14.6 | 28 | A |
| 233 | D | C | 50.2 | 6.8 | 17.9 | 21 | A |
| 233 | D | O | 50.7 | 7.9 | 17.9 | 22 | A |
| 234 | Q | N | 49.2 | 6.6 | 18.9 | 20 | A |
| 234 | Q | CA | 48.8 | 7.6 | 19.9 | 20 | A |
| 234 | Q | CB | 47.7 | 7.0 | 20.8 | 21 | A |
| 234 | Q | CG | 47.2 | 8.0 | 21.8 | 22 | A |
| 234 | Q | CD | 46.7 | 9.2 | 21.2 | 22 | A |
| 234 | Q | OE1 | 45.9 | 9.2 | 20.2 | 23 | A |
| 234 | Q | NE2 | 47.0 | 10.4 | 21.8 | 21 | A |
| 234 | Q | C | 50.0 | 8.0 | 20.7 | 20 | A |
| 234 | Q | O | 50.3 | 9.1 | 21.0 | 20 | A |
| 235 | L | N | 50.8 | 6.9 | 21.1 | 20 | A |
| 235 | L | CA | 52.2 | 7.2 | 21.9 | 20 | A |
| 235 | L | CB | 52.6 | 5.8 | 22.4 | 17 | A |
| 235 | L | CG | 53.8 | 5.9 | 23.3 | 19 | A |
| 235 | L | CD1 | 53.5 | 6.7 | 24.5 | 18 | A |
| 235 | L | CD2 | 54.1 | 4.4 | 23.7 | 18 | A |
| 235 | L | C | 53.0 | 8.0 | 21.2 | 19 | A |
| 235 | L | O | 53.7 | 8.9 | 21.8 | 18 | A |
| 236 | N | N | 53.2 | 7.9 | 19.9 | 19 | A |
| 236 | N | CA | 54.1 | 8.6 | 19.1 | 19 | A |
| 236 | N | CB | 54.3 | 8.0 | 17.7 | 23 | A |
| 236 | N | CG | 55.1 | 6.7 | 17.8 | 27 | A |
| 236 | N | OD1 | 56.1 | 6.6 | 18.5 | 29 | A |
| 236 | N | ND2 | 54.6 | 5.7 | 17.0 | 27 | A |
| 236 | N | C | 53.8 | 10.1 | 19.0 | 18 | A |
| 236 | N | O | 54.7 | 10.9 | 19.0 | 21 | A |
| 237 | H | N | 52.5 | 10.4 | 18.9 | 16 | A |
| 237 | H | CA | 52.1 | 11.8 | 18.9 | 14 | A |
| 237 | H | CB | 50.6 | 11.9 | 18.5 | 13 | A |
| 237 | H | CG | 50.3 | 11.6 | 17.1 | 12 | A |
| 237 | H | CD2 | 50.1 | 10.4 | 16.5 | 12 | A |
| 237 | H | ND1 | 50.2 | 12.5 | 16.1 | 12 | A |
| 237 | H | CE1 | 50.0 | 11.9 | 14.9 | 10 | A |
| 237 | H | NE2 | 49.9 | 10.6 | 15.1 | 15 | A |
| 237 | H | C | 52.3 | 12.5 | 20.2 | 13 | A |
| 237 | H | O | 52.6 | 13.7 | 20.3 | 17 | A |
| 238 | I | N | 52.2 | 11.7 | 21.3 | 12 | A |
| 238 | I | CA | 52.5 | 12.2 | 22.6 | 13 | A |
| 238 | I | CB | 52.1 | 11.2 | 23.7 | 10 | A |
| 238 | I | CG2 | 52.6 | 11.7 | 25.1 | 8 | A |
| 238 | I | CG1 | 50.6 | 11.1 | 23.6 | 11 | A |
| 238 | I | CD1 | 50.0 | 10.0 | 24.6 | 9 | A |
| 238 | I | C | 54.0 | 12.5 | 22.7 | 13 | A |
| 238 | I | O | 54.4 | 13.6 | 23.1 | 13 | A |
| 239 | L | N | 54.9 | 11.6 | 22.3 | 15 | A |
| 239 | L | CA | 56.3 | 11.8 | 22.4 | 17 | A |
| 239 | L | CB | 57.1 | 10.5 | 22.1 | 15 | A |
| 239 | L | CG | 56.8 | 9.4 | 23.1 | 19 | A |
| 239 | L | CD1 | 57.8 | 8.3 | 22.9 | 18 | A |
| 239 | L | CD2 | 57.0 | 10.0 | 24.5 | 16 | A |
| 239 | L | C | 56.7 | 12.9 | 21.4 | 17 | A |
| 239 | L | O | 57.7 | 13.5 | 21.5 | 15 | A |
| 240 | G | N | 55.9 | 13.1 | 20.4 | 19 | A |
| 240 | G | CA | 56.1 | 14.1 | 19.4 | 20 | A |
| 240 | G | C | 56.1 | 15.5 | 20.0 | 21 | A |
| 240 | G | O | 56.7 | 16.4 | 19.5 | 20 | A |
| 241 | I | N | 55.4 | 15.6 | 21.1 | 21 | A |
| 241 | I | CA | 55.3 | 16.9 | 21.8 | 19 | A |
| 241 | I | CB | 53.9 | 17.2 | 22.2 | 19 | A |
| 241 | I | CG2 | 53.8 | 18.5 | 23.1 | 18 | A |
| 241 | I | CG1 | 53.0 | 17.4 | 21.0 | 21 | A |
| 241 | I | CD1 | 53.4 | 18.6 | 20.1 | 21 | A |
| 241 | I | C | 56.2 | 16.9 | 23.1 | 19 | A |
| 241 | I | O | 57.0 | 17.9 | 23.3 | 18 | A |
| 242 | L | N | 56.1 | 15.9 | 24.0 | 20 | A |
| 242 | L | CA | 56.9 | 15.9 | 25.2 | 20 | A |
| 242 | L | CB | 56.3 | 14.9 | 26.2 | 20 | A |
| 242 | L | CG | 54.9 | 15.1 | 26.7 | 24 | A |
| 242 | L | CD1 | 54.7 | 14.3 | 27.9 | 20 | A |
| 242 | L | CD2 | 54.6 | 16.6 | 27.0 | 22 | A |
| 242 | L | C | 58.4 | 15.5 | 25.0 | 20 | A |
| 242 | L | O | 59.2 | 15.8 | 25.8 | 18 | A |
| 243 | G | N | 58.6 | 14.8 | 23.9 | 19 | A |
| 243 | G | CA | 59.9 | 14.3 | 23.6 | 18 | A |
| 243 | G | C | 60.0 | 12.9 | 24.3 | 20 | A |
| 243 | G | O | 59.1 | 12.5 | 25.0 | 19 | A |
| 244 | S | N | 61.2 | 12.3 | 24.1 | 20 | A |
| 244 | S | CA | 61.4 | 11.0 | 24.8 | 22 | A |
| 244 | S | CB | 62.7 | 10.4 | 24.3 | 21 | A |
| 244 | S | OG | 62.7 | 10.1 | 23.0 | 27 | A |
| 244 | S | C | 61.4 | 11.1 | 26.3 | 22 | A |
| 244 | S | O | 61.8 | 12.2 | 26.8 | 21 | A |
| 245 | P | N | 60.9 | 10.1 | 27.0 | 24 | A |
| 245 | P | CD | 60.4 | 8.8 | 26.6 | 22 | A |
| 245 | P | CA | 60.9 | 10.3 | 28.5 | 25 | A |
| 245 | P | CB | 60.1 | 9.0 | 29.0 | 23 | A |
| 245 | P | CG | 59.5 | 8.4 | 27.7 | 27 | A |
| 245 | P | C | 62.3 | 10.3 | 29.0 | 25 | A |
| 245 | P | O | 63.2 | 9.8 | 28.4 | 25 | A |
| 246 | S | N | 62.5 | 10.9 | 30.2 | 27 | A |
| 246 | S | CA | 63.8 | 11.0 | 30.8 | 28 | A |
| 246 | S | CB | 63.8 | 11.9 | 32.0 | 25 | A |
| 246 | S | OG | 63.0 | 11.3 | 33.0 | 25 | A |
| 246 | S | C | 64.2 | 9.5 | 31.2 | 32 | A |
| 246 | S | O | 63.3 | 8.7 | 31.4 | 30 | A |
| 247 | Q | N | 65.4 | 9.2 | 31.4 | 37 | A |
| 247 | Q | CA | 65.9 | 7.9 | 31.8 | 41 | A |
| 247 | Q | CB | 67.4 | 7.9 | 32.0 | 43 | A |
| 247 | Q | CG | 68.0 | 6.5 | 31.8 | 50 | A |
| 247 | Q | CD | 67.5 | 5.5 | 32.8 | 54 | A |
| 247 | Q | OE1 | 67.5 | 5.7 | 34.0 | 56 | A |
| 247 | Q | NE2 | 67.1 | 4.3 | 32.3 | 55 | A |
| 247 | Q | C | 65.1 | 7.5 | 33.1 | 40 | A |
| 247 | Q | O | 64.7 | 6.4 | 33.2 | 38 | A |
| 248 | E | N | 64.9 | 8.5 | 34.0 | 41 | A |
| 248 | E | CA | 64.3 | 8.2 | 35.2 | 42 | A |
| 248 | E | CB | 64.4 | 9.5 | 36.1 | 44 | A |
| 248 | E | CG | 63.7 | 9.4 | 37.5 | 49 | A |
| 248 | E | CD | 64.1 | 10.6 | 38.4 | 53 | A |
| 248 | E | OE1 | 65.2 | 10.7 | 38.8 | 54 | A |
| 248 | E | OE2 | 63.1 | 11.4 | 38.7 | 54 | A |
| 248 | E | C | 62.8 | 7.9 | 35.1 | 41 | A |
| 248 | E | O | 62.3 | 7.0 | 35.8 | 42 | A |
| 249 | D | N | 62.1 | 8.5 | 34.1 | 38 | A |
| 249 | D | CA | 60.7 | 8.2 | 33.9 | 36 | A |
| 249 | D | CB | 60.0 | 9.3 | 33.0 | 33 | A |
| 249 | D | CG | 60.0 | 10.6 | 33.6 | 33 | A |
| 249 | D | OD1 | 59.8 | 10.7 | 34.9 | 32 | A |
| 249 | D | OD2 | 60.0 | 11.6 | 32.9 | 35 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 249 | D | C | 60.6 | 6.8 | 33.2 | 35 | A |
|---|---|---|---|---|---|---|---|
| 249 | D | O | 59.6 | 6.1 | 33.5 | 35 | A |
| 250 | L | N | 61.5 | 6.5 | 32.3 | 35 | A |
| 250 | L | CA | 61.6 | 5.3 | 31.6 | 36 | A |
| 250 | L | CB | 62.8 | 5.2 | 30.7 | 35 | A |
| 250 | L | CG | 62.5 | 4.8 | 29.2 | 39 | A |
| 250 | L | CD1 | 62.0 | 3.4 | 29.1 | 41 | A |
| 250 | L | CD2 | 61.6 | 5.8 | 28.6 | 41 | A |
| 250 | L | C | 61.7 | 4.1 | 32.6 | 36 | A |
| 250 | L | O | 61.0 | 3.1 | 32.5 | 36 | A |
| 251 | N | N | 62.5 | 4.3 | 33.7 | 36 | A |
| 251 | N | CA | 62.7 | 3.3 | 34.7 | 38 | A |
| 251 | N | CB | 63.9 | 3.7 | 35.5 | 39 | A |
| 251 | N | CG | 65.2 | 3.5 | 34.8 | 41 | A |
| 251 | N | OD1 | 66.2 | 3.9 | 35.2 | 42 | A |
| 251 | N | ND2 | 65.1 | 3.0 | 33.5 | 38 | A |
| 251 | N | C | 61.5 | 3.1 | 35.6 | 38 | A |
| 251 | N | O | 61.4 | 2.1 | 36.3 | 41 | A |
| 252 | C | N | 60.5 | 3.9 | 35.5 | 35 | A |
| 252 | C | CA | 59.3 | 3.8 | 36.3 | 35 | A |
| 252 | C | CB | 58.6 | 5.1 | 36.6 | 33 | A |
| 252 | C | SG | 59.4 | 6.2 | 37.7 | 31 | A |
| 252 | C | C | 58.3 | 2.8 | 35.7 | 35 | A |
| 252 | C | O | 57.4 | 2.3 | 36.3 | 33 | A |
| 253 | I | N | 58.6 | 2.5 | 34.4 | 35 | A |
| 253 | I | CA | 57.8 | 1.5 | 33.6 | 34 | A |
| 253 | I | CB | 58.0 | 1.7 | 32.1 | 33 | A |
| 253 | I | CG2 | 57.3 | 0.6 | 31.3 | 31 | A |
| 253 | I | CG1 | 57.6 | 3.1 | 31.6 | 30 | A |
| 253 | I | CD1 | 56.2 | 3.4 | 31.9 | 28 | A |
| 253 | I | C | 58.2 | 0.2 | 34.1 | 36 | A |
| 253 | I | O | 59.4 | −0.2 | 33.8 | 37 | A |
| 254 | I | N | 57.4 | −0.6 | 34.7 | 37 | A |
| 254 | I | CA | 57.7 | −1.9 | 35.2 | 39 | A |
| 254 | I | CB | 56.8 | −2.3 | 36.4 | 40 | A |
| 254 | I | CG2 | 57.2 | −3.7 | 36.9 | 37 | A |
| 254 | I | CG1 | 57.0 | −1.3 | 37.5 | 40 | A |
| 254 | I | CD1 | 56.0 | −1.4 | 38.6 | 43 | A |
| 254 | I | C | 57.6 | −3.0 | 34.1 | 41 | A |
| 254 | I | O | 58.4 | −3.8 | 34.0 | 42 | A |
| 255 | N | N | 56.5 | −2.9 | 33.4 | 40 | A |
| 255 | N | CA | 56.2 | −3.9 | 32.3 | 40 | A |
| 255 | N | CB | 54.9 | −3.5 | 31.5 | 41 | A |
| 255 | N | CG | 54.6 | −4.5 | 30.4 | 43 | A |
| 255 | N | OD1 | 54.0 | −5.5 | 30.6 | 43 | A |
| 255 | N | ND2 | 55.0 | −4.1 | 29.2 | 42 | A |
| 255 | N | C | 57.4 | −3.9 | 31.3 | 39 | A |
| 255 | N | O | 57.6 | −2.8 | 30.7 | 38 | A |
| 256 | L | N | 58.1 | −5.0 | 31.2 | 38 | A |
| 256 | L | CA | 59.3 | −5.0 | 30.4 | 38 | A |
| 256 | L | CB | 60.1 | −6.3 | 30.7 | 39 | A |
| 256 | L | CG | 61.2 | −6.1 | 31.7 | 39 | A |
| 256 | L | CD1 | 60.8 | −5.2 | 32.9 | 37 | A |
| 256 | L | CD2 | 61.7 | −7.5 | 32.1 | 39 | A |
| 256 | L | C | 59.0 | −4.9 | 28.9 | 38 | A |
| 256 | L | O | 59.9 | −4.5 | 28.1 | 38 | A |
| 257 | K | N | 57.8 | −5.4 | 28.4 | 36 | A |
| 257 | K | CA | 57.5 | −5.3 | 27.0 | 37 | A |
| 257 | K | CB | 56.3 | −6.0 | 26.7 | 39 | A |
| 257 | K | CG | 56.1 | −7.3 | 27.5 | 49 | A |
| 257 | K | CD | 57.3 | −8.3 | 27.4 | 52 | A |
| 257 | K | CE | 57.2 | −9.4 | 28.3 | 55 | A |
| 257 | K | NZ | 55.9 | −10.3 | 28.1 | 55 | A |
| 257 | K | C | 57.4 | −3.8 | 26.7 | 35 | A |
| 257 | K | O | 57.9 | −3.3 | 25.7 | 36 | A |
| 258 | A | N | 56.7 | −3.1 | 27.6 | 31 | A |
| 258 | A | CA | 56.5 | −1.7 | 27.4 | 29 | A |
| 258 | A | CB | 55.5 | −1.2 | 28.5 | 28 | A |
| 258 | A | C | 57.8 | −0.9 | 27.6 | 29 | A |
| 258 | A | O | 58.1 | −0.1 | 26.8 | 26 | A |
| 259 | R | N | 58.5 | −1.3 | 28.6 | 30 | A |
| 259 | R | CA | 59.8 | −0.6 | 28.8 | 31 | A |
| 259 | R | CB | 60.6 | −1.3 | 30.0 | 33 | A |
| 259 | R | CG | 61.6 | −0.3 | 30.7 | 40 | A |
| 259 | R | CD | 62.7 | −1.0 | 31.3 | 46 | A |
| 259 | R | NE | 63.0 | −0.5 | 32.7 | 51 | A |
| 259 | R | CZ | 62.3 | −0.9 | 33.7 | 53 | A |
| 259 | R | NH1 | 61.3 | −1.8 | 33.7 | 54 | A |
| 259 | R | NH2 | 62.6 | −0.3 | 34.9 | 54 | A |
| 259 | R | C | 60.7 | −0.8 | 27.6 | 29 | A |
| 259 | R | O | 61.1 | 0.2 | 27.0 | 30 | A |
| 260 | N | N | 60.9 | −2.0 | 27.1 | 28 | A |
| 260 | N | CA | 61.7 | −2.3 | 26.0 | 29 | A |
| 260 | N | CB | 61.9 | −3.8 | 25.8 | 30 | A |
| 260 | N | CG | 62.8 | −4.4 | 26.9 | 29 | A |
| 260 | N | OD1 | 63.9 | −3.9 | 27.3 | 30 | A |
| 260 | N | ND2 | 62.4 | −5.5 | 27.4 | 31 | A |
| 260 | N | C | 61.2 | −1.7 | 24.7 | 29 | A |
| 260 | N | O | 61.9 | −1.4 | 23.8 | 29 | A |
| 261 | Y | N | 59.8 | −1.5 | 24.6 | 28 | A |
| 261 | Y | CA | 59.3 | −0.8 | 23.4 | 29 | A |
| 261 | Y | CB | 57.7 | −0.9 | 23.5 | 26 | A |
| 261 | Y | CG | 57.1 | −0.1 | 22.4 | 26 | A |
| 261 | Y | CD1 | 57.2 | −0.5 | 21.0 | 26 | A |
| 261 | Y | CE1 | 56.6 | 0.2 | 20.0 | 27 | A |
| 261 | Y | CD2 | 56.5 | 1.1 | 22.6 | 27 | A |
| 261 | Y | CE2 | 55.9 | 1.9 | 21.6 | 23 | A |
| 261 | Y | CZ | 55.9 | 1.4 | 20.3 | 25 | A |
| 261 | Y | OH | 55.4 | 2.2 | 19.3 | 23 | A |
| 261 | Y | C | 59.7 | 0.6 | 23.4 | 30 | A |
| 261 | Y | O | 60.1 | 1.2 | 22.4 | 32 | A |
| 262 | L | N | 59.7 | 1.3 | 24.6 | 30 | A |
| 262 | L | CA | 60.1 | 2.7 | 24.7 | 29 | A |
| 262 | L | CB | 59.9 | 3.2 | 26.1 | 26 | A |
| 262 | L | CG | 58.5 | 3.7 | 26.5 | 30 | A |
| 262 | L | CD1 | 58.5 | 4.2 | 27.9 | 29 | A |
| 262 | L | CD2 | 58.0 | 4.7 | 25.5 | 31 | A |
| 262 | L | C | 61.6 | 2.9 | 24.3 | 31 | A |
| 262 | L | O | 62.0 | 3.8 | 23.7 | 29 | A |
| 263 | L | N | 62.4 | 1.9 | 24.7 | 34 | A |
| 263 | L | CA | 63.8 | 1.9 | 24.4 | 36 | A |
| 263 | L | CB | 64.6 | 0.9 | 25.2 | 35 | A |
| 263 | L | CG | 65.0 | 1.1 | 26.7 | 39 | A |
| 263 | L | CD1 | 65.7 | 2.4 | 26.8 | 37 | A |
| 263 | L | CD2 | 63.7 | 1.2 | 27.6 | 39 | A |
| 263 | L | C | 64.1 | 1.7 | 22.9 | 36 | A |
| 263 | L | O | 65.2 | 2.1 | 22.4 | 37 | A |
| 264 | S | N | 63.1 | 1.1 | 22.3 | 33 | A |
| 264 | S | CA | 63.3 | 0.9 | 20.8 | 33 | A |
| 264 | S | CB | 62.3 | −0.3 | 20.4 | 32 | A |
| 264 | S | OG | 61.1 | 0.2 | 20.0 | 32 | A |
| 264 | S | C | 63.0 | 2.1 | 20.0 | 33 | A |
| 264 | S | O | 63.6 | 2.3 | 18.9 | 32 | A |
| 265 | L | N | 62.1 | 2.9 | 20.5 | 35 | A |
| 265 | L | CA | 61.7 | 4.2 | 19.8 | 35 | A |
| 265 | L | CB | 60.6 | 4.9 | 20.5 | 35 | A |
| 265 | L | CG | 59.1 | 4.4 | 20.2 | 38 | A |
| 265 | L | CD1 | 59.0 | 2.9 | 20.0 | 36 | A |
| 265 | L | CD2 | 58.2 | 4.8 | 21.4 | 34 | A |
| 265 | L | C | 62.9 | 5.1 | 19.5 | 35 | A |
| 265 | L | O | 63.7 | 5.4 | 20.4 | 34 | A |
| 266 | P | N | 62.9 | 5.5 | 18.3 | 36 | A |
| 266 | P | CD | 62.1 | 5.5 | 17.2 | 36 | A |
| 266 | P | CA | 64.0 | 6.7 | 18.0 | 36 | A |
| 266 | P | CB | 63.8 | 6.9 | 16.5 | 37 | A |
| 266 | P | CG | 62.4 | 6.7 | 16.3 | 38 | A |
| 266 | P | C | 63.7 | 7.9 | 18.8 | 36 | A |
| 266 | P | O | 62.6 | 8.4 | 18.9 | 36 | A |
| 267 | H | N | 64.8 | 8.5 | 19.4 | 34 | A |
| 267 | H | CA | 64.7 | 9.7 | 20.2 | 34 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | | | | | | | | | |
|---|---|---|---|---|---|---|---|---|---|---|---|---|---|---|---|
| 267 | H | CB | 66.2 | 10.1 | 20.6 | 33 | A | 275 | R | N | 55.7 | 27.5 | 22.0 | 37 | A |
| 267 | H | CG | 66.3 | 11.2 | 21.5 | 34 | A | 275 | R | CA | 56.0 | 27.4 | 20.6 | 37 | A |
| 267 | H | CD2 | 66.4 | 11.2 | 22.9 | 32 | A | 275 | R | CB | 57.1 | 26.5 | 20.2 | 42 | A |
| 267 | H | ND1 | 66.2 | 12.6 | 21.2 | 33 | A | 275 | R | CG | 57.3 | 26.3 | 18.7 | 45 | A |
| 267 | H | CE1 | 66.3 | 13.3 | 22.3 | 32 | A | 275 | R | CD | 58.5 | 25.5 | 18.4 | 47 | A |
| 267 | H | NE2 | 66.4 | 12.5 | 23.3 | 33 | A | 275 | R | NE | 59.7 | 26.3 | 18.2 | 52 | A |
| 267 | H | C | 64.0 | 10.9 | 19.6 | 33 | A | 275 | R | CZ | 60.9 | 25.8 | 17.7 | 55 | A |
| 267 | H | O | 64.1 | 11.1 | 18.4 | 33 | A | 275 | R | NH1 | 61.0 | 24.5 | 17.4 | 57 | A |
| 268 | K | N | 63.3 | 11.6 | 20.4 | 34 | A | 275 | R | NH2 | 61.9 | 26.7 | 17.5 | 54 | A |
| 268 | K | CA | 62.5 | 12.8 | 20.0 | 34 | A | 275 | R | C | 54.7 | 26.9 | 19.9 | 36 | A |
| 268 | K | CB | 61.0 | 12.5 | 19.9 | 33 | A | 275 | R | O | 54.4 | 27.4 | 18.8 | 35 | A |
| 268 | K | CG | 60.5 | 11.6 | 18.8 | 34 | A | 276 | L | N | 54.0 | 26.0 | 20.5 | 34 | A |
| 268 | K | CD | 59.1 | 11.9 | 18.5 | 36 | A | 276 | L | CA | 52.7 | 25.4 | 20.0 | 31 | A |
| 268 | K | CE | 58.5 | 11.0 | 17.5 | 36 | A | 276 | L | CB | 52.4 | 24.1 | 20.6 | 32 | A |
| 268 | K | NZ | 57.9 | 9.8 | 18.1 | 40 | A | 276 | L | CG | 53.4 | 22.9 | 20.5 | 33 | A |
| 268 | K | C | 62.8 | 13.9 | 21.0 | 34 | A | 276 | L | CD1 | 53.1 | 21.9 | 21.6 | 33 | A |
| 268 | K | O | 62.9 | 13.6 | 22.2 | 34 | A | 276 | L | CD2 | 53.3 | 22.3 | 19.2 | 32 | A |
| 269 | N | N | 62.8 | 15.2 | 20.6 | 36 | A | 276 | L | C | 51.6 | 26.4 | 20.2 | 31 | A |
| 269 | N | CA | 63.1 | 16.3 | 21.5 | 35 | A | 276 | L | O | 50.6 | 26.5 | 19.4 | 32 | A |
| 269 | N | CB | 64.1 | 17.3 | 20.9 | 39 | A | 277 | F | N | 51.7 | 27.1 | 21.3 | 29 | A |
| 269 | N | CG | 65.1 | 17.7 | 22.0 | 46 | A | 277 | F | CA | 50.6 | 28.1 | 21.7 | 30 | A |
| 269 | N | OD1 | 64.8 | 18.2 | 23.1 | 45 | A | 277 | F | CB | 49.9 | 27.6 | 22.9 | 28 | A |
| 269 | N | ND2 | 66.4 | 17.5 | 21.6 | 47 | A | 277 | F | CG | 49.5 | 26.1 | 22.8 | 26 | A |
| 269 | N | C | 61.7 | 17.0 | 21.9 | 32 | A | 277 | F | CD1 | 48.4 | 25.8 | 22.0 | 26 | A |
| 269 | N | O | 60.8 | 16.9 | 21.1 | 30 | A | 277 | F | CD2 | 50.1 | 25.1 | 23.6 | 23 | A |
| 270 | K | N | 61.7 | 17.6 | 23.0 | 32 | A | 277 | F | CE1 | 48.1 | 24.4 | 21.9 | 25 | A |
| 270 | K | CA | 60.5 | 18.3 | 23.5 | 32 | A | 277 | F | CE2 | 49.7 | 23.8 | 23.5 | 23 | A |
| 270 | K | CB | 60.7 | 18.5 | 25.0 | 34 | A | 277 | F | CZ | 48.7 | 23.4 | 22.6 | 24 | A |
| 270 | K | CG | 59.4 | 19.3 | 25.7 | 37 | A | 277 | F | C | 51.2 | 29.4 | 22.0 | 31 | A |
| 270 | K | CD | 59.7 | 19.7 | 27.1 | 35 | A | 277 | F | O | 51.4 | 29.8 | 23.2 | 30 | A |
| 270 | K | CE | 58.5 | 20.4 | 27.7 | 37 | A | 278 | P | N | 51.6 | 30.2 | 21.0 | 33 | A |
| 270 | K | NZ | 57.3 | 19.5 | 27.7 | 39 | A | 278 | P | CD | 51.6 | 29.9 | 19.5 | 33 | A |
| 270 | K | C | 60.2 | 19.6 | 22.8 | 33 | A | 278 | P | CA | 52.2 | 31.5 | 21.2 | 35 | A |
| 270 | K | O | 61.0 | 20.5 | 22.8 | 33 | A | 278 | P | CB | 52.7 | 31.9 | 19.8 | 35 | A |
| 271 | V | N | 59.0 | 19.7 | 22.2 | 32 | A | 278 | P | CG | 52.8 | 30.6 | 19.0 | 34 | A |
| 271 | V | CA | 58.6 | 20.9 | 21.6 | 33 | A | 278 | P | C | 51.2 | 32.5 | 21.7 | 36 | A |
| 271 | V | CB | 57.5 | 20.6 | 20.5 | 33 | A | 278 | P | O | 51.6 | 33.5 | 22.2 | 36 | A |
| 271 | V | CG1 | 57.0 | 21.9 | 19.8 | 32 | A | 279 | N | N | 50.0 | 32.1 | 21.6 | 39 | A |
| 271 | V | CG2 | 58.1 | 19.6 | 19.5 | 34 | A | 279 | N | CA | 48.8 | 32.9 | 22.0 | 39 | A |
| 271 | V | C | 58.0 | 21.8 | 22.7 | 32 | A | 279 | N | CB | 47.6 | 32.5 | 21.2 | 39 | A |
| 271 | V | O | 57.1 | 21.5 | 23.3 | 34 | A | 279 | N | CG | 47.3 | 31.0 | 21.3 | 40 | A |
| 272 | P | N | 58.7 | 23.0 | 22.9 | 31 | A | 279 | N | OD1 | 48.1 | 30.1 | 20.9 | 29 | A |
| 272 | P | CD | 59.8 | 23.6 | 22.1 | 31 | A | 279 | N | ND2 | 46.2 | 30.6 | 22.0 | 37 | A |
| 272 | P | CA | 58.2 | 23.9 | 23.9 | 31 | A | 279 | N | C | 48.5 | 32.8 | 23.5 | 39 | A |
| 272 | P | CB | 59.1 | 25.1 | 23.8 | 29 | A | 279 | N | O | 48.1 | 33.7 | 24.2 | 39 | A |
| 272 | P | CG | 59.6 | 25.0 | 22.4 | 32 | A | 280 | A | N | 48.5 | 31.5 | 24.0 | 37 | A |
| 272 | P | C | 56.7 | 24.3 | 23.8 | 29 | A | 280 | A | CA | 48.2 | 31.1 | 25.3 | 32 | A |
| 272 | P | O | 56.2 | 24.5 | 22.7 | 29 | A | 280 | A | CB | 48.5 | 29.7 | 25.5 | 29 | A |
| 273 | W | N | 56.1 | 24.5 | 24.9 | 29 | A | 280 | A | C | 48.7 | 32.0 | 26.5 | 32 | A |
| 273 | W | CA | 54.7 | 24.9 | 24.9 | 29 | A | 280 | A | O | 49.9 | 32.4 | 26.4 | 33 | A |
| 273 | W | CB | 54.1 | 24.8 | 26.4 | 25 | A | 281 | D | N | 47.9 | 32.1 | 27.5 | 32 | A |
| 273 | W | CG | 54.2 | 23.5 | 27.1 | 24 | A | 281 | D | CA | 48.3 | 32.8 | 28.7 | 31 | A |
| 273 | W | CD2 | 53.5 | 22.3 | 26.6 | 18 | A | 281 | D | CB | 47.0 | 32.8 | 29.6 | 34 | A |
| 273 | W | CE2 | 53.8 | 21.3 | 27.5 | 18 | A | 281 | D | CG | 47.3 | 33.5 | 31.0 | 36 | A |
| 273 | W | CE3 | 52.5 | 22.0 | 25.6 | 17 | A | 281 | D | OD1 | 48.1 | 32.9 | 31.8 | 35 | A |
| 273 | W | CD1 | 54.9 | 23.1 | 28.1 | 20 | A | 281 | D | OD2 | 46.8 | 34.6 | 31.2 | 41 | A |
| 273 | W | NE1 | 54.7 | 21.8 | 28.4 | 19 | A | 281 | D | C | 49.4 | 32.0 | 29.4 | 31 | A |
| 273 | W | CZ2 | 53.3 | 20.0 | 27.4 | 18 | A | 281 | D | O | 49.4 | 30.8 | 29.4 | 29 | A |
| 273 | W | CZ3 | 52.0 | 20.7 | 25.5 | 17 | A | 282 | S | N | 50.4 | 32.7 | 29.9 | 29 | A |
| 273 | W | CH2 | 52.4 | 19.7 | 26.4 | 17 | A | 282 | S | CA | 51.6 | 32.0 | 30.5 | 30 | A |
| 273 | W | C | 54.5 | 26.2 | 24.3 | 30 | A | 282 | S | CB | 52.5 | 33.1 | 31.1 | 31 | A |
| 273 | W | O | 53.6 | 26.4 | 23.5 | 32 | A | 282 | S | OG | 53.0 | 34.0 | 30.1 | 40 | A |
| 274 | N | N | 55.3 | 27.2 | 24.7 | 31 | A | 282 | S | C | 51.2 | 31.0 | 31.6 | 28 | A |
| 274 | N | CA | 55.2 | 28.5 | 24.1 | 35 | A | 282 | S | O | 51.7 | 29.9 | 31.6 | 27 | A |
| 274 | N | CB | 56.0 | 29.6 | 24.9 | 36 | A | 283 | K | N | 50.3 | 31.4 | 32.5 | 26 | A |
| 274 | N | CG | 57.5 | 29.4 | 24.8 | 40 | A | 283 | K | CA | 49.9 | 30.5 | 33.6 | 25 | A |
| 274 | N | OD1 | 58.0 | 28.9 | 23.8 | 41 | A | 283 | K | CB | 49.0 | 31.3 | 34.5 | 26 | A |
| 274 | N | ND2 | 58.2 | 29.9 | 25.8 | 40 | A | 283 | K | CG | 49.7 | 32.5 | 35.2 | 31 | A |
| 274 | N | C | 55.5 | 28.6 | 22.6 | 36 | A | 283 | K | CD | 48.7 | 33.4 | 36.0 | 33 | A |
| 274 | N | O | 55.5 | 29.7 | 22.1 | 36 | A | 283 | K | CE | 49.5 | 34.4 | 36.7 | 36 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 283 | K | NZ | 48.5 | 35.3 | 37.5 | 38 | A |
| 283 | K | C | 49.1 | 29.3 | 33.0 | 24 | A |
| 283 | K | O | 49.2 | 28.2 | 33.6 | 21 | A |
| 284 | A | N | 48.4 | 29.5 | 32.0 | 21 | A |
| 284 | A | CA | 47.6 | 28.4 | 31.4 | 23 | A |
| 284 | A | CB | 46.7 | 29.0 | 30.3 | 21 | A |
| 284 | A | C | 48.6 | 27.4 | 30.8 | 24 | A |
| 284 | A | O | 48.3 | 26.2 | 30.8 | 25 | A |
| 285 | L | N | 49.7 | 27.8 | 30.3 | 23 | A |
| 285 | L | CA | 50.7 | 26.9 | 29.7 | 23 | A |
| 285 | L | CB | 51.6 | 27.6 | 28.7 | 20 | A |
| 285 | L | CG | 51.1 | 28.0 | 27.4 | 25 | A |
| 285 | L | CD1 | 52.2 | 28.5 | 26.4 | 26 | A |
| 285 | L | CD2 | 50.3 | 26.9 | 26.8 | 23 | A |
| 285 | L | C | 51.4 | 26.3 | 30.8 | 20 | A |
| 285 | L | O | 51.9 | 25.1 | 30.7 | 22 | A |
| 286 | D | N | 51.6 | 27.0 | 31.9 | 19 | A |
| 286 | D | CA | 52.3 | 26.4 | 33.1 | 20 | A |
| 286 | D | CB | 52.6 | 27.4 | 34.1 | 19 | A |
| 286 | D | CG | 53.6 | 26.9 | 35.2 | 25 | A |
| 286 | D | OD1 | 54.7 | 26.6 | 34.8 | 29 | A |
| 286 | D | OD2 | 53.2 | 26.7 | 36.4 | 27 | A |
| 286 | D | C | 51.5 | 25.2 | 33.6 | 21 | A |
| 286 | D | O | 52.0 | 24.1 | 33.9 | 23 | A |
| 287 | L | N | 50.2 | 25.5 | 33.8 | 19 | A |
| 287 | L | CA | 49.3 | 24.5 | 34.3 | 20 | A |
| 287 | L | CB | 47.9 | 25.1 | 34.6 | 20 | A |
| 287 | L | CG | 46.8 | 24.1 | 35.1 | 21 | A |
| 287 | L | CD1 | 47.3 | 23.3 | 36.2 | 19 | A |
| 287 | L | CD2 | 45.6 | 24.9 | 35.4 | 19 | A |
| 287 | L | C | 49.2 | 23.3 | 33.3 | 20 | A |
| 287 | L | O | 49.2 | 22.1 | 33.7 | 23 | A |
| 288 | L | N | 49.1 | 23.7 | 32.0 | 20 | A |
| 288 | L | CA | 49.0 | 22.6 | 30.9 | 20 | A |
| 288 | L | CB | 49.0 | 23.3 | 29.6 | 19 | A |
| 288 | L | CG | 49.0 | 22.3 | 28.4 | 17 | A |
| 288 | L | CD1 | 47.7 | 21.6 | 28.2 | 17 | A |
| 288 | L | CD2 | 49.3 | 23.1 | 27.1 | 16 | A |
| 288 | L | C | 50.2 | 21.7 | 31.0 | 22 | A |
| 288 | L | O | 50.0 | 20.5 | 30.9 | 24 | A |
| 289 | D | N | 51.4 | 22.2 | 31.2 | 21 | A |
| 289 | D | CA | 52.6 | 21.4 | 31.3 | 20 | A |
| 289 | D | CB | 53.8 | 22.3 | 31.6 | 20 | A |
| 289 | D | CG | 55.1 | 21.5 | 31.8 | 20 | A |
| 289 | D | OD1 | 55.5 | 20.7 | 31.0 | 22 | A |
| 289 | D | OD2 | 55.7 | 21.7 | 32.9 | 26 | A |
| 289 | D | C | 52.5 | 20.4 | 32.5 | 21 | A |
| 289 | D | O | 52.9 | 19.2 | 32.3 | 21 | A |
| 290 | K | N | 52.0 | 20.8 | 33.6 | 23 | A |
| 290 | K | CA | 51.8 | 20.0 | 34.8 | 23 | A |
| 290 | K | CB | 51.5 | 20.8 | 36.0 | 25 | A |
| 290 | K | CG | 52.7 | 21.7 | 36.5 | 27 | A |
| 290 | K | CD | 52.4 | 22.6 | 37.6 | 28 | A |
| 290 | K | CE | 53.6 | 23.5 | 38.0 | 29 | A |
| 290 | K | NZ | 54.2 | 24.2 | 36.9 | 32 | A |
| 290 | K | C | 50.8 | 18.9 | 34.6 | 22 | A |
| 290 | K | O | 50.9 | 17.8 | 35.2 | 23 | A |
| 291 | M | N | 49.7 | 19.2 | 33.8 | 21 | A |
| 291 | M | CA | 48.7 | 18.2 | 33.6 | 20 | A |
| 291 | M | CB | 47.4 | 18.9 | 33.1 | 20 | A |
| 291 | M | CG | 46.9 | 20.0 | 34.0 | 24 | A |
| 291 | M | SD | 45.3 | 20.5 | 33.5 | 26 | A |
| 291 | M | CE | 44.4 | 19.8 | 34.8 | 27 | A |
| 291 | M | C | 49.1 | 17.2 | 32.5 | 19 | A |
| 291 | M | O | 48.8 | 16.0 | 32.6 | 17 | A |
| 292 | L | N | 49.9 | 17.6 | 31.6 | 17 | A |
| 292 | L | CA | 50.4 | 16.7 | 30.5 | 17 | A |
| 292 | L | CB | 50.4 | 17.4 | 29.2 | 12 | A |
| 292 | L | CG | 49.0 | 17.7 | 28.6 | 14 | A |
| 292 | L | CD1 | 49.0 | 18.3 | 27.2 | 11 | A |
| 292 | L | CD2 | 48.1 | 16.5 | 28.6 | 12 | A |
| 292 | L | C | 51.8 | 16.2 | 30.8 | 16 | A |
| 292 | L | O | 52.7 | 16.2 | 30.0 | 20 | A |
| 293 | T | N | 52.1 | 15.8 | 32.1 | 16 | A |
| 293 | T | CA | 53.4 | 15.3 | 32.5 | 19 | A |
| 293 | T | CB | 53.6 | 15.6 | 34.0 | 19 | A |
| 293 | T | OG1 | 53.8 | 17.0 | 34.2 | 19 | A |
| 293 | T | CG2 | 54.9 | 14.8 | 34.5 | 15 | A |
| 293 | T | C | 53.4 | 13.8 | 32.2 | 21 | A |
| 293 | T | O | 52.4 | 13.1 | 32.6 | 20 | A |
| 294 | F | N | 54.4 | 13.3 | 31.6 | 19 | A |
| 294 | F | CA | 54.5 | 11.8 | 31.3 | 20 | A |
| 294 | F | CB | 55.9 | 11.6 | 30.7 | 19 | A |
| 294 | F | CG | 56.0 | 10.2 | 30.0 | 20 | A |
| 294 | F | CD1 | 55.5 | 10.1 | 28.7 | 21 | A |
| 294 | F | CD2 | 56.5 | 9.1 | 30.6 | 18 | A |
| 294 | F | CE1 | 55.6 | 8.8 | 28.0 | 22 | A |
| 294 | F | CE2 | 56.6 | 7.9 | 30.0 | 21 | A |
| 294 | F | CZ | 56.1 | 7.7 | 28.7 | 19 | A |
| 294 | F | C | 54.3 | 10.9 | 32.5 | 23 | A |
| 294 | F | O | 53.4 | 10.1 | 32.5 | 24 | A |
| 295 | N | N | 55.2 | 11.1 | 33.5 | 23 | A |
| 295 | N | CA | 55.2 | 10.3 | 34.7 | 23 | A |
| 295 | N | CB | 56.5 | 10.5 | 35.5 | 24 | A |
| 295 | N | CG | 56.7 | 9.5 | 36.6 | 26 | A |
| 295 | N | OD1 | 55.7 | 9.2 | 37.3 | 26 | A |
| 295 | N | ND2 | 57.9 | 9.1 | 36.9 | 24 | A |
| 295 | N | C | 54.0 | 10.6 | 35.5 | 25 | A |
| 295 | N | O | 53.9 | 11.7 | 36.1 | 25 | A |
| 296 | P | N | 53.0 | 9.7 | 35.6 | 25 | A |
| 296 | P | CD | 53.0 | 8.4 | 35.0 | 23 | A |
| 296 | P | CA | 51.8 | 10.0 | 36.3 | 24 | A |
| 296 | P | CB | 51.0 | 8.7 | 36.2 | 23 | A |
| 296 | P | CG | 52.0 | 7.7 | 35.9 | 25 | A |
| 296 | P | C | 52.0 | 10.3 | 37.8 | 27 | A |
| 296 | P | O | 51.2 | 11.0 | 38.5 | 28 | A |
| 297 | H | N | 53.2 | 9.9 | 38.3 | 30 | A |
| 297 | H | CA | 53.5 | 10.1 | 39.7 | 34 | A |
| 297 | H | CB | 54.7 | 9.2 | 40.1 | 39 | A |
| 297 | H | CG | 54.4 | 7.8 | 40.0 | 45 | A |
| 297 | H | CD2 | 53.3 | 7.1 | 40.2 | 46 | A |
| 297 | H | ND1 | 55.4 | 6.8 | 39.8 | 47 | A |
| 297 | H | CE1 | 54.8 | 5.6 | 39.7 | 50 | A |
| 297 | H | NE2 | 53.6 | 5.8 | 40.0 | 48 | A |
| 297 | H | C | 53.9 | 11.6 | 39.9 | 32 | A |
| 297 | H | O | 53.7 | 12.2 | 41.0 | 32 | A |
| 298 | K | N | 54.5 | 12.2 | 38.9 | 32 | A |
| 298 | K | CA | 54.9 | 13.6 | 38.9 | 30 | A |
| 298 | K | CB | 56.1 | 13.8 | 38.0 | 32 | A |
| 298 | K | CG | 57.4 | 13.1 | 38.5 | 38 | A |
| 298 | K | CD | 57.9 | 13.8 | 39.8 | 45 | A |
| 298 | K | CE | 59.1 | 13.1 | 40.3 | 48 | A |
| 298 | K | NZ | 59.5 | 13.7 | 41.6 | 51 | A |
| 298 | K | C | 53.7 | 14.5 | 38.4 | 28 | A |
| 298 | K | O | 53.8 | 15.7 | 38.5 | 29 | A |
| 299 | R | N | 52.7 | 13.8 | 37.9 | 25 | A |
| 299 | R | CA | 51.6 | 14.6 | 37.3 | 23 | A |
| 299 | R | CB | 50.7 | 13.7 | 36.5 | 21 | A |
| 299 | R | CG | 49.7 | 14.5 | 35.6 | 23 | A |
| 299 | R | CD | 49.5 | 13.8 | 34.3 | 20 | A |
| 299 | R | NE | 48.8 | 12.6 | 34.3 | 20 | A |
| 299 | R | CZ | 49.2 | 11.5 | 33.8 | 21 | A |
| 299 | R | NH1 | 50.4 | 11.3 | 33.3 | 16 | A |
| 299 | R | NH2 | 48.4 | 10.4 | 33.9 | 22 | A |
| 299 | R | C | 50.8 | 15.3 | 38.5 | 21 | A |
| 299 | R | O | 50.5 | 14.6 | 39.5 | 19 | A |
| 300 | I | N | 50.4 | 16.5 | 38.2 | 20 | A |
| 300 | I | CA | 49.7 | 17.3 | 39.2 | 18 | A |
| 300 | I | CB | 49.5 | 18.8 | 38.7 | 19 | A |
| 300 | I | CG2 | 48.4 | 18.8 | 37.6 | 20 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| Residue | AA | Atom | x | y | z | B | Chain |
|---|---|---|---|---|---|---|---|
| 300 | I | CG1 | 49.2 | 19.7 | 39.8 | 22 | A |
| 300 | I | CD1 | 49.0 | 21.2 | 39.4 | 22 | A |
| 300 | I | C | 48.3 | 16.7 | 39.5 | 16 | A |
| 300 | I | O | 47.6 | 16.2 | 38.5 | 18 | A |
| 301 | E | N | 47.9 | 16.7 | 40.7 | 15 | A |
| 301 | E | CA | 46.6 | 16.2 | 41.1 | 15 | A |
| 301 | E | CB | 46.7 | 15.5 | 42.5 | 18 | A |
| 301 | E | CG | 47.7 | 14.4 | 42.5 | 23 | A |
| 301 | E | CD | 47.8 | 13.8 | 43.9 | 30 | A |
| 301 | E | OE1 | 48.2 | 14.5 | 44.9 | 28 | A |
| 301 | E | OE2 | 47.6 | 12.5 | 44.0 | 32 | A |
| 301 | E | C | 45.5 | 17.3 | 41.0 | 15 | A |
| 301 | E | O | 45.8 | 18.4 | 40.9 | 12 | A |
| 302 | V | N | 44.2 | 16.9 | 41.2 | 14 | A |
| 302 | V | CA | 43.1 | 17.8 | 41.1 | 13 | A |
| 302 | V | CB | 41.8 | 17.1 | 41.0 | 13 | A |
| 302 | V | CG1 | 41.4 | 16.5 | 42.4 | 11 | A |
| 302 | V | CG2 | 40.7 | 18.0 | 40.5 | 12 | A |
| 302 | V | C | 43.1 | 19.0 | 42.0 | 14 | A |
| 302 | V | O | 42.7 | 20.1 | 41.6 | 15 | A |
| 303 | E | N | 43.4 | 18.8 | 43.3 | 16 | A |
| 303 | E | CA | 43.4 | 19.9 | 44.3 | 18 | A |
| 303 | E | CB | 43.7 | 19.4 | 45.7 | 22 | A |
| 303 | E | CG | 43.3 | 18.0 | 46.0 | 34 | A |
| 303 | E | CD | 44.2 | 16.9 | 45.4 | 35 | A |
| 303 | E | OE1 | 45.4 | 16.9 | 45.7 | 36 | A |
| 303 | E | OE2 | 43.6 | 16.0 | 44.7 | 34 | A |
| 303 | E | C | 44.4 | 21.0 | 43.9 | 20 | A |
| 303 | E | O | 44.2 | 22.2 | 43.9 | 21 | A |
| 304 | Q | N | 45.6 | 20.5 | 43.6 | 19 | A |
| 304 | Q | CA | 46.8 | 21.3 | 43.2 | 19 | A |
| 304 | Q | CB | 48.0 | 20.4 | 43.1 | 21 | A |
| 304 | Q | CG | 48.3 | 19.7 | 44.4 | 26 | A |
| 304 | Q | CD | 49.1 | 18.4 | 44.3 | 37 | A |
| 304 | Q | OE1 | 49.2 | 17.7 | 45.3 | 41 | A |
| 304 | Q | NE2 | 49.5 | 18.1 | 43.1 | 34 | A |
| 304 | Q | C | 46.5 | 22.0 | 41.9 | 19 | A |
| 304 | Q | O | 47.0 | 23.2 | 41.7 | 19 | A |
| 305 | A | N | 45.8 | 21.4 | 40.9 | 17 | A |
| 305 | A | CA | 45.6 | 22.0 | 39.6 | 18 | A |
| 305 | A | CB | 45.0 | 21.0 | 38.6 | 12 | A |
| 305 | A | C | 44.6 | 23.1 | 39.9 | 18 | A |
| 305 | A | O | 44.7 | 24.2 | 39.4 | 21 | A |
| 306 | L | N | 43.6 | 22.9 | 40.7 | 17 | A |
| 306 | L | CA | 42.6 | 23.9 | 41.0 | 18 | A |
| 306 | L | CB | 41.5 | 23.4 | 42.0 | 18 | A |
| 306 | L | CG | 40.3 | 22.7 | 41.3 | 18 | A |
| 306 | L | CD1 | 39.5 | 21.8 | 42.2 | 18 | A |
| 306 | L | CD2 | 39.3 | 23.7 | 40.7 | 15 | A |
| 306 | L | C | 43.3 | 25.0 | 41.7 | 15 | A |
| 306 | L | O | 43.0 | 26.2 | 41.5 | 14 | A |
| 307 | A | N | 44.3 | 24.7 | 42.5 | 16 | A |
| 307 | A | CA | 45.1 | 25.7 | 43.3 | 17 | A |
| 307 | A | CB | 45.8 | 25.0 | 44.5 | 9 | A |
| 307 | A | C | 46.2 | 26.4 | 42.5 | 17 | A |
| 307 | A | O | 46.9 | 27.3 | 43.0 | 18 | A |
| 308 | H | N | 46.3 | 26.1 | 41.2 | 19 | A |
| 308 | H | CA | 47.2 | 26.8 | 40.3 | 21 | A |
| 308 | H | CB | 47.3 | 26.0 | 39.0 | 20 | A |
| 308 | H | CG | 48.4 | 26.4 | 38.1 | 23 | A |
| 308 | H | CD2 | 49.7 | 26.0 | 38.0 | 21 | A |
| 308 | H | ND1 | 48.3 | 27.5 | 37.3 | 25 | A |
| 308 | H | CE1 | 49.5 | 27.7 | 36.6 | 23 | A |
| 308 | H | NE2 | 50.3 | 26.8 | 37.1 | 24 | A |
| 308 | H | C | 46.9 | 28.2 | 40.1 | 22 | A |
| 308 | H | O | 45.8 | 28.6 | 40.0 | 22 | A |
| 309 | P | N | 48.0 | 29.1 | 39.9 | 24 | A |
| 309 | P | CD | 49.4 | 28.8 | 40.1 | 23 | A |
| 309 | P | CA | 47.8 | 30.5 | 39.7 | 25 | A |
| 309 | P | CB | 49.2 | 31.0 | 39.4 | 23 | A |
| 309 | P | CG | 50.0 | 30.1 | 40.3 | 23 | A |
| 309 | P | C | 46.8 | 30.8 | 38.6 | 24 | A |
| 309 | P | O | 46.2 | 31.9 | 38.6 | 24 | A |
| 310 | Y | N | 46.7 | 29.9 | 37.6 | 24 | A |
| 310 | Y | CA | 45.8 | 30.2 | 36.5 | 25 | A |
| 310 | Y | CB | 46.1 | 29.2 | 35.4 | 22 | A |
| 310 | Y | CG | 45.2 | 29.4 | 34.1 | 22 | A |
| 310 | Y | CD1 | 45.2 | 30.6 | 33.5 | 20 | A |
| 310 | Y | CE1 | 44.4 | 30.8 | 32.4 | 20 | A |
| 310 | Y | CD2 | 44.4 | 28.4 | 33.7 | 21 | A |
| 310 | Y | CE2 | 43.5 | 28.6 | 32.5 | 25 | A |
| 310 | Y | CZ | 43.6 | 29.8 | 31.9 | 25 | A |
| 310 | Y | OH | 42.8 | 30.1 | 30.8 | 25 | A |
| 310 | Y | C | 44.3 | 30.2 | 36.8 | 23 | A |
| 310 | Y | O | 43.5 | 30.8 | 36.1 | 25 | A |
| 311 | L | N | 44.0 | 29.6 | 38.0 | 22 | A |
| 311 | L | CA | 42.5 | 29.5 | 38.4 | 21 | A |
| 311 | L | CB | 42.1 | 28.1 | 38.6 | 18 | A |
| 311 | L | CG | 42.2 | 27.2 | 37.4 | 19 | A |
| 311 | L | CD1 | 42.1 | 25.7 | 37.8 | 16 | A |
| 311 | L | CD2 | 41.2 | 27.6 | 36.3 | 20 | A |
| 311 | L | C | 42.3 | 30.3 | 39.7 | 21 | A |
| 311 | L | O | 41.3 | 30.1 | 40.3 | 17 | A |
| 312 | E | N | 43.2 | 31.2 | 40.0 | 23 | A |
| 312 | E | CA | 43.1 | 32.0 | 41.2 | 27 | A |
| 312 | E | CB | 44.3 | 32.9 | 41.4 | 31 | A |
| 312 | E | CG | 44.4 | 34.0 | 40.4 | 41 | A |
| 312 | E | CD | 45.8 | 34.7 | 40.4 | 46 | A |
| 312 | E | OE1 | 46.3 | 35.1 | 41.5 | 49 | A |
| 312 | E | OE2 | 46.4 | 34.8 | 39.3 | 46 | A |
| 312 | E | C | 41.8 | 32.8 | 41.4 | 25 | A |
| 312 | E | O | 41.4 | 33.1 | 42.5 | 26 | A |
| 313 | Q | N | 41.2 | 33.3 | 40.3 | 26 | A |
| 313 | Q | CA | 40.0 | 34.1 | 40.4 | 28 | A |
| 313 | Q | CB | 39.8 | 34.9 | 39.2 | 29 | A |
| 313 | Q | CG | 39.3 | 34.1 | 38.0 | 36 | A |
| 313 | Q | CD | 39.2 | 35.0 | 36.7 | 43 | A |
| 313 | Q | OE1 | 38.3 | 35.8 | 36.6 | 43 | A |
| 313 | Q | NE2 | 40.1 | 34.7 | 35.7 | 39 | A |
| 313 | Q | C | 38.8 | 33.2 | 40.8 | 26 | A |
| 313 | Q | O | 37.8 | 33.8 | 41.1 | 25 | A |
| 314 | Y | N | 38.9 | 31.9 | 40.6 | 25 | A |
| 314 | Y | CA | 37.8 | 31.0 | 40.9 | 24 | A |
| 314 | Y | CB | 37.5 | 30.1 | 39.7 | 24 | A |
| 314 | Y | CG | 37.0 | 30.9 | 38.5 | 23 | A |
| 314 | Y | CD1 | 35.7 | 31.6 | 38.6 | 22 | A |
| 314 | Y | CE1 | 35.2 | 32.3 | 37.6 | 21 | A |
| 314 | Y | CD2 | 37.7 | 31.1 | 37.3 | 20 | A |
| 314 | Y | CE2 | 37.2 | 31.9 | 36.3 | 22 | A |
| 314 | Y | CZ | 36.0 | 32.5 | 36.4 | 22 | A |
| 314 | Y | OH | 35.5 | 33.2 | 35.4 | 27 | A |
| 314 | Y | C | 38.0 | 30.0 | 42.1 | 24 | A |
| 314 | Y | O | 37.1 | 29.7 | 42.8 | 26 | A |
| 315 | Y | N | 39.3 | 29.5 | 42.3 | 22 | A |
| 315 | Y | CA | 39.6 | 28.6 | 43.3 | 19 | A |
| 315 | Y | CB | 41.1 | 28.3 | 43.4 | 18 | A |
| 315 | Y | CG | 41.5 | 27.3 | 44.4 | 19 | A |
| 315 | Y | CD1 | 40.8 | 26.1 | 44.5 | 18 | A |
| 315 | Y | CE1 | 41.2 | 25.1 | 45.5 | 17 | A |
| 315 | Y | CD2 | 42.6 | 27.5 | 45.2 | 19 | A |
| 315 | Y | CE2 | 43.0 | 26.5 | 46.2 | 17 | A |
| 315 | Y | CZ | 42.3 | 25.3 | 46.3 | 20 | A |
| 315 | Y | OH | 42.7 | 24.4 | 47.2 | 19 | A |
| 315 | Y | C | 39.1 | 29.0 | 44.7 | 18 | A |
| 315 | Y | O | 39.5 | 30.0 | 45.2 | 17 | A |
| 316 | D | N | 38.3 | 28.1 | 45.3 | 18 | A |
| 316 | D | CA | 37.7 | 28.4 | 46.6 | 18 | A |
| 316 | D | CB | 36.7 | 29.5 | 46.5 | 18 | A |
| 316 | D | CG | 35.8 | 29.6 | 47.7 | 20 | A |
| 316 | D | OD1 | 36.3 | 29.4 | 48.8 | 24 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 316 | D | OD2 | 34.6 | 29.9 | 47.5 | 19 | A |
| 316 | D | C | 37.1 | 27.1 | 47.2 | 18 | A |
| 316 | D | O | 35.9 | 26.8 | 46.9 | 17 | A |
| 317 | P | N | 37.8 | 26.4 | 48.0 | 18 | A |
| 317 | P | CD | 39.3 | 26.5 | 48.1 | 18 | A |
| 317 | P | CA | 37.3 | 25.2 | 48.7 | 18 | A |
| 317 | P | CB | 38.4 | 24.8 | 49.6 | 17 | A |
| 317 | P | CG | 39.5 | 25.8 | 49.4 | 20 | A |
| 317 | P | C | 36.0 | 25.3 | 49.4 | 19 | A |
| 317 | P | O | 35.3 | 24.3 | 49.7 | 21 | A |
| 318 | S | N | 35.5 | 26.5 | 49.8 | 17 | A |
| 318 | S | CA | 34.3 | 26.7 | 50.5 | 15 | A |
| 318 | S | CB | 34.2 | 28.0 | 51.3 | 15 | A |
| 318 | S | OG | 34.2 | 29.1 | 50.4 | 12 | A |
| 318 | S | C | 33.1 | 26.6 | 49.5 | 16 | A |
| 318 | S | O | 31.9 | 26.7 | 49.9 | 16 | A |
| 319 | D | N | 33.3 | 26.4 | 48.2 | 14 | A |
| 319 | D | CA | 32.3 | 26.4 | 47.2 | 15 | A |
| 319 | D | CB | 32.2 | 27.7 | 46.4 | 17 | A |
| 319 | D | CG | 31.0 | 27.7 | 45.5 | 19 | A |
| 319 | D | OD1 | 29.9 | 27.1 | 45.9 | 19 | A |
| 319 | D | OD2 | 31.0 | 28.4 | 44.5 | 20 | A |
| 319 | D | C | 32.7 | 25.2 | 46.2 | 16 | A |
| 319 | D | O | 32.4 | 25.3 | 45.0 | 18 | A |
| 320 | E | N | 33.4 | 24.2 | 46.8 | 15 | A |
| 320 | E | CA | 33.9 | 23.1 | 46.0 | 18 | A |
| 320 | E | CB | 35.4 | 23.2 | 45.8 | 15 | A |
| 320 | E | CG | 35.8 | 24.1 | 44.5 | 17 | A |
| 320 | E | CD | 37.2 | 24.6 | 44.6 | 18 | A |
| 320 | E | OE1 | 38.1 | 23.9 | 45.3 | 16 | A |
| 320 | E | OE2 | 37.5 | 25.6 | 44.0 | 22 | A |
| 320 | E | C | 33.5 | 21.8 | 46.7 | 17 | A |
| 320 | E | O | 34.4 | 21.2 | 47.3 | 17 | A |
| 321 | P | N | 32.3 | 21.4 | 46.7 | 19 | A |
| 321 | P | CD | 31.1 | 22.1 | 46.0 | 17 | A |
| 321 | P | CA | 31.8 | 20.2 | 47.4 | 20 | A |
| 321 | P | CB | 30.4 | 20.1 | 47.1 | 18 | A |
| 321 | P | CG | 30.2 | 20.9 | 45.8 | 20 | A |
| 321 | P | C | 32.6 | 19.0 | 47.1 | 21 | A |
| 321 | P | O | 33.0 | 18.7 | 45.9 | 20 | A |
| 322 | I | N | 32.8 | 18.2 | 48.1 | 21 | A |
| 322 | I | CA | 33.5 | 16.9 | 47.9 | 24 | A |
| 322 | I | CB | 34.8 | 16.7 | 48.8 | 26 | A |
| 322 | I | CG2 | 35.9 | 17.6 | 48.3 | 22 | A |
| 322 | I | CG1 | 34.5 | 17.2 | 50.3 | 26 | A |
| 322 | I | CD1 | 33.6 | 16.2 | 51.0 | 31 | A |
| 322 | I | C | 32.4 | 15.8 | 48.3 | 25 | A |
| 322 | I | O | 31.4 | 16.2 | 48.8 | 25 | A |
| 323 | A | N | 32.7 | 14.5 | 48.0 | 25 | A |
| 323 | A | CA | 31.8 | 13.5 | 48.3 | 26 | A |
| 323 | A | CB | 32.2 | 12.2 | 47.5 | 19 | A |
| 323 | A | C | 31.7 | 13.2 | 49.8 | 28 | A |
| 323 | A | O | 32.7 | 13.1 | 50.5 | 30 | A |
| 324 | E | N | 30.5 | 13.0 | 50.3 | 32 | A |
| 324 | E | CA | 30.4 | 12.7 | 51.7 | 37 | A |
| 324 | E | CB | 29.1 | 13.2 | 52.3 | 42 | A |
| 324 | E | CG | 27.8 | 12.8 | 51.7 | 46 | A |
| 324 | E | CD | 26.6 | 13.6 | 52.2 | 50 | A |
| 324 | E | OE1 | 26.4 | 13.5 | 53.4 | 49 | A |
| 324 | E | OE2 | 25.9 | 14.3 | 51.4 | 52 | A |
| 324 | E | C | 30.5 | 11.2 | 52.1 | 36 | A |
| 324 | E | O | 31.1 | 10.8 | 53.1 | 34 | A |
| 325 | A | N | 30.0 | 10.4 | 51.2 | 35 | A |
| 325 | A | CA | 30.1 | 8.9 | 51.3 | 35 | A |
| 325 | A | CB | 28.7 | 8.3 | 51.5 | 34 | A |
| 325 | A | C | 30.9 | 8.3 | 50.1 | 33 | A |
| 325 | A | O | 30.2 | 7.8 | 49.2 | 30 | A |
| 326 | P | N | 32.2 | 8.5 | 50.1 | 32 | A |
| 326 | P | CD | 33.0 | 9.2 | 51.1 | 33 | A |
| 326 | P | CA | 33.1 | 7.9 | 49.0 | 33 | A |
| 326 | P | CB | 34.5 | 8.3 | 49.6 | 33 | A |
| 326 | P | CG | 34.3 | 9.5 | 50.3 | 33 | A |
| 326 | P | C | 32.8 | 6.4 | 48.8 | 35 | A |
| 326 | P | O | 32.8 | 5.7 | 49.8 | 34 | A |
| 327 | F | N | 32.7 | 6.0 | 47.6 | 33 | A |
| 327 | F | CA | 32.5 | 4.6 | 47.2 | 33 | A |
| 327 | F | CB | 32.4 | 4.4 | 45.7 | 34 | A |
| 327 | F | CG | 31.1 | 4.9 | 45.2 | 36 | A |
| 327 | F | CD1 | 30.0 | 4.2 | 45.4 | 36 | A |
| 327 | F | CD2 | 31.1 | 6.0 | 44.4 | 36 | A |
| 327 | F | CE1 | 28.7 | 4.6 | 44.9 | 37 | A |
| 327 | F | CE2 | 29.9 | 6.5 | 43.9 | 36 | A |
| 327 | F | CZ | 28.7 | 5.8 | 44.1 | 38 | A |
| 327 | F | C | 33.7 | 3.8 | 47.8 | 32 | A |
| 327 | F | O | 34.8 | 4.2 | 47.9 | 30 | A |
| 328 | K | N | 33.3 | 2.6 | 48.2 | 34 | A |
| 328 | K | CA | 34.3 | 1.6 | 48.8 | 38 | A |
| 328 | K | CB | 33.9 | 1.3 | 50.2 | 40 | A |
| 328 | K | CG | 34.2 | 2.4 | 51.2 | 42 | A |
| 328 | K | CD | 35.7 | 2.7 | 51.3 | 43 | A |
| 328 | K | CE | 36.1 | 3.9 | 52.1 | 46 | A |
| 328 | K | NZ | 37.6 | 4.1 | 52.0 | 45 | A |
| 328 | K | C | 34.5 | 0.4 | 48.0 | 38 | A |
| 328 | K | O | 33.6 | −0.0 | 47.2 | 34 | A |
| 329 | F | N | 35.6 | −0.3 | 48.2 | 42 | A |
| 329 | F | CA | 36.0 | −1.5 | 47.5 | 45 | A |
| 329 | F | CB | 37.2 | −2.2 | 48.2 | 44 | A |
| 329 | F | CG | 37.7 | −3.4 | 47.5 | 47 | A |
| 329 | F | CD1 | 38.5 | −3.3 | 46.4 | 48 | A |
| 329 | F | CD2 | 37.4 | −4.7 | 48.0 | 49 | A |
| 329 | F | CE1 | 39.0 | −4.4 | 45.8 | 50 | A |
| 329 | F | CE2 | 37.9 | −5.8 | 47.4 | 50 | A |
| 329 | F | CZ | 38.7 | −5.7 | 46.3 | 51 | A |
| 329 | F | C | 34.9 | −2.5 | 47.4 | 47 | A |
| 329 | F | O | 34.7 | −3.1 | 46.3 | 47 | A |
| 330 | D | N | 34.1 | −2.8 | 48.4 | 49 | A |
| 330 | D | CA | 33.1 | −3.7 | 48.5 | 51 | A |
| 330 | D | CB | 32.4 | −3.7 | 49.8 | 55 | A |
| 330 | D | CG | 32.3 | −2.3 | 50.4 | 59 | A |
| 330 | D | OD1 | 31.7 | −1.4 | 49.8 | 61 | A |
| 330 | D | OD2 | 32.8 | −2.1 | 51.5 | 58 | A |
| 330 | D | C | 32.0 | −3.6 | 47.3 | 50 | A |
| 330 | D | O | 31.3 | −4.6 | 47.1 | 52 | A |
| 331 | M | N | 31.9 | −2.5 | 46.7 | 48 | A |
| 331 | M | CA | 31.0 | −2.4 | 45.6 | 46 | A |
| 331 | M | CB | 30.1 | −1.1 | 45.8 | 47 | A |
| 331 | M | CG | 30.9 | 0.2 | 45.7 | 49 | A |
| 331 | M | SD | 31.3 | 0.6 | 44.0 | 51 | A |
| 331 | M | CE | 29.8 | 1.4 | 43.4 | 51 | A |
| 331 | M | C | 31.6 | −2.4 | 44.2 | 45 | A |
| 331 | M | O | 31.0 | −2.1 | 43.2 | 45 | A |
| 332 | E | N | 32.9 | −2.7 | 44.2 | 44 | A |
| 332 | E | CA | 33.7 | −2.8 | 42.9 | 43 | A |
| 332 | E | CB | 35.2 | −2.5 | 43.2 | 41 | A |
| 332 | E | CG | 35.5 | −1.1 | 43.4 | 39 | A |
| 332 | E | CD | 37.0 | −1.0 | 43.7 | 39 | A |
| 332 | E | OE1 | 37.8 | −1.5 | 43.0 | 36 | A |
| 332 | E | OE2 | 37.3 | −0.3 | 44.7 | 35 | A |
| 332 | E | C | 33.5 | −4.2 | 42.3 | 45 | A |
| 332 | E | O | 33.7 | −4.3 | 41.1 | 44 | A |
| 333 | L | N | 33.2 | −5.1 | 43.1 | 47 | A |
| 333 | L | CA | 33.0 | −6.5 | 42.7 | 48 | A |
| 333 | L | CB | 33.1 | −7.4 | 43.9 | 50 | A |
| 333 | L | CG | 34.4 | −7.5 | 44.7 | 53 | A |
| 333 | L | CD1 | 34.8 | −6.2 | 45.1 | 53 | A |
| 333 | L | CD2 | 34.2 | −8.5 | 45.9 | 53 | A |
| 333 | L | C | 31.7 | −6.8 | 41.9 | 46 | A |
| 333 | L | O | 30.8 | −7.4 | 42.4 | 46 | A |
| 334 | D | N | 31.7 | −6.3 | 40.7 | 43 | A |
| 334 | D | CA | 30.5 | −6.5 | 39.8 | 42 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| | | | | | | | |
|---|---|---|---|---|---|---|---|
| 334 | D | CB | 30.1 | −5.1 | 39.2 | 42 | A |
| 334 | D | CG | 31.2 | −4.3 | 38.5 | 41 | A |
| 334 | D | OD1 | 32.1 | −5.0 | 37.9 | 39 | A |
| 334 | D | OD2 | 31.1 | −3.1 | 38.5 | 40 | A |
| 334 | D | C | 30.9 | −7.4 | 38.6 | 42 | A |
| 334 | D | O | 30.1 | −7.4 | 37.6 | 39 | A |
| 335 | D | N | 31.9 | −8.2 | 38.8 | 42 | A |
| 335 | D | CA | 32.3 | −9.1 | 37.7 | 44 | A |
| 335 | D | CB | 33.8 | −9.5 | 37.9 | 45 | A |
| 335 | D | CG | 34.3 | −10.4 | 36.7 | 46 | A |
| 335 | D | OD1 | 33.8 | −10.2 | 35.6 | 46 | A |
| 335 | D | OD2 | 35.1 | −11.3 | 37.0 | 45 | A |
| 335 | D | C | 31.4 | −10.3 | 37.9 | 45 | A |
| 335 | D | O | 31.9 | −11.4 | 38.2 | 44 | A |
| 336 | L | N | 30.1 | −10.1 | 37.7 | 45 | A |
| 336 | L | CA | 29.1 | −11.2 | 37.9 | 47 | A |
| 336 | L | CB | 28.1 | −10.7 | 39.0 | 48 | A |
| 336 | L | CG | 28.6 | −10.1 | 40.2 | 48 | A |
| 336 | L | CD1 | 27.5 | −9.4 | 41.0 | 48 | A |
| 336 | L | CD2 | 29.4 | −11.1 | 41.1 | 48 | A |
| 336 | L | C | 28.3 | −11.4 | 36.6 | 48 | A |
| 336 | L | O | 28.4 | −10.6 | 35.6 | 47 | A |
| 337 | P | N | 27.6 | −12.6 | 36.5 | 49 | A |
| 337 | P | CD | 27.4 | −13.6 | 37.6 | 49 | A |
| 337 | P | CA | 26.8 | −12.9 | 35.3 | 49 | A |
| 337 | P | CB | 26.0 | −14.2 | 35.8 | 48 | A |
| 337 | P | CG | 26.9 | −14.8 | 36.8 | 49 | A |
| 337 | P | C | 25.9 | −11.8 | 34.9 | 49 | A |
| 337 | P | O | 25.5 | −11.0 | 35.8 | 48 | A |
| 338 | K | N | 25.6 | −11.7 | 33.6 | 50 | A |
| 338 | K | CA | 24.7 | −10.6 | 33.2 | 52 | A |
| 338 | K | CB | 24.7 | −10.5 | 31.7 | 52 | A |
| 338 | K | CG | 24.2 | −11.7 | 30.9 | 53 | A |
| 338 | K | CD | 24.5 | −11.7 | 29.4 | 53 | A |
| 338 | K | CE | 23.7 | −12.6 | 28.6 | 54 | A |
| 338 | K | NZ | 23.7 | −14.0 | 29.1 | 54 | A |
| 338 | K | C | 23.3 | −10.8 | 33.7 | 54 | A |
| 338 | K | O | 22.4 | −10.0 | 33.4 | 54 | A |
| 339 | E | N | 23.1 | −11.9 | 34.4 | 53 | A |
| 339 | E | CA | 21.8 | −12.2 | 35.0 | 53 | A |
| 339 | E | CB | 21.6 | −13.8 | 35.2 | 53 | A |
| 339 | E | CG | 21.4 | −14.5 | 33.9 | 54 | A |
| 339 | E | CD | 22.5 | −14.4 | 32.9 | 56 | A |
| 339 | E | OE1 | 23.7 | −14.7 | 33.3 | 56 | A |
| 339 | E | OE2 | 22.2 | −14.1 | 31.7 | 57 | A |
| 339 | E | C | 21.7 | −11.6 | 36.3 | 52 | A |
| 339 | E | O | 20.6 | −11.0 | 36.7 | 51 | A |
| 340 | K | N | 22.7 | −11.7 | 37.1 | 51 | A |
| 340 | K | CA | 22.8 | −11.1 | 38.5 | 51 | A |
| 340 | K | CB | 24.1 | −11.5 | 39.2 | 53 | A |
| 340 | K | CG | 23.8 | −12.3 | 40.4 | 56 | A |
| 340 | K | CD | 23.2 | −11.4 | 41.5 | 59 | A |
| 340 | K | CE | 22.6 | −12.3 | 42.6 | 62 | A |
| 340 | K | NZ | 21.5 | −13.1 | 42.1 | 61 | A |
| 340 | K | C | 22.8 | −9.6 | 38.3 | 51 | A |
| 340 | K | O | 22.1 | −8.8 | 39.0 | 51 | A |
| 341 | L | N | 23.6 | −9.1 | 37.3 | 50 | A |
| 341 | L | CA | 23.7 | −7.7 | 37.0 | 49 | A |
| 341 | L | CB | 24.7 | −7.5 | 35.9 | 49 | A |
| 341 | L | CG | 26.1 | −7.8 | 36.4 | 48 | A |
| 341 | L | CD1 | 27.1 | −7.7 | 35.2 | 48 | A |
| 341 | L | CD2 | 26.6 | −6.8 | 37.5 | 47 | A |
| 341 | L | C | 22.3 | −7.1 | 36.6 | 49 | A |
| 341 | L | O | 22.1 | −5.9 | 36.8 | 49 | A |
| 342 | K | N | 21.5 | −7.9 | 35.9 | 50 | A |
| 342 | K | CA | 20.2 | −7.4 | 35.5 | 50 | A |
| 342 | K | CB | 19.5 | −8.3 | 34.5 | 51 | A |
| 342 | K | CG | 18.1 | −7.9 | 34.0 | 52 | A |
| 342 | K | CD | 17.5 | −8.7 | 32.9 | 51 | A |
| 342 | K | CE | 16.2 | −8.1 | 32.5 | 50 | A |
| 342 | K | NZ | 15.6 | −8.8 | 31.3 | 50 | A |
| 342 | K | C | 19.3 | −7.2 | 36.7 | 50 | A |
| 342 | K | O | 18.5 | −6.3 | 36.8 | 50 | A |
| 343 | E | N | 19.4 | −8.2 | 37.6 | 50 | A |
| 343 | E | CA | 18.7 | −8.1 | 38.9 | 51 | A |
| 343 | E | CB | 19.0 | −9.3 | 39.7 | 53 | A |
| 343 | E | CG | 18.4 | −10.7 | 39.1 | 57 | A |
| 343 | E | CD | 19.0 | −11.9 | 39.8 | 60 | A |
| 343 | E | OE1 | 18.9 | −12.0 | 41.1 | 62 | A |
| 343 | E | OE2 | 19.6 | −12.7 | 39.1 | 61 | A |
| 343 | E | C | 19.0 | −6.8 | 39.6 | 50 | A |
| 343 | E | O | 18.2 | −6.1 | 40.0 | 50 | A |
| 344 | L | N | 20.3 | −6.6 | 39.8 | 47 | A |
| 344 | L | CA | 20.9 | −5.4 | 40.4 | 43 | A |
| 344 | L | CB | 22.4 | −5.5 | 40.4 | 40 | A |
| 344 | L | CG | 23.1 | −6.6 | 41.2 | 41 | A |
| 344 | L | CD1 | 24.6 | −6.7 | 40.9 | 38 | A |
| 344 | L | CD2 | 22.9 | −6.4 | 42.7 | 39 | A |
| 344 | L | C | 20.4 | −4.2 | 39.8 | 42 | A |
| 344 | L | O | 20.0 | −3.2 | 40.5 | 42 | A |
| 345 | I | N | 20.3 | −4.1 | 38.5 | 43 | A |
| 345 | I | CA | 19.9 | −2.9 | 37.7 | 42 | A |
| 345 | I | CB | 20.1 | −3.1 | 36.2 | 40 | A |
| 345 | I | CG2 | 19.3 | −2.0 | 35.5 | 39 | A |
| 345 | I | CG1 | 21.5 | −3.0 | 35.9 | 40 | A |
| 345 | I | CD1 | 21.8 | −3.1 | 34.4 | 39 | A |
| 345 | I | C | 18.4 | −2.7 | 38.0 | 44 | A |
| 345 | I | O | 17.9 | −1.6 | 38.3 | 43 | A |
| 346 | F | N | 17.6 | −3.8 | 38.0 | 48 | A |
| 346 | F | CA | 16.2 | −3.8 | 38.3 | 49 | A |
| 346 | F | CB | 15.6 | −5.2 | 38.3 | 50 | A |
| 346 | F | CG | 14.1 | −5.2 | 38.5 | 52 | A |
| 346 | F | CD1 | 13.2 | −4.9 | 37.5 | 52 | A |
| 346 | F | CD2 | 13.6 | −5.5 | 39.8 | 52 | A |
| 346 | F | CE1 | 11.9 | −4.9 | 37.6 | 52 | A |
| 346 | F | CE2 | 12.2 | −5.5 | 40.0 | 52 | A |
| 346 | F | CZ | 11.3 | −5.2 | 38.9 | 53 | A |
| 346 | F | C | 16.0 | −3.1 | 39.7 | 48 | A |
| 346 | F | O | 15.1 | −2.3 | 39.8 | 46 | A |
| 347 | E | N | 16.8 | −3.5 | 40.6 | 50 | A |
| 347 | E | CA | 16.7 | −3.0 | 42.0 | 53 | A |
| 347 | E | CB | 17.7 | −3.8 | 42.8 | 55 | A |
| 347 | E | CG | 17.6 | −3.6 | 44.3 | 59 | A |
| 347 | E | CD | 18.7 | −4.5 | 45.0 | 62 | A |
| 347 | E | OE1 | 18.6 | −5.7 | 44.9 | 63 | A |
| 347 | E | OE2 | 19.5 | −3.9 | 45.7 | 64 | A |
| 347 | E | C | 17.1 | −1.5 | 42.1 | 54 | A |
| 347 | E | O | 16.2 | −0.7 | 42.5 | 54 | A |
| 348 | E | N | 18.2 | −1.2 | 41.6 | 53 | A |
| 348 | E | CA | 18.7 | 0.2 | 41.6 | 51 | A |
| 348 | E | CB | 20.1 | 0.3 | 40.9 | 49 | A |
| 348 | E | CG | 21.3 | −0.2 | 41.7 | 47 | A |
| 348 | E | CD | 21.6 | 0.7 | 42.9 | 46 | A |
| 348 | E | OE1 | 21.8 | 1.9 | 42.7 | 43 | A |
| 348 | E | OE2 | 21.6 | 0.2 | 44.0 | 48 | A |
| 348 | E | C | 17.7 | 1.2 | 40.9 | 52 | A |
| 348 | E | O | 17.8 | 2.4 | 41.2 | 53 | A |
| 349 | T | N | 16.9 | 0.7 | 40.0 | 51 | A |
| 349 | T | CA | 15.9 | 1.6 | 39.4 | 51 | A |
| 349 | T | CB | 15.8 | 1.2 | 37.9 | 50 | A |
| 349 | T | OG1 | 15.2 | −0.1 | 37.7 | 47 | A |
| 349 | T | CG2 | 17.1 | 1.3 | 37.2 | 51 | A |
| 349 | T | C | 14.5 | 1.5 | 40.0 | 52 | A |
| 349 | T | O | 13.6 | 2.2 | 39.6 | 52 | A |
| 350 | A | N | 14.3 | 0.6 | 41.0 | 52 | A |
| 350 | A | CA | 13.1 | 0.4 | 41.6 | 53 | A |
| 350 | A | CB | 13.2 | −0.6 | 42.7 | 53 | A |
| 350 | A | C | 12.5 | 1.7 | 42.2 | 55 | A |
| 350 | A | O | 11.4 | 2.1 | 42.0 | 54 | A |
| 351 | R | N | 13.4 | 2.4 | 43.0 | 57 | A |

TABLE 2-continued

Structural Coordinates of Ah$_6$-ERK2 [di-phosphorlylated, SEQ ID NO: 5] crystals.
The following table contains one line for each atom in one Phosphorylated ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Phosphorylated. The coordinates are arranged in two side-by-side columns.

| 351 | R | CA  | 13.0 | 3.7  | 43.6 | 59 | A |
|-----|---|-----|------|------|------|----|---|
| 351 | R | CB  | 14.2 | 4.4  | 44.1 | 61 | A |
| 351 | R | CG  | 15.0 | 5.2  | 43.0 | 62 | A |
| 351 | R | CD  | 15.5 | 6.5  | 43.5 | 62 | A |
| 351 | R | NE  | 16.9 | 6.5  | 43.9 | 62 | A |
| 351 | R | CZ  | 17.5 | 7.5  | 44.5 | 62 | A |
| 351 | R | NH1 | 16.9 | 8.6  | 44.7 | 62 | A |
| 351 | R | NH2 | 18.8 | 7.4  | 44.8 | 61 | A |
| 351 | R | C   | 12.2 | 4.6  | 42.7 | 60 | A |
| 351 | R | O   | 11.3 | 5.4  | 43.1 | 61 | A |
| 352 | F | N   | 12.5 | 4.6  | 41.4 | 62 | A |
| 352 | F | CA  | 11.8 | 5.4  | 40.4 | 63 | A |
| 352 | F | CB  | 12.7 | 5.8  | 39.2 | 62 | A |
| 352 | F | CG  | 13.9 | 6.6  | 39.6 | 62 | A |
| 352 | F | CD1 | 13.7 | 8.0  | 39.8 | 61 | A |
| 352 | F | CD2 | 15.2 | 6.1  | 39.8 | 60 | A |
| 352 | F | CE1 | 14.8 | 8.8  | 40.2 | 60 | A |
| 352 | F | CE2 | 16.2 | 6.9  | 40.2 | 60 | A |
| 352 | F | CZ  | 16.1 | 8.3  | 40.3 | 59 | A |
| 352 | F | C   | 10.5 | 4.9  | 39.9 | 64 | A |
| 352 | F | O   | 9.8  | 5.6  | 39.1 | 63 | A |
| 353 | Q | N   | 10.2 | 3.7  | 40.3 | 66 | A |
| 353 | Q | CA  | 8.9  | 3.0  | 39.8 | 70 | A |
| 353 | Q | CB  | 8.8  | 1.6  | 40.3 | 69 | A |
| 353 | Q | CG  | 9.6  | 0.6  | 39.4 | 68 | A |
| 353 | Q | CD  | 8.9  | 0.5  | 38.1 | 69 | A |
| 353 | Q | OE1 | 9.0  | 1.4  | 37.3 | 69 | A |
| 353 | Q | NE2 | 8.3  | -0.7 | 37.7 | 69 | A |
| 353 | Q | C   | 7.7  | 3.8  | 40.4 | 72 | A |
| 353 | Q | O   | 7.7  | 4.3  | 41.5 | 73 | A |
| 354 | P | N   | 6.6  | 3.9  | 39.5 | 75 | A |
| 354 | P | CD  | 6.5  | 3.3  | 38.2 | 75 | A |
| 354 | P | CA  | 5.4  | 4.6  | 39.9 | 77 | A |
| 354 | P | CB  | 4.4  | 4.2  | 38.8 | 77 | A |
| 354 | P | CG  | 5.3  | 4.1  | 37.6 | 77 | A |
| 354 | P | C   | 4.9  | 4.2  | 41.3 | 80 | A |
| 354 | P | O   | 4.8  | 3.1  | 41.7 | 80 | A |
| 355 | G | N   | 4.6  | 5.3  | 42.1 | 84 | A |
| 355 | G | CA  | 4.1  | 5.1  | 43.5 | 89 | A |
| 355 | G | C   | 5.0  | 4.3  | 44.4 | 92 | A |
| 355 | G | O   | 4.5  | 3.7  | 45.4 | 92 | A |
| 356 | Y | N   | 6.3  | 4.2  | 44.1 | 95 | A |

Example 15

Ah$_6$-ERK2 [Di-Phosphorlylated] Structure Determination

The crystal structure was solved using molecular replacement using the search models 2ERK from the PDB. Refinement was done using the program CNX.

| Theoretical number of reflections | 113961 |
|---|---|
| Resolution Limits | 30.0-1.97 Å |
| Number of unobserved reflections | 19851 (17.4%) |
| Number of reflections in working set | 89428 (78.5%) |
| Number of reflections in test set | 4682 (4.1%) |
| Number of protein residues | 1388 |
| Number of solvent atoms | 718 |
| R-factor | 0.249 |
| R-free | 0.298 |
| RMSD bond length | 0.014 Å |
| RMSD bond angles | 1.49° |

Example 16

Preparation of Ah$_6$-ERK2 [Di-Thiophosphorlylated]

Di-thiophosphorylated ERK2 was prepared by incubation of 16 mg of 5 µM ERK2 with 200 nM MEK1P (active MEK1) and 50 µM ATPγS for 208 minutes, at 25° C. in 50 mM sodium Hepes Buffer, pH 7.5, 2.5 mM MgCl$_2$, 3 mM DTT, 4 mM Tris HCl, 2% (w/v) glycerol, 0.2 mM EDTA, and 0.05 M NaCl. The reaction was quenched with 25 mM EDTA. The product was dialyzed at 4° C. versus MonoQ buffer (25 mM Tris-Cl, pH 7.8 (rt), 0.05 M NaCl, 1 mM EDTA, 10% (v/v) glycerol, and 5 mM DTT) and applied to a MonoQ HR 10/10 column (Amersham/Pharmacia) at 4° C. The column was washed with 1 bed volume of MonoQ buffer and eluted with a linear 30 bed volume gradient between MonoQ Buffer and MonoQ Buffer with 0.5 M NaCl. The yield was 10 mg of di-thiophosphorylated ERA.

Pure di-thiophosphorylated ERK2 was prepared for crystallography by extensive dialysis versus 20 mM Tris-Cl, pH 7.5 (rt), 0.2 M NaCl, 0.03% sodium azide and 5 mM DTT at 4° C., centrifugation at 200,000×g for 40 minutes, and concentration to 11 mg/ml of protein on a YM10 membrane (Millipore).

Example 17

Crystallization of Ah$_6$-ERK2 [Di-Thiophosphorlylated]

The Ah$_6$-ERK2 [di-thiophosphortylated] was crystallized using a hanging-drop vapor diffusion method. The protein (0.5 µl; 10 mg/ml) in 20 mM Tris-HCl, pH 7.5, 0.20 M sodium chloride, 0.03% sodium azide, 5 mM DTT buffer was mixed with an equal volume of precipitant solution containing 10 mM sodium citrate, pH 5.8, 20% iso-propanol placed on the underside of a siliconized glass coverslip and sealed in close proximity to 1 ml of the precipitant solution. Crystallization plates were incubated at 4°; crystals grew over 4-30 days.

Example 18

Photomicrograph of Ah$_6$-ERK2 [Di-Thiophosphorlylated] Crystals

A photomicrograph of Ah$_6$-ERK2 [di-thiophosphorlylated crystals was taken (magnification about 200×). Rectangular rod crystals (0.02×0.2 mm) were observed.

Example 19

Crystallographic Analysis of Ah$_6$-ERK2 [Di-Thiophosphorylated]

Prior to data collection, crystals were washed with the reservoir solution of the crystallization setup and transferred into the same solution with 20% glycerol added. The crystals were then flash-cooled in a nitrogen stream at 95 K. X-ray diffraction was collected using a Rigaku generator equipped with a Raxis 4++ detector. Data were integrated and scaled using the HKL package.

Data Collection Statistics:

| Resolution | 30.0-2.35 Å |
|---|---|
| No. of collected reflections | 82289 |
| No. of unique reflections (F >= 0) | 21197 |

-continued

| | |
|---|---|
| R-sym | 11.3% |
| Percent of theoretical (l/s >= 1) | 99.7% |
| Unit Cell | a = 92.892 Å, b = 92.892 Å, c = 99.829 Å, α = β = 90° γ = 120° |
| Space Group | P3₂21 (number 154) |
| Asymmetric unit | 1 molecule |

TABLE 3

Structural Coordinates of Ah₆-ERK2 [di-thiophosphorylated, SEQ ID NO: 5] Crystals
The following table contains one line for each atom in one Thiophosphorylated Erk2 kinase tetramer. The columns are: 1) residue number, 2) 1-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | | |
|---|---|---|---|---|---|---|---|
| 6 | A | CB | 2.1 | 5.2 | 18.2 | 90 | A |
| 6 | A | C | 0.2 | 5.6 | 19.8 | 90 | A |
| 6 | A | O | 0.6 | 5.6 | 21.0 | 90 | A |
| 6 | A | N | 1.7 | 7.4 | 19.2 | 90 | A |
| 6 | A | CA | 1.1 | 6.2 | 18.7 | 90 | A |
| 7 | A | N | -0.9 | 5.0 | 19.4 | 89 | A |
| 7 | A | CA | -1.8 | 4.3 | 20.3 | 88 | A |
| 7 | A | CB | -2.5 | 3.2 | 19.6 | 88 | A |
| 7 | A | C | -1.1 | 3.9 | 21.6 | 86 | A |
| 7 | A | O | -1.4 | 4.3 | 22.7 | 87 | A |
| 8 | G | N | -0.2 | 3.0 | 21.4 | 84 | A |
| 8 | G | CA | 0.6 | 2.4 | 22.5 | 81 | A |
| 8 | G | C | 1.9 | 3.3 | 22.7 | 78 | A |
| 8 | G | O | 1.8 | 4.4 | 23.1 | 78 | A |
| 9 | P | N | 3.0 | 2.7 | 22.5 | 76 | A |
| 9 | P | CD | 3.3 | 1.3 | 22.1 | 75 | A |
| 9 | P | CA | 4.3 | 3.4 | 22.6 | 73 | A |
| 9 | P | CB | 5.3 | 2.2 | 22.7 | 74 | A |
| 9 | P | CG | 4.7 | 1.2 | 21.7 | 75 | A |
| 9 | P | C | 4.6 | 4.3 | 21.5 | 71 | A |
| 9 | P | O | 4.2 | 4.2 | 20.4 | 71 | A |
| 10 | E | N | 5.4 | 5.4 | 21.8 | 69 | A |
| 10 | E | CA | 5.7 | 6.4 | 20.8 | 66 | A |
| 10 | E | CB | 6.2 | 7.7 | 21.5 | 67 | A |
| 10 | E | CG | 5.2 | 8.2 | 22.5 | 67 | A |
| 10 | E | CD | 5.7 | 9.5 | 23.2 | 67 | A |
| 10 | E | OE1 | 5.9 | 10.5 | 22.5 | 65 | A |
| 10 | E | OE2 | 5.8 | 9.5 | 24.4 | 66 | A |
| 10 | E | C | 6.9 | 5.8 | 20.0 | 65 | A |
| 10 | E | O | 7.7 | 5.0 | 20.5 | 64 | A |
| 11 | M | N | 7.0 | 6.3 | 18.8 | 64 | A |
| 11 | M | CA | 8.0 | 5.8 | 17.9 | 62 | A |
| 11 | M | CB | 7.4 | 5.1 | 16.7 | 61 | A |
| 11 | M | CG | 6.4 | 4.0 | 17.0 | 59 | A |
| 11 | M | SD | 7.1 | 2.6 | 17.9 | 58 | A |
| 11 | M | CE | 8.1 | 1.8 | 16.6 | 59 | A |
| 11 | M | C | 9.0 | 6.8 | 17.4 | 61 | A |
| 11 | M | O | 8.6 | 8.0 | 17.1 | 61 | A |
| 12 | V | N | 10.3 | 6.5 | 17.3 | 61 | A |
| 12 | V | CA | 11.3 | 7.4 | 16.8 | 60 | A |
| 12 | V | CB | 12.1 | 8.0 | 17.9 | 60 | A |
| 12 | V | CG1 | 13.4 | 8.7 | 17.4 | 59 | A |
| 12 | V | CG2 | 11.3 | 8.9 | 18.7 | 59 | A |
| 12 | V | C | 12.2 | 6.5 | 15.9 | 60 | A |
| 12 | V | O | 12.8 | 5.6 | 16.4 | 61 | A |
| 13 | R | N | 12.2 | 6.8 | 14.6 | 59 | A |
| 13 | R | CA | 13.0 | 6.1 | 13.7 | 59 | A |
| 13 | R | CB | 14.5 | 6.3 | 13.9 | 59 | A |
| 13 | R | CG | 15.0 | 7.8 | 13.6 | 58 | A |
| 13 | R | CD | 16.5 | 7.9 | 13.7 | 58 | A |
| 13 | R | NE | 17.0 | 8.9 | 12.8 | 57 | A |
| 13 | R | CZ | 18.3 | 8.9 | 12.4 | 59 | A |
| 13 | R | NH1 | 19.1 | 7.9 | 12.8 | 58 | A |
| 13 | R | NH2 | 18.7 | 9.8 | 11.5 | 58 | A |

TABLE 3-continued

Structural Coordinates of Ah₆-ERK2 [di-thiophosphorylated, SEQ ID NO: 5] Crystals
The following table contains one line for each atom in one Thiophosphorylated Erk2 kinase tetramer. The columns are: 1) residue number, 2) 1-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | | |
|---|---|---|---|---|---|---|---|
| 13 | R | C | 12.8 | 4.6 | 13.8 | 59 | A |
| 13 | R | O | 13.7 | 3.8 | 14.0 | 59 | A |
| 14 | G | N | 11.5 | 4.2 | 13.6 | 58 | A |
| 14 | G | CA | 11.1 | 2.8 | 13.6 | 58 | A |
| 14 | G | C | 11.4 | 2.1 | 14.9 | 58 | A |
| 14 | G | O | 11.2 | 0.8 | 15.0 | 59 | A |
| 15 | Q | N | 11.9 | 2.8 | 15.9 | 57 | A |
| 15 | Q | CA | 12.2 | 2.1 | 17.2 | 55 | A |
| 15 | Q | CB | 13.6 | 2.5 | 17.7 | 56 | A |
| 15 | Q | CG | 14.7 | 1.9 | 17.0 | 58 | A |
| 15 | Q | CD | 15.9 | 1.6 | 17.9 | 60 | A |
| 15 | Q | OE1 | 17.0 | 1.3 | 17.5 | 62 | A |
| 15 | Q | NE2 | 15.7 | 1.7 | 19.2 | 59 | A |
| 15 | Q | C | 11.2 | 2.5 | 18.3 | 54 | A |
| 15 | Q | O | 10.4 | 3.5 | 18.2 | 52 | A |
| 16 | V | N | 11.1 | 1.6 | 19.3 | 52 | A |
| 16 | V | CA | 10.2 | 1.9 | 20.4 | 52 | A |
| 16 | V | CB | 9.7 | 0.6 | 21.1 | 52 | A |
| 16 | V | CG1 | 8.9 | 0.9 | 22.3 | 51 | A |
| 16 | V | CG2 | 8.9 | -0.2 | 20.1 | 55 | A |
| 16 | V | C | 10.9 | 2.7 | 21.5 | 51 | A |
| 16 | V | O | 11.9 | 2.4 | 22.0 | 49 | A |
| 17 | F | N | 10.3 | 3.9 | 21.7 | 51 | A |
| 17 | F | CA | 10.8 | 4.8 | 22.7 | 50 | A |
| 17 | F | CB | 11.1 | 6.2 | 22.1 | 49 | A |
| 17 | F | CG | 12.4 | 6.8 | 22.6 | 48 | A |
| 17 | F | CD1 | 13.6 | 6.3 | 22.3 | 47 | A |
| 17 | F | CD2 | 12.4 | 7.8 | 23.5 | 48 | A |
| 17 | F | CE1 | 14.8 | 6.8 | 22.8 | 45 | A |
| 17 | F | CE2 | 13.5 | 8.4 | 24.1 | 48 | A |
| 17 | F | CZ | 14.8 | 7.9 | 23.7 | 47 | A |
| 17 | F | C | 9.6 | 5.0 | 23.7 | 50 | A |
| 17 | F | O | 9.0 | 6.0 | 23.8 | 50 | A |
| 18 | D | N | 9.3 | 3.8 | 24.4 | 50 | A |
| 18 | D | CA | 8.2 | 3.7 | 25.3 | 50 | A |
| 18 | D | CB | 7.9 | 2.3 | 25.5 | 49 | A |
| 18 | D | CG | 6.6 | 2.1 | 26.3 | 52 | A |
| 18 | D | OD1 | 5.7 | 2.9 | 26.1 | 52 | A |
| 18 | D | OD2 | 6.5 | 1.1 | 27.0 | 53 | A |
| 18 | D | C | 8.4 | 4.4 | 26.7 | 49 | A |
| 18 | D | O | 8.6 | 3.7 | 27.7 | 49 | A |
| 19 | V | N | 8.3 | 5.7 | 26.7 | 49 | A |
| 19 | V | CA | 8.5 | 6.5 | 27.9 | 50 | A |
| 19 | V | CB | 9.5 | 7.7 | 27.7 | 48 | A |
| 19 | V | CG1 | 10.9 | 7.2 | 27.5 | 46 | A |
| 19 | V | CG2 | 9.0 | 8.5 | 26.6 | 47 | A |
| 19 | V | C | 7.2 | 7.0 | 28.5 | 51 | A |
| 19 | V | O | 7.0 | 8.2 | 28.7 | 51 | A |
| 20 | G | N | 6.3 | 6.0 | 28.8 | 51 | A |
| 20 | G | CA | 5.0 | 6.4 | 29.3 | 50 | A |
| 20 | G | C | 4.3 | 7.6 | 28.7 | 49 | A |
| 20 | G | O | 4.6 | 8.0 | 27.6 | 48 | A |
| 21 | P | N | 3.4 | 8.2 | 29.5 | 49 | A |
| 21 | P | CD | 2.7 | 7.6 | 30.6 | 49 | A |
| 21 | P | CA | 2.7 | 9.4 | 29.0 | 49 | A |
| 21 | P | CB | 1.3 | 9.3 | 29.7 | 47 | A |
| 21 | P | CG | 1.7 | 8.7 | 31.0 | 47 | A |
| 21 | P | C | 3.4 | 10.7 | 29.4 | 48 | A |
| 21 | P | O | 3.2 | 11.7 | 28.7 | 48 | A |
| 22 | R | N | 4.1 | 10.7 | 30.5 | 48 | A |
| 22 | R | CA | 4.8 | 11.9 | 31.0 | 48 | A |
| 22 | R | CB | 5.6 | 11.5 | 32.2 | 48 | A |
| 22 | R | CG | 6.4 | 12.7 | 32.9 | 48 | A |
| 22 | R | CD | 7.1 | 12.3 | 34.1 | 47 | A |
| 22 | R | NE | 8.0 | 13.3 | 34.6 | 47 | A |
| 22 | R | CZ | 8.8 | 13.2 | 35.7 | 48 | A |
| 22 | R | NH1 | 8.9 | 12.0 | 36.3 | 46 | A |
| 22 | R | NH2 | 9.5 | 14.2 | 36.1 | 47 | A |
| 22 | R | C | 5.8 | 12.5 | 30.0 | 49 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | |
|---|---|---|---|---|---|---|
| 22 | R | O | 5.8 | 13.8 | 29.9 | 50 | A |
| 23 | Y | N | 6.5 | 11.7 | 29.2 | 47 | A |
| 23 | Y | CA | 7.4 | 12.3 | 28.2 | 46 | A |
| 23 | Y | CB | 8.7 | 11.5 | 28.3 | 43 | A |
| 23 | Y | CG | 9.3 | 11.6 | 29.7 | 39 | A |
| 23 | Y | CD1 | 9.9 | 12.8 | 30.2 | 39 | A |
| 23 | Y | CE1 | 10.4 | 12.9 | 31.5 | 38 | A |
| 23 | Y | CD2 | 9.2 | 10.6 | 30.6 | 40 | A |
| 23 | Y | CE2 | 9.8 | 10.6 | 31.9 | 37 | A |
| 23 | Y | CZ | 10.3 | 11.8 | 32.3 | 38 | A |
| 23 | Y | OH | 10.9 | 11.9 | 33.6 | 37 | A |
| 23 | Y | C | 6.8 | 12.1 | 26.8 | 46 | A |
| 23 | Y | O | 6.4 | 11.1 | 26.4 | 47 | A |
| 24 | T | N | 6.8 | 13.2 | 26.1 | 48 | A |
| 24 | T | CA | 6.2 | 13.2 | 24.7 | 51 | A |
| 24 | T | CB | 4.8 | 13.7 | 24.7 | 51 | A |
| 24 | T | OG1 | 4.8 | 15.2 | 24.9 | 52 | A |
| 24 | T | CG2 | 4.0 | 13.1 | 25.8 | 49 | A |
| 24 | T | C | 7.0 | 14.1 | 23.8 | 52 | A |
| 24 | T | O | 8.2 | 14.4 | 24.0 | 55 | A |
| 25 | N | N | 6.4 | 14.4 | 22.6 | 53 | A |
| 25 | N | CA | 7.0 | 15.2 | 21.6 | 54 | A |
| 25 | N | CB | 6.9 | 16.7 | 22.0 | 55 | A |
| 25 | N | CG | 5.5 | 17.0 | 22.3 | 57 | A |
| 25 | N | OD1 | 4.6 | 16.9 | 21.5 | 56 | A |
| 25 | N | ND2 | 5.3 | 17.5 | 23.6 | 56 | A |
| 25 | N | C | 8.5 | 14.9 | 21.4 | 56 | A |
| 25 | N | O | 9.3 | 15.8 | 21.1 | 56 | A |
| 26 | L | N | 8.8 | 13.6 | 21.5 | 57 | A |
| 26 | L | CA | 10.2 | 13.1 | 21.3 | 57 | A |
| 26 | L | CB | 10.2 | 11.6 | 21.1 | 56 | A |
| 26 | L | CG | 10.2 | 10.7 | 22.4 | 57 | A |
| 26 | L | CD1 | 9.2 | 11.3 | 23.4 | 57 | A |
| 26 | L | CD2 | 9.8 | 9.3 | 22.0 | 57 | A |
| 26 | L | C | 10.9 | 13.8 | 20.1 | 57 | A |
| 26 | L | O | 10.2 | 14.2 | 19.2 | 58 | A |
| 27 | S | N | 12.2 | 13.8 | 20.1 | 58 | A |
| 27 | S | CA | 13.0 | 14.4 | 19.0 | 58 | A |
| 27 | S | CB | 13.0 | 15.9 | 19.2 | 58 | A |
| 27 | S | OG | 13.7 | 16.5 | 18.0 | 57 | A |
| 27 | S | C | 14.4 | 13.8 | 19.0 | 58 | A |
| 27 | S | O | 15.2 | 14.2 | 19.8 | 59 | A |
| 28 | Y | N | 14.6 | 12.9 | 18.1 | 57 | A |
| 28 | Y | CA | 15.9 | 12.2 | 17.9 | 57 | A |
| 28 | Y | CB | 16.0 | 11.4 | 16.7 | 56 | A |
| 28 | Y | CG | 17.2 | 10.7 | 16.4 | 55 | A |
| 28 | Y | CD1 | 17.5 | 9.5 | 17.1 | 56 | A |
| 28 | Y | CE1 | 18.7 | 8.8 | 16.9 | 55 | A |
| 28 | Y | CD2 | 18.2 | 11.1 | 15.5 | 56 | A |
| 28 | Y | CE2 | 19.4 | 10.5 | 15.3 | 56 | A |
| 28 | Y | CZ | 19.6 | 9.3 | 16.0 | 56 | A |
| 28 | Y | OH | 20.8 | 8.6 | 15.7 | 56 | A |
| 28 | Y | C | 17.1 | 13.2 | 17.9 | 56 | A |
| 28 | Y | O | 17.0 | 14.3 | 17.3 | 56 | A |
| 29 | I | N | 18.2 | 12.8 | 18.6 | 55 | A |
| 29 | I | CA | 19.4 | 13.7 | 18.6 | 54 | A |
| 29 | I | CB | 19.6 | 14.4 | 19.9 | 55 | A |
| 29 | I | CG2 | 18.5 | 15.5 | 20.0 | 56 | A |
| 29 | I | CG1 | 19.5 | 13.5 | 21.1 | 55 | A |
| 29 | I | CD1 | 19.4 | 14.2 | 22.5 | 54 | A |
| 29 | I | C | 20.7 | 12.9 | 18.3 | 53 | A |
| 29 | I | O | 21.7 | 13.4 | 17.8 | 52 | A |
| 30 | G | N | 20.6 | 11.6 | 18.5 | 52 | A |
| 30 | G | CA | 21.8 | 10.7 | 18.2 | 51 | A |
| 30 | G | C | 21.8 | 9.4 | 18.8 | 51 | A |
| 30 | G | O | 21.0 | 9.0 | 19.7 | 50 | A |
| 31 | E | N | 22.8 | 8.5 | 18.4 | 52 | A |
| 31 | E | CA | 22.9 | 7.2 | 18.9 | 53 | A |
| 31 | E | CB | 23.5 | 6.3 | 17.8 | 53 | A |
| 31 | E | CG | 22.6 | 6.0 | 16.6 | 54 | A |
| 31 | E | CD | 21.3 | 5.3 | 17.1 | 55 | A |
| 31 | E | OE1 | 21.4 | 4.3 | 17.7 | 55 | A |
| 31 | E | OE2 | 20.2 | 5.8 | 16.7 | 55 | A |
| 31 | E | C | 23.9 | 7.2 | 20.1 | 54 | A |
| 31 | E | O | 24.9 | 7.9 | 20.1 | 53 | A |
| 32 | G | N | 23.6 | 6.3 | 21.1 | 54 | A |
| 32 | G | CA | 24.4 | 6.2 | 22.3 | 54 | A |
| 32 | G | C | 25.0 | 4.8 | 22.3 | 54 | A |
| 32 | G | O | 24.7 | 4.0 | 21.4 | 55 | A |
| 33 | A | N | 25.9 | 4.6 | 23.3 | 54 | A |
| 33 | A | CA | 26.6 | 3.3 | 23.4 | 53 | A |
| 33 | A | CB | 27.3 | 3.2 | 24.7 | 53 | A |
| 33 | A | C | 25.7 | 2.1 | 23.2 | 53 | A |
| 33 | A | O | 25.9 | 1.3 | 22.3 | 53 | A |
| 34 | Y | N | 24.6 | 2.1 | 23.9 | 52 | A |
| 34 | Y | CA | 23.7 | 0.9 | 23.8 | 52 | A |
| 34 | Y | CB | 23.7 | 0.1 | 25.1 | 52 | A |
| 34 | Y | CG | 25.0 | 0.0 | 25.8 | 53 | A |
| 34 | Y | CD1 | 26.1 | −0.6 | 25.1 | 53 | A |
| 34 | Y | CE1 | 27.4 | −0.7 | 25.6 | 54 | A |
| 34 | Y | CD2 | 25.3 | 0.5 | 27.0 | 52 | A |
| 34 | Y | CE2 | 26.5 | 0.4 | 27.6 | 53 | A |
| 34 | Y | CZ | 27.6 | −0.1 | 26.9 | 54 | A |
| 34 | Y | OH | 28.9 | −0.2 | 27.5 | 53 | A |
| 34 | Y | C | 22.2 | 1.3 | 23.5 | 51 | A |
| 34 | Y | O | 21.3 | 0.6 | 23.9 | 50 | A |
| 35 | G | N | 22.0 | 2.3 | 22.7 | 49 | A |
| 35 | G | CA | 20.7 | 2.8 | 22.3 | 49 | A |
| 35 | G | C | 20.7 | 4.2 | 21.8 | 48 | A |
| 35 | G | O | 21.7 | 4.9 | 21.8 | 50 | A |
| 36 | M | N | 19.5 | 4.7 | 21.3 | 46 | A |
| 36 | M | CA | 19.4 | 6.0 | 20.9 | 45 | A |
| 36 | M | CB | 18.5 | 6.1 | 19.7 | 46 | A |
| 36 | M | CG | 17.0 | 5.8 | 20.0 | 46 | A |
| 36 | M | SD | 15.9 | 6.6 | 18.8 | 49 | A |
| 36 | M | CE | 16.1 | 5.5 | 17.3 | 48 | A |
| 36 | M | C | 19.0 | 7.0 | 21.9 | 44 | A |
| 36 | M | O | 18.4 | 6.7 | 23.0 | 41 | A |
| 37 | V | N | 19.4 | 8.3 | 21.7 | 44 | A |
| 37 | V | CA | 19.1 | 9.4 | 22.6 | 45 | A |
| 37 | V | CB | 20.5 | 10.1 | 23.1 | 45 | A |
| 37 | V | CG1 | 20.2 | 11.1 | 24.1 | 43 | A |
| 37 | V | CG2 | 21.4 | 9.0 | 23.6 | 44 | A |
| 37 | V | C | 18.2 | 10.4 | 22.0 | 45 | A |
| 37 | V | O | 18.4 | 10.8 | 20.9 | 43 | A |
| 38 | C | N | 17.1 | 10.7 | 22.7 | 46 | A |
| 38 | C | CA | 16.2 | 11.7 | 22.2 | 47 | A |
| 38 | C | CB | 14.8 | 11.0 | 21.9 | 47 | A |
| 38 | C | SG | 14.9 | 9.8 | 20.6 | 49 | A |
| 38 | C | C | 15.9 | 12.8 | 23.3 | 47 | A |
| 38 | C | O | 16.3 | 12.7 | 24.4 | 48 | A |
| 39 | S | N | 15.2 | 13.9 | 22.8 | 48 | A |
| 39 | S | CA | 14.9 | 14.9 | 23.8 | 49 | A |
| 39 | S | CB | 15.4 | 16.3 | 23.2 | 48 | A |
| 39 | S | OG | 14.9 | 16.6 | 22.0 | 47 | A |
| 39 | S | C | 13.4 | 15.0 | 23.8 | 50 | A |
| 39 | S | O | 12.7 | 15.2 | 22.8 | 51 | A |
| 40 | A | N | 12.8 | 14.6 | 25.0 | 51 | A |
| 40 | A | CA | 11.4 | 14.6 | 25.2 | 51 | A |
| 40 | A | CB | 11.0 | 13.5 | 26.1 | 50 | A |
| 40 | A | C | 11.0 | 15.9 | 25.8 | 54 | A |
| 40 | A | O | 11.7 | 16.9 | 25.9 | 52 | A |
| 41 | Y | N | 9.7 | 16.0 | 26.3 | 57 | A |
| 41 | Y | CA | 9.1 | 17.1 | 26.9 | 60 | A |
| 41 | Y | CB | 8.2 | 17.9 | 26.0 | 63 | A |
| 41 | Y | CG | 7.4 | 19.0 | 26.7 | 66 | A |
| 41 | Y | CD1 | 8.0 | 20.2 | 26.9 | 67 | A |
| 41 | Y | CE1 | 7.4 | 21.2 | 27.6 | 68 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 41 | Y | CD2 | 6.1 | 18.8 | 27.2 | 67 | A |
| --- | --- | --- | --- | --- | --- | --- | --- |
| 41 | Y | CE2 | 5.5 | 19.8 | 27.9 | 69 | A |
| 41 | Y | CZ | 6.1 | 21.0 | 28.1 | 69 | A |
| 41 | Y | OH | 5.4 | 22.0 | 28.8 | 70 | A |
| 41 | Y | C | 8.4 | 16.6 | 28.2 | 60 | A |
| 41 | Y | O | 7.3 | 16.1 | 28.1 | 61 | A |
| 42 | D | N | 9.0 | 16.8 | 29.3 | 60 | A |
| 42 | D | CA | 8.4 | 16.4 | 30.5 | 60 | A |
| 42 | D | CB | 9.3 | 16.6 | 31.8 | 59 | A |
| 42 | D | CG | 8.9 | 15.8 | 33.0 | 59 | A |
| 42 | D | OD1 | 7.7 | 15.4 | 33.1 | 59 | A |
| 42 | D | OD2 | 9.8 | 15.5 | 33.8 | 58 | A |
| 42 | D | C | 7.1 | 17.2 | 30.7 | 61 | A |
| 42 | D | O | 7.1 | 18.4 | 30.6 | 62 | A |
| 43 | N | N | 6.0 | 16.5 | 30.8 | 60 | A |
| 43 | N | CA | 4.7 | 17.2 | 30.9 | 60 | A |
| 43 | N | CB | 3.6 | 16.3 | 30.4 | 60 | A |
| 43 | N | CG | 3.6 | 16.1 | 28.9 | 60 | A |
| 43 | N | OD1 | 3.5 | 17.0 | 28.2 | 60 | A |
| 43 | N | ND2 | 3.8 | 14.8 | 28.5 | 59 | A |
| 43 | N | C | 4.5 | 17.5 | 32.4 | 60 | A |
| 43 | N | O | 3.6 | 18.3 | 32.7 | 61 | A |
| 44 | L | N | 5.3 | 17.0 | 33.3 | 60 | A |
| 44 | L | CA | 5.2 | 17.3 | 34.7 | 59 | A |
| 44 | L | CB | 5.8 | 16.1 | 35.5 | 57 | A |
| 44 | L | CG | 6.0 | 16.3 | 37.0 | 57 | A |
| 44 | L | CD1 | 4.9 | 17.2 | 37.6 | 57 | A |
| 44 | L | CD2 | 6.2 | 15.0 | 37.7 | 55 | A |
| 44 | L | C | 6.0 | 18.5 | 35.0 | 59 | A |
| 44 | L | O | 5.5 | 19.5 | 35.6 | 60 | A |
| 45 | N | N | 7.3 | 18.5 | 34.7 | 58 | A |
| 45 | N | CA | 8.2 | 19.7 | 35.0 | 56 | A |
| 45 | N | CB | 9.6 | 19.3 | 35.3 | 55 | A |
| 45 | N | CG | 9.6 | 18.3 | 36.5 | 53 | A |
| 45 | N | OD1 | 8.9 | 18.4 | 37.5 | 53 | A |
| 45 | N | ND2 | 10.5 | 17.3 | 36.4 | 53 | A |
| 45 | N | C | 8.2 | 20.6 | 33.8 | 56 | A |
| 45 | N | O | 9.1 | 21.4 | 33.6 | 57 | A |
| 46 | K | N | 7.2 | 20.5 | 32.9 | 56 | A |
| 46 | K | CA | 7.1 | 21.3 | 31.7 | 57 | A |
| 46 | K | CB | 6.2 | 22.5 | 31.9 | 58 | A |
| 46 | K | CG | 4.8 | 22.2 | 32.4 | 60 | A |
| 46 | K | CD | 4.7 | 21.8 | 33.8 | 60 | A |
| 46 | K | CE | 3.3 | 21.7 | 34.3 | 60 | A |
| 46 | K | NZ | 2.4 | 20.8 | 33.5 | 60 | A |
| 46 | K | C | 8.4 | 21.7 | 31.0 | 57 | A |
| 46 | K | O | 8.5 | 22.7 | 30.3 | 56 | A |
| 47 | V | N | 9.5 | 20.9 | 31.1 | 55 | A |
| 47 | V | CA | 10.7 | 21.2 | 30.5 | 54 | A |
| 47 | V | CB | 11.8 | 21.5 | 31.6 | 54 | A |
| 47 | V | CG1 | 11.6 | 22.8 | 32.2 | 55 | A |
| 47 | V | CG2 | 11.9 | 20.3 | 32.6 | 54 | A |
| 47 | V | C | 11.2 | 20.1 | 29.6 | 53 | A |
| 47 | V | O | 11.0 | 18.9 | 29.9 | 53 | A |
| 48 | R | N | 11.8 | 20.4 | 28.5 | 52 | A |
| 48 | R | CA | 12.3 | 19.4 | 27.6 | 52 | A |
| 48 | R | CB | 12.6 | 20.0 | 26.2 | 53 | A |
| 48 | R | CG | 11.4 | 20.3 | 25.4 | 52 | A |
| 48 | R | CD | 11.7 | 20.7 | 24.0 | 53 | A |
| 48 | R | NE | 12.2 | 19.6 | 23.1 | 53 | A |
| 48 | R | CZ | 11.6 | 18.5 | 22.8 | 54 | A |
| 48 | R | NH1 | 10.3 | 18.4 | 23.3 | 53 | A |
| 48 | R | NH2 | 12.1 | 17.6 | 22.1 | 53 | A |
| 48 | R | C | 13.6 | 18.8 | 28.2 | 52 | A |
| 48 | R | O | 14.5 | 19.6 | 28.4 | 53 | A |
| 49 | V | N | 13.6 | 17.6 | 28.5 | 51 | A |
| 49 | V | CA | 14.7 | 16.9 | 29.1 | 48 | A |
| 49 | V | CB | 14.3 | 15.9 | 30.2 | 48 | A |
| 49 | V | CG1 | 13.7 | 16.7 | 31.4 | 48 | A |
| 49 | V | CG2 | 13.2 | 14.9 | 29.7 | 48 | A |
| 49 | V | C | 15.4 | 16.1 | 28.0 | 47 | A |
| 49 | V | O | 15.2 | 16.3 | 26.8 | 46 | A |
| 50 | A | N | 16.3 | 15.2 | 28.4 | 45 | A |
| 50 | A | CA | 17.1 | 14.4 | 27.5 | 42 | A |
| 50 | A | CB | 18.5 | 14.8 | 27.5 | 42 | A |
| 50 | A | C | 16.9 | 13.0 | 28.0 | 39 | A |
| 50 | A | O | 16.9 | 12.7 | 29.2 | 38 | A |
| 51 | I | N | 16.7 | 12.0 | 27.1 | 38 | A |
| 51 | I | CA | 16.5 | 10.6 | 27.5 | 37 | A |
| 51 | I | CB | 15.0 | 10.2 | 27.4 | 37 | A |
| 51 | I | CG2 | 14.8 | 8.8 | 27.9 | 34 | A |
| 51 | I | CG1 | 14.2 | 11.2 | 28.2 | 35 | A |
| 51 | I | CD1 | 12.7 | 10.9 | 28.1 | 38 | A |
| 51 | I | C | 17.3 | 9.7 | 26.6 | 37 | A |
| 51 | I | O | 17.4 | 9.9 | 25.4 | 37 | A |
| 52 | K | N | 18.0 | 8.7 | 27.2 | 37 | A |
| 52 | K | CA | 18.7 | 7.7 | 26.4 | 37 | A |
| 52 | K | CB | 20.2 | 7.9 | 26.6 | 39 | A |
| 52 | K | CG | 20.7 | 7.6 | 28.0 | 41 | A |
| 52 | K | CD | 22.0 | 8.4 | 28.2 | 45 | A |
| 52 | K | CE | 22.8 | 8.0 | 29.4 | 49 | A |
| 52 | K | NZ | 23.7 | 6.8 | 29.1 | 50 | A |
| 52 | K | C | 18.2 | 6.3 | 26.6 | 35 | A |
| 52 | K | O | 18.0 | 5.9 | 27.8 | 32 | A |
| 53 | K | N | 17.9 | 5.6 | 25.6 | 35 | A |
| 53 | K | CA | 17.4 | 4.3 | 25.6 | 36 | A |
| 53 | K | CB | 16.6 | 3.9 | 24.4 | 36 | A |
| 53 | K | CG | 15.8 | 2.6 | 24.5 | 37 | A |
| 53 | K | CD | 15.1 | 2.3 | 23.2 | 36 | A |
| 53 | K | CE | 14.7 | 0.9 | 23.1 | 36 | A |
| 53 | K | NZ | 14.2 | 0.6 | 21.7 | 35 | A |
| 53 | K | C | 18.6 | 3.3 | 25.7 | 36 | A |
| 53 | K | O | 19.5 | 3.4 | 24.9 | 35 | A |
| 54 | I | N | 18.6 | 2.5 | 26.7 | 37 | A |
| 54 | I | CA | 19.8 | 1.6 | 26.9 | 37 | A |
| 54 | I | CB | 20.5 | 2.0 | 28.2 | 36 | A |
| 54 | I | CG2 | 21.8 | 1.1 | 28.4 | 34 | A |
| 54 | I | CG1 | 20.9 | 3.4 | 28.1 | 36 | A |
| 54 | I | CD1 | 21.6 | 4.0 | 29.4 | 38 | A |
| 54 | I | C | 19.3 | 0.1 | 27.0 | 37 | A |
| 54 | I | O | 18.5 | −0.2 | 27.9 | 39 | A |
| 55 | S | N | 19.8 | −0.7 | 26.1 | 40 | A |
| 55 | S | CA | 19.4 | −2.1 | 26.0 | 43 | A |
| 55 | S | CB | 18.8 | −2.4 | 24.7 | 43 | A |
| 55 | S | OG | 17.9 | −1.3 | 24.3 | 41 | A |
| 55 | S | C | 20.7 | −2.9 | 26.1 | 44 | A |
| 55 | S | O | 21.3 | −3.3 | 25.1 | 46 | A |
| 56 | P | N | 21.2 | −3.1 | 27.4 | 45 | A |
| 56 | P | CD | 20.8 | −2.4 | 28.6 | 45 | A |
| 56 | P | CA | 22.5 | −3.8 | 27.6 | 45 | A |
| 56 | P | CB | 23.1 | −3.0 | 28.7 | 46 | A |
| 56 | P | CG | 22.0 | −2.7 | 29.6 | 45 | A |
| 56 | P | C | 22.4 | −5.3 | 28.1 | 47 | A |
| 56 | P | O | 23.4 | −6.0 | 27.9 | 48 | A |
| 57 | F | N | 21.3 | −5.7 | 28.6 | 48 | A |
| 57 | F | CA | 21.1 | −7.0 | 29.1 | 49 | A |
| 57 | F | CB | 19.6 | −7.2 | 29.4 | 49 | A |
| 57 | F | CG | 19.1 | −6.1 | 30.3 | 50 | A |
| 57 | F | CD1 | 19.6 | −5.8 | 31.6 | 51 | A |
| 57 | F | CD2 | 18.1 | −5.2 | 29.8 | 51 | A |
| 57 | F | CE1 | 19.1 | −4.8 | 32.3 | 51 | A |
| 57 | F | CE2 | 17.7 | −4.1 | 30.5 | 51 | A |
| 57 | F | CZ | 18.2 | −3.9 | 31.8 | 50 | A |
| 57 | F | C | 21.6 | −8.2 | 28.3 | 49 | A |
| 57 | F | O | 21.6 | −9.3 | 28.8 | 50 | A |
| 58 | E | N | 22.1 | −8.0 | 27.1 | 50 | A |
| 58 | E | CA | 22.6 | −9.1 | 26.3 | 51 | A |
| 58 | E | CB | 22.5 | −8.7 | 24.8 | 53 | A |

TABLE 3-continued

Structural Coordinates of Ah₆-ERK2 [di-thiophosphorylated, SEQ ID NO: 5] Crystals The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 58 | E | CG  | 21.1 | -8.4  | 24.3 | 56 | A |
|----|---|-----|------|-------|------|----|---|
| 58 | E | CD  | 20.2 | -9.6  | 24.3 | 58 | A |
| 58 | E | OE1 | 20.4 | -10.5 | 23.5 | 59 | A |
| 58 | E | OE2 | 19.2 | -9.6  | 25.1 | 58 | A |
| 58 | E | C   | 24.1 | -9.5  | 26.6 | 51 | A |
| 58 | E | O   | 24.4 | -10.6 | 26.6 | 51 | A |
| 59 | H | N   | 24.9 | -8.5  | 27.0 | 50 | A |
| 59 | H | CA  | 26.3 | -8.7  | 27.3 | 49 | A |
| 59 | H | CB  | 27.2 | -8.0  | 26.4 | 51 | A |
| 59 | H | CG  | 26.9 | -8.2  | 24.9 | 54 | A |
| 59 | H | CD2 | 27.6 | -8.8  | 24.0 | 54 | A |
| 59 | H | ND1 | 25.7 | -7.8  | 24.3 | 54 | A |
| 59 | H | CE1 | 25.7 | -8.1  | 23.1 | 55 | A |
| 59 | H | NE2 | 26.9 | -8.8  | 22.8 | 56 | A |
| 59 | H | C   | 26.6 | -8.3  | 28.8 | 48 | A |
| 59 | H | O   | 26.0 | -7.4  | 29.3 | 48 | A |
| 60 | Q | N   | 27.5 | -9.0  | 29.4 | 47 | A |
| 60 | Q | CA  | 27.9 | -8.7  | 30.8 | 46 | A |
| 60 | Q | CB  | 28.9 | -9.8  | 31.3 | 45 | A |
| 60 | Q | CG  | 29.6 | -9.3  | 32.6 | 46 | A |
| 60 | Q | CD  | 30.9 | -10.0 | 32.8 | 46 | A |
| 60 | Q | OE1 | 31.8 | -10.0 | 32.0 | 48 | A |
| 60 | Q | NE2 | 31.1 | -10.6 | 34.0 | 46 | A |
| 60 | Q | C   | 28.6 | -7.3  | 30.9 | 46 | A |
| 60 | Q | O   | 28.3 | -6.6  | 31.8 | 48 | A |
| 61 | T | N   | 29.5 | -7.0  | 30.0 | 46 | A |
| 61 | T | CA  | 30.2 | -5.8  | 30.1 | 47 | A |
| 61 | T | CB  | 31.4 | -5.7  | 29.1 | 45 | A |
| 61 | T | OG1 | 31.0 | -5.9  | 27.8 | 50 | A |
| 61 | T | CG2 | 32.4 | -6.9  | 29.5 | 44 | A |
| 61 | T | C   | 29.3 | -4.6  | 29.8 | 47 | A |
| 61 | T | O   | 29.5 | -3.5  | 30.3 | 48 | A |
| 62 | Y | N   | 28.2 | -4.8  | 29.0 | 46 | A |
| 62 | Y | CA  | 27.3 | -3.8  | 28.8 | 46 | A |
| 62 | Y | CB  | 26.3 | -4.3  | 27.7 | 49 | A |
| 62 | Y | CG  | 26.8 | -4.1  | 26.3 | 51 | A |
| 62 | Y | CD1 | 28.2 | -4.1  | 26.0 | 51 | A |
| 62 | Y | CE1 | 28.7 | -4.0  | 24.7 | 52 | A |
| 62 | Y | CD2 | 26.0 | -4.0  | 25.2 | 51 | A |
| 62 | Y | CE2 | 26.5 | -3.9  | 23.9 | 51 | A |
| 62 | Y | CZ  | 27.8 | -3.8  | 23.7 | 51 | A |
| 62 | Y | OH  | 28.3 | -3.7  | 22.4 | 51 | A |
| 62 | Y | C   | 26.5 | -3.6  | 30.1 | 45 | A |
| 62 | Y | O   | 26.2 | -2.5  | 30.4 | 44 | A |
| 63 | C | N   | 26.2 | -4.7  | 30.8 | 43 | A |
| 63 | C | CA  | 25.5 | -4.6  | 32.1 | 41 | A |
| 63 | C | CB  | 25.1 | -6.0  | 32.5 | 42 | A |
| 63 | C | SG  | 23.7 | -6.7  | 31.6 | 41 | A |
| 63 | C | C   | 26.4 | -4.0  | 33.2 | 40 | A |
| 63 | C | O   | 25.8 | -3.1  | 33.9 | 39 | A |
| 64 | Q | N   | 27.6 | -4.3  | 33.2 | 39 | A |
| 64 | Q | CA  | 28.6 | -3.7  | 34.2 | 38 | A |
| 64 | Q | CB  | 30.0 | -4.2  | 34.0 | 39 | A |
| 64 | Q | CG  | 30.3 | -5.6  | 34.6 | 42 | A |
| 64 | Q | CD  | 31.8 | -5.9  | 34.4 | 44 | A |
| 64 | Q | OE1 | 32.3 | -5.9  | 33.2 | 45 | A |
| 64 | Q | NE2 | 32.5 | -6.2  | 35.4 | 44 | A |
| 64 | Q | C   | 28.6 | -2.2  | 34.2 | 37 | A |
| 64 | Q | O   | 28.4 | -1.6  | 35.2 | 37 | A |
| 65 | R | N   | 28.7 | -1.7  | 33.0 | 36 | A |
| 65 | R | CA  | 28.8 | -0.3  | 32.7 | 37 | A |
| 65 | R | CB  | 29.3 | 0.0   | 31.3 | 36 | A |
| 65 | R | CG  | 30.7 | -0.5  | 31.1 | 37 | A |
| 65 | R | CD  | 31.2 | -0.4  | 29.7 | 38 | A |
| 65 | R | NE  | 32.6 | -0.7  | 29.6 | 40 | A |
| 65 | R | CZ  | 33.3 | -0.8  | 28.4 | 41 | A |
| 65 | R | NH1 | 32.7 | -0.5  | 27.3 | 38 | A |
| 65 | R | NH2 | 34.6 | -1.2  | 28.5 | 38 | A |
| 65 | R | C   | 27.5 | 0.5   | 33.0 | 37 | A |
| 65 | R | O   | 27.5 | 1.6   | 33.4 | 39 | A |
| 66 | T | N   | 26.4 | -0.2  | 32.7 | 37 | A |
| 66 | T | CA  | 25.1 | 0.4   | 32.9 | 35 | A |
| 66 | T | CB  | 24.0 | -0.5  | 32.3 | 35 | A |
| 66 | T | OG1 | 24.1 | -0.5  | 30.9 | 35 | A |
| 66 | T | CG2 | 22.6 | -0.0  | 32.7 | 33 | A |
| 66 | T | C   | 24.8 | 0.5   | 34.4 | 34 | A |
| 66 | T | O   | 24.3 | 1.6   | 34.9 | 35 | A |
| 67 | L | N   | 25.2 | -0.5  | 35.2 | 32 | A |
| 67 | L | CA  | 25.0 | -0.5  | 36.7 | 31 | A |
| 67 | L | CB  | 25.3 | -1.9  | 37.2 | 30 | A |
| 67 | L | CG  | 24.6 | -2.5  | 38.5 | 31 | A |
| 67 | L | CD1 | 25.6 | -2.5  | 39.6 | 29 | A |
| 67 | L | CD2 | 23.4 | -1.7  | 38.9 | 28 | A |
| 67 | L | C   | 25.9 | 0.5   | 37.3 | 32 | A |
| 67 | L | O   | 25.5 | 1.3   | 38.2 | 30 | A |
| 68 | R | N   | 27.2 | 0.6   | 36.8 | 31 | A |
| 68 | R | CA  | 28.1 | 1.5   | 37.3 | 28 | A |
| 68 | R | CB  | 29.5 | 1.4   | 36.6 | 24 | A |
| 68 | R | CG  | 30.3 | 0.2   | 37.2 | 23 | A |
| 68 | R | CD  | 31.5 | -0.2  | 36.3 | 20 | A |
| 68 | R | NE  | 32.3 | -1.3  | 36.8 | 18 | A |
| 68 | R | CZ  | 33.3 | -1.9  | 36.2 | 19 | A |
| 68 | R | NH1 | 33.7 | -1.4  | 35.0 | 17 | A |
| 68 | R | NH2 | 33.9 | -2.9  | 36.8 | 19 | A |
| 68 | R | C   | 27.7 | 3.0   | 37.1 | 26 | A |
| 68 | R | O   | 27.6 | 3.7   | 38.1 | 25 | A |
| 69 | E | N   | 27.4 | 3.4   | 35.9 | 27 | A |
| 69 | E | CA  | 26.9 | 4.7   | 35.6 | 28 | A |
| 69 | E | CB  | 26.5 | 4.9   | 34.2 | 30 | A |
| 69 | E | CG  | 25.8 | 6.2   | 33.9 | 33 | A |
| 69 | E | CD  | 26.0 | 6.6   | 32.4 | 35 | A |
| 69 | E | OE1 | 25.6 | 5.8   | 31.5 | 36 | A |
| 69 | E | OE2 | 26.5 | 7.7   | 32.2 | 34 | A |
| 69 | E | C   | 25.8 | 5.1   | 36.5 | 29 | A |
| 69 | E | O   | 25.8 | 6.2   | 37.1 | 30 | A |
| 70 | I | N   | 24.8 | 4.2   | 36.7 | 26 | A |
| 70 | I | CA  | 23.6 | 4.4   | 37.5 | 25 | A |
| 70 | I | CB  | 22.6 | 3.3   | 37.3 | 25 | A |
| 70 | I | CG2 | 21.4 | 3.4   | 38.3 | 22 | A |
| 70 | I | CG1 | 22.1 | 3.2   | 35.9 | 22 | A |
| 70 | I | CD1 | 21.3 | 2.0   | 35.6 | 20 | A |
| 70 | I | C   | 23.9 | 4.6   | 39.0 | 25 | A |
| 70 | I | O   | 23.5 | 5.6   | 39.6 | 28 | A |
| 71 | K | N   | 24.6 | 3.6   | 39.6 | 25 | A |
| 71 | K | CA  | 24.9 | 3.7   | 41.0 | 28 | A |
| 71 | K | CB  | 25.7 | 2.5   | 41.5 | 30 | A |
| 71 | K | CG  | 24.9 | 1.2   | 41.4 | 33 | A |
| 71 | K | CD  | 25.6 | -0.0  | 41.9 | 34 | A |
| 71 | K | CE  | 26.0 | 0.1   | 43.4 | 37 | A |
| 71 | K | NZ  | 26.6 | -1.2  | 43.9 | 38 | A |
| 71 | K | C   | 25.7 | 5.0   | 41.3 | 29 | A |
| 71 | K | O   | 25.4 | 5.8   | 42.2 | 29 | A |
| 72 | I | N   | 26.7 | 5.2   | 40.5 | 27 | A |
| 72 | I | CA  | 27.5 | 6.4   | 40.6 | 26 | A |
| 72 | I | CB  | 28.7 | 6.4   | 39.6 | 26 | A |
| 72 | I | CG2 | 29.4 | 7.9   | 39.6 | 22 | A |
| 72 | I | CG1 | 29.7 | 5.4   | 40.0 | 22 | A |
| 72 | I | CD1 | 30.7 | 5.0   | 38.9 | 23 | A |
| 72 | I | C   | 26.7 | 7.7   | 40.5 | 25 | A |
| 72 | I | O   | 26.8 | 8.6   | 41.4 | 25 | A |
| 73 | L | N   | 26.1 | 7.9   | 39.3 | 24 | A |
| 73 | L | CA  | 25.3 | 9.1   | 39.0 | 26 | A |
| 73 | L | CB  | 24.8 | 9.1   | 37.6 | 25 | A |
| 73 | L | CG  | 25.4 | 10.1  | 36.7 | 25 | A |
| 73 | L | CD1 | 26.9 | 10.3  | 36.9 | 22 | A |
| 73 | L | CD2 | 25.1 | 9.8   | 35.2 | 22 | A |
| 73 | L | C   | 24.1 | 9.3   | 39.9 | 27 | A |
| 73 | L | O   | 23.6 | 10.4  | 40.1 | 29 | A |

TABLE 3-continued

Structural Coordinates of Ah₆-ERK2 [di-thiophosphorylated, SEQ ID NO: 5] Crystals The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | | |
|---|---|---|---|---|---|---|---|
| 74 | L | N   | 23.6 | 8.2  | 40.5 | 27 | A |
| 74 | L | CA  | 22.4 | 8.3  | 41.4 | 29 | A |
| 74 | L | CB  | 21.8 | 6.9  | 41.6 | 27 | A |
| 74 | L | CG  | 20.3 | 6.7  | 41.3 | 30 | A |
| 74 | L | CD1 | 19.8 | 7.7  | 40.2 | 24 | A |
| 74 | L | CD2 | 20.1 | 5.3  | 40.8 | 30 | A |
| 74 | L | C   | 22.9 | 8.8  | 42.8 | 29 | A |
| 74 | L | O   | 22.2 | 9.6  | 43.4 | 29 | A |
| 75 | R | N   | 24.1 | 8.5  | 43.1 | 30 | A |
| 75 | R | CA  | 24.7 | 9.0  | 44.4 | 31 | A |
| 75 | R | CB  | 25.8 | 8.0  | 44.9 | 34 | A |
| 75 | R | CG  | 26.3 | 8.4  | 46.3 | 38 | A |
| 75 | R | CD  | 27.3 | 7.5  | 46.9 | 40 | A |
| 75 | R | NE  | 26.7 | 6.2  | 47.2 | 42 | A |
| 75 | R | CZ  | 27.3 | 5.3  | 48.0 | 43 | A |
| 75 | R | NH1 | 28.4 | 5.5  | 48.6 | 44 | A |
| 75 | R | NH2 | 26.7 | 4.1  | 48.3 | 42 | A |
| 75 | R | C   | 25.3 | 10.4 | 44.3 | 30 | A |
| 75 | R | O   | 25.2 | 11.2 | 45.3 | 29 | A |
| 76 | F | N   | 25.9 | 10.7 | 43.2 | 27 | A |
| 76 | F | CA  | 26.6 | 12.0 | 43.0 | 26 | A |
| 76 | F | CB  | 27.3 | 12.0 | 41.7 | 23 | A |
| 76 | F | CG  | 28.7 | 11.4 | 41.8 | 22 | A |
| 76 | F | CD1 | 29.1 | 10.7 | 42.9 | 19 | A |
| 76 | F | CD2 | 29.5 | 11.4 | 40.7 | 21 | A |
| 76 | F | CE1 | 30.3 | 10.1 | 43.0 | 21 | A |
| 76 | F | CE2 | 30.8 | 10.8 | 40.8 | 22 | A |
| 76 | F | CZ  | 31.2 | 10.2 | 41.9 | 20 | A |
| 76 | F | C   | 25.6 | 13.2 | 43.0 | 26 | A |
| 76 | F | O   | 24.5 | 13.1 | 42.5 | 26 | A |
| 77 | R | N   | 26.0 | 14.3 | 43.6 | 28 | A |
| 77 | R | CA  | 25.2 | 15.5 | 43.7 | 29 | A |
| 77 | R | CB  | 24.6 | 15.6 | 45.1 | 34 | A |
| 77 | R | CG  | 25.6 | 15.7 | 46.2 | 42 | A |
| 77 | R | CD  | 25.4 | 14.7 | 47.4 | 48 | A |
| 77 | R | NE  | 26.6 | 14.0 | 47.7 | 53 | A |
| 77 | R | CZ  | 27.7 | 14.5 | 48.2 | 55 | A |
| 77 | R | NH1 | 27.8 | 15.8 | 48.5 | 57 | A |
| 77 | R | NH2 | 28.8 | 13.8 | 48.5 | 55 | A |
| 77 | R | C   | 26.1 | 16.8 | 43.5 | 26 | A |
| 77 | R | O   | 26.7 | 17.3 | 44.5 | 25 | A |
| 78 | H | N   | 26.3 | 17.2 | 42.3 | 24 | A |
| 78 | H | CA  | 27.2 | 18.3 | 42.0 | 22 | A |
| 78 | H | CB  | 28.7 | 17.8 | 41.8 | 19 | A |
| 78 | H | CG  | 29.7 | 18.8 | 41.7 | 21 | A |
| 78 | H | CD2 | 30.1 | 19.7 | 40.8 | 18 | A |
| 78 | H | ND1 | 30.5 | 19.1 | 42.8 | 21 | A |
| 78 | H | CE1 | 31.4 | 20.0 | 42.5 | 20 | A |
| 78 | H | NE2 | 31.1 | 20.4 | 41.3 | 22 | A |
| 78 | H | C   | 26.8 | 19.1 | 40.8 | 22 | A |
| 78 | H | O   | 26.3 | 18.6 | 39.8 | 21 | A |
| 79 | E | N   | 27.0 | 20.4 | 40.9 | 21 | A |
| 79 | E | CA  | 26.6 | 21.4 | 39.8 | 21 | A |
| 79 | E | CB  | 26.9 | 22.8 | 40.2 | 23 | A |
| 79 | E | CG  | 26.1 | 23.3 | 41.4 | 27 | A |
| 79 | E | CD  | 26.5 | 24.7 | 41.8 | 30 | A |
| 79 | E | OE1 | 25.7 | 25.4 | 42.4 | 32 | A |
| 79 | E | OE2 | 27.6 | 25.2 | 41.4 | 32 | A |
| 79 | E | C   | 27.3 | 21.1 | 38.5 | 22 | A |
| 79 | E | O   | 26.7 | 21.4 | 37.4 | 21 | A |
| 80 | N | N   | 28.5 | 20.5 | 38.5 | 21 | A |
| 80 | N | CA  | 29.2 | 20.2 | 37.3 | 21 | A |
| 80 | N | CB  | 30.7 | 20.7 | 37.4 | 19 | A |
| 80 | N | CG  | 30.8 | 22.2 | 37.8 | 21 | A |
| 80 | N | OD1 | 31.3 | 22.5 | 38.9 | 22 | A |
| 80 | N | ND2 | 30.2 | 23.1 | 37.0 | 15 | A |
| 80 | N | C   | 29.2 | 18.8 | 36.8 | 22 | A |
| 80 | N | O   | 30.0 | 18.3 | 36.0 | 22 | A |
| 81 | I | N   | 28.2 | 18.0 | 37.4 | 20 | A |
| 81 | I | CA  | 28.1 | 16.6 | 37.0 | 18 | A |
| 81 | I | CB  | 28.4 | 15.7 | 38.2 | 20 | A |
| 81 | I | CG2 | 28.2 | 14.2 | 37.8 | 15 | A |
| 81 | I | CG1 | 29.9 | 15.9 | 38.6 | 18 | A |
| 81 | I | CD1 | 30.4 | 15.0 | 39.7 | 18 | A |
| 81 | I | C   | 26.6 | 16.3 | 36.6 | 18 | A |
| 81 | I | O   | 25.7 | 16.5 | 37.5 | 15 | A |
| 82 | I | N   | 26.4 | 15.9 | 35.4 | 19 | A |
| 82 | I | CA  | 25.0 | 15.6 | 35.0 | 21 | A |
| 82 | I | CB  | 25.0 | 14.9 | 33.6 | 22 | A |
| 82 | I | CG2 | 25.5 | 13.5 | 33.6 | 20 | A |
| 82 | I | CG1 | 23.5 | 15.0 | 33.0 | 23 | A |
| 82 | I | CD1 | 22.9 | 16.4 | 33.0 | 23 | A |
| 82 | I | C   | 24.4 | 14.6 | 36.0 | 21 | A |
| 82 | I | O   | 25.1 | 13.7 | 36.6 | 22 | A |
| 83 | G | N   | 23.1 | 14.7 | 36.3 | 24 | A |
| 83 | G | CA  | 22.5 | 13.8 | 37.2 | 26 | A |
| 83 | G | C   | 21.3 | 13.0 | 36.5 | 29 | A |
| 83 | G | O   | 21.0 | 13.3 | 35.3 | 30 | A |
| 84 | I | N   | 20.8 | 12.0 | 37.1 | 31 | A |
| 84 | I | CA  | 19.6 | 11.3 | 36.6 | 31 | A |
| 84 | I | CB  | 19.8 | 9.8  | 36.8 | 32 | A |
| 84 | I | CG2 | 18.6 | 9.0  | 36.2 | 31 | A |
| 84 | I | CG1 | 21.1 | 9.3  | 36.2 | 29 | A |
| 84 | I | CD1 | 21.3 | 7.8  | 36.4 | 28 | A |
| 84 | I | C   | 18.4 | 11.8 | 37.2 | 32 | A |
| 84 | I | O   | 18.2 | 11.5 | 38.4 | 33 | A |
| 85 | N | N   | 17.5 | 12.4 | 36.5 | 34 | A |
| 85 | N | CA  | 16.2 | 12.9 | 37.1 | 36 | A |
| 85 | N | CB  | 15.7 | 14.1 | 36.3 | 35 | A |
| 85 | N | CG  | 16.8 | 15.0 | 35.8 | 37 | A |
| 85 | N | OD1 | 17.8 | 15.2 | 36.5 | 35 | A |
| 85 | N | ND2 | 16.6 | 15.6 | 34.6 | 37 | A |
| 85 | N | C   | 15.1 | 11.8 | 37.2 | 38 | A |
| 85 | N | O   | 14.2 | 12.0 | 38.0 | 39 | A |
| 86 | D | N   | 15.2 | 10.7 | 36.4 | 38 | A |
| 86 | D | CA  | 14.2 | 9.7  | 36.4 | 38 | A |
| 86 | D | CB  | 12.9 | 10.3 | 35.9 | 35 | A |
| 86 | D | CG  | 11.7 | 9.3  | 36.0 | 35 | A |
| 86 | D | OD1 | 11.7 | 8.4  | 36.8 | 33 | A |
| 86 | D | OD2 | 10.8 | 9.5  | 35.1 | 36 | A |
| 86 | D | C   | 14.7 | 8.5  | 35.6 | 39 | A |
| 86 | D | O   | 15.5 | 8.6  | 34.7 | 41 | A |
| 87 | I | N   | 14.1 | 7.3  | 35.8 | 39 | A |
| 87 | I | CA  | 14.4 | 6.1  | 35.1 | 40 | A |
| 87 | I | CB  | 15.4 | 5.2  | 35.9 | 38 | A |
| 87 | I | CG2 | 15.6 | 3.9  | 35.1 | 37 | A |
| 87 | I | CG1 | 16.8 | 6.0  | 36.0 | 37 | A |
| 87 | I | CD1 | 17.8 | 5.2  | 36.7 | 36 | A |
| 87 | I | C   | 13.1 | 5.3  | 34.8 | 42 | A |
| 87 | I | O   | 12.5 | 4.8  | 35.8 | 41 | A |
| 88 | I | N   | 12.8 | 5.1  | 33.6 | 43 | A |
| 88 | I | CA  | 11.7 | 4.3  | 33.1 | 44 | A |
| 88 | I | CB  | 10.9 | 5.0  | 32.0 | 44 | A |
| 88 | I | CG2 | 9.9  | 4.1  | 31.4 | 44 | A |
| 88 | I | CG1 | 10.3 | 6.3  | 32.5 | 43 | A |
| 88 | I | CD1 | 9.6  | 7.2  | 31.4 | 43 | A |
| 88 | I | C   | 12.1 | 2.9  | 32.7 | 45 | A |
| 88 | I | O   | 12.8 | 2.8  | 31.7 | 44 | A |
| 89 | R | N   | 11.5 | 1.9  | 33.3 | 46 | A |
| 89 | R | CA  | 11.8 | 0.5  | 32.9 | 47 | A |
| 89 | R | CB  | 13.1 | -0.0 | 33.6 | 48 | A |
| 89 | R | CG  | 13.2 | 0.1  | 35.1 | 47 | A |
| 89 | R | CD  | 12.2 | -0.9 | 35.8 | 48 | A |
| 89 | R | NE  | 12.6 | -1.1 | 37.2 | 51 | A |
| 89 | R | CZ  | 11.8 | -1.7 | 38.1 | 51 | A |
| 89 | R | NH1 | 10.7 | -2.2 | 37.7 | 52 | A |
| 89 | R | NH2 | 12.3 | -1.8 | 39.4 | 49 | A |
| 89 | R | C   | 10.6 | -0.4 | 33.3 | 49 | A |

TABLE 3-continued

Structural Coordinates of Ah$_6$-ERK2 [di-thiophosphorylated, SEQ ID NO: 5] Crystals The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| Res | AA | Atom | x | y | z | B | Chain |
|---|---|---|---|---|---|---|---|
| 89 | R | O | 9.8 | −0.1 | 34.2 | 49 | A |
| 90 | A | N | 10.4 | −1.5 | 32.6 | 50 | A |
| 90 | A | CA | 9.3 | −2.4 | 32.8 | 51 | A |
| 90 | A | CB | 9.6 | −3.7 | 32.0 | 51 | A |
| 90 | A | C | 9.0 | −2.8 | 34.3 | 52 | A |
| 90 | A | O | 9.9 | −2.9 | 35.1 | 52 | A |
| 91 | P | N | 7.7 | −2.9 | 34.6 | 52 | A |
| 91 | P | CD | 6.6 | −2.7 | 33.6 | 53 | A |
| 91 | P | CA | 7.2 | −3.2 | 35.9 | 52 | A |
| 91 | P | CB | 5.7 | −3.3 | 35.7 | 52 | A |
| 91 | P | CG | 5.4 | −2.4 | 34.6 | 52 | A |
| 91 | P | C | 7.8 | −4.5 | 36.4 | 52 | A |
| 91 | P | O | 8.0 | −4.7 | 37.6 | 51 | A |
| 92 | T | N | 8.0 | −5.5 | 35.5 | 52 | A |
| 92 | T | CA | 8.5 | −6.8 | 35.9 | 55 | A |
| 92 | T | CB | 7.5 | −7.9 | 35.6 | 55 | A |
| 92 | T | OG1 | 7.5 | −8.1 | 34.1 | 56 | A |
| 92 | T | CG2 | 6.1 | −7.6 | 36.0 | 55 | A |
| 92 | T | C | 9.8 | −7.0 | 35.2 | 56 | A |
| 92 | T | O | 9.9 | −6.7 | 34.0 | 56 | A |
| 93 | I | N | 10.8 | −7.6 | 35.9 | 56 | A |
| 93 | I | CA | 12.1 | −7.9 | 35.3 | 57 | A |
| 93 | I | CB | 12.9 | −8.7 | 36.3 | 58 | A |
| 93 | I | CG2 | 12.3 | −10.0 | 36.5 | 57 | A |
| 93 | I | CG1 | 14.4 | −8.9 | 35.7 | 58 | A |
| 93 | I | CD1 | 15.4 | −9.4 | 36.7 | 59 | A |
| 93 | I | C | 12.1 | −8.5 | 33.9 | 57 | A |
| 93 | I | O | 12.8 | −8.1 | 33.0 | 57 | A |
| 94 | E | N | 11.3 | −9.6 | 33.8 | 57 | A |
| 94 | E | CA | 11.2 | −10.3 | 32.5 | 56 | A |
| 94 | E | CB | 10.1 | −11.4 | 32.5 | 56 | A |
| 94 | E | CG | 10.5 | −12.6 | 33.3 | 56 | A |
| 94 | E | CD | 10.6 | −12.4 | 34.8 | 57 | A |
| 94 | E | OE1 | 9.7 | −11.7 | 35.4 | 55 | A |
| 94 | E | OE2 | 11.5 | −12.9 | 35.4 | 56 | A |
| 94 | E | C | 10.8 | −9.3 | 31.4 | 55 | A |
| 94 | E | O | 11.3 | −9.4 | 30.3 | 55 | A |
| 95 | Q | N | 10.0 | −8.3 | 31.7 | 56 | A |
| 95 | Q | CA | 9.5 | −7.4 | 30.7 | 56 | A |
| 95 | Q | CB | 8.3 | −6.7 | 31.1 | 58 | A |
| 95 | Q | CG | 7.1 | −7.6 | 31.4 | 60 | A |
| 95 | Q | CD | 5.8 | −6.8 | 31.8 | 60 | A |
| 95 | Q | OE1 | 5.2 | −6.1 | 31.0 | 62 | A |
| 95 | Q | NE2 | 5.5 | −6.9 | 33.1 | 60 | A |
| 95 | Q | C | 10.6 | −6.3 | 30.4 | 55 | A |
| 95 | Q | O | 10.5 | −5.5 | 29.5 | 57 | A |
| 96 | M | N | 11.6 | −6.2 | 31.3 | 53 | A |
| 96 | M | CA | 12.7 | −5.2 | 31.1 | 51 | A |
| 96 | M | CB | 13.3 | −4.9 | 32.5 | 50 | A |
| 96 | M | CG | 14.4 | −3.8 | 32.5 | 47 | A |
| 96 | M | SD | 15.0 | −3.5 | 34.1 | 44 | A |
| 96 | M | CE | 16.0 | −4.9 | 34.4 | 42 | A |
| 96 | M | C | 13.7 | −5.6 | 30.1 | 50 | A |
| 96 | M | O | 14.6 | −6.5 | 30.3 | 48 | A |
| 97 | K | N | 13.7 | −5.0 | 28.9 | 51 | A |
| 97 | K | CA | 14.6 | −5.2 | 27.9 | 52 | A |
| 97 | K | CB | 13.9 | −5.5 | 26.6 | 54 | A |
| 97 | K | CG | 12.7 | −6.5 | 26.7 | 56 | A |
| 97 | K | CD | 13.3 | −7.9 | 27.0 | 59 | A |
| 97 | K | CE | 12.1 | −8.9 | 27.1 | 60 | A |
| 97 | K | NZ | 12.7 | −10.3 | 27.3 | 61 | A |
| 97 | K | C | 15.4 | −3.9 | 27.7 | 51 | A |
| 97 | K | O | 16.5 | −3.9 | 27.2 | 52 | A |
| 98 | D | N | 14.8 | −2.8 | 28.1 | 49 | A |
| 98 | D | CA | 15.4 | −1.5 | 27.9 | 48 | A |
| 98 | D | CB | 14.7 | −0.8 | 26.8 | 49 | A |
| 98 | D | CG | 14.5 | −1.6 | 25.6 | 50 | A |
| 98 | D | OD1 | 15.5 | −2.1 | 25.0 | 51 | A |
| 98 | D | OD2 | 13.3 | −1.9 | 25.2 | 51 | A |
| 98 | D | C | 15.2 | −0.6 | 29.2 | 47 | A |
| 98 | D | O | 14.4 | −0.9 | 30.0 | 49 | A |
| 99 | V | N | 16.1 | 0.4 | 29.2 | 46 | A |
| 99 | V | CA | 16.0 | 1.3 | 30.3 | 43 | A |
| 99 | V | CB | 17.2 | 1.0 | 31.3 | 43 | A |
| 99 | V | CG1 | 17.1 | 2.0 | 32.5 | 42 | A |
| 99 | V | CG2 | 17.1 | −0.4 | 31.8 | 42 | A |
| 99 | V | C | 16.2 | 2.7 | 29.8 | 42 | A |
| 99 | V | O | 17.1 | 3.0 | 28.9 | 42 | A |
| 100 | Y | N | 15.3 | 3.6 | 30.2 | 39 | A |
| 100 | Y | CA | 15.4 | 5.0 | 29.7 | 38 | A |
| 100 | Y | CB | 14.1 | 5.4 | 29.1 | 38 | A |
| 100 | Y | CG | 13.5 | 4.6 | 28.0 | 37 | A |
| 100 | Y | CD1 | 12.9 | 3.3 | 28.3 | 37 | A |
| 100 | Y | CE1 | 12.4 | 2.5 | 27.3 | 37 | A |
| 100 | Y | CD2 | 13.6 | 4.9 | 26.7 | 37 | A |
| 100 | Y | CE2 | 13.2 | 4.2 | 25.6 | 38 | A |
| 100 | Y | CZ | 12.6 | 2.9 | 25.9 | 38 | A |
| 100 | Y | OH | 12.0 | 2.2 | 24.9 | 40 | A |
| 100 | Y | C | 15.8 | 5.9 | 30.8 | 38 | A |
| 100 | Y | O | 15.0 | 6.2 | 31.8 | 39 | A |
| 101 | I | N | 17.0 | 6.5 | 30.7 | 36 | A |
| 101 | I | CA | 17.5 | 7.4 | 31.7 | 34 | A |
| 101 | I | CB | 19.0 | 7.2 | 32.0 | 34 | A |
| 101 | I | CG2 | 19.5 | 8.1 | 33.1 | 33 | A |
| 101 | I | CG1 | 19.2 | 5.7 | 32.4 | 35 | A |
| 101 | I | CD1 | 20.7 | 5.3 | 32.6 | 34 | A |
| 101 | I | C | 17.2 | 8.8 | 31.3 | 34 | A |
| 101 | I | O | 17.7 | 9.3 | 30.3 | 33 | A |
| 102 | V | N | 16.5 | 9.5 | 32.1 | 34 | A |
| 102 | V | CA | 16.2 | 10.9 | 31.9 | 35 | A |
| 102 | V | CB | 14.7 | 11.3 | 32.4 | 37 | A |
| 102 | V | CG1 | 14.4 | 12.7 | 32.0 | 38 | A |
| 102 | V | CG2 | 13.7 | 10.4 | 31.8 | 37 | A |
| 102 | V | C | 17.2 | 11.8 | 32.6 | 34 | A |
| 102 | V | O | 17.5 | 11.6 | 33.7 | 35 | A |
| 103 | Q | N | 17.7 | 12.8 | 31.8 | 32 | A |
| 103 | Q | CA | 18.6 | 13.8 | 32.4 | 32 | A |
| 103 | Q | CB | 20.1 | 13.3 | 32.0 | 30 | A |
| 103 | Q | CG | 20.5 | 12.0 | 32.5 | 29 | A |
| 103 | Q | CD | 21.9 | 11.6 | 32.1 | 29 | A |
| 103 | Q | OE1 | 22.2 | 11.5 | 30.9 | 29 | A |
| 103 | Q | NE2 | 22.8 | 11.5 | 33.1 | 33 | A |
| 103 | Q | C | 18.3 | 15.1 | 31.8 | 33 | A |
| 103 | Q | O | 17.5 | 15.3 | 30.9 | 33 | A |
| 104 | D | N | 18.9 | 16.2 | 32.4 | 33 | A |
| 104 | D | CA | 18.7 | 17.5 | 31.9 | 33 | A |
| 104 | D | CB | 19.4 | 18.6 | 32.8 | 34 | A |
| 104 | D | CG | 18.8 | 18.7 | 34.2 | 36 | A |
| 104 | D | OD1 | 17.6 | 18.7 | 34.3 | 37 | A |
| 104 | D | OD2 | 19.6 | 18.8 | 35.1 | 36 | A |
| 104 | D | C | 19.2 | 17.7 | 30.5 | 34 | A |
| 104 | D | O | 20.3 | 17.1 | 30.1 | 34 | A |
| 105 | L | N | 18.5 | 18.4 | 29.7 | 34 | A |
| 105 | L | CA | 18.8 | 18.7 | 28.3 | 33 | A |
| 105 | L | CB | 17.6 | 18.9 | 27.5 | 32 | A |
| 105 | L | CG | 17.7 | 19.4 | 26.1 | 33 | A |
| 105 | L | CD1 | 18.5 | 18.3 | 25.3 | 32 | A |
| 105 | L | CD2 | 16.4 | 19.7 | 25.4 | 33 | A |
| 105 | L | C | 19.7 | 19.9 | 28.2 | 34 | A |
| 105 | L | O | 19.2 | 21.0 | 28.4 | 35 | A |
| 106 | M | N | 21.0 | 19.7 | 28.0 | 34 | A |
| 106 | M | CA | 21.9 | 20.9 | 27.9 | 33 | A |
| 106 | M | CB | 23.4 | 20.4 | 28.2 | 33 | A |
| 106 | M | CG | 23.6 | 20.0 | 29.7 | 32 | A |
| 106 | M | SD | 23.2 | 21.3 | 30.9 | 29 | A |
| 106 | M | CE | 24.7 | 22.1 | 31.1 | 29 | A |
| 106 | M | C | 21.9 | 21.4 | 26.4 | 34 | A |
| 106 | M | O | 21.5 | 20.7 | 25.5 | 35 | A |

TABLE 3-continued

Structural Coordinates of Ah$_6$-ERK2 [di-thiophosphorylated, SEQ ID NO: 5] Crystals The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 107 | E | N   | 22.3 | 22.7 | 26.3 | 36 | A |
|-----|---|-----|------|------|------|----|---|
| 107 | E | CA  | 22.2 | 23.4 | 25.0 | 35 | A |
| 107 | E | CB  | 22.5 | 24.8 | 25.3 | 39 | A |
| 107 | E | CG  | 21.9 | 25.8 | 24.3 | 46 | A |
| 107 | E | CD  | 21.1 | 26.9 | 25.0 | 50 | A |
| 107 | E | OE1 | 21.4 | 27.3 | 26.2 | 47 | A |
| 107 | E | OE2 | 20.0 | 27.3 | 24.5 | 53 | A |
| 107 | E | C   | 23.2 | 22.9 | 24.0 | 35 | A |
| 107 | E | O   | 22.9 | 22.8 | 22.8 | 35 | A |
| 108 | T | N   | 24.4 | 22.5 | 24.4 | 32 | A |
| 108 | T | CA  | 25.5 | 22.1 | 23.5 | 27 | A |
| 108 | T | CB  | 26.0 | 23.3 | 22.7 | 25 | A |
| 108 | T | OG1 | 26.8 | 22.9 | 21.6 | 25 | A |
| 108 | T | CG2 | 26.9 | 24.2 | 23.6 | 24 | A |
| 108 | T | C   | 26.6 | 21.4 | 24.3 | 27 | A |
| 108 | T | O   | 26.4 | 21.1 | 25.5 | 24 | A |
| 109 | D | N   | 27.7 | 21.2 | 23.7 | 24 | A |
| 109 | D | CA  | 28.9 | 20.6 | 24.4 | 25 | A |
| 109 | D | CB  | 28.9 | 19.0 | 24.1 | 25 | A |
| 109 | D | CG  | 29.2 | 18.6 | 22.7 | 25 | A |
| 109 | D | OD1 | 30.2 | 19.1 | 22.1 | 25 | A |
| 109 | D | OD2 | 28.4 | 17.8 | 22.1 | 21 | A |
| 109 | D | C   | 30.2 | 21.2 | 23.9 | 26 | A |
| 109 | D | O   | 30.1 | 22.0 | 22.9 | 28 | A |
| 110 | L | N   | 31.3 | 20.9 | 24.5 | 26 | A |
| 110 | L | CA  | 32.5 | 21.6 | 24.2 | 24 | A |
| 110 | L | CB  | 33.6 | 21.2 | 25.2 | 22 | A |
| 110 | L | CG  | 34.9 | 22.0 | 25.1 | 19 | A |
| 110 | L | CD1 | 34.7 | 23.5 | 25.1 | 18 | A |
| 110 | L | CD2 | 35.9 | 21.6 | 26.2 | 19 | A |
| 110 | L | C   | 33.0 | 21.2 | 22.8 | 25 | A |
| 110 | L | O   | 33.6 | 22.0 | 22.1 | 28 | A |
| 111 | Y | N   | 32.8 | 19.9 | 22.4 | 23 | A |
| 111 | Y | CA  | 33.2 | 19.4 | 21.1 | 24 | A |
| 111 | Y | CB  | 32.7 | 18.0 | 20.9 | 26 | A |
| 111 | Y | CG  | 32.9 | 17.4 | 19.5 | 31 | A |
| 111 | Y | CD1 | 34.2 | 17.0 | 19.1 | 31 | A |
| 111 | Y | CE1 | 34.4 | 16.5 | 17.8 | 33 | A |
| 111 | Y | CD2 | 31.9 | 17.4 | 18.6 | 34 | A |
| 111 | Y | CE2 | 32.1 | 16.9 | 17.3 | 35 | A |
| 111 | Y | CZ  | 33.3 | 16.4 | 16.9 | 37 | A |
| 111 | Y | OH  | 33.5 | 15.9 | 15.6 | 40 | A |
| 111 | Y | C   | 32.6 | 20.4 | 20.0 | 24 | A |
| 111 | Y | O   | 33.4 | 21.0 | 19.3 | 24 | A |
| 112 | K | N   | 31.3 | 20.5 | 20.0 | 23 | A |
| 112 | K | CA  | 30.7 | 21.3 | 19.0 | 26 | A |
| 112 | K | CB  | 29.1 | 21.2 | 19.1 | 28 | A |
| 112 | K | CG  | 28.6 | 19.8 | 18.6 | 31 | A |
| 112 | K | CD  | 27.1 | 19.8 | 18.6 | 35 | A |
| 112 | K | CE  | 26.5 | 19.5 | 19.9 | 36 | A |
| 112 | K | NZ  | 25.1 | 19.1 | 19.7 | 39 | A |
| 112 | K | C   | 31.1 | 22.8 | 19.1 | 27 | A |
| 112 | K | O   | 31.1 | 23.5 | 18.1 | 27 | A |
| 113 | L | N   | 31.3 | 23.3 | 20.3 | 28 | A |
| 113 | L | CA  | 31.7 | 24.7 | 20.5 | 29 | A |
| 113 | L | CB  | 31.7 | 25.0 | 22.0 | 28 | A |
| 113 | L | CG  | 31.4 | 26.4 | 22.5 | 32 | A |
| 113 | L | CD1 | 31.9 | 26.5 | 23.9 | 31 | A |
| 113 | L | CD2 | 32.2 | 27.4 | 21.6 | 34 | A |
| 113 | L | C   | 33.0 | 25.0 | 19.9 | 31 | A |
| 113 | L | O   | 33.1 | 26.0 | 19.1 | 30 | A |
| 114 | L | N   | 34.0 | 24.1 | 20.2 | 30 | A |
| 114 | L | CA  | 35.3 | 24.3 | 19.6 | 29 | A |
| 114 | L | CB  | 36.3 | 23.3 | 20.3 | 28 | A |
| 114 | L | CG  | 36.7 | 23.6 | 21.7 | 24 | A |
| 114 | L | CD1 | 37.6 | 22.5 | 22.2 | 20 | A |
| 114 | L | CD2 | 37.4 | 25.0 | 21.8 | 22 | A |
| 114 | L | C   | 35.4 | 24.2 | 18.1 | 31 | A |
| 114 | L | O   | 36.3 | 24.7 | 17.5 | 32 | A |
| 115 | K | N   | 34.4 | 23.5 | 17.6 | 34 | A |
| 115 | K | CA  | 34.3 | 23.2 | 16.2 | 36 | A |
| 115 | K | CB  | 33.5 | 22.0 | 15.9 | 36 | A |
| 115 | K | CG  | 33.5 | 21.4 | 14.6 | 42 | A |
| 115 | K | CD  | 32.8 | 20.0 | 14.5 | 46 | A |
| 115 | K | CE  | 31.3 | 20.2 | 14.9 | 48 | A |
| 115 | K | NZ  | 30.6 | 21.2 | 14.1 | 50 | A |
| 115 | K | C   | 33.8 | 24.4 | 15.4 | 38 | A |
| 115 | K | O   | 33.8 | 24.5 | 14.2 | 37 | A |
| 116 | T | N   | 33.3 | 25.4 | 16.1 | 38 | A |
| 116 | T | CA  | 32.7 | 26.6 | 15.5 | 39 | A |
| 116 | T | CB  | 31.2 | 26.5 | 15.5 | 40 | A |
| 116 | T | OG1 | 30.7 | 26.4 | 16.8 | 41 | A |
| 116 | T | CG2 | 30.8 | 25.2 | 14.7 | 39 | A |
| 116 | T | C   | 33.0 | 27.9 | 16.2 | 40 | A |
| 116 | T | O   | 32.5 | 28.9 | 15.8 | 41 | A |
| 117 | Q | N   | 33.9 | 27.9 | 17.2 | 40 | A |
| 117 | Q | CA  | 34.2 | 29.2 | 17.9 | 41 | A |
| 117 | Q | CB  | 33.1 | 29.4 | 18.9 | 44 | A |
| 117 | Q | CG  | 33.4 | 30.5 | 20.0 | 50 | A |
| 117 | Q | CD  | 33.1 | 31.9 | 19.5 | 55 | A |
| 117 | Q | OE1 | 32.4 | 32.1 | 18.5 | 57 | A |
| 117 | Q | NE2 | 33.6 | 32.9 | 20.2 | 57 | A |
| 117 | Q | C   | 35.6 | 29.1 | 18.6 | 39 | A |
| 117 | Q | O   | 36.0 | 28.1 | 19.2 | 37 | A |
| 118 | H | N   | 36.3 | 30.3 | 18.5 | 39 | A |
| 118 | H | CA  | 37.6 | 30.4 | 19.1 | 38 | A |
| 118 | H | CB  | 38.5 | 31.3 | 18.3 | 39 | A |
| 118 | H | CG  | 39.9 | 31.5 | 18.9 | 43 | A |
| 118 | H | CD2 | 41.1 | 31.0 | 18.7 | 44 | A |
| 118 | H | ND1 | 40.0 | 32.4 | 20.0 | 45 | A |
| 118 | H | CE1 | 41.3 | 32.3 | 20.4 | 44 | A |
| 118 | H | NE2 | 41.9 | 31.5 | 19.7 | 45 | A |
| 118 | H | C   | 37.3 | 31.1 | 20.5 | 37 | A |
| 118 | H | O   | 36.9 | 32.2 | 20.6 | 40 | A |
| 119 | L | N   | 37.6 | 30.4 | 21.6 | 33 | A |
| 119 | L | CA  | 37.4 | 30.8 | 22.9 | 31 | A |
| 119 | L | CB  | 37.4 | 29.7 | 23.9 | 26 | A |
| 119 | L | CG  | 36.4 | 28.5 | 23.6 | 23 | A |
| 119 | L | CD1 | 36.7 | 27.4 | 24.6 | 21 | A |
| 119 | L | CD2 | 35.0 | 29.0 | 23.7 | 22 | A |
| 119 | L | C   | 38.4 | 31.9 | 23.4 | 31 | A |
| 119 | L | O   | 39.6 | 31.8 | 23.1 | 31 | A |
| 120 | S | N   | 37.9 | 32.8 | 24.2 | 32 | A |
| 120 | S | CA  | 38.8 | 33.8 | 24.8 | 31 | A |
| 120 | S | CB  | 38.0 | 35.1 | 25.2 | 31 | A |
| 120 | S | OG  | 37.0 | 34.7 | 26.2 | 33 | A |
| 120 | S | C   | 39.4 | 33.2 | 26.1 | 31 | A |
| 120 | S | O   | 38.9 | 32.2 | 26.6 | 31 | A |
| 121 | N | N   | 40.4 | 33.9 | 26.6 | 29 | A |
| 121 | N | CA  | 41.1 | 33.3 | 27.8 | 30 | A |
| 121 | N | CB  | 42.2 | 34.3 | 28.1 | 30 | A |
| 121 | N | CG  | 43.1 | 33.7 | 29.3 | 30 | A |
| 121 | N | OD1 | 43.4 | 34.4 | 30.2 | 35 | A |
| 121 | N | ND2 | 43.4 | 32.4 | 29.1 | 28 | A |
| 121 | N | C   | 40.1 | 33.2 | 28.9 | 30 | A |
| 121 | N | O   | 40.2 | 32.3 | 29.7 | 28 | A |
| 122 | D | N   | 39.2 | 34.1 | 29.0 | 29 | A |
| 122 | D | CA  | 38.2 | 34.1 | 30.1 | 31 | A |
| 122 | D | CB  | 37.3 | 35.4 | 30.2 | 34 | A |
| 122 | D | CG  | 38.1 | 36.6 | 30.4 | 37 | A |
| 122 | D | OD1 | 39.0 | 36.6 | 31.3 | 38 | A |
| 122 | D | OD2 | 37.9 | 37.6 | 29.7 | 42 | A |
| 122 | D | C   | 37.3 | 32.9 | 30.1 | 30 | A |
| 122 | D | O   | 37.1 | 32.3 | 31.2 | 29 | A |
| 123 | H | N   | 36.8 | 32.5 | 28.9 | 29 | A |
| 123 | H | CA  | 36.0 | 31.3 | 28.8 | 28 | A |
| 123 | H | CB  | 35.4 | 31.2 | 27.4 | 30 | A |
| 123 | H | CG  | 34.2 | 32.1 | 27.2 | 34 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 123 | H | CD2 | 32.9 | 31.8 | 27.0 | 35 | A |
|---|---|---|---|---|---|---|---|
| 123 | H | ND1 | 34.3 | 33.5 | 27.2 | 38 | A |
| 123 | H | CE1 | 33.1 | 34.0 | 27.0 | 37 | A |
| 123 | H | NE2 | 32.2 | 33.0 | 26.9 | 37 | A |
| 123 | H | C | 36.8 | 30.1 | 29.2 | 26 | A |
| 123 | H | O | 36.4 | 29.3 | 30.0 | 28 | A |
| 124 | I | N | 37.9 | 29.9 | 28.5 | 23 | A |
| 124 | I | CA | 38.8 | 28.8 | 28.8 | 22 | A |
| 124 | I | CB | 40.1 | 29.0 | 28.0 | 19 | A |
| 124 | I | CG2 | 41.1 | 27.9 | 28.5 | 21 | A |
| 124 | I | CG1 | 39.9 | 28.9 | 26.5 | 18 | A |
| 124 | I | CD1 | 41.1 | 29.3 | 25.7 | 14 | A |
| 124 | I | C | 39.0 | 28.6 | 30.3 | 21 | A |
| 124 | I | O | 38.8 | 27.6 | 30.8 | 20 | A |
| 125 | C | N | 39.5 | 29.7 | 30.9 | 20 | A |
| 125 | C | CA | 39.8 | 29.7 | 32.3 | 21 | A |
| 125 | C | CB | 40.2 | 31.1 | 32.8 | 23 | A |
| 125 | C | SG | 40.6 | 31.2 | 34.5 | 25 | A |
| 125 | C | C | 38.6 | 29.3 | 33.1 | 22 | A |
| 125 | C | O | 38.7 | 28.5 | 34.1 | 22 | A |
| 126 | Y | N | 37.4 | 29.8 | 32.8 | 20 | A |
| 126 | Y | CA | 36.2 | 29.4 | 33.5 | 20 | A |
| 126 | Y | CB | 35.1 | 30.4 | 33.2 | 22 | A |
| 126 | Y | CG | 33.8 | 30.1 | 33.9 | 23 | A |
| 126 | Y | CD1 | 33.7 | 29.8 | 35.3 | 25 | A |
| 126 | Y | CE1 | 32.5 | 29.6 | 35.9 | 26 | A |
| 126 | Y | CD2 | 32.5 | 30.2 | 33.2 | 25 | A |
| 126 | Y | CE2 | 31.3 | 30.0 | 33.9 | 26 | A |
| 126 | Y | CZ | 31.4 | 29.7 | 35.2 | 26 | A |
| 126 | Y | OH | 30.2 | 29.4 | 35.9 | 31 | A |
| 126 | Y | C | 35.7 | 28.0 | 33.2 | 19 | A |
| 126 | Y | O | 35.3 | 27.3 | 34.1 | 18 | A |
| 127 | F | N | 35.9 | 27.5 | 32.0 | 18 | A |
| 127 | F | CA | 35.5 | 26.2 | 31.6 | 18 | A |
| 127 | F | CB | 35.6 | 26.0 | 30.1 | 18 | A |
| 127 | F | CG | 34.4 | 26.5 | 29.3 | 21 | A |
| 127 | F | CD1 | 33.2 | 26.7 | 29.9 | 17 | A |
| 127 | F | CD2 | 34.6 | 26.9 | 27.9 | 17 | A |
| 127 | F | CE1 | 32.1 | 27.2 | 29.1 | 18 | A |
| 127 | F | CE2 | 33.5 | 27.4 | 27.2 | 19 | A |
| 127 | F | CZ | 32.3 | 27.5 | 27.8 | 19 | A |
| 127 | F | C | 36.4 | 25.2 | 32.3 | 16 | A |
| 127 | F | O | 36.0 | 24.1 | 32.7 | 14 | A |
| 128 | L | N | 37.7 | 25.6 | 32.4 | 16 | A |
| 128 | L | CA | 38.7 | 24.7 | 33.0 | 17 | A |
| 128 | L | CB | 40.1 | 25.2 | 32.8 | 17 | A |
| 128 | L | CG | 41.1 | 24.3 | 33.4 | 18 | A |
| 128 | L | CD1 | 41.2 | 23.0 | 32.6 | 21 | A |
| 128 | L | CD2 | 42.5 | 25.0 | 33.4 | 21 | A |
| 128 | L | C | 38.3 | 24.5 | 34.5 | 18 | A |
| 128 | L | O | 38.4 | 23.4 | 35.0 | 16 | A |
| 129 | Y | N | 38.0 | 25.7 | 35.1 | 18 | A |
| 129 | Y | CA | 37.7 | 25.6 | 36.5 | 17 | A |
| 129 | Y | CB | 37.2 | 27.0 | 37.0 | 17 | A |
| 129 | Y | CG | 36.8 | 27.0 | 38.4 | 16 | A |
| 129 | Y | CD1 | 37.7 | 26.6 | 39.4 | 18 | A |
| 129 | Y | CE1 | 37.3 | 26.5 | 40.8 | 19 | A |
| 129 | Y | CD2 | 35.4 | 27.2 | 38.8 | 17 | A |
| 129 | Y | CE2 | 35.0 | 27.1 | 40.2 | 16 | A |
| 129 | Y | CZ | 36.0 | 26.8 | 41.1 | 18 | A |
| 129 | Y | OH | 35.7 | 26.6 | 42.5 | 15 | A |
| 129 | Y | C | 36.6 | 24.6 | 36.8 | 19 | A |
| 129 | Y | O | 36.7 | 23.7 | 37.6 | 18 | A |
| 130 | Q | N | 35.5 | 24.8 | 36.1 | 19 | A |
| 130 | Q | CA | 34.3 | 23.9 | 36.2 | 20 | A |
| 130 | Q | CB | 33.2 | 24.3 | 35.3 | 22 | A |
| 130 | Q | CG | 32.7 | 25.7 | 35.6 | 20 | A |
| 130 | Q | CD | 31.5 | 26.1 | 34.8 | 23 | A |
| 130 | Q | OE1 | 30.4 | 25.7 | 35.1 | 25 | A |
| 130 | Q | NE2 | 31.7 | 26.9 | 33.8 | 22 | A |
| 130 | Q | C | 34.6 | 22.4 | 36.0 | 19 | A |
| 130 | Q | O | 34.1 | 21.5 | 36.6 | 21 | A |
| 131 | I | N | 35.5 | 22.1 | 35.0 | 18 | A |
| 131 | I | CA | 35.9 | 20.8 | 34.7 | 17 | A |
| 131 | I | CB | 36.8 | 20.6 | 33.5 | 16 | A |
| 131 | I | CG2 | 37.3 | 19.2 | 33.4 | 18 | A |
| 131 | I | CG1 | 36.1 | 21.0 | 32.2 | 18 | A |
| 131 | I | CD1 | 37.1 | 21.3 | 31.0 | 13 | A |
| 131 | I | C | 36.6 | 20.2 | 35.9 | 15 | A |
| 131 | I | O | 36.3 | 19.0 | 36.3 | 13 | A |
| 132 | L | N | 37.5 | 20.9 | 36.5 | 14 | A |
| 132 | L | CA | 38.3 | 20.5 | 37.6 | 12 | A |
| 132 | L | CB | 39.6 | 21.3 | 37.8 | 10 | A |
| 132 | L | CG | 40.6 | 21.2 | 36.7 | 12 | A |
| 132 | L | CD1 | 41.7 | 22.2 | 36.9 | 8 | A |
| 132 | L | CD2 | 41.1 | 19.7 | 36.6 | 10 | A |
| 132 | L | C | 37.5 | 20.5 | 38.9 | 10 | A |
| 132 | L | O | 37.8 | 19.7 | 39.8 | 15 | A |
| 133 | R | N | 36.5 | 21.4 | 39.0 | 13 | A |
| 133 | R | CA | 35.7 | 21.4 | 40.2 | 11 | A |
| 133 | R | CB | 34.7 | 22.6 | 40.1 | 12 | A |
| 133 | R | CG | 33.9 | 22.9 | 41.4 | 12 | A |
| 133 | R | CD | 33.2 | 24.2 | 41.3 | 14 | A |
| 133 | R | NE | 32.2 | 24.5 | 42.4 | 17 | A |
| 133 | R | CZ | 30.9 | 24.5 | 42.3 | 20 | A |
| 133 | R | NH1 | 30.4 | 24.2 | 41.1 | 21 | A |
| 133 | R | NH2 | 30.1 | 24.7 | 43.3 | 15 | A |
| 133 | R | C | 34.9 | 20.1 | 40.2 | 12 | A |
| 133 | R | O | 34.8 | 19.4 | 41.2 | 12 | A |
| 134 | G | N | 34.3 | 19.8 | 39.0 | 13 | A |
| 134 | G | CA | 33.5 | 18.6 | 38.9 | 14 | A |
| 134 | G | C | 34.4 | 17.4 | 39.1 | 16 | A |
| 134 | G | O | 34.0 | 16.4 | 39.8 | 15 | A |
| 135 | L | N | 35.6 | 17.4 | 38.6 | 15 | A |
| 135 | L | CA | 36.6 | 16.3 | 38.7 | 16 | A |
| 135 | L | CB | 37.8 | 16.4 | 37.8 | 15 | A |
| 135 | L | CG | 38.8 | 15.2 | 37.8 | 17 | A |
| 135 | L | CD1 | 38.0 | 14.0 | 37.2 | 17 | A |
| 135 | L | CD2 | 40.0 | 15.5 | 36.8 | 11 | A |
| 135 | L | C | 37.0 | 16.1 | 40.2 | 16 | A |
| 135 | L | O | 37.4 | 15.0 | 40.6 | 15 | A |
| 136 | K | N | 37.1 | 17.2 | 40.9 | 15 | A |
| 136 | K | CA | 37.5 | 17.2 | 42.3 | 14 | A |
| 136 | K | CB | 37.6 | 18.6 | 42.8 | 15 | A |
| 136 | K | CG | 37.8 | 18.7 | 44.3 | 14 | A |
| 136 | K | CD | 37.9 | 20.1 | 44.8 | 15 | A |
| 136 | K | CE | 37.9 | 20.2 | 46.3 | 14 | A |
| 136 | K | NZ | 38.1 | 21.6 | 46.7 | 14 | A |
| 136 | K | C | 36.5 | 16.3 | 43.1 | 15 | A |
| 136 | K | O | 36.9 | 15.5 | 43.9 | 12 | A |
| 137 | Y | N | 35.2 | 16.6 | 42.8 | 17 | A |
| 137 | Y | CA | 34.2 | 15.9 | 43.5 | 17 | A |
| 137 | Y | CB | 32.8 | 16.5 | 43.2 | 18 | A |
| 137 | Y | CG | 31.6 | 15.7 | 43.7 | 20 | A |
| 137 | Y | CD1 | 31.1 | 16.1 | 45.0 | 20 | A |
| 137 | Y | CE1 | 30.0 | 15.4 | 45.5 | 19 | A |
| 137 | Y | CD2 | 31.1 | 14.6 | 43.1 | 19 | A |
| 137 | Y | CE2 | 30.0 | 13.9 | 43.6 | 21 | A |
| 137 | Y | CZ | 29.5 | 14.3 | 44.8 | 22 | A |
| 137 | Y | OH | 28.4 | 13.6 | 45.3 | 27 | A |
| 137 | Y | C | 34.2 | 14.4 | 43.1 | 19 | A |
| 137 | Y | O | 34.2 | 13.5 | 44.0 | 17 | A |
| 138 | I | N | 34.4 | 14.1 | 41.8 | 19 | A |
| 138 | I | CA | 34.4 | 12.7 | 41.3 | 20 | A |
| 138 | I | CB | 34.7 | 12.7 | 39.8 | 19 | A |
| 138 | I | CG2 | 34.8 | 11.2 | 39.3 | 22 | A |
| 138 | I | CG1 | 33.6 | 13.4 | 39.0 | 18 | A |
| 138 | I | CD1 | 33.9 | 13.6 | 37.6 | 16 | A |

TABLE 3-continued

Structural Coordinates of Ah$_6$-ERK2 [di-thiophosphorylated, SEQ ID NO: 5] Crystals The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| Residue | AA | Atom | x | y | z | B | Chain |
|---|---|---|---|---|---|---|---|
| 138 | I | C | 35.6 | 11.9 | 42.0 | 21 | A |
| 138 | I | O | 35.3 | 10.9 | 42.6 | 22 | A |
| 139 | H | N | 36.8 | 12.5 | 42.0 | 20 | A |
| 139 | H | CA | 37.9 | 11.9 | 42.6 | 21 | A |
| 139 | H | CB | 39.2 | 12.7 | 42.3 | 20 | A |
| 139 | H | CG | 39.7 | 12.4 | 40.9 | 21 | A |
| 139 | H | CD2 | 39.3 | 11.6 | 39.9 | 21 | A |
| 139 | H | ND1 | 40.9 | 12.9 | 40.5 | 21 | A |
| 139 | H | CE1 | 41.2 | 12.5 | 39.2 | 19 | A |
| 139 | H | NE2 | 40.2 | 11.7 | 38.9 | 25 | A |
| 139 | H | C | 37.8 | 11.7 | 44.1 | 19 | A |
| 139 | H | O | 38.4 | 10.8 | 44.7 | 19 | A |
| 140 | S | N | 37.1 | 12.6 | 44.8 | 19 | A |
| 140 | S | CA | 36.9 | 12.5 | 46.2 | 15 | A |
| 140 | S | CB | 36.2 | 13.7 | 46.8 | 15 | A |
| 140 | S | OG | 34.9 | 13.8 | 46.3 | 14 | A |
| 140 | S | C | 36.1 | 11.3 | 46.5 | 17 | A |
| 140 | S | O | 36.1 | 10.7 | 47.6 | 17 | A |
| 141 | A | N | 35.3 | 10.8 | 45.6 | 17 | A |
| 141 | A | CA | 34.4 | 9.7 | 45.7 | 18 | A |
| 141 | A | CB | 33.1 | 9.9 | 44.9 | 16 | A |
| 141 | A | C | 35.1 | 8.3 | 45.3 | 19 | A |
| 141 | A | O | 34.5 | 7.3 | 45.3 | 23 | A |
| 142 | N | N | 36.4 | 8.4 | 44.9 | 20 | A |
| 142 | N | CA | 37.1 | 7.2 | 44.5 | 20 | A |
| 142 | N | CB | 37.0 | 6.1 | 45.5 | 22 | A |
| 142 | N | CG | 37.6 | 6.4 | 46.8 | 26 | A |
| 142 | N | OD1 | 38.7 | 7.1 | 46.9 | 25 | A |
| 142 | N | ND2 | 37.0 | 5.9 | 47.9 | 26 | A |
| 142 | N | C | 36.7 | 6.7 | 43.1 | 19 | A |
| 142 | N | O | 37.1 | 5.6 | 42.7 | 19 | A |
| 143 | V | N | 36.1 | 7.6 | 42.4 | 16 | A |
| 143 | V | CA | 35.6 | 7.3 | 41.0 | 16 | A |
| 143 | V | CB | 34.2 | 7.8 | 40.7 | 17 | A |
| 143 | V | CG1 | 33.9 | 7.7 | 39.3 | 16 | A |
| 143 | V | CG2 | 33.2 | 7.1 | 41.6 | 16 | A |
| 143 | V | C | 36.6 | 7.8 | 40.0 | 19 | A |
| 143 | V | O | 37.2 | 8.9 | 40.2 | 17 | A |
| 144 | L | N | 36.9 | 7.1 | 38.9 | 20 | A |
| 144 | L | CA | 37.7 | 7.5 | 37.8 | 19 | A |
| 144 | L | CB | 38.8 | 6.5 | 37.4 | 19 | A |
| 144 | L | CG | 39.7 | 5.6 | 38.3 | 20 | A |
| 144 | L | CD1 | 41.0 | 5.4 | 37.5 | 14 | A |
| 144 | L | CD2 | 40.0 | 6.4 | 39.6 | 19 | A |
| 144 | L | C | 36.7 | 7.6 | 36.7 | 20 | A |
| 144 | L | O | 36.0 | 6.7 | 36.4 | 20 | A |
| 145 | H | N | 36.7 | 8.8 | 36.0 | 19 | A |
| 145 | H | CA | 35.7 | 8.9 | 34.9 | 17 | A |
| 145 | H | CB | 35.6 | 10.4 | 34.5 | 15 | A |
| 145 | H | CG | 34.6 | 10.6 | 33.4 | 16 | A |
| 145 | H | CD2 | 33.4 | 11.2 | 33.5 | 13 | A |
| 145 | H | ND1 | 34.9 | 10.3 | 32.1 | 16 | A |
| 145 | H | CE1 | 33.8 | 10.7 | 31.4 | 17 | A |
| 145 | H | NE2 | 32.9 | 11.2 | 32.2 | 15 | A |
| 145 | H | C | 36.2 | 8.0 | 33.8 | 19 | A |
| 145 | H | O | 35.4 | 7.2 | 33.3 | 18 | A |
| 146 | R | N | 37.4 | 8.2 | 33.3 | 20 | A |
| 146 | R | CA | 38.0 | 7.4 | 32.2 | 18 | A |
| 146 | R | CB | 37.8 | 6.0 | 32.4 | 22 | A |
| 146 | R | CG | 38.4 | 5.3 | 33.6 | 19 | A |
| 146 | R | CD | 37.6 | 4.1 | 33.8 | 19 | A |
| 146 | R | NE | 38.4 | 2.9 | 34.0 | 18 | A |
| 146 | R | CZ | 37.9 | 1.7 | 34.1 | 21 | A |
| 146 | R | NH1 | 36.6 | 1.5 | 33.9 | 13 | A |
| 146 | R | NH2 | 38.7 | 0.7 | 34.2 | 21 | A |
| 146 | R | C | 37.7 | 7.8 | 30.8 | 18 | A |
| 146 | R | O | 38.2 | 7.2 | 29.9 | 20 | A |
| 147 | D | N | 36.7 | 8.7 | 30.6 | 16 | A |
| 147 | D | CA | 36.4 | 9.0 | 29.2 | 17 | A |
| 147 | D | CB | 35.2 | 8.2 | 28.8 | 15 | A |
| 147 | D | CG | 35.1 | 8.1 | 27.2 | 19 | A |
| 147 | D | OD1 | 36.2 | 8.5 | 26.6 | 14 | A |
| 147 | D | OD2 | 34.1 | 7.7 | 26.7 | 17 | A |
| 147 | D | C | 36.2 | 10.5 | 29.0 | 18 | A |
| 147 | D | O | 35.2 | 10.9 | 28.3 | 19 | A |
| 148 | L | N | 37.0 | 11.3 | 29.7 | 16 | A |
| 148 | L | CA | 36.9 | 12.7 | 29.6 | 16 | A |
| 148 | L | CB | 37.8 | 13.4 | 30.7 | 16 | A |
| 148 | L | CG | 37.1 | 13.9 | 32.0 | 17 | A |
| 148 | L | CD1 | 35.8 | 13.3 | 32.2 | 16 | A |
| 148 | L | CD2 | 38.0 | 13.7 | 33.1 | 13 | A |
| 148 | L | C | 37.4 | 13.2 | 28.2 | 18 | A |
| 148 | L | O | 38.5 | 12.8 | 27.8 | 17 | A |
| 149 | K | N | 36.5 | 14.0 | 27.6 | 18 | A |
| 149 | K | CA | 36.8 | 14.5 | 26.2 | 19 | A |
| 149 | K | CB | 36.8 | 13.4 | 25.2 | 18 | A |
| 149 | K | CG | 35.5 | 12.6 | 25.2 | 18 | A |
| 149 | K | CD | 35.5 | 11.6 | 24.0 | 17 | A |
| 149 | K | CE | 34.3 | 10.6 | 24.0 | 14 | A |
| 149 | K | NZ | 34.3 | 9.9 | 22.7 | 19 | A |
| 149 | K | C | 35.8 | 15.6 | 25.9 | 20 | A |
| 149 | K | O | 34.7 | 15.7 | 26.5 | 22 | A |
| 150 | P | N | 36.1 | 16.5 | 25.0 | 18 | A |
| 150 | P | CD | 37.3 | 16.5 | 24.1 | 16 | A |
| 150 | P | CA | 35.2 | 17.6 | 24.7 | 19 | A |
| 150 | P | CB | 35.8 | 18.2 | 23.4 | 19 | A |
| 150 | P | CG | 37.2 | 17.9 | 23.5 | 19 | A |
| 150 | P | C | 33.7 | 17.3 | 24.6 | 19 | A |
| 150 | P | O | 32.9 | 18.1 | 25.1 | 21 | A |
| 151 | S | N | 33.3 | 16.2 | 23.9 | 20 | A |
| 151 | S | CA | 31.9 | 15.9 | 23.7 | 20 | A |
| 151 | S | CB | 31.7 | 14.8 | 22.6 | 21 | A |
| 151 | S | OG | 32.2 | 13.6 | 23.0 | 29 | A |
| 151 | S | C | 31.2 | 15.4 | 25.0 | 20 | A |
| 151 | S | O | 30.0 | 15.2 | 25.0 | 21 | A |
| 152 | N | N | 32.0 | 15.2 | 26.1 | 21 | A |
| 152 | N | CA | 31.4 | 14.7 | 27.3 | 19 | A |
| 152 | N | CB | 32.2 | 13.6 | 27.9 | 21 | A |
| 152 | N | CG | 31.9 | 12.3 | 27.3 | 20 | A |
| 152 | N | OD1 | 30.9 | 12.1 | 26.6 | 24 | A |
| 152 | N | ND2 | 32.7 | 11.3 | 27.5 | 18 | A |
| 152 | N | C | 31.3 | 15.9 | 28.3 | 19 | A |
| 152 | N | O | 31.2 | 15.7 | 29.5 | 21 | A |
| 153 | L | N | 31.5 | 17.1 | 27.8 | 21 | A |
| 153 | L | CA | 31.4 | 18.3 | 28.6 | 21 | A |
| 153 | L | CB | 32.7 | 19.1 | 28.4 | 20 | A |
| 153 | L | CG | 34.0 | 18.3 | 28.9 | 21 | A |
| 153 | L | CD1 | 35.2 | 19.2 | 28.8 | 21 | A |
| 153 | L | CD2 | 33.8 | 17.9 | 30.4 | 19 | A |
| 153 | L | C | 30.3 | 19.1 | 28.0 | 21 | A |
| 153 | L | O | 30.4 | 19.8 | 27.0 | 23 | A |
| 154 | L | N | 29.1 | 19.0 | 28.7 | 20 | A |
| 154 | L | CA | 27.9 | 19.7 | 28.2 | 20 | A |
| 154 | L | CB | 26.7 | 19.0 | 28.8 | 19 | A |
| 154 | L | CG | 26.8 | 17.5 | 28.5 | 20 | A |
| 154 | L | CD1 | 25.6 | 16.7 | 29.1 | 18 | A |
| 154 | L | CD2 | 26.9 | 17.3 | 27.0 | 19 | A |
| 154 | L | C | 27.9 | 21.2 | 28.7 | 20 | A |
| 154 | L | O | 28.4 | 21.5 | 29.8 | 19 | A |
| 155 | L | N | 27.4 | 22.1 | 27.8 | 21 | A |
| 155 | L | CA | 27.3 | 23.5 | 28.1 | 25 | A |
| 155 | L | CB | 28.3 | 24.2 | 27.3 | 25 | A |
| 155 | L | CG | 29.9 | 24.3 | 27.4 | 24 | A |
| 155 | L | CD1 | 30.4 | 24.3 | 28.4 | 25 | A |
| 155 | L | CD2 | 30.5 | 24.1 | 26.1 | 16 | A |
| 155 | L | C | 26.0 | 24.0 | 27.8 | 26 | A |
| 155 | L | O | 25.1 | 23.4 | 27.2 | 24 | A |
| 156 | N | N | 25.7 | 25.3 | 28.2 | 28 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 156 | N | CA | 24.5 | 26.0 | 27.9 | 29 | A |
|---|---|---|---|---|---|---|---|
| 156 | N | CB | 23.5 | 25.9 | 29.1 | 28 | A |
| 156 | N | CG | 23.9 | 26.5 | 30.3 | 31 | A |
| 156 | N | OD1 | 24.7 | 27.5 | 30.3 | 33 | A |
| 156 | N | ND2 | 23.4 | 26.0 | 31.5 | 27 | A |
| 156 | N | C | 24.9 | 27.4 | 27.7 | 30 | A |
| 156 | N | O | 26.1 | 27.8 | 27.9 | 30 | A |
| 157 | T | N | 24.0 | 28.2 | 27.2 | 32 | A |
| 157 | T | CA | 24.2 | 29.6 | 26.8 | 33 | A |
| 157 | T | CB | 22.8 | 30.3 | 26.6 | 36 | A |
| 157 | T | OG1 | 22.2 | 29.7 | 25.4 | 41 | A |
| 157 | T | CG2 | 23.0 | 31.8 | 26.2 | 36 | A |
| 157 | T | C | 25.0 | 30.4 | 27.8 | 32 | A |
| 157 | T | O | 25.8 | 31.3 | 27.5 | 33 | A |
| 158 | T | N | 24.7 | 30.2 | 29.1 | 28 | A |
| 158 | T | CA | 25.4 | 31.0 | 30.2 | 27 | A |
| 158 | T | CB | 24.4 | 31.1 | 31.4 | 27 | A |
| 158 | T | OG1 | 23.8 | 29.9 | 31.7 | 31 | A |
| 158 | T | CG2 | 23.4 | 32.2 | 31.1 | 29 | A |
| 158 | T | C | 26.7 | 30.4 | 30.7 | 26 | A |
| 158 | T | O | 27.2 | 30.8 | 31.7 | 21 | A |
| 159 | C | N | 27.3 | 29.5 | 29.9 | 26 | A |
| 159 | C | CA | 28.6 | 28.9 | 30.2 | 25 | A |
| 159 | C | CB | 29.6 | 30.0 | 30.5 | 27 | A |
| 159 | C | SG | 30.0 | 31.1 | 29.1 | 29 | A |
| 159 | C | C | 28.6 | 27.9 | 31.4 | 25 | A |
| 159 | C | O | 29.6 | 27.6 | 31.9 | 28 | A |
| 160 | D | N | 27.4 | 27.3 | 31.7 | 26 | A |
| 160 | D | CA | 27.4 | 26.3 | 32.7 | 26 | A |
| 160 | D | CB | 26.0 | 26.0 | 33.2 | 30 | A |
| 160 | D | CG | 25.3 | 27.1 | 33.9 | 30 | A |
| 160 | D | OD1 | 25.9 | 27.5 | 35.0 | 32 | A |
| 160 | D | OD2 | 24.3 | 27.6 | 33.5 | 31 | A |
| 160 | D | C | 28.0 | 25.1 | 32.1 | 25 | A |
| 160 | D | O | 27.7 | 24.9 | 30.9 | 26 | A |
| 161 | L | N | 28.8 | 24.3 | 32.8 | 21 | A |
| 161 | L | CA | 29.4 | 23.1 | 32.2 | 19 | A |
| 161 | L | CB | 30.9 | 23.4 | 32.1 | 18 | A |
| 161 | L | CG | 31.7 | 22.2 | 31.5 | 17 | A |
| 161 | L | CD1 | 33.0 | 22.7 | 30.9 | 16 | A |
| 161 | L | CD2 | 31.9 | 21.2 | 32.6 | 13 | A |
| 161 | L | C | 29.1 | 22.0 | 33.1 | 17 | A |
| 161 | L | O | 29.1 | 22.1 | 34.4 | 15 | A |
| 162 | K | N | 28.8 | 20.8 | 32.5 | 18 | A |
| 162 | K | CA | 28.6 | 19.6 | 33.3 | 20 | A |
| 162 | K | CB | 27.1 | 19.3 | 33.3 | 20 | A |
| 162 | K | CG | 26.2 | 20.1 | 34.2 | 19 | A |
| 162 | K | CD | 25.2 | 19.3 | 34.9 | 21 | A |
| 162 | K | CE | 24.4 | 20.0 | 35.9 | 19 | A |
| 162 | K | NZ | 23.4 | 20.9 | 35.2 | 19 | A |
| 162 | K | C | 29.3 | 18.4 | 32.6 | 20 | A |
| 162 | K | O | 29.2 | 18.2 | 31.4 | 19 | A |
| 163 | I | N | 29.9 | 17.6 | 33.5 | 20 | A |
| 163 | I | CA | 30.6 | 16.4 | 33.0 | 20 | A |
| 163 | I | CB | 31.7 | 15.9 | 34.0 | 19 | A |
| 163 | I | CG2 | 32.3 | 14.6 | 33.6 | 16 | A |
| 163 | I | CG1 | 32.8 | 17.0 | 34.1 | 19 | A |
| 163 | I | CD1 | 33.8 | 16.7 | 35.2 | 19 | A |
| 163 | I | C | 29.5 | 15.3 | 32.9 | 21 | A |
| 163 | I | O | 28.8 | 15.0 | 33.9 | 22 | A |
| 164 | C | N | 29.4 | 14.6 | 31.8 | 21 | A |
| 164 | C | CA | 28.4 | 13.6 | 31.6 | 21 | A |
| 164 | C | CB | 27.3 | 14.0 | 30.6 | 19 | A |
| 164 | C | SG | 27.9 | 14.1 | 28.9 | 23 | A |
| 164 | C | C | 29.1 | 12.3 | 31.1 | 19 | A |
| 164 | C | O | 30.4 | 12.3 | 31.1 | 18 | A |
| 165 | D | N | 28.3 | 11.3 | 30.8 | 23 | A |
| 165 | D | CA | 28.8 | 10.0 | 30.2 | 25 | A |
| 165 | D | CB | 29.4 | 10.3 | 28.8 | 26 | A |
| 165 | D | CG | 29.6 | 9.0 | 28.0 | 32 | A |
| 165 | D | OD1 | 30.1 | 9.0 | 26.9 | 33 | A |
| 165 | D | OD2 | 29.3 | 7.9 | 28.6 | 32 | A |
| 165 | D | C | 29.8 | 9.3 | 31.1 | 25 | A |
| 165 | D | O | 31.0 | 9.3 | 30.9 | 26 | A |
| 166 | F | N | 29.2 | 8.7 | 32.1 | 25 | A |
| 166 | F | CA | 30.0 | 7.9 | 33.1 | 24 | A |
| 166 | F | CB | 29.5 | 8.1 | 34.5 | 22 | A |
| 166 | F | CG | 29.9 | 9.4 | 35.1 | 21 | A |
| 166 | F | CD1 | 29.4 | 10.6 | 34.6 | 20 | A |
| 166 | F | CD2 | 30.8 | 9.4 | 36.2 | 18 | A |
| 166 | F | CE1 | 29.8 | 11.8 | 35.2 | 19 | A |
| 166 | F | CE2 | 31.2 | 10.6 | 36.8 | 18 | A |
| 166 | F | CZ | 30.7 | 11.9 | 36.3 | 19 | A |
| 166 | F | C | 29.9 | 6.4 | 32.8 | 24 | A |
| 166 | F | O | 30.0 | 5.6 | 33.6 | 23 | A |
| 167 | G | N | 29.7 | 6.1 | 31.5 | 25 | A |
| 167 | G | CA | 29.6 | 4.7 | 31.0 | 27 | A |
| 167 | G | C | 30.9 | 4.0 | 31.3 | 28 | A |
| 167 | G | O | 30.9 | 2.8 | 31.5 | 31 | A |
| 168 | L | N | 32.0 | 4.6 | 31.2 | 27 | A |
| 168 | L | CA | 33.3 | 4.0 | 31.4 | 27 | A |
| 168 | L | CB | 34.3 | 4.4 | 30.4 | 30 | A |
| 168 | L | CG | 35.6 | 3.6 | 30.1 | 37 | A |
| 168 | L | CD1 | 35.2 | 2.2 | 29.6 | 37 | A |
| 168 | L | CD2 | 36.4 | 4.3 | 29.0 | 39 | A |
| 168 | L | C | 33.8 | 4.3 | 32.8 | 25 | A |
| 168 | L | O | 34.9 | 3.7 | 33.2 | 24 | A |
| 169 | A | N | 33.1 | 5.1 | 33.6 | 25 | A |
| 169 | A | CA | 33.5 | 5.4 | 35.0 | 24 | A |
| 169 | A | CB | 32.6 | 6.4 | 35.6 | 23 | A |
| 169 | A | C | 33.6 | 4.1 | 35.9 | 25 | A |
| 169 | A | O | 33.0 | 3.1 | 35.6 | 23 | A |
| 170 | R | N | 34.4 | 4.2 | 36.9 | 25 | A |
| 170 | R | CA | 34.6 | 3.1 | 37.8 | 26 | A |
| 170 | R | CB | 35.6 | 2.1 | 37.2 | 29 | A |
| 170 | R | CG | 36.1 | 1.0 | 38.1 | 33 | A |
| 170 | R | CD | 37.5 | 0.6 | 37.6 | 34 | A |
| 170 | R | NE | 37.7 | −0.9 | 37.7 | 37 | A |
| 170 | R | CZ | 37.9 | −1.5 | 38.8 | 37 | A |
| 170 | R | NH1 | 37.9 | −0.9 | 40.0 | 41 | A |
| 170 | R | NH2 | 38.1 | −2.8 | 38.8 | 42 | A |
| 170 | R | C | 35.1 | 3.5 | 39.2 | 26 | A |
| 170 | R | O | 35.6 | 4.6 | 39.3 | 28 | A |
| 171 | V | N | 34.9 | 2.7 | 40.2 | 26 | A |
| 171 | V | CA | 35.3 | 2.9 | 41.5 | 24 | A |
| 171 | V | CB | 34.3 | 2.4 | 42.6 | 22 | A |
| 171 | V | CG1 | 34.8 | 2.5 | 44.0 | 24 | A |
| 171 | V | CG2 | 33.0 | 3.2 | 42.5 | 21 | A |
| 171 | V | C | 36.6 | 2.2 | 41.8 | 24 | A |
| 171 | V | O | 36.8 | 1.0 | 41.4 | 20 | A |
| 172 | A | N | 37.5 | 2.9 | 42.5 | 24 | A |
| 172 | A | CA | 38.8 | 2.3 | 42.8 | 26 | A |
| 172 | A | CB | 39.9 | 2.6 | 41.8 | 26 | A |
| 172 | A | C | 39.2 | 2.7 | 44.2 | 28 | A |
| 172 | A | O | 39.8 | 3.8 | 44.4 | 30 | A |
| 173 | D | N | 38.9 | 1.9 | 45.2 | 28 | A |
| 173 | D | CA | 39.1 | 2.2 | 46.6 | 30 | A |
| 173 | D | CB | 38.5 | 1.2 | 47.5 | 31 | A |
| 173 | D | CG | 38.3 | 1.6 | 48.9 | 32 | A |
| 173 | D | OD1 | 39.2 | 2.3 | 49.4 | 30 | A |
| 173 | D | OD2 | 37.4 | 1.2 | 49.5 | 34 | A |
| 173 | D | C | 40.6 | 2.3 | 46.9 | 33 | A |
| 173 | D | O | 41.3 | 1.3 | 46.8 | 33 | A |
| 174 | P | N | 41.1 | 3.5 | 47.3 | 35 | A |
| 174 | P | CD | 40.4 | 4.6 | 47.8 | 35 | A |
| 174 | P | CA | 42.6 | 3.6 | 47.6 | 38 | A |
| 174 | P | CB | 42.7 | 5.1 | 48.1 | 37 | A |
| 174 | P | CG | 41.4 | 5.7 | 47.7 | 37 | A |

TABLE 3-continued

Structural Coordinates of Ah₆-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| Res | AA | Atom | X | Y | Z | B | Chain |
|---|---|---|---|---|---|---|---|
| 174 | P | C | 43.1 | 2.6 | 48.6 | 40 | A |
| 174 | P | O | 44.3 | 2.3 | 48.6 | 42 | A |
| 175 | D | N | 42.2 | 2.1 | 49.5 | 41 | A |
| 175 | D | CA | 42.6 | 1.2 | 50.6 | 43 | A |
| 175 | D | CB | 41.5 | 1.0 | 51.6 | 42 | A |
| 175 | D | CG | 41.3 | 2.3 | 52.4 | 43 | A |
| 175 | D | OD1 | 42.3 | 3.0 | 52.6 | 43 | A |
| 175 | D | OD2 | 40.2 | 2.4 | 52.9 | 42 | A |
| 175 | D | C | 43.0 | −0.2 | 50.0 | 44 | A |
| 175 | D | O | 43.5 | −1.1 | 50.7 | 45 | A |
| 176 | H | N | 42.8 | −0.4 | 48.7 | 44 | A |
| 176 | H | CA | 43.1 | −1.6 | 48.0 | 45 | A |
| 176 | H | CB | 41.9 | −2.4 | 47.6 | 45 | A |
| 176 | H | CG | 41.1 | −3.0 | 48.7 | 47 | A |
| 176 | H | CD2 | 40.3 | −2.4 | 49.6 | 49 | A |
| 176 | H | ND1 | 41.0 | −4.3 | 48.9 | 48 | A |
| 176 | H | CE1 | 40.2 | −4.5 | 49.9 | 49 | A |
| 176 | H | NE2 | 39.8 | −3.4 | 50.4 | 50 | A |
| 176 | H | C | 44.1 | −1.4 | 46.9 | 45 | A |
| 176 | H | O | 43.8 | −0.6 | 46.0 | 46 | A |
| 177 | D | N | 45.2 | −2.2 | 46.8 | 45 | A |
| 177 | D | CA | 46.1 | −2.1 | 45.7 | 45 | A |
| 177 | D | CB | 47.4 | −3.0 | 46.0 | 48 | A |
| 177 | D | CG | 48.2 | −3.2 | 44.8 | 50 | A |
| 177 | D | OD1 | 48.6 | −2.2 | 44.1 | 51 | A |
| 177 | D | OD2 | 48.4 | −4.4 | 44.5 | 51 | A |
| 177 | D | C | 45.4 | −2.6 | 44.5 | 44 | A |
| 177 | D | O | 45.0 | −3.8 | 44.4 | 43 | A |
| 178 | H | N | 45.2 | −1.8 | 43.5 | 40 | A |
| 178 | H | CA | 44.6 | −2.2 | 42.3 | 38 | A |
| 178 | H | CB | 43.6 | −1.0 | 41.8 | 37 | A |
| 178 | H | CG | 42.3 | −1.0 | 42.5 | 36 | A |
| 178 | H | CD2 | 41.1 | −1.4 | 42.1 | 33 | A |
| 178 | H | ND1 | 42.2 | −0.5 | 43.8 | 36 | A |
| 178 | H | CE1 | 40.9 | −0.7 | 44.1 | 36 | A |
| 178 | H | NE2 | 40.2 | −1.2 | 43.1 | 34 | A |
| 178 | H | C | 45.5 | −2.6 | 41.2 | 35 | A |
| 178 | H | O | 45.0 | −2.8 | 40.1 | 36 | A |
| 179 | T | N | 46.8 | −2.7 | 41.5 | 34 | A |
| 179 | T | CA | 47.7 | −3.1 | 40.5 | 35 | A |
| 179 | T | CB | 49.1 | −3.4 | 41.1 | 36 | A |
| 179 | T | OG1 | 49.5 | −2.3 | 41.9 | 37 | A |
| 179 | T | CG2 | 50.2 | −3.6 | 40.0 | 35 | A |
| 179 | T | C | 47.2 | −4.4 | 39.8 | 35 | A |
| 179 | T | O | 47.0 | −5.4 | 40.5 | 35 | A |
| 180 | G | N | 47.1 | −4.4 | 38.5 | 34 | A |
| 180 | G | CA | 46.7 | −5.5 | 37.7 | 33 | A |
| 180 | G | C | 45.2 | −5.7 | 37.7 | 35 | A |
| 180 | G | O | 44.7 | −6.7 | 37.1 | 36 | A |
| 181 | F | N | 44.4 | −4.8 | 38.2 | 35 | A |
| 181 | F | CA | 42.9 | −5.0 | 38.2 | 37 | A |
| 181 | F | CB | 42.4 | −4.9 | 39.7 | 40 | A |
| 181 | F | CG | 42.9 | −6.0 | 40.6 | 43 | A |
| 181 | F | CD1 | 42.9 | −7.3 | 40.2 | 45 | A |
| 181 | F | CD2 | 43.4 | −5.6 | 41.8 | 43 | A |
| 181 | F | CE1 | 43.4 | −8.3 | 41.1 | 45 | A |
| 181 | F | CE2 | 43.9 | −6.5 | 42.7 | 43 | A |
| 181 | F | CZ | 43.9 | −7.9 | 42.4 | 46 | A |
| 181 | F | C | 42.0 | −4.1 | 37.4 | 35 | A |
| 181 | F | O | 40.8 | −4.3 | 37.3 | 37 | A |
| 182 | L | N | 42.6 | −3.1 | 36.7 | 34 | A |
| 182 | L | CA | 41.8 | −2.2 | 35.9 | 33 | A |
| 182 | L | CB | 42.3 | −0.8 | 36.0 | 34 | A |
| 182 | L | CG | 42.5 | −0.3 | 37.4 | 34 | A |
| 182 | L | CD1 | 43.1 | 1.1 | 37.4 | 34 | A |
| 182 | L | CD2 | 41.2 | −0.3 | 38.2 | 33 | A |
| 182 | L | C | 41.6 | −2.6 | 34.4 | 33 | A |
| 182 | L | O | 42.5 | −3.2 | 33.9 | 34 | A |
| 183 | X | N | 40.5 | −2.2 | 33.8 | 33 | A |
| 183 | X | CA | 40.2 | −2.5 | 32.5 | 30 | A |
| 183 | X | CB | 38.9 | −2.0 | 32.0 | 31 | A |
| 183 | X | OG1 | 37.9 | −2.8 | 32.8 | 33 | A |
| 183 | X | CG2 | 38.6 | −2.3 | 30.6 | 26 | A |
| 183 | X | C | 41.3 | −1.9 | 31.6 | 30 | A |
| 183 | X | O | 41.7 | −0.8 | 31.8 | 28 | A |
| 183 | X | S | 37.5 | −2.3 | 34.2 | 32 | A |
| 183 | X | P | 36.9 | −3.9 | 35.2 | 37 | A |
| 183 | X | O1 | 37.0 | −3.6 | 36.8 | 40 | A |
| 183 | X | O2 | 35.5 | −4.3 | 34.9 | 39 | A |
| 183 | X | O3 | 37.9 | −5.1 | 34.9 | 41 | A |
| 184 | E | N | 41.8 | −2.7 | 30.7 | 30 | A |
| 184 | E | CA | 42.9 | −2.3 | 29.8 | 33 | A |
| 184 | E | CB | 43.5 | −3.5 | 29.1 | 33 | A |
| 184 | E | CG | 44.9 | −3.4 | 28.7 | 39 | A |
| 184 | E | CD | 45.5 | −4.6 | 28.2 | 41 | A |
| 184 | E | OE1 | 45.3 | −5.7 | 28.9 | 41 | A |
| 184 | E | OE2 | 46.2 | −4.6 | 27.2 | 45 | A |
| 184 | E | C | 42.7 | −1.2 | 28.8 | 33 | A |
| 184 | E | O | 43.5 | −0.1 | 28.8 | 37 | A |
| 185 | Z | N | 41.8 | −1.3 | 27.9 | 30 | A |
| 185 | Z | CA | 41.5 | −0.4 | 26.8 | 29 | A |
| 185 | Z | CB | 41.0 | −1.3 | 25.6 | 29 | A |
| 185 | Z | CG | 41.0 | −0.6 | 24.2 | 26 | A |
| 185 | Z | CD1 | 42.1 | −0.2 | 23.5 | 27 | A |
| 185 | Z | CE1 | 42.0 | 0.4 | 22.2 | 24 | A |
| 185 | Z | CD2 | 39.7 | −0.4 | 23.6 | 26 | A |
| 185 | Z | CE2 | 39.6 | 0.2 | 22.3 | 26 | A |
| 185 | Z | CZ | 40.8 | 0.5 | 21.6 | 25 | A |
| 185 | Z | OH | 40.6 | 1.0 | 20.3 | 27 | A |
| 185 | Z | C | 40.5 | 0.7 | 27.1 | 30 | A |
| 185 | Z | O | 39.4 | 0.7 | 26.6 | 31 | A |
| 185 | Z | S | 41.0 | 2.5 | 20.0 | 30 | A |
| 185 | Z | P | 43.0 | 2.4 | 19.5 | 26 | A |
| 185 | Z | O1 | 43.6 | 3.9 | 19.5 | 38 | A |
| 185 | Z | O2 | 43.2 | 1.8 | 18.1 | 38 | A |
| 185 | Z | O3 | 43.8 | 1.6 | 20.6 | 38 | A |
| 186 | V | N | 40.9 | 1.6 | 27.9 | 29 | A |
| 186 | V | CA | 40.0 | 2.7 | 28.4 | 26 | A |
| 186 | V | CB | 40.0 | 2.8 | 29.9 | 29 | A |
| 186 | V | CG1 | 39.5 | 1.5 | 30.5 | 29 | A |
| 186 | V | CG2 | 41.4 | 3.1 | 30.4 | 29 | A |
| 186 | V | C | 40.4 | 4.1 | 27.8 | 25 | A |
| 186 | V | O | 41.4 | 4.4 | 27.3 | 18 | A |
| 187 | A | N | 39.4 | 5.0 | 27.9 | 24 | A |
| 187 | A | CA | 39.5 | 6.4 | 27.4 | 23 | A |
| 187 | A | CB | 40.8 | 7.0 | 28.0 | 23 | A |
| 187 | A | C | 39.5 | 6.4 | 25.9 | 23 | A |
| 187 | A | O | 39.8 | 5.4 | 25.3 | 25 | A |
| 188 | T | N | 39.1 | 7.6 | 25.3 | 22 | A |
| 188 | T | CA | 39.1 | 7.7 | 23.9 | 20 | A |
| 188 | T | CB | 38.2 | 8.9 | 23.5 | 21 | A |
| 188 | T | OG1 | 36.8 | 8.5 | 23.9 | 21 | A |
| 188 | T | CG2 | 38.2 | 9.1 | 22.0 | 18 | A |
| 188 | T | C | 40.6 | 8.0 | 23.5 | 21 | A |
| 188 | T | O | 41.2 | 8.9 | 24.1 | 19 | A |
| 189 | R | N | 41.0 | 7.3 | 22.5 | 20 | A |
| 189 | R | CA | 42.4 | 7.4 | 22.0 | 20 | A |
| 189 | R | CB | 42.5 | 6.9 | 20.5 | 21 | A |
| 189 | R | CG | 44.0 | 6.7 | 20.1 | 21 | A |
| 189 | R | CD | 44.1 | 6.6 | 18.6 | 24 | A |
| 189 | R | NE | 43.2 | 5.6 | 18.0 | 24 | A |
| 189 | R | CZ | 42.7 | 5.7 | 16.8 | 25 | A |
| 189 | R | NH1 | 42.9 | 6.8 | 16.1 | 20 | A |
| 189 | R | NH2 | 41.8 | 4.8 | 16.4 | 23 | A |
| 189 | R | C | 43.1 | 8.7 | 22.1 | 19 | A |
| 189 | R | O | 44.1 | 8.8 | 22.8 | 18 | A |
| 190 | W | N | 42.6 | 9.8 | 21.5 | 18 | A |
| 190 | W | CA | 43.3 | 11.0 | 21.5 | 19 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 190 | W | CB  | 42.6 | 12.1 | 20.7 | 17 | A |
| --- | - | --- | ---- | ---- | ---- | -- | - |
| 190 | W | CG  | 42.4 | 11.8 | 19.3 | 20 | A |
| 190 | W | CD2 | 41.6 | 12.5 | 18.3 | 18 | A |
| 190 | W | CE2 | 41.8 | 11.9 | 17.1 | 19 | A |
| 190 | W | CE3 | 40.7 | 13.6 | 18.4 | 22 | A |
| 190 | W | CD1 | 43.1 | 10.9 | 18.6 | 19 | A |
| 190 | W | NE1 | 42.7 | 10.9 | 17.2 | 19 | A |
| 190 | W | CZ2 | 41.1 | 12.4 | 15.9 | 18 | A |
| 190 | W | CZ3 | 40.0 | 14.0 | 17.3 | 21 | A |
| 190 | W | CH2 | 40.2 | 13.4 | 16.0 | 21 | A |
| 190 | W | C   | 43.5 | 11.6 | 23.0 | 17 | A |
| 190 | W | O   | 44.5 | 12.3 | 23.2 | 19 | A |
| 191 | Y | N   | 42.7 | 11.1 | 23.9 | 17 | A |
| 191 | Y | CA  | 42.7 | 11.6 | 25.3 | 16 | A |
| 191 | Y | CB  | 41.3 | 12.1 | 25.7 | 15 | A |
| 191 | Y | CG  | 40.7 | 13.1 | 24.7 | 19 | A |
| 191 | Y | CD1 | 40.0 | 12.6 | 23.6 | 20 | A |
| 191 | Y | CE1 | 39.6 | 13.5 | 22.6 | 19 | A |
| 191 | Y | CD2 | 41.0 | 14.4 | 24.9 | 20 | A |
| 191 | Y | CE2 | 40.6 | 15.3 | 23.9 | 16 | A |
| 191 | Y | CZ  | 39.9 | 14.9 | 22.8 | 20 | A |
| 191 | Y | OH  | 39.6 | 15.7 | 21.7 | 18 | A |
| 191 | Y | C   | 43.3 | 10.5 | 26.3 | 15 | A |
| 191 | Y | O   | 43.2 | 10.7 | 27.5 | 14 | A |
| 192 | R | N   | 43.9 | 9.5  | 25.7 | 15 | A |
| 192 | R | CA  | 44.5 | 8.4  | 26.5 | 15 | A |
| 192 | R | CB  | 44.5 | 7.2  | 25.5 | 18 | A |
| 192 | R | CG  | 44.6 | 5.8  | 26.2 | 20 | A |
| 192 | R | CD  | 43.6 | 4.9  | 25.6 | 22 | A |
| 192 | R | NE  | 43.9 | 4.4  | 24.2 | 26 | A |
| 192 | R | CZ  | 43.1 | 3.9  | 23.4 | 25 | A |
| 192 | R | NH1 | 41.8 | 3.8  | 23.7 | 20 | A |
| 192 | R | NH2 | 43.5 | 3.5  | 22.2 | 22 | A |
| 192 | R | C   | 45.8 | 8.7  | 27.0 | 14 | A |
| 192 | R | O   | 46.8 | 9.1  | 26.3 | 17 | A |
| 193 | A | N   | 46.0 | 8.6  | 28.4 | 13 | A |
| 193 | A | CA  | 47.3 | 8.8  | 29.0 | 13 | A |
| 193 | A | CB  | 47.1 | 8.8  | 30.5 | 15 | A |
| 193 | A | C   | 48.3 | 7.8  | 28.6 | 16 | A |
| 193 | A | O   | 47.9 | 6.7  | 28.3 | 12 | A |
| 194 | P | N   | 49.6 | 8.2  | 28.6 | 16 | A |
| 194 | P | CD  | 50.2 | 9.4  | 29.2 | 12 | A |
| 194 | P | CA  | 50.6 | 7.2  | 28.2 | 16 | A |
| 194 | P | CB  | 51.9 | 8.0  | 28.5 | 15 | A |
| 194 | P | CG  | 51.5 | 9.4  | 28.5 | 15 | A |
| 194 | P | C   | 50.6 | 5.9  | 29.0 | 18 | A |
| 194 | P | O   | 50.8 | 4.8  | 28.5 | 18 | A |
| 195 | E | N   | 50.4 | 6.0  | 30.3 | 17 | A |
| 195 | E | CA  | 50.4 | 4.9  | 31.2 | 18 | A |
| 195 | E | CB  | 50.3 | 5.3  | 32.7 | 16 | A |
| 195 | E | CG  | 49.0 | 5.9  | 33.1 | 15 | A |
| 195 | E | CD  | 49.1 | 7.4  | 33.1 | 18 | A |
| 195 | E | OE1 | 49.9 | 8.0  | 32.5 | 21 | A |
| 195 | E | OE2 | 48.2 | 8.0  | 33.8 | 20 | A |
| 195 | E | C   | 49.3 | 3.8  | 30.9 | 19 | A |
| 195 | E | O   | 49.5 | 2.6  | 31.2 | 21 | A |
| 196 | I | N   | 48.2 | 4.2  | 30.2 | 20 | A |
| 196 | I | CA  | 47.2 | 3.3  | 29.9 | 21 | A |
| 196 | I | CB  | 46.0 | 4.0  | 29.2 | 23 | A |
| 196 | I | CG2 | 45.1 | 3.0  | 28.5 | 22 | A |
| 196 | I | CG1 | 45.2 | 4.7  | 30.4 | 23 | A |
| 196 | I | CD1 | 44.2 | 5.7  | 29.9 | 22 | A |
| 196 | I | C   | 47.8 | 2.3  | 28.8 | 23 | A |
| 196 | I | O   | 47.4 | 1.1  | 28.8 | 24 | A |
| 197 | M | N   | 48.8 | 2.8  | 28.1 | 25 | A |
| 197 | M | CA  | 49.5 | 2.0  | 27.1 | 22 | A |
| 197 | M | CB  | 50.1 | 2.8  | 25.9 | 24 | A |
| 197 | M | CG  | 49.1 | 3.1  | 24.8 | 28 | A |
| 197 | M | SD  | 48.1 | 4.6  | 25.0 | 32 | A |
| 197 | M | CE  | 49.3 | 5.8  | 24.5 | 29 | A |
| 197 | M | C   | 50.7 | 1.3  | 27.7 | 23 | A |
| 197 | M | O   | 51.1 | 0.2  | 27.3 | 21 | A |
| 198 | L | N   | 51.4 | 2.0  | 28.7 | 24 | A |
| 198 | L | CA  | 52.6 | 1.4  | 29.3 | 25 | A |
| 198 | L | CB  | 53.6 | 2.6  | 29.5 | 26 | A |
| 198 | L | CG  | 54.4 | 3.2  | 28.4 | 28 | A |
| 198 | L | CD1 | 54.5 | 2.3  | 27.2 | 24 | A |
| 198 | L | CD2 | 53.8 | 4.5  | 28.0 | 27 | A |
| 198 | L | C   | 52.5 | 0.6  | 30.6 | 24 | A |
| 198 | L | O   | 53.4 | -0.1 | 30.9 | 25 | A |
| 199 | N | N   | 51.4 | 0.8  | 31.3 | 24 | A |
| 199 | N | CA  | 51.1 | 0.1  | 32.5 | 24 | A |
| 199 | N | CB  | 51.4 | 1.0  | 33.7 | 24 | A |
| 199 | N | CG  | 51.3 | 0.3  | 35.1 | 25 | A |
| 199 | N | OD1 | 51.3 | 1.0  | 36.1 | 25 | A |
| 199 | N | ND2 | 51.3 | -1.0 | 35.0 | 23 | A |
| 199 | N | C   | 49.6 | -0.3 | 32.5 | 27 | A |
| 199 | N | O   | 48.8 | -0.0 | 33.4 | 27 | A |
| 200 | S | N   | 49.2 | -0.8 | 31.3 | 29 | A |
| 200 | S | CA  | 47.9 | -1.2 | 30.9 | 31 | A |
| 200 | S | CB  | 47.9 | -2.3 | 29.9 | 33 | A |
| 200 | S | OG  | 48.5 | -3.5 | 30.4 | 35 | A |
| 200 | S | C   | 46.9 | -1.5 | 32.0 | 30 | A |
| 200 | S | O   | 45.7 | -1.2 | 31.9 | 31 | A |
| 201 | K | N   | 47.3 | -2.2 | 33.1 | 27 | A |
| 201 | K | CA  | 46.4 | -2.6 | 34.1 | 28 | A |
| 201 | K | CB  | 46.2 | -4.1 | 34.2 | 28 | A |
| 201 | K | CG  | 45.9 | -4.7 | 32.8 | 29 | A |
| 201 | K | CD  | 45.0 | -6.0 | 33.0 | 32 | A |
| 201 | K | CE  | 43.7 | -5.7 | 33.6 | 35 | A |
| 201 | K | NZ  | 42.8 | -6.9 | 33.8 | 36 | A |
| 201 | K | C   | 46.6 | -2.0 | 35.5 | 26 | A |
| 201 | K | O   | 46.0 | -2.4 | 36.5 | 24 | A |
| 202 | G | N   | 47.6 | -1.1 | 35.6 | 23 | A |
| 202 | G | CA  | 47.9 | -0.5 | 36.9 | 23 | A |
| 202 | G | C   | 47.9 | 1.0  | 36.9 | 24 | A |
| 202 | G | O   | 48.5 | 1.6  | 37.7 | 24 | A |
| 203 | Y | N   | 47.1 | 1.6  | 36.0 | 25 | A |
| 203 | Y | CA  | 47.0 | 3.1  | 35.9 | 24 | A |
| 203 | Y | CB  | 46.4 | 3.5  | 34.6 | 22 | A |
| 203 | Y | CG  | 45.1 | 2.9  | 34.3 | 21 | A |
| 203 | Y | CD1 | 43.9 | 3.5  | 34.8 | 19 | A |
| 203 | Y | CE1 | 42.7 | 3.0  | 34.5 | 14 | A |
| 203 | Y | CD2 | 45.0 | 1.8  | 33.4 | 18 | A |
| 203 | Y | CE2 | 43.7 | 1.3  | 33.2 | 13 | A |
| 203 | Y | CZ  | 42.6 | 1.8  | 33.7 | 15 | A |
| 203 | Y | OH  | 41.3 | 1.3  | 33.5 | 16 | A |
| 203 | Y | C   | 46.1 | 3.5  | 37.1 | 25 | A |
| 203 | Y | O   | 45.5 | 2.7  | 37.8 | 25 | A |
| 204 | T | N   | 46.1 | 4.8  | 37.3 | 24 | A |
| 204 | T | CA  | 45.2 | 5.4  | 38.4 | 20 | A |
| 204 | T | CB  | 46.1 | 6.0  | 39.5 | 22 | A |
| 204 | T | OG1 | 46.8 | 7.1  | 39.0 | 21 | A |
| 204 | T | CG2 | 47.1 | 5.0  | 40.1 | 21 | A |
| 204 | T | C   | 44.3 | 6.5  | 37.9 | 21 | A |
| 204 | T | O   | 44.3 | 6.7  | 36.7 | 20 | A |
| 205 | K | N   | 43.7 | 7.1  | 38.8 | 21 | A |
| 205 | K | CA  | 42.8 | 8.3  | 38.6 | 22 | A |
| 205 | K | CB  | 42.3 | 8.8  | 39.9 | 26 | A |
| 205 | K | CG  | 43.4 | 9.5  | 40.7 | 29 | A |
| 205 | K | CD  | 43.1 | 9.5  | 42.2 | 33 | A |
| 205 | K | CE  | 41.8 | 10.2 | 42.6 | 34 | A |
| 205 | K | NZ  | 41.4 | 9.9  | 44.0 | 36 | A |
| 205 | K | C   | 43.5 | 9.4  | 37.8 | 20 | A |
| 205 | K | O   | 42.8 | 10.2 | 37.2 | 20 | A |
| 206 | S | N   | 44.8 | 9.5  | 37.9 | 20 | A |
| 206 | S | CA  | 45.4 | 10.6 | 37.2 | 20 | A |
| 206 | S | CB  | 46.9 | 10.8 | 37.6 | 23 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) 1-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 206 | S | OG  | 47.8 | 9.8  | 37.1 | 27 | A |
|-----|---|-----|------|------|------|----|---|
| 206 | S | C   | 45.3 | 10.6 | 35.7 | 19 | A |
| 206 | S | O   | 45.7 | 11.6 | 35.0 | 21 | A |
| 207 | I | N   | 44.8 | 9.5  | 35.1 | 16 | A |
| 207 | I | CA  | 44.6 | 9.5  | 33.7 | 17 | A |
| 207 | I | CB  | 44.2 | 8.1  | 33.1 | 17 | A |
| 207 | I | CG2 | 45.1 | 7.0  | 33.6 | 15 | A |
| 207 | I | CG1 | 42.7 | 7.8  | 33.6 | 20 | A |
| 207 | I | CD1 | 42.2 | 6.4  | 33.1 | 19 | A |
| 207 | I | C   | 43.5 | 10.5 | 33.3 | 17 | A |
| 207 | I | O   | 43.4 | 11.0 | 32.2 | 19 | A |
| 208 | D | N   | 42.7 | 10.8 | 34.3 | 17 | A |
| 208 | D | CA  | 41.6 | 11.8 | 34.1 | 16 | A |
| 208 | D | CB  | 40.6 | 11.8 | 35.2 | 16 | A |
| 208 | D | CG  | 39.6 | 10.6 | 35.2 | 16 | A |
| 208 | D | OD1 | 39.3 | 10.2 | 34.1 | 12 | A |
| 208 | D | OD2 | 39.3 | 10.1 | 36.3 | 19 | A |
| 208 | D | C   | 42.2 | 13.2 | 34.0 | 17 | A |
| 208 | D | O   | 41.8 | 14.0 | 33.2 | 17 | A |
| 209 | I | N   | 43.3 | 13.4 | 34.8 | 15 | A |
| 209 | I | CA  | 44.0 | 14.7 | 34.7 | 16 | A |
| 209 | I | CB  | 45.0 | 14.8 | 35.9 | 16 | A |
| 209 | I | CG2 | 45.9 | 16.1 | 35.6 | 17 | A |
| 209 | I | CG1 | 44.4 | 14.9 | 37.2 | 16 | A |
| 209 | I | CD1 | 43.6 | 16.2 | 37.5 | 18 | A |
| 209 | I | C   | 44.7 | 14.9 | 33.4 | 16 | A |
| 209 | I | O   | 44.7 | 16.0 | 32.8 | 17 | A |
| 210 | W | N   | 45.2 | 13.8 | 32.9 | 16 | A |
| 210 | W | CA  | 45.9 | 13.8 | 31.6 | 16 | A |
| 210 | W | CB  | 46.4 | 12.4 | 31.2 | 16 | A |
| 210 | W | CG  | 47.0 | 12.4 | 29.9 | 14 | A |
| 210 | W | CD2 | 48.4 | 12.7 | 29.5 | 11 | A |
| 210 | W | CE2 | 48.4 | 12.6 | 28.1 | 13 | A |
| 210 | W | CE3 | 49.5 | 13.0 | 30.2 | 13 | A |
| 210 | W | CD1 | 46.3 | 12.2 | 28.7 | 14 | A |
| 210 | W | NE1 | 47.2 | 12.3 | 27.6 | 13 | A |
| 210 | W | CZ2 | 49.6 | 12.8 | 27.4 | 15 | A |
| 210 | W | CZ3 | 50.7 | 13.2 | 29.6 | 13 | A |
| 210 | W | CH2 | 50.8 | 13.1 | 28.2 | 14 | A |
| 210 | W | C   | 44.9 | 14.2 | 30.5 | 16 | A |
| 210 | W | O   | 45.2 | 15.0 | 29.6 | 14 | A |
| 211 | S | N   | 43.7 | 13.7 | 30.6 | 17 | A |
| 211 | S | CA  | 42.6 | 14.0 | 29.7 | 17 | A |
| 211 | S | CB  | 41.4 | 13.2 | 30.0 | 17 | A |
| 211 | S | OG  | 41.6 | 11.8 | 29.7 | 14 | A |
| 211 | S | C   | 42.3 | 15.5 | 29.7 | 17 | A |
| 211 | S | O   | 42.2 | 16.1 | 28.7 | 18 | A |
| 212 | V | N   | 42.1 | 16.0 | 30.9 | 15 | A |
| 212 | V | CA  | 41.7 | 17.4 | 31.1 | 16 | A |
| 212 | V | CB  | 41.6 | 17.8 | 32.5 | 17 | A |
| 212 | V | CG1 | 41.4 | 19.4 | 32.6 | 17 | A |
| 212 | V | CG2 | 40.5 | 17.1 | 33.2 | 15 | A |
| 212 | V | C   | 42.9 | 18.2 | 30.4 | 19 | A |
| 212 | V | O   | 42.6 | 19.3 | 29.8 | 17 | A |
| 213 | G | N   | 44.1 | 17.7 | 30.5 | 20 | A |
| 213 | G | CA  | 45.2 | 18.3 | 29.9 | 19 | A |
| 213 | G | C   | 45.0 | 18.4 | 28.4 | 19 | A |
| 213 | G | O   | 45.2 | 19.5 | 27.8 | 23 | A |
| 214 | C | N   | 44.6 | 17.3 | 27.8 | 17 | A |
| 214 | C | CA  | 44.4 | 17.3 | 26.3 | 17 | A |
| 214 | C | CB  | 44.0 | 15.9 | 25.8 | 16 | A |
| 214 | C | SG  | 45.2 | 14.7 | 26.1 | 16 | A |
| 214 | C | C   | 43.3 | 18.3 | 26.0 | 17 | A |
| 214 | C | O   | 43.3 | 19.0 | 25.0 | 18 | A |
| 215 | I | N   | 42.3 | 18.4 | 26.9 | 20 | A |
| 215 | I | CA  | 41.1 | 19.3 | 26.6 | 19 | A |
| 215 | I | CB  | 40.0 | 18.9 | 27.6 | 16 | A |
| 215 | I | CG2 | 38.9 | 20.0 | 27.6 | 12 | A |
| 215 | I | CG1 | 39.4 | 17.6 | 27.3 | 13 | A |
| 215 | I | CD1 | 38.6 | 17.0 | 28.4 | 14 | A |
| 215 | I | C   | 41.5 | 20.7 | 26.8 | 20 | A |
| 215 | I | O   | 41.0 | 21.6 | 26.0 | 22 | A |
| 216 | L | N   | 42.4 | 21.1 | 27.7 | 20 | A |
| 216 | L | CA  | 42.8 | 22.4 | 27.8 | 21 | A |
| 216 | L | CB  | 43.9 | 22.5 | 29.0 | 20 | A |
| 216 | L | CG  | 44.0 | 23.9 | 29.7 | 20 | A |
| 216 | L | CD1 | 45.5 | 24.0 | 30.1 | 20 | A |
| 216 | L | CD2 | 43.6 | 25.1 | 28.9 | 15 | A |
| 216 | L | C   | 43.5 | 22.8 | 26.5 | 22 | A |
| 216 | L | O   | 43.2 | 23.9 | 25.9 | 23 | A |
| 217 | A | N   | 44.4 | 22.0 | 26.0 | 22 | A |
| 217 | A | CA  | 45.2 | 22.3 | 24.8 | 21 | A |
| 217 | A | CB  | 46.1 | 21.1 | 24.5 | 22 | A |
| 217 | A | C   | 44.2 | 22.5 | 23.6 | 22 | A |
| 217 | A | O   | 44.4 | 23.3 | 22.8 | 22 | A |
| 218 | E | N   | 43.1 | 21.7 | 23.6 | 21 | A |
| 218 | E | CA  | 42.1 | 21.9 | 22.5 | 22 | A |
| 218 | E | CB  | 41.1 | 20.7 | 22.5 | 20 | A |
| 218 | E | CG  | 40.8 | 20.3 | 21.1 | 23 | A |
| 218 | E | CD  | 40.1 | 18.9 | 21.0 | 22 | A |
| 218 | E | OE1 | 40.7 | 17.9 | 21.6 | 20 | A |
| 218 | E | OE2 | 39.1 | 18.8 | 20.4 | 24 | A |
| 218 | E | C   | 41.4 | 23.2 | 22.6 | 22 | A |
| 218 | E | O   | 41.1 | 23.9 | 21.6 | 23 | A |
| 219 | M | N   | 41.1 | 23.7 | 23.9 | 21 | A |
| 219 | M | CA  | 40.4 | 25.0 | 24.1 | 22 | A |
| 219 | M | CB  | 40.8 | 25.1 | 25.6 | 19 | A |
| 219 | M | CG  | 38.9 | 24.2 | 26.0 | 22 | A |
| 219 | M | SD  | 38.1 | 24.7 | 27.6 | 17 | A |
| 219 | M | CE  | 39.2 | 24.0 | 28.8 | 18 | A |
| 219 | M | C   | 41.3 | 26.1 | 23.7 | 21 | A |
| 219 | M | O   | 40.9 | 27.2 | 23.3 | 23 | A |
| 220 | L | N   | 42.6 | 25.9 | 23.8 | 22 | A |
| 220 | L | CA  | 43.6 | 26.9 | 23.4 | 22 | A |
| 220 | L | CB  | 44.9 | 26.6 | 24.1 | 19 | A |
| 220 | L | CG  | 45.0 | 26.8 | 25.7 | 16 | A |
| 220 | L | CD1 | 46.2 | 26.1 | 26.2 | 13 | A |
| 220 | L | CD2 | 45.0 | 28.3 | 26.0 | 16 | A |
| 220 | L | C   | 43.9 | 27.0 | 21.9 | 21 | A |
| 220 | L | O   | 44.3 | 28.1 | 21.5 | 22 | A |
| 221 | S | N   | 43.6 | 26.0 | 21.2 | 21 | A |
| 221 | S | CA  | 43.9 | 26.1 | 19.7 | 22 | A |
| 221 | S | CB  | 45.2 | 25.4 | 19.5 | 26 | A |
| 221 | S | OG  | 45.1 | 24.0 | 19.7 | 29 | A |
| 221 | S | C   | 42.8 | 25.4 | 18.8 | 23 | A |
| 221 | S | O   | 43.0 | 25.4 | 17.6 | 25 | A |
| 222 | N | N   | 41.7 | 24.9 | 19.4 | 21 | A |
| 222 | N | CA  | 40.7 | 24.3 | 18.6 | 23 | A |
| 222 | N | CB  | 40.1 | 25.3 | 17.6 | 21 | A |
| 222 | N | CG  | 39.4 | 26.4 | 18.4 | 22 | A |
| 222 | N | OD1 | 40.1 | 27.4 | 18.9 | 20 | A |
| 222 | N | ND2 | 38.1 | 26.4 | 18.5 | 22 | A |
| 222 | N | C   | 41.2 | 23.1 | 17.7 | 22 | A |
| 222 | N | O   | 40.8 | 22.9 | 16.6 | 22 | A |
| 223 | R | N   | 42.2 | 22.4 | 18.3 | 23 | A |
| 223 | R | CA  | 42.7 | 21.3 | 17.5 | 25 | A |
| 223 | R | CB  | 43.9 | 21.8 | 16.7 | 30 | A |
| 223 | R | CG  | 44.2 | 21.0 | 15.4 | 37 | A |
| 223 | R | CD  | 45.6 | 21.3 | 14.9 | 42 | A |
| 223 | R | NE  | 46.6 | 20.5 | 15.7 | 47 | A |
| 223 | R | CZ  | 46.7 | 19.1 | 15.6 | 48 | A |
| 223 | R | NH1 | 45.9 | 18.5 | 14.8 | 48 | A |
| 223 | R | NH2 | 47.6 | 18.5 | 16.4 | 44 | A |
| 223 | R | C   | 43.2 | 20.2 | 18.5 | 22 | A |
| 223 | R | O   | 43.8 | 20.6 | 19.6 | 22 | A |
| 224 | P | N   | 42.9 | 18.9 | 18.2 | 20 | A |
| 224 | P | CD  | 42.1 | 18.3 | 17.2 | 19 | A |
| 224 | P | CA  | 43.4 | 17.9 | 19.2 | 16 | A |

TABLE 3-continued

Structural Coordinates of Ah$_6$-ERK2 [di-thiophosphorylated, SEQ ID NO: 5] Crystals The following table contains one line for each atom in one Thiophosphorylated Erk2 kinase tetramer. The columns are: 1) residue number, 2) 1-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| Residue | AA | Atom | X | Y | Z | B | Chain |
|---|---|---|---|---|---|---|---|
| 224 | P | CB | 42.8 | 16.6 | 18.8 | 13 | A |
| 224 | P | CG | 42.6 | 16.9 | 17.2 | 22 | A |
| 224 | P | C | 44.9 | 18.0 | 19.2 | 14 | A |
| 224 | P | O | 45.5 | 18.1 | 18.1 | 13 | A |
| 225 | I | N | 45.5 | 17.9 | 20.3 | 12 | A |
| 225 | I | CA | 47.0 | 18.0 | 20.4 | 14 | A |
| 225 | I | CB | 47.4 | 18.5 | 21.9 | 16 | A |
| 225 | I | CG2 | 46.9 | 17.5 | 22.9 | 16 | A |
| 225 | I | CG1 | 48.9 | 18.8 | 22.0 | 19 | A |
| 225 | I | CD1 | 49.3 | 19.9 | 21.2 | 23 | A |
| 225 | I | C | 47.7 | 16.6 | 20.1 | 16 | A |
| 225 | I | O | 48.8 | 16.6 | 19.5 | 15 | A |
| 226 | F | N | 47.1 | 15.5 | 20.4 | 16 | A |
| 226 | F | CA | 47.6 | 14.2 | 20.1 | 13 | A |
| 226 | F | CB | 47.9 | 13.5 | 21.4 | 14 | A |
| 226 | F | CG | 48.8 | 14.2 | 22.4 | 14 | A |
| 226 | F | CD1 | 50.0 | 14.9 | 22.0 | 15 | A |
| 226 | F | CD2 | 48.4 | 14.3 | 23.7 | 13 | A |
| 226 | F | CE1 | 50.7 | 15.5 | 22.9 | 14 | A |
| 226 | F | CE2 | 49.1 | 15.0 | 24.6 | 14 | A |
| 226 | F | CZ | 50.3 | 15.6 | 24.3 | 10 | A |
| 226 | F | C | 46.7 | 13.4 | 19.3 | 15 | A |
| 226 | F | O | 46.1 | 12.4 | 19.7 | 13 | A |
| 227 | P | N | 46.5 | 13.7 | 18.0 | 15 | A |
| 227 | P | CD | 47.1 | 14.9 | 17.3 | 14 | A |
| 227 | P | CA | 45.6 | 12.9 | 17.1 | 17 | A |
| 227 | P | CB | 45.3 | 14.0 | 16.0 | 14 | A |
| 227 | P | CG | 46.5 | 14.7 | 15.8 | 14 | A |
| 227 | P | C | 46.1 | 11.6 | 16.6 | 19 | A |
| 227 | P | O | 46.3 | 11.5 | 15.3 | 20 | A |
| 228 | G | N | 46.4 | 10.7 | 17.4 | 18 | A |
| 228 | G | CA | 46.9 | 9.4 | 17.0 | 19 | A |
| 228 | G | C | 45.9 | 8.7 | 16.1 | 20 | A |
| 228 | G | O | 44.7 | 8.8 | 16.3 | 21 | A |
| 229 | K | N | 46.4 | 7.9 | 15.2 | 20 | A |
| 229 | K | CA | 45.5 | 7.2 | 14.2 | 22 | A |
| 229 | K | CB | 46.2 | 7.3 | 12.8 | 24 | A |
| 229 | K | CG | 46.4 | 8.7 | 12.4 | 28 | A |
| 229 | K | CD | 47.3 | 8.8 | 11.2 | 34 | A |
| 229 | K | CE | 47.4 | 10.2 | 10.6 | 34 | A |
| 229 | K | NZ | 48.3 | 10.3 | 9.5 | 35 | A |
| 229 | K | C | 45.2 | 5.7 | 14.6 | 21 | A |
| 229 | K | O | 44.2 | 5.2 | 14.2 | 23 | A |
| 230 | H | N | 46.1 | 5.1 | 15.4 | 21 | A |
| 230 | H | CA | 45.9 | 3.8 | 15.8 | 21 | A |
| 230 | H | CB | 46.7 | 2.8 | 14.9 | 21 | A |
| 230 | H | CG | 46.3 | 2.9 | 13.5 | 25 | A |
| 230 | H | CD2 | 46.9 | 3.4 | 12.4 | 24 | A |
| 230 | H | ND1 | 45.0 | 2.4 | 13.0 | 26 | A |
| 230 | H | CE1 | 44.9 | 2.7 | 11.7 | 26 | A |
| 230 | H | NE2 | 46.1 | 3.3 | 11.3 | 24 | A |
| 230 | H | C | 46.4 | 3.7 | 17.2 | 19 | A |
| 230 | H | O | 47.0 | 4.7 | 17.8 | 20 | A |
| 231 | Y | N | 46.3 | 2.5 | 17.9 | 21 | A |
| 231 | Y | CA | 46.7 | 2.3 | 19.2 | 20 | A |
| 231 | Y | CB | 46.6 | 0.8 | 19.6 | 18 | A |
| 231 | Y | CG | 46.8 | 0.5 | 21.1 | 21 | A |
| 231 | Y | CD1 | 46.0 | 1.0 | 22.0 | 19 | A |
| 231 | Y | CE1 | 46.1 | 0.8 | 23.4 | 22 | A |
| 231 | Y | CD2 | 47.9 | −0.3 | 21.5 | 23 | A |
| 231 | Y | CE2 | 48.0 | −0.6 | 22.8 | 22 | A |
| 231 | Y | CZ | 47.2 | −0.0 | 23.8 | 21 | A |
| 231 | Y | OH | 47.3 | −0.4 | 25.1 | 24 | A |
| 231 | Y | C | 48.1 | 2.8 | 19.6 | 19 | A |
| 231 | Y | O | 48.2 | 3.8 | 20.4 | 15 | A |
| 232 | L | N | 49.1 | 2.3 | 19.0 | 19 | A |
| 232 | L | CA | 50.5 | 2.7 | 19.3 | 20 | A |
| 232 | L | CB | 51.5 | 1.6 | 18.7 | 20 | A |
| 232 | L | CG | 51.3 | 0.2 | 19.3 | 22 | A |
| 232 | L | CD1 | 52.4 | −0.7 | 18.7 | 23 | A |
| 232 | L | CD2 | 51.5 | 0.2 | 20.8 | 21 | A |
| 232 | L | C | 50.8 | 4.0 | 18.7 | 22 | A |
| 232 | L | O | 51.7 | 4.8 | 19.3 | 19 | A |
| 233 | D | N | 50.2 | 4.4 | 17.6 | 22 | A |
| 233 | D | CA | 50.5 | 5.7 | 17.0 | 22 | A |
| 233 | D | CB | 49.7 | 5.9 | 15.7 | 22 | A |
| 233 | D | CG | 50.0 | 7.1 | 14.9 | 25 | A |
| 233 | D | OD1 | 51.2 | 7.3 | 14.6 | 25 | A |
| 233 | D | OD2 | 49.1 | 8.0 | 14.7 | 27 | A |
| 233 | D | C | 50.2 | 6.8 | 17.9 | 21 | A |
| 233 | D | O | 50.8 | 7.9 | 17.9 | 22 | A |
| 234 | Q | N | 49.3 | 6.6 | 18.8 | 20 | A |
| 234 | Q | CA | 48.9 | 7.6 | 19.8 | 20 | A |
| 234 | Q | CB | 47.7 | 7.0 | 20.7 | 21 | A |
| 234 | Q | CG | 47.2 | 7.9 | 21.8 | 23 | A |
| 234 | Q | CD | 46.7 | 9.2 | 21.2 | 24 | A |
| 234 | Q | OE1 | 46.0 | 9.2 | 20.1 | 26 | A |
| 234 | Q | NE2 | 46.9 | 10.4 | 21.9 | 22 | A |
| 234 | Q | C | 50.1 | 8.0 | 20.7 | 20 | A |
| 234 | Q | O | 50.3 | 9.1 | 20.9 | 21 | A |
| 235 | L | N | 50.8 | 7.0 | 21.1 | 20 | A |
| 235 | L | CA | 52.0 | 7.2 | 21.9 | 20 | A |
| 235 | L | CB | 52.6 | 5.9 | 22.4 | 19 | A |
| 235 | L | CG | 53.8 | 5.9 | 23.3 | 20 | A |
| 235 | L | CD1 | 53.5 | 6.7 | 24.6 | 19 | A |
| 235 | L | CD2 | 54.1 | 4.4 | 23.7 | 19 | A |
| 235 | L | C | 53.0 | 8.1 | 21.2 | 20 | A |
| 235 | L | O | 53.7 | 8.9 | 21.8 | 19 | A |
| 236 | N | N | 53.1 | 7.9 | 19.9 | 19 | A |
| 236 | N | CA | 54.1 | 8.6 | 19.1 | 20 | A |
| 236 | N | CB | 54.3 | 8.1 | 17.7 | 24 | A |
| 236 | N | CG | 55.0 | 6.8 | 17.7 | 27 | A |
| 236 | N | OD1 | 56.1 | 6.6 | 18.4 | 29 | A |
| 236 | N | ND2 | 54.6 | 5.8 | 16.9 | 28 | A |
| 236 | N | C | 53.8 | 10.1 | 19.0 | 19 | A |
| 236 | N | O | 54.7 | 11.0 | 19.1 | 21 | A |
| 237 | H | N | 52.5 | 10.4 | 18.9 | 17 | A |
| 237 | H | CA | 52.1 | 11.8 | 18.9 | 15 | A |
| 237 | H | CB | 50.6 | 11.9 | 18.5 | 13 | A |
| 237 | H | CG | 50.3 | 11.6 | 17.1 | 13 | A |
| 237 | H | CD2 | 50.1 | 10.4 | 16.5 | 13 | A |
| 237 | H | ND1 | 50.2 | 12.6 | 16.1 | 14 | A |
| 237 | H | CE1 | 50.0 | 12.0 | 15.0 | 10 | A |
| 237 | H | NE2 | 50.0 | 10.7 | 15.1 | 16 | A |
| 237 | H | C | 52.3 | 12.5 | 20.2 | 13 | A |
| 237 | H | O | 52.6 | 13.7 | 20.3 | 18 | A |
| 238 | I | N | 52.3 | 11.7 | 21.3 | 12 | A |
| 238 | I | CA | 52.5 | 12.3 | 22.6 | 13 | A |
| 238 | I | CB | 52.1 | 11.2 | 23.7 | 11 | A |
| 238 | I | CG2 | 52.6 | 11.7 | 25.1 | 8 | A |
| 238 | I | CG1 | 50.6 | 11.1 | 23.6 | 11 | A |
| 238 | I | CD1 | 50.0 | 10.1 | 24.6 | 9 | A |
| 238 | I | C | 54.0 | 12.5 | 22.7 | 13 | A |
| 238 | I | O | 54.4 | 13.7 | 23.1 | 13 | A |
| 239 | L | N | 54.9 | 11.6 | 22.4 | 15 | A |
| 239 | L | CA | 56.3 | 11.8 | 22.4 | 17 | A |
| 239 | L | CB | 57.1 | 10.5 | 22.1 | 16 | A |
| 239 | L | CG | 56.8 | 9.4 | 23.1 | 19 | A |
| 239 | L | CD1 | 57.7 | 8.2 | 22.9 | 18 | A |
| 239 | L | CD2 | 56.9 | 10.0 | 24.5 | 18 | A |
| 239 | L | C | 56.7 | 12.9 | 21.4 | 17 | A |
| 239 | L | O | 57.7 | 13.5 | 21.6 | 16 | A |
| 240 | G | N | 55.9 | 13.1 | 20.4 | 18 | A |
| 240 | G | CA | 56.1 | 14.1 | 19.4 | 19 | A |
| 240 | G | C | 56.1 | 15.5 | 20.0 | 21 | A |
| 240 | G | O | 56.7 | 16.4 | 19.5 | 20 | A |
| 241 | I | N | 55.4 | 15.6 | 21.2 | 20 | A |
| 241 | I | CA | 55.3 | 16.9 | 21.9 | 19 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | | |
|---|---|---|---|---|---|---|---|
| 241 | I | CB | 53.9 | 17.2 | 22.3 | 20 | A |
| 241 | I | CG2 | 53.8 | 18.5 | 23.1 | 19 | A |
| 241 | I | CG1 | 53.0 | 17.4 | 21.0 | 21 | A |
| 241 | I | CD1 | 53.5 | 18.6 | 20.2 | 21 | A |
| 241 | I | C | 56.2 | 16.9 | 23.1 | 19 | A |
| 241 | I | O | 57.0 | 17.9 | 23.3 | 18 | A |
| 242 | L | N | 56.1 | 15.9 | 24.0 | 19 | A |
| 242 | L | CA | 56.9 | 15.9 | 25.2 | 19 | A |
| 242 | L | CB | 56.3 | 14.9 | 26.2 | 19 | A |
| 242 | L | CG | 54.9 | 15.1 | 26.7 | 23 | A |
| 242 | L | CD1 | 54.7 | 14.3 | 27.9 | 19 | A |
| 242 | L | CD2 | 54.6 | 16.6 | 26.9 | 21 | A |
| 242 | L | C | 58.4 | 15.5 | 25.0 | 19 | A |
| 242 | L | O | 59.3 | 15.8 | 25.8 | 17 | A |
| 243 | G | N | 58.6 | 14.8 | 23.9 | 18 | A |
| 243 | G | CA | 60.0 | 14.3 | 23.6 | 18 | A |
| 243 | G | C | 60.1 | 13.0 | 24.3 | 20 | A |
| 243 | G | O | 59.1 | 12.6 | 25.0 | 19 | A |
| 244 | S | N | 61.2 | 12.3 | 24.1 | 20 | A |
| 244 | S | CA | 61.4 | 11.0 | 24.8 | 23 | A |
| 244 | S | CB | 62.7 | 10.4 | 24.4 | 22 | A |
| 244 | S | OG | 62.7 | 10.1 | 23.0 | 26 | A |
| 244 | S | C | 61.3 | 11.1 | 26.3 | 22 | A |
| 244 | S | O | 61.7 | 12.2 | 26.9 | 21 | A |
| 245 | P | N | 60.9 | 10.1 | 27.0 | 24 | A |
| 245 | P | CD | 60.4 | 8.8 | 26.6 | 23 | A |
| 245 | P | CA | 60.9 | 10.3 | 28.5 | 25 | A |
| 245 | P | CB | 60.1 | 9.0 | 29.0 | 24 | A |
| 245 | P | CG | 59.4 | 8.5 | 27.7 | 27 | A |
| 245 | P | C | 62.3 | 10.3 | 29.0 | 25 | A |
| 245 | P | O | 63.2 | 9.8 | 28.4 | 25 | A |
| 246 | S | N | 62.5 | 10.9 | 30.2 | 28 | A |
| 246 | S | CA | 63.8 | 11.0 | 30.8 | 29 | A |
| 246 | S | CB | 63.8 | 11.9 | 32.0 | 27 | A |
| 246 | S | OG | 63.0 | 11.3 | 33.1 | 26 | A |
| 246 | S | C | 64.1 | 9.6 | 31.2 | 32 | A |
| 246 | S | O | 63.2 | 8.7 | 31.4 | 31 | A |
| 247 | Q | N | 65.4 | 9.3 | 31.3 | 36 | A |
| 247 | Q | CA | 65.9 | 7.9 | 31.7 | 40 | A |
| 247 | Q | CB | 67.4 | 7.9 | 31.9 | 42 | A |
| 247 | Q | CG | 68.0 | 6.6 | 31.9 | 47 | A |
| 247 | Q | CD | 67.5 | 5.7 | 33.1 | 51 | A |
| 247 | Q | OE1 | 67.5 | 6.1 | 34.2 | 53 | A |
| 247 | Q | NE2 | 67.2 | 4.5 | 32.8 | 52 | A |
| 247 | Q | C | 65.1 | 7.5 | 33.0 | 39 | A |
| 247 | Q | O | 64.7 | 6.4 | 33.2 | 37 | A |
| 248 | E | N | 65.0 | 8.5 | 33.9 | 40 | A |
| 248 | E | CA | 64.3 | 8.3 | 35.2 | 41 | A |
| 248 | E | CB | 64.4 | 9.5 | 36.1 | 43 | A |
| 248 | E | CG | 63.5 | 9.6 | 37.3 | 48 | A |
| 248 | E | CD | 63.8 | 10.8 | 38.2 | 52 | A |
| 248 | E | OE1 | 64.7 | 10.7 | 39.1 | 53 | A |
| 248 | E | OE2 | 63.1 | 11.8 | 38.0 | 53 | A |
| 248 | E | C | 62.8 | 7.9 | 35.0 | 40 | A |
| 248 | E | O | 62.3 | 7.0 | 35.7 | 40 | A |
| 249 | D | N | 62.1 | 8.5 | 34.1 | 36 | A |
| 249 | D | CA | 60.7 | 8.2 | 33.9 | 35 | A |
| 249 | D | CB | 60.0 | 9.2 | 33.0 | 32 | A |
| 249 | D | CG | 60.0 | 10.6 | 33.6 | 32 | A |
| 249 | D | OD1 | 59.8 | 10.7 | 34.8 | 31 | A |
| 249 | D | OD2 | 60.1 | 11.6 | 32.9 | 34 | A |
| 249 | D | C | 60.6 | 6.8 | 33.2 | 34 | A |
| 249 | D | O | 59.6 | 6.1 | 33.5 | 34 | A |
| 250 | L | N | 61.5 | 6.5 | 32.4 | 34 | A |
| 250 | L | CA | 61.6 | 5.2 | 31.6 | 36 | A |
| 250 | L | CB | 62.8 | 5.2 | 30.7 | 35 | A |
| 250 | L | CG | 62.6 | 4.9 | 29.2 | 38 | A |
| 250 | L | CD1 | 61.9 | 3.6 | 29.0 | 40 | A |
| 250 | L | CD2 | 61.7 | 6.0 | 28.6 | 40 | A |
| 250 | L | C | 61.7 | 4.1 | 32.6 | 36 | A |
| 250 | L | O | 61.0 | 3.1 | 32.5 | 36 | A |
| 251 | N | N | 62.5 | 4.3 | 33.7 | 36 | A |
| 251 | N | CA | 62.7 | 3.3 | 34.7 | 37 | A |
| 251 | N | CB | 63.9 | 3.6 | 35.5 | 38 | A |
| 251 | N | CG | 65.2 | 3.5 | 34.7 | 40 | A |
| 251 | N | OD1 | 66.3 | 4.0 | 35.2 | 41 | A |
| 251 | N | ND2 | 65.1 | 3.0 | 33.5 | 38 | A |
| 251 | N | C | 61.5 | 3.0 | 35.6 | 38 | A |
| 251 | N | O | 61.5 | 2.1 | 36.4 | 39 | A |
| 252 | C | N | 60.5 | 3.9 | 35.6 | 35 | A |
| 252 | C | CA | 59.3 | 3.8 | 36.4 | 34 | A |
| 252 | C | CB | 58.6 | 5.1 | 36.6 | 33 | A |
| 252 | C | SG | 59.4 | 6.2 | 37.7 | 31 | A |
| 252 | C | C | 58.4 | 2.8 | 35.7 | 34 | A |
| 252 | C | O | 57.4 | 2.2 | 36.3 | 32 | A |
| 253 | I | N | 58.6 | 2.5 | 34.4 | 35 | A |
| 253 | I | CA | 57.8 | 1.5 | 33.6 | 34 | A |
| 253 | I | CB | 58.1 | 1.7 | 32.1 | 33 | A |
| 253 | I | CG2 | 57.3 | 0.6 | 31.4 | 32 | A |
| 253 | I | CG1 | 57.7 | 3.1 | 31.7 | 31 | A |
| 253 | I | CD1 | 56.3 | 3.5 | 31.9 | 28 | A |
| 253 | I | C | 58.3 | 0.2 | 34.1 | 36 | A |
| 253 | I | O | 59.4 | -0.2 | 33.8 | 36 | A |
| 254 | I | N | 57.4 | -0.6 | 34.7 | 37 | A |
| 254 | I | CA | 57.7 | -1.9 | 35.2 | 39 | A |
| 254 | I | CB | 56.8 | -2.3 | 36.4 | 40 | A |
| 254 | I | CG2 | 57.2 | -3.7 | 36.9 | 38 | A |
| 254 | I | CG1 | 57.0 | -1.2 | 37.5 | 41 | A |
| 254 | I | CD1 | 55.9 | -1.3 | 38.5 | 44 | A |
| 254 | I | C | 57.6 | -3.0 | 34.1 | 41 | A |
| 254 | I | O | 58.4 | -3.8 | 33.9 | 42 | A |
| 255 | N | N | 56.4 | -2.9 | 33.4 | 40 | A |
| 255 | N | CA | 56.2 | -3.9 | 32.3 | 39 | A |
| 255 | N | CB | 54.9 | -3.5 | 31.5 | 40 | A |
| 255 | N | CG | 54.6 | -4.5 | 30.4 | 41 | A |
| 255 | N | OD1 | 54.0 | -5.6 | 30.6 | 41 | A |
| 255 | N | ND2 | 55.0 | -4.2 | 29.2 | 40 | A |
| 255 | N | C | 57.4 | -3.9 | 31.3 | 39 | A |
| 255 | N | O | 57.6 | -2.8 | 30.7 | 38 | A |
| 256 | L | N | 58.1 | -5.0 | 31.2 | 37 | A |
| 256 | L | CA | 59.3 | -5.0 | 30.4 | 38 | A |
| 256 | L | CB | 60.1 | -6.3 | 30.7 | 39 | A |
| 256 | L | CG | 61.2 | -6.1 | 31.7 | 40 | A |
| 256 | L | CD1 | 60.8 | -5.2 | 32.8 | 38 | A |
| 256 | L | CD2 | 61.7 | -7.4 | 32.2 | 39 | A |
| 256 | L | C | 59.0 | -5.0 | 28.9 | 37 | A |
| 256 | L | O | 59.9 | -4.5 | 28.1 | 37 | A |
| 257 | K | N | 57.8 | -5.4 | 28.4 | 35 | A |
| 257 | K | CA | 57.5 | -5.3 | 27.0 | 36 | A |
| 257 | K | CB | 56.2 | -6.0 | 26.6 | 38 | A |
| 257 | K | CG | 56.1 | -7.3 | 27.5 | 48 | A |
| 257 | K | CD | 57.3 | -8.3 | 27.4 | 51 | A |
| 257 | K | CE | 57.1 | -9.4 | 28.4 | 54 | A |
| 257 | K | NZ | 55.9 | -10.3 | 28.1 | 54 | A |
| 257 | K | C | 57.3 | -3.8 | 26.7 | 34 | A |
| 257 | K | O | 57.7 | -3.3 | 25.6 | 35 | A |
| 258 | A | N | 56.7 | -3.1 | 27.6 | 31 | A |
| 258 | A | CA | 56.5 | -1.6 | 27.5 | 28 | A |
| 258 | A | CB | 55.5 | -1.2 | 28.5 | 27 | A |
| 258 | A | C | 57.8 | -0.9 | 27.6 | 28 | A |
| 258 | A | O | 58.1 | -0.1 | 26.8 | 26 | A |
| 259 | R | N | 58.6 | -1.3 | 28.6 | 30 | A |
| 259 | R | CA | 59.8 | -0.6 | 28.8 | 30 | A |
| 259 | R | CB | 60.2 | -1.2 | 30.0 | 32 | A |
| 259 | R | CG | 61.6 | -0.3 | 30.5 | 40 | A |
| 259 | R | CD | 62.8 | -1.0 | 31.3 | 46 | A |
| 259 | R | NE | 62.9 | -0.5 | 32.7 | 50 | A |
| 259 | R | CZ | 62.2 | -1.0 | 33.7 | 52 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) 1-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 259 | R | NH1  | 61.2 | −1.9 | 33.4 | 53 | A |
|-----|---|------|------|------|------|----|---|
| 259 | R | NH2  | 62.4 | −0.5 | 34.9 | 53 | A |
| 259 | R | C    | 60.7 | −0.8 | 27.6 | 28 | A |
| 259 | R | O    | 61.1 | 0.2  | 27.0 | 28 | A |
| 260 | N | N    | 60.9 | −2.0 | 27.1 | 28 | A |
| 260 | N | CA   | 61.7 | −2.3 | 26.0 | 28 | A |
| 260 | N | CB   | 61.9 | −3.8 | 25.8 | 30 | A |
| 260 | N | CG   | 62.8 | −4.4 | 26.9 | 30 | A |
| 260 | N | OD1  | 63.8 | −3.9 | 27.2 | 31 | A |
| 260 | N | ND2  | 62.3 | −5.6 | 27.4 | 31 | A |
| 260 | N | C    | 61.2 | −1.7 | 24.7 | 29 | A |
| 260 | N | O    | 61.9 | −1.3 | 23.8 | 29 | A |
| 261 | Y | N    | 59.9 | −1.5 | 24.6 | 28 | A |
| 261 | Y | CA   | 59.3 | −0.8 | 23.4 | 29 | A |
| 261 | Y | CB   | 57.8 | −0.9 | 23.5 | 27 | A |
| 261 | Y | CG   | 57.1 | −0.1 | 22.4 | 27 | A |
| 261 | Y | CD1  | 57.2 | −0.6 | 21.0 | 26 | A |
| 261 | Y | CE1  | 56.6 | 0.2  | 20.0 | 27 | A |
| 261 | Y | CD2  | 56.5 | 1.1  | 22.6 | 28 | A |
| 261 | Y | CE2  | 55.9 | 1.8  | 21.6 | 24 | A |
| 261 | Y | CZ   | 55.9 | 1.4  | 20.3 | 25 | A |
| 261 | Y | OH   | 55.4 | 2.2  | 19.3 | 23 | A |
| 261 | Y | C    | 59.7 | 0.6  | 23.4 | 30 | A |
| 261 | Y | O    | 60.0 | 1.2  | 22.4 | 32 | A |
| 262 | L | N    | 59.7 | 1.3  | 24.6 | 30 | A |
| 262 | L | CA   | 60.1 | 2.7  | 24.7 | 30 | A |
| 262 | L | CB   | 59.9 | 3.2  | 26.1 | 28 | A |
| 262 | L | CG   | 58.5 | 3.7  | 26.5 | 31 | A |
| 262 | L | CD1  | 58.5 | 4.2  | 27.9 | 31 | A |
| 262 | L | CD2  | 58.0 | 4.7  | 25.5 | 33 | A |
| 262 | L | C    | 61.6 | 2.9  | 24.3 | 31 | A |
| 262 | L | O    | 62.0 | 3.9  | 23.8 | 30 | A |
| 263 | L | N    | 62.4 | 1.9  | 24.7 | 34 | A |
| 263 | L | CA   | 63.8 | 1.9  | 24.4 | 36 | A |
| 263 | L | CB   | 64.6 | 0.8  | 25.2 | 35 | A |
| 263 | L | CG   | 64.9 | 1.1  | 26.7 | 39 | A |
| 263 | L | CD1  | 65.8 | 2.4  | 26.8 | 37 | A |
| 263 | L | CD2  | 63.7 | 1.2  | 27.5 | 39 | A |
| 263 | L | C    | 64.1 | 1.7  | 22.9 | 35 | A |
| 263 | L | O    | 65.1 | 2.1  | 22.4 | 36 | A |
| 264 | S | N    | 63.1 | 1.1  | 22.2 | 33 | A |
| 264 | S | CA   | 63.2 | 0.8  | 20.8 | 33 | A |
| 264 | S | CB   | 62.3 | −0.3 | 20.4 | 32 | A |
| 264 | S | OG   | 61.0 | 0.3  | 19.9 | 32 | A |
| 264 | S | C    | 63.0 | 2.1  | 20.0 | 33 | A |
| 264 | S | O    | 63.6 | 2.3  | 18.9 | 31 | A |
| 265 | L | N    | 62.1 | 2.9  | 20.5 | 34 | A |
| 265 | L | CA   | 61.7 | 4.2  | 19.7 | 35 | A |
| 265 | L | CB   | 60.6 | 4.9  | 20.5 | 34 | A |
| 265 | L | CG   | 59.1 | 4.4  | 20.3 | 37 | A |
| 265 | L | CD1  | 59.1 | 2.9  | 20.1 | 36 | A |
| 265 | L | CD2  | 58.3 | 4.8  | 21.5 | 33 | A |
| 265 | L | C    | 62.9 | 5.1  | 19.5 | 35 | A |
| 265 | L | O    | 63.7 | 5.4  | 20.4 | 34 | A |
| 266 | P | N    | 63.0 | 5.7  | 18.3 | 36 | A |
| 266 | P | CD   | 62.1 | 5.5  | 17.2 | 35 | A |
| 266 | P | CA   | 64.1 | 6.6  | 18.0 | 36 | A |
| 266 | P | CB   | 63.9 | 6.8  | 16.5 | 36 | A |
| 266 | P | CG   | 62.4 | 6.7  | 16.3 | 37 | A |
| 266 | P | C    | 63.8 | 7.9  | 18.8 | 36 | A |
| 266 | P | O    | 62.6 | 8.4  | 18.9 | 35 | A |
| 267 | H | N    | 64.8 | 8.5  | 19.4 | 34 | A |
| 267 | H | CA   | 64.8 | 9.7  | 20.2 | 34 | A |
| 267 | H | CB   | 66.2 | 10.1 | 20.6 | 34 | A |
| 267 | H | CG   | 66.2 | 11.3 | 21.5 | 34 | A |
| 267 | H | CD2  | 66.3 | 11.3 | 22.9 | 32 | A |
| 267 | H | ND1  | 66.2 | 12.6 | 21.1 | 33 | A |
| 267 | H | CE1  | 66.3 | 13.4 | 22.2 | 32 | A |
| 267 | H | NE2  | 66.4 | 12.6 | 23.3 | 33 | A |
| 267 | H | C    | 64.0 | 10.9 | 19.6 | 34 | A |
| 267 | H | O    | 64.0 | 11.1 | 18.4 | 34 | A |
| 268 | K | N    | 63.3 | 11.6 | 20.4 | 34 | A |
| 268 | K | CA   | 62.5 | 12.8 | 20.0 | 35 | A |
| 268 | K | CB   | 61.0 | 12.5 | 19.9 | 35 | A |
| 268 | K | CG   | 60.5 | 11.6 | 18.9 | 35 | A |
| 268 | K | CD   | 59.1 | 11.9 | 18.5 | 37 | A |
| 268 | K | CE   | 58.5 | 10.9 | 17.5 | 37 | A |
| 268 | K | NZ   | 57.9 | 9.7  | 18.2 | 41 | A |
| 268 | K | C    | 62.8 | 13.9 | 21.0 | 35 | A |
| 268 | K | O    | 62.9 | 13.6 | 22.2 | 34 | A |
| 269 | N | N    | 62.8 | 15.2 | 20.6 | 37 | A |
| 269 | N | CA   | 63.0 | 16.3 | 21.5 | 36 | A |
| 269 | N | CB   | 64.1 | 17.3 | 21.0 | 39 | A |
| 269 | N | CG   | 65.1 | 17.6 | 22.0 | 46 | A |
| 269 | N | OD1  | 64.8 | 18.1 | 23.2 | 45 | A |
| 269 | N | ND2  | 66.4 | 17.4 | 21.7 | 47 | A |
| 269 | N | C    | 61.7 | 17.0 | 21.9 | 33 | A |
| 269 | N | O    | 60.8 | 17.0 | 21.1 | 31 | A |
| 270 | K | N    | 61.7 | 17.6 | 23.1 | 33 | A |
| 270 | K | CA   | 60.5 | 18.2 | 23.6 | 33 | A |
| 270 | K | CB   | 60.6 | 18.5 | 25.1 | 34 | A |
| 270 | K | CG   | 59.4 | 19.2 | 25.7 | 37 | A |
| 270 | K | CD   | 59.6 | 19.6 | 27.2 | 36 | A |
| 270 | K | CE   | 58.4 | 20.3 | 27.7 | 38 | A |
| 270 | K | NZ   | 57.2 | 19.4 | 27.8 | 39 | A |
| 270 | K | C    | 60.2 | 19.6 | 22.9 | 33 | A |
| 270 | K | O    | 61.0 | 20.5 | 22.9 | 34 | A |
| 271 | V | N    | 59.0 | 19.7 | 22.2 | 33 | A |
| 271 | V | CA   | 58.6 | 20.9 | 21.6 | 33 | A |
| 271 | V | CB   | 57.5 | 20.6 | 20.5 | 34 | A |
| 271 | V | CG1  | 57.1 | 21.9 | 19.8 | 33 | A |
| 271 | V | CG2  | 58.0 | 19.6 | 19.5 | 34 | A |
| 271 | V | C    | 58.0 | 21.8 | 22.7 | 33 | A |
| 271 | V | O    | 57.1 | 21.5 | 23.3 | 35 | A |
| 272 | P | N    | 58.6 | 23.0 | 22.9 | 32 | A |
| 272 | P | CD   | 59.7 | 23.6 | 22.1 | 32 | A |
| 272 | P | CA   | 58.2 | 23.9 | 23.9 | 31 | A |
| 272 | P | CB   | 59.1 | 25.1 | 23.8 | 30 | A |
| 272 | P | CG   | 59.5 | 25.1 | 22.4 | 33 | A |
| 272 | P | C    | 56.7 | 24.3 | 23.8 | 30 | A |
| 272 | P | O    | 56.2 | 24.6 | 22.7 | 30 | A |
| 273 | W | N    | 56.0 | 24.4 | 24.9 | 30 | A |
| 273 | W | CA   | 54.6 | 24.8 | 25.0 | 30 | A |
| 273 | W | CB   | 54.1 | 24.8 | 26.4 | 26 | A |
| 273 | W | CG   | 54.2 | 23.5 | 27.1 | 24 | A |
| 273 | W | CD2  | 53.5 | 22.3 | 26.7 | 19 | A |
| 273 | W | CE2  | 53.8 | 21.3 | 27.6 | 19 | A |
| 273 | W | CE3  | 52.6 | 22.0 | 25.6 | 18 | A |
| 273 | W | CD1  | 54.9 | 23.1 | 28.2 | 21 | A |
| 273 | W | NE1  | 54.7 | 21.8 | 28.5 | 18 | A |
| 273 | W | CZ2  | 53.3 | 20.0 | 27.5 | 19 | A |
| 273 | W | CZ3  | 52.1 | 20.7 | 25.5 | 17 | A |
| 273 | W | CH2  | 52.4 | 19.7 | 26.4 | 18 | A |
| 273 | W | C    | 54.5 | 26.2 | 24.3 | 31 | A |
| 273 | W | O    | 53.6 | 26.4 | 23.5 | 32 | A |
| 274 | N | N    | 55.3 | 27.2 | 24.7 | 31 | A |
| 274 | N | CA   | 55.2 | 28.5 | 24.2 | 35 | A |
| 274 | N | CB   | 56.0 | 29.6 | 25.0 | 36 | A |
| 274 | N | CG   | 57.5 | 29.4 | 24.8 | 39 | A |
| 274 | N | OD1  | 58.0 | 28.9 | 23.8 | 40 | A |
| 274 | N | ND2  | 58.2 | 29.9 | 25.7 | 39 | A |
| 274 | N | C    | 55.5 | 28.6 | 22.7 | 35 | A |
| 274 | N | O    | 55.4 | 29.7 | 22.1 | 35 | A |
| 275 | R | N    | 55.7 | 27.5 | 22.0 | 36 | A |
| 275 | R | CA   | 55.9 | 27.5 | 20.6 | 37 | A |
| 275 | R | CB   | 57.1 | 26.6 | 20.2 | 42 | A |
| 275 | R | CG   | 57.3 | 26.4 | 18.7 | 45 | A |
| 275 | R | CD   | 58.5 | 25.6 | 18.3 | 47 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| Res | AA | Atom | X | Y | Z | B | Chain |
|---|---|---|---|---|---|---|---|
| 275 | R | NE  | 59.7 | 26.3 | 18.1 | 52 | A |
| 275 | R | CZ  | 60.8 | 25.9 | 17.6 | 55 | A |
| 275 | R | NH1 | 60.9 | 24.6 | 17.2 | 57 | A |
| 275 | R | NH2 | 61.9 | 26.6 | 17.4 | 54 | A |
| 275 | R | C   | 54.7 | 26.9 | 19.9 | 36 | A |
| 275 | R | O   | 54.3 | 27.4 | 18.8 | 35 | A |
| 276 | L | N   | 54.0 | 26.0 | 20.5 | 34 | A |
| 276 | L | CA  | 52.7 | 25.4 | 20.0 | 32 | A |
| 276 | L | CB  | 52.4 | 24.1 | 20.6 | 32 | A |
| 276 | L | CG  | 53.4 | 22.9 | 20.6 | 34 | A |
| 276 | L | CD1 | 53.0 | 21.9 | 21.7 | 33 | A |
| 276 | L | CD2 | 53.4 | 22.3 | 19.2 | 32 | A |
| 276 | L | C   | 51.6 | 26.4 | 20.2 | 31 | A |
| 276 | L | O   | 50.6 | 26.5 | 19.4 | 32 | A |
| 277 | F | N   | 51.6 | 27.1 | 21.3 | 29 | A |
| 277 | F | CA  | 50.6 | 28.1 | 21.7 | 30 | A |
| 277 | F | CB  | 49.9 | 27.6 | 22.9 | 28 | A |
| 277 | F | CG  | 49.5 | 26.1 | 22.8 | 26 | A |
| 277 | F | CD1 | 48.4 | 25.7 | 22.0 | 26 | A |
| 277 | F | CD2 | 50.1 | 25.2 | 23.6 | 23 | A |
| 277 | F | CE1 | 48.1 | 24.4 | 21.9 | 26 | A |
| 277 | F | CE2 | 49.7 | 23.8 | 23.5 | 24 | A |
| 277 | F | CZ  | 48.7 | 23.4 | 22.6 | 25 | A |
| 277 | F | C   | 51.2 | 29.4 | 22.0 | 31 | A |
| 277 | F | O   | 51.4 | 29.8 | 23.2 | 30 | A |
| 278 | P | N   | 51.6 | 30.2 | 21.0 | 32 | A |
| 278 | P | CD  | 51.6 | 29.9 | 19.5 | 32 | A |
| 278 | P | CA  | 52.3 | 31.5 | 21.2 | 34 | A |
| 278 | P | CB  | 52.8 | 31.9 | 19.8 | 33 | A |
| 278 | P | CG  | 52.8 | 30.6 | 19.0 | 32 | A |
| 278 | P | C   | 51.2 | 32.5 | 21.7 | 35 | A |
| 278 | P | O   | 51.6 | 33.5 | 22.3 | 35 | A |
| 279 | N | N   | 50.0 | 32.1 | 21.6 | 38 | A |
| 279 | N | CA  | 48.8 | 32.9 | 22.0 | 38 | A |
| 279 | N | CB  | 47.6 | 32.5 | 21.2 | 38 | A |
| 279 | N | CG  | 47.3 | 31.0 | 21.3 | 40 | A |
| 279 | N | OD1 | 48.1 | 30.1 | 20.9 | 30 | A |
| 279 | N | ND2 | 46.2 | 30.7 | 22.0 | 38 | A |
| 279 | N | C   | 48.5 | 32.8 | 23.5 | 38 | A |
| 279 | N | O   | 48.2 | 33.7 | 24.2 | 38 | A |
| 280 | A | N   | 48.5 | 31.5 | 23.9 | 36 | A |
| 280 | A | CA  | 48.2 | 31.2 | 25.3 | 31 | A |
| 280 | A | CB  | 48.5 | 29.7 | 25.5 | 29 | A |
| 280 | A | C   | 48.7 | 32.0 | 26.5 | 32 | A |
| 280 | A | O   | 49.9 | 32.4 | 26.5 | 32 | A |
| 281 | D | N   | 47.9 | 32.1 | 27.5 | 31 | A |
| 281 | D | CA  | 48.2 | 32.8 | 28.7 | 31 | A |
| 281 | D | CB  | 47.0 | 32.9 | 29.6 | 33 | A |
| 281 | D | CG  | 47.3 | 33.5 | 30.9 | 35 | A |
| 281 | D | OD1 | 48.0 | 32.9 | 31.8 | 35 | A |
| 281 | D | OD2 | 46.7 | 34.6 | 31.2 | 41 | A |
| 281 | D | C   | 49.4 | 32.0 | 29.3 | 30 | A |
| 281 | D | O   | 49.3 | 30.8 | 29.3 | 29 | A |
| 282 | S | N   | 50.4 | 32.7 | 29.9 | 29 | A |
| 282 | S | CA  | 51.5 | 32.0 | 30.5 | 29 | A |
| 282 | S | CB  | 52.5 | 33.0 | 31.0 | 30 | A |
| 282 | S | OG  | 53.0 | 33.8 | 30.0 | 38 | A |
| 282 | S | C   | 51.2 | 31.0 | 31.6 | 27 | A |
| 282 | S | O   | 51.8 | 29.9 | 31.6 | 26 | A |
| 283 | K | N   | 50.3 | 31.4 | 32.5 | 25 | A |
| 283 | K | CA  | 49.9 | 30.5 | 33.6 | 24 | A |
| 283 | K | CB  | 49.0 | 31.3 | 34.5 | 25 | A |
| 283 | K | CG  | 49.7 | 32.4 | 35.2 | 29 | A |
| 283 | K | CD  | 48.7 | 33.3 | 36.0 | 30 | A |
| 283 | K | CE  | 49.5 | 34.4 | 36.8 | 32 | A |
| 283 | K | NZ  | 48.6 | 35.2 | 37.7 | 33 | A |
| 283 | K | C   | 49.1 | 29.3 | 33.0 | 24 | A |
| 283 | K | O   | 49.2 | 28.2 | 33.5 | 22 | A |
| 284 | A | N   | 48.3 | 29.5 | 32.0 | 21 | A |
| 284 | A | CA  | 47.6 | 28.5 | 31.3 | 23 | A |
| 284 | A | CB  | 46.7 | 29.0 | 30.2 | 22 | A |
| 284 | A | C   | 48.6 | 27.4 | 30.8 | 24 | A |
| 284 | A | O   | 48.3 | 26.2 | 30.9 | 26 | A |
| 285 | L | N   | 49.7 | 27.9 | 30.3 | 23 | A |
| 285 | L | CA  | 50.7 | 27.0 | 29.7 | 23 | A |
| 285 | L | CB  | 51.6 | 27.7 | 28.7 | 21 | A |
| 285 | L | CG  | 51.1 | 28.1 | 27.4 | 25 | A |
| 285 | L | CD1 | 52.2 | 28.5 | 26.4 | 25 | A |
| 285 | L | CD2 | 50.3 | 26.9 | 26.8 | 23 | A |
| 285 | L | C   | 51.5 | 26.3 | 30.8 | 21 | A |
| 285 | L | O   | 51.9 | 25.2 | 30.7 | 22 | A |
| 286 | D | N   | 51.6 | 27.0 | 32.0 | 19 | A |
| 286 | D | CA  | 52.3 | 26.4 | 33.1 | 21 | A |
| 286 | D | CB  | 52.6 | 27.4 | 34.2 | 20 | A |
| 286 | D | CG  | 53.6 | 26.8 | 35.2 | 25 | A |
| 286 | D | OD1 | 54.7 | 26.4 | 34.9 | 29 | A |
| 286 | D | OD2 | 53.2 | 26.8 | 36.4 | 27 | A |
| 286 | D | C   | 51.5 | 25.2 | 33.6 | 22 | A |
| 286 | D | O   | 52.0 | 24.1 | 33.8 | 23 | A |
| 287 | L | N   | 50.2 | 25.5 | 33.8 | 20 | A |
| 287 | L | CA  | 49.3 | 24.4 | 34.3 | 21 | A |
| 287 | L | CB  | 47.9 | 25.0 | 34.6 | 21 | A |
| 287 | L | CG  | 46.8 | 24.1 | 35.1 | 21 | A |
| 287 | L | CD1 | 47.3 | 23.3 | 36.3 | 20 | A |
| 287 | L | CD2 | 45.6 | 25.0 | 35.4 | 20 | A |
| 287 | L | C   | 49.2 | 23.3 | 33.3 | 21 | A |
| 287 | L | O   | 49.2 | 22.1 | 33.6 | 23 | A |
| 288 | L | N   | 49.1 | 23.6 | 32.0 | 20 | A |
| 288 | L | CA  | 49.0 | 22.6 | 30.9 | 20 | A |
| 288 | L | CB  | 49.1 | 23.3 | 29.6 | 19 | A |
| 288 | L | CG  | 49.1 | 22.3 | 28.4 | 18 | A |
| 288 | L | CD1 | 47.7 | 21.6 | 28.2 | 18 | A |
| 288 | L | CD2 | 49.4 | 23.0 | 27.1 | 16 | A |
| 288 | L | C   | 50.2 | 21.7 | 31.0 | 22 | A |
| 288 | L | O   | 50.0 | 20.4 | 30.9 | 23 | A |
| 289 | D | N   | 51.4 | 22.2 | 31.2 | 21 | A |
| 289 | D | CA  | 52.6 | 21.4 | 31.3 | 20 | A |
| 289 | D | CB  | 53.8 | 22.3 | 31.6 | 21 | A |
| 289 | D | CG  | 55.1 | 21.5 | 31.9 | 20 | A |
| 289 | D | OD1 | 55.5 | 20.7 | 31.0 | 23 | A |
| 289 | D | OD2 | 55.7 | 21.7 | 32.9 | 26 | A |
| 289 | D | C   | 52.5 | 20.4 | 32.4 | 21 | A |
| 289 | D | O   | 52.9 | 29.2 | 32.3 | 21 | A |
| 290 | K | N   | 52.0 | 10.8 | 33.6 | 22 | A |
| 290 | K | CA  | 51.8 | 19.9 | 34.8 | 22 | A |
| 290 | K | CB  | 51.5 | 20.8 | 36.0 | 24 | A |
| 290 | K | CG  | 52.7 | 21.7 | 36.4 | 26 | A |
| 290 | K | CD  | 52.4 | 22.7 | 37.5 | 27 | A |
| 290 | K | CE  | 53.6 | 23.4 | 38.0 | 28 | A |
| 290 | K | NZ  | 54.3 | 24.1 | 36.9 | 30 | A |
| 290 | K | C   | 50.8 | 18.9 | 34.6 | 22 | A |
| 290 | K | O   | 50.9 | 17.8 | 35.1 | 23 | A |
| 291 | M | N   | 49.7 | 19.2 | 33.8 | 20 | A |
| 291 | M | CA  | 48.7 | 18.2 | 33.6 | 21 | A |
| 291 | M | CB  | 47.4 | 18.9 | 33.1 | 21 | A |
| 291 | M | CG  | 46.9 | 20.0 | 34.0 | 24 | A |
| 291 | M | SD  | 45.3 | 20.5 | 33.5 | 26 | A |
| 291 | M | CE  | 44.4 | 19.8 | 34.8 | 26 | A |
| 291 | M | C   | 49.1 | 17.1 | 32.5 | 19 | A |
| 291 | M | O   | 48.8 | 16.0 | 32.6 | 17 | A |
| 292 | L | N   | 49.9 | 17.6 | 31.6 | 17 | A |
| 292 | L | CA  | 50.4 | 16.7 | 30.5 | 17 | A |
| 292 | L | CB  | 50.4 | 17.4 | 29.2 | 13 | A |
| 292 | L | CG  | 49.0 | 17.7 | 28.6 | 14 | A |
| 292 | L | CD1 | 49.0 | 18.2 | 27.2 | 11 | A |
| 292 | L | CD2 | 48.1 | 16.5 | 28.7 | 12 | A |
| 292 | L | C   | 51.8 | 16.2 | 30.8 | 16 | A |
| 292 | L | O   | 52.7 | 16.2 | 30.0 | 19 | A |

TABLE 3-continued

Structural Coordinates of Ah₆-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| 293 | T | N   | 52.1 | 15.8 | 32.1 | 16 | A |
|-----|---|-----|------|------|------|----|---|
| 293 | T | CA  | 53.4 | 15.3 | 32.5 | 19 | A |
| 293 | T | CB  | 53.6 | 15.6 | 34.0 | 20 | A |
| 293 | T | OG1 | 53.9 | 17.0 | 34.1 | 20 | A |
| 293 | T | CG2 | 54.9 | 14.8 | 34.5 | 16 | A |
| 293 | T | C   | 53.4 | 13.8 | 32.2 | 20 | A |
| 293 | T | O   | 52.4 | 13.1 | 32.6 | 19 | A |
| 294 | F | N   | 54.4 | 13.3 | 31.6 | 19 | A |
| 294 | F | CA  | 54.6 | 11.9 | 31.3 | 20 | A |
| 294 | F | CB  | 55.9 | 11.6 | 30.7 | 20 | A |
| 294 | F | CG  | 56.0 | 10.2 | 30.0 | 21 | A |
| 294 | F | CD1 | 55.6 | 10.1 | 28.7 | 22 | A |
| 294 | F | CD2 | 56.5 | 9.1  | 30.7 | 20 | A |
| 294 | F | CE1 | 55.7 | 8.8  | 28.0 | 23 | A |
| 294 | F | CE2 | 56.6 | 7.9  | 30.0 | 21 | A |
| 294 | F | CZ  | 56.2 | 7.7  | 28.7 | 19 | A |
| 294 | F | C   | 54.3 | 10.9 | 32.5 | 23 | A |
| 294 | F | O   | 53.4 | 10.1 | 32.5 | 25 | A |
| 295 | N | N   | 55.3 | 11.0 | 33.4 | 24 | A |
| 295 | N | CA  | 55.2 | 10.2 | 34.6 | 23 | A |
| 295 | N | CB  | 56.5 | 10.5 | 35.5 | 25 | A |
| 295 | N | CG  | 56.7 | 9.5  | 36.6 | 27 | A |
| 295 | N | OD1 | 55.7 | 9.1  | 37.2 | 28 | A |
| 295 | N | ND2 | 57.9 | 9.2  | 36.9 | 25 | A |
| 295 | N | C   | 54.0 | 10.6 | 35.5 | 26 | A |
| 295 | N | O   | 53.9 | 11.7 | 36.0 | 25 | A |
| 296 | P | N   | 53.0 | 9.7  | 35.6 | 25 | A |
| 296 | P | CD  | 53.0 | 8.3  | 35.0 | 23 | A |
| 296 | P | CA  | 51.8 | 10.0 | 36.3 | 25 | A |
| 296 | P | CB  | 51.0 | 8.7  | 36.1 | 24 | A |
| 296 | P | CG  | 52.0 | 7.7  | 35.9 | 25 | A |
| 296 | P | C   | 52.0 | 10.3 | 37.8 | 27 | A |
| 296 | P | O   | 51.2 | 11.0 | 38.4 | 28 | A |
| 297 | H | N   | 53.1 | 9.8  | 38.3 | 29 | A |
| 297 | H | CA  | 53.5 | 10.1 | 39.7 | 33 | A |
| 297 | H | CB  | 54.7 | 9.2  | 40.1 | 38 | A |
| 297 | H | CG  | 54.4 | 7.7  | 40.0 | 44 | A |
| 297 | H | CD2 | 53.2 | 7.0  | 40.1 | 45 | A |
| 297 | H | ND1 | 55.4 | 6.8  | 39.7 | 46 | A |
| 297 | H | CE1 | 54.8 | 5.6  | 39.7 | 49 | A |
| 297 | H | NE2 | 53.5 | 5.7  | 39.9 | 48 | A |
| 297 | H | C   | 53.9 | 11.6 | 39.9 | 31 | A |
| 297 | H | O   | 53.6 | 12.1 | 41.0 | 31 | A |
| 298 | K | N   | 54.4 | 12.1 | 38.9 | 30 | A |
| 298 | K | CA  | 54.9 | 13.5 | 38.9 | 29 | A |
| 298 | K | CB  | 56.1 | 13.7 | 38.0 | 30 | A |
| 298 | K | CG  | 57.4 | 13.1 | 38.5 | 37 | A |
| 298 | K | CD  | 57.8 | 13.8 | 39.8 | 43 | A |
| 298 | K | CE  | 59.1 | 13.2 | 40.3 | 46 | A |
| 298 | K | NZ  | 59.5 | 13.9 | 41.6 | 47 | A |
| 298 | K | C   | 53.7 | 14.4 | 38.4 | 27 | A |
| 298 | K | O   | 53.8 | 15.7 | 38.5 | 28 | A |
| 299 | R | N   | 52.7 | 13.8 | 37.9 | 25 | A |
| 299 | R | CA  | 51.6 | 14.6 | 37.4 | 22 | A |
| 299 | R | CB  | 50.7 | 13.7 | 36.5 | 20 | A |
| 299 | R | CG  | 49.7 | 14.4 | 35.6 | 22 | A |
| 299 | R | CD  | 49.6 | 13.8 | 34.3 | 20 | A |
| 299 | R | NE  | 48.8 | 12.6 | 34.3 | 21 | A |
| 299 | R | CZ  | 49.2 | 11.4 | 33.8 | 22 | A |
| 299 | R | NH1 | 50.4 | 11.3 | 33.3 | 17 | A |
| 299 | R | NH2 | 48.3 | 10.4 | 33.8 | 23 | A |
| 299 | R | C   | 50.8 | 15.3 | 38.5 | 21 | A |
| 299 | R | O   | 50.5 | 14.7 | 39.5 | 20 | A |
| 300 | I | N   | 50.4 | 16.5 | 38.2 | 20 | A |
| 300 | I | CA  | 49.7 | 17.3 | 39.2 | 18 | A |
| 300 | I | CB  | 49.5 | 18.8 | 38.7 | 19 | A |
| 300 | I | CG2 | 48.4 | 18.8 | 37.6 | 20 | A |
| 300 | I | CG1 | 49.2 | 19.8 | 39.8 | 21 | A |
| 300 | I | CD1 | 49.1 | 21.2 | 39.4 | 21 | A |
| 300 | I | C   | 48.3 | 16.7 | 39.5 | 16 | A |
| 300 | I | O   | 47.6 | 16.2 | 38.6 | 18 | A |
| 301 | E | N   | 47.9 | 16.8 | 40.7 | 16 | A |
| 301 | E | CA  | 46.6 | 16.2 | 41.1 | 15 | A |
| 301 | E | CB  | 46.7 | 15.6 | 42.5 | 18 | A |
| 301 | E | CG  | 47.7 | 14.4 | 42.6 | 24 | A |
| 301 | E | CD  | 47.8 | 13.8 | 43.9 | 30 | A |
| 301 | E | OE1 | 48.2 | 14.5 | 44.9 | 29 | A |
| 301 | E | OE2 | 47.5 | 12.6 | 44.1 | 32 | A |
| 301 | E | C   | 45.5 | 17.3 | 41.0 | 16 | A |
| 301 | E | O   | 45.8 | 18.5 | 40.8 | 13 | A |
| 302 | V | N   | 44.2 | 16.9 | 41.2 | 14 | A |
| 302 | V | CA  | 43.1 | 17.8 | 41.1 | 15 | A |
| 302 | V | CB  | 41.8 | 17.1 | 41.0 | 15 | A |
| 302 | V | CG1 | 41.4 | 16.4 | 42.3 | 11 | A |
| 302 | V | CG2 | 40.7 | 18.0 | 40.5 | 14 | A |
| 302 | V | C   | 43.0 | 19.0 | 42.0 | 15 | A |
| 302 | V | O   | 42.7 | 20.1 | 41.6 | 16 | A |
| 303 | E | N   | 43.4 | 18.8 | 43.3 | 17 | A |
| 303 | E | CA  | 43.4 | 19.9 | 44.3 | 19 | A |
| 303 | E | CB  | 43.7 | 19.4 | 45.7 | 22 | A |
| 303 | E | CG  | 43.3 | 18.0 | 46.0 | 33 | A |
| 303 | E | CD  | 44.2 | 16.9 | 45.3 | 35 | A |
| 303 | E | OE1 | 45.5 | 17.0 | 45.6 | 35 | A |
| 303 | E | OE2 | 43.7 | 16.1 | 44.6 | 34 | A |
| 303 | E | C   | 44.4 | 21.0 | 43.9 | 20 | A |
| 303 | E | O   | 44.2 | 22.2 | 43.9 | 21 | A |
| 304 | Q | N   | 45.6 | 20.5 | 43.6 | 20 | A |
| 304 | Q | CA  | 46.8 | 21.3 | 43.2 | 20 | A |
| 304 | Q | CB  | 48.0 | 20.4 | 43.1 | 21 | A |
| 304 | Q | CG  | 48.3 | 19.7 | 44.4 | 25 | A |
| 304 | Q | CD  | 49.1 | 18.4 | 44.3 | 35 | A |
| 304 | Q | OE1 | 49.3 | 17.6 | 45.2 | 39 | A |
| 304 | Q | NE2 | 49.5 | 18.0 | 43.0 | 32 | A |
| 304 | Q | C   | 46.5 | 22.0 | 41.9 | 19 | A |
| 304 | Q | O   | 47.0 | 23.1 | 41.7 | 19 | A |
| 305 | A | N   | 45.8 | 21.4 | 40.9 | 17 | A |
| 305 | A | CA  | 45.5 | 22.0 | 39.7 | 17 | A |
| 305 | A | CB  | 45.0 | 21.0 | 38.7 | 12 | A |
| 305 | A | C   | 44.6 | 23.1 | 39.9 | 18 | A |
| 305 | A | O   | 44.7 | 24.2 | 39.4 | 20 | A |
| 306 | L | N   | 43.6 | 22.9 | 40.8 | 16 | A |
| 306 | L | CA  | 42.6 | 23.9 | 41.1 | 18 | A |
| 306 | L | CB  | 41.5 | 23.4 | 42.0 | 18 | A |
| 306 | L | CG  | 40.3 | 22.7 | 41.3 | 18 | A |
| 306 | L | CD1 | 39.6 | 21.8 | 42.3 | 19 | A |
| 306 | L | CD2 | 39.3 | 23.7 | 40.7 | 17 | A |
| 306 | L | C   | 43.4 | 25.1 | 41.8 | 16 | A |
| 306 | L | O   | 43.0 | 26.2 | 41.6 | 16 | A |
| 307 | A | N   | 44.4 | 24.7 | 42.6 | 17 | A |
| 307 | A | CA  | 45.2 | 25.7 | 43.3 | 17 | A |
| 307 | A | CB  | 45.9 | 25.0 | 44.5 | 11 | A |
| 307 | A | C   | 46.2 | 26.4 | 42.5 | 17 | A |
| 307 | A | O   | 47.0 | 27.2 | 43.0 | 18 | A |
| 308 | H | N   | 46.3 | 26.1 | 41.2 | 19 | A |
| 308 | H | CA  | 47.2 | 26.8 | 40.3 | 21 | A |
| 308 | H | CB  | 47.3 | 26.0 | 39.0 | 20 | A |
| 308 | H | CG  | 48.4 | 26.4 | 38.1 | 23 | A |
| 308 | H | CD2 | 49.7 | 26.0 | 38.0 | 21 | A |
| 308 | H | ND1 | 48.3 | 27.5 | 37.3 | 25 | A |
| 308 | H | CE1 | 49.5 | 27.7 | 36.7 | 22 | A |
| 308 | H | NE2 | 50.3 | 26.8 | 37.1 | 23 | A |
| 308 | H | C   | 46.9 | 28.2 | 40.0 | 22 | A |
| 308 | H | O   | 45.7 | 28.6 | 39.9 | 21 | A |
| 309 | P | N   | 48.0 | 29.1 | 39.9 | 24 | A |
| 309 | P | CD  | 49.4 | 28.8 | 40.2 | 22 | A |
| 309 | P | CA  | 47.8 | 30.5 | 39.7 | 24 | A |
| 309 | P | CB  | 49.2 | 31.0 | 39.4 | 23 | A |
| 309 | P | CG  | 50.0 | 30.1 | 40.4 | 23 | A |

TABLE 3-continued

Structural Coordinates of Ah₆-ERK2 [di-thiophosphorylated, SEQ ID NO: 5] Crystals The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | | |
|---|---|---|---|---|---|---|---|
| 309 | P | C | 46.8 | 30.8 | 38.6 | 24 | A |
| 309 | P | O | 46.1 | 31.9 | 38.6 | 24 | A |
| 310 | Y | N | 46.7 | 30.0 | 37.6 | 24 | A |
| 310 | Y | CA | 45.8 | 30.2 | 36.4 | 24 | A |
| 310 | Y | CB | 46.1 | 29.2 | 35.3 | 21 | A |
| 310 | Y | CG | 45.2 | 29.4 | 34.1 | 21 | A |
| 310 | Y | CD1 | 45.2 | 30.7 | 33.5 | 19 | A |
| 310 | Y | CE1 | 44.4 | 30.9 | 32.3 | 20 | A |
| 310 | Y | CD2 | 44.4 | 28.4 | 33.6 | 21 | A |
| 310 | Y | CE2 | 43.5 | 28.7 | 32.5 | 23 | A |
| 310 | Y | CZ | 43.6 | 29.9 | 31.9 | 23 | A |
| 310 | Y | OH | 42.8 | 30.1 | 30.8 | 23 | A |
| 310 | Y | C | 44.3 | 30.2 | 36.8 | 23 | A |
| 310 | Y | O | 43.5 | 30.8 | 36.1 | 25 | A |
| 311 | L | N | 44.0 | 29.6 | 37.9 | 21 | A |
| 311 | L | CA | 42.6 | 29.6 | 38.4 | 21 | A |
| 311 | L | CB | 42.1 | 28.1 | 38.6 | 18 | A |
| 311 | L | CG | 42.3 | 27.2 | 37.3 | 19 | A |
| 311 | L | CD1 | 42.1 | 25.7 | 37.7 | 15 | A |
| 311 | L | CD2 | 41.2 | 27.6 | 36.3 | 20 | A |
| 311 | L | C | 42.3 | 30.3 | 39.6 | 21 | A |
| 311 | L | O | 41.3 | 30.1 | 40.3 | 17 | A |
| 312 | E | N | 43.2 | 31.3 | 40.0 | 22 | A |
| 312 | E | CA | 43.1 | 32.0 | 41.2 | 26 | A |
| 312 | E | CB | 44.3 | 32.9 | 41.4 | 31 | A |
| 312 | E | CG | 44.5 | 34.0 | 40.3 | 39 | A |
| 312 | E | CD | 45.9 | 34.6 | 40.3 | 44 | A |
| 312 | E | OE1 | 46.4 | 35.0 | 41.4 | 47 | A |
| 312 | E | OE2 | 46.5 | 34.8 | 39.2 | 44 | A |
| 312 | E | C | 41.8 | 32.9 | 41.4 | 25 | A |
| 312 | E | O | 41.4 | 33.1 | 42.5 | 25 | A |
| 313 | Q | N | 41.2 | 33.3 | 40.3 | 25 | A |
| 313 | Q | CA | 40.0 | 34.1 | 40.4 | 27 | A |
| 313 | Q | CB | 39.8 | 34.9 | 39.2 | 27 | A |
| 313 | Q | CG | 39.3 | 34.1 | 38.0 | 34 | A |
| 313 | Q | CD | 39.2 | 34.9 | 36.7 | 40 | A |
| 313 | Q | OE1 | 38.3 | 35.8 | 36.6 | 42 | A |
| 313 | Q | NE2 | 40.1 | 34.7 | 35.7 | 36 | A |
| 313 | Q | C | 38.8 | 33.2 | 40.7 | 25 | A |
| 313 | Q | O | 37.7 | 33.8 | 41.1 | 24 | A |
| 314 | Y | N | 38.9 | 31.9 | 40.6 | 24 | A |
| 314 | Y | CA | 37.8 | 31.0 | 40.9 | 24 | A |
| 314 | Y | CB | 37.5 | 30.1 | 39.7 | 23 | A |
| 314 | Y | CG | 37.0 | 30.9 | 38.5 | 23 | A |
| 314 | Y | CD1 | 35.7 | 31.6 | 38.6 | 22 | A |
| 314 | Y | CE1 | 35.2 | 32.3 | 37.5 | 22 | A |
| 314 | Y | CD2 | 37.7 | 31.1 | 37.3 | 21 | A |
| 314 | Y | CE2 | 37.2 | 31.8 | 36.3 | 24 | A |
| 314 | Y | CZ | 36.0 | 32.5 | 36.4 | 24 | A |
| 314 | Y | OH | 35.5 | 33.2 | 35.4 | 27 | A |
| 314 | Y | C | 38.0 | 30.0 | 42.1 | 24 | A |
| 314 | Y | O | 37.1 | 29.7 | 42.8 | 27 | A |
| 315 | Y | N | 39.3 | 29.5 | 42.2 | 22 | A |
| 315 | Y | CA | 39.6 | 28.5 | 43.3 | 19 | A |
| 315 | Y | CB | 41.1 | 28.3 | 43.3 | 18 | A |
| 315 | Y | CG | 41.5 | 27.3 | 44.4 | 19 | A |
| 315 | Y | CD1 | 40.8 | 26.1 | 44.5 | 18 | A |
| 315 | Y | CE1 | 41.2 | 25.1 | 45.5 | 17 | A |
| 315 | Y | CD2 | 42.6 | 27.5 | 45.2 | 19 | A |
| 315 | Y | CE2 | 43.0 | 26.5 | 46.1 | 18 | A |
| 315 | Y | CZ | 42.3 | 25.3 | 46.3 | 20 | A |
| 315 | Y | OH | 42.7 | 24.4 | 47.2 | 19 | A |
| 315 | Y | C | 39.1 | 28.9 | 44.7 | 18 | A |
| 315 | Y | O | 39.5 | 30.0 | 45.2 | 18 | A |
| 316 | D | N | 38.3 | 28.1 | 45.2 | 19 | A |
| 316 | D | CA | 37.7 | 28.4 | 46.6 | 19 | A |
| 316 | D | CB | 36.7 | 29.5 | 46.5 | 18 | A |
| 316 | D | CG | 35.8 | 29.6 | 47.7 | 21 | A |
| 316 | D | OD1 | 36.3 | 29.4 | 48.8 | 25 | A |
| 316 | D | OD2 | 34.6 | 29.9 | 47.6 | 19 | A |
| 316 | D | C | 37.1 | 27.1 | 47.2 | 19 | A |
| 316 | D | O | 35.9 | 26.8 | 46.8 | 19 | A |
| 317 | P | N | 37.8 | 26.4 | 48.0 | 19 | A |
| 317 | P | CD | 39.3 | 26.5 | 48.1 | 19 | A |
| 317 | P | CA | 37.3 | 25.2 | 48.7 | 19 | A |
| 317 | P | CB | 38.4 | 24.8 | 49.7 | 18 | A |
| 317 | P | CG | 39.6 | 25.8 | 49.4 | 20 | A |
| 317 | P | C | 35.9 | 25.3 | 49.4 | 19 | A |
| 317 | P | O | 35.3 | 24.3 | 49.6 | 21 | A |
| 318 | S | N | 35.5 | 26.6 | 49.8 | 17 | A |
| 318 | S | CA | 34.2 | 26.7 | 50.5 | 15 | A |
| 318 | S | CB | 34.2 | 28.0 | 51.3 | 14 | A |
| 318 | S | OG | 34.2 | 29.2 | 50.4 | 12 | A |
| 318 | S | C | 33.0 | 26.6 | 49.5 | 15 | A |
| 318 | S | O | 31.9 | 26.7 | 49.9 | 15 | A |
| 319 | D | N | 33.3 | 26.5 | 48.2 | 14 | A |
| 319 | D | CA | 32.3 | 26.3 | 47.2 | 16 | A |
| 319 | D | CB | 32.2 | 27.7 | 46.4 | 18 | A |
| 319 | D | CG | 30.9 | 27.7 | 45.5 | 20 | A |
| 319 | D | OD1 | 29.9 | 27.1 | 45.9 | 20 | A |
| 319 | D | OD2 | 31.0 | 28.4 | 44.5 | 21 | A |
| 319 | D | C | 32.7 | 25.2 | 46.2 | 17 | A |
| 319 | D | O | 32.4 | 25.3 | 45.0 | 19 | A |
| 320 | E | N | 33.4 | 24.2 | 46.8 | 15 | A |
| 320 | E | CA | 33.9 | 23.1 | 46.0 | 18 | A |
| 320 | E | CB | 35.4 | 23.2 | 45.8 | 15 | A |
| 320 | E | CG | 35.8 | 24.1 | 44.6 | 18 | A |
| 320 | E | CD | 37.2 | 24.6 | 44.6 | 18 | A |
| 320 | E | OE1 | 38.1 | 23.9 | 45.3 | 17 | A |
| 320 | E | OE2 | 37.5 | 25.6 | 44.0 | 23 | A |
| 320 | E | C | 33.6 | 21.8 | 46.7 | 18 | A |
| 320 | E | O | 34.4 | 21.2 | 47.3 | 18 | A |
| 321 | P | N | 32.3 | 21.4 | 46.7 | 20 | A |
| 321 | P | CD | 31.2 | 22.1 | 46.0 | 18 | A |
| 321 | P | CA | 31.9 | 20.2 | 47.4 | 20 | A |
| 321 | P | CB | 30.4 | 20.1 | 47.0 | 18 | A |
| 321 | P | CG | 30.2 | 20.9 | 45.8 | 21 | A |
| 321 | P | C | 32.6 | 18.9 | 47.1 | 21 | A |
| 321 | P | O | 33.0 | 18.7 | 45.9 | 20 | A |
| 322 | I | N | 32.9 | 18.1 | 48.1 | 22 | A |
| 322 | I | CA | 33.5 | 16.8 | 47.9 | 25 | A |
| 322 | I | CB | 34.8 | 16.7 | 48.9 | 27 | A |
| 322 | I | CG2 | 35.9 | 17.6 | 48.3 | 24 | A |
| 322 | I | CG1 | 34.5 | 17.2 | 50.3 | 27 | A |
| 322 | I | CD1 | 33.6 | 16.2 | 51.0 | 32 | A |
| 322 | I | C | 32.5 | 15.8 | 48.3 | 27 | A |
| 322 | I | O | 31.4 | 16.1 | 48.8 | 26 | A |
| 323 | A | N | 32.7 | 14.5 | 48.0 | 26 | A |
| 323 | A | CA | 31.8 | 13.4 | 48.3 | 27 | A |
| 323 | A | CB | 32.2 | 12.2 | 47.5 | 21 | A |
| 323 | A | C | 31.7 | 13.1 | 49.8 | 29 | A |
| 323 | A | O | 32.7 | 13.0 | 50.4 | 31 | A |
| 324 | E | N | 30.5 | 13.0 | 50.3 | 33 | A |
| 324 | E | CA | 30.4 | 12.7 | 51.7 | 37 | A |
| 324 | E | CB | 29.1 | 13.3 | 52.3 | 41 | A |
| 324 | E | CG | 27.8 | 12.8 | 51.7 | 44 | A |
| 324 | E | CD | 26.6 | 13.5 | 52.3 | 47 | A |
| 324 | E | OE1 | 26.4 | 13.4 | 53.5 | 46 | A |
| 324 | E | OE2 | 25.9 | 14.1 | 51.5 | 50 | A |
| 324 | E | C | 30.5 | 11.2 | 52.1 | 36 | A |
| 324 | E | O | 31.0 | 10.9 | 53.1 | 34 | A |
| 325 | A | N | 30.0 | 10.4 | 51.1 | 35 | A |
| 325 | A | CA | 30.1 | 8.9 | 51.3 | 35 | A |
| 325 | A | CB | 28.7 | 8.3 | 51.5 | 34 | A |
| 325 | A | C | 30.9 | 8.3 | 50.1 | 33 | A |
| 325 | A | O | 30.3 | 7.7 | 49.3 | 31 | A |
| 326 | P | N | 32.2 | 8.5 | 50.1 | 32 | A |
| 326 | P | CD | 33.0 | 9.2 | 51.1 | 33 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | | |
|---|---|---|---|---|---|---|---|
| 326 | P | CA | 33.1 | 7.9 | 49.0 | 33 | A |
| 326 | P | CB | 34.5 | 8.2 | 49.6 | 33 | A |
| 326 | P | CG | 34.3 | 9.5 | 50.3 | 33 | A |
| 326 | P | C | 32.9 | 6.4 | 48.8 | 34 | A |
| 326 | P | O | 32.8 | 5.7 | 49.8 | 34 | A |
| 327 | F | N | 32.8 | 6.0 | 47.6 | 33 | A |
| 327 | F | CA | 32.6 | 4.6 | 47.3 | 33 | A |
| 327 | F | CB | 32.4 | 4.4 | 45.8 | 33 | A |
| 327 | F | CG | 31.1 | 4.9 | 45.2 | 34 | A |
| 327 | F | CD1 | 30.0 | 4.2 | 45.4 | 35 | A |
| 327 | F | CD2 | 31.1 | 6.1 | 44.4 | 34 | A |
| 327 | F | CE1 | 28.8 | 4.7 | 44.9 | 35 | A |
| 327 | F | CE2 | 29.9 | 6.5 | 43.9 | 33 | A |
| 327 | F | CZ | 28.7 | 5.8 | 44.1 | 37 | A |
| 327 | F | C | 33.7 | 3.7 | 47.8 | 32 | A |
| 327 | F | O | 34.8 | 4.2 | 47.8 | 30 | A |
| 328 | K | N | 33.3 | 2.5 | 48.3 | 34 | A |
| 328 | K | CA | 34.3 | 1.6 | 48.8 | 37 | A |
| 328 | K | CB | 33.9 | 1.3 | 50.3 | 39 | A |
| 328 | K | CG | 34.2 | 2.4 | 51.3 | 41 | A |
| 328 | K | CD | 35.7 | 2.7 | 51.3 | 43 | A |
| 328 | K | CE | 36.1 | 3.8 | 52.1 | 45 | A |
| 328 | K | NZ | 37.6 | 4.1 | 52.0 | 44 | A |
| 328 | K | C | 34.5 | 0.4 | 48.0 | 38 | A |
| 328 | K | O | 33.6 | −0.0 | 47.2 | 34 | A |
| 329 | F | N | 35.6 | −0.3 | 48.2 | 41 | A |
| 329 | F | CA | 36.0 | −1.5 | 47.5 | 44 | A |
| 329 | F | CB | 37.2 | −2.2 | 48.2 | 44 | A |
| 329 | F | CG | 37.7 | −3.4 | 47.5 | 47 | A |
| 329 | F | CD1 | 38.5 | −3.3 | 46.4 | 47 | A |
| 329 | F | CD2 | 37.4 | −4.7 | 48.0 | 48 | A |
| 329 | F | CE1 | 39.0 | −4.4 | 45.8 | 49 | A |
| 329 | F | CE2 | 37.8 | −5.8 | 47.4 | 49 | A |
| 329 | F | CZ | 38.6 | −5.7 | 46.2 | 50 | A |
| 329 | F | C | 34.9 | −2.5 | 47.3 | 46 | A |
| 329 | F | O | 34.7 | −3.1 | 46.2 | 46 | A |
| 330 | D | N | 34.2 | −2.8 | 48.4 | 48 | A |
| 330 | D | CA | 33.1 | −3.8 | 48.4 | 51 | A |
| 330 | D | CB | 32.4 | −3.8 | 49.8 | 54 | A |
| 330 | D | CG | 32.2 | −2.4 | 50.3 | 58 | A |
| 330 | D | OD1 | 31.6 | −1.5 | 49.7 | 59 | A |
| 330 | D | OD2 | 32.8 | −2.1 | 51.5 | 58 | A |
| 330 | D | C | 32.1 | −3.7 | 47.3 | 50 | A |
| 330 | D | O | 31.4 | −4.7 | 47.0 | 51 | A |
| 331 | M | N | 31.9 | −2.5 | 46.7 | 48 | A |
| 331 | M | CA | 31.0 | −2.3 | 45.6 | 46 | A |
| 331 | M | CB | 30.1 | −1.1 | 45.8 | 47 | A |
| 331 | M | CG | 30.9 | 0.2 | 45.7 | 49 | A |
| 331 | M | SD | 31.3 | 0.7 | 44.0 | 51 | A |
| 331 | M | CE | 29.7 | 1.3 | 43.5 | 53 | A |
| 331 | M | C | 31.6 | −2.4 | 44.2 | 45 | A |
| 331 | M | O | 31.0 | −2.1 | 43.2 | 45 | A |
| 332 | E | N | 32.9 | −2.7 | 44.2 | 43 | A |
| 332 | E | CA | 33.7 | −2.8 | 42.9 | 42 | A |
| 332 | E | CB | 35.2 | −2.6 | 43.2 | 40 | A |
| 332 | E | CG | 35.5 | −1.1 | 43.4 | 38 | A |
| 332 | E | CD | 37.0 | −1.0 | 43.8 | 38 | A |
| 332 | E | OE1 | 37.8 | −1.6 | 43.1 | 36 | A |
| 332 | E | OE2 | 37.3 | −0.2 | 44.7 | 35 | A |
| 332 | E | C | 33.5 | −4.2 | 42.3 | 44 | A |
| 332 | E | O | 33.6 | −4.4 | 41.1 | 44 | A |
| 333 | L | N | 33.3 | −5.2 | 43.2 | 46 | A |
| 333 | L | CA | 33.1 | −6.5 | 42.8 | 47 | A |
| 333 | L | CB | 33.1 | −7.5 | 44.0 | 50 | A |
| 333 | L | CG | 34.4 | −7.5 | 44.8 | 53 | A |
| 333 | L | CD1 | 34.9 | −6.2 | 45.2 | 53 | A |
| 333 | L | CD2 | 34.2 | −8.4 | 46.0 | 54 | A |
| 333 | L | C | 31.8 | −6.8 | 41.9 | 45 | A |
| 333 | L | O | 30.9 | −7.3 | 42.5 | 45 | A |
| 334 | D | N | 31.9 | −6.4 | 40.7 | 44 | A |
| 334 | D | CA | 30.7 | −6.6 | 39.8 | 43 | A |
| 334 | D | CB | 30.2 | −5.3 | 39.3 | 43 | A |
| 334 | D | CG | 31.2 | −4.5 | 38.6 | 43 | A |
| 334 | D | OD1 | 32.1 | −5.0 | 37.9 | 40 | A |
| 334 | D | OD2 | 31.2 | −3.2 | 38.6 | 42 | A |
| 334 | D | C | 31.0 | −7.6 | 38.6 | 43 | A |
| 334 | D | O | 30.2 | −7.5 | 37.6 | 40 | A |
| 335 | D | N | 32.0 | −8.4 | 38.6 | 45 | A |
| 335 | D | CA | 32.3 | −9.3 | 37.5 | 48 | A |
| 335 | D | CB | 33.7 | −9.8 | 37.6 | 50 | A |
| 335 | D | CG | 34.6 | −8.9 | 38.4 | 54 | A |
| 335 | D | OD1 | 35.1 | −7.8 | 37.9 | 57 | A |
| 335 | D | OD2 | 34.8 | −9.2 | 39.6 | 55 | A |
| 335 | D | C | 31.4 | −10.5 | 37.8 | 47 | A |
| 335 | D | O | 31.8 | −11.6 | 38.1 | 47 | A |
| 336 | L | N | 30.1 | −10.2 | 37.7 | 47 | A |
| 336 | L | CA | 29.0 | −11.2 | 37.9 | 48 | A |
| 336 | L | CB | 28.0 | −10.7 | 38.9 | 48 | A |
| 336 | L | CG | 28.6 | −10.1 | 40.2 | 49 | A |
| 336 | L | CD1 | 27.5 | −9.4 | 41.0 | 49 | A |
| 336 | L | CD2 | 29.3 | −11.1 | 41.1 | 49 | A |
| 336 | L | C | 28.3 | −11.5 | 36.6 | 48 | A |
| 336 | L | O | 28.3 | −10.7 | 35.6 | 47 | A |
| 337 | P | N | 27.5 | −12.6 | 36.5 | 49 | A |
| 337 | P | CD | 27.3 | −13.6 | 37.6 | 49 | A |
| 337 | P | CA | 26.7 | −13.0 | 35.3 | 49 | A |
| 337 | P | CB | 25.9 | −14.2 | 35.8 | 48 | A |
| 337 | P | CG | 26.8 | −14.8 | 36.8 | 48 | A |
| 337 | P | C | 25.8 | −11.8 | 34.9 | 48 | A |
| 337 | P | O | 25.4 | −11.0 | 35.8 | 48 | A |
| 338 | K | N | 25.5 | −11.7 | 33.7 | 49 | A |
| 338 | K | CA | 24.7 | −10.6 | 33.2 | 52 | A |
| 338 | K | CB | 24.7 | −10.5 | 31.7 | 51 | A |
| 338 | K | CG | 24.1 | −11.7 | 30.9 | 53 | A |
| 338 | K | CD | 24.6 | −11.8 | 29.5 | 53 | A |
| 338 | K | CE | 23.6 | −12.6 | 28.6 | 54 | A |
| 338 | K | NZ | 23.3 | −13.9 | 29.2 | 53 | A |
| 338 | K | C | 23.3 | −10.8 | 33.7 | 53 | A |
| 338 | K | O | 22.4 | −10.0 | 33.5 | 54 | A |
| 339 | E | N | 23.1 | −11.9 | 34.5 | 53 | A |
| 339 | E | CA | 21.8 | −12.2 | 35.0 | 53 | A |
| 339 | E | CB | 21.6 | −13.7 | 35.2 | 53 | A |
| 339 | E | CG | 21.3 | −14.5 | 34.0 | 54 | A |
| 339 | E | CD | 22.4 | −14.4 | 33.0 | 56 | A |
| 339 | E | OE1 | 23.6 | −14.7 | 33.3 | 57 | A |
| 339 | E | OE2 | 22.2 | −14.1 | 31.8 | 57 | A |
| 339 | E | C | 21.7 | −11.5 | 36.4 | 52 | A |
| 339 | E | O | 20.7 | −10.9 | 36.7 | 51 | A |
| 340 | K | N | 22.7 | −11.7 | 37.2 | 51 | A |
| 340 | K | CA | 22.8 | −11.1 | 38.5 | 51 | A |
| 340 | K | CB | 24.1 | −11.5 | 39.2 | 53 | A |
| 340 | K | CG | 23.9 | −12.4 | 40.4 | 56 | A |
| 340 | K | CD | 23.4 | −11.7 | 41.6 | 58 | A |
| 340 | K | CE | 22.8 | −12.6 | 42.6 | 61 | A |
| 340 | K | NZ | 21.6 | −13.4 | 42.1 | 61 | A |
| 340 | K | C | 22.8 | −9.6 | 38.3 | 52 | A |
| 340 | K | O | 22.1 | −8.8 | 39.0 | 52 | A |
| 341 | L | N | 23.6 | −9.1 | 37.3 | 50 | A |
| 341 | L | CA | 23.7 | −7.7 | 37.0 | 49 | A |
| 341 | L | CB | 24.7 | −7.5 | 35.9 | 49 | A |
| 341 | L | CG | 26.1 | −7.8 | 36.3 | 48 | A |
| 341 | L | CD1 | 27.1 | −7.7 | 35.2 | 48 | A |
| 341 | L | CD2 | 26.6 | −6.9 | 37.4 | 47 | A |
| 341 | L | C | 22.3 | −7.1 | 36.6 | 49 | A |
| 341 | L | O | 22.1 | −5.9 | 36.9 | 49 | A |
| 342 | K | N | 21.5 | −7.9 | 35.9 | 50 | A |
| 342 | K | CA | 20.2 | −7.4 | 35.5 | 50 | A |
| 342 | K | CB | 19.5 | −8.3 | 34.5 | 50 | A |

TABLE 3-continued

Structural Coordinates of Ah$_6$-ERK2 [di-thiophosphorylated, SEQ ID NO: 5] Crystals
The following table contains one line for each atom in one Thiophosphorylated Erk2 kinase tetramer. The columns are: 1) residue number, 2) l-letter amino acid code, 3) atom name, 4) x-coordinate, 5) y-coordinate, 6) z-coordinate, 7) B-factor, 8) Chain ID. Residues A183 and A185 (Amino Acid Code X and Z) are Thiophosphorylated. The coordinates are arranged in two side-by-side columns.

| | | | | | | |
|---|---|---|---|---|---|---|
| 342 | K | CG | 18.1 | −7.8 | 34.0 | 51 | A |
| 342 | K | CD | 17.5 | −8.7 | 32.9 | 49 | A |
| 342 | K | CE | 16.2 | −8.1 | 32.5 | 49 | A |
| 342 | K | NZ | 15.6 | −8.7 | 31.3 | 48 | A |
| 342 | K | C | 19.3 | −7.2 | 36.7 | 49 | A |
| 342 | K | O | 18.5 | −6.3 | 36.8 | 49 | A |
| 343 | E | N | 19.5 | −8.2 | 37.6 | 49 | A |
| 343 | E | CA | 18.7 | −8.1 | 38.9 | 50 | A |
| 343 | E | CB | 19.0 | −9.3 | 39.7 | 52 | A |
| 343 | E | CG | 18.4 | −10.6 | 39.2 | 56 | A |
| 343 | E | CD | 19.0 | −11.8 | 39.9 | 58 | A |
| 343 | E | OE1 | 18.9 | −11.9 | 41.1 | 59 | A |
| 343 | E | OE2 | 19.5 | −12.7 | 39.2 | 59 | A |
| 343 | E | C | 19.0 | −6.8 | 39.6 | 49 | A |
| 343 | E | O | 18.2 | −6.1 | 40.0 | 50 | A |
| 344 | L | N | 20.3 | −6.6 | 39.8 | 47 | A |
| 344 | L | CA | 20.9 | −5.4 | 40.4 | 43 | A |
| 344 | L | CB | 22.4 | −5.4 | 40.4 | 41 | A |
| 344 | L | CG | 23.1 | −6.6 | 41.2 | 42 | A |
| 344 | L | CD1 | 24.5 | −6.7 | 40.8 | 40 | A |
| 344 | L | CD2 | 22.9 | −6.4 | 42.7 | 39 | A |
| 344 | L | C | 20.3 | −4.1 | 39.8 | 42 | A |
| 344 | L | O | 19.9 | −3.2 | 40.5 | 42 | A |
| 345 | I | N | 20.3 | −4.1 | 38.5 | 42 | A |
| 345 | I | CA | 19.8 | −2.9 | 37.8 | 41 | A |
| 345 | I | CB | 20.0 | −3.0 | 36.2 | 40 | A |
| 345 | I | CG2 | 19.3 | −1.9 | 35.5 | 40 | A |
| 345 | I | CG1 | 21.5 | −3.0 | 35.9 | 40 | A |
| 345 | I | CD1 | 21.8 | −3.1 | 34.4 | 39 | A |
| 345 | I | C | 18.4 | −2.7 | 38.1 | 44 | A |
| 345 | I | O | 17.9 | −1.6 | 38.4 | 43 | A |
| 346 | F | N | 17.6 | −3.8 | 38.0 | 47 | A |
| 346 | F | CA | 16.2 | −3.7 | 38.3 | 49 | A |
| 346 | F | CB | 15.6 | −5.2 | 38.3 | 50 | A |
| 346 | F | CG | 14.1 | −5.2 | 38.5 | 52 | A |
| 346 | F | CD1 | 13.2 | −4.9 | 37.4 | 52 | A |
| 346 | F | CD2 | 13.6 | −5.5 | 39.7 | 52 | A |
| 346 | F | CE1 | 11.8 | −4.9 | 37.6 | 53 | A |
| 346 | F | CE2 | 12.2 | −5.5 | 39.9 | 52 | A |
| 346 | F | CZ | 11.3 | −5.2 | 38.9 | 52 | A |
| 346 | F | C | 15.9 | −3.1 | 39.6 | 48 | A |
| 346 | F | O | 15.1 | −2.2 | 39.8 | 46 | A |
| 347 | E | N | 16.7 | −3.5 | 40.6 | 50 | A |
| 347 | E | CA | 16.7 | −3.0 | 41.9 | 53 | A |
| 347 | E | CB | 17.7 | −3.8 | 42.8 | 54 | A |
| 347 | E | CG | 17.6 | −3.6 | 44.3 | 58 | A |
| 347 | E | CD | 18.6 | −4.5 | 45.0 | 60 | A |
| 347 | E | OE1 | 18.6 | −5.8 | 44.8 | 61 | A |
| 347 | E | OE2 | 19.5 | −4.0 | 45.7 | 62 | A |
| 347 | E | C | 17.0 | −1.5 | 42.0 | 53 | A |
| 347 | E | O | 16.2 | −0.7 | 42.5 | 54 | A |
| 348 | E | N | 18.2 | −1.2 | 41.5 | 52 | A |
| 348 | E | CA | 18.7 | 0.2 | 41.6 | 50 | A |
| 348 | E | CB | 20.0 | 0.3 | 40.8 | 48 | A |
| 348 | E | CG | 21.2 | −0.2 | 41.6 | 46 | A |
| 348 | E | CD | 21.6 | 0.7 | 42.9 | 45 | A |
| 348 | E | OE1 | 21.8 | 1.9 | 42.7 | 42 | A |
| 348 | E | OE2 | 21.6 | 0.1 | 44.0 | 46 | A |
| 348 | E | C | 17.7 | 1.2 | 40.9 | 51 | A |
| 348 | E | O | 17.7 | 2.4 | 41.2 | 52 | A |
| 349 | T | N | 16.8 | 0.7 | 40.0 | 50 | A |
| 349 | T | CA | 15.9 | 1.6 | 39.4 | 50 | A |
| 349 | T | CB | 15.7 | 1.2 | 37.9 | 48 | A |
| 349 | T | OG1 | 15.2 | −0.1 | 37.7 | 46 | A |
| 349 | T | CG2 | 17.0 | 1.3 | 37.2 | 49 | A |
| 349 | T | C | 14.5 | 1.5 | 40.0 | 50 | A |
| 349 | T | O | 13.6 | 2.3 | 39.7 | 50 | A |
| 350 | A | N | 14.3 | 0.6 | 41.0 | 51 | A |
| 350 | A | CA | 13.0 | 0.4 | 41.7 | 52 | A |
| 350 | A | CB | 13.2 | −0.6 | 42.8 | 52 | A |
| 350 | A | C | 12.5 | 1.7 | 42.2 | 54 | A |
| 350 | A | O | 11.3 | 2.1 | 42.0 | 53 | A |
| 351 | R | N | 13.3 | 2.4 | 43.0 | 56 | A |
| 351 | R | CA | 12.9 | 3.7 | 43.6 | 59 | A |
| 351 | R | CB | 14.2 | 4.5 | 44.1 | 60 | A |
| 351 | R | CG | 14.9 | 5.2 | 43.0 | 61 | A |
| 351 | R | CD | 15.5 | 6.5 | 43.5 | 62 | A |
| 351 | R | NE | 16.8 | 6.4 | 44.0 | 62 | A |
| 351 | R | CZ | 17.5 | 7.4 | 44.5 | 62 | A |
| 351 | R | NH1 | 16.9 | 8.6 | 44.6 | 62 | A |
| 351 | R | NH2 | 18.8 | 7.3 | 44.9 | 61 | A |
| 351 | R | C | 12.1 | 4.6 | 42.7 | 60 | A |
| 351 | R | O | 11.2 | 5.3 | 43.1 | 60 | A |
| 352 | F | N | 12.5 | 4.6 | 41.4 | 61 | A |
| 352 | F | CA | 11.8 | 5.4 | 40.4 | 63 | A |
| 352 | F | CB | 12.7 | 5.8 | 39.3 | 62 | A |
| 352 | F | CG | 13.9 | 6.6 | 39.6 | 62 | A |
| 352 | F | CD1 | 13.7 | 8.0 | 39.9 | 61 | A |
| 352 | F | CD2 | 15.1 | 6.1 | 39.8 | 61 | A |
| 352 | F | CE1 | 14.7 | 8.8 | 40.2 | 61 | A |
| 352 | F | CE2 | 16.2 | 6.9 | 40.2 | 61 | A |
| 352 | F | CZ | 16.0 | 8.3 | 40.4 | 60 | A |
| 352 | F | C | 10.5 | 4.9 | 39.9 | 64 | A |
| 352 | F | O | 9.8 | 5.5 | 39.1 | 64 | A |
| 353 | Q | N | 10.1 | 3.7 | 40.3 | 66 | A |
| 353 | Q | CA | 8.9 | 3.0 | 39.8 | 70 | A |
| 353 | Q | CB | 8.8 | 1.6 | 40.3 | 70 | A |
| 353 | Q | CG | 9.6 | 0.6 | 39.4 | 68 | A |
| 353 | Q | CD | 9.0 | 0.5 | 38.0 | 69 | A |
| 353 | Q | OE1 | 9.1 | 1.4 | 37.3 | 69 | A |
| 353 | Q | NE2 | 8.4 | −0.7 | 37.7 | 69 | A |
| 353 | Q | C | 7.7 | 3.8 | 40.4 | 73 | A |
| 353 | Q | O | 7.7 | 4.3 | 41.5 | 73 | A |
| 354 | P | N | 6.6 | 3.9 | 39.6 | 75 | A |
| 354 | P | CD | 6.5 | 3.3 | 38.2 | 76 | A |
| 354 | P | CA | 5.4 | 4.6 | 40.0 | 77 | A |
| 354 | P | CB | 4.4 | 4.1 | 38.9 | 77 | A |
| 354 | P | CG | 5.2 | 4.0 | 37.7 | 76 | A |
| 354 | P | C | 4.9 | 4.3 | 41.4 | 80 | A |
| 354 | P | O | 4.8 | 3.1 | 41.8 | 80 | A |
| 355 | G | N | 4.6 | 5.4 | 42.1 | 83 | A |
| 355 | G | CA | 4.1 | 5.2 | 43.5 | 88 | A |
| 355 | G | C | 5.0 | 4.4 | 44.4 | 91 | A |
| 355 | G | O | 4.5 | 3.9 | 45.5 | 91 | A |

Example 20

Ah$_6$-ERK2 [Di-Thiophosphorlylated] Structure Determination

The crystal structure was solved using molecular replacement using the search models 2ERK from the PDB. Refinement was done using the program CNX.

| | |
|---|---|
| Theoretical number of reflections | 21186 |
| Resolution Limits | 30.0-2.35 Å |
| Number of unobserved reflections | 100 (0.5%) |
| Number of reflections in working set | 19999 (94.4%) |
| Number of reflections in test set | 1087 (5.1%) |
| Number of protein residues | 350 |
| Number of solvent atoms | 0 |

-continued

| | |
|---|---|
| R-factor | 0.25.9 |
| R-free | 0.281 |
| RMSD bond length | 0.0071 Å |
| RMSD bond angles | 1.34 |

Example 21

Preparation of Ah$_6$-ERK2 [Un-Phosphorlylated] Form 1-Olomoucine Complex by Soaking and Crystallographic Analysis To a drop of Ah$_6$-ERK2 [un-phosphorlylated] form 1 crystals as described in example 5 was added 0.1 ul of 100 mM olomoucine DMSO solution. The drop was subsequently incubated at 22° C. for 24 hours. Prior to data collection, a soaked crystal was washed with the reservoir solution of the crystallization setup and transferred into the same solution with 20% glycerol added. The crystals were then flash-cooled in a nitrogen stream at 95 K or in liquid nitrogen. X-ray diffraction was collected using a Rigaku generator equipped with a Raxis 4 detector. Data were integrated and scaled using the HKL package.

Data Collection Statistics:

| | |
|---|---|
| Resolution | 30.0-2.00 Å |
| No. of collected reflections | 405433 |
| No. of unique reflections (F >= 0) | 50033 |
| R-sym | 8.6% |
| Percent of theoretical (I/s >= 1) | 94.2% |
| Unit Cell | a = 70.622 Å, b = 92.154 Å, c = 63.103 Å, α = β = γ = 90° |
| Space Group | P2$_1$2$_1$2 (Number 18) |
| Asymmetric unit | 1 molecule |

TABLE 4

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 6 | A | CB | 39.9 | 17.3 | −21.9 | 77 | A |
|---|---|---|---|---|---|---|---|
| 6 | A | C | 40.2 | 16.0 | −19.8 | 78 | A |
| 6 | A | O | 40.5 | 16.5 | −18.7 | 78 | A |
| 6 | A | N | 41.2 | 15.2 | −21.9 | 77 | A |
| 6 | A | CA | 40.8 | 16.4 | −21.1 | 77 | A |
| 7 | A | N | 39.2 | 15.1 | −19.8 | 78 | A |
| 7 | A | CA | 38.5 | 14.6 | −18.6 | 78 | A |
| 7 | A | CB | 39.2 | 13.4 | −18.0 | 77 | A |
| 7 | A | C | 38.3 | 15.7 | −17.6 | 77 | A |
| 7 | A | O | 37.6 | 16.8 | −17.9 | 77 | A |
| 8 | G | N | 38.8 | 15.5 | −16.4 | 77 | A |
| 8 | G | CA | 38.7 | 16.5 | −15.4 | 76 | A |
| 8 | G | C | 39.4 | 16.1 | −14.1 | 75 | A |
| 8 | G | O | 39.8 | 14.9 | −14.0 | 75 | A |
| 9 | P | N | 39.5 | 16.9 | −13.1 | 75 | A |
| 9 | P | CD | 38.9 | 18.3 | −13.0 | 74 | A |
| 9 | P | CA | 40.1 | 16.6 | −11.8 | 74 | A |
| 9 | P | CB | 40.1 | 17.9 | −11.0 | 74 | A |
| 9 | P | CG | 38.8 | 18.5 | −11.5 | 74 | A |
| 9 | P | C | 39.4 | 15.5 | −11.0 | 74 | A |
| 9 | P | O | 38.1 | 15.4 | −11.1 | 74 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 10 | E | N | 40.1 | 14.6 | −10.4 | 73 | A |
|---|---|---|---|---|---|---|---|
| 10 | E | CA | 39.5 | 13.5 | −9.6 | 73 | A |
| 10 | E | CB | 40.6 | 12.6 | −9.1 | 73 | A |
| 10 | E | CG | 41.3 | 11.7 | −10.2 | 75 | A |
| 10 | E | CD | 42.2 | 10.7 | −9.6 | 76 | A |
| 10 | E | OE1 | 41.7 | 9.8 | −8.8 | 75 | A |
| 10 | E | OE2 | 43.4 | 10.7 | −9.8 | 76 | A |
| 10 | E | C | 38.7 | 14.0 | −8.5 | 72 | A |
| 10 | E | O | 39.1 | 15.0 | −7.8 | 72 | A |
| 11 | M | N | 37.6 | 13.4 | −8.2 | 71 | A |
| 11 | M | CA | 36.8 | 13.8 | −7.0 | 71 | A |
| 11 | M | CB | 35.3 | 14.0 | −7.5 | 71 | A |
| 11 | M | CG | 35.2 | 15.1 | −8.6 | 70 | A |
| 11 | M | SD | 35.5 | 16.7 | −8.1 | 70 | A |
| 11 | M | CE | 33.9 | 17.2 | −7.5 | 69 | A |
| 11 | M | C | 36.8 | 12.7 | −6.0 | 71 | A |
| 11 | M | O | 37.0 | 11.5 | −6.3 | 71 | A |
| 12 | V | N | 36.5 | 13.1 | −4.7 | 70 | A |
| 12 | V | CA | 36.5 | 12.2 | −3.6 | 70 | A |
| 12 | V | CB | 37.8 | 12.1 | −2.9 | 70 | A |
| 12 | V | CG1 | 37.7 | 11.2 | −1.7 | 71 | A |
| 12 | V | CG2 | 38.9 | 11.5 | −3.9 | 70 | A |
| 12 | V | C | 35.4 | 12.7 | −2.6 | 71 | A |
| 12 | V | O | 35.7 | 13.7 | −1.9 | 72 | A |
| 13 | R | N | 34.3 | 12.0 | −2.6 | 71 | A |
| 13 | R | CA | 33.2 | 12.4 | −1.7 | 71 | A |
| 13 | R | CB | 33.7 | 12.4 | −0.2 | 72 | A |
| 13 | R | CG | 33.7 | 11.0 | 0.4 | 74 | A |
| 13 | R | CD | 34.7 | 10.1 | −0.2 | 75 | A |
| 13 | R | NE | 34.7 | 8.8 | 0.4 | 76 | A |
| 13 | R | CZ | 35.5 | 7.8 | 0.1 | 76 | A |
| 13 | R | NH1 | 36.4 | 7.9 | −0.9 | 75 | A |
| 13 | R | NH2 | 35.5 | 6.6 | 0.7 | 75 | A |
| 13 | R | C | 32.7 | 13.8 | −2.0 | 71 | A |
| 13 | R | O | 32.5 | 14.7 | −1.1 | 71 | A |
| 14 | G | N | 32.5 | 14.0 | −3.3 | 70 | A |
| 14 | G | CA | 31.9 | 15.3 | −3.8 | 70 | A |
| 14 | G | C | 33.0 | 16.4 | −3.9 | 70 | A |
| 14 | G | O | 32.7 | 17.4 | −4.6 | 70 | A |
| 15 | Q | N | 34.1 | 16.3 | −3.2 | 69 | A |
| 15 | Q | CA | 35.1 | 17.4 | −3.2 | 67 | A |
| 15 | Q | CB | 35.7 | 17.6 | −1.8 | 69 | A |
| 15 | Q | CG | 34.7 | 17.9 | −0.8 | 71 | A |
| 15 | Q | CD | 35.3 | 18.3 | 0.5 | 73 | A |
| 15 | Q | OE1 | 36.2 | 17.6 | 1.1 | 73 | A |
| 15 | Q | NE2 | 34.9 | 19.4 | 1.1 | 73 | A |
| 15 | Q | C | 36.2 | 17.0 | −4.2 | 65 | A |
| 15 | Q | O | 36.4 | 15.9 | −4.6 | 65 | A |
| 16 | V | N | 36.9 | 18.1 | −4.7 | 63 | A |
| 16 | V | CA | 38.0 | 17.9 | −5.7 | 61 | A |
| 16 | V | CB | 38.2 | 19.2 | −6.5 | 62 | A |
| 16 | V | CG1 | 39.3 | 19.0 | −7.5 | 61 | A |
| 16 | V | CG2 | 36.9 | 19.7 | −7.1 | 61 | A |
| 16 | V | C | 39.3 | 17.6 | −5.0 | 61 | A |
| 16 | V | O | 39.7 | 18.3 | −4.1 | 60 | A |
| 17 | F | N | 39.8 | 16.4 | −5.4 | 60 | A |
| 17 | F | CA | 41.1 | 16.0 | −4.8 | 59 | A |
| 17 | F | CB | 40.9 | 14.8 | −3.9 | 57 | A |
| 17 | F | CG | 42.0 | 14.6 | −2.9 | 55 | A |
| 17 | F | CD1 | 42.0 | 15.3 | −1.7 | 53 | A |
| 17 | F | CD2 | 43.1 | 13.8 | −3.2 | 55 | A |
| 17 | F | CE1 | 43.0 | 15.1 | −0.8 | 54 | A |
| 17 | F | CE2 | 44.2 | 13.7 | −2.3 | 55 | A |
| 17 | F | CZ | 44.1 | 14.3 | −1.0 | 53 | A |
| 17 | F | C | 42.0 | 15.6 | −6.0 | 59 | A |
| 17 | F | O | 42.2 | 14.5 | −6.3 | 59 | A |
| 18 | D | N | 42.5 | 16.7 | −6.7 | 59 | A |
| 18 | D | CA | 43.3 | 16.5 | −7.9 | 60 | A |
| 18 | D | CB | 43.0 | 17.5 | −8.9 | 61 | A |
| 18 | D | CG | 43.5 | 17.2 | −10.3 | 61 | A |

TABLE 4-continued

Structural Coordinates of Ah₆-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 18 | D | OD1 | 43.3 | 16.1 | −10.7 | 61 | A |
|---|---|---|---|---|---|---|---|
| 18 | D | OD2 | 44.2 | 18.1 | −10.9 | 61 | A |
| 18 | D | C | 44.8 | 16.5 | −7.6 | 60 | A |
| 18 | D | O | 45.4 | 17.5 | −7.6 | 60 | A |
| 19 | V | N | 45.3 | 15.3 | −7.3 | 61 | A |
| 19 | V | CA | 46.8 | 15.2 | −6.9 | 62 | A |
| 19 | V | CB | 47.0 | 14.4 | −5.7 | 61 | A |
| 19 | V | CG1 | 46.3 | 15.0 | −4.5 | 61 | A |
| 19 | V | CG2 | 46.5 | 12.9 | −5.9 | 61 | A |
| 19 | V | C | 47.5 | 14.5 | −8.1 | 63 | A |
| 19 | V | O | 48.7 | 14.4 | −8.1 | 63 | A |
| 20 | G | N | 46.7 | 14.0 | −9.0 | 64 | A |
| 20 | G | CA | 47.2 | 13.3 | −10.2 | 65 | A |
| 20 | G | C | 48.4 | 14.0 | −10.8 | 65 | A |
| 20 | G | O | 48.6 | 15.2 | −10.5 | 66 | A |
| 21 | P | N | 49.2 | 13.3 | −11.6 | 66 | A |
| 21 | P | CD | 50.1 | 13.9 | −12.5 | 66 | A |
| 21 | P | CA | 49.0 | 11.9 | −11.9 | 66 | A |
| 21 | P | CB | 49.3 | 11.8 | −13.4 | 66 | A |
| 21 | P | CG | 50.5 | 12.7 | −13.4 | 66 | A |
| 21 | P | C | 49.8 | 10.9 | −11.1 | 66 | A |
| 21 | P | O | 49.5 | 9.7 | −10.9 | 66 | A |
| 22 | R | N | 50.9 | 11.4 | −10.6 | 65 | A |
| 22 | R | CA | 51.9 | 10.7 | −9.8 | 63 | A |
| 22 | R | CB | 53.0 | 11.6 | −9.3 | 62 | A |
| 22 | R | CG | 54.0 | 10.9 | −8.4 | 62 | A |
| 22 | R | CD | 55.1 | 11.9 | −7.9 | 61 | A |
| 22 | R | NE | 56.0 | 11.2 | −6.9 | 62 | A |
| 22 | R | CZ | 57.0 | 11.9 | −6.3 | 61 | A |
| 22 | R | NH1 | 57.2 | 13.2 | −6.5 | 62 | A |
| 22 | R | NH2 | 57.7 | 11.2 | −5.4 | 62 | A |
| 22 | R | C | 51.2 | 9.9 | −8.6 | 63 | A |
| 22 | R | O | 51.9 | 9.1 | −8.0 | 63 | A |
| 23 | Y | N | 50.0 | 10.3 | −8.3 | 63 | A |
| 23 | Y | CA | 49.3 | 9.6 | −7.2 | 64 | A |
| 23 | Y | CB | 49.2 | 10.6 | −6.0 | 61 | A |
| 23 | Y | CG | 50.6 | 11.2 | −5.6 | 58 | A |
| 23 | Y | CD1 | 51.6 | 10.5 | −5.0 | 57 | A |
| 23 | Y | CE1 | 52.8 | 11.0 | −4.6 | 54 | A |
| 23 | Y | CD2 | 50.9 | 12.6 | −6.0 | 56 | A |
| 23 | Y | CE2 | 52.1 | 13.1 | −5.6 | 53 | A |
| 23 | Y | CZ | 53.1 | 12.3 | −5.0 | 54 | A |
| 23 | Y | OH | 54.3 | 12.9 | −4.7 | 51 | A |
| 23 | Y | C | 47.9 | 9.2 | −7.6 | 66 | A |
| 23 | Y | O | 47.1 | 10.0 | −8.2 | 66 | A |
| 24 | T | N | 47.5 | 8.0 | −7.2 | 68 | A |
| 24 | T | CA | 46.1 | 7.5 | −7.5 | 70 | A |
| 24 | T | CB | 46.1 | 6.7 | −8.8 | 71 | A |
| 24 | T | OG1 | 47.1 | 5.6 | −8.7 | 71 | A |
| 24 | T | CG2 | 46.4 | 7.6 | −10.0 | 71 | A |
| 24 | T | C | 45.5 | 6.7 | −6.3 | 71 | A |
| 24 | T | O | 46.2 | 6.5 | −5.3 | 72 | A |
| 25 | N | N | 44.3 | 6.1 | −6.6 | 73 | A |
| 25 | N | CA | 43.7 | 5.3 | −5.6 | 74 | A |
| 25 | N | CB | 44.5 | 4.0 | −5.2 | 75 | A |
| 25 | N | CG | 44.6 | 3.1 | −6.4 | 76 | A |
| 25 | N | OD1 | 45.2 | 3.4 | −7.5 | 76 | A |
| 25 | N | ND2 | 44.2 | 1.9 | −6.2 | 76 | A |
| 25 | N | C | 43.3 | 6.0 | −4.3 | 74 | A |
| 25 | N | O | 43.4 | 5.5 | −3.2 | 74 | A |
| 26 | L | N | 43.0 | 7.3 | −4.4 | 75 | A |
| 26 | L | CA | 42.6 | 8.1 | −3.3 | 76 | A |
| 26 | L | CB | 42.2 | 9.5 | −3.8 | 76 | A |
| 26 | L | CG | 43.1 | 10.2 | −4.8 | 76 | A |
| 26 | L | CD1 | 42.5 | 11.4 | −5.4 | 76 | A |
| 26 | L | CD2 | 44.4 | 10.5 | −4.1 | 75 | A |
| 26 | L | C | 41.5 | 7.5 | −2.4 | 76 | A |
| 26 | L | O | 40.5 | 7.0 | −2.9 | 77 | A |
| 27 | S | N | 41.8 | 7.5 | −1.1 | 75 | A |
| 27 | S | CA | 40.8 | 7.0 | −0.2 | 75 | A |
| 27 | S | CB | 41.3 | 5.5 | 0.2 | 75 | A |
| 27 | S | OG | 40.3 | 5.0 | 1.1 | 75 | A |
| 27 | S | C | 40.7 | 7.8 | 1.1 | 75 | A |
| 27 | S | O | 41.7 | 8.2 | 1.7 | 74 | A |
| 28 | Y | N | 39.5 | 8.3 | 1.4 | 75 | A |
| 28 | Y | CA | 39.2 | 9.1 | 2.5 | 76 | A |
| 28 | Y | CB | 37.7 | 9.3 | 2.7 | 75 | A |
| 28 | Y | CG | 37.4 | 10.4 | 3.7 | 75 | A |
| 28 | Y | CD1 | 37.5 | 11.8 | 3.2 | 75 | A |
| 28 | Y | CE1 | 37.2 | 12.8 | 4.1 | 76 | A |
| 28 | Y | CD2 | 36.9 | 10.2 | 5.0 | 75 | A |
| 28 | Y | CE2 | 36.6 | 11.3 | 5.8 | 76 | A |
| 28 | Y | CZ | 36.8 | 12.6 | 5.4 | 76 | A |
| 28 | Y | OH | 36.5 | 13.6 | 6.2 | 77 | A |
| 28 | Y | C | 39.9 | 8.6 | 3.8 | 76 | A |
| 28 | Y | O | 40.0 | 7.4 | 4.0 | 76 | A |
| 29 | I | N | 40.4 | 9.5 | 4.6 | 76 | A |
| 29 | I | CA | 41.0 | 9.2 | 5.9 | 77 | A |
| 29 | I | CB | 42.5 | 9.2 | 5.8 | 76 | A |
| 29 | I | CG2 | 43.2 | 8.8 | 7.1 | 77 | A |
| 29 | I | CG1 | 43.0 | 8.3 | 4.7 | 75 | A |
| 29 | I | CD1 | 44.5 | 8.3 | 4.5 | 74 | A |
| 29 | I | C | 40.6 | 10.1 | 7.0 | 78 | A |
| 29 | I | O | 40.6 | 9.8 | 8.2 | 79 | A |
| 30 | G | N | 40.3 | 11.4 | 6.7 | 79 | A |
| 30 | G | CA | 39.9 | 12.4 | 7.6 | 81 | A |
| 30 | G | C | 40.0 | 13.8 | 7.0 | 83 | A |
| 30 | G | O | 40.3 | 13.9 | 5.8 | 83 | A |
| 31 | E | N | 39.6 | 14.8 | 7.8 | 84 | A |
| 31 | E | CA | 39.5 | 16.1 | 7.3 | 86 | A |
| 31 | E | CB | 38.1 | 16.5 | 6.7 | 86 | A |
| 31 | E | CG | 38.1 | 17.7 | 5.8 | 87 | A |
| 31 | E | CD | 36.7 | 18.0 | 5.3 | 87 | A |
| 31 | E | OE1 | 35.7 | 18.1 | 6.1 | 87 | A |
| 31 | E | OE2 | 36.6 | 18.1 | 4.0 | 87 | A |
| 31 | E | C | 39.9 | 17.2 | 8.3 | 87 | A |
| 31 | E | O | 40.6 | 16.8 | 9.3 | 87 | A |
| 32 | G | N | 39.4 | 18.4 | 8.2 | 88 | A |
| 32 | G | CA | 39.7 | 19.5 | 9.1 | 88 | A |
| 32 | G | C | 39.1 | 20.8 | 8.7 | 89 | A |
| 32 | G | O | 38.6 | 20.9 | 7.6 | 89 | A |
| 36 | M | N | 40.6 | 17.7 | 3.8 | 53 | A |
| 36 | M | CA | 40.5 | 16.3 | 3.4 | 55 | A |
| 36 | M | CB | 39.6 | 16.1 | 2.2 | 56 | A |
| 36 | M | CG | 39.4 | 14.7 | 1.7 | 59 | A |
| 36 | M | SD | 38.1 | 14.5 | 0.5 | 63 | A |
| 36 | M | CE | 38.8 | 15.1 | −1.0 | 63 | A |
| 36 | M | C | 41.8 | 15.6 | 3.2 | 55 | A |
| 36 | M | O | 42.7 | 16.0 | 2.5 | 54 | A |
| 37 | V | N | 42.0 | 14.4 | 3.9 | 55 | A |
| 37 | V | CA | 43.2 | 13.6 | 3.8 | 55 | A |
| 37 | V | CB | 43.9 | 13.4 | 5.1 | 54 | A |
| 37 | V | CG1 | 45.2 | 12.7 | 5.0 | 53 | A |
| 37 | V | CG2 | 44.1 | 14.8 | 5.8 | 53 | A |
| 37 | V | C | 42.9 | 12.3 | 3.1 | 57 | A |
| 37 | V | O | 42.0 | 11.6 | 3.6 | 57 | A |
| 38 | C | N | 43.7 | 11.9 | 2.1 | 58 | A |
| 38 | C | CA | 43.5 | 10.7 | 1.5 | 60 | A |
| 38 | C | CB | 43.0 | 10.9 | 0.0 | 61 | A |
| 38 | C | SG | 41.4 | 11.6 | −0.1 | 63 | A |
| 38 | C | C | 44.9 | 9.9 | 1.4 | 61 | A |
| 38 | C | O | 45.9 | 10.5 | 1.3 | 60 | A |
| 39 | S | N | 44.8 | 8.6 | 1.4 | 62 | A |
| 39 | S | CA | 45.9 | 7.7 | 1.3 | 64 | A |
| 39 | S | CB | 45.7 | 6.4 | 2.0 | 65 | A |
| 39 | S | OG | 44.6 | 5.7 | 1.6 | 64 | A |
| 39 | S | C | 46.0 | 7.4 | −0.2 | 66 | A |
| 39 | S | O | 45.2 | 6.7 | −0.8 | 67 | A |
| 40 | A | N | 47.0 | 8.0 | −0.9 | 67 | A |
| 40 | A | CA | 47.2 | 7.9 | −2.3 | 68 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 40 | A | CB | 47.5 | 9.2 | -3.0 | 68 | A |
|---|---|---|---|---|---|---|---|
| 40 | A | C | 48.3 | 6.9 | -2.6 | 69 | A |
| 40 | A | O | 49.2 | 6.7 | -1.8 | 70 | A |
| 41 | Y | N | 48.2 | 6.2 | -3.7 | 70 | A |
| 41 | Y | CA | 49.3 | 5.3 | -4.1 | 71 | A |
| 41 | Y | CB | 48.7 | 4.2 | -5.0 | 72 | A |
| 41 | Y | CG | 49.6 | 3.0 | -5.3 | 73 | A |
| 41 | Y | CD1 | 49.9 | 2.1 | -4.3 | 73 | A |
| 41 | Y | CE1 | 50.8 | 1.0 | -4.6 | 74 | A |
| 41 | Y | CD2 | 50.3 | 2.9 | -6.5 | 74 | A |
| 41 | Y | CE2 | 51.2 | 1.9 | -6.8 | 74 | A |
| 41 | Y | CZ | 51.4 | 1.0 | -5.8 | 75 | A |
| 41 | Y | OH | 52.3 | -0.0 | -6.0 | 75 | A |
| 41 | Y | C | 50.3 | 6.0 | -4.9 | 70 | A |
| 41 | Y | O | 50.1 | 6.4 | -6.1 | 70 | A |
| 42 | D | N | 51.4 | 6.3 | -4.3 | 70 | A |
| 42 | D | CA | 52.5 | 7.1 | -5.0 | 70 | A |
| 42 | D | CB | 53.7 | 7.2 | -4.1 | 70 | A |
| 42 | D | CG | 54.8 | 8.1 | -4.7 | 70 | A |
| 42 | D | OD1 | 55.2 | 7.7 | -5.8 | 70 | A |
| 42 | D | OD2 | 55.3 | 9.0 | -4.0 | 70 | A |
| 42 | D | C | 52.9 | 6.2 | -6.2 | 71 | A |
| 42 | D | O | 53.7 | 5.3 | -6.1 | 71 | A |
| 43 | N | N | 52.4 | 6.6 | -7.4 | 71 | A |
| 43 | N | CA | 52.7 | 5.8 | -8.6 | 71 | A |
| 43 | N | CB | 51.7 | 6.3 | -9.7 | 71 | A |
| 43 | N | CG | 50.2 | 6.1 | -9.3 | 71 | A |
| 43 | N | OD1 | 49.8 | 5.0 | -9.0 | 72 | A |
| 43 | N | ND2 | 49.5 | 7.2 | -9.4 | 72 | A |
| 43 | N | C | 54.1 | 6.0 | -9.0 | 71 | A |
| 43 | N | O | 54.4 | 5.9 | -10.2 | 71 | A |
| 44 | L | N | 55.0 | 6.3 | -8.1 | 70 | A |
| 44 | L | CA | 56.4 | 6.5 | -8.4 | 68 | A |
| 44 | L | CB | 56.8 | 7.9 | -8.3 | 67 | A |
| 44 | L | CG | 58.3 | 8.3 | -8.7 | 66 | A |
| 44 | L | CD1 | 58.3 | 9.8 | -8.9 | 65 | A |
| 44 | L | CD2 | 59.2 | 7.9 | -7.5 | 65 | A |
| 44 | L | C | 57.2 | 5.7 | -7.3 | 69 | A |
| 44 | L | O | 57.1 | 6.0 | -6.1 | 68 | A |
| 46 | K | N | 55.9 | 3.6 | -5.8 | 68 | A |
| 46 | K | CA | 55.7 | 2.2 | -5.7 | 69 | A |
| 46 | K | CB | 57.0 | 1.4 | -5.9 | 70 | A |
| 46 | K | CG | 58.0 | 1.6 | -4.8 | 71 | A |
| 46 | K | CD | 58.8 | 2.9 | -4.9 | 71 | A |
| 46 | K | CE | 58.1 | 4.1 | -4.2 | 71 | A |
| 46 | K | NZ | 58.9 | 5.3 | -4.4 | 71 | A |
| 46 | K | C | 55.2 | 1.9 | -4.2 | 67 | A |
| 46 | K | O | 55.0 | 0.7 | -3.9 | 68 | A |
| 47 | V | N | 55.0 | 3.0 | -3.5 | 65 | A |
| 47 | V | CA | 54.5 | 2.8 | -2.1 | 62 | A |
| 47 | V | CB | 55.6 | 3.1 | -1.1 | 63 | A |
| 47 | V | CG1 | 56.2 | 4.5 | -1.3 | 63 | A |
| 47 | V | CG2 | 55.1 | 3.0 | 0.3 | 63 | A |
| 47 | V | C | 53.4 | 3.9 | -1.9 | 60 | A |
| 47 | V | O | 53.4 | 4.9 | -2.4 | 59 | A |
| 48 | R | N | 52.4 | 3.5 | -1.0 | 57 | A |
| 48 | R | CA | 51.3 | 4.4 | -0.7 | 57 | A |
| 48 | R | CB | 50.1 | 3.7 | -0.2 | 57 | A |
| 48 | R | CG | 49.6 | 2.6 | -1.1 | 58 | A |
| 48 | R | CD | 48.2 | 2.2 | -0.6 | 60 | A |
| 48 | R | NE | 47.2 | 3.1 | -1.0 | 61 | A |
| 48 | R | CZ | 46.1 | 3.4 | -0.2 | 62 | A |
| 48 | R | NH1 | 46.0 | 2.8 | 1.0 | 63 | A |
| 48 | R | NH2 | 45.2 | 4.2 | -0.7 | 62 | A |
| 48 | R | C | 51.8 | 5.5 | 0.3 | 53 | A |
| 48 | R | O | 52.6 | 5.2 | 1.2 | 52 | A |
| 49 | V | N | 51.3 | 6.7 | 0.1 | 49 | A |
| 49 | V | CA | 51.6 | 7.8 | 0.9 | 45 | A |
| 49 | V | CB | 52.5 | 8.9 | 0.2 | 44 | A |
| 49 | V | CG1 | 53.8 | 8.3 | -0.3 | 42 | A |
| 49 | V | CG2 | 51.7 | 9.4 | -1.0 | 46 | A |
| 49 | V | C | 50.3 | 8.5 | 1.4 | 42 | A |
| 49 | V | O | 49.2 | 8.1 | 1.1 | 41 | A |
| 50 | A | N | 50.5 | 9.5 | 2.3 | 39 | A |
| 50 | A | CA | 49.4 | 10.3 | 2.8 | 37 | A |
| 50 | A | CB | 49.5 | 10.4 | 4.3 | 35 | A |
| 50 | A | C | 49.4 | 11.6 | 2.1 | 36 | A |
| 50 | A | O | 50.5 | 12.3 | 2.0 | 33 | A |
| 51 | I | N | 48.3 | 12.1 | 1.6 | 36 | A |
| 51 | I | CA | 48.2 | 13.4 | 1.0 | 36 | A |
| 51 | I | CB | 47.9 | 13.3 | -0.5 | 35 | A |
| 51 | I | CG2 | 47.7 | 14.7 | -1.1 | 33 | A |
| 51 | I | CG1 | 49.0 | 12.6 | -1.3 | 37 | A |
| 51 | I | CD1 | 48.8 | 12.4 | -2.8 | 38 | A |
| 51 | I | C | 47.1 | 14.3 | 1.7 | 35 | A |
| 51 | I | O | 46.0 | 13.9 | 1.8 | 35 | A |
| 52 | K | N | 47.6 | 15.4 | 2.1 | 35 | A |
| 52 | K | CA | 46.7 | 16.4 | 2.8 | 36 | A |
| 52 | K | CB | 47.4 | 16.8 | 4.1 | 38 | A |
| 52 | K | CG | 46.6 | 17.8 | 4.9 | 41 | A |
| 52 | K | CD | 47.6 | 18.7 | 5.7 | 44 | A |
| 52 | K | CE | 48.6 | 17.9 | 6.5 | 44 | A |
| 52 | K | NZ | 49.4 | 18.8 | 7.4 | 43 | A |
| 52 | K | C | 46.4 | 17.6 | 1.9 | 35 | A |
| 52 | K | O | 47.3 | 18.3 | 1.5 | 33 | A |
| 53 | K | N | 45.1 | 17.8 | 1.7 | 35 | A |
| 53 | K | CA | 44.7 | 18.9 | 0.9 | 36 | A |
| 53 | K | CB | 43.4 | 18.6 | 0.0 | 39 | A |
| 53 | K | CG | 42.9 | 19.8 | -0.8 | 42 | A |
| 53 | K | CD | 41.6 | 19.5 | -1.5 | 42 | A |
| 53 | K | CE | 41.2 | 20.7 | -2.3 | 44 | A |
| 53 | K | NZ | 39.9 | 20.5 | -3.1 | 45 | A |
| 53 | K | C | 44.4 | 20.1 | 1.8 | 35 | A |
| 53 | K | O | 43.6 | 20.0 | 2.7 | 36 | A |
| 54 | I | N | 45.0 | 21.2 | 1.5 | 34 | A |
| 54 | I | CA | 44.8 | 22.4 | 2.3 | 35 | A |
| 54 | I | CB | 46.2 | 22.9 | 2.9 | 34 | A |
| 54 | I | CG2 | 46.0 | 24.0 | 3.9 | 34 | A |
| 54 | I | CG1 | 46.8 | 21.7 | 3.6 | 35 | A |
| 54 | I | CD1 | 48.2 | 22.0 | 4.2 | 35 | A |
| 54 | I | C | 44.3 | 23.6 | 1.5 | 34 | A |
| 54 | I | O | 44.7 | 23.9 | 0.4 | 33 | A |
| 55 | S | N | 43.3 | 24.3 | 2.0 | 35 | A |
| 55 | S | CA | 42.6 | 25.4 | 1.4 | 36 | A |
| 55 | S | CB | 41.2 | 25.0 | 0.9 | 35 | A |
| 55 | S | OG | 41.3 | 23.9 | 0.1 | 36 | A |
| 55 | S | C | 42.5 | 26.5 | 2.5 | 36 | A |
| 55 | S | O | 41.5 | 26.7 | 3.1 | 38 | A |
| 56 | P | N | 43.6 | 27.3 | 2.7 | 37 | A |
| 56 | P | CD | 45.0 | 26.9 | 2.2 | 38 | A |
| 56 | P | CA | 43.7 | 28.3 | 3.7 | 37 | A |
| 56 | P | CB | 45.0 | 28.0 | 4.4 | 37 | A |
| 56 | P | CG | 45.9 | 27.8 | 3.1 | 38 | A |
| 56 | P | C | 43.7 | 29.8 | 3.2 | 37 | A |
| 56 | P | O | 43.6 | 30.7 | 4.0 | 36 | A |
| 57 | F | N | 43.9 | 30.0 | 1.9 | 37 | A |
| 57 | F | CA | 44.0 | 31.3 | 1.4 | 38 | A |
| 57 | F | CB | 44.2 | 31.2 | -0.1 | 35 | A |
| 57 | F | CG | 45.4 | 30.4 | -0.5 | 32 | A |
| 57 | F | CD1 | 46.7 | 30.7 | 0.0 | 32 | A |
| 57 | F | CD2 | 45.3 | 29.2 | -1.3 | 31 | A |
| 57 | F | CE1 | 47.8 | 29.9 | -0.2 | 30 | A |
| 57 | F | CE2 | 46.4 | 28.4 | -1.5 | 31 | A |
| 57 | F | CZ | 47.6 | 28.7 | -1.0 | 30 | A |
| 57 | F | C | 42.9 | 32.4 | 1.7 | 39 | A |
| 57 | F | O | 43.1 | 33.5 | 1.4 | 38 | A |
| 58 | E | N | 41.7 | 31.9 | 2.2 | 42 | A |
| 58 | E | CA | 40.6 | 32.8 | 2.5 | 46 | A |
| 58 | E | CB | 39.3 | 32.0 | 2.4 | 47 | A |
| 58 | E | CG | 39.0 | 31.7 | 0.9 | 53 | A |

TABLE 4-continued

Structural Coordinates of Ah₆-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 58 | E | CD | 38.7 | 30.2 | 0.8 | 58 | A |
|---|---|---|---|---|---|---|---|
| 58 | E | OE1 | 37.7 | 29.7 | 1.4 | 60 | A |
| 58 | E | OE2 | 39.5 | 29.5 | 0.0 | 59 | A |
| 58 | E | C | 40.7 | 33.4 | 3.9 | 46 | A |
| 58 | E | O | 39.9 | 34.2 | 4.3 | 46 | A |
| 59 | H | N | 41.8 | 33.1 | 4.7 | 46 | A |
| 59 | H | CA | 42.0 | 33.6 | 6.0 | 46 | A |
| 59 | H | CB | 41.3 | 32.8 | 7.0 | 48 | A |
| 59 | H | CG | 39.8 | 32.8 | 6.9 | 51 | A |
| 59 | H | CD2 | 38.9 | 31.8 | 6.5 | 51 | A |
| 59 | H | ND1 | 39.0 | 33.9 | 7.1 | 51 | A |
| 59 | H | CE1 | 37.7 | 33.6 | 6.8 | 52 | A |
| 59 | H | NE2 | 37.7 | 32.4 | 6.5 | 51 | A |
| 59 | H | C | 43.5 | 33.7 | 6.4 | 45 | A |
| 59 | H | O | 44.3 | 32.8 | 6.1 | 45 | A |
| 60 | Q | N | 43.9 | 34.8 | 7.0 | 44 | A |
| 60 | Q | CA | 45.2 | 35.1 | 7.4 | 46 | A |
| 60 | Q | CB | 45.4 | 36.4 | 8.1 | 46 | A |
| 60 | Q | CG | 46.8 | 36.6 | 8.7 | 48 | A |
| 60 | Q | CD | 46.9 | 37.9 | 9.6 | 50 | A |
| 60 | Q | OE1 | 46.0 | 38.2 | 10.4 | 52 | A |
| 60 | Q | NE2 | 47.9 | 38.7 | 9.3 | 51 | A |
| 60 | Q | C | 45.8 | 34.0 | 8.4 | 45 | A |
| 60 | Q | O | 46.9 | 33.5 | 8.2 | 45 | A |
| 61 | T | N | 44.9 | 33.6 | 9.3 | 45 | A |
| 61 | T | CA | 45.3 | 32.6 | 10.3 | 45 | A |
| 61 | T | CB | 44.2 | 32.4 | 11.4 | 45 | A |
| 61 | T | OG1 | 43.0 | 32.0 | 10.7 | 49 | A |
| 61 | T | CG2 | 44.0 | 33.7 | 12.2 | 44 | A |
| 61 | T | C | 45.7 | 31.3 | 9.7 | 45 | A |
| 61 | T | O | 46.7 | 30.7 | 10.0 | 45 | A |
| 62 | Y | N | 44.8 | 30.8 | 8.8 | 44 | A |
| 62 | Y | CA | 45.1 | 29.5 | 8.1 | 44 | A |
| 62 | Y | CB | 43.9 | 29.1 | 7.2 | 48 | A |
| 62 | Y | CG | 42.6 | 28.9 | 8.0 | 52 | A |
| 62 | Y | CD1 | 42.6 | 28.0 | 9.1 | 55 | A |
| 62 | Y | CE1 | 41.4 | 27.8 | 9.8 | 58 | A |
| 62 | Y | CD2 | 41.5 | 29.6 | 7.7 | 55 | A |
| 62 | Y | CE2 | 40.3 | 29.4 | 8.4 | 58 | A |
| 62 | Y | CZ | 40.3 | 28.6 | 9.5 | 59 | A |
| 62 | Y | OH | 39.1 | 28.4 | 10.2 | 61 | A |
| 62 | Y | C | 46.4 | 29.6 | 7.3 | 42 | A |
| 62 | Y | O | 47.1 | 28.6 | 7.1 | 39 | A |
| 63 | C | N | 46.6 | 30.8 | 6.7 | 38 | A |
| 63 | C | CA | 47.8 | 31.0 | 5.9 | 38 | A |
| 63 | C | CB | 47.7 | 32.4 | 5.2 | 37 | A |
| 63 | C | SG | 46.6 | 32.4 | 3.8 | 33 | A |
| 63 | C | C | 49.1 | 31.0 | 6.8 | 37 | A |
| 63 | C | O | 50.1 | 30.4 | 6.4 | 36 | A |
| 64 | Q | N | 49.0 | 31.6 | 7.9 | 35 | A |
| 64 | Q | CA | 50.1 | 31.7 | 8.8 | 35 | A |
| 64 | Q | CB | 49.8 | 32.6 | 10.1 | 37 | A |
| 64 | Q | CG | 49.5 | 34.0 | 9.7 | 40 | A |
| 64 | Q | CD | 49.1 | 34.8 | 10.9 | 44 | A |
| 64 | Q | OE1 | 48.2 | 34.5 | 11.6 | 45 | A |
| 64 | Q | NE2 | 49.8 | 36.0 | 11.1 | 44 | A |
| 64 | Q | C | 50.5 | 30.2 | 9.3 | 33 | A |
| 64 | Q | O | 51.6 | 29.8 | 9.3 | 34 | A |
| 65 | R | N | 49.4 | 29.5 | 9.7 | 32 | A |
| 65 | R | CA | 49.6 | 28.1 | 10.2 | 33 | A |
| 65 | R | CB | 48.3 | 27.6 | 10.7 | 34 | A |
| 65 | R | CG | 47.6 | 28.4 | 11.8 | 38 | A |
| 65 | R | CD | 48.4 | 28.7 | 13.0 | 41 | A |
| 65 | R | NE | 47.6 | 29.5 | 14.0 | 44 | A |
| 65 | R | CZ | 48.1 | 29.9 | 15.2 | 45 | A |
| 65 | R | NH1 | 49.3 | 29.5 | 15.6 | 46 | A |
| 65 | R | NH2 | 47.3 | 30.6 | 16.0 | 42 | A |
| 65 | R | C | 50.1 | 27.2 | 9.1 | 32 | A |
| 65 | R | O | 51.1 | 26.4 | 9.3 | 29 | A |
| 66 | T | N | 49.6 | 27.3 | 7.9 | 29 | A |
| 66 | T | CA | 50.0 | 26.5 | 6.7 | 29 | A |
| 66 | T | CB | 49.2 | 26.8 | 5.5 | 30 | A |
| 66 | T | OG1 | 47.8 | 26.4 | 5.7 | 29 | A |
| 66 | T | CG2 | 49.8 | 26.1 | 4.3 | 29 | A |
| 66 | T | C | 51.5 | 26.8 | 6.4 | 28 | A |
| 66 | T | O | 52.3 | 25.9 | 6.2 | 27 | A |
| 67 | L | N | 51.8 | 28.1 | 6.4 | 26 | A |
| 67 | L | CA | 53.2 | 28.5 | 6.1 | 25 | A |
| 67 | L | CB | 53.2 | 30.0 | 5.9 | 25 | A |
| 67 | L | CG | 54.6 | 30.6 | 5.6 | 24 | A |
| 67 | L | CD1 | 55.1 | 30.0 | 4.3 | 26 | A |
| 67 | L | CD2 | 54.5 | 32.1 | 5.5 | 26 | A |
| 67 | L | C | 54.2 | 28.1 | 7.1 | 26 | A |
| 67 | L | O | 55.3 | 27.7 | 6.8 | 25 | A |
| 68 | R | N | 53.8 | 28.2 | 8.4 | 25 | A |
| 68 | R | CA | 54.7 | 27.8 | 9.5 | 28 | A |
| 68 | R | CB | 54.1 | 28.0 | 10.9 | 30 | A |
| 68 | R | CG | 53.9 | 29.5 | 11.2 | 34 | A |
| 68 | R | CD | 54.6 | 29.9 | 12.5 | 37 | A |
| 68 | R | NE | 54.3 | 31.3 | 12.9 | 38 | A |
| 68 | R | CZ | 53.1 | 31.7 | 13.1 | 38 | A |
| 68 | R | NH1 | 52.0 | 30.9 | 13.0 | 38 | A |
| 68 | R | NH2 | 52.9 | 33.0 | 13.4 | 38 | A |
| 68 | R | C | 55.1 | 26.3 | 9.3 | 26 | A |
| 68 | R | O | 56.3 | 25.9 | 9.4 | 26 | A |
| 69 | E | N | 54.1 | 25.5 | 9.2 | 25 | A |
| 69 | E | CA | 54.3 | 24.0 | 9.0 | 27 | A |
| 69 | E | CB | 53.0 | 23.3 | 8.8 | 26 | A |
| 69 | E | CG | 53.3 | 21.8 | 8.7 | 30 | A |
| 69 | E | CD | 52.0 | 20.9 | 8.8 | 31 | A |
| 69 | E | OE1 | 51.1 | 21.1 | 8.0 | 36 | A |
| 69 | E | OE2 | 52.0 | 20.1 | 9.8 | 27 | A |
| 69 | E | C | 55.2 | 23.7 | 7.8 | 27 | A |
| 69 | E | O | 56.1 | 22.9 | 8.0 | 26 | A |
| 70 | I | N | 54.9 | 24.3 | 6.7 | 25 | A |
| 70 | I | CA | 55.8 | 24.1 | 5.5 | 25 | A |
| 70 | I | CB | 55.2 | 24.8 | 4.3 | 24 | A |
| 70 | I | CG2 | 56.1 | 24.7 | 3.1 | 25 | A |
| 70 | I | CG1 | 53.8 | 24.2 | 3.9 | 23 | A |
| 70 | I | CD1 | 53.1 | 24.9 | 2.7 | 27 | A |
| 70 | I | C | 57.2 | 24.4 | 5.7 | 24 | A |
| 70 | I | O | 58.1 | 23.6 | 5.5 | 25 | A |
| 71 | K | N | 57.4 | 25.7 | 6.2 | 26 | A |
| 71 | K | CA | 58.8 | 26.2 | 6.4 | 26 | A |
| 71 | K | CB | 58.8 | 27.6 | 6.9 | 28 | A |
| 71 | K | CG | 58.2 | 28.6 | 6.0 | 33 | A |
| 71 | K | CD | 58.4 | 30.0 | 6.5 | 36 | A |
| 71 | K | CE | 59.9 | 30.4 | 6.4 | 39 | A |
| 71 | K | NZ | 60.1 | 31.8 | 6.8 | 42 | A |
| 71 | K | C | 59.6 | 25.3 | 7.4 | 26 | A |
| 71 | K | O | 60.7 | 24.9 | 7.1 | 25 | A |
| 72 | I | N | 58.9 | 24.9 | 8.5 | 23 | A |
| 72 | I | CA | 59.5 | 24.1 | 9.5 | 24 | A |
| 72 | I | CB | 58.6 | 24.0 | 10.8 | 25 | A |
| 72 | I | CG2 | 59.1 | 23.0 | 11.7 | 26 | A |
| 72 | I | CG1 | 58.7 | 25.4 | 11.5 | 26 | A |
| 72 | I | CD1 | 57.7 | 25.6 | 12.6 | 27 | A |
| 72 | I | C | 59.8 | 22.7 | 9.0 | 23 | A |
| 72 | I | O | 61.0 | 22.2 | 9.1 | 25 | A |
| 73 | L | N | 58.8 | 22.0 | 8.5 | 21 | A |
| 73 | L | CA | 59.0 | 20.6 | 8.1 | 23 | A |
| 73 | L | CB | 57.7 | 20.0 | 7.7 | 22 | A |
| 73 | L | CG | 56.7 | 19.8 | 8.9 | 22 | A |
| 73 | L | CD1 | 55.5 | 19.0 | 8.5 | 23 | A |
| 73 | L | CD2 | 57.4 | 19.2 | 10.1 | 22 | A |
| 73 | L | C | 59.9 | 20.5 | 6.9 | 24 | A |
| 73 | L | O | 60.6 | 19.4 | 6.7 | 26 | A |
| 74 | L | N | 60.1 | 21.5 | 6.1 | 25 | A |
| 74 | L | CA | 61.0 | 21.4 | 4.9 | 26 | A |
| 74 | L | CB | 60.7 | 22.5 | 3.9 | 24 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 74 | L | CG   | 59.4 | 22.3 | 3.0  | 24 | A |
|----|---|------|------|------|------|----|---|
| 74 | L | CD1  | 59.4 | 23.4 | 2.0  | 23 | A |
| 74 | L | CD2  | 59.5 | 20.9 | 2.4  | 24 | A |
| 74 | L | C    | 62.4 | 21.5 | 5.4  | 27 | A |
| 74 | L | O    | 63.3 | 21.0 | 4.8  | 28 | A |
| 75 | R | N    | 62.6 | 22.2 | 6.6  | 27 | A |
| 75 | R | CA   | 63.9 | 22.4 | 7.1  | 29 | A |
| 75 | R | CB   | 64.1 | 23.7 | 7.8  | 31 | A |
| 75 | R | CG   | 65.5 | 23.9 | 8.3  | 37 | A |
| 75 | R | CD   | 65.8 | 25.2 | 9.1  | 40 | A |
| 75 | R | NE   | 65.6 | 26.4 | 8.2  | 42 | A |
| 75 | R | CZ   | 65.9 | 27.6 | 8.6  | 41 | A |
| 75 | R | NH1  | 66.5 | 27.8 | 9.7  | 40 | A |
| 75 | R | NH2  | 65.7 | 28.6 | 7.8  | 43 | A |
| 75 | R | C    | 64.3 | 21.2 | 8.0  | 28 | A |
| 75 | R | O    | 65.5 | 21.0 | 8.3  | 30 | A |
| 76 | F | N    | 63.3 | 20.5 | 8.5  | 26 | A |
| 76 | F | CA   | 63.6 | 19.4 | 9.4  | 24 | A |
| 76 | F | CB   | 62.4 | 19.2 | 10.4 | 20 | A |
| 76 | F | CG   | 62.3 | 20.2 | 11.5 | 18 | A |
| 76 | F | CD1  | 63.2 | 21.2 | 11.6 | 18 | A |
| 76 | F | CD2  | 61.3 | 20.1 | 12.5 | 19 | A |
| 76 | F | CE1  | 63.2 | 22.2 | 12.6 | 19 | A |
| 76 | F | CE2  | 61.3 | 21.0 | 13.5 | 20 | A |
| 76 | F | CZ   | 62.2 | 22.0 | 13.6 | 16 | A |
| 76 | F | C    | 63.8 | 18.0 | 8.7  | 24 | A |
| 76 | F | O    | 63.2 | 17.8 | 7.6  | 22 | A |
| 77 | R | N    | 64.6 | 17.2 | 9.3  | 23 | A |
| 77 | R | CA   | 64.9 | 15.9 | 8.8  | 25 | A |
| 77 | R | CB   | 66.1 | 15.9 | 7.8  | 28 | A |
| 77 | R | CG   | 66.3 | 14.6 | 7.0  | 36 | A |
| 77 | R | CD   | 67.4 | 14.8 | 6.0  | 43 | A |
| 77 | R | NE   | 67.6 | 13.5 | 5.2  | 49 | A |
| 77 | R | CZ   | 68.1 | 12.4 | 5.7  | 51 | A |
| 77 | R | NH1  | 68.3 | 12.3 | 7.0  | 51 | A |
| 77 | R | NH2  | 68.2 | 11.3 | 4.9  | 52 | A |
| 77 | R | C    | 65.3 | 15.0 | 10.0 | 23 | A |
| 77 | R | O    | 66.4 | 15.1 | 10.5 | 22 | A |
| 78 | H | N    | 64.3 | 14.2 | 10.5 | 21 | A |
| 78 | H | CA   | 64.5 | 13.4 | 11.7 | 21 | A |
| 78 | H | CB   | 64.3 | 14.3 | 12.9 | 19 | A |
| 78 | H | CG   | 64.6 | 13.6 | 14.2 | 20 | A |
| 78 | H | CD2  | 65.7 | 13.8 | 15.0 | 19 | A |
| 78 | H | ND1  | 63.8 | 12.6 | 14.8 | 19 | A |
| 78 | H | CE1  | 64.4 | 12.2 | 15.9 | 20 | A |
| 78 | H | NE2  | 65.6 | 12.9 | 16.1 | 19 | A |
| 78 | H | C    | 63.6 | 12.2 | 11.6 | 20 | A |
| 78 | H | O    | 62.4 | 12.3 | 11.2 | 18 | A |
| 79 | E | N    | 64.1 | 11.1 | 12.1 | 19 | A |
| 79 | E | CA   | 63.3 | 9.8  | 12.0 | 21 | A |
| 79 | E | CB   | 64.1 | 8.7  | 12.7 | 24 | A |
| 79 | E | CG   | 65.4 | 8.3  | 12.0 | 31 | A |
| 79 | E | CD   | 65.9 | 7.0  | 12.5 | 34 | A |
| 79 | E | OE1  | 65.8 | 6.7  | 13.7 | 33 | A |
| 79 | E | OE2  | 66.4 | 6.2  | 11.7 | 38 | A |
| 79 | E | C    | 61.9 | 9.9  | 12.8 | 18 | A |
| 79 | E | O    | 61.0 | 9.3  | 12.3 | 17 | A |
| 80 | N | N    | 61.9 | 10.7 | 13.9 | 17 | A |
| 80 | N | CA   | 60.7 | 10.8 | 14.6 | 17 | A |
| 80 | N | CB   | 61.0 | 10.7 | 16.1 | 16 | A |
| 80 | N | CG   | 61.7 | 9.4  | 16.5 | 15 | A |
| 80 | N | OD1  | 62.9 | 9.5  | 16.9 | 17 | A |
| 80 | N | ND2  | 61.1 | 8.3  | 16.3 | 15 | A |
| 80 | N | C    | 59.8 | 12.0 | 14.3 | 18 | A |
| 80 | N | O    | 59.0 | 12.4 | 15.1 | 18 | A |
| 81 | I | N    | 60.1 | 12.6 | 13.2 | 19 | A |
| 81 | I | CA   | 59.4 | 13.8 | 12.8 | 20 | A |
| 81 | I | CB   | 60.3 | 15.1 | 12.8 | 21 | A |
| 81 | I | CG2  | 59.5 | 16.3 | 12.2 | 19 | A |
| 81 | I | CG1  | 60.7 | 15.3 | 14.2 | 21 | A |
| 81 | I | CD1  | 61.7 | 16.5 | 14.3 | 21 | A |
| 81 | I | C    | 58.9 | 13.5 | 11.4 | 20 | A |
| 81 | I | O    | 59.7 | 13.2 | 10.5 | 20 | A |
| 82 | I | N    | 57.5 | 13.7 | 11.2 | 20 | A |
| 82 | I | CA   | 57.0 | 13.4 | 9.8  | 22 | A |
| 82 | I | CB   | 55.4 | 13.6 | 9.8  | 22 | A |
| 82 | I | CG2  | 55.0 | 15.0 | 9.9  | 20 | A |
| 82 | I | CG1  | 54.9 | 13.0 | 8.5  | 22 | A |
| 82 | I | CD1  | 55.0 | 11.4 | 8.4  | 20 | A |
| 82 | I | C    | 57.6 | 14.5 | 8.9  | 23 | A |
| 82 | I | O    | 57.7 | 15.6 | 9.3  | 25 | A |
| 83 | G | N    | 58.0 | 14.1 | 7.7  | 26 | A |
| 83 | G | CA   | 58.6 | 15.1 | 6.8  | 29 | A |
| 83 | G | C    | 57.5 | 15.4 | 5.7  | 29 | A |
| 83 | G | O    | 56.4 | 15.0 | 5.8  | 29 | A |
| 84 | I | N    | 58.0 | 16.2 | 4.8  | 29 | A |
| 84 | I | CA   | 57.1 | 16.6 | 3.7  | 28 | A |
| 84 | I | CB   | 56.9 | 18.1 | 3.5  | 27 | A |
| 84 | I | CG2  | 56.3 | 18.4 | 2.2  | 26 | A |
| 84 | I | CG1  | 56.0 | 18.6 | 4.6  | 27 | A |
| 84 | I | CD1  | 55.8 | 20.1 | 4.6  | 24 | A |
| 84 | I | C    | 57.9 | 16.0 | 2.5  | 29 | A |
| 84 | I | O    | 59.0 | 16.5 | 2.2  | 28 | A |
| 85 | N | N    | 57.3 | 15.0 | 1.8  | 28 | A |
| 85 | N | CA   | 57.9 | 14.4 | 0.6  | 31 | A |
| 85 | N | CB   | 57.3 | 13.0 | 0.4  | 31 | A |
| 85 | N | CG   | 57.5 | 12.1 | 1.6  | 31 | A |
| 85 | N | OD1  | 57.0 | 11.0 | 1.7  | 31 | A |
| 85 | N | ND2  | 58.2 | 12.6 | 2.6  | 29 | A |
| 85 | N | C    | 57.7 | 15.2 | −0.7 | 32 | A |
| 85 | N | O    | 58.6 | 15.1 | −1.5 | 31 | A |
| 86 | D | N    | 56.6 | 15.9 | −0.7 | 32 | A |
| 86 | D | CA   | 56.3 | 16.7 | −1.9 | 32 | A |
| 86 | D | CB   | 56.0 | 15.7 | −3.1 | 32 | A |
| 86 | D | CG   | 55.7 | 16.3 | −4.4 | 33 | A |
| 86 | D | OD1  | 56.3 | 17.4 | −4.7 | 36 | A |
| 86 | D | OD2  | 54.8 | 15.8 | −5.1 | 36 | A |
| 86 | D | C    | 55.1 | 17.6 | −1.6 | 30 | A |
| 86 | D | O    | 54.4 | 17.4 | −0.7 | 28 | A |
| 87 | I | N    | 55.0 | 18.7 | −2.4 | 30 | A |
| 87 | I | CA   | 54.0 | 19.7 | −2.3 | 28 | A |
| 87 | I | CB   | 54.4 | 21.0 | −1.6 | 28 | A |
| 87 | I | CG2  | 53.3 | 21.9 | −1.5 | 25 | A |
| 87 | I | CG1  | 55.0 | 20.7 | −0.3 | 27 | A |
| 87 | I | CD1  | 55.5 | 21.9 | 0.4  | 27 | A |
| 87 | I | C    | 53.4 | 19.9 | −3.7 | 31 | A |
| 87 | I | O    | 54.2 | 20.3 | −4.6 | 30 | A |
| 88 | I | N    | 52.1 | 19.8 | −3.8 | 30 | A |
| 88 | I | CA   | 51.4 | 20.0 | −5.1 | 31 | A |
| 88 | I | CB   | 50.5 | 18.8 | −5.4 | 33 | A |
| 88 | I | CG2  | 49.8 | 19.0 | −6.8 | 34 | A |
| 88 | I | CG1  | 51.4 | 17.5 | −5.5 | 34 | A |
| 88 | I | CD1  | 50.6 | 16.2 | −5.6 | 35 | A |
| 88 | I | C    | 50.5 | 21.2 | −5.1 | 30 | A |
| 88 | I | O    | 49.8 | 21.5 | −4.2 | 31 | A |
| 89 | R | N    | 50.7 | 22.1 | −6.1 | 30 | A |
| 89 | R | CA   | 49.9 | 23.3 | −6.3 | 28 | A |
| 89 | R | CB   | 50.3 | 24.3 | −5.2 | 28 | A |
| 89 | R | CG   | 51.7 | 24.7 | −5.1 | 28 | A |
| 89 | R | CD   | 52.3 | 25.5 | −6.2 | 27 | A |
| 89 | R | NE   | 53.5 | 26.2 | −5.9 | 28 | A |
| 89 | R | CZ   | 54.3 | 26.8 | −6.8 | 30 | A |
| 89 | R | NH1  | 54.0 | 26.7 | −8.1 | 26 | A |
| 89 | R | NH2  | 55.4 | 27.4 | −6.4 | 28 | A |
| 89 | R | C    | 50.1 | 23.8 | −7.7 | 29 | A |
| 89 | R | O    | 51.0 | 23.4 | −8.4 | 28 | A |
| 90 | A | N    | 49.2 | 24.7 | −8.1 | 28 | A |
| 90 | A | CA   | 49.2 | 25.3 | −9.4 | 27 | A |
| 90 | A | CB   | 48.0 | 26.2 | −9.6 | 25 | A |
| 90 | A | C    | 50.5 | 26.0 | −9.8 | 28 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 90 | A | O | 51.2 | 26.5 | −8.9 | 28 | A | 99 | V | CG2 | 49.1 | 25.3 | −1.5 | 33 | A |
|---|---|---|---|---|---|---|---|---|---|---|---|---|---|---|---|
| 91 | P | N | 50.8 | 26.1 | −11.1 | 29 | A | 99 | V | C | 47.9 | 21.7 | −1.1 | 31 | A |
| 91 | P | CD | 50.1 | 25.6 | −12.2 | 30 | A | 99 | V | O | 47.3 | 21.5 | −0.1 | 31 | A |
| 91 | P | CA | 52.0 | 26.8 | −11.5 | 29 | A | 100 | Y | N | 48.5 | 20.7 | −1.8 | 30 | A |
| 91 | P | CB | 52.1 | 26.4 | −13.0 | 29 | A | 100 | Y | CA | 48.5 | 19.3 | −1.3 | 30 | A |
| 91 | P | CG | 50.7 | 26.3 | −13.4 | 28 | A | 100 | Y | CB | 48.2 | 18.3 | −2.4 | 32 | A |
| 91 | P | C | 52.1 | 28.3 | −11.3 | 28 | A | 100 | Y | CG | 46.8 | 18.5 | −3.1 | 36 | A |
| 91 | P | O | 53.2 | 28.9 | −11.3 | 29 | A | 100 | Y | CD1 | 46.7 | 19.6 | −4.1 | 37 | A |
| 92 | T | N | 50.9 | 28.9 | −11.0 | 26 | A | 100 | Y | CE1 | 45.4 | 19.7 | −4.7 | 39 | A |
| 92 | T | CA | 50.9 | 30.3 | −10.8 | 26 | A | 100 | Y | CD2 | 45.7 | 17.7 | −2.8 | 37 | A |
| 92 | T | CB | 50.2 | 31.1 | −12.0 | 26 | A | 100 | Y | CE2 | 44.5 | 17.9 | −3.5 | 38 | A |
| 92 | T | OG1 | 48.8 | 30.8 | −12.1 | 25 | A | 100 | Y | CZ | 44.4 | 18.9 | −4.4 | 40 | A |
| 92 | T | CG2 | 50.9 | 30.7 | −13.3 | 23 | A | 100 | Y | OH | 43.2 | 19.1 | −5.0 | 42 | A |
| 92 | T | C | 50.1 | 30.6 | −9.5 | 27 | A | 100 | Y | C | 49.9 | 19.0 | −0.8 | 30 | A |
| 92 | T | O | 49.3 | 29.9 | −9.1 | 27 | A | 100 | Y | O | 50.9 | 19.1 | −1.4 | 27 | A |
| 93 | I | N | 50.4 | 31.8 | −8.9 | 28 | A | 101 | I | N | 49.9 | 18.5 | 0.5 | 29 | A |
| 93 | I | CA | 49.7 | 32.2 | −7.7 | 30 | A | 101 | I | CA | 51.1 | 18.1 | 1.1 | 29 | A |
| 93 | I | CB | 50.3 | 33.5 | −7.1 | 33 | A | 101 | I | CB | 51.2 | 18.7 | 2.6 | 30 | A |
| 93 | I | CG2 | 50.2 | 34.6 | −8.2 | 34 | A | 101 | I | CG2 | 52.5 | 18.2 | 3.3 | 28 | A |
| 93 | I | CG1 | 49.6 | 33.9 | −5.8 | 35 | A | 101 | I | CG1 | 51.2 | 20.2 | 2.5 | 29 | A |
| 93 | I | CD1 | 50.2 | 35.0 | −5.1 | 37 | A | 101 | I | CD1 | 51.3 | 20.9 | 3.8 | 32 | A |
| 93 | I | C | 48.2 | 32.4 | −8.0 | 29 | A | 101 | I | C | 51.3 | 16.6 | 1.2 | 28 | A |
| 93 | I | O | 47.4 | 32.0 | −7.2 | 28 | A | 101 | I | O | 50.4 | 15.9 | 1.8 | 28 | A |
| 94 | E | N | 47.9 | 33.0 | −9.1 | 29 | A | 102 | V | N | 52.3 | 16.0 | 0.6 | 28 | A |
| 94 | E | CA | 46.5 | 33.2 | −9.5 | 29 | A | 102 | V | CA | 52.5 | 14.6 | 0.6 | 27 | A |
| 94 | E | CB | 46.4 | 34.0 | −10.9 | 31 | A | 102 | V | CB | 53.1 | 14.1 | −0.8 | 27 | A |
| 94 | E | CG | 47.1 | 35.3 | −10.9 | 33 | A | 102 | V | CG1 | 53.2 | 12.6 | −0.9 | 27 | A |
| 94 | E | CD | 48.5 | 35.3 | −11.3 | 35 | A | 102 | V | CG2 | 52.3 | 14.7 | −1.9 | 26 | A |
| 94 | E | OE1 | 49.2 | 34.3 | −11.1 | 35 | A | 102 | V | C | 53.5 | 14.2 | 1.7 | 26 | A |
| 94 | E | OE2 | 49.0 | 36.4 | −11.7 | 37 | A | 102 | V | O | 54.6 | 14.8 | 1.8 | 25 | A |
| 94 | E | C | 45.7 | 32.0 | −9.6 | 29 | A | 103 | Q | N | 53.1 | 13.1 | 2.4 | 26 | A |
| 94 | E | O | 44.5 | 32.0 | −9.2 | 29 | A | 103 | Q | CA | 53.9 | 12.7 | 3.5 | 27 | A |
| 95 | Q | N | 46.3 | 30.9 | −10.0 | 27 | A | 103 | Q | CB | 53.4 | 13.3 | 4.9 | 26 | A |
| 95 | Q | CA | 45.5 | 29.6 | −10.2 | 27 | A | 103 | Q | CG | 53.3 | 14.8 | 4.8 | 24 | A |
| 95 | Q | CB | 46.0 | 28.8 | −11.4 | 27 | A | 103 | Q | CD | 52.8 | 15.4 | 6.1 | 24 | A |
| 95 | Q | CG | 46.1 | 29.7 | −12.6 | 29 | A | 103 | Q | OE1 | 51.6 | 15.2 | 6.4 | 25 | A |
| 95 | Q | CD | 46.7 | 28.9 | −13.8 | 30 | A | 103 | Q | NE2 | 53.6 | 16.1 | 6.9 | 22 | A |
| 95 | Q | OE1 | 46.0 | 28.1 | −14.4 | 31 | A | 103 | Q | C | 53.9 | 11.2 | 3.6 | 27 | A |
| 95 | Q | NE2 | 48.0 | 29.0 | −14.0 | 30 | A | 103 | Q | O | 53.0 | 10.5 | 3.1 | 26 | A |
| 95 | Q | C | 45.6 | 28.7 | −8.9 | 27 | A | 104 | D | N | 54.9 | 10.6 | 4.3 | 28 | A |
| 95 | Q | O | 45.0 | 27.7 | −8.9 | 25 | A | 104 | D | CA | 54.9 | 9.1 | 4.5 | 29 | A |
| 96 | M | N | 46.5 | 29.1 | −8.0 | 26 | A | 104 | D | CB | 56.1 | 8.7 | 5.4 | 31 | A |
| 96 | M | CA | 46.6 | 28.3 | −6.8 | 27 | A | 104 | D | CG | 57.5 | 8.9 | 4.8 | 31 | A |
| 96 | M | CB | 48.0 | 28.6 | −6.1 | 25 | A | 104 | D | OD1 | 57.5 | 8.9 | 3.5 | 33 | A |
| 96 | M | CG | 48.2 | 27.9 | −4.8 | 25 | A | 104 | D | OD2 | 58.4 | 9.1 | 5.5 | 31 | A |
| 96 | M | SD | 49.9 | 28.1 | −4.1 | 27 | A | 104 | D | C | 53.6 | 8.7 | 5.2 | 28 | A |
| 96 | M | CE | 49.9 | 29.8 | −3.6 | 25 | A | 104 | D | O | 53.2 | 9.4 | 6.1 | 28 | A |
| 96 | M | C | 45.5 | 28.6 | −5.7 | 27 | A | 105 | L | N | 53.1 | 7.6 | 4.7 | 28 | A |
| 96 | M | O | 45.5 | 29.7 | −5.1 | 26 | A | 105 | L | CA | 51.8 | 7.1 | 5.3 | 29 | A |
| 97 | K | N | 44.6 | 27.7 | −5.6 | 28 | A | 105 | L | CB | 51.1 | 6.2 | 4.2 | 29 | A |
| 97 | K | CA | 43.5 | 27.9 | −4.6 | 31 | A | 105 | L | CG | 49.9 | 5.5 | 4.7 | 29 | A |
| 97 | K | CB | 42.2 | 27.7 | −5.3 | 33 | A | 105 | L | CD1 | 48.7 | 6.5 | 4.9 | 29 | A |
| 97 | K | CG | 41.9 | 28.7 | −6.4 | 35 | A | 105 | L | CD2 | 49.4 | 4.5 | 3.6 | 30 | A |
| 97 | K | CD | 42.2 | 30.1 | −5.9 | 39 | A | 105 | L | C | 52.1 | 6.2 | 6.5 | 29 | A |
| 97 | K | CE | 42.2 | 31.2 | −7.0 | 43 | A | 105 | L | O | 52.9 | 5.3 | 6.5 | 29 | A |
| 97 | K | NZ | 42.8 | 32.5 | −6.6 | 41 | A | 106 | M | N | 51.4 | 6.5 | 7.6 | 29 | A |
| 97 | K | C | 43.7 | 26.8 | −3.5 | 30 | A | 106 | M | CA | 51.5 | 5.8 | 8.8 | 30 | A |
| 97 | K | O | 43.0 | 27.0 | −2.4 | 30 | A | 106 | M | CB | 51.8 | 6.7 | 10.0 | 29 | A |
| 98 | D | N | 44.5 | 25.8 | −3.7 | 30 | A | 106 | M | CG | 53.1 | 7.5 | 9.9 | 29 | A |
| 98 | D | CA | 44.7 | 24.8 | −2.7 | 32 | A | 106 | M | SD | 54.6 | 6.4 | 9.8 | 31 | A |
| 98 | D | CB | 43.8 | 23.5 | −3.0 | 32 | A | 106 | M | CE | 54.9 | 6.1 | 11.6 | 28 | A |
| 98 | D | CG | 42.4 | 23.9 | −3.4 | 36 | A | 106 | M | C | 50.2 | 5.0 | 9.0 | 29 | A |
| 98 | D | OD1 | 42.2 | 24.3 | −4.6 | 37 | A | 106 | M | O | 49.1 | 5.4 | 8.5 | 30 | A |
| 98 | D | OD2 | 41.5 | 23.7 | −2.6 | 37 | A | 107 | E | N | 50.2 | 4.0 | 9.8 | 30 | A |
| 98 | D | C | 46.2 | 24.4 | −2.8 | 31 | A | 107 | E | CA | 49.0 | 3.1 | 10.0 | 30 | A |
| 98 | D | O | 46.9 | 24.7 | −3.7 | 30 | A | 107 | E | CB | 49.4 | 1.7 | 10.4 | 34 | A |
| 99 | V | N | 46.6 | 23.6 | −1.8 | 31 | A | 107 | E | CG | 50.2 | 1.0 | 9.3 | 38 | A |
| 99 | V | CA | 47.9 | 23.1 | −1.7 | 31 | A | 107 | E | CD | 50.9 | −0.2 | 9.9 | 41 | A |
| 99 | V | CB | 48.9 | 23.9 | −0.9 | 33 | A | 107 | E | OE1 | 50.3 | −1.1 | 10.5 | 44 | A |
| 99 | V | CG1 | 50.2 | 23.3 | −0.7 | 35 | A | 107 | E | OE2 | 52.2 | −0.3 | 9.7 | 43 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 107 | E | C   | 48.0 | 3.6  | 11.0 | 30 | A |
|-----|---|-----|------|------|------|----|---|
| 107 | E | O   | 46.8 | 3.4  | 10.8 | 30 | A |
| 108 | T | N   | 48.4 | 4.3  | 12.0 | 26 | A |
| 108 | T | CA  | 47.5 | 4.9  | 13.0 | 25 | A |
| 108 | T | CB  | 46.9 | 3.7  | 13.9 | 24 | A |
| 108 | T | OG1 | 45.9 | 4.2  | 14.8 | 27 | A |
| 108 | T | CG2 | 48.1 | 3.1  | 14.8 | 26 | A |
| 108 | T | C   | 48.2 | 5.9  | 13.8 | 23 | A |
| 108 | T | O   | 49.3 | 6.4  | 13.5 | 20 | A |
| 109 | D | N   | 47.5 | 6.4  | 14.9 | 24 | A |
| 109 | D | CA  | 48.1 | 7.4  | 15.8 | 23 | A |
| 109 | D | CB  | 47.5 | 8.8  | 15.5 | 25 | A |
| 109 | D | CG  | 46.0 | 8.9  | 15.8 | 26 | A |
| 109 | D | OD1 | 45.5 | 8.4  | 16.8 | 29 | A |
| 109 | D | OD2 | 45.3 | 9.4  | 14.9 | 29 | A |
| 109 | D | C   | 47.8 | 6.9  | 17.2 | 22 | A |
| 109 | D | O   | 47.0 | 6.0  | 17.4 | 20 | A |
| 110 | L | N   | 48.5 | 7.5  | 18.2 | 22 | A |
| 110 | L | CA  | 48.4 | 7.1  | 19.6 | 21 | A |
| 110 | L | CB  | 49.4 | 7.9  | 20.5 | 21 | A |
| 110 | L | CG  | 49.4 | 7.4  | 21.9 | 21 | A |
| 110 | L | CD1 | 49.9 | 6.0  | 22.0 | 19 | A |
| 110 | L | CD2 | 50.3 | 8.3  | 22.7 | 18 | A |
| 110 | L | C   | 47.0 | 7.2  | 20.1 | 22 | A |
| 110 | L | O   | 46.5 | 6.4  | 20.9 | 21 | A |
| 111 | Y | N   | 46.3 | 8.2  | 19.6 | 23 | A |
| 111 | Y | CA  | 44.9 | 8.5  | 20.0 | 27 | A |
| 111 | Y | CB  | 44.3 | 9.7  | 19.3 | 28 | A |
| 111 | Y | CG  | 42.9 | 10.0 | 19.7 | 34 | A |
| 111 | Y | CD1 | 42.5 | 10.5 | 20.9 | 36 | A |
| 111 | Y | CE1 | 41.2 | 10.7 | 21.2 | 40 | A |
| 111 | Y | CD2 | 41.9 | 9.7  | 18.7 | 36 | A |
| 111 | Y | CE2 | 40.5 | 9.8  | 19.0 | 40 | A |
| 111 | Y | CZ  | 40.2 | 10.4 | 20.3 | 41 | A |
| 111 | Y | OH  | 38.8 | 10.5 | 20.6 | 44 | A |
| 111 | Y | C   | 44.0 | 7.3  | 19.7 | 27 | A |
| 111 | Y | O   | 43.3 | 6.7  | 20.6 | 26 | A |
| 112 | K | N   | 44.0 | 6.9  | 18.4 | 27 | A |
| 112 | K | CA  | 43.2 | 5.8  | 18.0 | 29 | A |
| 112 | K | CB  | 43.3 | 5.6  | 16.5 | 30 | A |
| 112 | K | CG  | 42.6 | 4.3  | 16.0 | 36 | A |
| 112 | K | CD  | 42.6 | 4.2  | 14.5 | 41 | A |
| 112 | K | CE  | 41.6 | 5.1  | 13.8 | 46 | A |
| 112 | K | NZ  | 41.8 | 6.6  | 14.1 | 50 | A |
| 112 | K | C   | 43.6 | 4.5  | 18.7 | 28 | A |
| 112 | K | O   | 42.8 | 3.7  | 19.1 | 29 | A |
| 113 | L | N   | 44.9 | 4.3  | 18.8 | 27 | A |
| 113 | L | CA  | 45.5 | 3.1  | 19.5 | 28 | A |
| 113 | L | CB  | 47.0 | 3.1  | 19.4 | 28 | A |
| 113 | L | CG  | 47.7 | 1.9  | 20.0 | 28 | A |
| 113 | L | CD1 | 47.4 | 0.7  | 19.2 | 29 | A |
| 113 | L | CD2 | 49.2 | 2.1  | 20.1 | 28 | A |
| 113 | L | C   | 45.1 | 3.0  | 20.9 | 28 | A |
| 113 | L | O   | 44.8 | 1.9  | 21.4 | 27 | A |
| 114 | L | N   | 45.0 | 4.1  | 21.7 | 28 | A |
| 114 | L | CA  | 44.6 | 4.0  | 23.1 | 30 | A |
| 114 | L | CB  | 45.0 | 5.3  | 23.8 | 29 | A |
| 114 | L | CG  | 46.5 | 5.6  | 24.0 | 29 | A |
| 114 | L | CD1 | 46.7 | 7.0  | 24.7 | 24 | A |
| 114 | L | CD2 | 47.1 | 4.5  | 24.9 | 26 | A |
| 114 | L | C   | 43.1 | 3.8  | 23.3 | 31 | A |
| 114 | L | O   | 42.7 | 3.5  | 24.4 | 32 | A |
| 115 | K | N   | 42.4 | 3.8  | 22.2 | 34 | A |
| 115 | K | CA  | 40.9 | 3.5  | 22.3 | 38 | A |
| 115 | K | CB  | 40.2 | 4.1  | 21.1 | 39 | A |
| 115 | K | CG  | 39.9 | 5.6  | 21.2 | 44 | A |
| 115 | K | CD  | 39.0 | 6.1  | 20.1 | 48 | A |
| 115 | K | CE  | 38.4 | 7.5  | 20.4 | 51 | A |
| 115 | K | NZ  | 37.5 | 7.9  | 19.3 | 54 | A |
| 115 | K | C   | 40.7 | 2.0  | 22.3 | 39 | A |
| 115 | K | O   | 39.8 | 1.5  | 22.9 | 39 | A |
| 116 | T | N   | 41.7 | 1.3  | 21.7 | 40 | A |
| 116 | T | CA  | 41.6 | -0.1 | 21.5 | 42 | A |
| 116 | T | CB  | 41.8 | -0.5 | 20.0 | 43 | A |
| 116 | T | OG1 | 40.8 | -0.0 | 19.2 | 47 | A |
| 116 | T | CG2 | 41.9 | -2.0 | 19.9 | 46 | A |
| 116 | T | C   | 42.6 | -0.9 | 22.4 | 41 | A |
| 116 | T | O   | 42.2 | -2.1 | 22.8 | 40 | A |
| 117 | Q | N   | 43.7 | -0.4 | 22.6 | 39 | A |
| 117 | Q | CA  | 44.8 | -1.1 | 23.4 | 39 | A |
| 117 | Q | CB  | 46.0 | -1.4 | 22.5 | 41 | A |
| 117 | Q | CG  | 45.7 | -2.1 | 21.2 | 44 | A |
| 117 | Q | CD  | 45.2 | -3.6 | 21.4 | 47 | A |
| 117 | Q | OE1 | 46.0 | -4.4 | 22.0 | 48 | A |
| 117 | Q | NE2 | 44.1 | -3.9 | 21.0 | 49 | A |
| 117 | Q | C   | 45.3 | -0.5 | 24.7 | 38 | A |
| 117 | Q | O   | 45.4 | 0.7  | 24.8 | 36 | A |
| 118 | H | N   | 45.5 | -1.4 | 25.7 | 37 | A |
| 118 | H | CA  | 46.1 | -0.9 | 26.9 | 38 | A |
| 118 | H | CB  | 45.6 | -1.8 | 28.1 | 42 | A |
| 118 | H | CG  | 46.2 | -1.4 | 29.4 | 48 | A |
| 118 | H | CD2 | 45.6 | -1.0 | 30.6 | 50 | A |
| 118 | H | ND1 | 47.6 | -1.4 | 29.6 | 51 | A |
| 118 | H | CE1 | 47.8 | -1.1 | 30.8 | 51 | A |
| 118 | H | NE2 | 46.7 | -0.8 | 31.4 | 51 | A |
| 118 | H | C   | 47.5 | -1.3 | 26.6 | 36 | A |
| 118 | H | O   | 47.9 | -2.5 | 26.4 | 36 | A |
| 119 | L | N   | 48.4 | -0.3 | 26.7 | 32 | A |
| 119 | L | CA  | 49.8 | -0.5 | 26.4 | 28 | A |
| 119 | L | CB  | 50.5 | 0.8  | 25.9 | 27 | A |
| 119 | L | CG  | 49.9 | 1.4  | 24.6 | 27 | A |
| 119 | L | CD1 | 50.6 | 2.8  | 24.4 | 25 | A |
| 119 | L | CD2 | 50.0 | 0.5  | 23.4 | 29 | A |
| 119 | L | C   | 50.6 | -1.1 | 27.5 | 26 | A |
| 119 | L | O   | 50.5 | -0.6 | 28.7 | 24 | A |
| 120 | S | N   | 51.5 | -2.0 | 27.2 | 24 | A |
| 120 | S | CA  | 52.4 | -2.6 | 28.2 | 23 | A |
| 120 | S | CB  | 53.1 | -3.8 | 27.7 | 22 | A |
| 120 | S | OG  | 53.9 | -3.5 | 26.6 | 20 | A |
| 120 | S | C   | 53.4 | -1.5 | 28.5 | 22 | A |
| 120 | S | O   | 53.6 | -0.6 | 27.8 | 22 | A |
| 121 | N | N   | 54.1 | -1.7 | 29.7 | 21 | A |
| 121 | N | CA  | 55.2 | -0.7 | 30.1 | 23 | A |
| 121 | N | CB  | 55.8 | -1.1 | 31.4 | 22 | A |
| 121 | N | CG  | 56.9 | -0.2 | 31.8 | 24 | A |
| 121 | N | OD1 | 56.7 | 1.0  | 32.1 | 23 | A |
| 121 | N | ND2 | 58.2 | -0.7 | 31.7 | 22 | A |
| 121 | N | C   | 56.3 | -0.6 | 29.0 | 23 | A |
| 121 | N | O   | 56.7 | 0.5  | 28.8 | 22 | A |
| 122 | D | N   | 56.7 | -1.7 | 28.4 | 22 | A |
| 122 | D | CA  | 57.8 | -1.5 | 27.4 | 21 | A |
| 122 | D | CB  | 58.6 | -2.9 | 27.2 | 22 | A |
| 122 | D | CG  | 57.7 | -4.0 | 26.6 | 22 | A |
| 122 | D | OD1 | 56.5 | -3.8 | 26.3 | 19 | A |
| 122 | D | OD2 | 58.3 | -5.0 | 26.4 | 22 | A |
| 122 | D | C   | 57.4 | -0.8 | 26.1 | 20 | A |
| 122 | D | O   | 58.2 | -0.3 | 25.4 | 16 | A |
| 123 | H | N   | 56.1 | -0.9 | 25.8 | 20 | A |
| 123 | H | CA  | 55.6 | -0.1 | 24.6 | 21 | A |
| 123 | H | CB  | 54.2 | -0.6 | 24.2 | 21 | A |
| 123 | H | CG  | 54.1 | -1.7 | 23.3 | 22 | A |
| 123 | H | CD2 | 54.2 | -1.8 | 21.9 | 24 | A |
| 123 | H | ND1 | 54.0 | -3.0 | 23.7 | 22 | A |
| 123 | H | CE1 | 53.9 | -3.8 | 22.7 | 23 | A |
| 123 | H | NE2 | 54.1 | -3.1 | 21.6 | 24 | A |
| 123 | H | C   | 55.6 | 1.4  | 25.0 | 21 | A |
| 123 | H | O   | 56.0 | 2.2  | 24.2 | 21 | A |
| 124 | I | N   | 55.1 | 1.7  | 26.2 | 19 | A |
| 124 | I | CA  | 55.0 | 3.0  | 26.7 | 20 | A |
| 124 | I | CB  | 54.4 | 3.1  | 28.1 | 18 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 124 | I | CG2 | 54.5 | 4.5 | 28.7 | 17 | A |
|---|---|---|---|---|---|---|---|
| 124 | I | CG1 | 53.0 | 2.6 | 28.0 | 19 | A |
| 124 | I | CD1 | 52.2 | 2.7 | 29.4 | 19 | A |
| 124 | I | C | 56.4 | 3.7 | 26.8 | 21 | A |
| 124 | I | O | 56.6 | 4.8 | 26.3 | 21 | A |
| 125 | C | N | 57.4 | 2.9 | 27.3 | 19 | A |
| 125 | C | CA | 58.8 | 3.4 | 27.4 | 20 | A |
| 125 | C | CB | 59.6 | 2.3 | 28.1 | 20 | A |
| 125 | C | SG | 61.3 | 2.8 | 28.5 | 23 | A |
| 125 | C | C | 59.4 | 3.7 | 26.0 | 20 | A |
| 125 | C | O | 60.0 | 4.7 | 25.8 | 20 | A |
| 126 | Y | N | 59.2 | 2.8 | 25.1 | 20 | A |
| 126 | Y | CA | 59.7 | 3.0 | 23.7 | 20 | A |
| 126 | Y | CB | 59.5 | 1.7 | 22.9 | 20 | A |
| 126 | Y | CG | 60.2 | 1.8 | 21.5 | 24 | A |
| 126 | Y | CD1 | 61.5 | 2.1 | 21.4 | 24 | A |
| 126 | Y | CE1 | 62.1 | 2.1 | 20.1 | 23 | A |
| 126 | Y | CD2 | 59.5 | 1.5 | 20.4 | 22 | A |
| 126 | Y | CE2 | 60.0 | 1.5 | 19.1 | 24 | A |
| 126 | Y | CZ | 61.4 | 1.8 | 19.0 | 24 | A |
| 126 | Y | OH | 62.0 | 1.9 | 17.8 | 24 | A |
| 126 | Y | C | 59.0 | 4.2 | 23.0 | 20 | A |
| 126 | Y | O | 59.7 | 5.0 | 22.3 | 19 | A |
| 127 | F | N | 57.7 | 4.3 | 23.1 | 20 | A |
| 127 | F | CA | 57.0 | 5.4 | 22.5 | 19 | A |
| 127 | F | CB | 55.5 | 5.3 | 22.7 | 19 | A |
| 127 | F | CG | 54.9 | 4.2 | 21.8 | 22 | A |
| 127 | F | CD1 | 55.4 | 3.9 | 20.5 | 22 | A |
| 127 | F | CD2 | 53.7 | 3.5 | 22.2 | 23 | A |
| 127 | F | CE1 | 54.8 | 2.9 | 19.7 | 24 | A |
| 127 | F | CE2 | 53.1 | 2.5 | 21.4 | 23 | A |
| 127 | F | CZ | 53.7 | 2.2 | 20.2 | 23 | A |
| 127 | F | C | 57.5 | 6.8 | 23.1 | 19 | A |
| 127 | F | O | 57.7 | 7.7 | 22.4 | 17 | A |
| 128 | L | N | 57.5 | 6.8 | 24.5 | 18 | A |
| 128 | L | CA | 58.0 | 8.0 | 25.1 | 19 | A |
| 128 | L | CB | 58.0 | 7.8 | 26.7 | 19 | A |
| 128 | L | CG | 58.4 | 9.0 | 27.5 | 21 | A |
| 128 | L | CD1 | 57.5 | 10.2 | 27.2 | 21 | A |
| 128 | L | CD2 | 58.4 | 8.7 | 29.0 | 22 | A |
| 128 | L | C | 59.4 | 8.4 | 24.7 | 17 | A |
| 128 | L | O | 59.7 | 9.6 | 24.5 | 17 | A |
| 129 | Y | N | 60.2 | 7.4 | 24.5 | 16 | A |
| 129 | Y | CA | 61.6 | 7.7 | 24.1 | 17 | A |
| 129 | Y | CB | 62.4 | 6.4 | 24.0 | 18 | A |
| 129 | Y | CG | 63.8 | 6.6 | 23.4 | 19 | A |
| 129 | Y | CD1 | 64.8 | 7.2 | 24.2 | 17 | A |
| 129 | Y | CE1 | 66.0 | 7.5 | 23.6 | 17 | A |
| 129 | Y | CD2 | 64.1 | 6.2 | 22.1 | 19 | A |
| 129 | Y | CE2 | 65.4 | 6.5 | 21.6 | 19 | A |
| 129 | Y | CZ | 66.3 | 7.1 | 22.3 | 18 | A |
| 129 | Y | OH | 67.5 | 7.4 | 21.7 | 19 | A |
| 129 | Y | C | 61.6 | 8.4 | 22.7 | 17 | A |
| 129 | Y | O | 62.3 | 9.3 | 22.5 | 17 | A |
| 130 | Q | N | 60.8 | 7.8 | 21.8 | 15 | A |
| 130 | Q | CA | 60.8 | 8.4 | 20.5 | 17 | A |
| 130 | Q | CB | 60.0 | 7.5 | 19.5 | 16 | A |
| 130 | Q | CG | 60.6 | 6.2 | 19.3 | 15 | A |
| 130 | Q | CD | 59.8 | 5.4 | 18.3 | 17 | A |
| 130 | Q | OE1 | 59.9 | 5.5 | 17.1 | 17 | A |
| 130 | Q | NE2 | 58.9 | 4.5 | 18.8 | 15 | A |
| 130 | Q | C | 60.2 | 9.8 | 20.5 | 17 | A |
| 130 | Q | O | 60.6 | 10.7 | 19.7 | 16 | A |
| 131 | I | N | 59.2 | 10.0 | 21.3 | 16 | A |
| 131 | I | CA | 58.6 | 11.4 | 21.4 | 15 | A |
| 131 | I | CB | 57.5 | 11.4 | 22.5 | 14 | A |
| 131 | I | CG2 | 57.0 | 12.8 | 22.7 | 14 | A |
| 131 | I | CG1 | 56.3 | 10.6 | 22.0 | 12 | A |
| 131 | I | CD1 | 55.2 | 10.4 | 23.1 | 15 | A |
| 131 | I | C | 59.7 | 12.4 | 21.9 | 16 | A |
| 131 | I | O | 59.8 | 13.5 | 21.3 | 16 | A |
| 132 | L | N | 60.4 | 12.0 | 22.9 | 16 | A |
| 132 | L | CA | 61.5 | 12.9 | 23.4 | 16 | A |
| 132 | L | CB | 61.9 | 12.4 | 24.8 | 16 | A |
| 132 | L | CG | 60.9 | 12.5 | 25.9 | 19 | A |
| 132 | L | CD1 | 61.2 | 11.8 | 27.1 | 20 | A |
| 132 | L | CD2 | 60.7 | 14.0 | 26.2 | 19 | A |
| 132 | L | C | 62.7 | 13.0 | 22.5 | 17 | A |
| 132 | L | O | 63.3 | 14.1 | 22.4 | 17 | A |
| 133 | R | N | 62.9 | 12.0 | 21.7 | 17 | A |
| 133 | R | CA | 64.0 | 12.0 | 20.8 | 17 | A |
| 133 | R | CB | 64.3 | 10.6 | 20.1 | 17 | A |
| 133 | R | CG | 65.5 | 10.5 | 19.2 | 17 | A |
| 133 | R | CD | 65.8 | 9.0 | 18.9 | 19 | A |
| 133 | R | NE | 66.9 | 8.8 | 18.0 | 19 | A |
| 133 | R | CZ | 66.7 | 8.5 | 16.7 | 22 | A |
| 133 | R | NH1 | 65.5 | 8.5 | 16.2 | 20 | A |
| 133 | R | NH2 | 67.8 | 8.3 | 15.9 | 18 | A |
| 133 | R | C | 63.7 | 13.0 | 19.7 | 16 | A |
| 133 | R | O | 64.5 | 13.8 | 19.2 | 18 | A |
| 134 | G | N | 62.4 | 13.0 | 19.2 | 15 | A |
| 134 | G | CA | 62.0 | 13.9 | 18.2 | 14 | A |
| 134 | G | C | 61.9 | 15.3 | 18.7 | 15 | A |
| 134 | G | O | 62.3 | 16.3 | 18.1 | 17 | A |
| 135 | L | N | 61.4 | 15.4 | 20.0 | 13 | A |
| 135 | L | CA | 61.3 | 16.7 | 20.6 | 16 | A |
| 135 | L | CB | 60.5 | 16.6 | 21.9 | 16 | A |
| 135 | L | CG | 60.1 | 17.9 | 22.6 | 18 | A |
| 135 | L | CD1 | 59.3 | 18.7 | 21.6 | 17 | A |
| 135 | L | CD2 | 59.4 | 17.7 | 23.9 | 19 | A |
| 135 | L | C | 62.7 | 17.4 | 20.8 | 16 | A |
| 135 | L | O | 62.8 | 18.6 | 20.8 | 17 | A |
| 136 | K | N | 63.7 | 16.6 | 21.1 | 16 | A |
| 136 | K | CA | 65.0 | 17.1 | 21.3 | 15 | A |
| 136 | K | CB | 66.0 | 16.0 | 21.7 | 14 | A |
| 136 | K | CG | 67.5 | 16.5 | 21.8 | 15 | A |
| 136 | K | CD | 68.5 | 15.3 | 22.0 | 17 | A |
| 136 | K | CE | 69.9 | 15.9 | 22.0 | 17 | A |
| 136 | K | NZ | 70.9 | 14.8 | 22.2 | 17 | A |
| 136 | K | C | 65.5 | 17.8 | 20.1 | 16 | A |
| 136 | K | O | 66.1 | 18.9 | 20.1 | 17 | A |
| 137 | Y | N | 65.2 | 17.2 | 18.9 | 16 | A |
| 137 | Y | CA | 65.6 | 17.8 | 17.6 | 16 | A |
| 137 | Y | CB | 65.3 | 16.7 | 16.5 | 14 | A |
| 137 | Y | CG | 65.7 | 17.2 | 15.1 | 18 | A |
| 137 | Y | CD1 | 64.8 | 17.9 | 14.3 | 19 | A |
| 137 | Y | CE1 | 65.1 | 18.4 | 13.1 | 21 | A |
| 137 | Y | CD2 | 67.0 | 17.0 | 14.6 | 17 | A |
| 137 | Y | CE2 | 67.3 | 17.4 | 13.3 | 18 | A |
| 137 | Y | CZ | 66.4 | 18.1 | 12.6 | 21 | A |
| 137 | Y | OH | 66.7 | 18.5 | 11.3 | 20 | A |
| 137 | Y | C | 64.8 | 19.1 | 17.4 | 18 | A |
| 137 | Y | O | 65.4 | 20.1 | 17.1 | 18 | A |
| 138 | I | N | 63.5 | 19.0 | 17.6 | 16 | A |
| 138 | I | CA | 62.7 | 20.2 | 17.4 | 17 | A |
| 138 | I | CB | 61.2 | 19.9 | 17.8 | 17 | A |
| 138 | I | CG2 | 60.4 | 21.2 | 17.7 | 18 | A |
| 138 | I | CG1 | 60.6 | 18.8 | 16.8 | 13 | A |
| 138 | I | CD1 | 59.2 | 18.3 | 17.2 | 13 | A |
| 138 | I | C | 63.2 | 21.3 | 18.3 | 17 | A |
| 138 | I | O | 63.4 | 22.5 | 17.8 | 15 | A |
| 139 | H | N | 63.4 | 21.1 | 19.6 | 17 | A |
| 139 | H | CA | 63.9 | 22.1 | 20.5 | 16 | A |
| 139 | H | CB | 63.8 | 21.6 | 21.9 | 16 | A |
| 139 | H | CG | 62.4 | 21.6 | 22.5 | 16 | A |
| 139 | H | CD2 | 61.2 | 22.0 | 21.9 | 16 | A |
| 139 | H | ND1 | 62.1 | 21.2 | 23.8 | 15 | A |
| 139 | H | CE1 | 60.8 | 21.3 | 24.0 | 18 | A |
| 139 | H | NE2 | 60.2 | 21.8 | 22.9 | 16 | A |
| 139 | H | C | 65.3 | 22.6 | 20.2 | 17 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 139 | H | O | 65.6 | 23.8 | 20.4 | 17 | A |
|---|---|---|---|---|---|---|---|
| 140 | S | N | 66.1 | 21.7 | 19.7 | 17 | A |
| 140 | S | CA | 67.5 | 22.1 | 19.3 | 19 | A |
| 140 | S | CB | 68.4 | 20.9 | 18.9 | 16 | A |
| 140 | S | OG | 68.0 | 20.4 | 17.7 | 18 | A |
| 140 | S | C | 67.5 | 23.1 | 18.1 | 19 | A |
| 140 | S | O | 68.4 | 23.9 | 17.9 | 20 | A |
| 141 | A | N | 66.4 | 23.1 | 17.4 | 18 | A |
| 141 | A | CA | 66.2 | 24.0 | 16.3 | 21 | A |
| 141 | A | CB | 65.3 | 23.4 | 15.2 | 20 | A |
| 141 | A | C | 65.6 | 25.3 | 16.7 | 22 | A |
| 141 | A | O | 65.2 | 26.2 | 15.9 | 22 | A |
| 142 | N | N | 65.4 | 25.4 | 18.1 | 22 | A |
| 142 | N | CA | 64.7 | 26.6 | 18.7 | 23 | A |
| 142 | N | CB | 65.5 | 27.9 | 18.3 | 25 | A |
| 142 | N | CG | 65.2 | 29.0 | 19.2 | 28 | A |
| 142 | N | OD1 | 65.2 | 28.9 | 20.5 | 31 | A |
| 142 | N | ND2 | 65.0 | 30.2 | 18.7 | 28 | A |
| 142 | N | C | 63.3 | 26.7 | 18.3 | 22 | A |
| 142 | N | O | 62.7 | 27.8 | 18.1 | 22 | A |
| 143 | V | N | 62.7 | 25.6 | 18.1 | 21 | A |
| 143 | V | CA | 61.2 | 25.5 | 17.7 | 19 | A |
| 143 | V | CB | 61.1 | 24.7 | 16.3 | 20 | A |
| 143 | V | CG1 | 59.6 | 24.5 | 16.0 | 18 | A |
| 143 | V | CG2 | 61.7 | 25.6 | 15.2 | 21 | A |
| 143 | V | C | 60.4 | 24.8 | 18.7 | 20 | A |
| 143 | V | O | 60.9 | 23.9 | 19.4 | 18 | A |
| 144 | L | N | 59.1 | 25.2 | 18.8 | 18 | A |
| 144 | L | CA | 58.2 | 24.7 | 19.8 | 18 | A |
| 144 | L | CB | 57.6 | 25.8 | 20.7 | 17 | A |
| 144 | L | CG | 58.6 | 26.8 | 21.3 | 19 | A |
| 144 | L | CD1 | 57.9 | 27.9 | 22.0 | 18 | A |
| 144 | L | CD2 | 59.5 | 26.0 | 22.3 | 19 | A |
| 144 | L | C | 57.1 | 24.1 | 19.0 | 19 | A |
| 144 | L | O | 56.6 | 24.7 | 18.0 | 18 | A |
| 145 | H | N | 56.6 | 22.9 | 19.3 | 18 | A |
| 145 | H | CA | 55.5 | 22.2 | 18.6 | 18 | A |
| 145 | H | CB | 55.5 | 20.7 | 18.9 | 17 | A |
| 145 | H | CG | 54.5 | 20.0 | 18.1 | 18 | A |
| 145 | H | CD2 | 54.6 | 19.2 | 17.0 | 18 | A |
| 145 | H | ND1 | 53.1 | 20.1 | 18.4 | 15 | A |
| 145 | H | CE1 | 52.5 | 19.3 | 17.5 | 19 | A |
| 145 | H | NE2 | 53.3 | 18.8 | 16.7 | 18 | A |
| 145 | H | C | 54.2 | 22.9 | 19.0 | 17 | A |
| 145 | H | O | 53.4 | 23.3 | 18.1 | 19 | A |
| 146 | R | N | 54.0 | 23.0 | 20.3 | 16 | A |
| 146 | R | CA | 52.8 | 23.6 | 20.9 | 18 | A |
| 146 | R | CB | 52.7 | 25.0 | 20.4 | 19 | A |
| 146 | R | CG | 54.0 | 25.9 | 20.7 | 19 | A |
| 146 | R | CD | 53.9 | 27.3 | 20.0 | 22 | A |
| 146 | R | NE | 53.1 | 28.2 | 20.9 | 24 | A |
| 146 | R | CZ | 52.1 | 28.9 | 20.5 | 23 | A |
| 146 | R | NH1 | 51.5 | 28.7 | 19.3 | 24 | A |
| 146 | R | NH2 | 51.5 | 29.8 | 21.3 | 22 | A |
| 146 | R | C | 51.4 | 22.9 | 20.9 | 18 | A |
| 146 | R | O | 50.5 | 23.5 | 21.3 | 18 | A |
| 147 | D | N | 51.4 | 21.8 | 20.3 | 17 | A |
| 147 | D | CA | 50.1 | 21.0 | 20.2 | 17 | A |
| 147 | D | CB | 49.3 | 21.4 | 18.9 | 18 | A |
| 147 | D | CG | 47.9 | 21.1 | 19.0 | 22 | A |
| 147 | D | OD1 | 47.3 | 20.9 | 20.2 | 20 | A |
| 147 | D | OD2 | 47.2 | 21.0 | 18.0 | 23 | A |
| 147 | D | C | 50.3 | 19.5 | 20.3 | 16 | A |
| 147 | D | O | 49.7 | 18.7 | 19.6 | 15 | A |
| 148 | L | N | 51.3 | 19.1 | 21.1 | 15 | A |
| 148 | L | CA | 51.6 | 17.7 | 21.3 | 17 | A |
| 148 | L | CB | 52.9 | 17.5 | 22.0 | 15 | A |
| 148 | L | CG | 54.1 | 18.0 | 21.3 | 16 | A |
| 148 | L | CD1 | 55.3 | 18.1 | 22.3 | 16 | A |
| 148 | L | CD2 | 54.5 | 17.2 | 20.1 | 17 | A |
| 148 | L | C | 50.4 | 17.0 | 22.0 | 18 | A |
| 148 | L | O | 50.0 | 17.5 | 23.1 | 17 | A |
| 149 | K | N | 49.9 | 16.0 | 21.4 | 16 | A |
| 149 | K | CA | 48.8 | 15.2 | 22.0 | 18 | A |
| 149 | K | CB | 47.5 | 16.0 | 21.8 | 18 | A |
| 149 | K | CG | 47.2 | 16.3 | 20.3 | 19 | A |
| 149 | K | CD | 45.8 | 17.1 | 20.2 | 19 | A |
| 149 | K | CE | 45.6 | 17.6 | 18.8 | 19 | A |
| 149 | K | NZ | 44.3 | 18.3 | 18.7 | 23 | A |
| 149 | K | C | 48.8 | 13.9 | 21.3 | 18 | A |
| 149 | K | O | 49.4 | 13.8 | 20.2 | 20 | A |
| 150 | P | N | 48.1 | 12.9 | 21.8 | 20 | A |
| 150 | P | CD | 47.2 | 12.9 | 23.0 | 19 | A |
| 150 | P | CA | 48.0 | 11.5 | 21.1 | 19 | A |
| 150 | P | CB | 47.0 | 10.8 | 21.9 | 20 | A |
| 150 | P | CG | 47.1 | 11.4 | 23.3 | 21 | A |
| 150 | P | C | 47.8 | 11.5 | 19.6 | 21 | A |
| 150 | P | O | 48.4 | 10.8 | 18.9 | 20 | A |
| 151 | S | N | 46.8 | 12.3 | 19.2 | 21 | A |
| 151 | S | CA | 46.4 | 12.3 | 17.7 | 21 | A |
| 151 | S | CB | 45.1 | 13.1 | 17.5 | 22 | A |
| 151 | S | OG | 45.2 | 14.4 | 18.0 | 22 | A |
| 151 | S | C | 47.5 | 12.9 | 16.8 | 22 | A |
| 151 | S | O | 47.5 | 12.7 | 15.6 | 22 | A |
| 152 | N | N | 48.5 | 13.6 | 17.4 | 21 | A |
| 152 | N | CA | 49.6 | 14.2 | 16.6 | 20 | A |
| 152 | N | CB | 49.9 | 15.6 | 17.2 | 21 | A |
| 152 | N | CG | 49.0 | 16.6 | 16.6 | 24 | A |
| 152 | N | OD1 | 48.9 | 17.7 | 17.1 | 25 | A |
| 152 | N | ND2 | 48.2 | 16.3 | 15.6 | 20 | A |
| 152 | N | C | 50.8 | 13.3 | 16.7 | 18 | A |
| 152 | N | O | 51.9 | 13.7 | 16.3 | 19 | A |
| 153 | L | N | 50.7 | 12.0 | 17.1 | 18 | A |
| 153 | L | CA | 51.8 | 11.1 | 17.2 | 18 | A |
| 153 | L | CB | 52.0 | 10.6 | 18.6 | 17 | A |
| 153 | L | CG | 52.3 | 11.7 | 19.6 | 19 | A |
| 153 | L | CD1 | 52.5 | 11.1 | 21.0 | 16 | A |
| 153 | L | CD2 | 53.6 | 12.4 | 19.2 | 17 | A |
| 153 | L | C | 51.4 | 9.9 | 16.3 | 17 | A |
| 153 | L | O | 50.5 | 9.1 | 16.7 | 17 | A |
| 154 | L | N | 51.9 | 9.8 | 15.1 | 18 | A |
| 154 | L | CA | 51.6 | 8.7 | 14.1 | 19 | A |
| 154 | L | CB | 51.8 | 9.2 | 12.7 | 20 | A |
| 154 | L | CG | 51.0 | 10.5 | 12.3 | 25 | A |
| 154 | L | CD1 | 51.5 | 11.0 | 11.0 | 25 | A |
| 154 | L | CD2 | 49.5 | 10.1 | 12.2 | 27 | A |
| 154 | L | C | 52.5 | 7.5 | 14.4 | 20 | A |
| 154 | L | O | 53.6 | 7.6 | 14.7 | 20 | A |
| 155 | L | N | 51.9 | 6.3 | 14.2 | 21 | A |
| 155 | L | CA | 52.5 | 5.1 | 14.5 | 24 | A |
| 155 | L | CB | 52.0 | 4.5 | 15.8 | 24 | A |
| 155 | L | CG | 52.0 | 5.4 | 17.0 | 25 | A |
| 155 | L | CD1 | 51.1 | 4.8 | 18.1 | 24 | A |
| 155 | L | CD2 | 53.4 | 5.7 | 17.5 | 24 | A |
| 155 | L | C | 52.3 | 4.0 | 13.4 | 25 | A |
| 155 | L | O | 51.3 | 4.1 | 12.6 | 24 | A |
| 156 | N | N | 53.1 | 3.0 | 13.3 | 27 | A |
| 156 | N | CA | 53.0 | 1.9 | 12.4 | 29 | A |
| 156 | N | CB | 54.0 | 2.0 | 11.2 | 31 | A |
| 156 | N | CG | 55.4 | 2.0 | 11.7 | 35 | A |
| 156 | N | OD1 | 55.8 | 1.5 | 12.7 | 34 | A |
| 156 | N | ND2 | 56.3 | 2.7 | 10.8 | 36 | A |
| 156 | N | C | 53.2 | 0.6 | 13.2 | 30 | A |
| 156 | N | O | 53.5 | 0.7 | 14.4 | 28 | A |
| 157 | T | N | 53.0 | −0.5 | 12.6 | 33 | A |
| 157 | T | CA | 53.1 | −1.8 | 13.3 | 34 | A |
| 157 | T | CB | 52.6 | −3.0 | 12.5 | 36 | A |
| 157 | T | OG1 | 53.2 | −2.9 | 11.2 | 40 | A |
| 157 | T | CG2 | 51.1 | −3.0 | 12.4 | 37 | A |
| 157 | T | C | 54.5 | −2.1 | 13.9 | 33 | A |

TABLE 4-continued

Structural Coordinates of Ah₆-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| | | | | | | | |
|---|---|---|---|---|---|---|---|
| 157 | T | O | 54.7 | −2.8 | 14.8 | 34 | A |
| 158 | T | N | 55.5 | −1.5 | 13.2 | 31 | A |
| 158 | T | CA | 56.9 | −1.7 | 13.7 | 29 | A |
| 158 | T | CB | 57.9 | −1.5 | 12.6 | 31 | A |
| 158 | T | OG1 | 57.7 | −0.2 | 12.0 | 36 | A |
| 158 | T | CG2 | 57.8 | −2.6 | 11.5 | 33 | A |
| 158 | T | C | 57.2 | −0.8 | 14.9 | 26 | A |
| 158 | T | O | 58.3 | −0.7 | 15.4 | 24 | A |
| 159 | C | N | 56.1 | −0.1 | 15.3 | 24 | A |
| 159 | C | CA | 56.2 | 0.8 | 16.5 | 22 | A |
| 159 | C | CB | 56.7 | 0.1 | 17.7 | 25 | A |
| 159 | C | SG | 55.5 | −1.1 | 18.4 | 26 | A |
| 159 | C | C | 57.0 | 2.1 | 16.3 | 22 | A |
| 159 | C | O | 57.4 | 2.7 | 17.2 | 21 | A |
| 160 | D | N | 57.2 | 2.4 | 15.0 | 21 | A |
| 160 | D | CA | 57.9 | 3.6 | 14.7 | 21 | A |
| 160 | D | CB | 58.3 | 3.8 | 13.3 | 22 | A |
| 160 | D | CG | 59.4 | 2.8 | 12.9 | 23 | A |
| 160 | D | OD1 | 60.4 | 2.6 | 13.6 | 24 | A |
| 160 | D | OD2 | 59.3 | 2.2 | 11.8 | 27 | A |
| 160 | D | C | 56.9 | 4.7 | 15.1 | 20 | A |
| 160 | D | O | 55.7 | 4.6 | 14.8 | 18 | A |
| 161 | L | N | 57.4 | 5.8 | 15.6 | 18 | A |
| 161 | L | CA | 56.6 | 7.0 | 16.0 | 18 | A |
| 161 | L | CB | 56.5 | 7.1 | 17.5 | 20 | A |
| 161 | L | CG | 55.8 | 8.3 | 18.2 | 20 | A |
| 161 | L | CD1 | 55.4 | 7.9 | 19.6 | 21 | A |
| 161 | L | CD2 | 56.6 | 9.6 | 18.1 | 17 | A |
| 161 | L | C | 57.1 | 8.2 | 15.3 | 20 | A |
| 161 | L | O | 58.3 | 8.5 | 15.3 | 19 | A |
| 162 | K | N | 56.1 | 9.0 | 14.8 | 19 | A |
| 162 | K | CA | 56.5 | 10.3 | 14.1 | 20 | A |
| 162 | K | CB | 56.4 | 10.1 | 12.6 | 20 | A |
| 162 | K | CG | 57.5 | 9.2 | 12.0 | 23 | A |
| 162 | K | CD | 57.4 | 9.2 | 10.4 | 22 | A |
| 162 | K | CE | 58.3 | 8.1 | 9.8 | 25 | A |
| 162 | K | NZ | 59.7 | 8.4 | 10.1 | 25 | A |
| 162 | K | C | 55.5 | 11.4 | 14.6 | 19 | A |
| 162 | K | O | 54.3 | 11.2 | 14.6 | 17 | A |
| 163 | I | N | 56.1 | 12.5 | 15.0 | 18 | A |
| 163 | I | CA | 55.4 | 13.7 | 15.4 | 19 | A |
| 163 | I | CB | 56.3 | 14.6 | 16.2 | 19 | A |
| 163 | I | CG2 | 55.5 | 15.8 | 16.7 | 18 | A |
| 163 | I | CG1 | 56.9 | 13.8 | 17.4 | 18 | A |
| 163 | I | CD1 | 58.0 | 14.6 | 18.2 | 16 | A |
| 163 | I | C | 54.9 | 14.4 | 14.2 | 20 | A |
| 163 | I | O | 55.7 | 14.6 | 13.2 | 17 | A |
| 164 | C | N | 53.6 | 14.8 | 14.2 | 20 | A |
| 164 | C | CA | 53.1 | 15.6 | 13.0 | 21 | A |
| 164 | C | CB | 52.2 | 14.6 | 12.2 | 20 | A |
| 164 | C | SG | 50.7 | 14.1 | 13.0 | 28 | A |
| 164 | C | C | 52.3 | 16.8 | 13.5 | 20 | A |
| 164 | C | O | 52.2 | 17.1 | 14.7 | 18 | A |
| 165 | D | N | 51.8 | 17.5 | 12.5 | 21 | A |
| 165 | D | CA | 51.0 | 18.7 | 12.7 | 22 | A |
| 165 | D | CB | 49.8 | 18.4 | 13.5 | 27 | A |
| 165 | D | CG | 48.7 | 17.8 | 12.6 | 37 | A |
| 165 | D | OD1 | 49.0 | 16.8 | 11.9 | 40 | A |
| 165 | D | OD2 | 47.5 | 18.3 | 12.6 | 43 | A |
| 165 | D | C | 51.7 | 19.9 | 13.4 | 20 | A |
| 165 | D | O | 51.6 | 20.1 | 14.6 | 19 | A |
| 166 | F | N | 52.6 | 20.6 | 12.6 | 17 | A |
| 166 | F | CA | 53.3 | 21.7 | 13.2 | 19 | A |
| 166 | F | CB | 54.7 | 21.7 | 12.6 | 18 | A |
| 166 | F | CG | 55.6 | 20.7 | 13.2 | 22 | A |
| 166 | F | CD1 | 55.4 | 19.3 | 12.9 | 19 | A |
| 166 | F | CD2 | 56.6 | 21.0 | 14.0 | 20 | A |
| 166 | F | CE1 | 56.2 | 18.3 | 13.4 | 21 | A |
| 166 | F | CE2 | 57.4 | 20.0 | 14.6 | 19 | A |
| 166 | F | CZ | 57.2 | 18.7 | 14.3 | 19 | A |
| 166 | F | C | 52.6 | 23.0 | 12.8 | 19 | A |
| 166 | F | O | 53.3 | 24.1 | 12.7 | 20 | A |
| 167 | G | N | 51.3 | 23.0 | 12.7 | 20 | A |
| 167 | G | CA | 50.5 | 24.2 | 12.3 | 22 | A |
| 167 | G | C | 50.5 | 25.2 | 13.4 | 22 | A |
| 167 | G | O | 50.3 | 26.4 | 13.1 | 23 | A |
| 168 | L | N | 50.7 | 24.8 | 14.7 | 20 | A |
| 168 | L | CA | 50.7 | 25.8 | 15.7 | 22 | A |
| 168 | L | CB | 49.8 | 25.3 | 16.9 | 22 | A |
| 168 | L | CG | 48.3 | 25.2 | 16.6 | 24 | A |
| 168 | L | CD1 | 47.6 | 24.7 | 17.9 | 25 | A |
| 168 | L | CD2 | 47.8 | 26.5 | 16.1 | 24 | A |
| 168 | L | C | 52.1 | 26.0 | 16.3 | 20 | A |
| 168 | L | O | 52.3 | 26.7 | 17.3 | 22 | A |
| 169 | A | N | 53.1 | 25.5 | 15.6 | 19 | A |
| 169 | A | CA | 54.5 | 25.7 | 16.0 | 21 | A |
| 169 | A | CB | 55.4 | 24.8 | 15.1 | 21 | A |
| 169 | A | C | 55.0 | 27.1 | 15.9 | 23 | A |
| 169 | A | O | 54.5 | 27.9 | 15.1 | 25 | A |
| 170 | R | N | 55.9 | 27.5 | 16.7 | 23 | A |
| 170 | R | CA | 56.5 | 28.8 | 16.8 | 25 | A |
| 170 | R | CB | 55.8 | 29.7 | 17.8 | 27 | A |
| 170 | R | CG | 54.3 | 29.7 | 17.7 | 34 | A |
| 170 | R | CD | 53.8 | 30.4 | 16.4 | 39 | A |
| 170 | R | NE | 54.1 | 31.8 | 16.4 | 43 | A |
| 170 | R | CZ | 53.3 | 32.7 | 16.9 | 44 | A |
| 170 | R | NH1 | 52.1 | 32.3 | 17.4 | 44 | A |
| 170 | R | NH2 | 53.6 | 34.0 | 16.8 | 45 | A |
| 170 | R | C | 58.0 | 28.7 | 17.1 | 24 | A |
| 170 | R | O | 58.5 | 27.7 | 17.6 | 20 | A |
| 171 | V | N | 58.7 | 29.8 | 16.8 | 24 | A |
| 171 | V | CA | 60.1 | 29.9 | 17.2 | 22 | A |
| 171 | V | CB | 60.9 | 30.9 | 16.4 | 22 | A |
| 171 | V | CG1 | 62.3 | 31.1 | 16.9 | 20 | A |
| 171 | V | CG2 | 60.9 | 30.5 | 14.9 | 21 | A |
| 171 | V | C | 60.1 | 30.3 | 18.7 | 23 | A |
| 171 | V | O | 59.3 | 31.2 | 19.0 | 23 | A |
| 172 | A | N | 60.8 | 29.6 | 19.5 | 22 | A |
| 172 | A | CA | 60.8 | 29.9 | 20.9 | 22 | A |
| 172 | A | CB | 61.8 | 29.0 | 21.7 | 20 | A |
| 172 | A | C | 61.2 | 31.4 | 21.2 | 25 | A |
| 172 | A | O | 62.0 | 31.9 | 20.4 | 23 | A |
| 173 | D | N | 60.6 | 32.0 | 22.2 | 25 | A |
| 173 | D | CA | 60.8 | 33.4 | 22.5 | 27 | A |
| 173 | D | CB | 59.9 | 34.3 | 21.7 | 27 | A |
| 173 | D | CG | 60.2 | 35.7 | 21.8 | 27 | A |
| 173 | D | OD1 | 61.1 | 36.1 | 22.5 | 26 | A |
| 173 | D | OD2 | 59.6 | 36.5 | 21.1 | 27 | A |
| 173 | D | C | 60.6 | 33.6 | 24.0 | 27 | A |
| 173 | D | O | 59.7 | 34.3 | 24.4 | 25 | A |
| 174 | P | N | 61.4 | 33.0 | 24.8 | 29 | A |
| 174 | P | CD | 62.5 | 32.1 | 24.5 | 30 | A |
| 174 | P | CA | 61.3 | 33.1 | 26.3 | 32 | A |
| 174 | P | CB | 62.4 | 32.2 | 26.8 | 32 | A |
| 174 | P | CG | 63.4 | 32.2 | 25.7 | 32 | A |
| 174 | P | C | 61.3 | 34.5 | 26.8 | 34 | A |
| 174 | P | O | 60.8 | 34.7 | 28.0 | 34 | A |
| 175 | D | N | 61.8 | 35.5 | 26.1 | 36 | A |
| 175 | D | CA | 61.8 | 36.8 | 26.6 | 37 | A |
| 175 | D | CB | 62.9 | 37.7 | 25.8 | 40 | A |
| 175 | D | CG | 64.3 | 37.2 | 26.1 | 44 | A |
| 175 | D | OD1 | 64.6 | 37.0 | 27.3 | 46 | A |
| 175 | D | OD2 | 65.1 | 37.1 | 25.1 | 49 | A |
| 175 | D | C | 60.5 | 37.5 | 26.4 | 35 | A |
| 175 | D | O | 60.2 | 38.5 | 27.1 | 36 | A |
| 176 | H | N | 59.6 | 37.0 | 25.5 | 33 | A |
| 176 | H | CA | 58.3 | 37.6 | 25.3 | 31 | A |
| 176 | H | CB | 58.2 | 38.2 | 23.9 | 36 | A |
| 176 | H | CG | 59.3 | 39.1 | 23.5 | 40 | A |
| 176 | H | CD2 | 59.3 | 40.5 | 23.5 | 41 | A |

TABLE 4-continued

Structural Coordinates of Ah₆-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 176 | H | ND1 | 60.6 | 38.7 | 23.2 | 40 | A |
|---|---|---|---|---|---|---|---|
| 176 | H | CE1 | 61.3 | 39.8 | 23.0 | 41 | A |
| 176 | H | NE2 | 60.6 | 40.9 | 23.1 | 42 | A |
| 176 | H | C | 57.2 | 36.6 | 25.6 | 29 | A |
| 176 | H | O | 56.2 | 36.6 | 25.0 | 25 | A |
| 177 | D | N | 57.4 | 35.8 | 26.6 | 27 | A |
| 177 | D | CA | 56.5 | 34.7 | 27.0 | 28 | A |
| 177 | D | CB | 57.2 | 33.6 | 27.7 | 25 | A |
| 177 | D | CG | 56.3 | 32.4 | 28.0 | 25 | A |
| 177 | D | OD1 | 56.0 | 32.1 | 29.1 | 27 | A |
| 177 | D | OD2 | 55.9 | 31.7 | 27.0 | 28 | A |
| 177 | D | C | 55.4 | 35.2 | 27.9 | 28 | A |
| 177 | D | O | 54.3 | 34.6 | 28.0 | 26 | A |
| 178 | H | N | 55.6 | 36.4 | 28.6 | 30 | A |
| 178 | H | CA | 54.6 | 36.9 | 29.5 | 31 | A |
| 178 | H | CB | 55.2 | 37.9 | 30.4 | 36 | A |
| 178 | H | CG | 56.1 | 38.9 | 29.7 | 45 | A |
| 178 | H | CD2 | 56.0 | 40.3 | 29.6 | 48 | A |
| 178 | H | ND1 | 57.2 | 38.6 | 29.0 | 47 | A |
| 178 | H | CE1 | 57.8 | 39.7 | 28.5 | 49 | A |
| 178 | H | NE2 | 57.1 | 40.7 | 28.8 | 49 | A |
| 178 | H | C | 53.3 | 37.5 | 28.9 | 29 | A |
| 178 | H | O | 53.3 | 38.2 | 27.9 | 26 | A |
| 179 | T | N | 52.2 | 37.1 | 29.5 | 27 | A |
| 179 | T | CA | 50.9 | 37.6 | 29.2 | 25 | A |
| 179 | T | CB | 50.2 | 36.7 | 28.1 | 25 | A |
| 179 | T | OG1 | 49.0 | 37.3 | 27.6 | 25 | A |
| 179 | T | CG2 | 49.9 | 35.3 | 28.2 | 23 | A |
| 179 | T | C | 50.0 | 37.6 | 30.4 | 24 | A |
| 179 | T | O | 50.4 | 37.2 | 31.5 | 22 | A |
| 180 | G | N | 48.8 | 38.2 | 30.3 | 23 | A |
| 180 | G | CA | 48.0 | 38.3 | 31.5 | 24 | A |
| 180 | G | C | 47.2 | 37.0 | 31.9 | 23 | A |
| 180 | G | O | 47.3 | 36.0 | 31.2 | 24 | A |
| 181 | F | N | 46.6 | 37.1 | 33.1 | 22 | A |
| 181 | F | CA | 45.9 | 36.0 | 33.7 | 22 | A |
| 181 | F | CB | 45.4 | 36.5 | 35.1 | 21 | A |
| 181 | F | CG | 44.5 | 35.5 | 35.8 | 19 | A |
| 181 | F | CD1 | 44.9 | 34.2 | 36.0 | 20 | A |
| 181 | F | CD2 | 43.3 | 36.0 | 36.4 | 20 | A |
| 181 | F | CE1 | 44.1 | 33.3 | 36.7 | 22 | A |
| 181 | F | CE2 | 42.5 | 35.1 | 37.1 | 19 | A |
| 181 | F | CZ | 42.9 | 33.8 | 37.3 | 17 | A |
| 181 | F | C | 44.7 | 35.7 | 32.8 | 23 | A |
| 181 | F | O | 43.9 | 36.6 | 32.3 | 23 | A |
| 182 | L | N | 44.5 | 34.4 | 32.6 | 21 | A |
| 182 | L | CA | 43.4 | 33.9 | 31.8 | 22 | A |
| 182 | L | CB | 42.0 | 34.2 | 32.4 | 24 | A |
| 182 | L | CG | 41.8 | 33.6 | 33.8 | 24 | A |
| 182 | L | CD1 | 40.5 | 34.1 | 34.4 | 27 | A |
| 182 | L | CD2 | 41.8 | 32.1 | 33.8 | 23 | A |
| 182 | L | C | 43.3 | 34.4 | 30.3 | 24 | A |
| 182 | L | O | 42.3 | 34.8 | 29.8 | 24 | A |
| 183 | T | N | 44.5 | 34.4 | 29.7 | 27 | A |
| 183 | T | CA | 44.6 | 34.9 | 28.3 | 30 | A |
| 183 | T | CB | 46.0 | 35.4 | 27.9 | 31 | A |
| 183 | T | OG1 | 46.3 | 36.5 | 28.8 | 32 | A |
| 183 | T | CG2 | 46.1 | 35.8 | 26.5 | 32 | A |
| 183 | T | C | 44.2 | 33.7 | 27.4 | 30 | A |
| 183 | T | O | 44.8 | 32.6 | 27.5 | 31 | A |
| 184 | E | N | 43.4 | 34.0 | 26.4 | 32 | A |
| 184 | E | CA | 42.9 | 33.0 | 25.4 | 35 | A |
| 184 | E | CB | 42.1 | 33.6 | 24.3 | 37 | A |
| 184 | E | CG | 41.7 | 32.7 | 23.2 | 44 | A |
| 184 | E | CD | 40.7 | 33.3 | 22.2 | 47 | A |
| 184 | E | OE1 | 41.0 | 34.4 | 21.8 | 49 | A |
| 184 | E | OE2 | 39.7 | 32.6 | 21.9 | 47 | A |
| 184 | E | C | 44.1 | 32.2 | 24.8 | 34 | A |
| 184 | E | O | 45.2 | 32.8 | 24.5 | 35 | A |
| 185 | Y | N | 43.9 | 30.9 | 24.6 | 34 | A |
| 185 | Y | CA | 45.0 | 30.1 | 24.0 | 33 | A |
| 185 | Y | CB | 45.6 | 29.2 | 25.0 | 31 | A |
| 185 | Y | CG | 47.0 | 28.7 | 24.6 | 30 | A |
| 185 | Y | CD1 | 48.0 | 29.6 | 24.4 | 31 | A |
| 185 | Y | CE1 | 49.3 | 29.1 | 24.1 | 29 | A |
| 185 | Y | CD2 | 47.2 | 27.3 | 24.6 | 30 | A |
| 185 | Y | CE2 | 48.5 | 26.8 | 24.2 | 29 | A |
| 185 | Y | CZ | 49.5 | 27.7 | 24.0 | 29 | A |
| 185 | Y | OH | 50.8 | 27.3 | 23.7 | 26 | A |
| 185 | Y | C | 44.3 | 29.2 | 22.9 | 33 | A |
| 185 | Y | O | 43.1 | 28.8 | 23.0 | 33 | A |
| 186 | V | N | 45.1 | 28.8 | 21.9 | 33 | A |
| 186 | V | CA | 44.6 | 28.0 | 20.8 | 32 | A |
| 186 | V | CB | 45.1 | 28.6 | 19.4 | 34 | A |
| 186 | V | CG1 | 46.6 | 28.4 | 19.3 | 35 | A |
| 186 | V | CG2 | 44.4 | 27.9 | 18.3 | 35 | A |
| 186 | V | C | 44.8 | 26.5 | 20.9 | 31 | A |
| 186 | V | O | 44.0 | 25.8 | 20.4 | 32 | A |
| 187 | A | N | 45.9 | 26.1 | 21.4 | 28 | A |
| 187 | A | CA | 46.3 | 24.7 | 21.5 | 29 | A |
| 187 | A | CB | 47.7 | 24.5 | 22.1 | 28 | A |
| 187 | A | C | 45.3 | 23.9 | 22.4 | 27 | A |
| 187 | A | O | 44.7 | 24.4 | 23.3 | 26 | A |
| 188 | T | N | 45.2 | 22.6 | 22.0 | 26 | A |
| 188 | T | CA | 44.3 | 21.6 | 22.7 | 24 | A |
| 188 | T | CB | 44.6 | 20.2 | 22.2 | 24 | A |
| 188 | T | OG1 | 44.8 | 20.2 | 20.8 | 23 | A |
| 188 | T | CG2 | 43.5 | 19.3 | 22.6 | 23 | A |
| 188 | T | C | 44.3 | 21.8 | 24.2 | 24 | A |
| 188 | T | O | 45.4 | 21.5 | 24.8 | 23 | A |
| 189 | R | N | 43.2 | 22.1 | 24.7 | 22 | A |
| 189 | R | CA | 43.0 | 22.3 | 26.2 | 21 | A |
| 189 | R | CB | 41.5 | 22.5 | 26.5 | 23 | A |
| 189 | R | CG | 41.2 | 22.9 | 27.9 | 24 | A |
| 189 | R | CD | 39.7 | 22.8 | 28.2 | 25 | A |
| 189 | R | NE | 38.9 | 23.5 | 27.2 | 25 | A |
| 189 | R | CZ | 37.9 | 22.9 | 26.6 | 26 | A |
| 189 | R | NH1 | 37.5 | 21.7 | 27.0 | 26 | A |
| 189 | R | NH2 | 37.2 | 23.6 | 25.7 | 26 | A |
| 189 | R | C | 43.6 | 21.3 | 27.2 | 20 | A |
| 189 | R | O | 44.3 | 21.7 | 28.1 | 19 | A |
| 190 | W | N | 43.2 | 20.1 | 27.0 | 19 | A |
| 190 | W | CA | 43.7 | 19.0 | 27.9 | 20 | A |
| 190 | W | CB | 43.1 | 17.6 | 27.5 | 23 | A |
| 190 | W | CG | 41.6 | 17.5 | 27.5 | 25 | A |
| 190 | W | CD2 | 40.9 | 16.4 | 27.0 | 27 | A |
| 190 | W | CE2 | 39.5 | 16.7 | 27.3 | 28 | A |
| 190 | W | CE3 | 41.2 | 15.2 | 26.4 | 29 | A |
| 190 | W | CD1 | 40.7 | 18.4 | 28.1 | 25 | A |
| 190 | W | NE1 | 39.4 | 17.9 | 27.9 | 26 | A |
| 190 | W | CZ2 | 38.5 | 15.9 | 26.9 | 28 | A |
| 190 | W | CZ3 | 40.1 | 14.4 | 26.0 | 29 | A |
| 190 | W | CH2 | 38.8 | 14.7 | 26.3 | 30 | A |
| 190 | W | C | 45.2 | 18.9 | 28.1 | 20 | A |
| 190 | W | O | 45.6 | 18.2 | 29.1 | 22 | A |
| 191 | Y | N | 45.9 | 19.4 | 27.2 | 18 | A |
| 191 | Y | CA | 47.4 | 19.3 | 27.2 | 18 | A |
| 191 | Y | CB | 47.9 | 18.7 | 25.9 | 19 | A |
| 191 | Y | CG | 47.2 | 17.4 | 25.6 | 21 | A |
| 191 | Y | CD1 | 47.6 | 16.2 | 26.1 | 20 | A |
| 191 | Y | CE1 | 46.9 | 15.0 | 26.0 | 22 | A |
| 191 | Y | CD2 | 46.0 | 17.4 | 24.8 | 21 | A |
| 191 | Y | CE2 | 45.2 | 16.2 | 24.7 | 22 | A |
| 191 | Y | CZ | 45.7 | 15.0 | 25.3 | 23 | A |
| 191 | Y | OH | 44.9 | 13.8 | 25.2 | 22 | A |
| 191 | Y | C | 48.1 | 20.6 | 27.5 | 18 | A |
| 191 | Y | O | 49.3 | 20.7 | 27.3 | 17 | A |
| 192 | R | N | 47.3 | 21.6 | 27.9 | 19 | A |
| 192 | R | CA | 47.9 | 23.0 | 28.2 | 17 | A |
| 192 | R | CB | 46.8 | 24.1 | 28.2 | 16 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 192 | R | CG  | 46.1 | 24.3 | 26.9 | 18 | A | 201 | K | CG  | 51.9 | 35.3 | 25.4 | 27 | A |
|-----|---|-----|------|------|------|----|---|-----|---|-----|------|------|------|----|---|
| 192 | R | CD  | 45.0 | 25.3 | 27.0 | 16 | A | 201 | K | CD  | 52.5 | 36.3 | 24.5 | 29 | A |
| 192 | R | NE  | 44.3 | 25.5 | 25.7 | 18 | A | 201 | K | CE  | 51.9 | 37.7 | 24.8 | 34 | A |
| 192 | R | CZ  | 43.0 | 25.9 | 25.6 | 21 | A | 201 | K | NZ  | 52.5 | 38.7 | 23.8 | 36 | A |
| 192 | R | NH1 | 42.3 | 26.3 | 26.6 | 22 | A | 201 | K | C   | 52.2 | 31.4 | 25.1 | 23 | A |
| 192 | R | NH2 | 42.5 | 26.0 | 24.4 | 24 | A | 201 | K | O   | 52.0 | 31.2 | 23.9 | 21 | A |
| 192 | R | C   | 48.5 | 23.0 | 29.6 | 16 | A | 202 | G | N   | 53.0 | 30.6 | 25.9 | 21 | A |
| 192 | R | O   | 47.9 | 22.6 | 30.6 | 15 | A | 202 | G | CA  | 53.4 | 29.3 | 25.3 | 21 | A |
| 193 | A | N   | 49.8 | 23.5 | 29.7 | 16 | A | 202 | G | C   | 54.6 | 29.5 | 24.4 | 22 | A |
| 193 | A | CA  | 50.5 | 23.6 | 30.9 | 17 | A | 202 | G | O   | 54.7 | 28.7 | 23.3 | 21 | A |
| 193 | A | CB  | 51.9 | 24.1 | 30.7 | 16 | A | 203 | Y | N   | 55.5 | 30.4 | 24.7 | 21 | A |
| 193 | A | C   | 49.7 | 24.7 | 31.8 | 18 | A | 203 | Y | CA  | 56.7 | 30.6 | 23.8 | 23 | A |
| 193 | A | O   | 49.0 | 25.5 | 31.3 | 18 | A | 203 | Y | CB  | 56.9 | 32.1 | 23.6 | 26 | A |
| 194 | P | N   | 49.8 | 24.6 | 33.1 | 17 | A | 203 | Y | CG  | 55.8 | 32.8 | 22.8 | 28 | A |
| 194 | P | CD  | 50.6 | 23.6 | 33.9 | 19 | A | 203 | Y | CD1 | 54.9 | 32.2 | 22.0 | 31 | A |
| 194 | P | CA  | 49.1 | 25.5 | 34.0 | 18 | A | 203 | Y | CE1 | 53.9 | 32.6 | 21.2 | 32 | A |
| 194 | P | CB  | 49.5 | 25.0 | 35.4 | 18 | A | 203 | Y | CD2 | 55.6 | 34.2 | 22.7 | 33 | A |
| 194 | P | CG  | 50.8 | 24.4 | 35.2 | 19 | A | 203 | Y | CE2 | 54.7 | 34.8 | 21.9 | 34 | A |
| 194 | P | C   | 49.4 | 27.0 | 33.8 | 18 | A | 203 | Y | CZ  | 53.8 | 34.0 | 21.2 | 34 | A |
| 194 | P | O   | 48.5 | 27.8 | 33.8 | 17 | A | 203 | Y | OH  | 52.8 | 34.6 | 20.4 | 39 | A |
| 195 | E | N   | 50.7 | 27.3 | 33.5 | 18 | A | 203 | Y | C   | 58.0 | 30.0 | 24.4 | 23 | A |
| 195 | E | CA  | 51.1 | 28.7 | 33.2 | 18 | A | 203 | Y | O   | 59.1 | 30.5 | 24.0 | 23 | A |
| 195 | E | CB  | 52.6 | 28.8 | 33.1 | 17 | A | 204 | T | N   | 57.9 | 29.1 | 25.3 | 23 | A |
| 195 | E | CG  | 53.1 | 28.1 | 31.8 | 16 | A | 204 | T | CA  | 59.1 | 28.5 | 25.9 | 23 | A |
| 195 | E | CD  | 53.6 | 26.7 | 32.1 | 17 | A | 204 | T | CB  | 59.2 | 28.9 | 27.4 | 26 | A |
| 195 | E | OE1 | 53.1 | 26.1 | 33.1 | 17 | A | 204 | T | OG1 | 58.2 | 28.2 | 28.2 | 30 | A |
| 195 | E | OE2 | 54.4 | 26.1 | 31.4 | 17 | A | 204 | T | CG2 | 59.1 | 30.4 | 27.6 | 27 | A |
| 195 | E | C   | 50.4 | 29.3 | 32.0 | 19 | A | 204 | T | C   | 59.0 | 27.0 | 25.8 | 21 | A |
| 195 | E | O   | 50.3 | 30.6 | 31.9 | 21 | A | 204 | T | O   | 57.9 | 26.4 | 25.9 | 20 | A |
| 196 | I | N   | 49.8 | 28.5 | 31.1 | 18 | A | 205 | K | N   | 60.1 | 26.3 | 25.7 | 19 | A |
| 196 | I | CA  | 49.1 | 29.1 | 30.0 | 18 | A | 205 | K | CA  | 60.2 | 24.9 | 25.5 | 19 | A |
| 196 | I | CB  | 48.6 | 28.0 | 29.0 | 19 | A | 205 | K | CB  | 61.6 | 24.4 | 25.4 | 19 | A |
| 196 | I | CG2 | 47.6 | 28.6 | 28.1 | 21 | A | 205 | K | CG  | 62.4 | 25.0 | 24.2 | 18 | A |
| 196 | I | CG1 | 49.8 | 27.3 | 28.3 | 17 | A | 205 | K | CD  | 63.9 | 24.7 | 24.2 | 17 | A |
| 196 | I | CD1 | 50.7 | 28.3 | 27.5 | 18 | A | 205 | K | CE  | 64.6 | 25.4 | 23.1 | 21 | A |
| 196 | I | C   | 48.0 | 29.9 | 30.5 | 19 | A | 205 | K | NZ  | 66.0 | 25.1 | 23.1 | 19 | A |
| 196 | I | O   | 47.7 | 31.0 | 29.9 | 19 | A | 205 | K | C   | 59.4 | 24.1 | 26.6 | 17 | A |
| 197 | M | N   | 47.3 | 29.4 | 31.5 | 17 | A | 205 | K | O   | 58.9 | 23.0 | 26.3 | 18 | A |
| 197 | M | CA  | 46.1 | 30.1 | 32.1 | 20 | A | 206 | S | N   | 59.4 | 24.6 | 27.8 | 16 | A |
| 197 | M | CB  | 45.2 | 29.1 | 32.8 | 18 | A | 206 | S | CA  | 58.7 | 23.9 | 28.9 | 17 | A |
| 197 | M | CG  | 44.4 | 28.2 | 31.8 | 19 | A | 206 | S | CB  | 58.8 | 24.7 | 30.2 | 17 | A |
| 197 | M | SD  | 45.5 | 26.9 | 31.1 | 21 | A | 206 | S | OG  | 58.4 | 26.1 | 30.0 | 20 | A |
| 197 | M | CE  | 45.6 | 25.7 | 32.4 | 17 | A | 206 | S | C   | 57.2 | 23.6 | 28.6 | 17 | A |
| 197 | M | C   | 46.5 | 31.2 | 33.1 | 19 | A | 206 | S | O   | 56.6 | 22.7 | 29.1 | 16 | A |
| 197 | M | O   | 45.7 | 32.0 | 33.5 | 18 | A | 207 | I | N   | 56.6 | 24.4 | 27.6 | 16 | A |
| 198 | L | N   | 47.8 | 31.2 | 33.5 | 18 | A | 207 | I | CA  | 55.3 | 24.2 | 27.2 | 17 | A |
| 198 | L | CA  | 48.2 | 32.2 | 34.5 | 20 | A | 207 | I | CB  | 54.8 | 25.3 | 26.3 | 21 | A |
| 198 | L | CB  | 49.0 | 31.4 | 35.6 | 18 | A | 207 | I | CG2 | 55.1 | 24.9 | 24.8 | 23 | A |
| 198 | L | CG  | 48.2 | 30.3 | 36.3 | 20 | A | 207 | I | CG1 | 53.3 | 25.5 | 26.4 | 25 | A |
| 198 | L | CD1 | 49.1 | 29.4 | 37.1 | 20 | A | 207 | I | CD1 | 52.9 | 25.9 | 27.8 | 25 | A |
| 198 | L | CD2 | 47.0 | 30.9 | 37.2 | 18 | A | 207 | I | C   | 55.1 | 22.8 | 26.6 | 17 | A |
| 198 | L | C   | 49.1 | 33.3 | 34.1 | 20 | A | 207 | I | O   | 54.0 | 22.1 | 26.9 | 16 | A |
| 198 | L | O   | 48.9 | 34.4 | 34.5 | 21 | A | 208 | D | N   | 56.0 | 22.3 | 25.8 | 15 | A |
| 199 | N | N   | 50.1 | 33.0 | 33.2 | 21 | A | 208 | D | CA  | 56.0 | 21.0 | 25.2 | 14 | A |
| 199 | N | CA  | 51.0 | 34.1 | 32.7 | 21 | A | 208 | D | CB  | 57.0 | 20.9 | 24.0 | 14 | A |
| 199 | N | CB  | 52.0 | 34.4 | 33.8 | 21 | A | 208 | D | CG  | 56.6 | 21.7 | 22.8 | 16 | A |
| 199 | N | CG  | 52.8 | 33.2 | 34.2 | 23 | A | 208 | D | OD1 | 55.3 | 21.9 | 22.5 | 16 | A |
| 199 | N | OD1 | 53.1 | 32.3 | 33.4 | 25 | A | 208 | D | OD2 | 57.5 | 22.1 | 22.0 | 14 | A |
| 199 | N | ND2 | 53.1 | 33.1 | 35.5 | 23 | A | 208 | D | C   | 56.2 | 19.9 | 26.2 | 16 | A |
| 199 | N | C   | 51.8 | 33.8 | 31.5 | 22 | A | 208 | D | O   | 55.6 | 18.8 | 26.0 | 15 | A |
| 199 | N | O   | 52.7 | 34.6 | 31.1 | 22 | A | 209 | I | N   | 57.1 | 20.1 | 27.1 | 15 | A |
| 200 | S | N   | 51.5 | 32.7 | 30.7 | 21 | A | 209 | I | CA  | 57.4 | 19.1 | 28.1 | 14 | A |
| 200 | S | CA  | 52.3 | 32.4 | 29.6 | 21 | A | 209 | I | CB  | 58.5 | 19.5 | 29.1 | 17 | A |
| 200 | S | CB  | 53.0 | 31.0 | 29.8 | 19 | A | 209 | I | CG2 | 58.7 | 18.5 | 30.3 | 14 | A |
| 200 | S | OG  | 53.8 | 30.6 | 28.7 | 19 | A | 209 | I | CG1 | 59.8 | 19.7 | 28.3 | 16 | A |
| 200 | S | C   | 51.6 | 32.3 | 28.2 | 22 | A | 209 | I | CD1 | 60.3 | 18.4 | 27.7 | 18 | A |
| 200 | S | O   | 50.4 | 31.8 | 28.1 | 22 | A | 209 | I | C   | 56.1 | 18.7 | 28.9 | 15 | A |
| 201 | K | N   | 52.3 | 32.7 | 27.2 | 21 | A | 209 | I | O   | 55.9 | 17.6 | 29.2 | 15 | A |
| 201 | K | CA  | 51.8 | 32.7 | 25.8 | 22 | A | 210 | W | N   | 55.4 | 19.7 | 29.3 | 15 | A |
| 201 | K | CB  | 52.4 | 33.9 | 25.0 | 24 | A | 210 | W | CA  | 54.1 | 19.5 | 30.0 | 15 | A |

TABLE 4-continued

Structural Coordinates of Ah$_6$-ERK2 [non-phosphorlylated, SEQ ID NO: 5] (form 1)-olomoucine complex Crystals The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 210 | W | CB | 53.4 | 20.8 | 30.4 | 14 | A |
|---|---|---|---|---|---|---|---|
| 210 | W | CG | 52.1 | 20.6 | 31.0 | 14 | A |
| 210 | W | CD2 | 51.9 | 20.5 | 32.5 | 15 | A |
| 210 | W | CE2 | 50.5 | 20.2 | 32.6 | 16 | A |
| 210 | W | CE3 | 52.7 | 20.6 | 33.6 | 15 | A |
| 210 | W | CD1 | 50.9 | 20.4 | 30.4 | 14 | A |
| 210 | W | NE1 | 50.0 | 20.1 | 31.4 | 16 | A |
| 210 | W | CZ2 | 50.0 | 20.1 | 33.9 | 16 | A |
| 210 | W | CZ3 | 52.2 | 20.5 | 34.8 | 17 | A |
| 210 | W | CH2 | 50.8 | 20.2 | 35.0 | 15 | A |
| 210 | W | C | 53.2 | 18.6 | 29.1 | 15 | A |
| 210 | W | O | 52.6 | 17.6 | 29.7 | 15 | A |
| 211 | S | N | 53.1 | 18.9 | 27.9 | 15 | A |
| 211 | S | CA | 52.2 | 18.1 | 27.0 | 17 | A |
| 211 | S | CB | 52.2 | 18.7 | 25.6 | 18 | A |
| 211 | S | OG | 51.7 | 20.0 | 25.6 | 18 | A |
| 211 | S | C | 52.6 | 16.6 | 26.9 | 18 | A |
| 211 | S | O | 51.8 | 15.7 | 27.0 | 16 | A |
| 212 | V | N | 54.0 | 16.4 | 26.9 | 16 | A |
| 212 | V | CA | 54.5 | 15.1 | 26.8 | 19 | A |
| 212 | V | CB | 56.0 | 15.1 | 26.6 | 19 | A |
| 212 | V | CG1 | 56.6 | 13.7 | 26.8 | 21 | A |
| 212 | V | CG2 | 56.3 | 15.7 | 25.2 | 16 | A |
| 212 | V | C | 54.2 | 14.4 | 28.1 | 18 | A |
| 212 | V | O | 53.9 | 13.2 | 28.1 | 18 | A |
| 213 | G | N | 54.2 | 15.1 | 29.2 | 18 | A |
| 213 | G | CA | 53.9 | 14.5 | 30.5 | 18 | A |
| 213 | G | C | 52.4 | 14.1 | 30.5 | 17 | A |
| 213 | G | O | 52.1 | 13.1 | 31.1 | 15 | A |
| 214 | C | N | 51.6 | 14.9 | 29.9 | 17 | A |
| 214 | C | CA | 50.1 | 14.5 | 29.8 | 17 | A |
| 214 | C | CB | 49.3 | 15.7 | 29.2 | 18 | A |
| 214 | C | SG | 49.2 | 17.2 | 30.3 | 18 | A |
| 214 | C | C | 49.9 | 13.3 | 29.0 | 17 | A |
| 214 | C | O | 49.1 | 12.4 | 29.3 | 17 | A |
| 215 | I | N | 50.7 | 13.2 | 27.9 | 17 | A |
| 215 | I | CA | 50.6 | 12.0 | 27.0 | 17 | A |
| 215 | I | CB | 51.5 | 12.2 | 25.7 | 17 | A |
| 215 | I | CG2 | 51.5 | 10.9 | 24.9 | 17 | A |
| 215 | I | CG1 | 50.8 | 13.4 | 24.9 | 16 | A |
| 215 | I | CD1 | 51.7 | 13.9 | 23.8 | 13 | A |
| 215 | I | C | 51.1 | 10.8 | 27.7 | 18 | A |
| 215 | I | O | 50.5 | 9.7 | 27.6 | 18 | A |
| 216 | L | N | 52.2 | 10.9 | 28.5 | 17 | A |
| 216 | L | CA | 52.7 | 9.7 | 29.3 | 20 | A |
| 216 | L | CB | 53.9 | 10.1 | 30.0 | 17 | A |
| 216 | L | CG | 54.5 | 9.0 | 31.0 | 17 | A |
| 216 | L | CD1 | 54.7 | 7.7 | 30.3 | 15 | A |
| 216 | L | CD2 | 55.8 | 9.5 | 31.6 | 15 | A |
| 216 | L | C | 51.6 | 9.2 | 30.2 | 21 | A |
| 216 | L | O | 51.4 | 8.0 | 30.3 | 21 | A |
| 217 | A | N | 51.0 | 10.1 | 31.0 | 22 | A |
| 217 | A | CA | 49.9 | 9.8 | 31.9 | 21 | A |
| 217 | A | CB | 49.4 | 11.1 | 32.6 | 22 | A |
| 217 | A | C | 48.8 | 9.1 | 31.2 | 22 | A |
| 217 | A | O | 48.3 | 8.1 | 31.7 | 23 | A |
| 218 | E | N | 48.5 | 9.6 | 30.0 | 20 | A |
| 218 | E | CA | 47.4 | 9.0 | 29.2 | 20 | A |
| 218 | E | CB | 47.1 | 9.9 | 28.0 | 18 | A |
| 218 | E | CG | 45.7 | 9.6 | 27.4 | 21 | A |
| 218 | E | CD | 45.2 | 10.8 | 26.6 | 22 | A |
| 218 | E | OE1 | 45.6 | 11.9 | 26.8 | 22 | A |
| 218 | E | OE2 | 44.3 | 10.5 | 25.7 | 21 | A |
| 218 | E | C | 47.7 | 7.6 | 28.8 | 21 | A |
| 218 | E | O | 46.8 | 6.7 | 28.7 | 20 | A |
| 219 | M | N | 49.0 | 7.3 | 28.4 | 20 | A |
| 219 | M | CA | 49.4 | 6.0 | 28.0 | 21 | A |
| 219 | M | CB | 50.8 | 6.0 | 27.4 | 20 | A |
| 219 | M | CG | 51.0 | 6.6 | 26.0 | 19 | A |
| 219 | M | SD | 52.6 | 6.2 | 25.3 | 18 | A |
| 219 | M | CE | 53.7 | 7.3 | 26.2 | 18 | A |
| 219 | M | C | 49.3 | 5.0 | 29.1 | 23 | A |
| 219 | M | O | 49.1 | 3.8 | 29.0 | 23 | A |
| 220 | L | N | 49.5 | 5.6 | 30.3 | 23 | A |
| 220 | L | CA | 49.5 | 4.8 | 31.6 | 25 | A |
| 220 | L | CB | 50.2 | 5.6 | 32.7 | 22 | A |
| 220 | L | CG | 51.7 | 5.8 | 32.7 | 21 | A |
| 220 | L | CD1 | 52.1 | 6.7 | 33.8 | 18 | A |
| 220 | L | CD2 | 52.4 | 4.5 | 32.8 | 21 | A |
| 220 | L | C | 48.1 | 4.3 | 32.0 | 28 | A |
| 220 | L | O | 48.0 | 3.3 | 32.7 | 28 | A |
| 221 | S | N | 47.1 | 5.1 | 31.6 | 29 | A |
| 221 | S | CA | 45.7 | 4.7 | 32.0 | 30 | A |
| 221 | S | CB | 45.3 | 5.7 | 33.1 | 31 | A |
| 221 | S | OG | 45.3 | 7.0 | 32.6 | 34 | A |
| 221 | S | C | 44.7 | 4.7 | 30.9 | 30 | A |
| 221 | S | O | 43.5 | 4.3 | 31.2 | 31 | A |
| 222 | N | N | 45.0 | 5.1 | 29.7 | 29 | A |
| 222 | N | CA | 44.1 | 5.1 | 28.6 | 30 | A |
| 222 | N | CB | 43.4 | 3.8 | 28.4 | 30 | A |
| 222 | N | CG | 44.3 | 2.7 | 27.8 | 29 | A |
| 222 | N | OD1 | 44.4 | 2.6 | 26.6 | 30 | A |
| 222 | N | ND2 | 45.1 | 2.0 | 28.7 | 31 | A |
| 222 | N | C | 43.0 | 6.2 | 28.8 | 30 | A |
| 222 | N | O | 42.0 | 6.2 | 28.1 | 30 | A |
| 223 | R | N | 43.3 | 7.2 | 29.6 | 29 | A |
| 223 | R | CA | 42.4 | 8.3 | 29.9 | 29 | A |
| 223 | R | CB | 41.6 | 8.1 | 31.1 | 32 | A |
| 223 | R | CG | 42.4 | 8.0 | 32.4 | 39 | A |
| 223 | R | CD | 41.6 | 7.9 | 33.7 | 44 | A |
| 223 | R | NE | 42.4 | 7.5 | 34.9 | 50 | A |
| 223 | R | CZ | 43.4 | 8.2 | 35.4 | 51 | A |
| 223 | R | NH1 | 43.8 | 9.4 | 34.8 | 50 | A |
| 223 | R | NH2 | 44.1 | 7.8 | 36.4 | 51 | A |
| 223 | R | C | 43.2 | 9.6 | 30.0 | 26 | A |
| 223 | R | O | 44.3 | 9.6 | 30.6 | 24 | A |
| 224 | P | N | 42.7 | 10.7 | 29.5 | 25 | A |
| 224 | P | CD | 41.5 | 10.9 | 28.6 | 24 | A |
| 224 | P | CA | 43.4 | 12.0 | 29.6 | 24 | A |
| 224 | P | CB | 42.6 | 13.0 | 28.8 | 26 | A |
| 224 | P | CG | 41.2 | 12.3 | 28.8 | 26 | A |
| 224 | P | C | 43.5 | 12.3 | 31.1 | 23 | A |
| 224 | P | O | 42.5 | 12.1 | 31.8 | 23 | A |
| 225 | I | N | 44.7 | 12.7 | 31.6 | 22 | A |
| 225 | I | CA | 44.8 | 13.0 | 33.0 | 22 | A |
| 225 | I | CB | 46.4 | 13.1 | 33.4 | 20 | A |
| 225 | I | CG2 | 47.1 | 14.2 | 32.6 | 19 | A |
| 225 | I | CG1 | 46.5 | 13.3 | 34.9 | 21 | A |
| 225 | I | CD1 | 48.0 | 13.3 | 35.4 | 23 | A |
| 225 | I | C | 44.1 | 14.3 | 33.5 | 22 | A |
| 225 | I | O | 43.6 | 14.3 | 34.6 | 22 | A |
| 226 | F | N | 44.1 | 15.3 | 32.6 | 23 | A |
| 226 | F | CA | 43.4 | 16.6 | 33.0 | 22 | A |
| 226 | F | CB | 44.5 | 17.7 | 33.1 | 20 | A |
| 226 | F | CG | 45.6 | 17.4 | 34.0 | 19 | A |
| 226 | F | CD1 | 45.4 | 17.1 | 35.4 | 19 | A |
| 226 | F | CD2 | 46.9 | 17.4 | 33.6 | 18 | A |
| 226 | F | CE1 | 46.5 | 16.8 | 36.3 | 17 | A |
| 226 | F | CE2 | 48.0 | 17.2 | 34.5 | 18 | A |
| 226 | F | CZ | 47.8 | 16.9 | 35.8 | 17 | A |
| 226 | F | C | 42.4 | 16.9 | 31.9 | 22 | A |
| 226 | F | O | 42.6 | 17.8 | 31.1 | 21 | A |
| 227 | P | N | 41.2 | 16.3 | 31.9 | 23 | A |
| 227 | P | CD | 40.9 | 15.1 | 32.7 | 24 | A |
| 227 | P | CA | 40.2 | 16.5 | 30.9 | 24 | A |
| 227 | P | CB | 39.4 | 15.2 | 30.9 | 24 | A |
| 227 | P | CG | 39.5 | 14.8 | 32.3 | 23 | A |
| 227 | P | C | 39.3 | 17.7 | 31.3 | 25 | A |
| 227 | P | O | 38.1 | 17.6 | 31.4 | 26 | A |
| 228 | G | N | 39.9 | 18.9 | 31.3 | 24 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 228 | G | CA | 39.1 | 20.1 | 31.6 | 26 | A |
|---|---|---|---|---|---|---|---|
| 228 | G | C | 37.9 | 20.3 | 30.7 | 28 | A |
| 228 | G | O | 38.1 | 20.1 | 29.5 | 28 | A |
| 229 | K | N | 36.8 | 20.6 | 31.2 | 30 | A |
| 229 | K | CA | 35.5 | 20.8 | 30.5 | 33 | A |
| 229 | K | CB | 34.3 | 20.7 | 31.4 | 36 | A |
| 229 | K | CG | 34.1 | 19.3 | 32.0 | 42 | A |
| 229 | K | CD | 33.0 | 19.4 | 33.1 | 45 | A |
| 229 | K | CE | 32.6 | 18.0 | 33.5 | 49 | A |
| 229 | K | NZ | 33.7 | 17.1 | 34.0 | 51 | A |
| 229 | K | C | 35.5 | 22.1 | 29.7 | 32 | A |
| 229 | K | O | 34.9 | 22.2 | 28.6 | 34 | A |
| 230 | H | N | 36.2 | 23.1 | 30.3 | 31 | A |
| 230 | H | CA | 36.3 | 24.4 | 29.7 | 30 | A |
| 230 | H | CB | 35.1 | 25.3 | 30.0 | 29 | A |
| 230 | H | CG | 34.8 | 25.3 | 31.5 | 28 | A |
| 230 | H | CD2 | 35.3 | 26.1 | 32.5 | 27 | A |
| 230 | H | ND1 | 33.9 | 24.5 | 32.1 | 29 | A |
| 230 | H | CE1 | 33.8 | 24.8 | 33.4 | 27 | A |
| 230 | H | NE2 | 34.7 | 25.7 | 33.6 | 29 | A |
| 230 | H | C | 37.6 | 25.0 | 30.1 | 29 | A |
| 230 | H | O | 38.4 | 24.5 | 30.9 | 30 | A |
| 231 | Y | N | 37.9 | 26.2 | 29.6 | 28 | A |
| 231 | Y | CA | 39.1 | 27.0 | 29.9 | 27 | A |
| 231 | Y | CB | 39.0 | 28.4 | 29.4 | 27 | A |
| 231 | Y | CG | 40.3 | 29.2 | 29.4 | 26 | A |
| 231 | Y | CD1 | 40.7 | 29.8 | 30.6 | 25 | A |
| 231 | Y | CE1 | 41.9 | 30.5 | 30.7 | 26 | A |
| 231 | Y | CD2 | 41.2 | 29.2 | 28.3 | 28 | A |
| 231 | Y | CE2 | 42.4 | 29.9 | 28.4 | 25 | A |
| 231 | Y | CZ | 42.7 | 30.6 | 29.6 | 24 | A |
| 231 | Y | OH | 43.9 | 31.2 | 29.6 | 22 | A |
| 231 | Y | C | 39.7 | 27.0 | 31.3 | 29 | A |
| 231 | Y | O | 40.8 | 26.5 | 31.5 | 28 | A |
| 232 | L | N | 38.9 | 27.5 | 32.2 | 29 | A |
| 232 | L | CA | 39.4 | 27.6 | 33.6 | 30 | A |
| 232 | L | CB | 38.6 | 28.6 | 34.5 | 32 | A |
| 232 | L | CG | 39.1 | 28.7 | 35.9 | 34 | A |
| 232 | L | CD1 | 40.5 | 29.3 | 36.0 | 31 | A |
| 232 | L | CD2 | 38.1 | 29.7 | 36.7 | 35 | A |
| 232 | L | C | 39.4 | 26.2 | 34.3 | 29 | A |
| 232 | L | O | 40.1 | 25.9 | 35.2 | 30 | A |
| 233 | D | N | 38.4 | 25.4 | 33.9 | 27 | A |
| 233 | D | CA | 38.3 | 24.1 | 34.5 | 26 | A |
| 233 | D | CB | 37.1 | 23.3 | 33.8 | 26 | A |
| 233 | D | CG | 36.8 | 22.0 | 34.5 | 26 | A |
| 233 | D | OD1 | 36.7 | 22.1 | 35.8 | 27 | A |
| 233 | D | OD2 | 36.5 | 21.0 | 33.9 | 30 | A |
| 233 | D | C | 39.6 | 23.3 | 34.2 | 25 | A |
| 233 | D | O | 39.9 | 22.4 | 35.0 | 27 | A |
| 234 | Q | N | 40.3 | 23.6 | 33.2 | 24 | A |
| 234 | Q | CA | 41.6 | 23.0 | 32.9 | 23 | A |
| 234 | Q | CB | 42.2 | 23.5 | 31.6 | 23 | A |
| 234 | Q | CG | 43.4 | 22.7 | 31.1 | 20 | A |
| 234 | Q | CD | 43.0 | 21.3 | 30.9 | 22 | A |
| 234 | Q | OE1 | 41.9 | 20.9 | 30.5 | 20 | A |
| 234 | Q | NE2 | 44.0 | 20.4 | 31.2 | 19 | A |
| 234 | Q | C | 42.5 | 23.1 | 34.0 | 23 | A |
| 234 | Q | O | 43.2 | 22.2 | 34.4 | 21 | A |
| 235 | L | N | 42.5 | 24.4 | 34.6 | 24 | A |
| 235 | L | CA | 43.4 | 24.6 | 35.7 | 26 | A |
| 235 | L | CB | 43.5 | 26.2 | 35.9 | 27 | A |
| 235 | L | CG | 44.4 | 26.7 | 37.0 | 28 | A |
| 235 | L | CD1 | 45.8 | 26.1 | 36.8 | 28 | A |
| 235 | L | CD2 | 44.5 | 28.2 | 37.0 | 30 | A |
| 235 | L | C | 42.9 | 24.0 | 37.0 | 26 | A |
| 235 | L | O | 43.7 | 23.5 | 37.8 | 26 | A |
| 236 | N | N | 41.6 | 23.9 | 37.2 | 27 | A |
| 236 | N | CA | 41.0 | 23.2 | 38.3 | 27 | A |
| 236 | N | CB | 39.5 | 23.2 | 38.3 | 30 | A |
| 236 | N | CG | 38.8 | 24.5 | 38.4 | 34 | A |
| 236 | N | OD1 | 39.4 | 25.5 | 39.0 | 34 | A |
| 236 | N | ND2 | 37.6 | 24.6 | 38.0 | 33 | A |
| 236 | N | C | 41.5 | 21.7 | 38.4 | 25 | A |
| 236 | N | O | 41.7 | 21.2 | 39.4 | 24 | A |
| 237 | H | N | 41.5 | 21.1 | 37.2 | 25 | A |
| 237 | H | CA | 42.0 | 19.7 | 37.1 | 22 | A |
| 237 | H | CB | 41.7 | 19.2 | 35.7 | 25 | A |
| 237 | H | CG | 40.3 | 18.7 | 35.4 | 27 | A |
| 237 | H | CD2 | 39.2 | 19.4 | 35.1 | 26 | A |
| 237 | H | ND1 | 40.0 | 17.4 | 35.5 | 26 | A |
| 237 | H | CE1 | 38.7 | 17.2 | 35.3 | 29 | A |
| 237 | H | NE2 | 38.2 | 18.4 | 35.1 | 28 | A |
| 237 | H | C | 43.4 | 19.5 | 37.5 | 22 | A |
| 237 | H | O | 43.8 | 18.6 | 38.2 | 21 | A |
| 238 | I | N | 44.3 | 20.4 | 36.9 | 21 | A |
| 238 | I | CA | 45.7 | 20.4 | 37.2 | 20 | A |
| 238 | I | CB | 46.4 | 21.4 | 36.4 | 22 | A |
| 238 | I | CG2 | 47.9 | 21.4 | 36.7 | 20 | A |
| 238 | I | CG1 | 46.2 | 21.2 | 34.9 | 21 | A |
| 238 | I | CD1 | 46.8 | 22.3 | 34.0 | 19 | A |
| 238 | I | C | 46.0 | 20.6 | 38.7 | 23 | A |
| 238 | I | O | 46.7 | 19.8 | 39.3 | 20 | A |
| 239 | L | N | 45.4 | 21.6 | 39.3 | 22 | A |
| 239 | L | CA | 45.6 | 21.9 | 40.7 | 21 | A |
| 239 | L | CB | 45.1 | 23.3 | 41.1 | 21 | A |
| 239 | L | CG | 45.8 | 24.4 | 40.4 | 22 | A |
| 239 | L | CD1 | 45.3 | 25.7 | 40.9 | 22 | A |
| 239 | L | CD2 | 47.3 | 24.3 | 40.5 | 23 | A |
| 239 | L | C | 45.0 | 20.8 | 41.6 | 23 | A |
| 239 | L | O | 45.4 | 20.6 | 42.7 | 23 | A |
| 240 | G | N | 43.9 | 20.2 | 41.1 | 22 | A |
| 240 | G | CA | 43.3 | 19.1 | 41.8 | 24 | A |
| 240 | G | C | 44.2 | 17.9 | 42.1 | 25 | A |
| 240 | G | O | 44.0 | 17.2 | 43.1 | 26 | A |
| 241 | I | N | 45.1 | 17.7 | 41.2 | 24 | A |
| 241 | I | CA | 46.1 | 16.6 | 41.3 | 22 | A |
| 241 | I | CB | 46.3 | 15.9 | 40.0 | 22 | A |
| 241 | I | CG2 | 47.6 | 15.1 | 40.0 | 19 | A |
| 241 | I | CG1 | 45.1 | 15.0 | 39.7 | 23 | A |
| 241 | I | CD1 | 45.1 | 14.3 | 38.4 | 27 | A |
| 241 | I | C | 47.4 | 17.1 | 41.9 | 22 | A |
| 241 | I | O | 48.0 | 16.4 | 42.8 | 21 | A |
| 242 | L | N | 47.9 | 18.2 | 41.4 | 21 | A |
| 242 | L | CA | 49.2 | 18.7 | 41.9 | 21 | A |
| 242 | L | CB | 49.8 | 19.7 | 40.9 | 21 | A |
| 242 | L | CG | 50.9 | 19.3 | 40.0 | 21 | A |
| 242 | L | CD1 | 50.5 | 18.0 | 39.3 | 20 | A |
| 242 | L | CD2 | 51.2 | 20.4 | 39.0 | 17 | A |
| 242 | L | C | 49.1 | 19.4 | 43.3 | 22 | A |
| 242 | L | O | 50.1 | 19.5 | 44.0 | 21 | A |
| 243 | G | N | 47.9 | 19.8 | 43.7 | 23 | A |
| 243 | G | CA | 47.7 | 20.4 | 45.0 | 23 | A |
| 243 | G | C | 48.1 | 21.9 | 44.8 | 25 | A |
| 243 | G | O | 48.5 | 22.4 | 43.8 | 25 | A |
| 244 | S | N | 47.9 | 22.6 | 45.9 | 25 | A |
| 244 | S | CA | 48.2 | 24.1 | 46.0 | 25 | A |
| 244 | S | CB | 47.9 | 24.6 | 47.3 | 26 | A |
| 244 | S | OG | 46.5 | 24.4 | 47.7 | 24 | A |
| 244 | S | C | 49.7 | 24.3 | 45.7 | 25 | A |
| 244 | S | O | 50.6 | 23.6 | 46.1 | 25 | A |
| 245 | P | N | 50.0 | 25.4 | 44.9 | 26 | A |
| 245 | P | CD | 49.0 | 26.1 | 44.1 | 26 | A |
| 245 | P | CA | 51.4 | 25.7 | 44.5 | 25 | A |
| 245 | P | CB | 51.2 | 26.8 | 43.5 | 25 | A |
| 245 | P | CG | 49.9 | 26.5 | 42.9 | 27 | A |
| 245 | P | C | 52.1 | 26.3 | 45.8 | 25 | A |
| 245 | P | O | 51.6 | 27.0 | 46.6 | 21 | A |
| 246 | S | N | 53.4 | 25.9 | 45.9 | 26 | A |
| 246 | S | CA | 54.3 | 26.3 | 47.0 | 27 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 246 | S | CB  | 55.6 | 25.7 | 46.9 | 26 | A |
|-----|---|-----|------|------|------|----|---|
| 246 | S | OG  | 56.3 | 26.2 | 45.8 | 26 | A |
| 246 | S | C   | 54.4 | 27.8 | 47.0 | 27 | A |
| 246 | S | O   | 54.1 | 28.5 | 45.9 | 27 | A |
| 247 | Q | N   | 54.9 | 28.4 | 48.1 | 29 | A |
| 247 | Q | CA  | 55.0 | 29.8 | 48.1 | 33 | A |
| 247 | Q | CB  | 55.4 | 30.3 | 49.5 | 36 | A |
| 247 | Q | CG  | 55.7 | 31.8 | 49.7 | 40 | A |
| 247 | Q | CD  | 55.8 | 32.2 | 51.2 | 44 | A |
| 247 | Q | OE1 | 54.8 | 32.1 | 51.9 | 45 | A |
| 247 | Q | NE2 | 56.9 | 32.7 | 51.6 | 45 | A |
| 247 | Q | C   | 56.1 | 30.3 | 47.1 | 33 | A |
| 247 | Q | O   | 55.9 | 31.4 | 46.5 | 33 | A |
| 248 | E | N   | 57.2 | 29.6 | 47.0 | 34 | A |
| 248 | E | CA  | 58.2 | 29.9 | 46.0 | 36 | A |
| 248 | E | CB  | 59.4 | 29.0 | 46.1 | 40 | A |
| 248 | E | CG  | 60.5 | 29.3 | 45.1 | 44 | A |
| 248 | E | CD  | 61.7 | 28.5 | 45.4 | 47 | A |
| 248 | E | OE1 | 61.7 | 27.3 | 45.1 | 48 | A |
| 248 | E | OE2 | 62.8 | 29.1 | 45.8 | 51 | A |
| 248 | E | C   | 57.6 | 30.0 | 44.6 | 37 | A |
| 248 | E | O   | 58.0 | 30.8 | 43.8 | 37 | A |
| 249 | D | N   | 56.7 | 29.0 | 44.3 | 35 | A |
| 249 | D | CA  | 56.1 | 28.9 | 43.0 | 33 | A |
| 249 | D | CB  | 55.4 | 27.6 | 42.8 | 34 | A |
| 249 | D | CG  | 56.4 | 26.5 | 42.5 | 33 | A |
| 249 | D | OD1 | 57.6 | 26.8 | 42.5 | 32 | A |
| 249 | D | OD2 | 56.0 | 25.4 | 42.2 | 34 | A |
| 249 | D | C   | 55.1 | 30.1 | 42.8 | 33 | A |
| 249 | D | O   | 55.0 | 30.6 | 41.7 | 31 | A |
| 250 | L | N   | 54.5 | 30.5 | 43.9 | 34 | A |
| 250 | L | CA  | 53.5 | 31.6 | 43.8 | 36 | A |
| 250 | L | CB  | 52.7 | 31.7 | 45.1 | 37 | A |
| 250 | L | CG  | 51.3 | 31.1 | 45.1 | 38 | A |
| 250 | L | CD1 | 50.6 | 31.3 | 46.4 | 39 | A |
| 250 | L | CD2 | 50.5 | 31.7 | 44.0 | 39 | A |
| 250 | L | C   | 54.3 | 32.9 | 43.6 | 37 | A |
| 250 | L | O   | 53.8 | 33.8 | 42.9 | 37 | A |
| 251 | N | N   | 55.5 | 33.0 | 44.1 | 38 | A |
| 251 | N | CA  | 56.3 | 34.2 | 44.0 | 40 | A |
| 251 | N | CB  | 57.4 | 34.2 | 45.0 | 43 | A |
| 251 | N | CG  | 57.0 | 34.6 | 46.4 | 44 | A |
| 251 | N | OD1 | 56.3 | 35.5 | 46.6 | 46 | A |
| 251 | N | ND2 | 57.4 | 33.8 | 47.4 | 46 | A |
| 251 | N | C   | 56.9 | 34.3 | 42.5 | 40 | A |
| 251 | N | O   | 57.2 | 35.4 | 42.1 | 39 | A |
| 252 | C | N   | 56.9 | 33.1 | 41.8 | 40 | A |
| 252 | C | CA  | 57.4 | 33.1 | 40.5 | 40 | A |
| 252 | C | CB  | 57.9 | 31.7 | 40.1 | 40 | A |
| 252 | C | SG  | 59.6 | 31.4 | 40.8 | 46 | A |
| 252 | C | C   | 56.3 | 33.5 | 39.5 | 37 | A |
| 252 | C | O   | 56.5 | 33.7 | 38.3 | 36 | A |
| 253 | I | N   | 55.1 | 33.7 | 40.1 | 36 | A |
| 253 | I | CA  | 54.0 | 34.1 | 39.3 | 37 | A |
| 253 | I | CB  | 52.6 | 33.7 | 40.0 | 37 | A |
| 253 | I | CG2 | 51.7 | 34.9 | 40.2 | 36 | A |
| 253 | I | CG1 | 51.9 | 32.6 | 39.1 | 39 | A |
| 253 | I | CD1 | 52.7 | 31.3 | 39.0 | 37 | A |
| 253 | I | C   | 54.1 | 35.7 | 39.3 | 38 | A |
| 253 | I | O   | 54.1 | 36.3 | 40.4 | 40 | A |
| 254 | I | N   | 54.2 | 36.3 | 38.1 | 36 | A |
| 254 | I | CA  | 54.4 | 37.7 | 38.1 | 35 | A |
| 254 | I | CB  | 55.2 | 38.2 | 36.9 | 40 | A |
| 254 | I | CG2 | 56.6 | 37.6 | 36.9 | 44 | A |
| 254 | I | CG1 | 54.5 | 37.8 | 35.6 | 41 | A |
| 254 | I | CD1 | 55.1 | 38.5 | 34.3 | 44 | A |
| 254 | I | C   | 53.1 | 38.5 | 38.0 | 30 | A |
| 254 | I | O   | 53.0 | 39.7 | 38.4 | 29 | A |
| 255 | N | N   | 52.0 | 37.8 | 37.6 | 26 | A |
| 255 | N | CA  | 50.7 | 38.5 | 37.5 | 25 | A |
| 255 | N | CB  | 49.8 | 37.8 | 36.5 | 23 | A |
| 255 | N | CG  | 50.2 | 38.0 | 35.0 | 24 | A |
| 255 | N | OD1 | 50.7 | 39.1 | 34.7 | 23 | A |
| 255 | N | ND2 | 50.0 | 37.0 | 34.2 | 24 | A |
| 255 | N | C   | 50.0 | 38.7 | 38.8 | 23 | A |
| 255 | N | O   | 49.9 | 37.7 | 39.6 | 20 | A |
| 256 | L | N   | 49.6 | 39.9 | 39.1 | 23 | A |
| 256 | L | CA  | 48.9 | 40.2 | 40.3 | 23 | A |
| 256 | L | CB  | 48.5 | 41.7 | 40.3 | 23 | A |
| 256 | L | CG  | 47.5 | 42.2 | 41.3 | 24 | A |
| 256 | L | CD1 | 48.1 | 42.0 | 42.7 | 21 | A |
| 256 | L | CD2 | 47.2 | 43.7 | 41.1 | 24 | A |
| 256 | L | C   | 47.6 | 39.4 | 40.4 | 22 | A |
| 256 | L | O   | 47.3 | 38.8 | 41.4 | 20 | A |
| 257 | K | N   | 46.9 | 39.3 | 39.2 | 21 | A |
| 257 | K | CA  | 45.6 | 38.6 | 39.2 | 21 | A |
| 257 | K | CB  | 45.0 | 38.8 | 37.8 | 22 | A |
| 257 | K | CG  | 44.4 | 40.2 | 37.6 | 28 | A |
| 257 | K | CD  | 43.8 | 40.4 | 36.2 | 27 | A |
| 257 | K | CE  | 43.0 | 41.6 | 36.0 | 30 | A |
| 257 | K | NZ  | 42.4 | 41.7 | 34.7 | 27 | A |
| 257 | K | C   | 45.8 | 37.1 | 39.4 | 20 | A |
| 257 | K | O   | 45.0 | 36.4 | 40.0 | 19 | A |
| 258 | A | N   | 46.9 | 36.5 | 38.8 | 17 | A |
| 258 | A | CA  | 47.2 | 35.1 | 38.9 | 19 | A |
| 258 | A | CB  | 48.3 | 34.7 | 38.0 | 18 | A |
| 258 | A | C   | 47.5 | 34.8 | 40.4 | 20 | A |
| 258 | A | O   | 47.1 | 33.8 | 41.0 | 20 | A |
| 259 | R | N   | 48.3 | 35.7 | 41.0 | 20 | A |
| 259 | R | CA  | 48.7 | 35.5 | 42.4 | 22 | A |
| 259 | R | CB  | 49.7 | 36.6 | 42.8 | 25 | A |
| 259 | R | CG  | 49.9 | 36.6 | 44.3 | 32 | A |
| 259 | R | CD  | 50.9 | 37.7 | 44.7 | 40 | A |
| 259 | R | NE  | 52.2 | 37.5 | 44.0 | 46 | A |
| 259 | R | CZ  | 53.1 | 36.6 | 44.3 | 49 | A |
| 259 | R | NH1 | 52.9 | 35.8 | 45.4 | 51 | A |
| 259 | R | NH2 | 54.2 | 36.5 | 43.6 | 51 | A |
| 259 | R | C   | 47.5 | 35.5 | 43.3 | 20 | A |
| 259 | R | O   | 47.3 | 34.7 | 44.2 | 21 | A |
| 260 | N | N   | 46.6 | 36.5 | 43.1 | 18 | A |
| 260 | N | CA  | 45.4 | 36.7 | 43.9 | 19 | A |
| 260 | N | CB  | 44.7 | 38.0 | 43.5 | 19 | A |
| 260 | N | CG  | 45.4 | 39.3 | 44.0 | 21 | A |
| 260 | N | OD1 | 46.1 | 39.2 | 44.9 | 20 | A |
| 260 | N | ND2 | 45.0 | 40.4 | 43.4 | 20 | A |
| 260 | N | C   | 44.5 | 35.5 | 43.8 | 18 | A |
| 260 | N | O   | 44.0 | 35.0 | 44.8 | 17 | A |
| 261 | Y | N   | 44.3 | 35.0 | 42.5 | 19 | A |
| 261 | Y | CA  | 43.4 | 33.9 | 42.3 | 19 | A |
| 261 | Y | CB  | 43.4 | 33.5 | 40.8 | 20 | A |
| 261 | Y | CG  | 42.6 | 32.2 | 40.6 | 21 | A |
| 261 | Y | CD1 | 41.2 | 32.2 | 40.8 | 20 | A |
| 261 | Y | CE1 | 40.5 | 31.0 | 40.6 | 24 | A |
| 261 | Y | CD2 | 43.2 | 31.1 | 40.1 | 20 | A |
| 261 | Y | CE2 | 42.5 | 29.9 | 39.8 | 24 | A |
| 261 | Y | CZ  | 41.2 | 29.9 | 40.1 | 24 | A |
| 261 | Y | OH  | 40.4 | 28.7 | 39.9 | 26 | A |
| 261 | Y | C   | 43.9 | 32.6 | 43.1 | 18 | A |
| 261 | Y | O   | 43.2 | 32.0 | 43.9 | 18 | A |
| 262 | L | N   | 45.2 | 32.3 | 42.9 | 18 | A |
| 262 | L | CA  | 45.8 | 31.2 | 43.6 | 20 | A |
| 262 | L | CB  | 47.2 | 30.9 | 43.2 | 19 | A |
| 262 | L | CG  | 47.4 | 30.6 | 41.7 | 20 | A |
| 262 | L | CD1 | 48.9 | 30.5 | 41.3 | 19 | A |
| 262 | L | CD2 | 46.7 | 29.3 | 41.4 | 21 | A |
| 262 | L | C   | 45.7 | 31.3 | 45.1 | 20 | A |
| 262 | L | O   | 45.4 | 30.3 | 45.8 | 20 | A |
| 263 | L | N   | 46.0 | 32.5 | 45.7 | 21 | A |
| 263 | L | CA  | 45.9 | 32.7 | 47.1 | 22 | A |
| 263 | L | CB  | 46.5 | 34.1 | 47.5 | 22 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 263 | L | CG | 48.0 | 34.3 | 47.3 | 25 | A |
|---|---|---|---|---|---|---|---|
| 263 | L | CD1 | 48.3 | 35.8 | 47.6 | 24 | A |
| 263 | L | CD2 | 48.8 | 33.4 | 48.3 | 25 | A |
| 263 | L | C | 44.5 | 32.6 | 47.7 | 21 | A |
| 263 | L | O | 44.3 | 32.3 | 48.8 | 21 | A |
| 264 | S | N | 43.5 | 32.8 | 46.8 | 21 | A |
| 264 | S | CA | 42.1 | 32.7 | 47.2 | 20 | A |
| 264 | S | CB | 41.2 | 33.5 | 46.2 | 21 | A |
| 264 | S | OG | 41.0 | 32.8 | 45.0 | 17 | A |
| 264 | S | C | 41.6 | 31.3 | 47.3 | 21 | A |
| 264 | S | O | 40.5 | 31.1 | 47.8 | 20 | A |
| 265 | L | N | 42.3 | 30.3 | 46.7 | 21 | A |
| 265 | L | CA | 41.8 | 28.9 | 46.7 | 22 | A |
| 265 | L | CB | 42.5 | 28.2 | 45.6 | 22 | A |
| 265 | L | CG | 42.2 | 28.7 | 44.2 | 22 | A |
| 265 | L | CD1 | 43.0 | 27.9 | 43.1 | 19 | A |
| 265 | L | CD2 | 40.7 | 28.6 | 43.9 | 21 | A |
| 265 | L | C | 42.1 | 28.2 | 48.0 | 23 | A |
| 265 | L | O | 43.1 | 28.5 | 48.7 | 23 | A |
| 266 | P | N | 41.2 | 27.3 | 48.4 | 24 | A |
| 266 | P | CD | 39.9 | 27.0 | 47.8 | 24 | A |
| 266 | P | CA | 41.4 | 26.5 | 49.6 | 25 | A |
| 266 | P | CB | 40.1 | 25.7 | 49.7 | 25 | A |
| 266 | P | CG | 39.1 | 26.5 | 48.9 | 27 | A |
| 266 | P | C | 42.6 | 25.6 | 49.4 | 26 | A |
| 266 | P | O | 42.9 | 25.2 | 48.3 | 25 | A |
| 267 | H | N | 43.3 | 25.4 | 50.5 | 28 | A |
| 267 | H | CA | 44.5 | 24.6 | 50.4 | 30 | A |
| 267 | H | CB | 45.2 | 24.4 | 51.8 | 33 | A |
| 267 | H | CG | 46.4 | 23.5 | 51.7 | 35 | A |
| 267 | H | CD2 | 47.3 | 23.3 | 50.8 | 36 | A |
| 267 | H | ND1 | 46.8 | 22.8 | 52.8 | 37 | A |
| 267 | H | CE1 | 47.8 | 22.1 | 52.5 | 38 | A |
| 267 | H | NE2 | 48.2 | 22.3 | 51.3 | 37 | A |
| 267 | H | C | 44.2 | 23.2 | 49.9 | 30 | A |
| 267 | H | O | 43.2 | 22.6 | 50.4 | 30 | A |
| 268 | K | N | 44.9 | 22.7 | 48.9 | 30 | A |
| 268 | K | CA | 44.7 | 21.3 | 48.4 | 32 | A |
| 268 | K | CB | 44.1 | 21.5 | 46.9 | 35 | A |
| 268 | K | CG | 43.8 | 20.2 | 46.2 | 39 | A |
| 268 | K | CD | 42.6 | 19.5 | 46.8 | 40 | A |
| 268 | K | CE | 42.3 | 18.2 | 46.1 | 42 | A |
| 268 | K | NZ | 43.5 | 17.2 | 46.1 | 40 | A |
| 268 | K | C | 46.0 | 20.5 | 48.4 | 32 | A |
| 268 | K | O | 47.0 | 21.0 | 47.9 | 32 | A |
| 269 | N | N | 45.9 | 19.3 | 48.9 | 32 | A |
| 269 | N | CA | 47.1 | 18.5 | 48.9 | 33 | A |
| 269 | N | CB | 47.1 | 17.5 | 50.1 | 36 | A |
| 269 | N | CG | 47.5 | 18.1 | 51.4 | 37 | A |
| 269 | N | OD1 | 48.6 | 18.7 | 51.6 | 38 | A |
| 269 | N | ND2 | 46.5 | 18.1 | 52.4 | 39 | A |
| 269 | N | C | 47.4 | 17.7 | 47.6 | 32 | A |
| 269 | N | O | 46.5 | 17.3 | 46.9 | 29 | A |
| 270 | K | N | 48.7 | 17.5 | 47.4 | 33 | A |
| 270 | K | CA | 49.1 | 16.8 | 46.2 | 35 | A |
| 270 | K | CB | 50.6 | 16.7 | 46.1 | 36 | A |
| 270 | K | CG | 51.2 | 16.0 | 44.9 | 38 | A |
| 270 | K | CD | 52.7 | 15.9 | 44.9 | 40 | A |
| 270 | K | CE | 53.2 | 15.3 | 43.6 | 41 | A |
| 270 | K | NZ | 52.9 | 16.1 | 42.4 | 41 | A |
| 270 | K | C | 48.5 | 15.3 | 46.2 | 35 | A |
| 270 | K | O | 48.5 | 14.7 | 47.3 | 35 | A |
| 271 | V | N | 48.1 | 14.8 | 45.1 | 36 | A |
| 271 | V | CA | 47.6 | 13.4 | 45.0 | 36 | A |
| 271 | V | CB | 46.5 | 13.3 | 44.0 | 36 | A |
| 271 | V | CG1 | 46.1 | 11.9 | 43.8 | 37 | A |
| 271 | V | CG2 | 45.2 | 14.1 | 44.5 | 37 | A |
| 271 | V | C | 48.8 | 12.6 | 44.5 | 36 | A |
| 271 | V | O | 49.3 | 12.8 | 43.4 | 36 | A |
| 272 | P | N | 49.2 | 11.6 | 45.3 | 35 | A |
| 272 | P | CD | 48.5 | 11.2 | 46.6 | 35 | A |
| 272 | P | CA | 50.3 | 10.7 | 44.9 | 33 | A |
| 272 | P | CB | 50.2 | 9.6 | 46.0 | 35 | A |
| 272 | P | CG | 49.6 | 10.3 | 47.2 | 36 | A |
| 272 | P | C | 50.1 | 10.1 | 43.5 | 32 | A |
| 272 | P | O | 49.1 | 9.6 | 43.1 | 31 | A |
| 273 | W | N | 51.2 | 10.1 | 42.8 | 30 | A |
| 273 | W | CA | 51.2 | 9.5 | 41.5 | 29 | A |
| 273 | W | CB | 52.5 | 9.8 | 40.7 | 28 | A |
| 273 | W | CG | 52.8 | 11.2 | 40.5 | 27 | A |
| 273 | W | CD2 | 52.0 | 12.1 | 39.6 | 25 | A |
| 273 | W | CE2 | 52.7 | 13.4 | 39.7 | 26 | A |
| 273 | W | CE3 | 50.9 | 11.9 | 38.8 | 25 | A |
| 273 | W | CD1 | 53.8 | 12.0 | 41.0 | 27 | A |
| 273 | W | NE1 | 53.7 | 13.3 | 40.5 | 26 | A |
| 273 | W | CZ2 | 52.2 | 14.5 | 39.0 | 26 | A |
| 273 | W | CZ3 | 50.4 | 13.0 | 38.1 | 28 | A |
| 273 | W | CH2 | 51.0 | 14.3 | 38.2 | 27 | A |
| 273 | W | C | 50.9 | 8.0 | 41.5 | 29 | A |
| 273 | W | O | 50.2 | 7.5 | 40.6 | 28 | A |
| 274 | N | N | 51.4 | 7.3 | 42.5 | 30 | A |
| 274 | N | CA | 51.2 | 5.9 | 42.6 | 33 | A |
| 274 | N | CB | 52.1 | 5.2 | 43.6 | 37 | A |
| 274 | N | CG | 52.1 | 5.9 | 45.0 | 42 | A |
| 274 | N | OD1 | 51.0 | 6.0 | 45.6 | 44 | A |
| 274 | N | ND2 | 53.2 | 6.3 | 45.5 | 46 | A |
| 274 | N | C | 49.7 | 5.6 | 43.0 | 33 | A |
| 274 | N | O | 49.3 | 4.4 | 42.9 | 34 | A |
| 275 | R | N | 49.0 | 6.6 | 43.5 | 33 | A |
| 275 | R | CA | 47.6 | 6.3 | 43.8 | 33 | A |
| 275 | R | CB | 47.1 | 7.3 | 44.9 | 37 | A |
| 275 | R | CG | 47.6 | 6.9 | 46.3 | 43 | A |
| 275 | R | CD | 47.2 | 8.0 | 47.3 | 49 | A |
| 275 | R | NE | 45.8 | 8.2 | 47.3 | 53 | A |
| 275 | R | CZ | 45.2 | 9.0 | 48.2 | 55 | A |
| 275 | R | NH1 | 45.9 | 9.7 | 49.1 | 55 | A |
| 275 | R | NH2 | 43.8 | 9.2 | 48.1 | 56 | A |
| 275 | R | C | 46.7 | 6.5 | 42.5 | 32 | A |
| 275 | R | O | 45.7 | 5.8 | 42.3 | 31 | A |
| 276 | L | N | 47.2 | 7.4 | 41.6 | 30 | A |
| 276 | L | CA | 46.5 | 7.6 | 40.4 | 30 | A |
| 276 | L | CB | 46.9 | 8.9 | 39.7 | 31 | A |
| 276 | L | CG | 46.3 | 10.2 | 40.3 | 34 | A |
| 276 | L | CD1 | 46.9 | 11.4 | 39.6 | 35 | A |
| 276 | L | CD2 | 44.8 | 10.2 | 40.1 | 35 | A |
| 276 | L | C | 46.9 | 6.5 | 39.4 | 27 | A |
| 276 | L | O | 46.0 | 6.0 | 38.6 | 27 | A |
| 277 | F | N | 48.1 | 6.0 | 39.5 | 28 | A |
| 277 | F | CA | 48.6 | 5.0 | 38.6 | 28 | A |
| 277 | F | CB | 49.7 | 5.6 | 37.6 | 27 | A |
| 277 | F | CG | 49.1 | 6.8 | 36.9 | 26 | A |
| 277 | F | CD1 | 48.2 | 6.6 | 35.8 | 27 | A |
| 277 | F | CD2 | 49.6 | 8.1 | 37.2 | 26 | A |
| 277 | F | CE1 | 47.7 | 7.7 | 35.1 | 28 | A |
| 277 | F | CE2 | 49.1 | 9.2 | 36.4 | 27 | A |
| 277 | F | CZ | 48.1 | 8.9 | 35.4 | 26 | A |
| 277 | F | C | 49.3 | 3.9 | 39.5 | 29 | A |
| 277 | F | O | 50.5 | 3.8 | 39.6 | 29 | A |
| 278 | P | N | 48.5 | 3.1 | 40.2 | 31 | A |
| 278 | P | CD | 47.0 | 3.1 | 40.1 | 31 | A |
| 278 | P | CA | 49.0 | 2.0 | 41.0 | 31 | A |
| 278 | P | CB | 47.7 | 1.5 | 41.7 | 32 | A |
| 278 | P | CG | 46.7 | 1.7 | 40.7 | 31 | A |
| 278 | P | C | 49.7 | 0.9 | 40.4 | 32 | A |
| 278 | P | O | 50.5 | 0.2 | 41.0 | 34 | A |
| 279 | N | N | 49.5 | 0.7 | 39.1 | 33 | A |
| 279 | N | CA | 50.2 | −0.4 | 38.4 | 33 | A |
| 279 | N | CB | 49.2 | −1.2 | 37.5 | 34 | A |
| 279 | N | CG | 48.0 | −1.7 | 38.3 | 33 | A |
| 279 | N | OD1 | 46.9 | −1.6 | 37.9 | 35 | A |

TABLE 4-continued

Structural Coordinates of Ah$_6$-ERK2 [non-phosphorlylated, SEQ ID NO: 5] (form 1)-olomoucine complex Crystals The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 279 | N | ND2 | 48.3 | −2.2 | 39.5 | 32 | A |
|---|---|---|---|---|---|---|---|
| 279 | N | C | 51.4 | 0.1 | 37.5 | 32 | A |
| 279 | N | O | 52.0 | −0.7 | 36.8 | 31 | A |
| 280 | A | N | 51.6 | 1.4 | 37.5 | 31 | A |
| 280 | A | CA | 52.7 | 2.0 | 36.7 | 30 | A |
| 280 | A | CB | 52.5 | 3.5 | 36.5 | 28 | A |
| 280 | A | C | 54.1 | 1.8 | 37.3 | 29 | A |
| 280 | A | O | 54.3 | 1.7 | 38.5 | 28 | A |
| 281 | D | N | 55.1 | 1.7 | 36.4 | 29 | A |
| 281 | D | CA | 56.5 | 1.6 | 36.8 | 29 | A |
| 281 | D | CB | 57.4 | 1.5 | 35.5 | 32 | A |
| 281 | D | CG | 58.8 | 1.3 | 35.8 | 35 | A |
| 281 | D | OD1 | 59.4 | 2.0 | 36.6 | 38 | A |
| 281 | D | OD2 | 59.4 | 0.3 | 35.2 | 39 | A |
| 281 | D | C | 56.9 | 2.8 | 37.6 | 28 | A |
| 281 | D | O | 56.5 | 3.9 | 37.3 | 28 | A |
| 282 | S | N | 57.6 | 2.6 | 38.7 | 26 | A |
| 282 | S | CA | 57.9 | 3.7 | 39.6 | 28 | A |
| 282 | S | CB | 58.5 | 3.2 | 40.9 | 28 | A |
| 282 | S | OG | 59.8 | 2.6 | 40.7 | 34 | A |
| 282 | S | C | 58.9 | 4.7 | 38.9 | 27 | A |
| 282 | S | O | 58.9 | 5.9 | 39.3 | 26 | A |
| 283 | K | N | 59.7 | 4.2 | 38.0 | 27 | A |
| 283 | K | CA | 60.6 | 5.2 | 37.3 | 25 | A |
| 283 | K | CB | 61.7 | 4.4 | 36.5 | 27 | A |
| 283 | K | CG | 62.8 | 3.8 | 37.4 | 29 | A |
| 283 | K | CD | 63.8 | 3.0 | 36.7 | 32 | A |
| 283 | K | CE | 64.8 | 2.4 | 37.6 | 34 | A |
| 283 | K | NZ | 65.8 | 1.5 | 37.0 | 35 | A |
| 283 | K | C | 59.8 | 6.0 | 36.4 | 22 | A |
| 283 | K | O | 60.1 | 7.2 | 36.2 | 21 | A |
| 284 | A | N | 58.7 | 5.5 | 35.8 | 22 | A |
| 284 | A | CA | 57.9 | 6.2 | 34.9 | 22 | A |
| 284 | A | CB | 56.8 | 5.3 | 34.2 | 21 | A |
| 284 | A | C | 57.2 | 7.3 | 35.7 | 22 | A |
| 284 | A | O | 57.0 | 8.5 | 35.2 | 22 | A |
| 285 | L | N | 56.7 | 7.0 | 36.9 | 21 | A |
| 285 | L | CA | 56.0 | 8.0 | 37.7 | 21 | A |
| 285 | L | CB | 55.3 | 7.3 | 38.9 | 23 | A |
| 285 | L | CG | 54.2 | 6.3 | 38.6 | 22 | A |
| 285 | L | CD1 | 53.6 | 5.9 | 39.9 | 23 | A |
| 285 | L | CD2 | 53.2 | 6.9 | 37.6 | 22 | A |
| 285 | L | C | 57.0 | 9.1 | 38.2 | 21 | A |
| 285 | L | O | 56.6 | 10.2 | 38.4 | 23 | A |
| 286 | D | N | 58.2 | 8.7 | 38.4 | 21 | A |
| 286 | D | CA | 59.2 | 9.7 | 38.8 | 21 | A |
| 286 | D | CB | 60.5 | 9.1 | 39.2 | 22 | A |
| 286 | D | CG | 61.5 | 10.1 | 39.7 | 26 | A |
| 286 | D | OD1 | 62.4 | 10.5 | 38.9 | 25 | A |
| 286 | D | OD2 | 61.4 | 10.5 | 40.9 | 31 | A |
| 286 | D | C | 59.5 | 10.7 | 37.6 | 20 | A |
| 286 | D | O | 59.6 | 11.9 | 37.9 | 21 | A |
| 287 | L | N | 59.6 | 10.2 | 36.4 | 21 | A |
| 287 | L | CA | 59.8 | 11.1 | 35.3 | 21 | A |
| 287 | L | CB | 60.1 | 10.2 | 34.0 | 18 | A |
| 287 | L | CG | 60.3 | 10.9 | 32.7 | 20 | A |
| 287 | L | CD1 | 61.3 | 12.1 | 32.9 | 17 | A |
| 287 | L | CD2 | 60.8 | 10.0 | 31.6 | 19 | A |
| 287 | L | C | 58.5 | 11.9 | 35.0 | 20 | A |
| 287 | L | O | 58.5 | 13.1 | 34.8 | 22 | A |
| 288 | L | N | 57.3 | 11.2 | 35.2 | 20 | A |
| 288 | L | CA | 56.0 | 11.9 | 35.0 | 19 | A |
| 288 | L | CB | 54.9 | 10.9 | 35.3 | 19 | A |
| 288 | L | CG | 53.4 | 11.5 | 35.2 | 19 | A |
| 288 | L | CD1 | 53.2 | 12.0 | 33.8 | 15 | A |
| 288 | L | CD2 | 52.4 | 10.4 | 35.6 | 20 | A |
| 288 | L | C | 55.9 | 13.1 | 36.0 | 20 | A |
| 288 | L | O | 55.5 | 14.2 | 35.6 | 20 | A |
| 289 | D | N | 56.4 | 12.9 | 37.2 | 19 | A |
| 289 | D | CA | 56.4 | 13.9 | 38.2 | 19 | A |
| 289 | D | CB | 56.9 | 13.4 | 39.6 | 20 | A |
| 289 | D | CG | 56.9 | 14.4 | 40.7 | 21 | A |
| 289 | D | OD1 | 55.8 | 14.8 | 41.1 | 24 | A |
| 289 | D | OD2 | 58.0 | 14.8 | 41.1 | 23 | A |
| 289 | D | C | 57.2 | 15.1 | 37.8 | 18 | A |
| 289 | D | O | 56.8 | 16.3 | 38.0 | 17 | A |
| 290 | K | N | 58.3 | 14.9 | 37.2 | 18 | A |
| 290 | K | CA | 59.2 | 15.9 | 36.8 | 19 | A |
| 290 | K | CB | 60.6 | 15.4 | 36.5 | 18 | A |
| 290 | K | CG | 61.4 | 14.9 | 37.8 | 20 | A |
| 290 | K | CD | 62.7 | 14.3 | 37.4 | 24 | A |
| 290 | K | CE | 63.6 | 14.2 | 38.7 | 27 | A |
| 290 | K | NZ | 63.0 | 13.4 | 39.8 | 28 | A |
| 290 | K | C | 58.7 | 16.7 | 35.5 | 19 | A |
| 290 | K | O | 59.0 | 17.9 | 35.4 | 21 | A |
| 291 | M | N | 58.0 | 16.0 | 34.7 | 19 | A |
| 291 | M | CA | 57.4 | 16.7 | 33.5 | 19 | A |
| 291 | M | CB | 57.1 | 15.6 | 32.4 | 18 | A |
| 291 | M | CG | 58.2 | 14.8 | 31.9 | 22 | A |
| 291 | M | SD | 57.8 | 13.6 | 30.7 | 26 | A |
| 291 | M | CE | 58.5 | 14.3 | 29.3 | 28 | A |
| 291 | M | C | 56.2 | 17.5 | 33.8 | 19 | A |
| 291 | M | O | 55.9 | 18.5 | 33.2 | 18 | A |
| 292 | L | N | 55.4 | 17.0 | 34.8 | 19 | A |
| 292 | L | CA | 54.2 | 17.7 | 35.2 | 19 | A |
| 292 | L | CB | 53.1 | 16.7 | 35.5 | 19 | A |
| 292 | L | CG | 52.7 | 15.9 | 34.2 | 16 | A |
| 292 | L | CD1 | 51.5 | 15.0 | 34.5 | 16 | A |
| 292 | L | CD2 | 52.4 | 16.9 | 33.1 | 16 | A |
| 292 | L | C | 54.5 | 18.5 | 36.5 | 20 | A |
| 292 | L | O | 53.7 | 18.5 | 37.4 | 22 | A |
| 293 | T | N | 55.6 | 19.3 | 36.4 | 20 | A |
| 293 | T | CA | 56.0 | 20.1 | 37.5 | 20 | A |
| 293 | T | CB | 57.5 | 20.3 | 37.6 | 23 | A |
| 293 | T | OG1 | 58.1 | 19.1 | 38.0 | 26 | A |
| 293 | T | CG2 | 57.9 | 21.5 | 38.5 | 24 | A |
| 293 | T | C | 55.3 | 21.5 | 37.3 | 19 | A |
| 293 | T | O | 55.3 | 22.0 | 36.2 | 17 | A |
| 294 | F | N | 54.7 | 22.0 | 38.3 | 18 | A |
| 294 | F | CA | 53.9 | 23.3 | 38.2 | 19 | A |
| 294 | F | CB | 53.3 | 23.7 | 39.6 | 19 | A |
| 294 | F | CG | 52.5 | 24.9 | 39.6 | 20 | A |
| 294 | F | CD1 | 51.2 | 24.9 | 39.1 | 20 | A |
| 294 | F | CD2 | 53.0 | 26.2 | 39.9 | 20 | A |
| 294 | F | CE1 | 50.4 | 26.0 | 39.0 | 22 | A |
| 294 | F | CE2 | 52.2 | 27.3 | 39.8 | 20 | A |
| 294 | F | CZ | 50.9 | 27.3 | 39.4 | 21 | A |
| 294 | F | C | 54.7 | 24.5 | 37.7 | 19 | A |
| 294 | F | O | 54.3 | 25.1 | 36.7 | 18 | A |
| 295 | N | N | 55.8 | 24.7 | 38.3 | 20 | A |
| 295 | N | CA | 56.7 | 25.8 | 37.9 | 19 | A |
| 295 | N | CB | 57.7 | 26.2 | 39.0 | 22 | A |
| 295 | N | CG | 58.4 | 27.5 | 38.8 | 26 | A |
| 295 | N | OD1 | 58.7 | 27.8 | 37.7 | 25 | A |
| 295 | N | ND2 | 58.8 | 28.1 | 39.9 | 26 | A |
| 295 | N | C | 57.5 | 25.4 | 36.6 | 21 | A |
| 295 | N | O | 58.3 | 24.5 | 36.7 | 19 | A |
| 296 | P | N | 57.3 | 26.1 | 35.5 | 19 | A |
| 296 | P | CD | 56.3 | 27.2 | 35.3 | 21 | A |
| 296 | P | CA | 58.0 | 25.8 | 34.3 | 22 | A |
| 296 | P | CB | 57.4 | 28.3 | 33.3 | 19 | A |
| 296 | P | CG | 56.9 | 27.9 | 34.1 | 21 | A |
| 296 | P | C | 59.5 | 25.9 | 34.4 | 22 | A |
| 296 | P | O | 60.3 | 25.2 | 33.7 | 22 | A |
| 297 | H | N | 60.0 | 26.8 | 35.3 | 23 | A |
| 297 | H | CA | 61.5 | 26.9 | 35.5 | 25 | A |
| 297 | H | CB | 61.8 | 28.2 | 36.3 | 28 | A |
| 297 | H | CG | 61.2 | 29.4 | 35.7 | 32 | A |
| 297 | H | CD2 | 61.6 | 30.1 | 34.6 | 33 | A |
| 297 | H | ND1 | 60.1 | 30.1 | 36.1 | 34 | A |

TABLE 4-continued

Structural Coordinates of Ah₆-ERK2 [non-phosphorlylated, SEQ ID NO: 5] (form 1)-olomoucine complex Crystals The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| | | | | | | | |
|---|---|---|---|---|---|---|---|
| 297 | H | CE1 | 59.8 | 31.1 | 35.3 | 34 | A |
| 297 | H | NE2 | 60.7 | 31.2 | 34.4 | 35 | A |
| 297 | H | C | 62.1 | 25.7 | 36.2 | 26 | A |
| 297 | H | O | 63.3 | 25.5 | 36.1 | 26 | A |
| 298 | K | N | 61.2 | 25.0 | 36.9 | 24 | A |
| 298 | K | CA | 61.7 | 23.8 | 37.6 | 26 | A |
| 298 | K | CB | 61.0 | 23.7 | 39.0 | 26 | A |
| 298 | K | CG | 61.4 | 24.8 | 39.9 | 29 | A |
| 298 | K | CD | 60.6 | 24.6 | 41.2 | 33 | A |
| 298 | K | CE | 61.0 | 25.7 | 42.2 | 36 | A |
| 298 | K | NZ | 60.0 | 25.6 | 43.4 | 36 | A |
| 298 | K | C | 61.4 | 22.5 | 36.8 | 24 | A |
| 298 | K | O | 61.9 | 21.4 | 37.1 | 26 | A |
| 299 | R | N | 60.6 | 22.6 | 35.8 | 23 | A |
| 299 | R | CA | 60.2 | 21.5 | 35.0 | 22 | A |
| 299 | R | CB | 59.1 | 21.9 | 34.0 | 20 | A |
| 299 | R | CG | 58.4 | 20.8 | 33.3 | 19 | A |
| 299 | R | CD | 57.2 | 21.3 | 32.5 | 18 | A |
| 299 | R | NE | 56.3 | 22.1 | 33.4 | 15 | A |
| 299 | R | CZ | 55.5 | 23.1 | 33.0 | 16 | A |
| 299 | R | NH1 | 55.5 | 23.5 | 31.8 | 14 | A |
| 299 | R | NH2 | 54.8 | 23.7 | 33.9 | 18 | A |
| 299 | R | C | 61.4 | 20.9 | 34.2 | 22 | A |
| 299 | R | O | 62.2 | 21.7 | 33.7 | 22 | A |
| 300 | I | N | 61.5 | 19.6 | 34.1 | 22 | A |
| 300 | I | CA | 62.6 | 18.9 | 33.4 | 22 | A |
| 300 | I | CB | 62.4 | 17.4 | 33.6 | 21 | A |
| 300 | I | CG2 | 61.2 | 16.9 | 32.9 | 21 | A |
| 300 | I | CG1 | 63.7 | 16.7 | 33.1 | 21 | A |
| 300 | I | CD1 | 63.7 | 15.2 | 33.5 | 20 | A |
| 300 | I | C | 62.6 | 19.3 | 31.9 | 21 | A |
| 300 | I | O | 61.6 | 19.5 | 31.3 | 18 | A |
| 301 | E | N | 63.9 | 19.4 | 31.4 | 20 | A |
| 301 | E | CA | 64.0 | 19.8 | 30.0 | 20 | A |
| 301 | E | CB | 65.2 | 20.7 | 29.8 | 23 | A |
| 301 | E | CG | 65.1 | 22.1 | 30.4 | 26 | A |
| 301 | E | CD | 66.1 | 23.1 | 29.9 | 28 | A |
| 301 | E | OE1 | 67.0 | 22.7 | 29.0 | 30 | A |
| 301 | E | OE2 | 66.1 | 24.2 | 30.4 | 33 | A |
| 301 | E | C | 64.2 | 18.5 | 29.2 | 18 | A |
| 301 | E | O | 64.4 | 17.4 | 29.7 | 16 | A |
| 302 | V | N | 64.0 | 18.6 | 27.8 | 18 | A |
| 302 | V | CA | 64.1 | 17.4 | 27.0 | 17 | A |
| 302 | V | CB | 63.8 | 17.7 | 25.5 | 20 | A |
| 302 | V | CG1 | 65.0 | 18.4 | 24.9 | 19 | A |
| 302 | V | CG2 | 63.4 | 16.5 | 24.8 | 18 | A |
| 302 | V | C | 65.3 | 16.5 | 27.1 | 17 | A |
| 302 | V | O | 65.2 | 15.3 | 27.2 | 17 | A |
| 303 | E | N | 66.5 | 17.1 | 27.2 | 18 | A |
| 303 | E | CA | 67.7 | 16.3 | 27.3 | 19 | A |
| 303 | E | CB | 68.9 | 17.2 | 27.1 | 24 | A |
| 303 | E | CG | 69.0 | 17.8 | 25.7 | 28 | A |
| 303 | E | CD | 70.2 | 18.8 | 25.6 | 30 | A |
| 303 | E | OE1 | 70.2 | 19.8 | 26.4 | 32 | A |
| 303 | E | OE2 | 71.0 | 18.6 | 24.7 | 33 | A |
| 303 | E | C | 67.8 | 15.6 | 28.6 | 19 | A |
| 303 | E | O | 68.2 | 14.4 | 28.7 | 20 | A |
| 304 | Q | N | 67.3 | 16.2 | 29.7 | 21 | A |
| 304 | Q | CA | 67.3 | 15.6 | 31.0 | 20 | A |
| 304 | Q | CB | 66.8 | 16.7 | 32.1 | 23 | A |
| 304 | Q | CG | 67.8 | 17.8 | 32.4 | 24 | A |
| 304 | Q | CD | 67.2 | 18.8 | 33.3 | 27 | A |
| 304 | Q | OE1 | 66.3 | 19.6 | 33.0 | 23 | A |
| 304 | Q | NE2 | 67.7 | 18.7 | 34.6 | 25 | A |
| 304 | Q | C | 66.3 | 14.5 | 31.0 | 19 | A |
| 304 | Q | O | 66.5 | 13.4 | 31.7 | 19 | A |
| 305 | A | N | 65.1 | 14.7 | 30.4 | 19 | A |
| 305 | A | CA | 64.1 | 13.6 | 30.3 | 17 | A |
| 305 | A | CB | 62.9 | 14.2 | 29.6 | 17 | A |
| 305 | A | C | 64.7 | 12.4 | 29.6 | 17 | A |
| 305 | A | O | 64.5 | 11.3 | 30.1 | 18 | A |
| 306 | L | N | 65.4 | 12.6 | 28.5 | 17 | A |
| 306 | L | CA | 65.9 | 11.5 | 27.8 | 16 | A |
| 306 | L | CB | 66.7 | 12.0 | 26.5 | 16 | A |
| 306 | L | CG | 65.8 | 12.3 | 25.3 | 16 | A |
| 306 | L | CD1 | 66.5 | 13.2 | 24.3 | 13 | A |
| 306 | L | CD2 | 65.4 | 10.9 | 24.7 | 14 | A |
| 306 | L | C | 67.0 | 10.7 | 28.7 | 19 | A |
| 306 | L | O | 67.2 | 9.5 | 28.5 | 19 | A |
| 307 | A | N | 67.6 | 11.4 | 29.6 | 18 | A |
| 307 | A | CA | 68.6 | 10.9 | 30.5 | 18 | A |
| 307 | A | CB | 69.7 | 12.0 | 30.8 | 16 | A |
| 307 | A | C | 68.1 | 10.3 | 31.8 | 21 | A |
| 307 | A | O | 68.8 | 9.8 | 32.6 | 20 | A |
| 308 | H | N | 66.8 | 10.4 | 31.9 | 20 | A |
| 308 | H | CA | 66.1 | 9.9 | 33.1 | 20 | A |
| 308 | H | CB | 64.6 | 10.3 | 33.1 | 21 | A |
| 308 | H | CG | 63.9 | 9.9 | 34.4 | 21 | A |
| 308 | H | CD2 | 63.7 | 10.7 | 35.5 | 21 | A |
| 308 | H | ND1 | 63.5 | 8.7 | 34.7 | 20 | A |
| 308 | H | CE1 | 62.9 | 8.7 | 35.9 | 22 | A |
| 308 | H | NE2 | 63.0 | 9.9 | 36.4 | 22 | A |
| 308 | H | C | 66.2 | 8.3 | 33.2 | 21 | A |
| 308 | H | O | 66.3 | 7.7 | 32.1 | 21 | A |
| 309 | P | N | 66.4 | 7.7 | 34.4 | 22 | A |
| 309 | P | CD | 66.5 | 8.4 | 35.7 | 24 | A |
| 309 | P | CA | 66.5 | 6.3 | 34.5 | 22 | A |
| 309 | P | CB | 66.5 | 6.1 | 36.0 | 24 | A |
| 309 | P | CG | 67.2 | 7.3 | 36.5 | 24 | A |
| 309 | P | C | 65.4 | 5.4 | 33.8 | 22 | A |
| 309 | P | O | 65.6 | 4.3 | 33.4 | 21 | A |
| 310 | Y | N | 64.2 | 6.0 | 33.7 | 21 | A |
| 310 | Y | CA | 63.1 | 5.3 | 33.0 | 20 | A |
| 310 | Y | CB | 61.8 | 6.1 | 33.1 | 20 | A |
| 310 | Y | CG | 60.6 | 5.4 | 32.4 | 21 | A |
| 310 | Y | CD1 | 60.2 | 4.1 | 32.9 | 19 | A |
| 310 | Y | CE1 | 59.1 | 3.4 | 32.3 | 20 | A |
| 310 | Y | CD2 | 59.9 | 5.9 | 31.3 | 19 | A |
| 310 | Y | CE2 | 58.9 | 5.2 | 30.7 | 20 | A |
| 310 | Y | CZ | 58.5 | 4.0 | 31.2 | 20 | A |
| 310 | Y | OH | 57.4 | 3.3 | 30.6 | 19 | A |
| 310 | Y | C | 63.5 | 4.9 | 31.6 | 19 | A |
| 310 | Y | O | 63.0 | 3.9 | 31.1 | 18 | A |
| 311 | L | N | 64.2 | 5.8 | 30.9 | 20 | A |
| 311 | L | CA | 64.6 | 5.6 | 29.5 | 21 | A |
| 311 | L | CB | 64.3 | 6.9 | 28.7 | 21 | A |
| 311 | L | CG | 62.9 | 7.5 | 28.7 | 23 | A |
| 311 | L | CD1 | 62.9 | 8.8 | 28.0 | 25 | A |
| 311 | L | CD2 | 62.0 | 6.5 | 28.0 | 23 | A |
| 311 | L | C | 66.0 | 5.1 | 29.3 | 22 | A |
| 311 | L | O | 66.5 | 5.1 | 28.2 | 22 | A |
| 312 | E | N | 66.7 | 4.7 | 30.4 | 24 | A |
| 312 | E | CA | 68.1 | 4.3 | 30.3 | 27 | A |
| 312 | E | CB | 68.6 | 3.9 | 31.7 | 28 | A |
| 312 | E | CG | 67.9 | 2.7 | 32.2 | 34 | A |
| 312 | E | CD | 68.2 | 2.4 | 33.7 | 39 | A |
| 312 | E | OE1 | 69.4 | 2.4 | 34.0 | 39 | A |
| 312 | E | OE2 | 67.3 | 2.3 | 34.5 | 40 | A |
| 312 | E | C | 68.5 | 3.3 | 29.3 | 26 | A |
| 312 | E | O | 69.6 | 3.2 | 28.8 | 26 | A |
| 313 | Q | N | 67.5 | 2.4 | 28.9 | 26 | A |
| 313 | Q | CA | 67.8 | 1.4 | 27.9 | 27 | A |
| 313 | Q | CB | 66.8 | 0.2 | 28.0 | 29 | A |
| 313 | Q | CG | 65.4 | 0.6 | 27.6 | 32 | A |
| 313 | Q | CD | 64.4 | −0.5 | 27.8 | 35 | A |
| 313 | Q | OE1 | 64.5 | −1.5 | 27.2 | 36 | A |
| 313 | Q | NE2 | 63.5 | −0.3 | 28.8 | 34 | A |
| 313 | Q | C | 67.9 | 1.9 | 26.5 | 26 | A |
| 313 | Q | O | 68.4 | 1.2 | 25.6 | 26 | A |
| 314 | Y | N | 67.3 | 3.1 | 26.3 | 25 | A |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| | | | | | | | |
|---|---|---|---|---|---|---|---|
| 314 | Y | CA | 67.3 | 3.6 | 24.9 | 24 | A |
| 314 | Y | CB | 65.9 | 4.0 | 24.5 | 23 | A |
| 314 | Y | CG | 65.0 | 2.9 | 24.4 | 24 | A |
| 314 | Y | CD1 | 65.2 | 1.9 | 23.5 | 23 | A |
| 314 | Y | CE1 | 64.4 | 0.7 | 23.4 | 27 | A |
| 314 | Y | CD2 | 63.9 | 2.8 | 25.2 | 22 | A |
| 314 | Y | CE2 | 63.0 | 1.6 | 25.1 | 23 | A |
| 314 | Y | CZ | 63.3 | 0.6 | 24.2 | 24 | A |
| 314 | Y | OH | 62.5 | −0.5 | 24.1 | 25 | A |
| 314 | Y | C | 68.2 | 4.9 | 24.8 | 21 | A |
| 314 | Y | O | 68.7 | 5.2 | 23.8 | 21 | A |
| 315 | Y | N | 68.5 | 5.5 | 26.0 | 21 | A |
| 315 | Y | CA | 69.3 | 6.7 | 26.0 | 20 | A |
| 315 | Y | CB | 69.5 | 7.1 | 27.4 | 21 | A |
| 315 | Y | CG | 70.3 | 8.4 | 27.6 | 22 | A |
| 315 | Y | CD1 | 70.0 | 9.5 | 26.8 | 22 | A |
| 315 | Y | CE1 | 70.6 | 10.8 | 27.0 | 23 | A |
| 315 | Y | CD2 | 71.2 | 8.6 | 28.6 | 23 | A |
| 315 | Y | CE2 | 71.9 | 9.9 | 28.8 | 22 | A |
| 315 | Y | CZ | 71.5 | 10.9 | 28.0 | 22 | A |
| 315 | Y | OH | 72.1 | 12.1 | 28.2 | 23 | A |
| 315 | Y | C | 70.7 | 6.5 | 25.3 | 19 | A |
| 315 | Y | O | 71.4 | 5.6 | 25.7 | 17 | A |
| 316 | D | N | 70.9 | 7.3 | 24.3 | 20 | A |
| 316 | D | CA | 72.2 | 7.3 | 23.5 | 20 | A |
| 316 | D | CB | 72.2 | 6.2 | 22.5 | 20 | A |
| 316 | D | CG | 73.5 | 6.2 | 21.7 | 22 | A |
| 316 | D | OD1 | 74.4 | 6.9 | 22.0 | 20 | A |
| 316 | D | OD2 | 73.6 | 5.4 | 20.7 | 21 | A |
| 316 | D | C | 72.3 | 8.7 | 22.8 | 21 | A |
| 316 | D | O | 71.8 | 8.8 | 21.7 | 18 | A |
| 317 | P | N | 72.9 | 9.7 | 23.5 | 21 | A |
| 317 | P | CD | 73.6 | 9.6 | 24.8 | 19 | A |
| 317 | P | CA | 73.1 | 11.0 | 22.9 | 21 | A |
| 317 | P | CB | 73.9 | 11.7 | 23.9 | 23 | A |
| 317 | P | CG | 73.6 | 11.0 | 25.2 | 22 | A |
| 317 | P | C | 73.7 | 11.1 | 21.5 | 21 | A |
| 317 | P | O | 73.3 | 12.0 | 20.7 | 23 | A |
| 318 | S | N | 74.5 | 10.1 | 21.2 | 21 | A |
| 318 | S | CA | 75.2 | 10.1 | 19.9 | 20 | A |
| 318 | S | CB | 76.4 | 9.2 | 19.9 | 19 | A |
| 318 | S | OG | 76.0 | 7.8 | 20.0 | 22 | A |
| 318 | S | C | 74.2 | 9.6 | 18.8 | 21 | A |
| 318 | S | O | 74.4 | 9.8 | 17.6 | 18 | A |
| 319 | D | N | 73.1 | 9.0 | 19.3 | 20 | A |
| 319 | D | CA | 72.0 | 8.6 | 18.3 | 19 | A |
| 319 | D | CB | 71.8 | 7.1 | 18.5 | 19 | A |
| 319 | D | CG | 70.9 | 6.5 | 17.4 | 22 | A |
| 319 | D | OD1 | 71.1 | 6.8 | 16.2 | 19 | A |
| 319 | D | OD2 | 70.1 | 5.6 | 17.7 | 20 | A |
| 319 | D | C | 70.8 | 9.4 | 18.5 | 20 | A |
| 319 | D | O | 69.6 | 8.9 | 18.2 | 21 | A |
| 320 | E | N | 70.9 | 10.6 | 19.1 | 18 | A |
| 320 | E | CA | 69.8 | 11.5 | 19.3 | 19 | A |
| 320 | E | CB | 69.6 | 11.6 | 20.8 | 19 | A |
| 320 | E | CG | 68.9 | 10.3 | 21.4 | 19 | A |
| 320 | E | CD | 69.1 | 10.1 | 22.8 | 23 | A |
| 320 | E | OE1 | 69.6 | 11.1 | 23.5 | 23 | A |
| 320 | E | OE2 | 68.8 | 9.0 | 23.4 | 22 | A |
| 320 | E | C | 70.3 | 12.8 | 18.7 | 19 | A |
| 320 | E | O | 70.7 | 13.8 | 19.4 | 21 | A |
| 321 | P | N | 70.2 | 12.9 | 17.4 | 19 | A |
| 321 | P | CD | 69.6 | 11.9 | 16.5 | 19 | A |
| 321 | P | CA | 70.6 | 14.1 | 16.6 | 20 | A |
| 321 | P | CB | 70.5 | 13.7 | 15.1 | 20 | A |
| 321 | P | CG | 69.4 | 12.7 | 15.2 | 21 | A |
| 321 | P | C | 69.9 | 15.4 | 16.9 | 21 | A |
| 321 | P | O | 68.7 | 15.4 | 17.3 | 19 | A |
| 322 | I | N | 70.6 | 16.5 | 16.7 | 21 | A |
| 322 | I | CA | 70.1 | 17.8 | 16.9 | 22 | A |
| 322 | I | CB | 70.9 | 18.7 | 17.9 | 21 | A |
| 322 | I | CG2 | 70.9 | 18.0 | 19.3 | 21 | A |
| 322 | I | CG1 | 72.3 | 18.9 | 17.4 | 24 | A |
| 322 | I | CD1 | 73.1 | 19.9 | 18.2 | 25 | A |
| 322 | I | C | 70.1 | 18.5 | 15.5 | 23 | A |
| 322 | I | O | 70.8 | 18.1 | 14.6 | 22 | A |
| 323 | A | N | 69.4 | 19.6 | 15.4 | 24 | A |
| 323 | A | CA | 69.3 | 20.4 | 14.1 | 26 | A |
| 323 | A | CB | 68.1 | 21.4 | 14.2 | 23 | A |
| 323 | A | C | 70.6 | 21.1 | 13.8 | 27 | A |
| 323 | A | O | 71.3 | 21.7 | 14.6 | 25 | A |
| 324 | E | N | 70.9 | 21.1 | 12.5 | 31 | A |
| 324 | E | CA | 72.1 | 21.7 | 11.9 | 36 | A |
| 324 | E | CB | 72.4 | 21.2 | 10.6 | 39 | A |
| 324 | E | CG | 73.3 | 22.2 | 9.7 | 47 | A |
| 324 | E | CD | 73.7 | 21.6 | 8.4 | 51 | A |
| 324 | E | OE1 | 72.9 | 20.8 | 7.8 | 54 | A |
| 324 | E | OE2 | 74.8 | 21.9 | 7.9 | 52 | A |
| 324 | E | C | 71.8 | 23.2 | 11.8 | 38 | A |
| 324 | E | O | 72.5 | 24.1 | 12.3 | 38 | A |
| 325 | A | N | 70.6 | 23.5 | 11.3 | 39 | A |
| 325 | A | CA | 70.2 | 24.9 | 11.0 | 39 | A |
| 325 | A | CB | 69.9 | 25.1 | 9.5 | 40 | A |
| 325 | A | C | 69.0 | 25.3 | 11.8 | 38 | A |
| 325 | A | O | 67.8 | 25.2 | 11.4 | 37 | A |
| 326 | P | N | 69.2 | 25.8 | 13.1 | 37 | A |
| 326 | P | CD | 70.4 | 25.7 | 13.8 | 38 | A |
| 326 | P | CA | 68.1 | 26.2 | 14.0 | 37 | A |
| 326 | P | CB | 68.8 | 26.5 | 15.3 | 36 | A |
| 326 | P | CG | 70.0 | 25.6 | 15.2 | 38 | A |
| 326 | P | C | 67.4 | 27.5 | 13.4 | 37 | A |
| 326 | P | O | 68.1 | 28.3 | 12.7 | 34 | A |
| 327 | F | N | 66.2 | 27.7 | 13.8 | 38 | A |
| 327 | F | CA | 65.5 | 28.9 | 13.4 | 40 | A |
| 327 | F | CB | 63.9 | 28.7 | 13.4 | 38 | A |
| 327 | F | CG | 63.4 | 27.9 | 12.2 | 36 | A |
| 327 | F | CD1 | 63.0 | 28.6 | 11.1 | 36 | A |
| 327 | F | CD2 | 63.4 | 26.5 | 12.3 | 34 | A |
| 327 | F | CE1 | 62.6 | 27.9 | 10.0 | 35 | A |
| 327 | F | CE2 | 62.9 | 25.8 | 11.2 | 34 | A |
| 327 | F | CZ | 62.5 | 26.5 | 10.0 | 36 | A |
| 327 | F | C | 65.8 | 29.9 | 14.5 | 43 | A |
| 327 | F | O | 65.1 | 30.2 | 15.4 | 43 | A |
| 328 | K | N | 67.0 | 30.6 | 14.3 | 48 | A |
| 328 | K | CA | 67.5 | 31.6 | 15.2 | 51 | A |
| 328 | K | CB | 68.9 | 32.0 | 14.9 | 51 | A |
| 328 | K | CG | 69.9 | 30.9 | 14.9 | 53 | A |
| 328 | K | CD | 71.3 | 31.4 | 14.5 | 55 | A |
| 328 | K | CE | 71.4 | 31.9 | 13.1 | 55 | A |
| 328 | K | NZ | 71.0 | 30.9 | 12.1 | 55 | A |
| 328 | K | C | 66.6 | 32.8 | 15.4 | 53 | A |
| 328 | K | O | 66.5 | 33.3 | 16.5 | 54 | A |
| 329 | F | N | 66.0 | 33.3 | 14.3 | 55 | A |
| 329 | F | CA | 65.2 | 34.5 | 14.4 | 57 | A |
| 329 | F | CB | 65.7 | 35.5 | 13.4 | 59 | A |
| 329 | F | CG | 67.2 | 35.8 | 13.4 | 60 | A |
| 329 | F | CD1 | 68.0 | 35.0 | 12.7 | 61 | A |
| 329 | F | CD2 | 67.7 | 36.8 | 14.2 | 60 | A |
| 329 | F | CE1 | 69.4 | 35.2 | 12.8 | 61 | A |
| 329 | F | CE2 | 69.1 | 37.0 | 14.3 | 61 | A |
| 329 | F | CZ | 69.9 | 36.2 | 13.6 | 60 | A |
| 329 | F | C | 63.7 | 34.2 | 14.1 | 57 | A |
| 329 | F | O | 63.3 | 33.2 | 13.5 | 57 | A |
| 330 | D | N | 62.8 | 35.1 | 14.6 | 59 | A |
| 330 | D | CA | 61.4 | 34.9 | 14.5 | 60 | A |
| 330 | D | CB | 60.6 | 36.0 | 15.3 | 60 | A |
| 330 | D | CG | 61.0 | 35.9 | 16.8 | 61 | A |
| 330 | D | OD1 | 61.0 | 34.8 | 17.4 | 60 | A |
| 330 | D | OD2 | 61.4 | 37.0 | 17.3 | 61 | A |
| 330 | D | C | 61.1 | 35.1 | 13.0 | 60 | A |

TABLE 4-continued

Structural Coordinates of Ah₆-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 330 | D | O | 61.7 | 35.9 | 12.3 | 59 | A |
|---|---|---|---|---|---|---|---|
| 331 | M | N | 60.0 | 34.4 | 12.5 | 60 | A |
| 331 | M | CA | 59.6 | 34.5 | 11.1 | 61 | A |
| 331 | M | CB | 58.8 | 33.2 | 10.8 | 61 | A |
| 331 | M | CG | 59.4 | 31.9 | 11.2 | 61 | A |
| 331 | M | SD | 58.4 | 30.5 | 10.8 | 61 | A |
| 331 | M | CE | 59.6 | 29.6 | 9.7 | 61 | A |
| 331 | M | C | 58.7 | 35.7 | 10.9 | 61 | A |
| 331 | M | O | 58.6 | 36.2 | 9.7 | 60 | A |
| 332 | E | N | 58.2 | 36.3 | 11.9 | 61 | A |
| 332 | E | CA | 57.3 | 37.5 | 11.9 | 61 | A |
| 332 | E | CB | 58.2 | 38.7 | 11.8 | 62 | A |
| 332 | E | CG | 59.0 | 38.8 | 10.6 | 64 | A |
| 332 | E | CD | 60.4 | 39.4 | 10.9 | 65 | A |
| 332 | E | OE1 | 60.5 | 40.5 | 11.5 | 66 | A |
| 332 | E | OE2 | 61.4 | 38.8 | 10.5 | 66 | A |
| 332 | E | C | 56.3 | 37.4 | 10.8 | 61 | A |
| 332 | E | O | 56.4 | 38.1 | 9.8 | 61 | A |
| 333 | L | N | 55.2 | 36.6 | 11.0 | 60 | A |
| 333 | L | CA | 54.1 | 36.4 | 10.0 | 61 | A |
| 333 | L | CB | 54.0 | 34.9 | 9.7 | 58 | A |
| 333 | L | CG | 55.2 | 34.1 | 9.4 | 55 | A |
| 333 | L | CD1 | 54.9 | 32.7 | 9.3 | 55 | A |
| 333 | L | CD2 | 55.8 | 34.6 | 8.0 | 54 | A |
| 333 | L | C | 52.8 | 37.0 | 10.5 | 61 | A |
| 333 | L | O | 51.8 | 37.0 | 9.7 | 61 | A |
| 334 | D | N | 52.8 | 37.5 | 11.7 | 63 | A |
| 334 | D | CA | 51.6 | 38.0 | 12.3 | 64 | A |
| 334 | D | CB | 51.8 | 38.2 | 13.8 | 66 | A |
| 334 | D | CG | 53.0 | 39.0 | 14.1 | 69 | A |
| 334 | D | OD1 | 54.1 | 38.5 | 13.8 | 70 | A |
| 334 | D | OD2 | 52.9 | 40.1 | 14.8 | 71 | A |
| 334 | D | C | 51.1 | 39.3 | 11.7 | 63 | A |
| 334 | D | O | 49.9 | 39.6 | 11.6 | 62 | A |
| 335 | D | N | 52.0 | 40.1 | 11.3 | 62 | A |
| 335 | D | CA | 51.7 | 41.4 | 10.6 | 61 | A |
| 335 | D | CB | 52.7 | 42.5 | 11.0 | 64 | A |
| 335 | D | CG | 54.1 | 42.1 | 10.7 | 65 | A |
| 335 | D | OD1 | 55.1 | 42.9 | 10.8 | 66 | A |
| 335 | D | OD2 | 54.3 | 40.9 | 10.3 | 64 | A |
| 335 | D | C | 51.6 | 41.3 | 9.1 | 60 | A |
| 335 | D | O | 51.8 | 42.4 | 8.4 | 60 | A |
| 336 | L | N | 51.3 | 40.2 | 8.6 | 57 | A |
| 336 | L | CA | 51.2 | 40.0 | 7.1 | 54 | A |
| 336 | L | CB | 52.2 | 38.9 | 6.7 | 53 | A |
| 336 | L | CG | 53.7 | 39.1 | 7.0 | 53 | A |
| 336 | L | CD1 | 54.5 | 37.9 | 6.6 | 51 | A |
| 336 | L | CD2 | 54.2 | 40.3 | 6.4 | 53 | A |
| 336 | L | C | 49.8 | 39.6 | 6.7 | 52 | A |
| 336 | L | O | 49.2 | 38.7 | 7.2 | 52 | A |
| 337 | P | N | 49.3 | 40.3 | 5.6 | 50 | A |
| 337 | P | CD | 49.9 | 41.5 | 5.0 | 49 | A |
| 337 | P | CA | 48.0 | 40.0 | 5.1 | 48 | A |
| 337 | P | CB | 47.7 | 41.2 | 4.2 | 48 | A |
| 337 | P | CG | 49.0 | 41.6 | 3.7 | 49 | A |
| 337 | P | C | 48.0 | 38.7 | 4.4 | 46 | A |
| 337 | P | O | 49.0 | 38.3 | 3.9 | 45 | A |
| 338 | K | N | 46.8 | 38.1 | 4.3 | 45 | A |
| 338 | K | CA | 46.7 | 36.8 | 3.6 | 45 | A |
| 338 | K | CB | 45.3 | 36.2 | 3.6 | 46 | A |
| 338 | K | CG | 44.2 | 37.2 | 3.0 | 45 | A |
| 338 | K | CD | 42.9 | 36.5 | 3.0 | 48 | A |
| 338 | K | CE | 41.8 | 37.5 | 2.6 | 50 | A |
| 338 | K | NZ | 42.1 | 38.2 | 1.3 | 52 | A |
| 338 | K | C | 47.2 | 36.8 | 2.2 | 45 | A |
| 338 | K | O | 47.7 | 35.7 | 1.7 | 45 | A |
| 339 | E | N | 47.2 | 37.9 | 1.5 | 44 | A |
| 339 | E | CA | 47.7 | 38.0 | 0.1 | 43 | A |
| 339 | E | CB | 47.3 | 39.3 | -0.6 | 43 | A |
| 339 | E | CG | 45.9 | 39.6 | -0.6 | 46 | A |
| 339 | E | CD | 45.3 | 40.1 | 0.7 | 47 | A |
| 339 | E | OE1 | 45.8 | 41.0 | 1.3 | 47 | A |
| 339 | E | OE2 | 44.2 | 39.5 | 1.1 | 49 | A |
| 339 | E | C | 49.2 | 37.8 | 0.1 | 42 | A |
| 339 | E | O | 49.7 | 37.0 | -0.7 | 41 | A |
| 340 | K | N | 49.8 | 38.5 | 1.0 | 40 | A |
| 340 | K | CA | 51.3 | 38.4 | 1.2 | 39 | A |
| 340 | K | CB | 51.8 | 39.5 | 2.2 | 39 | A |
| 340 | K | CG | 53.3 | 39.4 | 2.5 | 39 | A |
| 340 | K | CD | 54.1 | 39.6 | 1.2 | 40 | A |
| 340 | K | CE | 55.5 | 39.3 | 1.5 | 41 | A |
| 340 | K | NZ | 56.3 | 39.3 | 0.2 | 45 | A |
| 340 | K | C | 51.7 | 37.0 | 1.6 | 37 | A |
| 340 | K | O | 52.7 | 36.5 | 1.2 | 37 | A |
| 341 | L | N | 50.9 | 36.4 | 2.5 | 36 | A |
| 341 | L | CA | 51.2 | 35.1 | 3.0 | 36 | A |
| 341 | L | CB | 50.2 | 34.7 | 4.2 | 34 | A |
| 341 | L | CG | 50.4 | 35.5 | 5.5 | 35 | A |
| 341 | L | CD1 | 49.4 | 35.2 | 6.5 | 33 | A |
| 341 | L | CD2 | 51.8 | 35.2 | 6.1 | 34 | A |
| 341 | L | C | 51.1 | 34.1 | 1.9 | 35 | A |
| 341 | L | O | 51.9 | 33.2 | 1.8 | 35 | A |
| 342 | K | N | 50.1 | 34.3 | 1.0 | 34 | A |
| 342 | K | CA | 49.9 | 33.4 | -0.1 | 35 | A |
| 342 | K | CB | 48.7 | 33.9 | -0.9 | 36 | A |
| 342 | K | CG | 48.3 | 32.9 | -2.0 | 36 | A |
| 342 | K | CD | 47.2 | 33.6 | -2.9 | 39 | A |
| 342 | K | CE | 46.4 | 32.5 | -3.6 | 39 | A |
| 342 | K | NZ | 47.2 | 31.6 | -4.4 | 41 | A |
| 342 | K | C | 51.1 | 33.4 | -1.0 | 33 | A |
| 342 | K | O | 51.5 | 32.4 | -1.5 | 34 | A |
| 343 | E | N | 51.8 | 34.6 | -1.1 | 34 | A |
| 343 | E | CA | 53.0 | 34.7 | -1.9 | 32 | A |
| 343 | E | CB | 53.4 | 36.1 | -2.1 | 36 | A |
| 343 | E | CG | 52.4 | 37.0 | -2.9 | 40 | A |
| 343 | E | CD | 52.8 | 38.4 | -2.9 | 42 | A |
| 343 | E | OE1 | 54.0 | 38.7 | -3.0 | 43 | A |
| 343 | E | OE2 | 51.8 | 39.3 | -2.7 | 45 | A |
| 343 | E | C | 54.1 | 33.9 | -1.3 | 32 | A |
| 343 | E | O | 55.0 | 33.3 | -2.0 | 31 | A |
| 344 | L | N | 54.2 | 34.0 | 0.0 | 31 | A |
| 344 | L | CA | 55.3 | 33.3 | 0.8 | 30 | A |
| 344 | L | CB | 55.3 | 33.7 | 2.2 | 31 | A |
| 344 | L | CG | 55.6 | 35.2 | 2.5 | 32 | A |
| 344 | L | CD1 | 55.3 | 35.6 | 3.9 | 33 | A |
| 344 | L | CD2 | 57.0 | 35.5 | 2.1 | 34 | A |
| 344 | L | C | 55.1 | 31.8 | 0.6 | 27 | A |
| 344 | L | O | 56.0 | 31.1 | 0.4 | 26 | A |
| 345 | I | N | 53.8 | 31.4 | 0.7 | 27 | A |
| 345 | I | CA | 53.5 | 30.0 | 0.5 | 27 | A |
| 345 | I | CB | 52.0 | 29.8 | 0.8 | 26 | A |
| 345 | I | CG2 | 51.6 | 28.4 | 0.4 | 25 | A |
| 345 | I | CG1 | 51.8 | 29.9 | 2.4 | 28 | A |
| 345 | I | CD1 | 50.3 | 29.8 | 2.8 | 25 | A |
| 345 | I | C | 53.8 | 29.5 | -0.9 | 27 | A |
| 345 | I | O | 54.3 | 28.4 | -1.1 | 26 | A |
| 346 | F | N | 53.6 | 30.4 | -1.9 | 27 | A |
| 346 | F | CA | 53.9 | 30.1 | -3.3 | 28 | A |
| 346 | F | CB | 53.4 | 31.2 | -4.2 | 29 | A |
| 346 | F | CG | 53.6 | 30.9 | -5.6 | 27 | A |
| 346 | F | CD1 | 52.7 | 30.0 | -6.3 | 25 | A |
| 346 | F | CD2 | 54.6 | 31.5 | -6.4 | 26 | A |
| 346 | F | CE1 | 52.9 | 29.7 | -7.7 | 27 | A |
| 346 | F | CE2 | 54.7 | 31.2 | -7.8 | 28 | A |
| 346 | F | CZ | 53.9 | 30.4 | -8.4 | 25 | A |
| 346 | F | C | 55.4 | 29.8 | -3.4 | 28 | A |
| 346 | F | O | 55.8 | 28.8 | -3.9 | 29 | A |
| 347 | E | N | 56.2 | 30.8 | -3.0 | 31 | A |
| 347 | E | CA | 57.6 | 30.8 | -3.1 | 33 | A |
| 347 | E | CB | 58.2 | 32.1 | -2.6 | 37 | A |

TABLE 4-continued

Structural Coordinates of Ah$_6$-ERK2 [non-phosphorlylated, SEQ ID NO: 5] (form 1)-olomoucine complex Crystals The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| | | | | | | | |
|---|---|---|---|---|---|---|---|
| 347 | E | CG | 57.6 | 33.3 | -3.2 | 43 | A |
| 347 | E | CD | 58.2 | 34.6 | -2.7 | 46 | A |
| 347 | E | OE1 | 58.2 | 34.8 | -1.4 | 46 | A |
| 347 | E | OE2 | 58.6 | 35.5 | -3.5 | 48 | A |
| 347 | E | C | 58.2 | 29.6 | -2.3 | 33 | A |
| 347 | E | O | 59.1 | 28.9 | -2.8 | 33 | A |
| 348 | E | N | 57.7 | 29.4 | -1.1 | 32 | A |
| 348 | E | CA | 58.1 | 28.3 | -0.2 | 32 | A |
| 348 | E | CB | 57.4 | 28.4 | 1.1 | 34 | A |
| 348 | E | CG | 58.1 | 27.7 | 2.3 | 35 | A |
| 348 | E | CD | 59.5 | 28.2 | 2.6 | 37 | A |
| 348 | E | OE1 | 59.6 | 29.4 | 2.7 | 33 | A |
| 348 | E | OE2 | 60.4 | 27.4 | 2.8 | 39 | A |
| 348 | E | C | 57.9 | 26.9 | -0.8 | 33 | A |
| 348 | E | O | 58.7 | 25.9 | -0.5 | 33 | A |
| 349 | T | N | 56.9 | 26.7 | -1.7 | 31 | A |
| 349 | T | CA | 56.6 | 25.5 | -2.3 | 30 | A |
| 349 | T | CB | 55.1 | 25.3 | -2.4 | 29 | A |
| 349 | T | OG1 | 54.5 | 26.4 | -3.0 | 25 | A |
| 349 | T | CG2 | 54.5 | 25.2 | -1.0 | 27 | A |
| 349 | T | C | 57.2 | 25.3 | -3.7 | 31 | A |
| 349 | T | O | 57.0 | 24.3 | -4.4 | 30 | A |
| 350 | A | N | 57.8 | 26.4 | -4.2 | 34 | A |
| 350 | A | CA | 58.4 | 26.4 | -5.6 | 37 | A |
| 350 | A | CB | 59.1 | 27.7 | -5.8 | 35 | A |
| 350 | A | C | 59.4 | 25.2 | -5.9 | 39 | A |
| 350 | A | O | 59.4 | 24.7 | -7.0 | 39 | A |
| 351 | R | N | 60.2 | 24.8 | -4.9 | 42 | A |
| 351 | R | CA | 61.2 | 23.8 | -5.1 | 43 | A |
| 351 | R | CB | 62.0 | 23.6 | -3.9 | 46 | A |
| 351 | R | CG | 61.2 | 23.4 | -2.6 | 50 | A |
| 351 | R | CD | 62.0 | 22.9 | -1.4 | 53 | A |
| 351 | R | NE | 62.6 | 21.6 | -1.7 | 58 | A |
| 351 | R | CZ | 63.3 | 20.9 | -0.8 | 59 | A |
| 351 | R | NH1 | 63.5 | 21.4 | 0.4 | 60 | A |
| 351 | R | NH2 | 63.8 | 19.7 | -1.1 | 60 | A |
| 351 | R | C | 60.6 | 22.4 | -5.6 | 43 | A |
| 351 | R | O | 61.4 | 21.6 | -6.1 | 44 | A |
| 352 | F | N | 59.3 | 22.2 | -5.5 | 42 | A |
| 352 | F | CA | 58.7 | 21.0 | -5.9 | 42 | A |
| 352 | F | CB | 57.7 | 20.6 | -4.8 | 42 | A |
| 352 | F | CG | 58.2 | 20.3 | -3.5 | 42 | A |
| 352 | F | CD1 | 58.9 | 19.1 | -3.3 | 42 | A |
| 352 | F | CD2 | 58.1 | 21.2 | -2.4 | 41 | A |
| 352 | F | CE1 | 59.5 | 18.8 | -2.0 | 41 | A |
| 352 | F | CE2 | 58.7 | 20.9 | -1.2 | 41 | A |
| 352 | F | CZ | 59.3 | 19.7 | -1.0 | 41 | A |
| 352 | F | C | 58.1 | 21.0 | -7.3 | 41 | A |
| 352 | F | O | 57.5 | 20.0 | -7.7 | 39 | A |
| 353 | Q | N | 58.2 | 22.1 | -8.0 | 43 | A |
| 353 | Q | CA | 57.7 | 22.2 | -9.3 | 47 | A |
| 353 | Q | CB | 57.4 | 23.7 | -9.7 | 46 | A |
| 353 | Q | CG | 56.3 | 24.3 | -8.9 | 44 | A |
| 353 | Q | CD | 55.0 | 23.7 | -9.2 | 43 | A |
| 353 | Q | OE1 | 54.5 | 22.8 | -8.4 | 43 | A |
| 353 | Q | NE2 | 54.3 | 24.1 | -10.3 | 44 | A |
| 353 | Q | C | 58.6 | 21.6 | -10.3 | 50 | A |
| 353 | Q | O | 59.8 | 21.8 | -10.3 | 50 | A |
| 354 | P | N | 58.0 | 20.8 | -11.3 | 52 | A |
| 354 | P | CD | 56.5 | 20.5 | -11.4 | 53 | A |
| 354 | P | CA | 58.7 | 20.1 | -12.3 | 54 | A |
| 354 | P | CB | 57.7 | 19.6 | -13.2 | 54 | A |
| 354 | P | CG | 56.5 | 19.3 | -12.3 | 54 | A |
| 354 | P | C | 59.7 | 21.1 | -13.0 | 55 | A |
| 354 | P | O | 59.2 | 22.1 | -13.5 | 56 | A |
| 355 | G | N | 61.0 | 20.8 | -13.0 | 57 | A |
| 355 | G | CA | 61.9 | 21.6 | -13.7 | 59 | A |
| 355 | G | C | 63.3 | 21.6 | -13.0 | 60 | A |
| 355 | G | O | 64.3 | 21.3 | -13.6 | 62 | A |
| 355 | G | OXT | 63.3 | 21.9 | -11.8 | 62 | A |
| 1 | O | OH2 | 52.9 | 20.9 | 23.0 | 17 | W |
| 3 | O | OH2 | 65.7 | 21.9 | 26.1 | 20 | W |
| 4 | O | OH2 | 67.2 | 13.4 | 18.4 | 12 | W |
| 5 | O | OH2 | 46.5 | 13.3 | 29.1 | 18 | W |
| 6 | O | OH2 | 63.2 | 21.1 | 26.4 | 17 | W |
| 7 | O | OH2 | 51.3 | 22.6 | 27.4 | 16 | W |
| 8 | O | OH2 | 61.7 | 14.6 | 9.1 | 19 | W |
| 9 | O | OH2 | 48.1 | 19.8 | 22.6 | 18 | W |
| 10 | O | OH2 | 60.4 | 17.0 | 8.7 | 20 | W |
| 11 | O | OH2 | 67.3 | 19.8 | 27.3 | 27 | W |
| 12 | O | OH2 | 46.5 | 27.9 | -17.8 | 21 | W |
| 13 | O | OH2 | 45.3 | 15.8 | 30.0 | 18 | W |
| 14 | O | OH2 | 60.7 | 22.1 | 30.6 | 20 | W |
| 15 | O | OH2 | 47.0 | 20.0 | 31.0 | 22 | W |
| 16 | O | OH2 | 45.2 | 25.6 | -17.5 | 30 | W |
| 17 | O | OH2 | 62.5 | 28.1 | 25.7 | 21 | W |
| 18 | O | OH2 | 61.8 | 22.6 | 28.3 | 21 | W |
| 19 | O | OH2 | 62.2 | 24.1 | 32.3 | 23 | W |
| 20 | O | OH2 | 47.0 | 24.8 | -6.5 | 19 | W |
| 21 | O | OH2 | 54.7 | 21.0 | 41.0 | 25 | W |
| 22 | O | OH2 | 68.1 | 7.5 | 30.2 | 20 | W |
| 23 | O | OH2 | 54.5 | 24.0 | 43.8 | 27 | W |
| 24 | O | OH2 | 60.6 | 1.1 | 15.7 | 25 | W |
| 25 | O | OH2 | 44.8 | 13.7 | 20.8 | 26 | W |
| 26 | O | OH2 | 42.6 | 26.0 | 29.6 | 18 | W |
| 27 | O | OH2 | 49.0 | 28.0 | -16.3 | 22 | W |
| 28 | O | OH2 | 56.2 | 27.5 | 29.9 | 17 | W |
| 29 | O | OH2 | 66.8 | 22.4 | 23.6 | 19 | W |
| 31 | O | OH2 | 56.9 | 23.4 | 40.8 | 23 | W |
| 32 | O | OH2 | 51.6 | 22.4 | 16.1 | 21 | W |
| 33 | O | OH2 | 40.9 | 22.5 | 22.9 | 26 | W |
| 34 | O | OH2 | 46.8 | 33.3 | 30.7 | 24 | W |
| 35 | O | OH2 | 61.6 | 18.7 | 37.3 | 23 | W |
| 36 | O | OH2 | 55.8 | 28.9 | 27.6 | 29 | W |
| 37 | O | OH2 | 54.7 | 23.0 | -5.5 | 25 | W |
| 38 | O | OH2 | 52.7 | 20.6 | -8.2 | 32 | W |
| 39 | O | OH2 | 51.9 | 22.9 | -10.9 | 31 | W |
| 40 | O | OH2 | 60.7 | 17.2 | 5.2 | 31 | W |
| 42 | O | OH2 | 49.8 | 41.3 | 33.4 | 21 | W |
| 43 | O | OH2 | 50.5 | 23.2 | 42.1 | 26 | W |
| 44 | O | OH2 | 48.0 | 22.0 | 24.6 | 27 | W |
| 45 | O | OH2 | 42.7 | 26.9 | -10.1 | 20 | W |
| 46 | O | OH2 | 64.8 | 2.1 | 30.0 | 24 | W |
| 47 | O | OH2 | 53.0 | 22.3 | 42.6 | 34 | W |
| 48 | O | OH2 | 52.6 | 18.9 | 43.1 | 39 | W |
| 49 | O | OH2 | 51.0 | -3.7 | 25.0 | 30 | W |
| 50 | O | OH2 | 59.3 | -6.0 | 28.9 | 19 | W |
| 51 | O | OH2 | 73.9 | 14.0 | 19.0 | 30 | W |
| 52 | O | OH2 | 45.8 | 9.7 | 32.8 | 31 | W |
| 53 | O | OH2 | 72.9 | 11.1 | 15.8 | 27 | W |
| 54 | O | OH2 | 67.0 | 26.9 | 21.1 | 37 | W |
| 55 | O | OH2 | 68.1 | 13.9 | 12.4 | 30 | W |
| 56 | O | OH2 | 73.4 | 15.5 | 16.5 | 26 | W |
| 57 | O | OH2 | 55.6 | 33.8 | 31.2 | 26 | W |
| 58 | O | OH2 | 51.3 | 28.6 | 14.1 | 70 | W |
| 59 | O | OH2 | 47.7 | 2.2 | 27.7 | 33 | W |
| 60 | O | OH2 | 73.2 | 16.1 | 21.6 | 45 | W |
| 61 | O | OH2 | 55.3 | 29.1 | 39.2 | 23 | W |
| 62 | O | OH2 | 61.0 | -1.2 | 28.9 | 32 | W |
| 63 | O | OH2 | 38.8 | 32.9 | 49.0 | 33 | W |
| 64 | O | OH2 | 71.2 | 23.0 | 16.9 | 49 | W |
| 65 | O | OH2 | 58.9 | 10.9 | 7.7 | 34 | W |
| 66 | O | OH2 | 54.4 | 17.2 | 39.7 | 32 | W |
| 67 | O | OH2 | 61.0 | 11.0 | 9.1 | 36 | W |
| 68 | O | OH2 | 70.7 | 28.2 | 11.6 | 44 | W |
| 69 | O | OH2 | 64.7 | 28.6 | 24.4 | 30 | W |
| 70 | O | OH2 | 65.4 | 30.3 | 22.7 | 41 | W |
| 71 | O | OH2 | 59.3 | 36.3 | 29.4 | 39 | W |
| 72 | O | OH2 | 60.6 | 18.2 | 39.9 | 32 | W |
| 73 | O | OH2 | 60.1 | 6.5 | 13.0 | 34 | W |

TABLE 4-continued

Structural Coordinates of Ah$_6$-ERK2 [non-phosphorlylated, SEQ ID NO: 5] (form 1)-olomoucine complex Crystals
The following table contains one line for each atom in one ERK2 kinase monomer. The columns are: 1) residue number, 2) l-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| 74 | O | OH2 | 51.3 | 21.1 | 45.7 | 48 | W |
|---|---|---|---|---|---|---|---|
| 75 | O | OH2 | 40.0 | 11.6 | 32.4 | 40 | W |
| 76 | O | OH2 | 52.8 | 33.4 | 52.8 | 44 | W |
| 77 | O | OH2 | 52.5 | 2.5 | 40.9 | 39 | W |
| 78 | O | OH2 | 58.1 | -0.4 | 39.8 | 37 | W |
| 79 | O | OH2 | 60.8 | -0.7 | 26.0 | 21 | W |
| 80 | O | OH2 | 69.1 | 3.8 | 21.6 | 34 | W |
| 81 | O | OH2 | 70.5 | 14.2 | 26.9 | 40 | W |
| 82 | O | OH2 | 70.2 | 13.4 | 24.3 | 21 | W |
| 83 | O | OH2 | 49.9 | 32.6 | 13.3 | 40 | W |
| 84 | O | OH2 | 45.9 | 35.0 | -5.7 | 36 | W |
| 85 | O | OH2 | 57.9 | 6.9 | 41.6 | 34 | W |
| 86 | O | OH2 | 48.7 | 22.2 | 15.3 | 41 | W |
| 87 | O | OH2 | 60.5 | 13.9 | 41.1 | 34 | W |
| 88 | O | OH2 | 63.0 | 32.2 | 11.0 | 44 | W |
| 89 | O | OH2 | 46.0 | 36.7 | -3.6 | 32 | W |
| 90 | O | OH2 | 50.0 | 32.4 | 22.5 | 37 | W |
| 91 | O | OH2 | 45.5 | 16.0 | 15.4 | 35 | W |
| 92 | O | OH2 | 52.9 | 27.4 | 36.4 | 26 | W |
| 93 | O | OH2 | 50.8 | 14.7 | 41.8 | 35 | W |
| 94 | O | OH2 | 42.4 | 37.5 | 40.1 | 28 | W |
| 95 | O | OH2 | 48.3 | 33.4 | 24.6 | 31 | W |
| 96 | O | OH2 | 67.3 | 20.1 | 22.4 | 24 | W |
| 97 | O | OH2 | 56.6 | 29.9 | 31.1 | 24 | W |
| 98 | O | OH2 | 49.7 | 1.6 | 34.4 | 44 | W |
| 99 | O | OH2 | 69.1 | 18.5 | 10.5 | 43 | W |
| 100 | O | OH2 | 41.5 | 26.3 | 39.6 | 31 | W |
| 101 | O | OH2 | 42.7 | 40.1 | 41.6 | 29 | W |
| 102 | O | OH2 | 71.2 | 9.0 | 14.9 | 27 | W |
| 103 | O | OH2 | 70.5 | 7.2 | 31.5 | 28 | W |
| 104 | O | OH2 | 56.9 | 12.3 | 5.1 | 23 | W |
| 105 | O | OH2 | 54.7 | -4.8 | 19.2 | 34 | W |
| 106 | O | OH2 | 61.4 | 26.4 | 28.9 | 32 | W |
| 107 | O | OH2 | 55.5 | 31.2 | 33.2 | 33 | W |
| 108 | O | OH2 | 68.8 | 9.2 | 12.9 | 33 | W |
| 109 | O | OH2 | 63.8 | 28.0 | 27.9 | 42 | W |
| 110 | O | OH2 | 47.7 | 32.1 | 27.1 | 27 | W |
| 111 | O | OH2 | 66.9 | 10.9 | 12.9 | 32 | W |
| 112 | O | OH2 | 63.4 | 35.4 | 23.7 | 29 | W |
| 113 | O | OH2 | 61.5 | 5.0 | 14.6 | 44 | W |
| 114 | O | OH2 | 79.0 | 22.3 | 8.1 | 50 | W |
| 115 | O | OH2 | 42.9 | 21.6 | -6.0 | 43 | W |
| 116 | O | OH2 | 58.9 | 26.3 | -9.4 | 53 | W |
| 117 | O | OH2 | 44.7 | 36.0 | -1.4 | 36 | W |
| 118 | O | OH2 | 54.9 | 35.1 | 13.3 | 45 | W |
| 119 | O | OH2 | 50.8 | 38.6 | -5.1 | 48 | W |
| 120 | O | OH2 | 51.0 | 24.9 | 23.5 | 28 | W |
| 121 | O | OH2 | 9999.0 | 1.0 | 0.0 | 0 | |
| 122 | O | OH2 | 54.8 | 19.2 | -7.6 | 44 | W |
| 123 | O | OH2 | 43.4 | 13.4 | 23.1 | 32 | W |
| 124 | O | OH2 | 39.5 | 25.7 | -2.5 | 53 | W |
| 125 | O | OH2 | 54.1 | 16.7 | -7.6 | 37 | W |
| 126 | O | OH2 | 43.0 | 11.8 | 36.0 | 45 | W |
| 127 | O | OH2 | 44.6 | 21.9 | 18.0 | 37 | W |
| 128 | O | OH2 | 71.5 | 3.8 | 20.2 | 39 | W |
| 129 | O | OH2 | 60.9 | 5.7 | 10.2 | 47 | W |
| 130 | O | OH2 | 42.1 | 28.3 | -0.0 | 31 | W |
| 131 | O | OH2 | 51.8 | 0.5 | 33.1 | 40 | W |
| 132 | O | OH2 | 67.4 | 26.8 | 25.6 | 35 | W |
| 133 | O | OH2 | 54.4 | 1.5 | 33.7 | 30 | W |
| 134 | O | OH2 | 61.1 | 0.4 | 31.1 | 35 | W |
| 135 | O | OH2 | 52.3 | 17.4 | 9.7 | 26 | W |
| 136 | O | OH2 | 41.0 | 19.0 | 24.7 | 30 | W |
| 137 | O | OH2 | 42.5 | 31.8 | 51.0 | 33 | W |
| 138 | O | OH2 | 61.8 | 1.1 | 34.3 | 48 | W |
| 139 | O | OH2 | 41.8 | 15.4 | 36.3 | 30 | W |
| 140 | O | OH2 | 56.5 | 9.2 | 41.8 | 46 | W |
| 141 | O | OH2 | 9999.0 | 1.0 | 0.0 | 0 | |
| 142 | O | OH2 | 63.2 | 27.6 | 6.2 | 55 | W |
| 143 | O | OH2 | 64.0 | 7.0 | 38.7 | 32 | W |
| 144 | O | OH2 | 48.4 | 2.3 | 36.7 | 36 | W |
| 145 | O | OH2 | 57.6 | 35.5 | 19.6 | 50 | W |
| 146 | O | OH2 | 9999.0 | 1.0 | 0.0 | 0 | |
| 147 | O | OH2 | 68.2 | 5.9 | 19.5 | 24 | W |
| 148 | O | OH2 | 49.1 | -4.0 | 30.1 | 45 | W |
| 149 | O | OH2 | 46.9 | 20.3 | -8.0 | 34 | W |
| 150 | O | OH2 | 55.3 | 24.3 | -12.8 | 36 | W |
| 151 | O | OH2 | 60.1 | 34.3 | 7.9 | 60 | W |
| 152 | O | OH2 | 53.0 | -4.2 | 16.6 | 47 | W |
| 153 | O | OH2 | 69.8 | 19.8 | 22.5 | 40 | W |
| 154 | O | OH2 | 42.1 | 16.7 | 39.0 | 29 | W |
| 155 | O | OH2 | 58.6 | 33.7 | 18.1 | 47 | W |
| 156 | O | OH2 | 57.0 | 28.6 | -8.6 | 33 | W |
| 157 | O | OH2 | 55.4 | 27.8 | -10.5 | 34 | W |
| 158 | O | OH2 | 50.1 | 17.7 | 49.6 | 46 | W |
| 159 | O | OH2 | 42.4 | 7.9 | 22.7 | 34 | W |
| 160 | O | OH2 | 55.3 | 3.8 | 42.5 | 43 | W |
| 161 | O | OH2 | 65.7 | 13.1 | 36.1 | 29 | W |
| 162 | O | OH2 | 44.2 | 25.2 | -6.6 | 31 | W |
| 163 | O | OH2 | 52.8 | 39.2 | 32.6 | 33 | W |
| 164 | O | OH2 | 57.7 | 32.8 | 33.9 | 60 | W |
| 165 | O | OH2 | 36.2 | 27.4 | 27.3 | 38 | W |
| 166 | O | OH2 | 68.3 | 21.3 | 8.2 | 57 | W |
| 167 | O | OH2 | 66.3 | 20.1 | 36.5 | 45 | W |
| 168 | O | OH2 | 52.0 | 40.5 | 27.1 | 42 | W |
| 169 | O | OH2 | 33.3 | 11.5 | -5.7 | 58 | W |
| 170 | O | OH2 | 51.0 | 14.6 | -9.1 | 50 | W |
| 171 | O | OH2 | 43.1 | 7.9 | 25.6 | 44 | W |
| 172 | O | OH2 | 62.4 | 30.9 | 8.8 | 60 | W |
| 173 | O | OH2 | 58.3 | 31.9 | 1.4 | 40 | W |
| 174 | O | OH2 | 48.0 | -3.4 | 23.9 | 45 | W |
| 175 | O | OH2 | 57.7 | 36.8 | 14.7 | 54 | W |
| 176 | O | OH2 | 58.0 | 27.3 | 48.9 | 41 | W |
| 177 | O | OH2 | 71.2 | 21.7 | 21.3 | 39 | W |
| 178 | O | OH2 | 52.4 | 34.9 | 37.2 | 32 | W |
| 179 | O | OH2 | 57.1 | 30.7 | 37.3 | 41 | W |
| 180 | O | OH2 | 76.0 | 4.4 | 19.9 | 33 | W |
| 181 | O | OH2 | 61.3 | 20.5 | 41.3 | 32 | W |
| 182 | O | OH2 | 48.5 | 36.8 | -3.1 | 45 | W |
| 183 | O | OH2 | 55.8 | 35.4 | 35.5 | 52 | W |
| 184 | O | OH2 | 70.1 | -2.3 | 24.0 | 57 | W |
| 185 | O | OH2 | 46.8 | 0.5 | 34.2 | 60 | W |
| 186 | O | OH2 | 68.5 | 26.1 | 19.3 | 48 | W |
| 187 | O | OH2 | 34.1 | 23.2 | 37.4 | 45 | W |
| 188 | O | OH2 | 66.9 | 4.6 | 15.1 | 39 | W |
| 189 | O | OH2 | 44.0 | 18.9 | 16.1 | 42 | W |
| 190 | O | OH2 | 44.9 | 39.6 | 6.0 | 70 | W |
| 191 | O | OH2 | 42.2 | 7.3 | -8.0 | 55 | W |
| 192 | O | OH2 | 62.4 | 6.6 | 40.9 | 40 | W |
| 193 | O | OH2 | 65.4 | 0.5 | 32.9 | 57 | W |
| 194 | O | OH2 | 58.0 | 18.2 | 40.5 | 55 | W |
| 195 | O | OH2 | 54.8 | 6.2 | 2.5 | 33 | W |
| 196 | O | OH2 | 66.1 | 5.2 | 39.2 | 36 | W |
| 197 | O | OH2 | 35.9 | 18.6 | 27.0 | 45 | W |
| 198 | O | OH2 | 61.0 | 19.4 | -8.8 | 52 | W |
| 199 | O | OH2 | 48.9 | 26.4 | 20.0 | 91 | W |
| 200 | O | OH2 | 57.7 | 43.4 | 28.5 | 74 | W |
| 201 | O | OH2 | 41.1 | 30.1 | 24.9 | 45 | W |
| 202 | O | OH2 | 58.8 | 22.1 | 41.9 | 34 | W |
| 203 | O | OH2 | 59.5 | 41.7 | 27.4 | 51 | W |
| 204 | O | OH2 | 42.3 | 36.8 | 25.9 | 36 | W |
| 205 | O | OH2 | 50.9 | 22.2 | 48.6 | 53 | W |
| 206 | O | OH2 | 33.3 | 20.7 | -5.9 | 60 | W |
| 207 | O | OH2 | 44.1 | 2.2 | 11.8 | 54 | W |
| 208 | O | OH2 | 62.2 | 13.4 | 6.8 | 44 | W |
| 209 | O | OH2 | 52.9 | 2.8 | 2.4 | 55 | W |
| 210 | O | OH2 | 62.8 | 30.0 | 29.4 | 52 | W |
| 211 | O | OH2 | 38.1 | 23.0 | -0.3 | 50 | W |
| 212 | O | OH2 | 62.0 | 7.6 | 8.9 | 48 | W |
| 213 | O | OH2 | 43.8 | 5.3 | -10.7 | 60 | W |

TABLE 4-continued

Structural Coordinates of Ah₆-ERK2 [non-phosphorlylated, SEQ ID NO: 5] (form 1)-olomoucine complex Crystals
The following table contains one line for each atom in one ERK2 kinase monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X and Z are SO4 and the olomoucine). The coordinates are arranged in two side-by-side columns.

| | | | | | | | |
|---|---|---|---|---|---|---|---|
| 214 | O | OH2 | 57.1 | 16.9 | −10.4 | 56 | W |
| 215 | O | OH2 | 63.8 | 25.2 | 45.5 | 48 | W |
| 216 | O | OH2 | 43.2 | 14.3 | 14.0 | 51 | W |
| 217 | O | OH2 | 37.3 | 25.4 | −1.1 | 78 | W |
| 218 | O | OH2 | 63.9 | 2.2 | 13.1 | 49 | W |
| 219 | O | OH2 | 60.8 | 32.8 | 46.9 | 60 | W |
| 220 | O | OH2 | 56.9 | 44.4 | 11.5 | 69 | W |
| 221 | O | OH2 | 39.2 | 39.8 | 2.4 | 48 | W |
| 222 | O | OH2 | 36.8 | 8.3 | −5.8 | 49 | W |
| 500 | X | S | 57.3 | 33.0 | 14.7 | 80 | W |
| 500 | X | O1 | 56.8 | 32.9 | 13.3 | 80 | W |
| 500 | X | O2 | 56.5 | 34.0 | 15.4 | 80 | W |
| 500 | X | O3 | 57.2 | 31.7 | 15.3 | 79 | W |
| 500 | X | O4 | 58.7 | 33.5 | 14.7 | 79 | W |
| 501 | X | S | 67.0 | 31.7 | 10.7 | 80 | W |
| 501 | X | O1 | 66.5 | 30.7 | 9.7 | 80 | W |
| 501 | X | O2 | 67.9 | 31.0 | 11.6 | 80 | W |
| 501 | X | O3 | 67.6 | 32.8 | 10.0 | 81 | W |
| 501 | X | O4 | 65.8 | 32.2 | 11.5 | 80 | W |
| 800 | Z | N | 50.1 | 11.3 | 7.8 | 36 | S |
| 800 | Z | C | 50.7 | 10.0 | 7.7 | 37 | S |
| 800 | Z | N1 | 49.9 | 8.9 | 7.7 | 36 | S |
| 800 | Z | C3A | 48.7 | 9.5 | 7.9 | 38 | S |
| 800 | Z | C7A | 48.8 | 10.9 | 8.0 | 37 | S |
| 800 | Z | C1 | 47.4 | 8.9 | 8.0 | 40 | S |
| 800 | Z | N2 | 46.2 | 9.7 | 8.2 | 42 | S |
| 800 | Z | C2 | 46.3 | 11.2 | 8.3 | 42 | S |
| 800 | Z | N3 | 47.6 | 11.8 | 8.2 | 40 | S |
| 800 | Z | C3 | 50.8 | 12.6 | 7.8 | 36 | S |
| 800 | Z | N4 | 45.1 | 11.9 | 8.5 | 45 | S |
| 800 | Z | C4 | 43.9 | 11.6 | 9.2 | 48 | S |
| 800 | Z | C5 | 44.2 | 11.1 | 10.7 | 50 | S |
| 800 | Z | O | 43.0 | 10.7 | 11.3 | 52 | S |
| 800 | Z | N5 | 47.2 | 7.4 | 8.0 | 42 | S |
| 800 | Z | C6 | 46.2 | 6.5 | 8.5 | 42 | S |
| 800 | Z | C7 | 46.3 | 7.4 | 10.9 | 41 | S |
| 800 | Z | C8 | 45.7 | 7.8 | 12.2 | 42 | S |
| 800 | Z | C9 | 44.3 | 7.6 | 12.4 | 43 | S |
| 800 | Z | C10 | 43.5 | 7.0 | 11.3 | 43 | S |
| 800 | Z | C11 | 44.1 | 6.7 | 10.1 | 42 | S |
| 800 | Z | C12 | 45.5 | 6.9 | 9.9 | 42 | S |

Example 22

Ah₆-ERK2 [Non-Phosphorlylated] (Form 1)-Olomoucine Complex Structure Determination The crystal structure was solved using molecular replacement using the search models 1ERK and 3ERK and 4ERK from the PDB. Refinement was done using the program CNX.

| | |
|---|---|
| Theoretical number of reflections | 28237 |
| Resolution Limits | 30.0-2.00 Å |
| Number of unobserved reflections | 891 (3.2%) |
| Number of reflections in working set | 25956 (91.9%) |
| Number of reflections in test set | 1390 (4.9%) |
| Number of protein residues | 346 |
| Number of solvent atoms | 219 |
| R-factor | 0.222 |
| R-free | 0.259 |
| RMSD bond length | 0.0061 Å |
| RMSD bond angles | 1.126° |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, Genbank Accession Numbers and publications are cited throughout this application, the disclosures of which are incorporated herein by reference in their entireties.

We claim:

1. A method for crystallizing a polypeptide comprising placing a non-liganded, non-phosphorylated polypeptide comprising SEQ ID NO:5 at a concentration of about 5 mg/mL to about 25 mg/mL in an aqueous buffered solution comprising 100 mM MES at a pH of from about 5.5 to about 6.7, from about 1% to about 8% polyethylene glycol (PEG) 400 (v/v), and about 2.4 M ammonium sulfate, and crystallizing the non-liganded, non-phosphorylated polypeptide comprising SEQ ID NO:5.

2. The method of claim 1 wherein the non-liganded, non-phosphorylated polypeptide comprising SEQ ID NO:5 is crystallized by a method selected from the group consisting of hanging-drop vapor diffusion and sitting drop vapor diffusion.

3. A method for crystallizing a polypeptide comprising placing a non-liganded, diphosphorylated or dithiophosphorylated polypeptide comprising SEQ ID NO:5, wherein Thr190 and Tyr192 of SEQ ID NO:5 are phosphorylated or wherein Thr190 and Tyr192 of SEQ ID NO:5 are thiophosphorylated, at a concentration of about 3 mg/mL to about 25 mg/mL in an aqueous buffered solution comprising 10 mM sodium citrate at a pH of from about 5 to about 6.2 and a concentration of from about 5% to about 30% isopropanol (v/v), and crystallizing the non-liganded, dephosphorylated or dithiophosphorylated polypeptide comprising SEQ ID NO:5.

4. The method of claim 3 wherein the non-liganded, diphosphorylated or dithiophosphorylated polypeptide comprising SEQ ID NO:5 is crystallized by a method selected from the group consisting of hanging-drop vapor diffusion and sitting drop vapor diffusion.

5. A method for soaking a ligand into a crystallized polypeptide comprising placing a non-liganded, non-phosphorylated polypeptide comprising SEQ ID NO:5 at a concentration of about 5 mg/mL to about 25 mg/mL in an aqueous buffered solution comprising 100 mM MES at a pH of from about 5.5 to about 6.7, from about 1% to about 8% polyethylene glycol (PEG) 400 (v/v), and about 2.4 M ammonium sulfate, and crystallizing the non-liganded, non-phosphorylated polypeptide comprising SEQ ID NO:5 by hanging drop vapor diffusion method and soaking said crystal in a solution comprising olomoucine, thereby soaking olomoucine into the crystallized non-liganded, non-phosphorylated polypeptide comprising SEQ ID NO:5.

* * * * *

SEQUENCE LISTING

<160> NUMBER OF SEQ ID NOS: 6

<210> SEQ ID NO 1
<211> LENGTH: 84
<212> TYPE: DNA
<213> ORGANISM: Artificial Sequence
<220> FEATURE:
<223> OTHER INFORMATION: Primer NpT7-5 mouse Erk2 forward

<400> SEQUENCE: 1
ccggaattct aaggaggttt aaccatggca catcaccatc accatcacat ggcggcggcg        60
gcggcggcgg gcccggagat ggtc                                              84

<210> SEQ ID NO 2
<211> LENGTH: 50

```
<212> TYPE: DNA
<213> ORGANISM: Artificial Sequence
<220> FEATURE:
<223> OTHER INFORMATION: Primer Mouse Erk2 reverse

<400> SEQUENCE: 2
cccaagcttt taagatctgt atcctggctg gaatctagca gtctcttcaa          50

<210> SEQ ID NO 3
<211> LENGTH: 366
<212> TYPE: PRT
<213> ORGANISM: Artificial Sequence
<220> FEATURE:
<223> OTHER INFORMATION: Met-Ala-His6-ERK2

<400> SEQUENCE: 3
```

Met Ala His His His His His His Met Ala Ala Ala Ala Ala Gly
1               5                   10                  15

Pro Glu Met Val Arg Gly Gln Val Phe Asp Val Gly Pro Arg Tyr Thr
            20                  25                  30

Asn Leu Ser Tyr Ile Gly Glu Gly Ala Tyr Gly Met Val Cys Ser Ala
            35                  40                  45

Tyr Asp Asn Leu Asn Lys Val Arg Val Ala Ile Lys Lys Ile Ser Pro
50                  55                  60

Phe Glu His Gln Thr Tyr Cys Gln Arg Thr Leu Arg Glu Ile Lys Ile
65                  70                  75                  80

Leu Leu Arg Phe Arg His Glu Asn Ile Ile Gly Ile Asn Asp Ile Ile
                85                  90                  95

Arg Ala Pro Thr Ile Glu Gln Met Lys Asp Val Tyr Ile Val Gln Asp
            100                 105                 110

Leu Met Glu Thr Asp Leu Tyr Lys Leu Leu Lys Thr Gln His Leu Ser
        115                 120                 125

Asn Asp His Ile Cys Tyr Phe Leu Tyr Gln Ile Leu Arg Gly Leu Lys
    130                 135                 140

Tyr Ile His Ser Ala Asn Val Leu His Arg Asp Leu Lys Pro Ser Asn
145                 150                 155                 160

Leu Leu Leu Asn Thr Thr Cys Asp Leu Lys Ile Cys Asp Phe Gly Leu
                165                 170                 175

Ala Arg Val Ala Asp Pro Asp His Asp His Thr Gly Phe Leu Thr Glu
            180                 185                 190

Tyr Val Ala Thr Arg Trp Tyr Arg Ala Pro Glu Ile Met Leu Asn Ser
        195                 200                 205

Lys Gly Tyr Thr Lys Ser Ile Asp Ile Trp Ser Val Gly Cys Ile Leu
    210                 215                 220

Ala Glu Met Leu Ser Asn Arg Pro Ile Phe Pro Gly Lys His Tyr Leu
225                 230                 235                 240

Asp Gln Leu Asn His Ile Leu Gly Ile Leu Gly Ser Pro Ser Gln Glu
                245                 250                 255

Asp Leu Asn Cys Ile Ile Asn Leu Lys Ala Arg Asn Tyr Leu Leu Ser
            260                 265                 270

Leu Pro His Lys Asn Lys Val Pro Trp Asn Arg Leu Phe Pro Asn Ala
        275                 280                 285

Asp Ser Lys Ala Leu Asp Leu Leu Asp Lys Met Leu Thr Phe Asn Pro
    290                 295                 300

His Lys Arg Ile Glu Val Glu Gln Ala Leu Ala His Pro Tyr Leu Glu
305                 310                 315                 320

```
Gln Tyr Tyr Asp Pro Ser Asp Glu Pro Ile Ala Glu Ala Pro Phe Lys
            325                 330                 335

Phe Asp Met Glu Leu Asp Asp Leu Pro Lys Glu Lys Leu Lys Glu Leu
            340                 345                 350

Ile Phe Glu Glu Thr Ala Arg Phe Gln Pro Gly Tyr Arg Ser
            355                 360                 365
```

<210> SEQ ID NO 4
<211> LENGTH: 1101
<212> TYPE: DNA
<213> ORGANISM: Artificial Sequence
<220> FEATURE:
<223> OTHER INFORMATION: Met-Ala-His6-ERK2

<400> SEQUENCE: 4

```
atggcacatc accatcacca tcacatggcg gcggcggcgg cggcgggccc ggagatggtc     60
cgcgggcagg tgttcgacgt agggccgcgc tacaccaacc tctcgtacat cggagaaggc    120
gcctacggca tggtttgctc tgcttatgat aatctcaaca agttcgagt  gctatcaag     180 aaaatcagtc cttttgagca ccagacctac tgtcaaagaa ccctaagaga gataaaaatc    240
ttactgcgct tcagacatga aacatcatt  ggcatcaatg acatcatccg ggcaccaacc    300
attgagcaaa tgaaagatgt atatatagta caggacctca tggagacgga cctttacaag    360
ctcttgaaga cacagcacct cagcaatgac acacatctgct attttcttta tcagatcctg    420
agagggctaa agtatatcca ttcagctaac gttctgcacc gtgacctcaa gccttccaac    480
ctcctgctga acaccacttg tgatctcaag atctgtgact tggccttgc  ccgtgttgca    540 gatccagatc atgatcacac agggttcttg acagagtacg tagccacacg ttggtacaga    600
gctccagaaa ttatgttgaa ctccaagggt tataccaagt ccattgatat ttggtctgtg    660
ggctgcatcc tggcagagat gctatccaac aggcctatct cccaggaaa  gcattacctt    720 gaccagctga atcacatcct gggtattctt ggatctccat acaggaaga  tctgaattgt    780 ataataaatt taaaagctag aaactatttg ctttctctcc cgcacaaaaa taaggtgcca    840
tggaacaggt tgttcccaaa tgctgactcc aaagctctgg atttactgga taaaatgttg    900
acatttaacc ctcacaagag gattgaagtt gaacaggctc tggcccaccc atacctggag    960
cagtattatg acccaagtga tgagcccatt gctgaagcgc cattcaagtt tgacatggag   1020
ttggacgact acctaaggaa gaagctcaaa gaactcattt ttgaagagac tgctagattc   1080
cagccaggat acagatctta a                                             1101
```

<210> SEQ ID NO 5
<211> LENGTH: 365
<212> TYPE: PRT
<213> ORGANISM: Artificial Sequence
<220> FEATURE:
<223> OTHER INFORMATION: Ala-His6-ERK2

<400> SEQUENCE: 5

```
Ala His His His His His His Met Ala Ala Ala Ala Ala Gly Pro
1               5                   10                  15

Glu Met Val Arg Gly Gln Val Phe Asp Val Gly Pro Arg Tyr Thr Asn
            20                  25                  30

Leu Ser Tyr Ile Gly Glu Gly Ala Tyr Gly Met Val Cys Ser Ala Tyr
        35                  40                  45
```

```
Asp Asn Leu Asn Lys Val Arg Val Ala Ile Lys Lys Ile Ser Pro Phe
        50                  55                  60

Glu His Gln Thr Tyr Cys Gln Arg Thr Leu Arg Glu Ile Lys Ile Leu
65                  70                  75                  80

Leu Arg Phe Arg His Glu Asn Ile Ile Gly Ile Asn Asp Ile Ile Arg
                85                  90                  95

Ala Pro Thr Ile Glu Gln Met Lys Asp Val Tyr Ile Val Gln Asp Leu
            100                 105                 110

Met Glu Thr Asp Leu Tyr Lys Leu Leu Lys Thr Gln His Leu Ser Asn
        115                 120                 125

Asp His Ile Cys Tyr Phe Leu Tyr Gln Ile Leu Arg Gly Leu Lys Tyr
    130                 135                 140

Ile His Ser Ala Asn Val Leu His Arg Asp Leu Lys Pro Ser Asn Leu
145                 150                 155                 160

Leu Leu Asn Thr Thr Cys Asp Leu Lys Ile Cys Asp Phe Gly Leu Ala
                165                 170                 175

Arg Val Ala Asp Pro Asp His Asp His Thr Gly Phe Leu Thr Glu Tyr
            180                 185                 190

Val Ala Thr Arg Trp Tyr Arg Ala Pro Glu Ile Met Leu Asn Ser Lys
        195                 200                 205

Gly Tyr Thr Lys Ser Ile Asp Ile Trp Ser Val Gly Cys Ile Leu Ala
    210                 215                 220

Glu Met Leu Ser Asn Arg Pro Ile Phe Pro Gly Lys His Tyr Leu Asp
225                 230                 235                 240

Gln Leu Asn His Ile Leu Gly Ile Leu Gly Ser Pro Ser Gln Glu Asp
                245                 250                 255

Leu Asn Cys Ile Ile Asn Leu Lys Ala Arg Asn Tyr Leu Leu Ser Leu
            260                 265                 270

Pro His Lys Asn Lys Val Pro Trp Asn Arg Leu Phe Pro Asn Ala Asp
        275                 280                 285

Ser Lys Ala Leu Asp Leu Leu Asp Lys Met Leu Thr Phe Asn Pro His
    290                 295                 300

Lys Arg Ile Glu Val Glu Gln Ala Leu Ala His Pro Tyr Leu Glu Gln
305                 310                 315                 320

Tyr Tyr Asp Pro Ser Asp Glu Pro Ile Ala Glu Ala Pro Phe Lys Phe
                325                 330                 335

Asp Met Glu Leu Asp Asp Leu Pro Lys Glu Lys Leu Lys Glu Leu Ile
            340                 345                 350

Phe Glu Glu Thr Ala Arg Phe Gln Pro Gly Tyr Arg Ser
        355                 360                 365

<210> SEQ ID NO 6
<211> LENGTH: 358
<212> TYPE: PRT
<213> ORGANISM: Mus sp.

<400> SEQUENCE: 6

Met Ala Ala Ala Ala Ala Gly Pro Glu Met Val Arg Gly Gln Val
1               5                   10                  15

Phe Asp Val Gly Pro Arg Tyr Thr Asn Leu Ser Tyr Ile Gly Glu Gly
                20                  25                  30

Ala Tyr Gly Met Val Cys Ser Ala Tyr Asp Asn Leu Asn Lys Val Arg
            35                  40                  45

Val Ala Ile Lys Lys Ile Ser Pro Phe Glu His Gln Thr Tyr Cys Gln
```

-continued

```
            50                  55                  60
Arg Thr Leu Arg Glu Ile Lys Ile Leu Leu Arg Phe Arg His Glu Asn
65                  70                  75                  80

Ile Ile Gly Ile Asn Asp Ile Ile Arg Ala Pro Thr Ile Glu Gln Met
                85                  90                  95

Lys Asp Val Tyr Ile Val Gln Asp Leu Met Glu Thr Asp Leu Tyr Lys
                100                 105                 110

Leu Leu Lys Thr Gln His Leu Ser Asn Asp His Ile Cys Tyr Phe Leu
            115                 120                 125

Tyr Gln Ile Leu Arg Gly Leu Lys Tyr Ile His Ser Ala Asn Val Leu
        130                 135                 140

His Arg Asp Leu Lys Pro Ser Asn Leu Leu Leu Asn Thr Thr Cys Asp
145                 150                 155                 160

Leu Lys Ile Cys Asp Phe Gly Leu Ala Arg Val Ala Asp Pro Asp His
                165                 170                 175

Asp His Thr Gly Phe Leu Thr Glu Tyr Val Ala Thr Arg Trp Tyr Arg
            180                 185                 190

Ala Pro Glu Ile Met Leu Asn Ser Lys Gly Tyr Thr Lys Ser Ile Asp
        195                 200                 205

Ile Trp Ser Val Gly Cys Ile Leu Ala Glu Met Leu Ser Asn Arg Pro
    210                 215                 220

Ile Phe Pro Gly Lys His Tyr Leu Asp Gln Leu Asn His Ile Leu Gly
225                 230                 235                 240

Ile Leu Gly Ser Pro Ser Gln Glu Asp Leu Asn Cys Ile Ile Asn Leu
                245                 250                 255

Lys Ala Arg Asn Tyr Leu Leu Ser Leu Pro His Lys Asn Lys Val Pro
            260                 265                 270

Trp Asn Arg Leu Phe Pro Asn Ala Asp Ser Lys Ala Leu Asp Leu Leu
        275                 280                 285

Asp Lys Met Leu Thr Phe Asn Pro His Lys Arg Ile Glu Val Glu Gln
    290                 295                 300

Ala Leu Ala His Pro Tyr Leu Glu Gln Tyr Tyr Asp Pro Ser Asp Glu
305                 310                 315                 320

Pro Ile Ala Glu Ala Pro Phe Lys Phe Asp Met Glu Leu Asp Asp Leu
                325                 330                 335

Pro Lys Glu Lys Leu Lys Glu Leu Ile Phe Glu Glu Thr Ala Arg Phe
            340                 345                 350

Gln Pro Gly Tyr Arg Ser
            355
```